United States Patent
Martini et al.

(10) Patent No.: US 12,239,742 B2
(45) Date of Patent: *Mar. 4, 2025

(54) POLYNUCLEOTIDES ENCODING CITRIN FOR THE TREATMENT OF CITRULLINEMIA TYPE 2

(71) Applicant: ModernaTX, Inc., Cambridge, MA (US)

(72) Inventors: Paolo Martini, Boston, MA (US); Stephen Hoge, Cambridge, MA (US); Kerry Benenato, Cambridge, MA (US); Vladimir Presnyak, Manchester, NH (US); Iain McFadyen, Medford, MA (US); Ellalahewage Sathyajith Kumarasinghe, Cambridge, MA (US); Jingsong Cao, Cambridge, MA (US); Lin Tung Guey, Lexington, MA (US); Staci Sabnis, Cambridge, MA (US)

(73) Assignee: ModernaTX, Inc., Cambridge, MA (US)

(*) Notice: Subject to any disclaimer, the term of this patent is extended or adjusted under 35 U.S.C. 154(b) by 711 days.

This patent is subject to a terminal disclaimer.

(21) Appl. No.: 17/154,325

(22) Filed: Jan. 21, 2021

(65) Prior Publication Data

US 2022/0071915 A1    Mar. 10, 2022

Related U.S. Application Data

(63) Continuation of application No. 16/302,360, filed as application No. PCT/US2017/033421 on May 18, 2017, now Pat. No. 10,993,918.

(60) Provisional application No. 62/338,479, filed on May 18, 2016.

(51) Int. Cl.
| | | |
|---|---|---|
| *C12N 15/11* | (2006.01) | |
| *A61K 9/00* | (2006.01) | |
| *A61K 9/51* | (2006.01) | |
| *A61P 13/00* | (2006.01) | |
| *C07K 14/47* | (2006.01) | |
| *A61K 38/00* | (2006.01) | |

(52) U.S. Cl.
CPC .......... *A61K 9/5123* (2013.01); *A61K 9/0019* (2013.01); *A61K 9/5146* (2013.01); *A61P 13/00* (2018.01); *C07K 14/47* (2013.01); *A61K 38/00* (2013.01)

(58) Field of Classification Search
CPC ............... A61K 47/549; A61K 48/005; A61K 31/7105; A61K 31/7125; A61K 48/0066; A61K 31/7088; C12N 15/11; C12N 15/67
See application file for complete search history.

(56) References Cited

U.S. PATENT DOCUMENTS

| | | |
|---|---|---|
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,220,792 B2 | 12/2015 | Chakraborty et al. |
| 9,233,141 B2 | 1/2016 | Chakraborty et al. |
| 9,814,760 B2 | 11/2017 | Bancel et al. |
| 2013/0259923 A1 | 10/2013 | Bancel et al. |
| 2014/0010861 A1* | 1/2014 | Bancel .................. C07K 14/62 536/23.4 |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0155486 A1 | 6/2014 | Gregory et al. |
| 2014/0193482 A1 | 7/2014 | Bancel et al. |
| 2014/0194494 A1 | 7/2014 | Bancel et al. |
| 2014/0200263 A1 | 7/2014 | Bancel et al. |
| 2018/0311381 A1 | 11/2018 | Bancel et al. |
| 2019/0298657 A1 | 10/2019 | Martini et al. |
| 2019/0298658 A1 | 10/2019 | Benenato et al. |
| 2019/0300906 A1 | 10/2019 | Martini et al. |

(Continued)

FOREIGN PATENT DOCUMENTS

| | | |
|---|---|---|
| JP | 2000316577 | 11/2000 |
| JP | 2004315469 | 11/2004 |

(Continued)

OTHER PUBLICATIONS

Cao et al., Citrin mRNA therapy improved metabolic and behavioral abnormalities in a mouse model of type II citrullinemia, abstract No. 26, Society for Inherited Metabolic Disorders, 40th Annual Meeting, Mar. 2018, San Diego, Ca, Molecular Genetics and Metabolism, vol. 123. (Year: 2018).*

Yasuda et al., "Identification of two novel mutations in the SLC25A13 gene and detection of seven mutations in 102 patients with adult-onset type 1 citrullinemia", Human Genetics, 2000, 107:537-545.

(Continued)

*Primary Examiner* — Dana H Shin
(74) *Attorney, Agent, or Firm* — Fish & Richardson P.C.

(57) ABSTRACT

The invention relates to mRNA therapy for the treatment of Citrullinemia Type 2 ("CTLN2"). mRNAs for use in the invention, when administered in vivo, encode human Citrin, isoforms thereof, functional fragments thereof, and fusion proteins comprising Citrin. mRNAs of the invention are preferably encapsulated in lipid nanoparticles (LNPs) to effect efficient delivery to cells and/or tissues in subjects, when administered thereto. mRNA therapies of the invention increase and/or restore deficient levels of Citrin expression and/or activity in subjects. mRNA therapies of the invention further decrease levels of biomarkers associated with deficient Citrin activity in subjects, namely ammonia and/or triglycerides.

3 Claims, 16 Drawing Sheets

Specification includes a Sequence Listing.

(56) References Cited

U.S. PATENT DOCUMENTS

| | | | |
|---|---|---|---|
| 2019/0390181 A1 | 12/2019 | Benenato et al. | |
| 2020/0078314 A1 | 3/2020 | Martini et al. | |
| 2020/0085916 A1 | 3/2020 | Martini et al. | |

FOREIGN PATENT DOCUMENTS

| | | |
|---|---|---|
| JP | 2006001868 | 1/2006 |
| JP | 2006036646 | 2/2006 |
| JP | 2015516143 | 8/2015 |
| WO | WO2011068810 | 6/2011 |
| WO | WO2013086373 | 6/2013 |
| WO | WO2013151665 | 10/2013 |
| WO | WO2013151666 | 10/2013 |
| WO | WO2015199952 | 12/2015 |
| WO | WO2017049245 | 3/2017 |
| WO | WO2014/144196 | 9/2018 |

OTHER PUBLICATIONS

Gustafsson C et al., "Codon bias and heterologous protein expression", Trends in Biotechnol, Elsevier Publications, Cambridge, GB, vol. 22, No. 7, Jul. 1, 2004, pp. 346-353.

Hayasaka et al., "Medium-chain triglyceride supplementation under a low-carbohydrate formula is a promising therapy for adult-onset type II citrullinemia", Mol. Genet. Metab. Rep., Jan. 2014, 1:42-50.

International Search Report and Written Opinion in International Application. No. PCT/US2017/033421, dated May 18, 2016, 15 pages.

Kimura et al., "Liver Transplantation versus conservative treatment for adult-onset type II citrullinemia: our experience and a review of the literature", Transplant Proc. Oct. 2013, 45(9):3432-3437.

Kobayashi, K. "Citrin deficiency." GeneReviews at GeneTests: Medical Genetics Information Resource, 2008, 29 pages.

Kogure, et al., "Three cases of adult-onset type 2 citrullinemia treated with different therapies: Efficacy of sodium pyruvate and low-carbohydrate diet: CTLN2 with sodium pyruvate treatment", Hepatology Research, vol. 44, No. 6, Jun. 2013, pp. 707-712.

Saheki et al., "Citrin/Mitochondrial Glycerol-3-phosphate Dehydrogenase Double Knock-out Mice Recapitulate Features of Human Citrin Deficiency", Journal of Biological Chemistry, vol. 282, No. 34, Aug. 24, 2007, pp. 25041-25052.

Saheki T, Song YZ. Citrin Deficiency. Sep. 16, 2005 GeneReviews [Internet]. Seattle (WA): University of Washington, Seattle; 1993-2019. Retrieved from: <URL> https://www.ncbi.nlm.nih.gov/books/NBK1181/.

Saheki T. et al., "Pathogenesis and Pathophysiology of Citrin (a Mitochondrial Aspartate Glutamate Carrier) Deficiency", Metabolic Brain Disease, Dec. 2002, vol. 17, pp. 335-346.

Saheki, T. et al., "Citrin Deficiency and Current Treatment Concepts", Molecular Genetics and Metabolism, 2010, vol. 100, pp. S59-S64.

Singaporian Search Report and Written Opinion in Singaporian Application No. 11201810162P, dated Apr. 7, 2020, 11 pages.

Song, et al., "SLC25A13 Gene Analysis in Citrin Deficiency: Sixteen Novel Mutations in East Asian Patients, and the Mutation Distribution in a Large Pediatric Cohort in China", PLOS One, vol. 8, No. 9, Sep. 19, 2013, p. e74544.

\* cited by examiner

FIG. 1A

SEQ ID NO: 1 (SLC25A13; Citrin, wt, isoform 1)

MAAAKVALTKRADPAELPTIPLKYASIERNGEFFMSPRDFVTRYLNIFGESQPNPKTVE
LLSGVVDQTKDGLISFQEFVAFESVLCAPDALFMVAQLFDKAGKGEVTFEDVKQVFGQ
TTIHQHIPFNWDSEFVQLNPGKERKRHLTYAEFTQFLLEIQLEHAKQAFVQRDNARTGR
VTAIDFRDIMVTIRPBVLTPFVEECLVAAAGGTTSHQVSFSYFNGFNGLLSNMELIRKI
YSTLAGTRKDVEVTKEEFVLAAQKFGQVTFMEVDILFQLADLYEPRGFMTLADIERIAP
LEEGTLPFNLAEAQRQKASGDSARPVLLQVAESAYRFGLGSVAGAVGATAVYPIDLVKT
RMQNQRSTGSFVGELMYKNSFDCFKKVLRYEGFFGLYRGLLPQLLGVAPEKAIKLTVND
FVRDKFMHKDGSVPLAARIIAGGCAGGSQVIFTNPLEIVKIRLQVAGEITTGPPVSALS
VVRDLGFFGIYKGAKACFLRDIPFSAIYFPCYAHVKASFANEDGQVSPGSLLLAGAIAG
MPAASLVTPADVIKTRLQVAARAGQTTYSGVIDCFRKILREEGPKALWKGAGARVFRSS
PQFGVTLLTYELLQRWFYIDFGGVRPMGSEPVPKSRINLPAPNPDHVGGYKLAVATFAG
IESKFGLYLPLFKPSVSTSKAIGGGP

See Calcium-binding mitochondrial carrier protein Aralar2, Uniprot Acc. No. Q9UJS0. This is the 'canonical' sequence. All positional information in related variants and isoforms refer to it.

FIG. 1B

| Feature | Position | Length | Description |
|---|---|---|---|
| Initiator Methionine | 1 | 1 | Removed |
| Calcium binding | 66 – 77 | 12 | Calcium binding site 1 |
| Calcium binding | 100 – 111 | 12 | Calcium binding site 2 |
| Calcium binding | 171 – 182 | 12 | Calcium binding site 3 |
| Transmembrane | 332 – 349 | 18 | Helical |
| Transmembrane | 393 – 412 | 20 | Helical |
| Transmembrane | 436 – 449 | 14 | Helical |
| Transmembrane | 485 – 504 | 20 | Helical |
| Transmembrane | 524 – 541 | 18 | Helical |
| Transmembrane | 581 – 600 | 20 | Helical |
| Domain | 51 – 86 | 36 | EF-hand 1 |
| Domain | 87 – 122 | 36 | EF-hand 2 |
| Domain | 125 – 157 | 33 | EF-hand 3 |
| Domain | 158 – 193 | 36 | EF-hand 4 |
| Repeat | 326 – 418 | 93 | Solcar 1 |
| Repeat | 426 – 510 | 85 | Solcar 2 |
| Repeat | 518 – 606 | 89 | Solcar 3 |

*All positional information refers to the 'canonical' sequence*

FIG. 1C

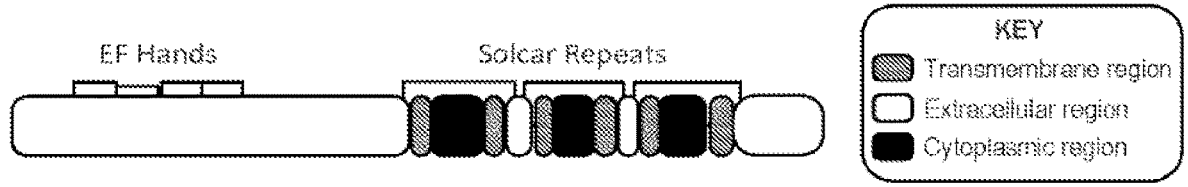

FIG. 1D

D. SEQ ID NO: 2

```
ATGGCGGCCGCCAAGGTGGCTTTAACCAAGAGAGCAGATCCAGCTGAGCTTAGAACAATATTTTTGA
AGTATGCAAGCATTCACAAAAACGGTGAATTTTTCATGTCCCCCAATGACTTTGTCACTCGATACTT
GAACATTTTTGGAGAAAGCCAGCCTAATCCAAAGACTGTGGAACTTTTAAGTGGAGTGGTGGATCAG
ACCAAAGATGGATTAATATCTTTTCAAGAATTTGTTGCCTTTGAATCTGTCCTGTGTGCCCCTGATG
CTTTGTTTAGGTAGCCTTTCAGCTGTTTGACAAAGCTGGCAAAGGAGAAGTAACTTTTCAGGATGT
TAAGCAAGTTTTTGGACAGACCACAATTCATCAACATATTCCATTTAACTGGGATTCAGAATTTGTG
CAACTACATTTTGGAAAAGAAAGAAAAAGACACCTGACATATGCGGAATTTACTCAGTTTTTATTGG
AAATACAACTGGAGCACGCAAAGCAAGCCTTTGTCCAACGGGACAATGCTAGGACTGGGAGAGTCAC
AGCCATCGACTTCCGAGACATCATGGTCACCATCCGCCCCATGTCTTGACTCCTTTGTAGAAGAA
TGTCTAGTAGCTGCTGCTGGAGGTACCACATCCCATCAAGTTAGTTTCTCCTATTTTAATGGATTTA
ATTCGCTCCTTAACAACATGGAACTCATTAGAAAGATCTATAGCACTCTGGCTGGCACCAGGAAAGA
TGTTGAAGTGACTAAGGAGGAGTTTGTTCTGGCAGCTCAGAAATTTGGTCAGGTACACCCATGGAA
GTTGACATCTTGTTTCAGTTAGCAGATTTATATGAGCCAAGGGGACGTATGACTTTAGCAGACATTG
AACGGATTGCTCCTCTGGAAGAGGGAACTCTGCCCTTTAACTTGGCTGAGGCCCAGAGCCAGAAGCC
CTCAGGTGATTCAGCTCGACCAGTTCTTCTACAAGTTGCAGAGTCGGCCTACAGGTTTGGTCTGGGT
TCTGTTGCTGGAGCTGTTGGAGCCACTGCTGTGTATCCTATCGATCTTGTAAAAACTCGAATGCAGA
ACCAACGATCAACTGGCTCTTTTGTGGGAGAACTCATGTATAAAAACAGCTTTGACTGTTTTAAGAA
AGTGCTACGCTATGAAGGCTTCTTTGCACTGTATAGAGGTCTGTTGCCACAGTTATTGGAGTTGCC
CCAGAGAAGGCCATAAAACTTACAGTGAACGATTTTGTGAGGGATAAATTTATGCACAAAGATGGTT
CGGTCCCACTTGCAGCAGAAATTCTTGCTGGAGGCTGCGCTGGAGGCTCCACGTCATTTTCACAAA
TCCTTTAGAAATCGTCAAGATCCGTTGCAAGTGGCAGGAGAAATCACCACTGGTCCTCGAGTCAGT
GCTCTGTCTGTCGTGCGGGACCTGGGGTTTTTTGGATCTACAAGGGTGCCAAAGCATCCTTTCTGC
GGGACATTCCTTTCTCGGCCATCTACTTTCCGTGCTATGCTCATGTGAAGGCTTCCTTTGCAAATGA
AGAATGGCAGGTTAGCCCAGGAAGCCTGCTCTTAGCTGGTGCCATAGCTGGTATGCCTGCAGCATCT
TTAGTGACCCCTGCTGATGTTATCAAGACGAGATTACAGGTGGCTGCCCGGGCTGGCCAAACCACTT
ACAGCGGAGTGATAGACTGCTTTAGAAAGATACTGCGTGAAGAAGGACCAAAAGCTCTGTGGAAGGG
AGCTGGTGCTCGTGTATTTCGATCCTCAGCCCAGTTTGGTGTAACTTTGCTGACTTACCGAATTGCTA
CAGCGATGGTCTACATTGATTTTGGAGGAGTAAAACCCATGGGATCAGAGCCAGTTCCTAAATCCA
GGATCAACCTGGCTGCCCCGAATCCTGATCACGTTGGGGGCTACAAACTGGCAGTTGCTACATTTGC
AGGGATTGAAAACAAATTTGGACTTTACCTACCTCTCTTCAAGCCATCAGTATCTACCTCAAAGGCT
ATTGGTGGAGGCCCA
```

FIG. 2A

SEQ ID NO: 3 (SLC25A13 ; Citrin, wt, isoform 2)

MAAAKVALTKRADPAELRTIFLKYASTEKNGEFFMSPNDFVTRYLNIFGESQPNFKTVE
LLSGVVDQTKDGLISFQEFVAFESVLCAPDALFMVAFQLFDKAGKGEVTFEDVKQVFGQ
TTIHQHIPFNWDSEFVQLHFGKERKRHLTYAEFTQFLLEIQLEHAKQAFVQRDNARTGR
VTAIDFFDIMVTIRPHVLTPFVEECLVAAAGGTTSHQVSFSYFNGFNSLLNMMELIKKI
YSTLAGTPKDVEVTKEEFVLAAQKFGQVTPMSVDILFQLADLYEPRGRMTLADIERIAP
LEEGTLPFNLAEAQRQQKASGLSAPPVLLQVAESAYRFGLGSVAGAVGATAVYPIDLVK
TRMQNQRSTGSFVGELMYKNSFDCFKKVLRYEGFFGLYRGLLPQLLGVAPEKAIKLTVN
DFVRDLFMEKDGSVPLAAEILAGGCAGGSQVIFTNPLEIVKIRLQVAGETTTSPRVSAL
SVVRDLGFFGIYKGAKACFLRDIPFSAIYFFCYAHVKASFANEDGQVSPGSLLLAGAIA
GMPAASLVTPADVIKTRLQVAARAGQTTYSSVIDCFRKTLREEGPKALWKGAGARVFRS
SPQFGVTLLTYELLQRWFYIDFGGVKPMGSEPVPKSPINLPAPNPDHVGGYKLAVATFA
GIENKFGLYLPLFKPSVSTSKAIGGGP

See Calcium-binding mitochondrial carrier protein Aralar2, Uniprot Acc. No. Q9UJS0-2. The sequence of this isoform differs from the canonical sequence as follows:    311-311: Q → QQ

FIG. 2B

| Feature | Position | Length | Description |
|---|---|---|---|
| Initiator Methionine | 1 | 1 | Removed |
| Calcium binding | 66 – 77 | 12 | Calcium binding site 1 |
| Calcium binding | 100 – 111 | 12 | Calcium binding site 2 |
| Calcium binding | 171 – 182 | 12 | Calcium binding site 3 |
| Transmembrane | 332 – 349 | 18 | Helical |
| Transmembrane | 393 – 412 | 20 | Helical |
| Transmembrane | 436 – 449 | 14 | Helical |
| Transmembrane | 485 – 504 | 20 | Helical |
| Transmembrane | 524 – 541 | 18 | Helical |
| Transmembrane | 581 – 600 | 20 | Helical |
| Domain | 51 – 86 | 36 | EF-hand 1 |
| Domain | 87 – 122 | 36 | EF-hand 2 |
| Domain | 125 – 157 | 33 | EF-hand 3 |
| Domain | 158 – 193 | 36 | EF-hand 4 |
| Repeat | 326 – 418 | 93 | Solcar 1 |
| Repeat | 426 – 510 | 85 | Solcar 2 |
| Repeat | 518 – 606 | 89 | Solcar 3 |

FIG. 2C

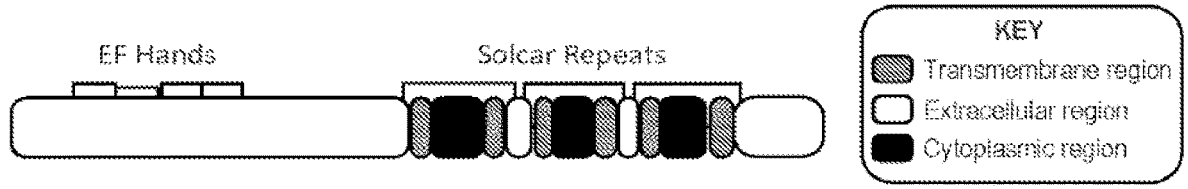

FIG. 2D

D. SEQ ID NO: 4

ATGGCGGCCGCCAAGGTGGCTTTAACCAAGAGAGCAGATCCAGCTGAGCTTAGAACAATATTTTTGA
AGTATGCAAGCATTGAGAAAAACGGTGAATTTTTCATGTCCCCCAATGACTTTGTCACTCGATACTT
GAACATTTTTGGAGAAAGCCAGCCTAATCCAAAGACTGTTGAACTTTTAAGTGGAGTGCTGGATCAG
ACCAAAGATGGATTAATATCTTTTCAAGAATTTGTTGCCTTTGAATCTGTCCTGTGTGCCCCTGATG
CTTTGTTTATGGTAGCCTTTCAGCTGTTTGACAAAGCTGGCAAAGGAGAAGTAACTTTTTGAGGATGT
TAAGCAAGTTTTTGGACAGACCACAATTCATCAACATATTCCATTTAACTGGGATTCAGAAATTTGTG
CAACTACATTTTGAAAAGAAAGAAAAAGACACCTGACATATGGGAATTTACTCAGTTTTTATTGG
AAATACAACTGGAGCACGCAAAGCAAGCCTTTGTGCAACGGGACAATGCTAGGACTGGGAGAGTCAC
AGCCATCGACTTCCGAGACATCATGGTCACCATCCGCCCCCATGTCTTGACTCCTTTTGTAGAAGAA
TGTCTAGTAGCTGCTGCTGGAGGTACCACATCCCATCAAGTTAGTTTCTCCTATTTTAATGGATTTA
ATTCGCTCCTTAACAACATGGAACTCATTAGAAAGATCTATAGCACTCTGGCTGGCACCAGGAAAGA
TGTTGAAGTGACTAAGGAGGAGTTTGTTCTGGCAGCTCAGAAATTGGTCAGGTTACACCCATGGAA
GTTGACATCTTGTTCAGTTAGCAGATTTATATGAGCCAAGGGACGTATGACCTTAGCAGACATTG
AACGGATTGCTCCTCTGGAAGAGGGAACTCTGCCCTTTAACTTGGCTGAGGCCCAGAGGCAGCAGAA
GGCCTCAGCTGATTCAGCTCGACCAGTTCTTCTACAAGTTGCAGAGTCGGCCTACAGGTTGGTCTG
GGTTCTGTTGCTGGAGCTGTTGGAGCCACTGCTGTGTAGCCTATCGATCTTGTAAAAACTCGAATGC
AGAACCAACGATCAACTGGCTCTTTTCTGGGAGAACTCATGTATAAAACAGCTTTGACTGTTTAA
GAAAGTGCTACGCTATGAAGGCTTCTTTGGACTGTATAGAGGTCTGTTGCCACAGTTATTGGGAGTT
GCCCCAGAGAAGGCCATAAAACTTACAGTCAACGATTTGTGAGGGATAAATTTATGCACAAAGATG
GTTCGGTCCCACTTGCAGCAGAAATTCTTGCTGGAGGCTGCGCTGGAGGCTCCCAGGTGATTTTCAC
AAATCCTTTAGAAATCGTCAAGATCCGTTTGCAAGTGGCAGGAGAAATCACCACTGGTCCTCGAGTC
AGTGCTCTGTCTGTCGTGCGGGACCTGGGGTTTTTTGGATCTACAAGGGTGCCAAAGCATGCTTTC
TGCGGGACATTCTTTCTCGGCCATCTACTTTCCGTGCTATGCTCATGTGAAGGCTTCCTTTGCAAA
TGAAGATGGGCAGTTAGCCCAGGAAGCCTGCTCTTAGCTGGTGCCATAGCTGGTATGCCTGCAGCA
TCTTTAGTGACCCCTGCTGATGTTATCAAGACGACATTACAGGTGCCTGCCCGGGCTGCCCAAACCA
CTTACAGCGGAGTGATAGACTGCTTTAGAAAGATACTGCGTGAAGAAGGACCAAAAGCTCTGTGGAA
GGCAGCTGGTGCTCGTGTATTTCGATCCTCACCCCAGTTTGGTGTAACTTTGCTGACTTACCAATTG
CTACAGCGATGGTTCTACATTGATTTGGAGGAGTAAAACCCATGGGATCAGAGCCAGTTCCTAAAT
CCAGGATCAACCTGCCTGCCCCGAATCCTGATCACGTTGGGGCTACAAACTGGCAGTTGCTACATT
TGCAGGGATTGAAAACAAATTTGGACTTTACCTACCTCTCTTCAAGCCATCAGTATCTACCTCAAAG
GCTATTGGTGGAGGCCCA

| Protein | Length | Theoretical Minimum U (%) | Theoretical Minimum U (abs) | | | | | | |
|---|---|---|---|---|---|---|---|---|---|
| Citrin Protein | 675 | 14.22% | 288 | | | | | | |

| Nucleic Acid | Length | U Content (abs) | U Content (%) | U Content v WT (%) | U Content v Theoretical Minimum (%) | UU pairs | UU pairs v WT (%) | UUU | UUUU | UUUUU |
|---|---|---|---|---|---|---|---|---|---|---|
| Citrin-WT | 2025 | 562 | 27.75% | 100.00% | 195.14% | 61 | 100.00% | 37 | 11 | 5 |
| Citrin-CO01 | 2025 | 343 | 16.94% | 61.03% | 119.10% | 43 | 70.49% | 10 | 3 | 0 |
| Citrin-CO02 | 2025 | 342 | 16.89% | 60.85% | 118.75% | 47 | 77.05% | 6 | 1 | 0 |
| Citrin-CO03 | 2025 | 352 | 17.38% | 62.63% | 122.22% | 41 | 67.21% | 13 | 0 | 0 |
| Citrin-CO04 | 2025 | 346 | 17.09% | 61.57% | 120.14% | 45 | 73.77% | 10 | 1 | 0 |
| Citrin-CO05 | 2025 | 346 | 17.09% | 61.57% | 120.14% | 42 | 68.85% | 12 | 0 | 2 |
| Citrin-CO06 | 2025 | 348 | 17.19% | 61.92% | 120.83% | 42 | 68.85% | 10 | 1 | 1 |
| Citrin-CO07 | 2025 | 347 | 17.14% | 61.74% | 120.49% | 43 | 70.49% | 12 | 1 | 0 |
| Citrin-CO08 | 2025 | 359 | 17.73% | 63.88% | 124.65% | 42 | 68.85% | 11 | 0 | 1 |
| Citrin-CO09 | 2025 | 356 | 17.58% | 63.35% | 123.61% | 42 | 68.85% | 9 | 2 | 1 |
| Citrin-CO10 | 2025 | 356 | 17.58% | 63.35% | 123.61% | 34 | 55.74% | 12 | 4 | 2 |
| Citrin-CO11 | 2025 | 339 | 16.74% | 60.32% | 117.71% | 40 | 65.57% | 7 | 2 | 1 |
| Citrin-CO12 | 2025 | 363 | 17.93% | 64.59% | 126.04% | 52 | 85.25% | 8 | 1 | 0 |
| Citrin-CO13 | 2025 | 355 | 17.53% | 63.17% | 123.26% | 45 | 73.77% | 10 | 0 | 1 |
| Citrin-CO14 | 2025 | 343 | 16.94% | 61.03% | 119.10% | 48 | 78.69% | 7 | 1 | 0 |
| Citrin-CO15 | 2025 | 339 | 16.74% | 60.32% | 117.71% | 48 | 78.69% | 1 | 3 | 2 |
| Citrin-CO16 | 2025 | 357 | 17.63% | 63.52% | 123.96% | 49 | 80.33% | 11 | 1 | 0 |
| Citrin-CO17 | 2025 | 349 | 17.23% | 62.10% | 121.18% | 45 | 73.77% | 8 | 2 | 0 |
| Citrin-CO18 | 2025 | 350 | 17.28% | 62.28% | 121.53% | 40 | 65.57% | 14 | 1 | 2 |
| Citrin-CO19 | 2025 | 342 | 16.89% | 60.85% | 118.75% | 46 | 75.41% | 8 | 1 | 0 |
| Citrin-CO20 | 2025 | 342 | 16.89% | 60.85% | 118.75% | 40 | 65.57% | 14 | 1 | 0 |
| Citrin-CO21 | 2025 | 344 | 16.99% | 61.21% | 119.44% | 42 | 68.85% | 9 | 0 | 0 |
| Citrin-CO22 | 2025 | 348 | 17.19% | 61.92% | 120.83% | 50 | 81.97% | 5 | 1 | 0 |
| Citrin-CO23 | 2025 | 339 | 16.74% | 60.32% | 117.71% | 43 | 70.49% | 11 | 1 | 0 |
| Citrin-CO24 | 2025 | 344 | 16.99% | 61.21% | 119.44% | 45 | 73.77% | 10 | 0 | 1 |
| Citrin-CO25 | 2025 | 345 | 17.04% | 61.39% | 119.79% | 41 | 67.21% | 13 | 1 | 0 |
| | MAX | 363 | 17.93% | 64.59% | 126.04% | 52 | 85.25% | 14 | 4 | 2 |
| | MIN | 339 | 16.74% | 60.32% | 117.71% | 34 | 55.74% | 1 | 0 | 0 |
| | AVERAGE | 347.76 | 17.17% | 61.88% | 120.75% | 43.8 | 71.80% | 9.64 | 1.16 | 0.56 |
| | MEDIAN | 346 | 17.09% | 61.57% | 120.14% | 43 | 70.49% | 10 | 1 | 0 |
| | STD DEV | 6.69 | 0.33% | 1.19% | 2.32% | 3.88 | 6.37% | | | |

FIG. 3

| Protein | Length | Theoretical Maximum G (%) | Theoretical Maximum G (abs) | | |
|---|---|---|---|---|---|
| Citrin Protein | 675 | 42.27% | 856 | | |

| Nucleic Acid | Length | G Content(abs) | G Content(%) | G Content v WT (%) | G Content v Theoretical Maximum (%) |
|---|---|---|---|---|---|
| Citrin-WT | 2025 | 499 | 24.64% | 100.00% | 58.29% |
| Citrin-CO01 | 2025 | 634 | 31.31% | 127.05% | 74.07% |
| Citrin-CO02 | 2025 | 610 | 30.12% | 122.24% | 71.26% |
| Citrin-CO03 | 2025 | 620 | 30.62% | 124.25% | 72.43% |
| Citrin-CO04 | 2025 | 605 | 29.88% | 121.24% | 70.68% |
| Citrin-CO05 | 2025 | 614 | 30.32% | 123.05% | 71.73% |
| Citrin-CO06 | 2025 | 611 | 30.17% | 122.44% | 71.38% |
| Citrin-CO07 | 2025 | 627 | 30.96% | 125.65% | 73.25% |
| Citrin-CO08 | 2025 | 619 | 30.57% | 124.05% | 72.31% |
| Citrin-CO09 | 2025 | 612 | 30.22% | 122.65% | 71.50% |
| Citrin-CO10 | 2025 | 619 | 30.57% | 124.05% | 72.31% |
| Citrin-CO11 | 2025 | 622 | 30.72% | 124.65% | 72.66% |
| Citrin-CO12 | 2025 | 627 | 30.96% | 125.65% | 73.25% |
| Citrin-CO13 | 2025 | 631 | 31.16% | 126.45% | 73.71% |
| Citrin-CO14 | 2025 | 626 | 30.91% | 125.45% | 73.13% |
| Citrin-CO15 | 2025 | 611 | 30.17% | 122.44% | 71.38% |
| Citrin-CO16 | 2025 | 626 | 30.91% | 125.45% | 73.13% |
| Citrin-CO17 | 2025 | 612 | 30.22% | 122.65% | 71.50% |
| Citrin-CO18 | 2025 | 647 | 31.95% | 129.66% | 75.58% |
| Citrin-CO19 | 2025 | 619 | 30.57% | 124.05% | 72.31% |
| Citrin-CO20 | 2025 | 614 | 30.32% | 123.05% | 71.73% |
| Citrin-CO21 | 2025 | 620 | 30.62% | 124.25% | 72.43% |
| Citrin-CO22 | 2025 | 620 | 30.62% | 124.25% | 72.43% |
| Citrin-CO23 | 2025 | 625 | 30.86% | 125.25% | 73.01% |
| Citrin-CO24 | 2025 | 619 | 30.57% | 124.05% | 72.31% |
| Citrin-CO25 | 2025 | 643 | 31.75% | 128.86% | 75.12% |
| | MAX | 647 | 31.95% | 129.66% | 75.58% |
| | MIN | 605 | 29.88% | 121.24% | 70.68% |
| | MEAN | 621.32 | 30.68% | 124.51% | 72.58% |
| | MEDIAN | 620 | 30.62% | 124.25% | 72.43% |
| | STD DEV | 10.04 | 0.50% | 2.01% | 1.17% |

FIG. 4

| Protein | Length | Theoretical Maximum C | Theoretical Maximum C (abs) | | |
|---|---|---|---|---|---|
| Citrin Protein | 675 | 44.49% | 901 | | |

| Nucleic Acid | Length | C Content(abs) | C Content(%) | C Content v WT (%) | C Content v Theoretical Maximum (%) |
|---|---|---|---|---|---|
| Citrin-WT | 2025 | 432 | 21.33% | 100.00% | 47.95% |
| Citrin-CO01 | 2025 | 652 | 32.20% | 150.93% | 72.36% |
| Citrin-CO02 | 2025 | 657 | 32.44% | 152.08% | 72.92% |
| Citrin-CO03 | 2025 | 640 | 31.60% | 148.15% | 71.03% |
| Citrin-CO04 | 2025 | 671 | 33.14% | 155.32% | 74.47% |
| Citrin-CO05 | 2025 | 671 | 33.14% | 155.32% | 74.47% |
| Citrin-CO06 | 2025 | 656 | 32.40% | 151.85% | 72.81% |
| Citrin-CO07 | 2025 | 639 | 31.56% | 147.92% | 70.92% |
| Citrin-CO08 | 2025 | 656 | 32.40% | 151.85% | 72.81% |
| Citrin-CO09 | 2025 | 652 | 32.20% | 150.93% | 72.36% |
| Citrin-CO10 | 2025 | 648 | 32.00% | 150.00% | 71.92% |
| Citrin-CO11 | 2025 | 657 | 32.44% | 152.08% | 72.92% |
| Citrin-CO12 | 2025 | 642 | 31.70% | 148.61% | 71.25% |
| Citrin-CO13 | 2025 | 628 | 31.01% | 145.37% | 69.70% |
| Citrin-CO14 | 2025 | 647 | 31.95% | 149.77% | 71.81% |
| Citrin-CO15 | 2025 | 668 | 32.99% | 154.63% | 74.14% |
| Citrin-CO16 | 2025 | 628 | 31.01% | 145.37% | 69.70% |
| Citrin-CO17 | 2025 | 647 | 31.95% | 149.77% | 71.81% |
| Citrin-CO18 | 2025 | 625 | 30.86% | 144.68% | 69.37% |
| Citrin-CO19 | 2025 | 646 | 31.90% | 149.54% | 71.70% |
| Citrin-CO20 | 2025 | 648 | 32.00% | 150.00% | 71.92% |
| Citrin-CO21 | 2025 | 650 | 32.10% | 150.46% | 72.14% |
| Citrin-CO22 | 2025 | 658 | 32.49% | 152.31% | 73.03% |
| Citrin-CO23 | 2025 | 655 | 32.35% | 151.62% | 72.70% |
| Citrin-CO24 | 2025 | 647 | 31.95% | 149.77% | 71.81% |
| Citrin-CO25 | 2025 | 628 | 31.01% | 145.37% | 69.70% |
| | MAX | 671 | 33.14% | 155.32% | 74.47% |
| | MIN | 625 | 30.86% | 144.68% | 69.37% |
| | AVERAGE | 648.64 | 32.03% | 150.15% | 71.99% |
| | MEDIAN | 648 | 32.00% | 150.00% | 71.92% |
| | STD DEV | 12.65 | 0.62% | 2.93% | 1.40% |

FIG. 5

| Protein | Length | Theoretical Maximum GC | Theoretical Maximum GC (abs) | | |
|---|---|---|---|---|---|
| Citrin Protein | 675 | 67.70% | 1371 | | |

| Nucleic Acid | Length | GC Content(abs) | GC Content(%) | GC Content v WT (%) | GC Content v Theoretical Maximum (%) |
|---|---|---|---|---|---|
| Citrin-WT | 2025 | 932 | 45.98% | 100.00% | 67.98% |
| Citrin-CO01 | 2025 | 1286 | 63.51% | 138.13% | 93.80% |
| Citrin-CO02 | 2025 | 1267 | 62.57% | 136.09% | 92.41% |
| Citrin-CO03 | 2025 | 1260 | 62.22% | 135.34% | 91.90% |
| Citrin-CO04 | 2025 | 1276 | 63.01% | 137.06% | 93.07% |
| Citrin-CO05 | 2025 | 1285 | 63.46% | 138.02% | 93.73% |
| Citrin-CO06 | 2025 | 1267 | 62.57% | 136.09% | 92.41% |
| Citrin-CO07 | 2025 | 1266 | 62.52% | 135.98% | 92.34% |
| Citrin-CO08 | 2025 | 1275 | 62.96% | 136.95% | 93.00% |
| Citrin-CO09 | 2025 | 1264 | 62.42% | 135.77% | 92.20% |
| Citrin-CO10 | 2025 | 1267 | 62.57% | 136.09% | 92.41% |
| Citrin-CO11 | 2025 | 1279 | 63.16% | 137.38% | 93.29% |
| Citrin-CO12 | 2025 | 1269 | 62.67% | 136.31% | 92.56% |
| Citrin-CO13 | 2025 | 1259 | 62.17% | 135.23% | 91.83% |
| Citrin-CO14 | 2025 | 1273 | 62.86% | 136.73% | 92.85% |
| Citrin-CO15 | 2025 | 1279 | 63.16% | 137.38% | 93.29% |
| Citrin-CO16 | 2025 | 1254 | 61.93% | 134.69% | 91.47% |
| Citrin-CO17 | 2025 | 1259 | 62.17% | 135.23% | 91.83% |
| Citrin-CO18 | 2025 | 1272 | 62.81% | 136.63% | 92.78% |
| Citrin-CO19 | 2025 | 1265 | 62.47% | 135.88% | 92.27% |
| Citrin-CO20 | 2025 | 1262 | 62.32% | 135.55% | 92.05% |
| Citrin-CO21 | 2025 | 1270 | 62.72% | 136.41% | 92.63% |
| Citrin-CO22 | 2025 | 1278 | 63.11% | 137.27% | 93.22% |
| Citrin-CO23 | 2025 | 1280 | 63.21% | 137.49% | 93.36% |
| Citrin-CO24 | 2025 | 1266 | 62.52% | 135.98% | 92.34% |
| Citrin-CO25 | 2025 | 1271 | 62.77% | 136.52% | 92.71% |
| | MAX | 1286 | 63.51% | 138.13% | 93.80% |
| | MIN | 1254 | 61.93% | 134.69% | 91.47% |
| | AVERAGE | 1269.96 | 62.71% | 136.41% | 92.63% |
| | MEDIAN | 1269 | 62.67% | 136.31% | 92.56% |
| | STD DEV | 8.33 | 0.41% | 0.89% | 0.61% |

FIG. 6

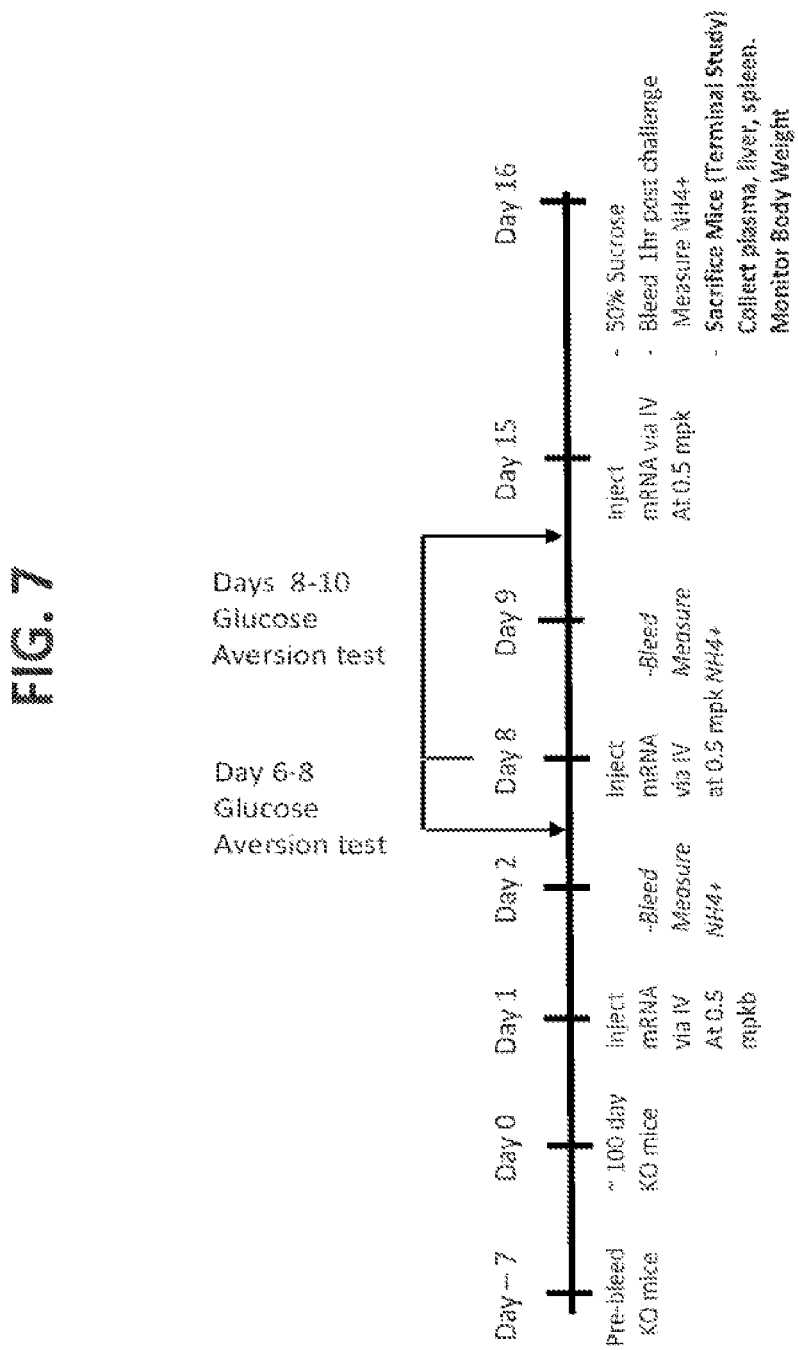

Before treatment

After treatment

POLYNUCLEOTIDES ENCODING CITRIN FOR THE TREATMENT OF CITRULLINEMIA TYPE 2

CROSS-REFERENCE TO RELATED APPLICATIONS

This application is a continuation of U.S. application Ser. No. 16/302,360, filed on Nov. 16, 2018, issued as U.S. Pat. No. 10,993,918, which is the National Stage of International Application No. PCT/US2017/033421, filed on May 18, 2017, which claims the priority benefit of U.S. Provisional Application No. 62/338,479, filed on May 18, 2016. The disclosures of the prior applications are incorporated herein by reference in their entirety.

REFERENCE TO A SEQUENCE LISTING SUBMITTED ELECTRONICALLY VIA EFS-WEB

The content of the electronically submitted sequence listing (Name: 3529_072PC02_Sequence Listing, Size: 181,746 bytes; and Date of Creation: May 16, 2017) is herein incorporated by reference in its entirety.

BACKGROUND

Citrullinemia is an autosomal recessive urea cycle disorder that causes abnormal buildup of ammonia and other toxic substances in the blood. Citrullinemia Type 2 ("CTLN2") is a form of Citrullinemia that is caused by mutation of the Solute Carrier Family 25, Member 13 gene ("SLC25A13"). CTLN2 is also known as Adult-Onset Citrullinemia Type 2 or Citrin Deficiency. CTLN2 causes nocturnal delirium, aggression, irritability, hyperactivity, delusions, disorientation, restlessness, drowsiness, loss of memory, flapping tremor, convulsive seizures, coma, or even death resulting from brain edema. Kobayashi, K. et al., GeneReviews (2008). CTLN2 is found in the Japanese population with an estimated incidence of 1 in 100,000 to 230,000. Additionally, CTLN2 has been reported in East Asian and Middle Eastern populations. Current treatments for CTLN2 attempt to control signs and symptoms by having individuals consume diets that are low in carbohydrates and high in proteins and fats. Also, treatment with arginine, sodium benzoate, or sodium phenylacetate removes ammonia from the blood. In serious cases, liver transplantation has been successful in treating CTLN2 and dialysis can be used to remove ammonia from the blood. Saheki, T. et al., Molec. Genet. Metab. 100 (Suppl. 1): S59-S64 (2010). Thus, most effective treatment for this disorder is liver transplantation, although many patients can be managed by a low-carbohydrate/high-protein diet. However, none of these treatments completely control the disorder.

The principal gene associated with CTLN2 is SLC25A13, which has two variants (Genbank Accession Nos. NM_001160210, NP_001153682: NM_014251, NP_055066; XM_006715831, XP_006715894; XM_011515727, XP_011514029). SLC25A13 encodes Citrin, which is a calcium-dependent mitochondrial solute carrier protein. Citrin is also known as Mitochondrial Aspartate Glutamate Carrier 2 or ARALAR2. Citrin plays a critical role in the urea cycle by catalyzing the mitochondrial uptake of glutamate and export of aspartate. Saheki, T. et al., Metab. Brain Dis. 17:335-346 (2002). Depending on the variant, the precursor form of human Citrin is either 676 or 675 amino acids, while its mature form is either 675 or 674 amino acids with the initiator methionine cleaved off.

A complete or partial loss of Citrin function leads to abnormal buildup of ammonia and other toxic substances in the blood. For example, loss of Citrin has been reported to lead to ammonia levels greater than 750 µg/dL, as compared to 49 µg/dL or less in normal individuals. Aside from liver transplant, treatment for CTLN2 generally focuses on managing the disease, e.g., through diet and nutritional support. There are currently no available therapeutics to treat CTLN2. Accordingly, there is a need for improved therapy to treat CTLN2.

BRIEF SUMMARY

The present invention provides mRNA therapeutics for the treatment of Citrullinemia Type 2 (CTLN2). The mRNA therapeutics of the invention are particularly well-suited for the treatment of CTLN2 as the technology provides for the intracellular delivery of mRNA encoding Citrin followed by de novo synthesis of functional Citrin protein within target cells. The instant invention features the incorporation of modified nucleotides within therapeutic mRNAs to (1) minimize unwanted immune activation (e.g., the innate immune response associated with the in vivo introduction of foreign nucleic acids) and (2) optimize the translation efficiency of mRNA to protein. Exemplary aspects of the invention feature a combination of nucleotide modifications to reduce the innate immune response and sequence optimization, in particular, within the open reading frame (ORF) of therapeutic mRNAs encoding Citrin to enhance protein expression.

In further embodiments, the mRNA therapeutic technology of the instant invention also features delivery of mRNA encoding Citrin via a lipid nanoparticle (LNP) delivery system. The instant invention features novel ionizable lipid-based LNPs which have improved properties when combined with mRNA encoding CTLN2 and administered in vivo, for example, cellular uptake, intracellular transport and/or endosomal release or endosomal escape. The LNPs of the invention also demonstrate reduced immunogenicity associated with the in vivo administration of LNPs.

In certain aspects, the invention relates to compositions and delivery formulations comprising a polynucleotide, e.g., a ribonucleic acid (RNA), e.g., a messenger RNA (mRNA), encoding Citrin and methods for treating Citrullinemia Type 2 (CTLN2) in a subject in need thereof by administering the same.

The present disclosure provides a pharmaceutical composition comprising a lipid nanoparticle encapsulated mRNA that comprises an open reading frame (ORF) encoding an Citrin polypeptide, wherein the composition is suitable for administration to a human subject in need of treatment for Citrullinemia Type 2 (CTLN2).

The present disclosure further provides a pharmaceutical composition comprising: (a) a mRNA that comprises (i) an open reading frame (ORF) encoding an Citrin polypeptide, wherein the ORF comprises at least one chemically modified nucleobase, sugar, backbone, or any combination thereof, (ii) an untranslated region (UTR) comprising a microRNA (miRNA) binding site; and (b) a delivery agent, wherein the pharmaceutical composition is suitable for administration to a human subject in need of treatment for Citrullinemia Type 2 (CTLN2).

The present disclosure further provides a pharmaceutical composition comprising an mRNA comprising an open reading frame (ORF) encoding a human Citrin polypeptide, wherein the composition when administered to a subject in need thereof as a single intravenous dose is sufficient to reduce blood and/or plasma levels of (i) ammonia at least 2-fold, at least 3-fold, at least 5-fold, at least 10-fold, at least 15-fold, at least 20-fold, or at least 50-fold compared to the subject's baseline level or a reference ammonia blood and/or plasma level, for at least 24 hours, at least 48 hours, at least 72 hours, at least 96 hours, or at least 120 hours post-administration; and/or (ii) triglycerides at least 1.5-fold, at least 2-fold, at least 3-fold, at least 4-fold, at least 5-fold, at least 10-fold, or at least 20-fold compared to the subject's baseline level or a reference triglyceride blood and/or plasma level, for at least 24 hours post-administration, at least 48 hours, at least 72 hours, at least 96 hours, or at least 120 hours post-administration.

The present disclosure further provides a pharmaceutical composition comprising an mRNA comprising an open reading frame (ORF) encoding a human Citrin polypeptide, wherein the composition when administered to a subject in need thereof as a single intravenous dose is sufficient to reduce blood and/or plasma levels of (i) ammonia at least 50%, at least 60%, at least 70%, at least 80%, at least 90%, at least 95% or at least 98%, at least 99%, or 100% compared to the subject's baseline level or a reference ammonia blood and/or plasma level (e.g., in a subject with CTLN2), for at least 24 hours, at least 48 hours, at least 72 hours, at least 96 hours, or at least 120 hours post-administration; and/or (ii) triglycerides at least 30%, at least 50%, at least 60%, at least 70%, at least 80%, at least 90%, at least 95% or at least 98%, at least 99%, or 100% compared to the subject's baseline level or a reference triglyceride blood and/or plasma level (e.g., in a subject with CTLN2), for at least 24 hours post-administration, at least 48 hours, at least 72 hours, at least 96 hours, or at least 120 hours post-administration.

The present disclosure further provides a pharmaceutical composition comprising an mRNA comprising an open reading frame (ORF) encoding a human Citrin polypeptide, wherein the composition when administered to a subject in need thereof as a single intravenous dose is sufficient to: (i) increase hepatic Citrin activity level at or above a normal physiological level for at least 24 hours, at least 48 hours, at least 72 hours, at least 96 hours, or at least 120 hours post-administration, and/or (ii) increase hepatic Citrin activity level to 50% or more of a reference hepatic Citrin activity level for at least 24 hours, at least 48 hours, at least 72 hours, or at least 96 hours post-administration.

In some embodiments, the pharmaceutical compositions disclosed herein further comprise a delivery agent.

In some aspects, the invention relates to a polynucleotide comprising an open reading frame (ORF) encoding a Citrin polypeptide, wherein the uracil or thymine content of the ORF relative to the theoretical minimum uracil or thymine content of a nucleotide sequence encoding the Citrin polypeptide (% $U_{TM}$ or % $T_{TM}$), is between about 100% and about 150%. In some aspects, the uracil or thymine content of the ORF relative to the uracil or thymine content of the corresponding wild-type ORF (% $U_{WT}$ or % $T_{WT}$) is less than 100%. In some aspects, the uracil or thymine content in the ORF relative to the total nucleotide content in the ORF (% $U_{TL}$ or % $T_{TL}$) is less than about 50%, less than about 40%, less than about 30%, or less than about 20%.

In some aspects, the guanine content of the ORF with respect to the theoretical maximum guanine content of a nucleotide sequence encoding the Citrin polypeptide (% $G_{TMX}$) is at least 69%, at least 70%, at least 75%, at least about 80%, at least about 85%, at least about 90%, at least about 95%, or about 100%. In some aspects, the cytosine content of the ORF relative to the theoretical maximum cytosine content of a nucleotide sequence encoding the Citrin polypeptide (% $C_{TMX}$) is at least 60%, at least 65%, at least about 70%, at least about 75%, at least about 80%, at least about 85%, at least about 90%, at least about 95%, or about 100%. In some aspects, the guanine and cytosine content (G/C) of the ORF relative to the theoretical maximum G/C content of a nucleotide sequence encoding the Citrin polypeptide (% $G/C_{TMX}$) is at least about 81%, at least about 85%, at least about 90%, at least about 95%, or about 100%. In some aspects, the G/C content in the ORF relative to the G/C content in the corresponding wild-type ORF (% $G/C_{WT}$) is at least 102%, at least 103%, at least 104%, at least 105%, at least 106%, at least 107%, at least 110%, at least 115%, at least 120%, at least 125%, at least 130%, at least 131%, at least 132%, at least 133%, or at least 134%. In some aspects, the average G/C content in the $3^{rd}$ codon position in the ORF is at least 30%, at least 35%, at least 40%, at least 41%, at least 42%, at least 43%, at least 44%, at least 45%, at least 46%, at least 47%, at least 48%, or at least 49% higher than the average G/C content in the $3^{rd}$ codon position in the corresponding wild-type ORF.

In some aspects, the ORF has at least 74%, at least 75%, at least 76%, at least 77%, at least 78%, at least 79%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NOs: 5-29, 129, 132, 135, or 138.

In some aspects, the Citrin polypeptide comprises an amino acid sequence at least about 95%, at least about 96%, at least about 97%, at least about 98%, at least about 99%, or about 100% identical to (i) the polypeptide sequence of wild type Citrin, isoform 1 (SEQ ID NO: 1), or (ii) the polypeptide sequence of wild type Citrin, isoform 2 (SEQ ID NO: 3), and wherein the Citrin polypeptide has aspartate or glutamate transport activity.

In some embodiments, the polynucleotide is single stranded. In some embodiments, the polynucleotide is double stranded. In some embodiments, the polynucleotide is DNA. In some embodiments, the polynucleotide is RNA. In some embodiments, the polynucleotide is mRNA. In some embodiments, the polynucleotide comprises at least one chemically modified nucleobase, sugar, backbone, or any combination thereof. In some embodiments, the at least one chemically modified nucleobase is selected from the group consisting of pseudouracil (ψ), N1-methylpseudouracil (m1ψ), 2-thiouracil (s2U), 4'-thiouracil, 5-methylcytosine, 5-methyluracil, and any combination thereof. In some embodiments, the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof. In some embodiments, the at least one chemically modified nucleobase is 5-methoxyuracil. In some embodiments, at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils. In some embodiments, at least about 25%, at least about 30%, at least about 40%, at least about 50%, at least about 60%, at least about 70%, at least about 80%, at least about 90%, at least about 95%, at least about 99%, or 100% of the uracils or thymines are chemically modified. In some embodiments, at least about 25%, at least about 30%, at least about 40%, at least about 50%, at least about 60%, at least about 70%, at least about 80%, at least about 90%, at least about 95%, at least about 99%, or 100% of the guanines are chemically modified. In some embodiments, at least about 25%, at least about 30%, at least about 40%, at least about 50%, at least about 60%, at least about 70%, at least about 80%, at least about 90%, at least about 95%, at least about 99%, or 100% of the cytosines are chemically modified. In some embodiments, at least about 25%, at least about 30%, at least about 40%, at least about 50%, at least about 60%, at least about 70%, at least about 80%, at least about 90%, at least about 95%, at least about 99%, or 100% of the adenines are chemically modified.

In some embodiments, the polynucleotide comprises at least two different microRNA (miR) binding sites.

In some embodiments, the microRNA is expressed in an immune cell of hematopoietic lineage or a cell that expresses TLR7 and/or TLR8 and secretes pro-inflammatory cytokines and/or chemokines, and wherein the polynucleotide (e.g., mRNA) comprises one or more modified nucleobases.

In some embodiments, the mRNA comprises at least one first microRNA binding site of a microRNA abundant in an immune cell of hematopoietic lineage and at least one second microRNA binding site is of a microRNA abundant in endothelial cells.

In some embodiments, the mRNA comprises multiple copies of a first microRNA binding site and at least one copy of a second microRNA binding site.

In some embodiments, the mRNA comprises first and second microRNA binding sites of the same microRNA.

In some embodiments, the microRNA binding sites are of the 3p and 5p arms of the same microRNA.

In some embodiments, the microRNA binding site comprises one or more nucleotide sequences selected from TABLE 3 or TABLE 4.

In some embodiments, the microRNA binding site binds to miR-126, miR-142, miR-144, miR-146, miR-150, miR-155, miR-16, miR-21, miR-223, miR-24, miR-27 or miR-26a, or any combination thereof.

In some embodiments, the microRNA binding site binds to miR126-3p, miR-142-3p, miR-142-5p, or miR-155, or any combination thereof.

In some embodiments, the microRNA binding site is a miR-126 binding site. In some embodiments, at least one microRNA binding site is a miR-142 binding site. In some embodiments, one microRNA binding site is a miR-126 binding site and the second microRNA binding site is for a microRNA selected from the group consisting of miR-142-3p, miR-142-5p, miR-146-3p, miR-146-5p, miR-155, miR-16, miR-21, miR-223, miR-24 and miR-27.

In some embodiments, the mRNA comprises at least one miR-126-3p binding site and at least one miR-142-3p binding site. In some embodiments, the mRNA comprises at least one miR-142-3p binding site and at least one 142-5p binding site.

In some embodiments, the microRNA binding sites are located in the 5' UTR, 3' UTR, or both the 5' UTR and 3' UTR of the mRNA. In some embodiments, the microRNA binding sites are located in the 3' UTR of the mRNA. In some embodiments, the microRNA binding sites are located in the 5' UTR of the mRNA. In some embodiments, the microRNA binding sites are located in both the 5' UTR and 3' UTR of the mRNA. In some embodiments, at least one microRNA binding site is located in the 3' UTR immediately adjacent to the stop codon of the coding region of the mRNA. In some embodiments, at least one microRNA binding site is located in the 3' UTR 70-80 bases downstream of the stop codon of the coding region of the mRNA. In some embodiments, at least one microRNA binding site is located in the 5' UTR immediately preceding the start codon of the coding region of the mRNA. In some embodiments, at least one microRNA binding site is located in the 5' UTR 15-20 nucleotides preceding the start codon of the coding region of the mRNA. In some embodiments, at least one microRNA binding site is located in the 5' UTR 70-80 nucleotides preceding the start codon of the coding region of the mRNA.

In some embodiments, the mRNA comprises multiple copies of the same microRNA binding site positioned immediately adjacent to each other or with a spacer of less than 5, 5-10, 10-15, or 15-20 nucleotides.

In some embodiments, the mRNA comprises multiple copies of the same microRNA binding site located in the 3' UTR, wherein the first microRNA binding site is positioned immediately adjacent to the stop codon and the second and third microRNA binding sites are positioned 30-40 bases downstream of the 3' most residue of the first microRNA binding site.

In some embodiments, the microRNA binding site comprises one or more nucleotide sequences selected from SEQ ID NO: 75 and SEQ ID NO: 77. In some embodiments, the miRNA binding site binds to miR-142. In some embodiments, the miRNA binding site binds to miR-142-3p or miR-142-5p. In certain embodiments, the miR-142 comprises SEQ ID NO: 73.

In some embodiments, the microRNA binding site comprises one or more nucleotide sequences selected from SEQ ID NO: 144 and SEQ ID NO:146. In some embodiments, the miRNA binding site binds to miR-126. In some embodiments, the miRNA binding site binds to miR-126-3p or miR-126-5p. In some embodiments, the miR-126 comprises SEQ ID NO: 142.

In some embodiments, the mRNA comprises a 3' UTR comprising a microRNA binding site that binds to miR-142, miR-126, or a combination thereof.

In some embodiments, the polynucleotide, e.g., mRNA, further comprises a 3' UTR. In some embodiments, the 3' UTR comprises a nucleic acid sequence at least about 90%, at least about 95%, at least about 96%, at least about 97%, at least about 98%, at least about 99%, or 100% identical to a 3'UTR sequence selected from the group consisting of SEQ ID NOs: 48-72, 80, 81, 102-105, 108-117, 124, 125, 147-157, or any combination thereof. In some embodiments, the miRNA binding site is located within the 3' UTR. In some embodiments, the 3' UTR comprises a nucleic acid sequence selected from the group consisting of SEQ ID NOs: 48-72, 80, 81, 102-105, 108-117, 124, 125, 147-157, and any combination thereof. In some embodiments, the mRNA comprises a 3' UTR comprising a nucleic acid sequence selected from the group consisting of SEQ ID NOs: 105, 147, 148, or any combination thereof. In some embodiments, the mRNA comprises a 3' UTR comprising a nucleic acid sequence of SEQ ID NO: 147. In some embodiments, the mRNA comprises a 3' UTR comprising a nucleic acid sequence of SEQ ID NO: 148.

In some embodiments, the polynucleotide, e.g., mRNA, further comprises a 5' UTR. In some embodiments, the 5' UTR comprises a nucleic acid sequence at least 90%, at least about 95%, at least about 96%, at least about 97%, at least about 98%, at least about 99%, or about 100% identical to a 5'UTR sequence selected from the group consisting of SEQ ID NO: 30-47, 79, 120-122, 126-128, or any combination thereof. In some embodiments, the 5' UTR comprises a sequence selected from the group consisting of SEQ ID NO: 30-47, 79, 120-122, 126-128, and any combination thereof. In some embodiments, the mRNA comprises a 5' UTR comprising the nucleic acid sequence of SEQ ID NO: 30.

In some embodiments, the polynucleotide, e.g., mRNA, further comprises a 5' terminal cap. In some embodiments, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof. In some embodiments, the 5' terminal cap comprises a Cap1.

In some embodiments, the polynucleotide, e.g., mRNA, further comprises a poly-A region. In some embodiments, the poly-A region is at least about 10, at least about 20, at least about 30, at least about 40, at least about 50, at least about 60, at least about 70, at least about 80, or at least about 90 nucleotides in length. In some embodiments, the poly-A region has about 10 to about 200, about 20 to about 180, about 50 to about 160, about 70 to about 140, about 80 to about 120 nucleotides in length.

In some aspects, the polynucleotide, e.g., mRNA, encodes a Citrin polypeptide that is fused to one or more heterologous polypeptides. In some aspects, the one or more heterologous polypeptides increase a pharmacokinetic property of the Citrin polypeptide. In some aspects, upon administration to a subject, the polynucleotide has (i) a longer plasma half-life: (ii) increased expression of a Citrin polypeptide encoded by the ORF; (iii) a lower frequency of arrested translation resulting in an expression fragment: (iv) greater structural stability: or (v) any combination thereof, relative to a corresponding polynucleotide comprising SEQ ID NO: 2 or 4.

In some embodiments, the polynucleotide, e.g., mRNA, comprises (i) a 5'-terminal cap: (ii) a 5'-UTR: (iii) an ORF encoding a Citrin polypeptide: (iv) a 3'-UTR; and (v) a poly-A region. In some embodiments, the 3'-UTR comprises a miRNA binding site. In some embodiments, the polynucleotide comprises a nucleic acid sequence selected from the group consisting of SEQ ID NO: 130, 133, 136, 139. In some embodiments the polynucleotide further comprises a 5'-terminal cap (e.g., Cap1) and a poly-A-tail region (e.g., about 100 nucleotides in length).

In some aspects, the invention relates to a method of producing a polynucleotide, e.g., mRNA, of the invention, the method comprising modifying an ORF encoding a Citrin polypeptide by substituting at least one uracil nucleobase with an adenine, guanine, or cytosine nucleobase, or by substituting at least one adenine, guanine, or cytosine nucleobase with a uracil nucleobase, wherein all the substitutions are synonymous substitutions. In some embodiments, the method further comprises replacing at least about 90%, at least about 95%, at least about 99%, or about 100% of uracils with 5-methoxyuracils.

The present disclosure also provides a composition comprising (a) a polynucleotide, e.g., mRNA, of the invention; and (b) a delivery agent. In some embodiments, the delivery agent comprises a lipidoid, a liposome, a lipoplex, a lipid nanoparticle, a polymeric compound, a peptide, a protein, a cell, a nanoparticle mimic, a nanotube, or a conjugate. In some embodiments, the delivery agent comprises a lipid nanoparticle. In some embodiments, the lipid nanoparticle comprises a lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatricontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), (13Z,16Z)—N,N-dimethyl-3-nonydocosa-13-16-dien-1-amine (L608), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2R)), (2S)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2S)), and any combinations thereof. In some embodiments, the lipid nanoparticle comprises DLin-MC3-DMA.

In some aspects, the delivery agent comprises a compound having the formula (I)

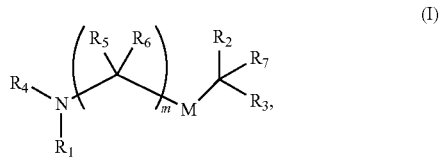

or a salt or stereoisomer thereof, wherein
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;
$R_7$ is selected from the group consisting of $C_{1-3}$ alkyl, $C_{2-3}$ alkenyl, and H;
$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —$(CH_2)_nQ$, —$(CH_2)_nCHQR$, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In some aspects, the delivery agent comprises a compound having the formula (I)

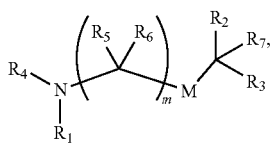

(I)

or a salt or stereoisomer thereof, wherein $R_1$ is selected from the group consisting of $C_{5-30}$ alkyl, $C_{5-20}$ alkenyl, —R*YR", —YR", and —R"M'R';

$R_2$ and $R_5$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —N(R)S(O)_2R, —$N(R)C(O)N(R)_2$, —$N(R)C(S)N(R)_2$, and —$N(R)R_8$, —$O(CH_2)_nOR$, —$N(R)C(=NR_9)N(R)_2$, —$N(R)C(=CHR_9)N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —$N(OR)C(=NR_9)N(R)_2$, —$N(OR)C(=CHR_9)N(R)_2$, —$C(=NR_9)N(R)_2$, —$C(=NR_9)R$, —C(O)N(R) OR, —$C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —$(CH_2)_nQ$, —$(CH_2)_nCHQR$, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In some embodiments, the delivery agent comprises a compound having the formula (I), or a salt or stereoisomer thereof, wherein $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —$N(R)S(O)_2R$, —$N(R)C(O)N(R)_2$, —$N(R)C(S)N(R)_2$, and —$C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —$(CH_2)_nQ$, —$(CH_2)_n$CHQR, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2. In some embodiments, the compound is of formula (IA)

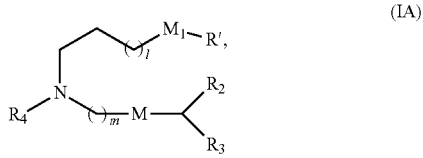

(IA)

or a salt or stereoisomer thereof, wherein
l is selected from 1, 2, 3, 4, and 5;
m is selected from 5, 6, 7, 8, and 9;
$M_1$ is a bond or M';
$R_4$ is unsubstituted $C_{1-3}$ alkyl, or —$(CH_2)_nQ$, in which n is 1, 2, 3, 4, or 5 and Q is OH, —$NHC(S)N(R)_2$, —$NHC(O)N(R)_2$, —$N(R)C(O)R$, —$N(R)S(O)_2R$, —$N(R)R_8$, —$NHC(=NR_9)N(R)_2$, —$NHC(=CHR_9)N(R)_2$, —$OC(O)N(R)_2$, —$N(R)C(O)OR$, heteroaryl, or heterocycloalkyl;
M and M' are independently selected from —C(O)O—, —OC(O)—, —C(O)N(R')—, —P(O)(OR')O—, an aryl group, and a heteroaryl group; and
$R_2$ and $R_3$ are independently selected from the group consisting of H, $C_{1-14}$ alkyl, and $C_{2-14}$ alkenyl.

In some embodiments, m is 5, 7, or 9. In some embodiments, the compound is of Formula (IA), or a salt or stereoisomer thereof, wherein
l is selected from 1, 2, 3, 4, and 5;
m is selected from 5, 6, 7, 8, and 9;
$M_1$ is a bond or M';
$R_4$ is unsubstituted $C_{1-3}$ alkyl, or —$(CH_2)_nQ$, in which n is 1, 2, 3, 4, or 5 and Q is OH, —$NHC(S)N(R)_2$, or —$NHC(O)N(R)_2$;
M and M' are independently selected from —C(O)O—, —OC(O)—, —C(O)N(R')—, —P(O)(OR')O—, an aryl group, and a heteroaryl group; and
$R_2$ and $R_3$ are independently selected from the group consisting of H, $C_{1-14}$ alkyl, and $C_{2-14}$ alkenyl.

In some embodiments, m is 5, 7, or 9.

In some embodiments, the compound is of Formula (II):

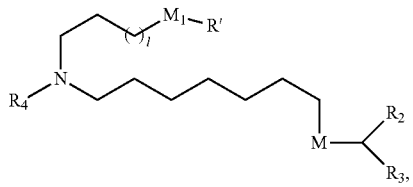

(II)

or a salt or stereoisomer thereof, wherein
l is selected from 1, 2, 3, 4, and 5;
$M_1$ is a bond or M';
$R_4$ is unsubstituted $C_{1-3}$ alkyl, or —$(CH_2)_nQ$, in which n is 2, 3 or 4 and Q is OH, —$NHC(S)N(R)_2$, —$NHC(O)N(R)_2$, —$N(R)C(O)R$, —$N(R)S(O)_2R$, —$N(R)R_8$, —$NHC(=NR_9)N(R)_2$, —$NHC(=CHR_9)N(R)_2$, —$OC(O)N(R)_2$, —$N(R)C(O)OR$, heteroaryl, or heterocycloalkyl;

In some embodiments, the compound is of Formula (II), or a salt or stereoisomer thereof, wherein
l is selected from 1, 2, 3, 4, and 5;
$M_1$ is a bond or M';
$R_4$ is unsubstituted $C_{1-3}$ alkyl, or —$(CH_2)_nQ$, in which n is 2, 3, or 4 and Q is OH, —$NHC(S)N(R)_2$, or —$NHC(O)N(R)_2$;
M and M' are independently selected from —C(O)O—, —OC(O)—, —C(O)N(R')—, —P(O)(OR')O—, an aryl group, and a heteroaryl group; and
$R_2$ and $R_3$ are independently selected from the group consisting of H, $C_{1-14}$ alkyl, and $C_{2-14}$ alkenyl.

In some embodiments, $M_1$ is M'.

In some embodiments, M and M' are independently —C(O)O— or —OC(O)—.

In some embodiments, l is 1, 3, or 5.

In some embodiments, the compound is selected from the group consisting of Compound 1 to Compound 232, salts and stereoisomers thereof, and any combination thereof.

In some embodiments, the compound is selected from the group consisting of Compound 1 to Compound 147, salts and stereoisomers thereof, and any combination thereof.

In some aspects, the compound is of the Formula (IIa),

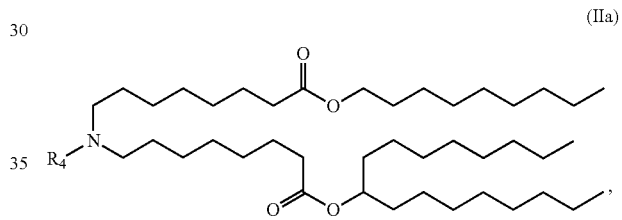

(IIa)

or a salt or stereoisomer thereof.

In some aspects, the compound is of the Formula (IIb),

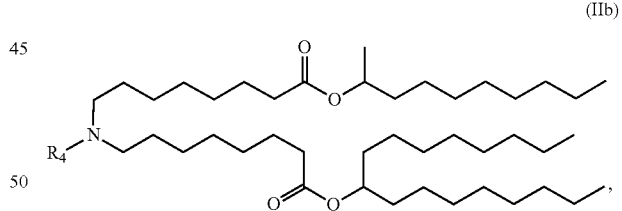

(IIb)

or a salt or stereoisomer thereof.

In some aspects, the compound is of the Formula (IIc) or (IIe),

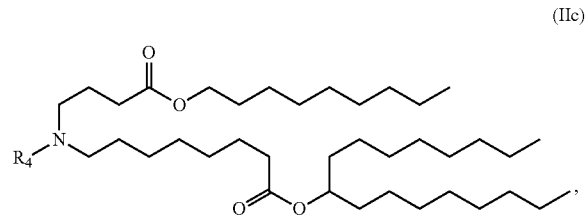

(IIc)

-continued (IIe)

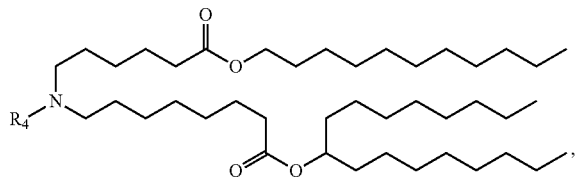

or a salt or stereoisomer thereof.

In some embodiments, $R_4$ is as described herein. In some embodiments, $R_4$ is selected from —$(CH_2)_nQ$ and —$(CH_2)_nCHQR$.

In some aspects, the compound is of the Formula (IId), (IId)

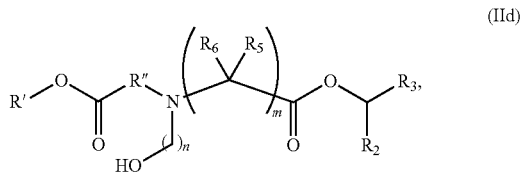

or a salt or stereoisomer thereof, wherein n is selected from 2, 3, and 4, and m, R', R", and $R_5$ through $R_6$ are as described herein. For example, each of $R_2$ and $R_3$ may be independently selected from the group consisting of $C_{5-14}$ alkyl and $C_{5-14}$ alkenyl.

In some embodiments, the compound is of the Formula (IId), or a salt or stereoisomer thereof, wherein $R_2$ and $R_3$ are independently selected from the group consisting of $C_{5-14}$ alkyl and $C_{5-14}$ alkenyl, n is selected from 2, 3, and 4, and R', R", $R_5$, $R_6$ and m are as defined herein.

In some embodiments, $R_2$ is $C_8$ alkyl.

In some embodiments, $R_3$ is $C_5$ alkyl, $C_6$ alkyl, $C_7$ alkyl, $C_8$ alkyl, or $C_9$ alkyl.

In some embodiments, m is 5, 7, or 9.

In some embodiments, each $R_5$ is H.

In some embodiments, each $R_6$ is H. In some embodiments, the delivery agent comprises a compound having the formula (III)

(III)

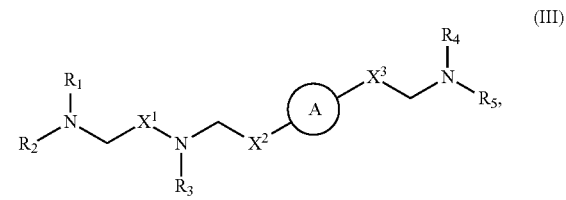

or salts or stereoisomers thereof, wherein
ring A is

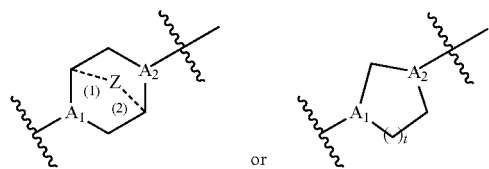

t is 1 or 2; or t $A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$X^1$, $X^2$, and $X^3$ are independently selected from the group consisting of a bond, —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl, wherein when ring A is

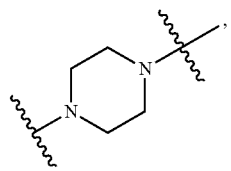

then
i) at least one of $X^1$, $X^2$, and $X^3$ is not —$CH_2$—; and/or
ii) at least one of $R_1$, $R_2$, $R_3$, $R_4$, and $R_5$ is —R"MR'.

In some embodiments, the compound is of any of formulae (IIIa1)-(IIIa6):

(IIIa1)

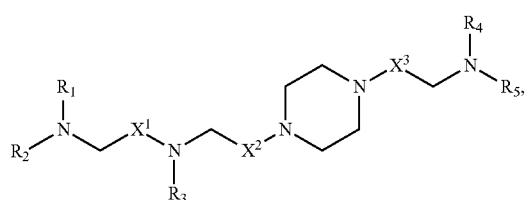

(IIIa2)

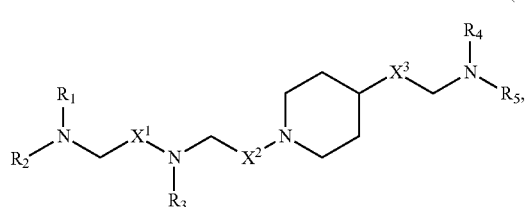

-continued

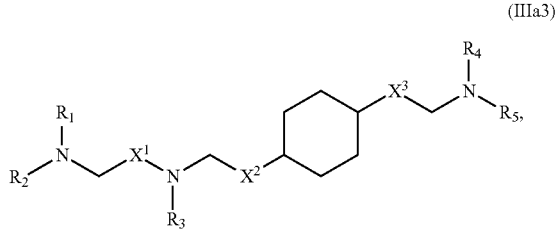
(IIIa3)

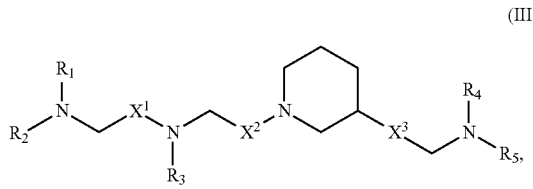
(IIIa4)

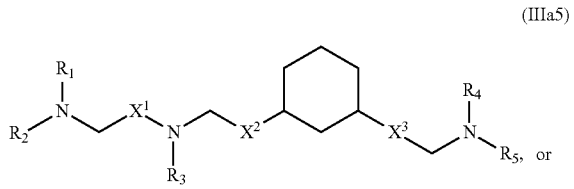
(IIIa5)

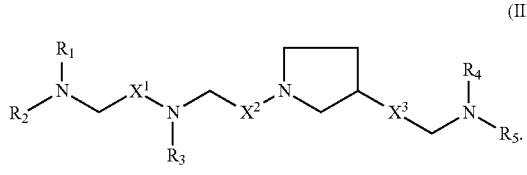
(IIIa6)

The compounds of Formula (III) or any of (IIIa1)-(IIIa6) include one or more of the following features when applicable.

In some embodiments, ring A is

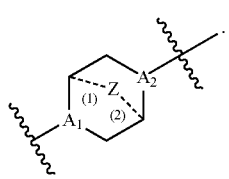

In some embodiments, ring A is

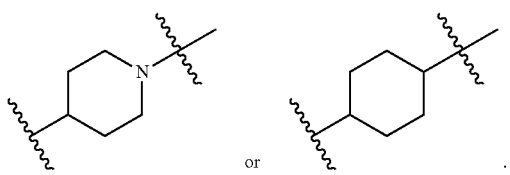 [SMILES: *C1CCN(*)CC1 ; *C1CCC(*)CC1]

In some embodiments, ring A is

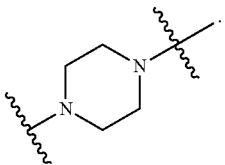 [SMILES: *N1CCN(*)CC1]

In some embodiments, ring A is

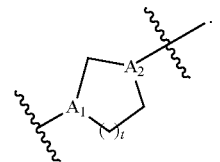

In some embodiments, ring A is

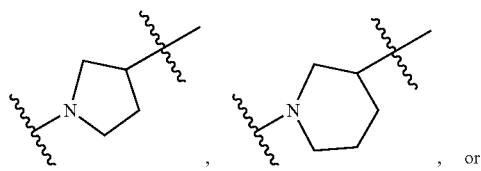

In some embodiments, ring A is

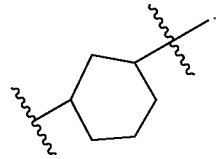

In some embodiments, ring A is

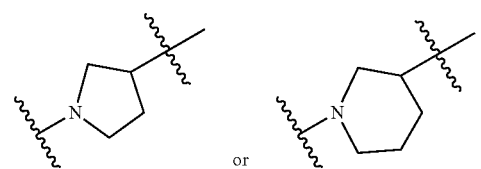 [SMILES: *C1CCN(*)C1 ; *C1CCCN(*)C1]

wherein ring, in which the N atom is connected with X2.

In some embodiments, Z is $CH_2$.
In some embodiments, Z is absent.
In some embodiments, at least one of $A_1$ and $A_2$ is N.
In some embodiments, each of $A_1$ and $A_2$ is N.
In some embodiments, each of $A_1$ and $A_2$ is CH.
In some embodiments, $A_1$ is N and $A_2$ is CH.
In some embodiments, $A_1$ is CH and $A_2$ is N.
In some embodiments, at least one of $X^1$, $X^2$, and $X^3$ is not —$CH_2$—. For example, in certain embodiments, $X^1$ is not —$CH_2$—. In some embodiments, at least one of $X^1$, $X^2$, and $X^3$ is —C(O)—.
In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.
In some embodiments, $X^3$ is —C(O)—, —C(O)O—, —OC(O)—, —C(O)—$CH_2$—, —$CH_2$—C(O)—, —C(O)

O—CH$_2$—, —OC(O)—CH$_2$—, —CH$_2$—C(O)O—, or —CH$_2$—OC(O)—. In other embodiments, X$^3$ is —CH$_2$—.

In some embodiments, X$^3$ is a bond or —(CH$_2$)$_2$—.

In some embodiments, R$_1$ and R$_2$ are the same. In certain embodiments, R$_1$, R$_2$, and R$_3$ are the same. In some embodiments, R$_4$ and R$_5$ are the same. In certain embodiments, R$_1$, R$_2$, R$_3$, R$_4$, and R$_5$ are the same.

In some embodiments, at least one of R$_1$, R$_2$, R$_3$, R$_4$, and R$_5$ is —R"MR'. In some embodiments, at most one of R$_1$, R$_2$, R$_3$, R$_4$, and R$_5$ is —R"MR'. For example, at least one of R$_1$, R$_2$, and R$_3$ may be —R"MR', and/or at least one of R$_4$ and R$_5$ is —R"MR'. In certain embodiments, at least one M is —C(O)O—. In some embodiments, each M is —C(O)O—. In some embodiments, at least one M is —OC(O)—. In some embodiments, each M is —OC(O)—. In some embodiments, at least one M is —OC(O)O—. In some embodiments, each M is —OC(O)O—. In some embodiments, at least one R" is C$_3$ alkyl. In certain embodiments, each R" is C$_3$ alkyl. In some embodiments, at least one R" is C$_5$ alkyl. In certain embodiments, each R" is C$_5$ alkyl. In some embodiments, at least one R" is C$_6$ alkyl. In certain embodiments, each R" is C$_6$ alkyl. In some embodiments, at least one R" is C$_7$ alkyl. In certain embodiments, each R" is C$_7$ alkyl. In some embodiments, at least one R' is C$_5$ alkyl. In certain embodiments, each R' is C$_5$ alkyl. In other embodiments, at least one R' is C$_1$ alkyl. In certain embodiments, each R' is C$_1$ alkyl. In some embodiments, at least one R' is C$_2$ alkyl. In certain embodiments, each R' is C$_2$ alkyl.

In some embodiments, at least one of R$_1$, R$_2$, R$_3$, R$_4$, and R$_5$ is C$_{12}$ alkyl. In certain embodiments, each of R$_1$, R$_2$, R$_3$, R$_4$, and R$_5$ are C$_{12}$ alkyl.

In some embodiments, the delivery agent comprises a compound having the formula (IV)

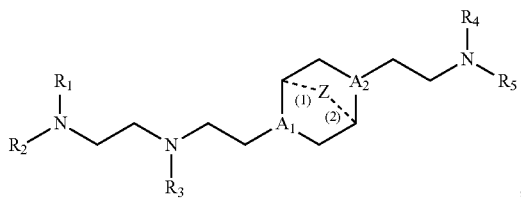

or salts or stereoisomer thereof, wherein

A$_1$ and A$_2$ are each independently selected from CH or N and at least one of A$_1$ and A$_2$ is N;

Z is CH$_2$ or absent wherein when Z is CH$_2$, the dashed lines (1) and (2) each represent a single bond; and when Z is absent, the dashed lines (1) and (2) are both absent;

R$_1$, R$_2$, R$_3$, R$_4$, and R$_5$ are independently selected from the group consisting of C$_{6-20}$ alkyl and C$_{6-20}$ alkenyl;

wherein when ring A is

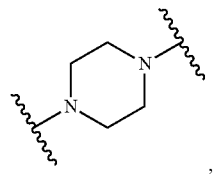 [SMILES: *N1CCN(*)CC1 ; ","]

then i) R$_1$, R$_2$, R$_3$, R$_4$, and R$_5$ are the same, wherein R$_1$ is not C$_{12}$ alkyl, C$_{18}$ alkyl, or C$_{18}$ alkenyl;

ii) only one of R$_1$, R$_2$, R$_3$, R$_4$, and R$_5$ is selected from C$_{6-20}$ alkenyl;

iii) at least one of R$_1$, R$_2$, R$_3$, R$_4$, and R$_5$ have a different number of carbon atoms than at least one other of R$_1$, R$_2$, R$_3$, R$_4$, and R$_5$;

iv) R$_1$, R$_2$, and R$_3$ are selected from C$_{6-20}$ alkenyl, and R$_4$ and R$_5$ are selected from C$_{6-20}$ alkyl; or v) R$_1$, R$_2$, and R$_3$ are selected from C$_{6-20}$ alkyl, and R$_4$ and R$_5$ are selected from C$_{6-20}$ alkenyl.

In some embodiments, the compound is of formula (IVa):

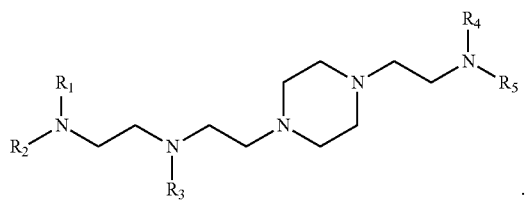

The compounds of Formula (IV) or (IVa) include one or more of the following features when applicable.

In some embodiments, Z is CH$_2$.

In some embodiments, Z is absent.

In some embodiments, at least one of A$_1$ and A$_2$ is N.

In some embodiments, each of A$_1$ and A$_2$ is N.

In some embodiments, each of A$_1$ and A$_2$ is CH.

In some embodiments, A$_1$ is N and A$_2$ is CH.

In some embodiments, A$_1$ is CH and A$_2$ is N.

In some embodiments, R$_1$, R$_2$, R$_3$, R$_4$, and R$_5$ are the same, and are not C$_{12}$ alkyl, C$_{18}$ alkyl, or C$_{18}$ alkenyl. In some embodiments, R$_1$, R$_2$, R$_3$, R$_4$, and R$_5$ are the same and are C$_9$ alkyl or C$_{14}$ alkyl.

In some embodiments, only one of R$_1$, R$_2$, R$_3$, R$_4$, and R$_5$ is selected from C$_{6-20}$ alkenyl. In certain such embodiments, R$_1$, R$_2$, R$_3$, R$_4$, and R$_5$ have the same number of carbon atoms. In some embodiments, R$_4$ is selected from C$_{5-20}$ alkenyl. For example, R$_4$ may be C$_{12}$ alkenyl or C$_{18}$ alkenyl.

In some embodiments, at least one of R$_1$, R$_2$, R$_3$, R$_4$, and R$_5$ have a different number of carbon atoms than at least one other of R$_1$, R$_2$, R$_3$, R$_4$, and R$_5$.

In certain embodiments, R$_1$, R$_2$, and R$_3$ are selected from C$_{6-20}$ alkenyl, and R$_4$ and R$_5$ are selected from C$_{6-20}$ alkyl. In other embodiments, R$_1$, R$_2$, and R$_3$ are selected from C$_{6-20}$ alkyl, and R$_4$ and R$_5$ are selected from C$_{6-20}$ alkenyl. In some embodiments, R$_1$, R$_2$, and R$_3$ have the same number of carbon atoms, and/or R$_4$ and R$_5$ have the same number of carbon atoms. For example, R$_1$, R$_2$, and R$_3$, or R$_4$ and R$_5$, may have 6, 8, 9, 12, 14, or 18 carbon atoms. In some embodiments, R$_1$, R$_2$, and R$_3$, or R$_4$ and R$_5$, are C$_{18}$ alkenyl (e.g., linoleyl). In some embodiments, R$_1$, R$_2$, and R$_3$, or R$_4$ and R$_5$, are alkyl groups including 6, 8, 9, 12, or 14 carbon atoms.

In some embodiments, R$_1$ has a different number of carbon atoms than R$_2$, R$_3$, R$_4$, and R$_5$. In other embodiments, R$_3$ has a different number of carbon atoms than R$_1$, R$_2$, R$_4$, and R$_5$. In further embodiments, R$_4$ has a different number of carbon atoms than R$_1$, R$_2$, R$_3$, and R$_5$.

In other embodiments, the delivery agent comprises a compound having the formula (V)

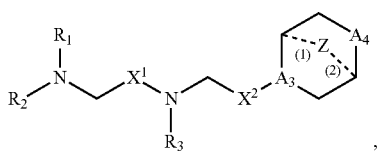

(V)

or salts or stereoisomers thereof, in which
A3 is CH or N;
A4 is CH$_2$ or NH; and at least one of A3 and A4 is N or NH;
Z is CH$_2$ or absent wherein when Z is CH$_2$, the dashed lines (1) and (2) each represent a single bond; and when Z is absent, the dashed lines (1) and (2) are both absent;
R$_1$, R$_2$, and R$_3$ are independently selected from the group consisting of C$_{5-20}$ alkyl, C$_{5-20}$ alkenyl, —R"MR', —R*YR", —YR", and —R*OR";
each M is independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
X$^1$ and X$^2$ are independently selected from the group consisting of —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;
each Y is independently a C$_{3-6}$ carbocycle;
each R* is independently selected from the group consisting of C$_{1-12}$ alkyl and C$_{2-12}$ alkenyl;
each R is independently selected from the group consisting of C$_{1-3}$ alkyl and a C$_{3-6}$ carbocycle;
each R' is independently selected from the group consisting of C$_{1-12}$ alkyl, C$_{2-12}$ alkenyl, and H; and
each R" is independently selected from the group consisting of C$_{3-12}$ alkyl and C$_{3-12}$ alkenyl.
In some embodiments, the compound is of formula (Va):

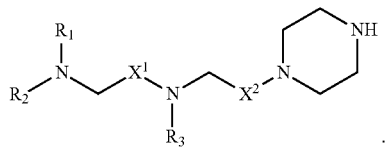

(Va)

The compounds of Formula (V) or (Va) include one or more of the following features when applicable.
In some embodiments, Z is CH$_2$.
In some embodiments, Z is absent.
In some embodiments, at least one of A$_3$ and A$_4$ is N or NH.
In some embodiments, A$_3$ is N and A$_4$ is NH.
In some embodiments, A$_3$ is N and A$_4$ is CH$_2$.
In some embodiments, A$_3$ is CH and A$_4$ is NH.
In some embodiments, at least one of X$^1$ and X$^2$ is not —CH$_2$—. For example, in certain embodiments, X$^1$ is not —CH$_2$—. In some embodiments, at least one of X$^1$ and X$^2$ is —C(O)—.

In some embodiments, X$^2$ is —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, or —CH$_2$—OC(O)—.

In some embodiments, R$_1$, R$_2$, and R$_3$ are independently selected from the group consisting of C$_{5-20}$ alkyl and C$_{5-20}$ alkenyl. In some embodiments, R$_1$, R$_2$, and R$_3$ are the same. In certain embodiments, R$_1$, R$_2$, and R$_3$ are C$_6$, C$_9$, C$_{12}$, or C$_{14}$ alkyl. In other embodiments, R$_1$, R$_2$, and R$_3$ are C$_{18}$ alkenyl. For example, R$_1$, R$_2$, and R$_3$ may be linoleyl.

In other embodiments, the delivery agent comprises a compound having the formula (VI):

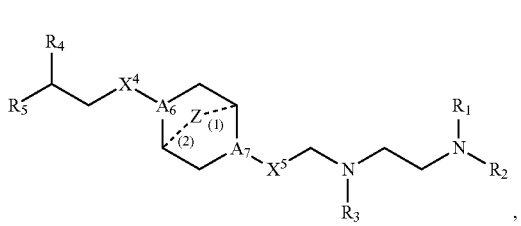

(VI)

or salts or stereoisomers thereof, in which
A$_6$ and A$_7$ are each independently selected from CH or N, wherein at least one of A$_6$ and A$_7$ is N;
Z is CH$_2$ or absent wherein when Z is CH$_2$, the dashed lines (1) and (2) each represent a single bond; and when Z is absent, the dashed lines (1) and (2) are both absent;
X$^4$ and X$^5$ are independently selected from the group consisting of —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;
R$_1$, R$_2$, R$_3$, R$_4$, and R$_5$ each are independently selected from the group consisting of C$_{5-20}$ alkyl, C$_{5-20}$ alkenyl, —R"MR', —R*YR", —YR", and —R*OR";
each M is independently selected from the group consisting of —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
each Y is independently a C$_{3-6}$ carbocycle;
each R* is independently selected from the group consisting of C$_{1-12}$ alkyl and C$_{2-12}$ alkenyl;
each R is independently selected from the group consisting of C$_{1-3}$ alkyl and a C$_{3-6}$ carbocycle;
each R' is independently selected from the group consisting of C$_{1-12}$ alkyl, C$_{2-12}$ alkenyl, and H; and
each R" is independently selected from the group consisting of C$_{3-12}$ alkyl and C$_{3-12}$ alkenyl.
In some embodiments, R$_1$, R$_2$, R$_3$, R$_4$, and R$_5$ each are independently selected from the group consisting of C$_{6-20}$ alkyl and C$_{6-20}$ alkenyl.
In some embodiments, R$_1$ and R$_2$ are the same. In certain embodiments, R$_1$, R$_2$, and R$_3$ are the same. In some embodiments, R$_4$ and R$_5$ are the same. In certain embodiments, R$_1$, R$_2$, R$_3$, R$_4$, and R$_5$ are the same.
In some embodiments, at least one of R$_1$, R$_2$, R$_3$, R$_4$, and R$_5$ is C$_{9-12}$ alkyl. In certain embodiments, each of R$_1$, R$_2$, R$_3$, R$_4$, and R$_5$ independently is C$_9$, C$_{12}$ or C$_{14}$ alkyl. In certain embodiments, each of R$_1$, R$_2$, R$_3$, R$_4$, and R$_5$ is C$_9$ alkyl.

In some embodiments, $A_6$ is N and $A_7$ is N. In some embodiments, A6 is CH and $A_7$ is N.

In some embodiments, $X^4$ is —$CH_2$— and $X^5$ is —C(O)—. In some embodiments, $X^4$ and $X^5$ are —C(O)—.

In some embodiments, when $A_6$ is N and $A_7$ is N, at least one of $X^4$ and $X^5$ is not —$CH_2$—, e.g., at least one of $X^4$ and $X^5$ is —C(O)—. In some embodiments, when A6 is N and $A_7$ is N, at least one of $R_1$, $R_2$, $R_3$, $R_4$, and $R_5$ is —R"MR'.

In some embodiments, at least one of $R_1$, $R_2$, $R_3$, $R_4$, and $R_5$ is not —R"MR'.

In some aspects, the composition is a nanoparticle composition. In some aspects, the delivery agent further comprises a phospholipid. In some embodiments, the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16:0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and any mixtures thereof.

In some embodiments, the delivery agent further comprises a structural lipid. In some embodiments, the structural lipid is selected from the group consisting of cholesterol, fecosterol, sitosterol, ergosterol, campesterol, stigmasterol, brassicasterol, tomatidine, ursolic acid, alpha-tocopherol, and any mixtures thereof.

In some embodiments, the delivery agent further comprises a PEG lipid. In some embodiments, the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and any mixtures thereof. In some embodiments, the PEG lipid has the formula:

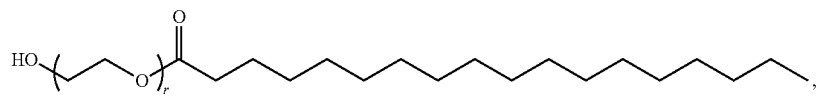

wherein r is an integer between 1 and 100. In some embodiments, the PEG lipid is Compound 428.

In some aspects, the delivery agent further comprises an ionizable lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-di en-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2S)).

In some embodiments, the delivery agent further comprises a phospholipid, a structural lipid, a PEG lipid, or any combination thereof. In some embodiments, the delivery agent comprises Compound 18, DSPC, Cholesterol, and Compound 428, e.g., with a mole ratio of about 50:10:38.5:1.5.

In some aspects, the composition is formulated for in vivo delivery. In some aspects, the composition is formulated for intramuscular, subcutaneous, or intradermal delivery.

The present disclosure further provides a polynucleotide comprising an mRNA comprising: (i) a 5' UTR, (ii) an open reading frame (ORF) encoding a human Citrin polypeptide, wherein the ORF comprises a nucleic acid sequence selected from the group consisting of SEQ ID NOs 5-29, 129, 132, 135, 138, and (iii) a 3' UTR comprising a microRNA binding site selected from miR-142, miR-126, or a combination thereof, wherein the mRNA comprises at least one chemically modified nucleobase.

The present disclosure further provides a polynucleotide comprising an mRNA comprising: (i) a 5'-terminal cap; (ii) a 5' UTR comprising a sequence selected from the group consisting of SEQ ID NO: 30-47, 79, 120-122, 126-128, and any combination thereof; (iii) an open reading frame (ORF) encoding a human Citrin polypeptide, wherein the ORF comprises a sequence selected from the group consisting of SEQ ID NOs: 5-29, 129, 132, 135, 138, wherein the mRNA comprises at least one chemically modified nucleobase selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof, and (iv) a 3' UTR comprising a nucleic acid sequence selected from the group consisting of SEQ ID NOs: 48-72, 80, 81, 102-105, 108-117, 124, 125, 147-157, and any combination thereof; and (v) a poly-A-region.

In some embodiments, the polynucleotide comprises a nucleic acid sequence selected from the group consisting of SEQ ID NO: 130, 133, 136, 139.

The present disclosure further provides a pharmaceutical composition comprising the polynucleotide, e.g., an mRNA, and a delivery agent. In some embodiments, the delivery agent is a lipid nanoparticle comprising Compound 18, Compound 236, a salt or a stereoisomer thereof, or any combination thereof. In some embodiments, the polynucleotide comprising a nucleotide sequence encoding a Citrin polypeptide disclosed herein is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

In one aspect of the embodiments disclosed herein, the subject is a human subject in need of treatment or prophylaxis for Citrullinemia Type 2 (CTLN2).

In one aspect of the embodiments disclosed herein, upon administration to the subject, the mRNA has: (i) a longer plasma half-life; (ii) increased expression of a Citrin polypeptide encoded by the ORF; (iii) a lower frequency of arrested translation resulting in an expression fragment; (iv) greater structural stability; or (v) any combination thereof, relative to a corresponding mRNA having the nucleic acid sequence of SEQ ID NO: 2 or 4 and/or administered as naked mRNA.

In some embodiments, a pharmaceutical composition or polynucleotide disclosed herein is suitable for administration as a single unit dose or a plurality of single unit doses.

In some embodiments, a pharmaceutical composition or polynucleotide disclosed herein is suitable for reducing the level of one or more biomarkers of CTLN2 in the subject.

In some embodiments, a pharmaceutical composition or polynucleotide disclosed herein is for use in treating, preventing or delaying the onset of CTLN2 signs or symptoms in the subject. In some embodiments, the signs or symptoms include nocturnal delirium, aggression, irritability, hyperactivity, delusions, disorientation, restlessness, drowsiness, loss of memory, flapping tremor, convulsive seizures, coma, brain edema, death, or a combination thereof.

In some aspects, the invention relates to a host cell comprising a polynucleotide of the invention. In some aspects, the host cell is a eukaryotic cell.

In some aspects, the invention relates to a vector comprising a polynucleotide of the invention.

In some aspects, the invention relates to a method of making a polynucleotide comprising enzymatically or chemically synthesizing a polynucleotide of the invention.

In some aspects, the invention relates to a method of expressing in vivo an active Citrin polypeptide in a subject in need thereof comprising administering to the subject an effective amount of a polynucleotide, composition, host cell, or vector of the invention.

In some aspects, the invention relates to a method of treating citrullinemia type 2 (CTLN2) in a subject in need thereof comprising administering to the subject a therapeutically effective amount of a polynucleotide, composition, host cell, or vector of the invention, wherein the administration alleviates the signs or symptoms of CTLN2 in the subject.

In some aspects, the invention relates to a method to prevent or delay the onset of CTLN2 signs or symptoms in a subject in need thereof comprising administering to the subject a prophylactically effective amount of a polynucleotide, composition, host cell, or vector of the invention before CTLN2 signs or symptoms manifest, wherein the administration prevents or delays the onset of CTLN2 signs or symptoms in the subject.

In some aspects, the invention relates to a method to ameliorate the signs or symptoms of CTLN2 in a subject in need thereof comprising administering to the subject a therapeutically effective amount of a polynucleotide, composition, host cell, or vector of the invention before CTLN2 signs or symptoms manifest, wherein the administration ameliorates CTLN2 signs or symptoms in the subject.

The present disclosure further provides a method of expressing a Citrin polypeptide in a human subject in need thereof comprising administering to the subject an effective amount of a pharmaceutical composition or a polynucleotide, e.g., an mRNA, described herein, wherein the pharmaceutical composition or polynucleotide is suitable for administrating as a single dose or as a plurality of single unit doses to the subject.

The present disclosure further provides a method of treating, preventing or delaying the onset of Citrullinemia Type 2 (CTLN2) signs or symptoms in a human subject in need thereof comprising administering to the subject an effective amount of a pharmaceutical composition or a polynucleotide, e.g., an mRNA, described herein, wherein the administration treats, prevents or delays the onset of one or more of the signs or symptoms of CTLN2 in the subject.

The present disclosure further provides a method for the treatment of Citrullinemia Type 2 (CTLN2), comprising administering to a human subject suffering from CTLN2 a single intravenous dose of a pharmaceutical composition or a polynucleotide, e.g., an mRNA, described herein.

The present disclosure further provides a method of reducing an ammonia and/or triglyceride blood and/or plasma level in a human subject comprising administering to the subject an effective amount of a pharmaceutical composition or a polynucleotide, e.g., an mRNA, described herein, wherein the administration reduces the ammonia and/or triglyceride plasma level in the subject. In some embodiments, (i) ammonia blood and/or plasma level is reduced at least 2-fold, at least 3-fold, at least 5-fold, at least 10-fold, at least 15 fold, at least 20-fold, at least 50-fold, at least 20%, at least 30%, at least 40%, at least 50%, at least 60%, at least 70%, at least 80%, at least 90%, at least 95% or at least 98%, at least 99%, or 100% compared to the subject's baseline level or a reference ammonia blood and/or plasma level, for at least 24 hours, at least 48 hours, at least 72 hours, at least 96 hours, or at least 120 hours post-administration; and/or (ii) triglyceride blood and/or plasma level is reduced at least 1.5-fold, 2-fold, at least 3-fold, at least 4-fold, at least 5-fold, at least 10-fold, at least 20-fold, at least 20%, at least 30%, at least 40%, at least 50%, at least 60%, at least 70%, at least 80%, at least 90%, at least 95% or at least 98%, at least 99%, or 100% compared to the subject's baseline level or a reference triglyceride blood and/or plasma level, for at least 24 hours, at least 48 hours, at least 72 hours, at least 96 hours, or at least 120 hours post-administration.

In some embodiments, after administration of the pharmaceutical composition or polynucleotide to the subject, e.g., within 12 hours, 24 hours, 36 hours, or 48 hours, the Citrin activity in the subject is increased at least 20%, at least 30%, at least 40%, at least 50%, at least 60%, at least 70%, at least 80%, at least 90%, at least 100%, at least 150%, at least 200%, at least 300%, at least 400%, at least 500%, or at least 600% compared to the subject's baseline Citrin activity.

In some embodiments, the Citrin activity is increased in the liver, and/or kidneys of the subject.

In some embodiments, the increased Citrin activity persists for greater than 24, 36, 48, 60, 72, or 96 hours post-administration.

In some embodiments, the pharmaceutical composition or polynucleotide is administered to the subject having citrullinemia type 2 (CTLN2).

In some embodiments, after administration of the pharmaceutical composition or polynucleotide to the subject, e.g, within 24 hours, the level of ammonia in the subject is reduced by at least about 100%, at least about 90%, at least about 80%, at least about 70%, at least about 60%, at least about 50%, at least about 40%, or at least about 30% compared to the subject's baseline ammonia level.

In some embodiments, the level of ammonia is reduced in the blood and/or plasma of the subject.

In some embodiments, after the administration to the subject the level of ammonia in the subject is reduced compared to the baseline level in the subject for at least one day, at least two days, at least three days, at least four days, at least five days, at least one week, at least two weeks, at least three weeks, or at least one month.

In some embodiments, after administration of the pharmaceutical composition or polynucleotide to the subject, e.g., within 24 hours, the level of triglycerides in the subject is reduced by at least about 100%, at least about 80%, at least about 60%, at least about 50%, at least about 40%, at least about 30%, at least about 20%, or at least about 10% compared to the subject's baseline triglycerides.

In some embodiments, the level of triglycerides is reduced in the plasma and/or liver of the subject.

In some embodiments, after the administration to the subject the level of triglycerides in the subject is reduced compared to the baseline level in the subject for at least one day, at least two days, at least three days, at least four days, at least five days, at least one week, at least two weeks, at least three weeks, or at least one month.

In some embodiments, the subject is symptomatic for CTLN2.

In some embodiments, the subject is presymptomatic for CTLN2.

In some embodiments, the Citrin polypeptide activity level is sufficient to prevent the onset of CTLN2 signs and/or symptoms.

In some embodiments, the pharmaceutical composition or polynucleotide is administered as a single dose of less than 1.5 mg/kg, less than 1.25 mg/kg, less than 1 mg/kg, or less than 0.75 mg/kg.

In some embodiments, the administration to the subject is about once a week, about once every two weeks, or about once a month.

In some embodiments, the pharmaceutical composition or polynucleotide is administered intravenously.

BRIEF DESCRIPTION OF THE DRAWINGS/FIGURES

FIGS. 1A-1D show the protein sequence (FIG. 1A), table with domain features (panel B), graphic representation of domain structure (FIG. 1C), and nucleic acid sequence (FIG. 1D) of isoform 1 of Citrin.

FIGS. 2A-2D show the protein sequence (FIG. 2A), table with domain features (FIG. 2B), graphic representation of domain structure (FIG. 2C), and nucleic acid sequence (FIG. 2D) of isoform 2 of Citrin.

FIG. 3 shows uracil (U) metrics corresponding to wild type isoform 1 of Citrin and 25 sequence optimized Citrin polynucleotides. The column labeled "U content (%)" corresponds to the % $U_{TL}$ parameter. The column labeled "U Content v. WT (%)" corresponds to % $U_{WT}$. The column labeled "U Content v. Theoretical Minimum (%)" corresponds to % $U_{TM}$. The column labeled "UU pairs v. WT (%)" corresponds to % $UU_{WT}$.

FIG. 4 shows guanine (G) metrics corresponding to wild type isoform 1 of Citrin and 25 sequence optimized Citrin polynucleotides. The column labeled "G Content (%)" corresponds to % Gn. The column labeled "G Content v. WT (%)" corresponds to % $G_{WT}$. The column labeled "G Content v. Theoretical Maximum (%)" corresponds to % $G_{TMX}$.

FIG. 5 shows cytosine (C) metrics corresponding to wild type isoform 1 of Citrin and 25 sequence optimized Citrin polynucleotides. The column labeled "C Content (%)" corresponds to % $C_{TL}$. The column labeled "C Content v. WT (%)" corresponds to % $C_{WT}$. The column labeled "C Content v. Theoretical Maximum (%)" corresponds to % $C_{TMX}$.

FIG. 6 shows guanine plus cytosine (G/C) metrics corresponding to wild type isoform 1 of Citrin and 25 sequence optimized Citrin polynucleotides. The column labeled "G/C Content (%)" corresponds to % $G/C_{TL}$. The column labeled "G/C Content v. WT (%)" corresponds to % $G/C_{WT}$. The column labeled "G/C Content v. Theoretical Maximum (%)" corresponds to % $G/C_{TMX}$.

FIG. 7 is an experimental design diagram showing the timing for administration of mRNA encoding Citrin or non-translated Factor IX (NTFIX) control mRNA to CTRN knockout and mGPD/CTRN double knockout mice and the timing for bleeding mice, taking body weight measurements, and collecting samples (plasma, liver, and spleen).

Figure 8:
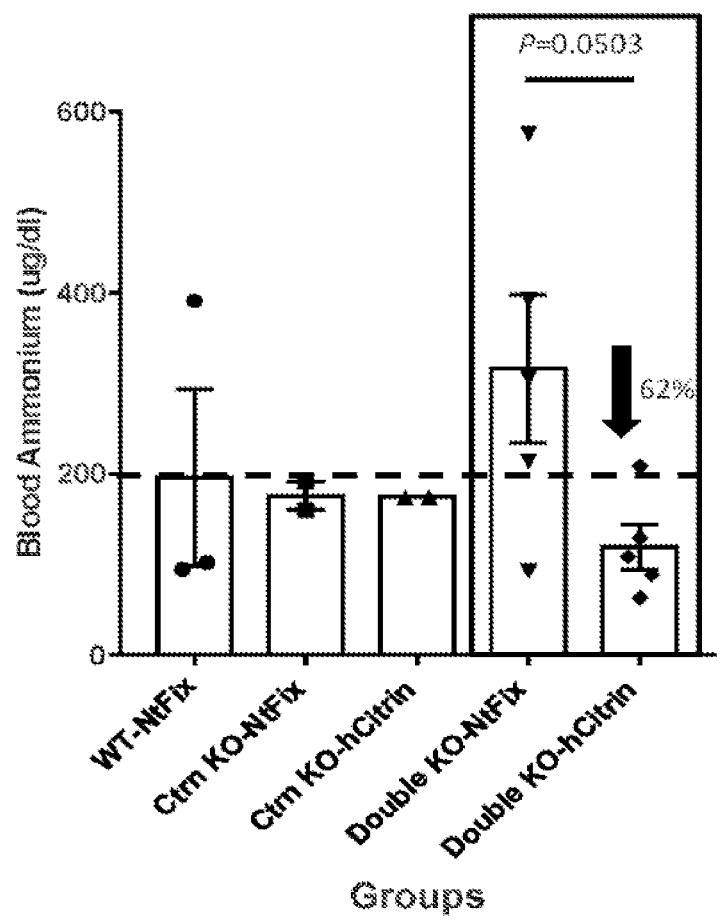

FIG. 8 shows blood ammonium levels (µg/dl) in CTRN knockout (Ctrn KO) and mGPD/CTRN (Double KO) mice administered mRNA (Construct #1) encoding human Citrin (hCitrin) or control mRNA encoding non-translated Factor IX (NtFix) according to the experimental design shown in FIG. 7. Blood ammonium levels for wild-type mice administered control NTFIX mRNA (WT-NtFix) are also shown.

Figure 9A:
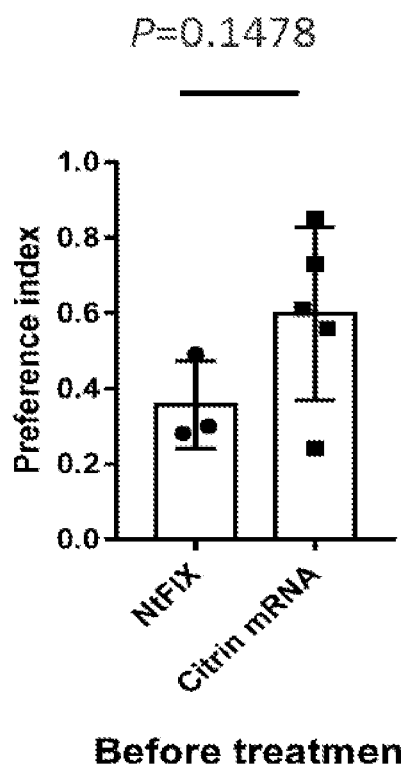
Figure 9B:
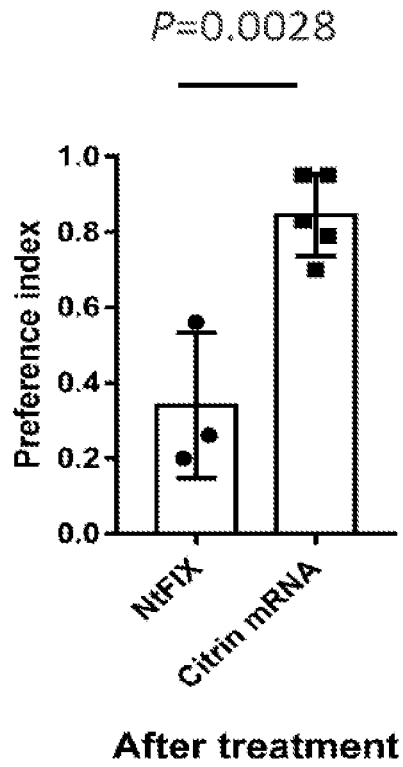

FIGS. 9A-9B show sucrose aversion (preference index) before mRNA administration (FIG. 9A) and after the second injection of mRNA (FIG. 9B) for mGPD/CTRN double knockout mice administered mRNA (Construct #1) encoding Citrin or control NTFIX mRNA.

Figure 10:
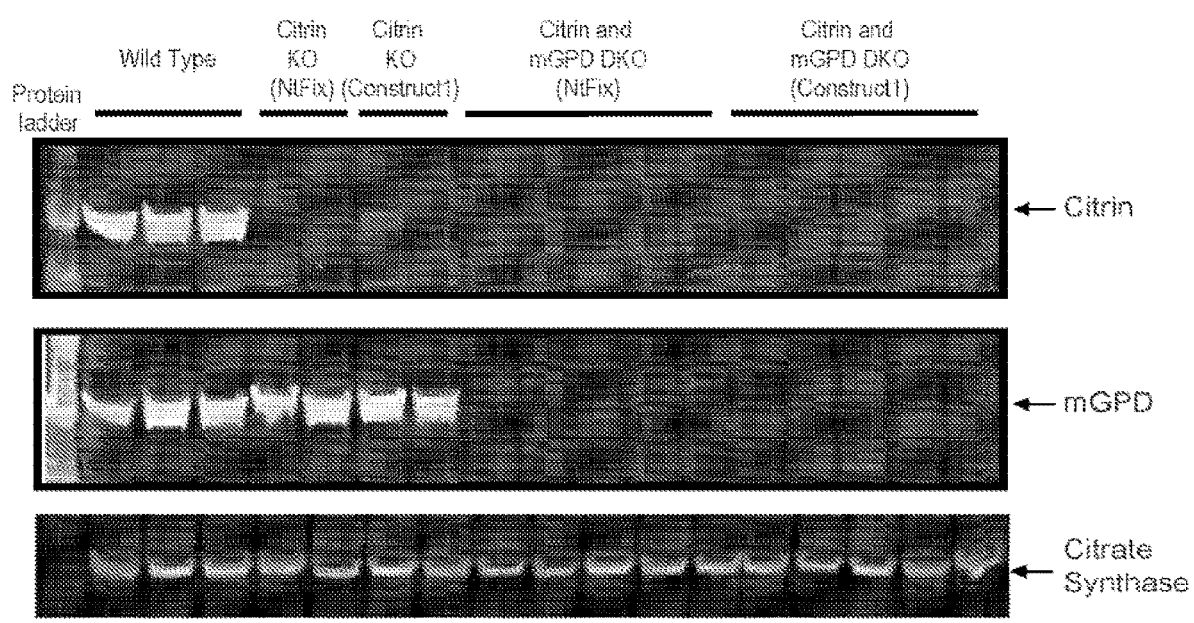

FIG. 10 shows protein expression levels of Citrin (top panel), mGPD (middle panel), and citrate synthase (bottom panel) in isolated liver mitochondria following administration of control mRNA (NTFIX) or mRNA encoding Citrin (Construct #1) to wild-type mice, CTRN knockout mice, and mGPD/CTRN knockout mice.

Figure 11:
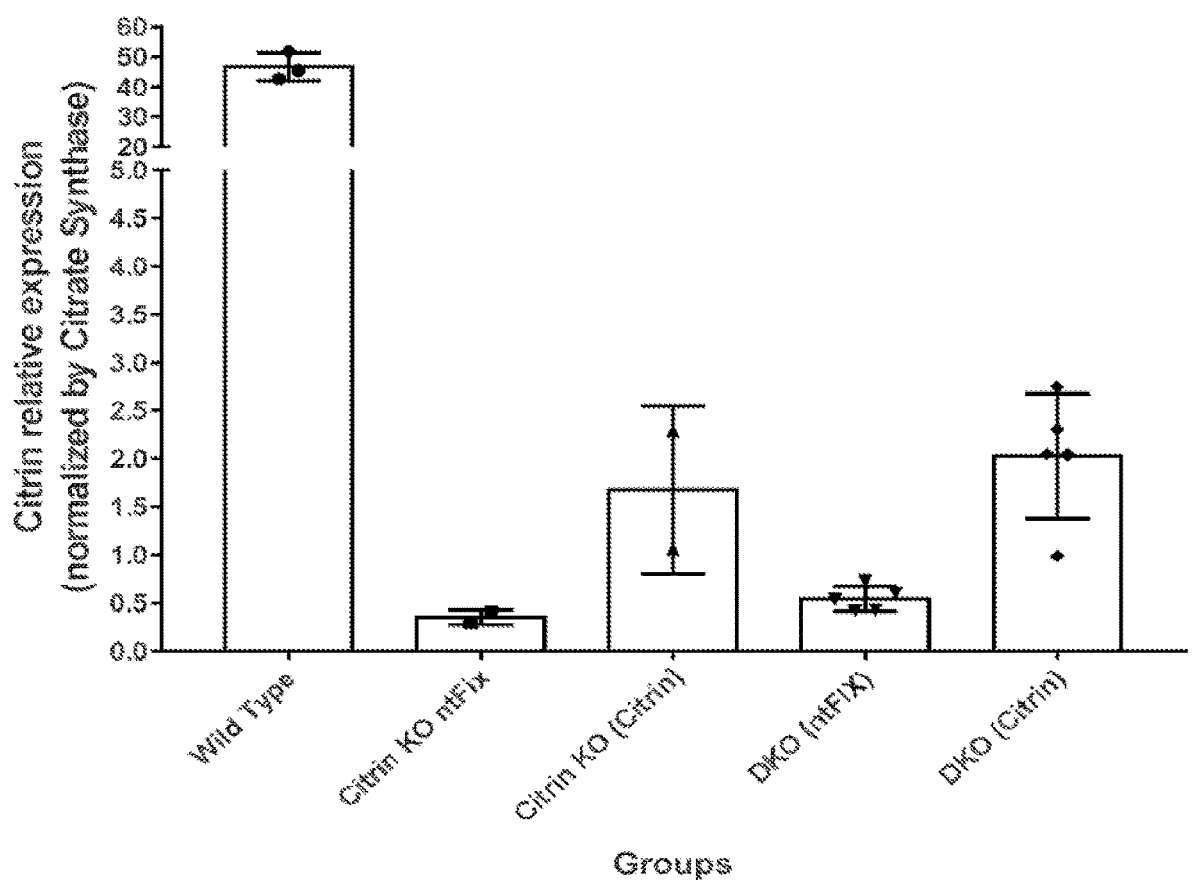

FIG. 11 shows a semi-quantitative analysis of protein expression levels of Citrin following administration of control mRNA (NTFIX) or mRNA encoding Citrin (Construct #1) to wild-type mice, CTRN knockout mice, and mGPD/CTRN knockout mice.

Figure 12:
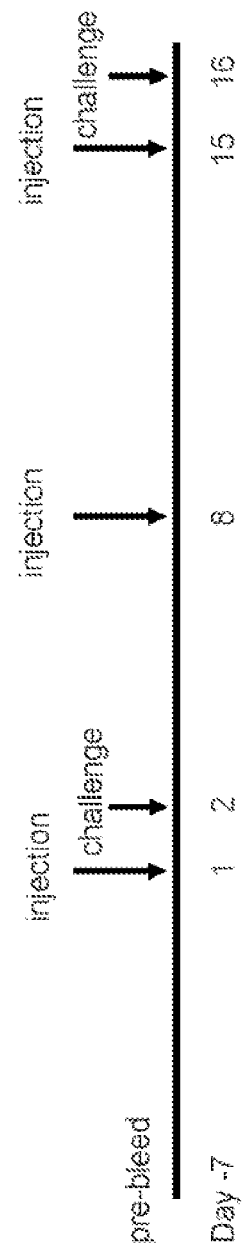

FIG. 12 is an experimental design diagram showing the timing of mRNA injection and sucrose challenge for the study described in Example 23.

Figure 13A:
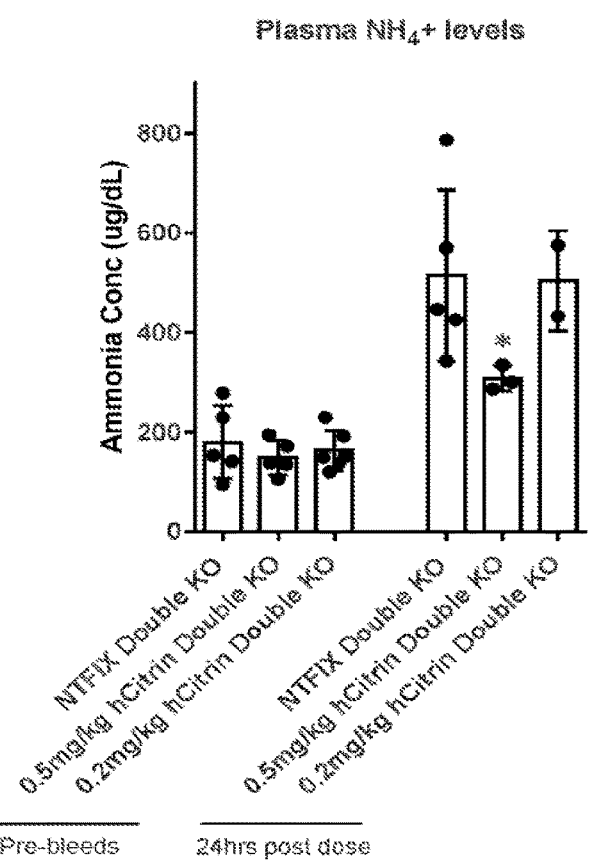
Figure 13B:
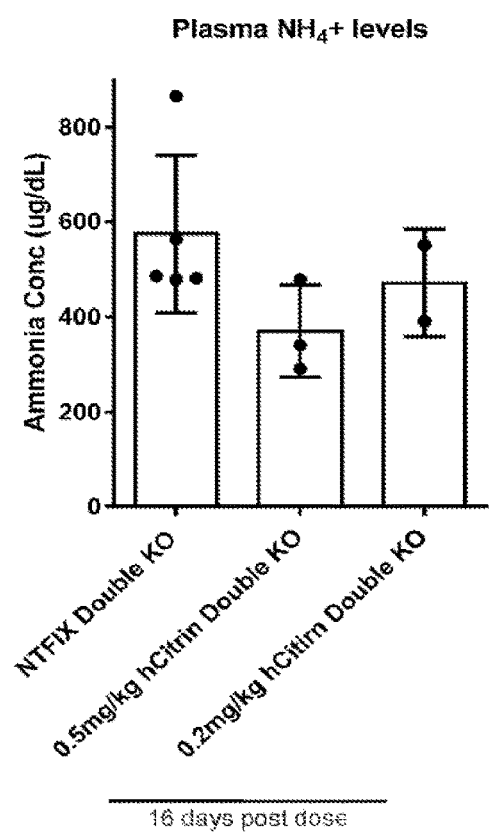

FIGS. 13A-13B show plasma ammonia concentration levels in mGPD/CTRN double knockout mice after injection of mRNA encoding human Citrin (0.5 mg/kg and 0.2 mg/kg) or control mRNA (NTFIX). FIG. 13A shows the plasma ammonia concentration prior to injection of mRNA and 24 hours post initial injection of mRNA. FIG. 13B shows the plasma ammonia concentration 16 days post initial injection of mRNA.

Figure 14A:
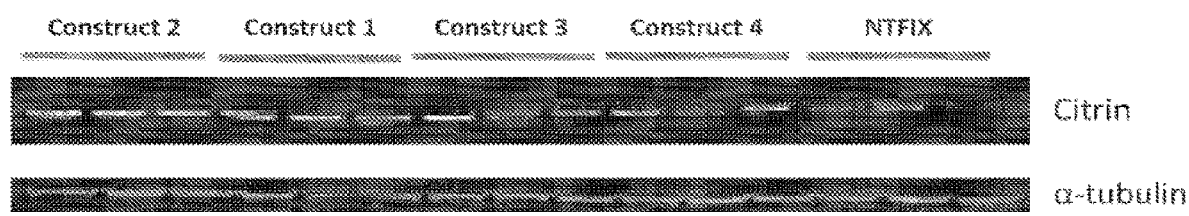
Figure 14B:
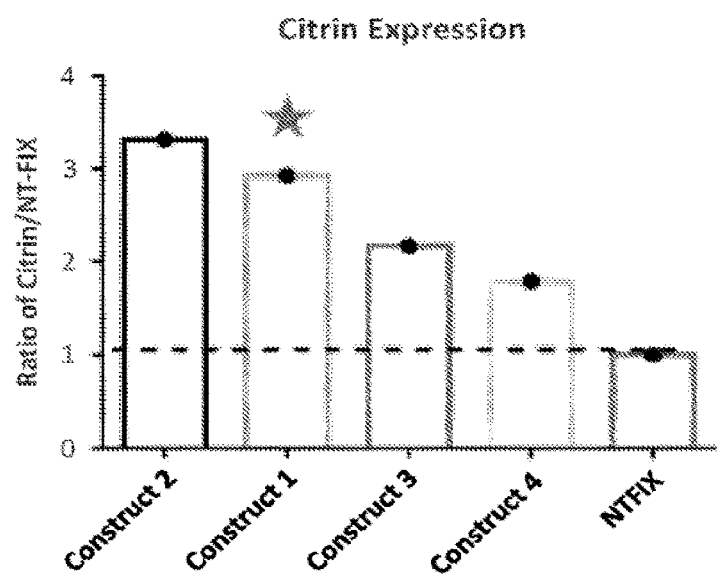

FIGS. 14A-14B show Citrin protein expression in liver mitochondria isolated from mice administered Citrin mRNA. FIG. 14A is a Western blot showing Citrin protein expression in liver mitochondria isolated from wild-type mice 24 hours post-injection with mRNA encoding human Citrin (Constructs #1, #2, #3 or #4) or with mRNA encoding NTFIX. α-tubulin is detected as a loading control. FIG. 14B shows a quantitative analysis of the ratio of protein expression levels of Citrin in liver mitochondria isolated from wild-type mice 24 hours post-injection with mRNA encoding Citrin (Constructs #1, 2, 3 or 4) to control mRNA (NTFIX).

DETAILED DESCRIPTION

The present invention provides mRNA therapeutics for the treatment of citrullinemia type 2 (CTLN2). CTLN2 is an autosomal recessive urea cycle disorder that causes abnormal buildup of ammonia and other toxic substances in the blood. CTLN2 is a form of citrullinemia that is caused by mutation of the Solute Carrier Family 25, Member 13 gene ("SLC25A13"). CTLN2 is also known as adult-onset citrullinemia type 2 or citrin deficiency. CTLN2 causes nocturnal delirium, aggression, irritability, hyperactivity, delusions, disorientation, restlessness, drowsiness, loss of memory, flapping tremor, convulsive seizures, coma, or even death resulting from brain edema. mRNA therapeutics are particularly well-suited for the treatment of CTLN2 as the technology provides for the intracellular delivery of mRNA encoding Citrin (the protein encoded by SLC25A13) followed by de novo synthesis of functional Citrin protein within target cells. After delivery of mRNA to the target cells, the desired Citrin protein is expressed by the cells' own translational machinery, and hence, fully functional Citrin protein replaces the defective or missing protein.

One challenge associated with delivering nucleic acid-based therapeutics (e.g., mRNA therapeutics) in vim stems from the innate immune response which can occur when the body's immune system encounters foreign nucleic acids. Foreign mRNAs can activate the immune system via recognition through toll-like receptors (TLRs), in particular TLR7/8, which is activated by single-stranded RNA (ssRNA). In nonimmune cells, the recognition of foreign mRNA can occur through the retinoic acid-inducible gene I (RIG-I). Immune recognition of foreign mRNAs can result in unwanted cytokine effects including interleukin-1β (IL-1β) production, tumor necrosis factor-α (TNF-α) distribution and a strong type I interferon (type I IFN) response. The instant invention features the incorporation of different modified nucleotides within therapeutic mRNAs to minimize the immune activation and optimize the translation efficiency of mRNA to protein. Particular aspects of the invention feature a combination of nucleotide modification to reduce the innate immune response and sequence optimization, in particular, within the open reading frame (ORF) of therapeutic mRNAs encoding Citrin to enhance protein expression.

Certain embodiments of the mRNA therapeutic technology of the instant invention also features delivery of mRNA encoding Citrin via a lipid nanoparticle (LNP) delivery system. Lipid nanoparticles (LNPs) are an ideal platform for the safe and effective delivery of mRNAs to target cells. LNPs have the unique ability to deliver nucleic acids by a mechanism involving cellular uptake, intracellular transport and endosomal release or endosomal escape. The instant invention features novel ionizable lipid-based LNPs combined with mRNA encoding Citrin which have improved properties when administered in vivo. Without being bound in theory, it is believed that the novel ionizable lipid-based LNP formulations of the invention have improved properties, for example, cellular uptake, intracellular transport and/or endosomal release or endosomal escape. LNPs administered by systemic route (e.g., intravenous (IV) administration), for example, in a first administration, can accelerate the clearance of subsequently injected LNPs, for example, in further administrations. This phenomenon is known as accelerated blood clearance (ABC) and is a key challenge, in particular, when replacing deficient proteins (e.g., Citrin) in a therapeutic context. This is because repeat administration of mRNA therapeutics is in most instances essential to maintain necessary levels of protein in target tissues in subjects (e.g., subjects suffering from CTLN2.) Repeat dosing challenges can be addressed on multiple levels. mRNA engineering and/or efficient delivery by LNPs can result in increased levels and or enhanced duration of protein (e.g., Citrin) being expressed following a first dose of administration, which in turn, can lengthen the time between first dose and subsequent dosing. It is known that the ABC phenomenon is, at least in part, transient in nature, with the immune responses underlying ABC resolving after sufficient time following systemic administration. As such, increasing the duration of protein expression and/or activity following systemic delivery of an mRNA therapeutic of the invention in one aspect, combats the ABC phenomenon. Moreover, LNPs can be engineered to avoid immune sensing and/or recognition and can thus further avoid ABC upon subsequent or repeat dosing. Exemplary aspect of the invention feature novel LNPs which have been engineered to have reduced ABC.

1. Citrin

The principal gene associated with CTLN2 is SLC25A13, which has two variants (Genbank Accession Nos. NM_001160210, NP 001153682; NM 014251, NP_055066; XM_006715831, XP_006715894; XM 011515727, XP 011514029). SLC25A13 encodes Citrin, which is a calcium-dependent mitochondrial solute carrier protein. Citrin is also known as Mitochondrial Aspartate Glutamate Carrier 2 or ARALAR2. Citrin plays a critical role in the urea cycle by catalyzing the mitochondrial uptake of glutamate and export of aspartate. Saheki, T. et al., Metab. Brain Dis. 17:335-346 (2002). Depending on the variant, the precursor form of human Citrin is either 676 or 675 amino acids, while its mature form is either 675 or 674 amino acids with the initiator methionine cleaved off.

In certain aspects, the invention provides a polynucleotide (e.g., a ribonucleic acid (RNA), e.g., a messenger RNA (mRNA)) comprising a nucleotide sequence (e.g., an open reading frame (ORF)) encoding a Citrin polypeptide. In some embodiments, the Citrin polypeptide of the invention is a wild type Citrin isoform 1 or 2 protein. In some embodiments, the Citrin polypeptide of the invention is a variant, a peptide or a polypeptide containing a substitution, and insertion and/or an addition, a deletion and/or a covalent modification with respect to a wild-type Citrin isoform 1 or 2 sequence. In some embodiments, sequence tags or amino acids, can be added to the sequences encoded by the polynucleotides of the invention (e.g., at the N-terminal or C-terminal ends), e.g., for localization. In some embodiments, amino acid residues located at the carboxy, amino terminal, or internal regions of a polypeptide of the invention can optionally be deleted providing for fragments.

In some embodiments, the polynucleotide (e.g., a RNA, e.g., an mRNA) comprising a nucleotide sequence (e.g., an ORF) of the invention encodes a substitutional variant of a Citrin isoform 1 or 2 sequence, which can comprise one, two, three or more than three substitutions. In some embodiments, the substitutional variant can comprise one or more conservative amino acids substitutions. In other embodiments, the variant is an insertional variant. In other embodiments, the variant is a deletional variant.

As recognized by those skilled in the art, Citrin isoform 1 or 2 protein fragments, functional protein domains, variants, and homologous proteins (orthologs) are also considered to be within the scope of the Citrin polypeptides of the invention. Nonlimiting examples of polypeptides encoded by the polynucleotides of the invention are shown in FIGS. 1 and 2. For example, FIG. 1 shows the amino acid sequence of human Citrin wild type isoform 1.

Certain compositions and methods presented in this disclosure refer to the protein or polynucleotide sequences of Citrin isoform 1. A person skilled in the art will understand that such disclosures are equally applicable to any other isoforms of Citrin known in the art.

2. Polynucleotides and Open Reading Frames (ORFs)

The instant invention features mRNAs for use in treating (i.e., prophylactically and/or therapeutically treating) CTLN2. The mRNAs featured for use in the invention are administered to subjects and encode Citrin proteins(s) in vivo. Accordingly, the invention relates to polynucleotides comprising an open reading frame of linked nucleosides encoding human Citrin, isoforms thereof, functional fragments thereof, and fusion proteins comprising Citrin. In some embodiments, the open reading frame is sequence-optimized. In particular embodiments, the invention provides sequence-optimized polynucleotides comprising nucleotides encoding the polypeptide sequence of isoforms 1 or 2 of human Citrin, or sequence having high sequence identity with those sequence optimized polynucleotides.

In certain aspects, the invention provides polynucleotides (e.g., a RNA, e.g., an mRNA) that comprise a nucleotide sequence (e.g., an ORF) encoding one or more Citrin polypeptides. In some embodiments, the encoded Citrin polypeptide of the invention can be selected from:
  (i) a fill length Citrin polypeptide (e.g., having the same or essentially the same length as wild-type Citrin isoform 1 or 2);
  (ii) a functional fragment of any of the Citrin isoforms described herein (e.g., a truncated (e.g., deletion of carboxy, amino terminal, or internal regions) sequence shorter than one of wild-type isoforms 1 or 2; but still retaining Citrin enzymatic activity);
  (iii) a variant thereof (e.g., full length or truncated isoform 1 or 2 proteins in which one or more amino acids have been replaced, e.g., variants that retain all or most of the Citrin activity of the polypeptide with respect to a reference isoform (such as, e.g., any natural or artificial variants known in the art); or
  (iv) a fusion protein comprising (i) a full length Citrin isoform 1 or 2 protein, a functional fragment or a variant thereof, and (ii) a heterologous protein.

In certain embodiments, the encoded Citrin polypeptide is a mammalian Citrin polypeptide, such as a human Citrin polypeptide, a functional fragment or a variant thereof.

In some embodiments, the polynucleotide (e.g., a RNA, e.g., an mRNA) of the invention increases Citrin protein expression levels and/or detectable Citrin enzymatic activity levels in cells when introduced in those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, compared to Citrin protein expression levels and/or detectable Citrin enzymatic activity levels in the cells prior to the administration of the polynucleotide of the invention. Citrin protein expression levels and/or Citrin enzymatic activity can be measured according to methods know in the art. In some embodiments, the polynucleotide is introduced to the cells in vitro. In some embodiments, the polynucleotide is introduced to the cells in vim.

In some embodiments, the polynucleotides (e.g., a RNA, e.g., an mRNA) of the invention comprise a nucleotide sequence (e.g., an ORF) that encodes a wild-type human Citrin, e.g., wild-type isoform 1 of human Citrin (SEQ ID NO: 1, see FIG. 1), or wild-type isoform 2 of human Citrin (SEQ ID NO: 3, see FIG. 2).

In some embodiments, the polynucleotide (e.g., a RNA, e.g., an mRNA) of the invention comprises a codon optimized nucleic acid sequence, wherein the open reading frame (ORF) of the codon optimized nucleic acid sequence is derived from a wild-type Citrin sequence (e.g., wild-type isoforms 1 or 2). For example, for polynucleotides of invention comprising a sequence optimized ORF encoding Citrin isoform 2, the corresponding wild type sequence is the native Citrin isoform 2. Similarly, for an sequence optimized mRNA encoding a functional fragment of isoform 1, the corresponding wild type sequence is the corresponding fragment from Citrin isoform 1.

In some embodiments, the polynucleotides (e.g., a RNA, e.g., an mRNA) of the invention comprise a nucleotide sequence encoding Citrin isoform 1 having the full length sequence of human Citrin isoform 1 (i.e., including the initiator methionine). In mature human Citrin isoform 1, the initiator methionine can be removed to yield a "mature Citrin" comprising amino acid residues of 2-606 of the translated product. The teachings of the present disclosure directed to the full sequence of human Citrin (amino acids 1-606) are also applicable to the mature form of human Citrin lacking the initiator methionine (amino acids 2-606). Thus, in some embodiments, the polynucleotides (e.g., a RNA, e.g., an mRNA) of the invention comprise a nucleotide sequence encoding Citrin isoform 1 having the mature sequence of human Citrin isoform 1 (i.e., lacking the initiator methionine). In some embodiments, the polynucleotide (e.g., a RNA, e.g., an mRNA) of the invention comprising a nucleotide sequence encoding Citrin isoform 1 having the full length or mature sequence of human Citrin isoform 1 is sequence optimized.

In some embodiments, the polynucleotides (e.g., a RNA, e.g., an mRNA) of the invention comprise a nucleotide sequence (e.g., an ORF) encoding a mutant Citrin polypeptide. In some embodiments, the polynucleotides of the invention comprise an ORF encoding a Citrin polypeptide that comprises at least one point mutation in the Citrin sequence and retains Citrin enzymatic activity. In some embodiments, the mutant Citrin polypeptide has a Citrin activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the Citrin activity of the corresponding wild-type Citrin (i.e., the same Citrin isoform but without the mutation(s)). In some embodiments, the polynucleotide (e.g., a RNA, e.g., an mRNA) of the invention comprising an ORF encoding a mutant Citrin polypeptide is sequence optimized.

In some embodiments, the polynucleotide (e.g., a RNA, e.g., an mRNA) of the invention comprises a nucleotide sequence (e.g., an ORF) that encodes a Citrin polypeptide with mutations that do not alter Citrin enzymatic activity.

Such mutant Citrin polypeptides can be referred to as function-neutral. In some embodiments, the polynucleotide comprises an ORF that encodes a mutant Citrin polypeptide comprising one or more function-neutral point mutations.

In some embodiments, the mutant Citrin polypeptide has higher Citrin enzymatic activity than the corresponding wild-type Citrin. In some embodiments, the mutant Citrin polypeptide has a Citrin activity that is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the activity of the corresponding wild-type Citrin (i.e., the same Citrin isoform but without the mutation(s)).

In some embodiments, the polynucleotides (e.g., a RNA, e.g., an mRNA) of the invention comprise a nucleotide sequence (e.g., an ORF) encoding a functional Citrin fragment, e.g., where one or more fragments correspond to a polypeptide subsequence of a wild type Citrin polypeptide and retain Citrin enzymatic activity. In some embodiments, the Citrin fragment has a Citrin activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the Citrin activity of the corresponding full length Citrin. In some embodiments, the polynucleotides (e.g., a RNA, e.g., an mRNA) of the invention comprising an ORF encoding a functional Citrin fragment is sequence optimized.

In some embodiments, the polynucleotide (e.g., a RNA, e.g., an mRNA) of the invention comprises a nucleotide sequence (e.g., an ORF) encoding a Citrin fragment that has higher Citrin enzymatic activity than the corresponding full length Citrin. Thus, in some embodiments the Citrin fragment has a Citrin activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the Citrin activity of the corresponding full length Citrin.

In some embodiments, the polynucleotide (e.g., a RNA, e.g., an mRNA) of the invention comprises a nucleotide sequence (e.g., an ORF) encoding a Citrin fragment that is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% shorter than wild-type isoform 1 or 2 of Citrin.

In some embodiments, the polynucleotide (e.g., a RNA, e.g., an mRNA) of the invention comprises a nucleotide sequence (e.g., an ORF) encoding a Citrin polypeptide (e.g., the wild-type sequence, functional fragment, or variant thereof), wherein the nucleotide sequence is at least 70%, at least 75%, at least 80%, at least 85%, at least 90%, at least 95%, at least 96%, at least 97%, at least 98%, at least 99%, or 100% identical to the sequence of SEQ ID NO:2 or 4 (see, e.g., panel D in FIGS. 1 and 2, respectively).

In some embodiments, the polynucleotide (e.g., a RNA, e.g., an mRNA) of the invention comprises a nucleotide sequence (e.g., an ORF) encoding a Citrin polypeptide (e.g., the wild-type sequence, functional fragment, or variant thereof), wherein the nucleotide sequence has at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 5-29, 129, 132, 135, and 138. See TABLE 2.

In some embodiments, the polynucleotide (e.g., a RNA, e.g., an mRNA) of the invention comprises a nucleotide sequence (e.g., an ORF) encoding a Citrin polypeptide (e.g., the wild-type sequence, functional fragment, or variant thereof), wherein the nucleotide sequence has 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 5-29, 129, 132, 135, and 138. See TABLE 2.

In some embodiments, the polynucleotide (e.g., a RNA, e.g., an mRNA) of the invention comprises an ORF encoding a Citrin polypeptide (e.g., the wild-type sequence, functional fragment, or variant thereof), wherein the polynucleotide comprises a nucleic acid sequence having 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 130, 133, 136, and 139. See TABLE 5.

In some embodiments, the polynucleotide (e.g., a RNA, e.g., an mRNA) of the invention comprises a nucleotide sequence (e.g., an ORF) encoding a Citrin polypeptide (e.g., the wild-type sequence, functional fragment, or variant thereof), wherein the nucleotide sequence is at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence of SEQ ID NO:2 or 4 (see, e.g, panel D in FIGS. 1 and 2, respectively).

In some embodiments the polynucleotide (e.g., a RNA, e.g., an mRNA) of the invention comprises a nucleotide sequence (e.g., an ORF) encoding a Citrin polypeptide (e.g., the wild-type sequence, functional fragment, or variant thereof), wherein the nucleotide sequence is between 70% and 90% identical; between 71% and 85% identical; between 72% and 84% identical; between 73% and 82% identical, between 73% and 80% identical, between 73% and 78%, or between 73% and 76% identical to the sequence of SEQ ID NO:2 or 4 (see, e.g., panel D in FIGS. 1 and 2, respectively).

In some embodiments, the polynucleotide (e.g., a RNA, e.g., an mRNA) of the invention comprises from about 900 to about 100,000 nucleotides (e.g., from 900 to 1,000, from 900 to 1,100, from 900 to 1,200, from 900 to 1,300, from 900 to 1,400, from 900 to 1,500, from 1,000 to 1,100, from 1,000 to 1,100, from 1,000 to 1,200, from 1,000 to 1,300, from 1,000 to 1,400, from 1,000 to 1,500, from 1,083 to 1,200, from 1,083 to 1,400, from 1,083 to 1,600, from 1,083 to 1,800, from 1,083 to 2,000, from 1,083 to 3,000, from 1,083 to 5,000, from 1,083 to 7,000, from 1,083 to 10,000, from 1,083 to 25,000, from 1,083 to 50,000, from 1,083 to 70,000, or from 1,083 to 100,000).

In some embodiments, the polynucleotide of the invention (e.g., a RNA, e.g., an mRNA) comprises a nucleotide sequence (e.g., an ORF) encoding a Citrin polypeptide (e.g., the wild-type sequence, functional fragment, or variant thereof), wherein the length of the nucleotide sequence (e.g., an ORF) is at least 500 nucleotides in length (e.g., at least or greater than about 500, 600, 700, 80, 900, 1,000, 1,050, 1,083, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the polynucleotide of the invention (e.g., a RNA, e.g., an mRNA) comprises a nucleotide sequence (e.g., an ORF) encoding a Citrin polypeptide (e.g., the wild-type sequence, functional fragment, or variant thereof) further comprises at least one nucleic acid sequence that is noncoding, e.g., a miRNA binding site. In some embodiments, the polynucleotide (e.g., a RNA, e.g., an mRNA) of the invention further comprises a 5'-UTR (e.g., selected from the sequences of SEQ ID NOs: 30-47, 79, 120-122, 126-128) and a 3'UTR (e.g., selected from the sequences of SEQ ID NOs: 48-72, 80, 81, 102-105, 108-117, 124, 125, 147-157). In some embodiments, the polynucleotide (e.g., a RNA, e.g., an mRNA) of the invention comprises a sequence selected from the group consisting of SEQ ID NO: 5-29, 129, 132, 135, and 138. In a further embodiment, the polynucleotide (e.g., a RNA, e.g., an mRNA) comprises a 5' terminal cap (e.g., Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof) and a poly-A-tail region (e.g., about 100 nucleotides in length). In a further embodiment, the polynucleotide (e.g., a RNA, e.g., an mRNA) a comprises a 3' UTR comprising a nucleic acid sequence selected from the group consisting of SEQ ID NOs: 105, 147, 148, or any combination thereof. In a further embodiment, the polynucleotide (e.g., a RNA, e.g., an mRNA) comprises a 3' UTR comprising a nucleic acid sequence of SEQ ID NO: 147. In a further embodiment, the polynucleotide (e.g., a RNA, e.g., an mRNA) comprises a 3' UTR comprising a nucleic acid sequence of SEQ ID NO: 148.

In some embodiments, the polynucleotide of the invention (e.g., a RNA, e.g., an mRNA) comprises a nucleotide sequence (e.g., an ORF) encoding a Citrin polypeptide is single stranded or double stranded.

In some embodiments, the polynucleotide of the invention comprising a nucleotide sequence (e.g., an ORF) encoding a Citrin polypeptide (e.g., the wild-type sequence, functional fragment, or variant thereof) is DNA or RNA. In some embodiments, the polynucleotide of the invention is RNA. In some embodiments, the polynucleotide of the invention is, or functions as, a messenger RNA (mRNA). In some embodiments, the mRNA comprises a nucleotide sequence (e.g., an ORF) that encodes at least one Citrin polypeptide, and is capable of being translated to produce the encoded Citrin polypeptide in vitro, in vivo, in situ or ex vivo.

In some embodiments, the polynucleotide of the invention (e.g., a RNA, e.g., an mRNA) comprises a sequence-optimized nucleotide sequence (e.g., an ORF) encoding a Citrin polypeptide (e.g., the wild-type sequence, functional fragment, or variant thereof), wherein the polynucleotide comprises at least one chemically modified nucleobase, e.g., 5-methoxyuracil. In some embodiments, the polynucleotide further comprises a miRNA binding site, e.g., a miRNA binding site that binds to miR-142 and/or a miRNA binding site that binds to miR-126. In some embodiments, the polynucleotide (e.g., a RNA, e.g., an mRNA) disclosed herein is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

3. Signal Sequences

The polynucleotides (e.g., a RNA, e.g., an mRNA) of the invention can also comprise nucleotide sequences that encode additional features that facilitate trafficking of the encoded polypeptides to therapeutically relevant sites. One such feature that aids in protein trafficking is the signal sequence, or targeting sequence. The peptides encoded by these signal sequences are known by a variety of names, including targeting peptides, transit peptides, and signal peptides. In some embodiments, the polynucleotide (e.g., a RNA, e.g., an mRNA) comprises a nucleotide sequence (e.g., an ORF) that encodes a signal peptide operably linked to a nucleotide sequence that encodes a Citrin polypeptide described herein.

In some embodiments, the "signal sequence" or "signal peptide" is a polynucleotide or polypeptide, respectively, which is from about 9 to 200 nucleotides (3-70 amino acids) in length that, optionally, is incorporated at the 5' (or N-terminus) of the coding region or the polypeptide, respectively. Addition of these sequences results in trafficking the encoded polypeptide to a desired site, such as the endoplasmic reticulum or the mitochondria through one or more targeting pathways. Some signal peptides are cleaved from the protein, for example by a signal peptidase after the proteins are transported to the desired site.

In some embodiments, the polynucleotide of the invention comprises a nucleotide sequence encoding a Citrin polypeptide, wherein the nucleotide sequence further comprises a 5' nucleic acid sequence encoding a heterologous signal peptide.

4. Fusion Proteins

In some embodiments, the polynucleotide of the invention (e.g., a RNA, e.g., an mRNA) can comprise more than one nucleic acid sequence (e.g., an ORF) encoding a polypeptide of interest. In some embodiments, polynucleotides of the invention comprise a single ORF encoding a Citrin polypeptide, a functional fragment, or a variant thereof. However, in some embodiments, the polynucleotide of the invention can comprise more than one ORF, for example, a first ORF encoding a Citrin polypeptide (a first polypeptide of interest), a functional fragment, or a variant thereof, and a second ORF expressing a second polypeptide of interest. In some embodiments, two or more polypeptides of interest can be genetically fused, i.e., two or more polypeptides can be encoded by the same ORF. In some embodiments, the polynucleotide can comprise a nucleic acid sequence encoding a linker (e.g., a $G_4S$ peptide linker or another linker known in the art) between two or more polypeptides of interest.

In some embodiments, a polynucleotide of the invention (e.g., a RNA, e.g., an mRNA) can comprise two, three, four, or more ORFs, each expressing a polypeptide of interest.

In some embodiments, the polynucleotide of the invention (e.g., a RNA, e.g., an mRNA) can comprise a first nucleic acid sequence (e.g., a first ORF) encoding a Citrin polypeptide and a second nucleic acid sequence (e.g., a second ORF) encoding a second polypeptide of interest.

5. Sequence Optimization of Nucleotide Sequence Encoding a Citrin Polypeptide In some embodiments, the polynucleotide (e.g., a RNA, e.g., an mRNA) of the invention is sequence optimized. In some embodiments, the polynucleotide (e.g., a RNA, e.g., an mRNA) of the invention comprises a nucleotide sequence (e.g., an ORF) encoding a Citrin polypeptide, a nucleotide sequence (e.g, an ORF) encoding another polypeptide of interest, a 5'-UTR, a 3'-UTR, a miRNA, a nucleotide sequence encoding a linker, or any combination thereof) that is sequence optimized.

A sequence-optimized nucleotide sequence, e.g., an codon-optimized mRNA sequence encoding a Citrin polypeptide, is a sequence comprising at least one synonymous nucleobase substitution with respect to a reference sequence (e.g., a wild type nucleotide sequence encoding a Citrin polypeptide).

A sequence-optimized nucleotide sequence can be partially or completely different in sequence from the reference sequence. For example, a reference sequence encoding polyserine uniformly encoded by TCT codons can be sequence-optimized by having 100% of its nucleobases substituted (for each codon, Tin position 1 replaced by A, C in position 2 replaced by G, and T in position 3 replaced by C) to yield a sequence encoding polyserine which would be uniformly encoded by AGC codons. The percentage of sequence identity obtained from a global pairwise alignment between the reference polyserine nucleic acid sequence and the sequence-optimized polyserine nucleic acid sequence would be 0%. However, the protein products from both sequences would be 100% identical.

Some sequence optimization (also sometimes referred to codon optimization) methods are known in the art (and discussed in more detail below) and can be useful to achieve one or more desired results. These results can include, e.g., matching codon frequencies in certain tissue targets and/or host organisms to ensure proper folding; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites; adjusting translational rates to allow the various domains of the protein to fold properly; and/or reducing or eliminating problem secondary structures within the polynucleotide. Sequence optimization tools, algorithms and services are known in the art, non-limiting examples include services from GeneArt (Life Technologies), DNA2.0 (Menlo Park CA) and/or proprietary methods.

Codon options for each amino acid are given in TABLE 1.

TABLE 1

Codon Options

| Amino Acid | Single Letter Code | Codon Options |
|---|---|---|
| Isoleucine | I | ATT, ATC, ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Selenocysteine | Sec | UGA in mRNA in presence of Selenocysteine insertion element (SECIS) |
| Stop codons | Stop | TAA, TAG, TGA |

In some embodiments, a polynucleotide (e.g., a RNA, e.g., an mRNA) of the invention comprises a sequence-optimized nucleotide sequence (e.g., an ORF) encoding a Citrin polypeptide, a functional fragment, or a variant thereof, wherein the Citrin polypeptide, functional fragment, or a variant thereof encoded by the sequence-optimized nucleotide sequence has improved properties (e.g., compared to a Citrin polypeptide, functional fragment, or a variant thereof encoded by a reference nucleotide sequence that is not sequence optimized), e.g., improved properties related to expression efficacy after administration in vivo. Such properties include, but are not limited to, improving nucleic acid stability (e.g., mRNA stability), increasing translation efficacy in the target tissue, reducing the number of truncated proteins expressed, improving the folding or prevent misfolding of the expressed proteins, reducing toxicity of the expressed products, reducing cell death caused by the expressed products, increasing and/or decreasing protein aggregation.

In some embodiments, the sequence-optimized nucleotide sequence is codon optimized for expression in human subjects, having structural and/or chemical features that avoid one or more of the problems in the art, for example, features which are useful for optimizing formulation and delivery of nucleic acid-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways.

In some embodiments, the polynucleotides of the invention comprise a nucleotide sequence (e.g., a nucleotide sequence (e.g, an ORF) encoding a Citrin polypeptide, a nucleotide sequence (e.g, an ORF) encoding another polypeptide of interest, a 5'-UTR, a 3'-UTR, a microRNA binding site, a nucleic acid sequence encoding a linker, or any combination thereof) that is sequence-optimized according to a method comprising:
  (i) substituting at least one codon in a reference nucleotide sequence (e.g., an ORF encoding a Citrin polypeptide)

with an alternative codon to increase or decrease uridine content to generate a uridine-modified sequence;
(ii) substituting at least one codon in a reference nucleotide sequence (e.g., an ORF encoding a Citrin polypeptide) with an alternative codon having a higher codon frequency in the synonymous codon set;
(iii) substituting at least one codon in a reference nucleotide sequence (e.g., an ORF encoding a Citrin polypeptide) with an alternative codon to increase G/C content; or
(iv) a combination thereof.

In some embodiments, the sequence-optimized nucleotide sequence (e.g., an ORF encoding a Citrin polypeptide) has at least one improved property with respect to the reference nucleotide sequence.

In some embodiments, the sequence optimization method is multiparametric and comprises one, two, three, four, or more methods disclosed herein and/or other optimization methods known in the art.

Features, which can be considered beneficial in some embodiments of the invention, can be encoded by or within regions of the polynucleotide and such regions can be upstream (5') to, downstream (3') to, or within the region that encodes the Citrin polypeptide. These regions can be incorporated into the polynucleotide before and/or after sequence-optimization of the protein encoding region or open reading frame (ORF). Examples of such features include, but are not limited to, untranslated regions (UTRs), microRNA sequences, Kozak sequences, oligo(dT) sequences, poly-A tail, and detectable tags and can include multiple cloning sites that can have XbaI recognition.

In some embodiments, the polynucleotide of the invention comprises a 5' UTR, a 3' UTR and/or a miRNA binding site. In some embodiments, the polynucleotide comprises two or more 5' UTRs and/or 3' UTRs, which can be the same or different sequences. In some embodiments, the polynucleotide comprises two or more miRNA, which can be the same or different sequences. Any portion of the 5' UTR, 3' UTR, and/or miRNA binding site, including none, can be sequence-optimized and can independently contain one or more different structural or chemical modifications, before and/or after sequence optimization.

In some embodiments, after optimization, the polynucleotide is reconstituted and transformed into a vector such as, but not limited to, plasmids, viruses, cosmids, and artificial chromosomes. For example, the optimized polynucleotide can be reconstituted and transformed into chemically competent *E. coli*, yeast, *neurospora*, maize, *drosophila*, etc. where high copy plasmid-like or chromosome structures occur by methods described herein.

6. Sequence-Optimized Nucleotide Sequences Encoding Citrin Polypeptides

In some embodiments, the polynucleotide of the invention comprises a sequence-optimized nucleotide sequence encoding a Citrin polypeptide disclosed herein. In some embodiments, the polynucleotide of the invention comprises an open reading frame (ORF) encoding a Citrin polypeptide, wherein the ORF has been sequence optimized.

Exemplary sequence-optimized nucleotide sequences encoding human Citrin isoform 1 are set forth as SEQ ID Nos: 5-29 (Citrin-CO01, Citrin-CO02, Citrin-CO03, Citrin-CO04, Citrin-CO05, Citrin-CO06, Citrin-CO07, Citrin-CO08, Citrin-CO09, Citrin-CO10, Citrin-CO11, Citrin-CO12, Citrin-CO13, Citrin-CO14, Citrin-CO15, Citrin-CO16, Citrin-CO17, Citrin-CO18, Citrin-CO19, Citrin-CO20, Citrin-CO21, Citrin-CO22, Citrin-CO23, Citrin-CO24, and Citrin-CO25, respectively. Further exemplary sequence optimized nucleotide sequences encoding human Citrin isoform 1 are shown in TABLE 2. In some embodiments, the sequence optimized Citrin sequences set forth as SEQ ID Nos: 5-29 or shown in TABLE 2, fragments, and variants thereof are used to practice the methods disclosed herein. In some embodiments, the sequence optimized Citrin sequences set forth as SEQ ID Nos: 5-29 or shown in TABLE 2, fragments and variants thereof are combined with or alternatives to the wild-type sequences disclosed in FIGS. 1-2.

Exemplary sequence optimized nucleotide sequence encoding human Citrin isoform 1 are set forth as SEQ ID Nos: 129 (Construct #1 ORF), 132 (Construct #2 ORF), 135 (Construct #3 ORF), and 138 (Construct #4 ORF). Further exemplary sequence optimized nucleotide sequences encoding human Citrin isoform 1 are shown in TABLE 2. In some embodiments, the sequence optimized Citrin sequences set forth as SEQ ID Nos: 129, 132, 135, and 138, or shown in TABLE 2, fragments, and variants thereof are used to practice the methods disclosed herein. In some embodiments, the sequence optimized Citrin sequences set forth as SEQ ID Nos: 129, 132, 135, and 138, or shown in TABLE 2, fragments and variants thereof are combined with or alternatives to the wild-type sequences disclosed in FIGS. 1-2.

In some embodiments, a polynucleotide of the present disclosure, for example a polynucleotide comprising an mRNA nucleotide sequence encoding a Citrin polypeptide, comprises from 5' to 3' end:
(i) a 5' cap provided herein, for example, CAP 1;
(ii) a 5' UTR, such as the sequences provided herein, for example, SEQ ID NO: 30;
(iii) an open reading frame encoding a Citrin polypeptide, e.g., a sequence optimized nucleic acid sequence encoding Citrin set forth as SEQ ID Nos: 5 to 29, 129, 132, 135, and 138, or shown in TABLE 2;
(iv) at least one stop codon;
(v) a 3' UTR, such as the sequences provided herein, for example, SEQ ID NO: 105, 147 and 148; and
(vi) a poly-A tail provided above.

TABLE 2

| | | |
|---|---|---|
| Sequence optimized sequences for human Citrin, isoform 1 ||| 
| SEQ ID NO | Name | Sequence |
| 5 | Citrin-CO01 | See Sequence Listing |
| 6 | Citrin-CO02 | See Sequence Listing |

TABLE 2-continued

Sequence optimized sequences for human Citrin, isoform 1

| SEQ ID NO | Name | Sequence |
|---|---|---|
| 7 | Citrin-CO03 | See Sequence Listing |
| 8 | Citrin-CO04 | See Sequence Listing |
| 9 | Citrin-CO05 | See Sequence Listing |
| 10 | Citrin-CO06 | See Sequence Listing |
| 11 | Citrin-CO07 | See Sequence Listing |
| 12 | Citrin-CO08 | See Sequence Listing |
| 13 | Citrin-CO09 | See Sequence Listing |
| 14 | Citrin-CO10 | See Sequence Listing |
| 15 | Citrin-CO11 | See Sequence Listing |
| 16 | Citrin-CO12 | See Sequence Listing |
| 17 | Citrin-CO13 | See Sequence Listing |
| 18 | Citrin-CO14 | See Sequence Listing |
| 19 | Citrin-CO15 | See Sequence Listing |
| 20 | Citrin-CO16 | See Sequence Listing |
| 21 | Citrin-CO17 | See Sequence Listing |
| 22 | Citrin-CO18 | See Sequence Listing |
| 23 | Citrin-CO19 | See Sequence Listing |
| 24 | Citrin-CO20 | See Sequence Listing |
| 25 | Citrin-CO21 | See Sequence Listing |
| 26 | Citrin-CO22 | See Sequence Listing |
| 27 | Citrin-CO23 | See Sequence Listing |
| 28 | Citrin-CO24 | See Sequence Listing |
| 29 | Citrin-CO25 | See Sequence Listing |
| 129 | Construct 1 ORF | AUGGCCGCCGCCAAGGUCGCCCUCACCAAGAGGGCGGACCCCGCGGAGCUCAGGACCAUCUUUCUCAAGU ACGCCUCCAUCGAGAAGAACGGGGAGUUCUUCAUGAGCCCGAACGAUUUCGUCACCAGGUACCUCAACAU CUUCGGCGAGAGCCAGCCCAACCCGAAGACCGUAGAGCUCCUCAGCGGCGUCGUCGACCAGACGAAGGAC GGACUCAUUAGCUUCCAGGAGUUCGUCGCCCUUCGAGAGCGUCCUCUGCGCGCCCCGACGCCCUCUUCAUGG |

TABLE 2-continued

Sequence optimized sequences for human Citrin, isoform 1

| SEQ ID NO | Name | Sequence |
|---|---|---|
| | | UCGCGUUCCAGCUGUUCGAUAAGGCCGGCAAGGGCGAGGUGACCUUUGAAGAUGUGAAGCAGGUGUUCGG
UCAGACCACCAUCCACCAGCACAUCCCUUUUAACUGGGACUCAGAAUUCGUCCAGCUGCACUUCGGCAAG
GAAAGGAAGCGCCAUCUGACCUACGCCGAGUUCACACAGUUUCUCCUGGAGAUCCAGCUGGAACACGCCA
AACAGGCGUUCGUUCAGCGGGACAACGCCAGGACCGGCCGGGUCACCGCGAUCGACUUCCGUGAUAUCAU
GGUGACCAUCAGGCCUCACGUCCUGACGCCCUUCGUGGAAGAGUGCCUGGUGGCCGCCGCGGGUGGGACC
ACGUCCACCAGGUGAGCUUCUCCUAUUUUAACGGGUUCAACAGCCUCCUCAACAACAUGGAGCUGAUCC
GGAAGAUCUAUAGCACCCUGGCCGGGACGCGCAAGGACGUCGAGGUGACCAAGGAAGAAUUCGUGCUGGC
CGCCCAGAAGUUUGGCCAGGUGACGCCCAUGGAGGUGGACAUCCUGUUCCAACUGGCGGACCUGUACGAA
CCCAGGGGCCGGAUGACCCUGGCCGACAUCGAGCGCAUUGCCCCGCUCGAGGAGGGCACCCUGCCCUUCA
ACCUGGCGGAGGCCCAGCGCCAGAAGGCCAGCGGGGACAGCGCCAGGCCCGUCCUGCUGCAGGUGGCCGA
GUCCGCGUACAGGUUCGGUCUGGGGAGCGUCGCGGGAGCCGUGGGUGCCACCGCCGUGUAUCCGAUCGAC
CUCGUGAAGACCCGUAUGCAGAAUCAGAGGUCCACCGGCAGCUUCGUGGGCGAGCUCAUGUACAAGAACU
CCUUCGACUGUUUCAAGAAGGUUCUCCGGUACGAGGGGUUCUUCGGCCUCUACCGGGGACUGCUACCCCA
GCUGCUCGGCGUGGCGCCCGAGAAGGCCAUCAAGCUCACGGUCAACGACUUUGUGCGGGACAAGUUCAUG
CACAAGGACGGCAGCGUCCCACUGGCCGCCGAGAUUCUGGCAGGCGGCUGCGCCGGAGGCAGCCAGGUCA
UCUUUUACCAACCCACUGGAGAUCGUGAAGAUCAGGCUGCAAGUGGCCGGGGAGAUUACCACCGGACCCCG
UGUGAGCGCCCUGAGCGUGGUGAGGGACCUUGGCUUCUUUGGCAUAUACAAGGGAGCCAAGGCCUGCUUU
CUGAGGGACAUCCCGUUUUCCGCAUAUACUUUCCCUGCUACGCCCACGUGAAAGCGAGCUUCGCCAACG
AGGACGGCCAGGUCAGUCCCGGCUCCCUACUGCUGGCCGGAGCCAUCGCGGGAUGCCGCCGCCAGCCU
GGUGACGCCCGGACGUUAUCAAGACCAGGCUGCAGGUGGCGGCCAGGGCGGGCCAGACCACCUACAGC
GGCGUGAUCGACUGCUUCCGCAAGAUCCUGCGGGAGGAGGGCCCAAGGCCCUGUGGAAAGGCGCCGGGG
CAAGGGUGUUCAGGAGCAGCCCACAGUUCGGGGUGACCCUGCUUACCUACGAACUGCUGCAGCGGUGGUU
CUAUAUCGACUUCGGGGAGGAGUCAAGCCCAUGGGAGUCCGAGCCUGUGCCAAGAGCAGGAUCAAUCUGCCC
GCGCCCAACCCAGACCACGUGGGAGGGUACAAACUGGCCGUGGCCACCUUCGCCGGAAUCGAGAACAAGU
UCGGCCUGUAUCUGCCCCUGUUCAAACCGUCCGUCUCCACCAGCAAGGCCAUCGGCGGAGGCCCC |
| 132 | Construct 2 ORF | AUGGCCGCCGCCAAGGUCGCCCUCACCAAGAGGGCGGACCCCGCGGAGCUCAGGACCAUCUUUCUCAAGU
ACGCCUCCAUCGAGAAGAACGGGGAGUUCUUCAUGAGCCCGAACGAUUUCGUCACCAGGUACCUCAACAU
CUUCGGCGAGAGCCAGCCCAACCCGAAGACCGUAGAGCUCCUCAGCGGCGUCGUCGACCAGACGAAGGAC
GGACUCAUUAGCUUCCAGGAGUUCGUCGCCUUCGAGAGCGUCCUCUGCGCCCCCGACGCCCUCUUCAUGG
UCGCGUUCCAGCUGUUCGAUAAGGCCGGCAAGGGCGAGGUGACCUUUGAAGAUGUGAAGCAGGUGUUCGG
UCAGACCACCAUCCACCAGCACAUCCCUUUUAACUGGGACUCAGAAUUCGUCCAGCUGCACUUCGGCAAG
GAAAGGAAGCGCCAUCUGACCUACGCCGAGUUCACACAGUUUCUCCUGGAGAUCCAGCUGGAACACGCCA
AACAGGCGUUCGUUCAGCGGGACAACGCCAGGACCGGCCGGGUCACCGCGAUCGACUUCCGUGAUAUCAU
GGUGACCAUCAGGCCUCACGUCCUGACCCCCUUCGUGGAAGAGUGCCUGGUGGCCGCCGCGGGUGGGACC
ACGUCCACCAGGUGAGCUUCUCCUAUUUUAACGGGUUCAACAGCCUCCUCAACAACAUGGAGCUGAUCC
GGAAGAUCUAUAGCACCCUGGCCGGGACGCGCAAGGACGUCGAGGUGACCAAGGAAGAAUUCGUGCUGGC
CGCCCAGAAGUUUGGCCAGGUGACCCCCAUGGAGGUGGACAUCCUGUUCCAACUGGCGGACCUGUACGAA
CCCAGGGGCCGGAUGACCCUGGCCGACAUCGAGCGCAUUGCCCCGCUCGAGGAGGGCACCCUGCCCUUCA
ACCUGGCGGAGGCCCAGCGCCAGAAGGCCAGCGGGGACAGCGCCAGGCCCGUCCUGCUGCAGGUGGCCGA
GUCCGCGUACAGGUUCGGUCUGGGGAGCGUCGCGGGAGCCGUGGGUGCCACCGCCGUGUAUCCGAUCGAC
CUCGUGAAGACCCGUAUGCAGAAUCAGAGGUCCACCGGCAGCUUCGUGGGCGAGCUCAUGUACAAGAACU
CCUUCGACUGUUUCAAGAAGGUUCUCCGGUACGAGGGGUUCUUCGGCCUCUACCGGGGGCUGCUACCCCA
GCUGCUCGGCGUGGCGCCCGAGAAGGCCAUCAAGCUCACGGUCAACGACUUUGUGCGGGACAAGUUCAUG
CACAAGGACGGCAGCGUCCCCCUGGCCGCCGAGAUUCUGGCAGGCGGCUGCGCCGGAGGCAGCCAGGUCA
UCUUUUACCAACCCCCUGGAGAUCGUGAAGAUCAGGCUGCAAGUGGCCGGGGAGAUUACCACCGGACCCCG
UGUGAGCGCCCUGAGCGUGGUGAGGGACCUUGGCUUCUUUGGCAUAUACAAGGGAGCCAAGGCCUGCUUU
CUGAGGGACAUCCCGUUUUCCGCAUAUACUUUCCCUGCUACGCCCACGUGAAAGCGAGCUUCGCCAACG
AGGACGCCCAGGUCAGUCCCGGCUCCCUACUGCUGGCCGGAGCCAUCGCGGGAUGCCGCCGCCAGCCU
GGUGACCCCGCGGACGUUAUCAAGACCAGGCUGCAGGUGGCGGCCAGGGCGGGCCAGACCACCUACAGC
GGCGUGAUCGACUGCUUCCGCAAGAUCCUGCGGGAGGAGGGCCCAAGGCCCUGUGGAAAGGCGCCGGGG
CAAGGGUGUUCAGGAGCAGCCCCCAGUUCGGGGUGACCCUGCUUACCUACGAACUGCUGCAGCGGUGGUU
CUAUAUCGACUUCGGGGAGUCAAGCCCAUGGGCUCCGAGCCUGUGCCAAGAGCAGGAUCAAUCUGCCC
GCCCCCAACCCAGACCACGUGGGAGGGUACAAACUGGCCGUGGCCACCUUCGCCGGAAUCGAGAACAAGU
UCGGCCUGUAUCUGCCCCUGUUCAAACCGUCCGUCUCCACCAGCAAGGCCAUCGGCGGGGGCCCC |
| 135 | Construct 3 ORF | AUGGCCGCCGCCAAGGUCGCACUCACCAAACGGGCCGACCCCGCCGAGCUCAGGACCAUCUUCCUCAAGU
ACGCCAGCAUCGAGAAGAACGGGGAGUUCUUCAUGAGCCCCAACGACUUCGUAACCAGGUACCUCAAUAU
CUUCGGCGAAAGCCAGCCCAACCCGAAGACCGUCGAGCUCCUCUCCGGGGUCGUCGAUCAGACCAAGGAC
GGGCUCAUCUCCUUCCAGGAGUUCGUGGCCUUCGAGUCCGUCCUCUGCGCCCCGGACGCCCUCUUCAUGG
UCGCUUCCAACUCUUCGAUAAGGCCGGGAAAGGCGAGGUGACCUUCGAAGAUGUGAAGCAGGUGUUCGG
CCAGACCACGAUCCACCAGCAUAUCCCCUUUAACUGGGACAGCGAGUUCGUGCAGCUGCACUUCGGCAAA
GAGAGGAAGAGGCACCUCACCUAUGCCGAAUUCACACAAUUCCUGCUCGAGAUUCAGCUGGAGCAUGCCA
AACAAGCCUUUGUCCAGCGGGACAACGCCAGGACCGGCAGGGUCACCGCGAUCGACUUUCGCGAUAUCAU
GGUGACCAUCAGGCCCCACGUGCUCACCCCCUUUGUGGAGGAGUGCCUGGUGCCCGCCGCCGGUGGGACG
ACCAGCACCAGGUGUCCUUCUCAUACUUCAACGGGUUCAACAGCCUGCUGAACAACAUGGAGCUGAUCC
GCAAGAUCUACUCCACCCUGGCCGGCACCAGGAAGGACGUGGAAGUGACCAAGGAGGAGUUCGUUCUCGC
CGCCCAGAAAUUCGGACAGGUGACCCCGAUGGAGGUGGACAUCCUCUUCCAGCUGGCCGAUCUCUACGAG
CCCCGGGGCCGGAUGACCCUCGCCGACAUCGAGCGCCCCCCUUGGAGGGGCACCCUCCCUUCA
ACCUGGCCGAGGCCCAGCGACAGAAAGCCAGCGGCGACAGUGCCAGGCCGGUCCUGCUGCAGGUGGCCGA
AUCCGCCUACAGAUUUGCCUGGGCAGCGUCGCCGGCGCAGUGGGCGCCACCGCCGUGUACCCGAUCGAC
CUGGUCAAGACCAGGAUGCAGAACCAGAGAAGCACCGGCUCCUUUGUGGGCGAGCUUAUGUACAAGAACA
GCUUCGACUGCUUCAAGAAGGUCCUGCGUUACGAGGGCUUCUUCGGGCUGUACCGGGGCCUGCUGCCGCA
GCUGCUAGGCGUCGCGCCCGAGAAGGCCAUUAAGCUGACCGUGAACGACUUCGUACGGGACAAAUUCAUG |

TABLE 2-continued

Sequence optimized sequences for human Citrin, isoform 1

| SEQ ID NO | Name | Sequence |
|---|---|---|
| | | CACAAGGACGGCAGUGUGCCCCUGGCCGCAGAGAUCCUGGCCGGGGGCUGUGCCGGCGGGUCCCAGGUGA<br>UCUUUACGAACCCCCUGGAGAUAGUGAAGAUCCGGCUGCAGGUGGCCGGGGAGAUCACCACCGGCCCCCG<br>GGUGUCCGCCCUGAGCGUCGUGAGGGAUCUGGGGUUCUUUGGCAUCUAUAAGGGUGCCAAGGCCUGCUUC<br>CUGCGUGACAUUCCCUUUAGCGCCAUCUACUUCCCCUGCUACGCCCAUGUCAAGGCCAGCUUCGCCAACG<br>AAGACGGACAGGUGAGCCCCGGGUCCCUGCUGCUGGCCGGCGCCAUCGCAGGGAUGCCGGCCGCCUCACU<br>GGUGACCCCGGCGGACGUGAUAAAGACGAGGCUGCAGGUGGCCGCCCGCGCAGGCCAGACCACGUACUCG<br>GGUGUGAUAGACUGCUUCCGGAAGAUCCUGAGGGAAGAAGGCCCCAAGGCCCUGUGGAAGGGGGCCGGCG<br>CCAGGGUGUUCCGCAGCAGCCCCCAGUUCGGGGUCACCCUGCUCACGUACGAGCUCCUGCAGAGGUGGUU<br>CUACAUCGACUUUGGCGGGGUCAAGCCCAUGGGCAGUGAGCCGGUGCCCAAGAGCCGGAUCAAUCUGCCC<br>GCCCCCAACCCUGACCACGUCGGCGGGUACAAACUGGCGGUGGCCACCUUCGCCGGCAUCGAGAACAAGU<br>UUGGCCUGUACCUGCCGCUGUUUAAGCCGUCCGUGAGCACCUCCAAGGCCAUCGGGGCGGCCCA |
| 138 | Construct 4 ORF | AUGGCCGCCGCUAAGGUCGCCCUCACGAAGCGGGCCGAUCCCGCCGAGCUCCGGACCAUCUUUCUCAAAU<br>ACGCCAGCAUCGAGAAGAACGGCGAGUUCUUCAUGUCCCCCAACGACUUCGUCACCAGGUACCUAAACAU<br>CUUCGGCGAGAGCCAGCCGAACCCCAAGACCGUCGAAUUGCUAUCGGGCGUCGUCGACCAGACCAAGGAC<br>GGGCUCAUCAGCUUCCAGGAGUUCGUCGCCUUCGAGUCCGUCCUCUGCGCCCCCGACGCCCUCUUCAUGG<br>UAGCAUUCCAGUUGUUCGACAAGGCCGGAAAGGGGGAGGUGACCUUCGAGGACGUGAAGCAGGUGUUGG<br>UCAGACCACCAUCCAUCAGCACAUCCCGUUUAACUGGGACUCGGAGUUCGUGCAGCUCCACUUCGGCAAG<br>GAACGAAAGCGGCACCUCACCUACGCCGAGUUCACCCAGUUCCUGCUGGAGAUCCAGCUGGAACACGCCA<br>AGCAGGCCUUCGUGCAGCGAGACAAUGCGAGGACCGGGCGCGUGACUGCCAUCGAUUUCAGGGACAUCAU<br>GGUGACCAUCCGGCCCCACGUGCUGACUCCCUUCGUGGAGGAGUGCCUGGUCGCAGCCGCCGGGGGUACC<br>ACCUCCCACCAGGUGAGCUUCAGCUACUUCAACGGCUUCAACAGCCUGCUCAACAACAUGGAACUGAUCC<br>GCAAGAUCUAUUCCACACUCGCCGGCACCAGGAAGGAUGUGGAGGUGACCAAGGAGGAGUUUGGUCUGGC<br>GGCCCAGAAGUUUGGGCAGGUCACCCCCAUGGAGGUGGACAUCCUCUUCCAGCUGGCCGACCUGUACGAG<br>CCCAGGGGCAGGAUGACCCUGGCCGACAUCGAACGAAUCGCCCCCCUGGAGGAGGGCACACUGCCCUUCA<br>ACCUGGCCGAGGCCCAGAGGCAGAAGGCCUCCGGCGACAGCGCCCGACCCGUGCUUCUGCAAGUGGCCGA<br>GAGCGCCUACCGCUUUGGCCUGGGAUCCGUGGCCGGCGCCGUCGGUGCCACCGCCGUGACCCAAUCGAC<br>CUAGUGAAGACACGCAUGCAGAACCAGCGCAGCACCGGCUCCUUUGUCGGGGAGCUGAUGUAUAAGAACA<br>GCUUCGACUGCUUCAAGAAGGUGCUGCGCUACGAGGGCUUCUUCGGCCUGUACAGGGGGCUGCUGCCCCA<br>ACUGCUGGGCGUGGCCCCCGAGAAGGCCAUCAAGCUGACCGUUAACGACUUCGUGCGAGACAAGUUCAUG<br>CACAAGGACGGCAGCGUGCCCUUGGCCGCAGAGAUACUGGCCGGGGGCUGCGCCGGCGGGUCGCAGGUGA<br>UCUUCACCAACCCCCUCGAGAUCGUAAAGAUCAGGCUCCAAGUGGCCGGGGAGAUCACCACCGGCCCCAG<br>GGUGUCCGCCCUGUCGGUGGUCAGGGACCUGGGGUUCUUCGGGAUAUACAAGGGCGCGAAGGCCUGCUUC<br>CUGAGGGACAUCCCCUUCAGCGCCAUCUACUUUCCCUGCUACGCCCACGUCAAGGCCAGCUUCGCCAACG<br>AGGAUGGCCAGGUGUCCCCGGGCUCCCUGCUCCUGGCCGGUGCUAUCGCGGGAAUGCCCGCCGCGAGCCU<br>GGUGACCCCGCCGAUGUGAUCAAGACCAGGCUGCAAGUCGCGGCGAGGGCCGGCAGACCACCUACUCC<br>GGGGUCAUCGAUUGCUUUAGGAAGAUCCUCCGGGAGGAGGGCCCAAGGCACUGUGGAAGGGGGCCGGGG<br>CCAGGGUGUUCCGUAGCUCCCCCAGUUUGGCGUGACCCUGCUGACCUACGAACUGCUGCAGAGGUGGUU<br>CUACAUCGACUUCGGGGCGUGAAGCCCAUGGGCUCCGAGCCGGUGCCUAAGAGCCGGAUCAAUCUGCCC<br>GCCCCCAACCCCGACCACGUGGGGGGCUACAAGCUGGCCGUGGCUACCUUCGCCGGUAUCGAGAACAAGU<br>UCGGCCUGUACCUGCCCCUGUUCAAGCCCUCCGUGAGCACGAGCAAGGCCAUCGGGGCGGCCCC |

The sequence-optimized nucleotide sequences disclosed herein are distinct from the corresponding wild type nucleotide acid sequences and from other known sequence-optimized nucleotide sequences, e.g., these sequence-optimized nucleic acids have unique compositional characteristics.

In some embodiments, the percentage of uracil or thymine nucleobases in a sequence-optimized nucleotide sequence (e.g., encoding a Citrin polypeptide, a functional fragment, or a variant thereof) is modified (e.g, reduced) with respect to the percentage of uracil or thymine nucleobases in the reference wild-type nucleotide sequence. Such a sequence is referred to as a uracil-modified or thymine-modified sequence. The percentage of uracil or thymine content in a nucleotide sequence can be determined by dividing the number of uracils or thymines in a sequence by the total number of nucleotides and multiplying by 100. In some embodiments, the sequence-optimized nucleotide sequence has a lower uracil or thymine content than the uracil or thymine content in the reference wild-type sequence. In some embodiments, the uracil or thymine content in a sequence-optimized nucleotide sequence of the invention is greater than the uracil or thymine content in the reference wild-type sequence and still maintain beneficial effects, e.g., increased expression and/or reduced Toll-Like Receptor (TLR) response when compared to the reference wild-type sequence.

The uracil or thymine content of wild-type Citrin isoform 1 is about 28%. In some embodiments, the uracil or thymine content of a uracil- or thymine-modified sequence encoding a Citrin polypeptide is less than 28%. In some embodiments, the uracil or thymine content of a uracil- or thymine-modified sequence encoding a Citrin polypeptide of the invention is less than 27%, less than 26%, less than 25%, less than 24%, less than 23%, less than 22%, less than 21%, less than 20%, less than 19%, less that 18%, less than 17%, less than 16%, less than 15%, less than 14%, less than 13%, less than 12%, less than 11%, or less than 10%. In some embodiments, the uracil or thymine content is not less than 18%, 17%, 16%, 15%, 14%, 13%, 12%, 11%, or 10%. The uracil or thymine content of a sequence disclosed herein, i.er., its total uracil or thymine content is abbreviated herein as % $U_{TL}$ or % $T_{TL}$.

In some embodiments, the uracil or thymine content (% $U_{TL}$ or % $T_{TL}$) of a uracil- or thymine-modified sequence encoding a Citrin polypeptide of the invention is between 15% and 20%, between 16% and 20%, between 16% and 19%, between 17% and 19%, or between 17% and 18%.

In some embodiments, the uracil or thymine content (% $U_{TL}$ or % $T_{TL}$) of a uracil- or thymine-modified sequence encoding a Citrin polypeptide of the invention is between 15% and 20%, between 15% and 19%, between 16% and 19%, or between 15% and 18%.

In a particular embodiment, the uracil or thymine content (% $U_{TL}$ or % $T_{TL}$) of a uracil- or thymine modified sequence encoding a Citrin polypeptide of the invention is between about 16% and about 18%.

A uracil- or thymine-modified sequence encoding a Citrin polypeptide of the invention can also be described according to its uracil or thymine content relative to the uracil or thymine content in the corresponding wild-type nucleic acid sequence (% $U_{WT}$ or % $T_{WT}$), or according to its uracil or thymine content relative to the theoretical minimum uracil or thymine content of a nucleic acid encoding the wild-type protein sequence (% $U_{TM}$ or (% $T_{TM}$).

The phrases "uracil or thymine content relative to the uracil or thymine content in the wild type nucleic acid sequence," refers to a parameter determined by dividing the number of uracils or thymines in a sequence-optimized nucleic acid by the total number of uracils or thymines in the corresponding wild-type nucleic acid sequence and multiplying by 100. This parameter is abbreviated herein as % $U_{WT}$ or % $T_{WT}$.

In some embodiments, the % $U_{WT}$ or % $T_{WT}$ of a uracil- or thymine-modified sequence encoding a Citrin polypeptide of the invention is above 50%, above 55%, above 60%, above 65%, above 70%, above 75%, above 80%, above 85%, above 90%, or above 95%.

In some embodiments, the % $U_{WT}$ or % $T_{WT}$ of a uracil- or thymine modified sequence encoding a Citrin polypeptide of the invention is between 50% and 85%, between 51% and 84%, between 52% and 83%, between 53% and 82%, between 54% and 81%, between 55% and 80%, between 56% and 79%, between 57% and 78%, between 58% and 77%, between 59% and 76%, between 60% and 75%, or between 60% and 74%.

In some embodiments, the % $U_{WT}$ or % $T_{WT}$ of a uracil- or thymine-modified sequence encoding a Citrin polypeptide of the invention is between 58% and 67%, between 59% and 66%, between 59% and 65%, or between 60% and 65%.

In a particular embodiment, the % $U_{WT}$ or % $T_{WT}$ of a uracil- or thymine-modified sequence encoding a Citrin polypeptide of the invention is between about 60% and about 65%.

Uracil- or thymine-content relative to the uracil or thymine theoretical minimum, refers to a parameter determined by dividing the number of uracils or thymines in a sequence-optimized nucleotide sequence by the total number of uracils or thymines in a hypothetical nucleotide sequence in which all the codons in the hypothetical sequence are replaced with synonymous codons having the lowest possible uracil or thymine content and multiplying by 100. This parameter is abbreviated herein as % $U_{TM}$ or % $T_{TM}$.

For DNA it is recognized that thymine is present instead of uracil, and one would substitute T where U appears. Thus, all the disclosures related to, e.g., % $U_{TM}$, % $U_{WT}$, or %$U_{TL}$, with respect to RNA are equally applicable to % $T_{TM}$, % $T_{WT}$, or %$T_{TL}$ with respect to DNA.

In some embodiments, the % $U_{TM}$ of a uracil-modified sequence encoding a Citrin polypeptide of the invention is below 300%, below 295%, below 290%, below 285%, below 280%, below 275%, below 270%, below 265%, below 260%, below 255%, below 250%, below 245%, below 240%, below 235%, below 230%, below 225%, below 220%, below 215%, below 200%, below 195%, below 190%, below 185%, below 180%, below 175%, below 170%, below 165%, below 160%, below 155%, below 150%, below 145%, below 140%, below 139%, below 138%, below 137%, below 136%, below 135%, below 134%, below 133%, below 132%, below 131%, below 130%, below 129%, below 128%, below 127%, below 126%, below 125%, below 124%, below 123%, below 122%, below 121%, below 120%, below 119%, below 118%, below 117%, below 116%, or below 115%.

In some embodiments, the % $U_{TM}$ of a uracil-modified sequence encoding a Citrin polypeptide of the invention is above 100%, above 101%, above 102%, above 103%, above 104%, above 105%, above 106%, above 107%, above 108%, above 109%, above 110%, above 111%, above 112%, above 113%, above 114%, above 115%, above 116%, above 117%, above 118%, above 119%, above 120%, above 121%, above 122%, above 123%, above 124%, above 125%, or above 126%.

In some embodiments, the % $U_{TM}$ of a uracil-modified sequence encoding a Citrin polypeptide of the invention is between 118% and 122%, between 117% and 123%, between 116% and 124%, between 115% and 125%, between 114% and 126%, between 113% and 127%, between 112% and 128%, between 111% and 129%, between 110% and 130%, between 109% and 131%, between 108% and 132%, between 107% and 133%, or between 106% and 134%.

In some embodiments, the % $U_{TM}$ of a uracil-modified sequence encoding a Citrin polypeptide of the invention is between about 117% and about 127%.

In some embodiments, a uracil-modified sequence encoding a Citrin polypeptide of the invention has a reduced number of consecutive uracils with respect to the corresponding wild-type nucleic acid sequence. For example, two consecutive leucines can be encoded by the sequence CUUUUG, which includes a four uracil cluster. Such a subsequence can be substituted, e.g., with CUGCUC, which removes the uracil cluster.

Phenylalanine can be encoded by UUC or UUU. Thus, even if phenylalanines encoded by UUU are replaced by UUC, the synonymous codon still contains a uracil pair (UU). Accordingly, the number of phenylalanines in a sequence establishes a minimum number of uracil pairs (UU) that cannot be eliminated without altering the number of phenylalanines in the encoded polypeptide. For example, if the polypeptide, e.g., wild type Citrin isoform 1, has, e.g., 49, 50, 51, 52, or 53 phenylalanines, the absolute minimum number of uracil pairs (UU) that a uracil-modified sequence encoding the polypeptide, e.g., wild type Citrin isoform 1, can contain is 49, 50, 51, 52, or 53, respectively.

Wild type Citrin isoform 1 contains 61 uracil pairs (UU), and 37 uracil triplets (UUU). In some embodiments, a uracil-modified sequence encoding a Citrin polypeptide of the invention has a reduced number of uracil triplets (UUU) with respect to the wild-type nucleic acid sequence. In some embodiments, a uracil-modified sequence encoding a Citrin polypeptide of the invention contains 15, 14, 13, 12, 11, 10, 9, 8, 7, 6, 5, 4, 3, 2, 1 or no uracil triplets (UUU).

In some embodiments, a uracil-modified sequence encoding a Citrin polypeptide has a reduced number of uracil pairs (UU) with respect to the number of uracil pairs (UU) in the wild-type nucleic acid sequence. In some embodiments, a uracil-modified sequence encoding a Citrin polypeptide of the invention has a number of uracil pairs (UU) corresponding to the minimum possible number of uracil pairs (UU) in the wild-type nucleic acid sequence, e.g., 9 uracil pairs in the case of wild type Citrin isoform 1.

In some embodiments, a uracil-modified sequence encoding a Citrin polypeptide of the invention has at least 1, 2, 3, 4, 5, 6, 7, 8, 9, 10, 11, 12, 13, 14, 15, 16, 17, 18, 19, 20, 21, 22, 23, 24, 25, 30, 35, 40 or 45 uracil pairs (UU) less than the number of uracil pairs (UU) in the wild-type nucleic acid sequence. In some embodiments, a uracil-modified sequence encoding a Citrin polypeptide of the invention has between 30 and 55 uracil pairs (UU), e.g., 34 and 52.

The phrase "uracil pairs (UU) relative to the uracil pairs (UU) in the wild type nucleic acid sequence," refers to a parameter determined by dividing the number of uracil pairs (UU) in a sequence-optimized nucleotide sequence by the total number of uracil pairs (UU) in the corresponding wild-type nucleotide sequence and multiplying by 100. This parameter is abbreviated herein as % $UU_{wt}$.

In some embodiments, a uracil-modified sequence encoding a Citrin polypeptide of the invention has a % $UU_{wt}$ less than 90%, less than 85%, less than 80%, less than 75%, less than 70%, less than 65%, less than 60%, less than 65%, less than 60%, less than 55%, less than 50%, less than 40%, less than 30%, or less than 20%.

In some embodiments, a uracil-modified sequence encoding a Citrin polypeptide has a % $UU_{wt}$ between 50% and 90%. In a particular embodiment, a uracil-modified sequence encoding a Citrin polypeptide of the invention has a % $UU_{wt}$ between 55% and 86%.

In some embodiments, the polynucleotide of the invention comprises a uracil-modified sequence encoding a Citrin polypeptide disclosed herein. In some embodiments, the uracil-modified sequence encoding a Citrin polypeptide comprises at least one chemically modified nucleobase, e.g., 5-methoxyuracil. In some embodiments, at least 95% of a nucleobase (e.g., uracil) in a uracil-modified sequence encoding a Citrin polypeptide of the invention are modified nucleobases. In some embodiments, at least 95% of uracil in a uracil-modified sequence encoding a Citrin polypeptide is 5-methoxyuracil. In some embodiments, the polynucleotide comprising a uracil-modified sequence further comprises a miRNA binding site, e.g., a miRNA binding site that binds to miR-142 and/or a miRNA binding site that binds to miR-126. In some embodiments, the polynucleotide (e.g., a RNA, e.g., an mRNA) comprising a uracil-modified sequence disclosed herein is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

In some embodiments, the "guanine content of the sequence optimized ORF encoding Citrin with respect to the theoretical maximum guanine content of a nucleotide sequence encoding the Citrin polypeptide," abbreviated as % $C_{TMX}$ is at least 59%, at least 60%, least 65, at least 69%, at least 70%, at least 75%, at least about 80%, at least about 85%, at least about 90%, at least about 95%, or about 100%. In some embodiments, the % $C_{TMX}$ is between about 70% and about 80%, between about 70% and about 79%, between about 70% and about 78%, or between about 70% and about 76%.

In some embodiments, the "cytosine content of the ORF relative to the theoretical maximum cytosine content of a nucleotide sequence encoding the Citrin polypeptide," abbreviated as % $C_{TMX}$, is at least 49%, at least 50%, at least 55%, at least 59%, at least 60%, at least about 65%, at least about 70%, at least about 75%, at least about 80%, at least about 85%, at least about 90%, at least about 95%, or about 100%. In some embodiments, the % $C_{TMX}$ is between about 60% and about 80%, between about 65% and about 80%, between about 65% and about 78%, or between about 69% and about 75%.

In some embodiments, the "guanine and cytosine content (G/C) of the ORF relative to the theoretical maximum G/C content in a nucleotide sequence encoding the Citrin polypeptide," abbreviated as % $G/C_{TMX}$ is at least about 68%, at least about 70%, at least about 75%, at least about 80%, at least about 85%, at least about 90%, at least about 95%, or about 100%. The % $G/C_{TMX}$ is between about 80% and about 100%, between about 85% and about 98%, between about 90% and about 95%, or between about 91% and about 94%.

In some embodiments, the "G/C content in the ORF relative to the G/C content in the corresponding wild-type ORF," abbreviated as % $G/C_{WT}$ is at least 102%, at least 103%, at least 104%, at least 105%, at least 106%, at least 107%, at least 110%, at least 115%, at least 120%, at least 125%, at least 130%, or at least 135%.

In some embodiments, the average G/C content in the 3rd codon position in the ORF is at least 20%, at least 21%, at least 22%, at least 23%, at least 24%, at least 25%, at least 26%, at least 27%, at least 28%, at least 29%, at least 30%, at least 35%, at least 40%, or at least 45% higher than the average G/C content in the 3rd codon position in the corresponding wild-type ORF.

In some embodiments, the polynucleotide of the invention comprises an open reading frame (ORF) encoding a Citrin polypeptide, wherein the ORF has been sequence optimized, and wherein each of % $U_{TL}$, % $U_{WT}$, % $U_{TM}$, % $G_{TL}$, % $G_{WT}$, % $G_{TMX}$, % $C_{TL}$, % $C_{WT}$, % $C_{TMX}$, % $G/C_{TL}$, % $G/C_{WT}$, or % $G/C_{TMX}$, alone or in a combination thereof is in a range between (i) a maximum corresponding to the parameter's maximum value (MAX) plus about 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV), and (ii) a minimum corresponding to the parameter's minimum value (MIN) less 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV).

7. Methods for Sequence Optimization

In some embodiments, a polynucleotide, e.g., mRNA, of the invention (e.g., a polynucleotide comprising a nucleotide sequence encoding a Citrin polypeptide (e.g., the wild-type sequence, functional fragment, or variant thereof) is sequence optimized. A sequence optimized nucleotide sequence (nucleotide sequence is also referred to as "nucleic acid" herein) comprises at least one codon modification with respect to a reference sequence (e.g., a wild-type sequence encoding a Citrin polypeptide). Thus, in a sequence optimized nucleic acid, at least one codon is different from a corresponding codon in a reference sequence (e.g., a wild-type sequence).

In general, sequence optimized nucleic acids are generated by at least a step comprising substituting codons in a reference sequence with synonymous codons (i.e., codons that encode the same amino acid). Such substitutions can be effected, for example, by applying a codon substitution map (i.e., a table providing the codons that will encode each amino acid in the codon optimized sequence), or by applying a set of rules (e.g., if glycine is next to neutral amino acid, glycine would be encoded by a certain codon, but if it is next to a polar amino acid, it would be encoded by another codon). In addition to codon substitutions (i.e., "codon optimization") the sequence optimization methods disclosed herein comprise additional optimization steps which are not strictly directed to codon optimization such as the removal of deleterious motifs (destabilizing motif substitution). Compositions and formulations comprising these sequence optimized nucleic acids (e.g., a RNA, e.g., an mRNA) can be administered to a subject in need thereof to facilitate in vivo expression of functionally active Citrin.

The recombinant expression of large molecules in cell cultures can be a challenging task with numerous limitations (e.g., poor protein expression levels, stalled translation resulting in truncated expression products, protein misfolding, etc.) These limitations can be reduced or avoided by administering the polynucleotides (e.g., a RNA, e.g., an mRNA), which encode a functionally active Citrin or compositions or formulations comprising the same to a patient suffering from Citrullinemia Type 2 (CTLN2), so the synthesis and delivery of the Citrin polypeptide to treat CTLN2 takes place endogenously.

Changing from an in vitro expression system (e.g., cell culture) to in vivo expression requires the redesign of the nucleic acid sequence encoding the therapeutic agent. Redesigning a naturally occurring gene sequence by choosing different codons without necessarily altering the encoded amino acid sequence can often lead to dramatic increases in protein expression levels (Gustafsson et al., 2004, Journal/Trends Biotechnol 22, 346-53). Variables such as codon adaptation index (CAI), mRNA secondary structures, cis-regulatory sequences, GC content and many other similar variables have been shown to somewhat correlate with protein expression levels (Villalobos et al., 2006, "Journal/BMC Bioinformatics 7, 285). However, due to the degeneracy of the genetic code, there are numerous different nucleic acid sequences that can all encode the same therapeutic agent. Each amino acid is encoded by up to six synonymous codons; and the choice between these codons influences gene expression. In addition, codon usage (i.e., the frequency with which different organisms use codons for expressing a polypeptide sequence) differs among organisms (for example, recombinant production of human or humanized therapeutic antibodies frequently takes place in hamster cell cultures).

In some embodiments, a reference nucleic acid sequence can be sequence optimized by applying a codon map. The skilled artisan will appreciate that the T bases in the codon maps disclosed below are present in DNA, whereas the T bases would be replaced by U bases in corresponding RNAs. For example, a sequence optimized nucleic acid disclosed herein in DNA form, e.g., a vector or an in-vitro translation (IVT) template, would have its T bases transcribed as U based in its corresponding transcribed mRNA. In this respect, both sequence optimized DNA sequences (comprising T) and their corresponding RNA sequences (comprising U) are considered sequence optimized nucleic acid of the present invention. A skilled artisan would also understand that equivalent codon-maps can be generated by replaced one or more bases with non-natural bases. Thus, e.g., a TTC codon (DNA map) would correspond to a UUC codon (RNA map), which in turn can correspond to a ΨΨC codon (RNA map in which U has been replaced with pseudouridine).

In one embodiment, a reference sequence encoding Citrin can be optimized by replacing all the codons encoding a certain amino acid with only one of the alternative codons provided in a codon map. For example, all the valines in the optimized sequence would be encoded by GTG or GTC or GTT.

Sequence optimized polynucleotides of the invention can be generated using one or more codon optimization methods, or a combination thereof. Sequence optimization methods which can be used to sequence optimize nucleic acid sequences are described in detail herein. This list of methods is not comprehensive or limiting.

It will be appreciated that the design principles and rules described for each one of the sequence optimization methods discussed below can be combined in many different ways, for example high G/C content sequence optimization for some regions or uridine content sequence optimization for other regions of the reference nucleic acid sequence, as well as targeted nucleotide mutations to minimize secondary structure throughout the sequence or to eliminate deleterious motifs.

The choice of potential combinations of sequence optimization methods can be, for example, dependent on the specific chemistry used to produce a synthetic polynucleotide. Such a choice can also depend on characteristics of the protein encoded by the sequence optimized nucleic acid, e.g., a full sequence, a functional fragment, or a fusion protein comprising Citrin, etc. In some embodiments, such a choice can depend on the specific tissue or cell targeted by the sequence optimized nucleic acid (e.g., a therapeutic synthetic mRNA).

The mechanisms of combining the sequence optimization methods or design rules derived from the application and analysis of the optimization methods can be either simple or complex. For example, the combination can be:

(i) Sequential: Each sequence optimization method or set of design rules applies to a different subsequence of the overall sequence, for example reducing uridine at codon positions 1 to 30 and then selecting high frequency codons for the remainder of the sequence;

(ii) Hierarchical: Several sequence optimization methods or sets of design rules are combined in a hierarchical, deterministic fashion. For example, use the most GC-rich codons, breaking ties (which are common) by choosing the most frequent of those codons.

(iii) Multifactorial/Multiparametric: Machine learning or other modeling techniques are used to design a single sequence that best satisfies multiple overlapping and possibly contradictory requirements. This approach would require the use of a computer applying a number of mathematical techniques, for example, genetic algorithms.

Ultimately, each one of these approaches can result in a specific set of rules which in many cases can be summarized in a single codon table, i.e., a sorted list of codons for each amino acid in the target protein (i.e., Citrin), with a specific rule or set of rules indicating how to select a specific codon for each amino acid position.

a. Uridine Content Optimization

The presence of local high concentrations of uridine in a nucleic acid sequence can have detrimental effects on translation, e.g., slow or prematurely terminated translation, especially when modified uridine analogs are used in the production of synthetic mRNAs. Furthermore, high uridine content can also reduce the in vivo half-life of synthetic mRNAs due to TLR activation.

Accordingly, a nucleic acid sequence can be sequence optimized using a method comprising at least one uridine content optimization step. Such a step comprises, e.g., substituting at least one codon in the reference nucleic acid with an alternative codon to generate a uridine-modified sequence, wherein the uridine-modified sequence has at least one of the following properties:

(i) increase or decrease in global uridine content;
(ii) increase or decrease in local uridine content (i.e., changes in uridine content are limited to specific subsequences);
(iii) changes in uridine distribution without altering the global uridine content;
(iv) changes in uridine clustering (e.g., number of clusters, location of clusters, or distance between clusters); or
(v) combinations thereof.

In some embodiments, the sequence optimization process comprises optimizing the global uridine content, i.e., optimizing the percentage of uridine nucleobases in the sequence optimized nucleic acid with respect to the percentage of uridine nucleobases in the reference nucleic acid sequence. For example, 30% of nucleobases can be uridines in the reference sequence and 10% of nucleobases can be uridines in the sequence optimized nucleic acid.

In other embodiments, the sequence optimization process comprises reducing the local uridine content in specific regions of a reference nucleic acid sequence, i.e., reducing the percentage of uridine nucleobases in a subsequence of the sequence optimized nucleic acid with respect to the percentage of uridine nucleobases in the corresponding subsequence of the reference nucleic acid sequence. For example, the reference nucleic acid sequence can have a 5'-end region (e.g., 30 codons) with a local uridine content of 30%, and the uridine content in that same region could be reduced to 10% in the sequence optimized nucleic acid.

In specific embodiments, codons can be replaced in the reference nucleic acid sequence to reduce or modify, for example, the number, size, location, or distribution of uridine clusters that could have deleterious effects on protein translation. Although as a general rule it is desirable to reduce the uridine content of the reference nucleic acid sequence, in certain embodiments the uridine content, and in particular the local uridine content, of some subsequences of the reference nucleic acid sequence can be increased.

The reduction of uridine content to avoid adverse effects on translation can be done in combination with other optimization methods disclosed here to achieve other design goals. For example, uridine content optimization can be combined with ramp design, since using the rarest codons for most amino acids will, with a few exceptions, reduce the U content.

In some embodiments, the uridine-modified sequence is designed to induce a lower Toll-Like Receptor (TLR) response when compared to the reference nucleic acid sequence. Several TLRs recognize and respond to nucleic acids. Double-stranded (ds)RNA, a frequent viral constituent, has been shown to activate TLR3. See Alexopoulou et al. (2001) Nature, 413:732-738 and Wang et al. (2004) Nat. Med., 10:1366-1373. Single-stranded (ss)RNA activates TLR7. See Diebold et al. (2004) Science 303:1529-1531. RNA oligonucleotides, for example RNA with phosphorothioate internucleotide linkages, are ligands of human TLR8. See Heil et al. (2004) Science 303:1526-1529. DNA containing unmethylated CpG motifs, characteristic of bacterial and viral DNA, activate TLR9. See Hemmi et al. (2000) Nature, 408: 740-745.

As used herein, the term "TLR response" is defined as the recognition of single-stranded RNA by a TLR7 receptor, and in some embodiments encompasses the degradation of the RNA and/or physiological responses caused by the recognition of the single-stranded RNA by the receptor. Methods to determine and quantitate the binding of an RNA to a TLR7 are known in the art. Similarly, methods to determine whether an RNA has triggered a TLR7-mediated physiological response (e.g., cytokine secretion) are well known in the art. In some embodiments, a TLR response can be mediated by TLR3, TLR8, or TLR9 instead of TLR7.

Suppression of TLR7-mediated response can be accomplished via nucleoside modification. RNA undergoes over hundred different nucleoside modifications in nature (see the RNA Modification Database, available at mods.ma.albany.edu). Human rRNA, for example, has ten times more pseudouridine ($\Psi$) and 25 times more 2'-O-methylated nucleosides than bacterial rRNA. Bacterial mRNA contains no nucleoside modifications, whereas mammalian mRNAs have modified nucleosides such as 5-methylcytidine (m5C), N6-methyladenosine (m6A), inosine and many 2'-O-methylated nucleosides in addition to N7-methylguanosine (m7G).

Uracil and ribose, the two defining features of RNA, are both necessary and sufficient for TLR7 stimulation, and short single-stranded RNA (ssRNA) act as TLR7 agonists in a sequence-independent manner as long as they contain several uridines in close proximity. See Diebold et al. (2006) Eur. J. Immunol. 36:3256-3267, which is herein incorporated by reference in its entirety. Accordingly, one or more of the optimization methods disclosed herein comprises reducing the uridine content (locally and/or locally) and/or reducing or modifying uridine clustering to reduce or to suppress a TLR7-mediated response.

In some embodiments, the TLR response (e.g., a response mediated by TLR7) caused by the uridine-modified sequence is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the TLR response caused by the reference nucleic acid sequence.

In some embodiments, the TLR response caused by the reference nucleic acid sequence is at least about 1-fold, at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 3-fold, at least about 4-fold, at least about 5-fold, at least about 6-fold, at least about 7-fold, at least about 8-fold, at least about 9-fold, or at least about 10-fold higher than the TLR response caused by the uridine-modified sequence.

In some embodiments, the uridine content (average global uridine content) (absolute or relative) of the uridine-modified sequence is higher than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% more uridine that the reference nucleic acid sequence.

In other embodiments, the uridine content (average global uridine content) (absolute or relative) of the uridine-modified sequence is lower than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% less uridine that the reference nucleic acid sequence.

In some embodiments, the uridine content (average global uridine content) (absolute or relative) of the uridine-modified sequence is less than 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the total nucleobases in the uridine-modified sequence. In some embodiments, the uridine content of the uridine-modified sequence is between about 10% and about 20%. In some particular embodiments, the uridine content of the uridine-modified sequence is between about 12% and about 16%.

In some embodiments, the uridine content of the reference nucleic acid sequence can be measured using a sliding window. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the sliding window is 20 nucleobases in length. Based on the uridine content measured with a sliding window, it is possible to generate a histogram representing the uridine content throughout the length of the reference nucleic acid sequence and sequence optimized nucleic acids.

In some embodiments, a reference nucleic acid sequence can be modified to reduce or eliminate peaks in the histogram that are above or below a certain percentage value. In some embodiments, the reference nucleic acid sequence can be modified to eliminate peaks in the sliding-window representation which are above 65%, 60%, 55%, 50%, 45%, 40%, 35%, or 30% uridine. In another embodiment, the reference nucleic acid sequence can be modified so no peaks are over 30% uridine in the sequence optimized nucleic acid, as measured using a 20 nucleobase sliding window. In some embodiments, the reference nucleic acid sequence can be modified so no more or no less than a predetermined number of peaks in the sequence optimized nucleic sequence, as measured using a 20 nucleobase sliding window, are above or below a certain threshold value. For example, in some embodiments, the reference nucleic acid sequence can be modified so no peaks or no more than 1, 2, 3, 4, 5, 6, 7, 8, 9 or 10 peaks in the sequence optimized nucleic acid are above 10%, 15%, 20%, 25% or 30% uridine. In another embodiment, the sequence optimized nucleic acid contains between 0 peaks and 2 peaks with uridine contents 30% of higher.

In some embodiments, a reference nucleic acid sequence can be sequence optimized to reduce the incidence of consecutive uridines. For example, two consecutive leucines could be encoded by the sequence CUUUUG, which would include a four uridine cluster. Such subsequence could be substituted with CUGCUC, which would effectively remove the uridine cluster. Accordingly, a reference nucleic sequence can be sequence optimized by reducing or eliminating uridine pairs (UU), uridine triplets (UUU) or uridine quadruplets (UUUU). Higher order combinations of U are not considered combinations of lower order combinations. Thus, for example, UUUU is strictly considered a quadruplet, not two consecutive U pairs; or UUUUUU is considered a sextuplet, not three consecutive U pairs, or two consecutive U triplets, etc.

In some embodiments, all uridine pairs (UU) and/or uridine triplets (UUU) and/or uridine quadruplets (UUUU) can be removed from the reference nucleic acid sequence. In other embodiments, uridine pairs (UU) and/or uridine triplets (UUU) and/or uridine quadruplets (UUUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 uridine pairs. In another particular embodiment, the sequence optimized nucleic acid contains no uridine pairs and/or triplets.

Phenylalanine codons, i.e., UUC or UUU, comprise a uridine pair or triples and therefore sequence optimization to reduce uridine content can at most reduce the phenylalanine U triplet to a phenylalanine U pair. In some embodiments, the occurrence of uridine pairs (UU) and/or uridine triplets (UUU) refers only to non-phenylalanine U pairs or triplets. Accordingly, in some embodiments, non-phenylalanine uridine pairs (UU) and/or uridine triplets (UUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 non-phenylalanine uridine pairs and/or triplets. In another particular embodiment, the sequence optimized nucleic acid contains no non-phenylalanine uridine pairs and/or triplets.

In some embodiments, the reduction in uridine combinations (e.g., pairs, triplets, quadruplets) in the sequence optimized nucleic acid can be expressed as a percentage reduction with respect to the uridine combinations present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine triplets present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine quadruplets present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine triplets present in the reference nucleic acid sequence.

In some embodiments, the uridine content in the sequence optimized sequence can be expressed with respect to the theoretical minimum uridine content in the sequence. The term "theoretical minimum uridine content" is defined as the uridine content of a nucleic acid sequence as a percentage of the sequence's length after all the codons in the sequence have been replaced with synonymous codon with the lowest uridine content. In some embodiments, the uridine content of the sequence optimized nucleic acid is identical to the theoretical minimum uridine content of the reference sequence (e.g., a wild type sequence). In some aspects, the uridine content of the sequence optimized nucleic acid is about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195% or about 200% of the theoretical minimum uridine content of the reference sequence (e.g., a wild type sequence).

In some embodiments, the uridine content of the sequence optimized nucleic acid is identical to the theoretical minimum uridine content of the reference sequence (e.g., a wild type sequence).

The reference nucleic acid sequence (e.g., a wild type sequence) can comprise uridine clusters which due to their number, size, location, distribution or combinations thereof have negative effects on translation. As used herein, the term "uridine cluster" refers to a subsequence in a reference nucleic acid sequence or sequence optimized nucleic sequence with contains a uridine content (usually described as a percentage) which is above a certain threshold. Thus, in certain embodiments, if a subsequence comprises more than about 10%, 15%, 20%, 25%, 30%, 35%, 40%, 45%, 50%, 55%, 60% or 65% uridine content, such subsequence would be considered a uridine cluster.

The negative effects of uridine clusters can be, for example, eliciting a TLR7 response. Thus, in some implementations of the nucleic acid sequence optimization methods disclosed herein it is desirable to reduce the number of clusters, size of clusters, location of clusters (e.g., close to the 5' and/or 3' end of a nucleic acid sequence), distance between clusters, or distribution of uridine clusters (e.g., a certain pattern of cluster along a nucleic acid sequence, distribution of clusters with respect to secondary structure elements in the expressed product, or distribution of clusters with respect to the secondary structure of an mRNA).

In some embodiments, the reference nucleic acid sequence comprises at least one uridine cluster, wherein said uridine cluster is a subsequence of the reference nucleic acid sequence wherein the percentage of total uridine nucleobases in said subsequence is above a predetermined threshold. In some embodiments, the length of the subsequence is at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleobases. In some embodiments, the subsequence is longer than 100 nucleobases. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

For example, an amino acid sequence comprising A, D, G, S and R could be encoded by the nucleic acid sequence (ICU, GAU, GGU, AGU, CGU. Although such sequence does not contain any uridine pairs, triplets, or quadruplets, one third of the nucleobases would be uridines. Such a uridine cluster could be removed by using alternative codons, for example, by using GCC, GAC, GGC, AGC, and CGC, which would contain no uridines.

In other embodiments, the reference nucleic acid sequence comprises at least one uridine cluster, wherein said uridine cluster is a subsequence of the reference nucleic acid sequence wherein the percentage of uridine nucleobases of said subsequence as measured using a sliding window that is above a predetermined threshold. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

In some embodiments, the reference nucleic acid sequence comprises at least two uridine clusters. In some embodiments, the uridine-modified sequence contains fewer uridine-rich clusters than the reference nucleic acid sequence. In some embodiments, the uridine-modified sequence contains more uridine-rich clusters than the reference nucleic acid sequence. In some embodiments, the uridine-modified sequence contains uridine-rich clusters with are shorter in length than corresponding uridine-rich clusters in the reference nucleic acid sequence. In other embodiments, the uridine-modified sequence contains uridine-rich clusters which are longer in length than the corresponding uridine-rich cluster in the reference nucleic acid sequence.

See, Kariko et al. (2005) Immunity 23:165-175; Kormann et al. (2010) Nature Biotechnology 29:154-157; or Sahin et al. (2014) Nature Reviews Drug Discovery|AOP, published online 19 Sep. 2014m doi: 10.1038/nrd4278; all of which are herein incorporated by reference their entireties.

b. Guanine/Cytosine (G/C) Content

A reference nucleic acid sequence can be sequence optimized using methods comprising altering the Guanine/Cytosine (G/C) content (absolute or relative) of the reference nucleic acid sequence. Such optimization can comprise altering (e.g., increasing or decreasing) the global G/C content (absolute or relative) of the reference nucleic acid sequence; introducing local changes in G/C content in the reference nucleic acid sequence (e.g., increase or decrease G/C in selected regions or subsequences in the reference nucleic acid sequence); altering the frequency, size, and distribution of G/C clusters in the reference nucleic acid sequence, or combinations thereof.

In some embodiments, the sequence optimized nucleic acid encoding Citrin comprises an overall increase in G/C content (absolute or relative) relative to the G/C content (absolute or relative) of the reference nucleic acid sequence. In some embodiments, the overall increase in G/C content (absolute or relative) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding Citrin comprises an overall decrease in G/C content (absolute or relative) relative to the G/C content of the reference nucleic acid sequence. In some embodiments, the overall decrease in G/C content (absolute or relative) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding Citrin comprises a local increase in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local increase in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the sequence optimized nucleic acid encoding Citrin comprises a local decrease in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local decrease in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the G/C content (absolute or relative) is increased or decreased in a subsequence which is at least about 5, 10, 15, 20, 25, 30, 35, 40, 45, 50, 55, 60, 65, 70, 75, 80, 85, 90, 95, or 100 nucleobases in length.

In some embodiments, the G/C content (absolute or relative) is increased or decreased in a subsequence which is at least about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleobases in length.

In some embodiments, the G/C content (absolute or relative) is increased or decreased in a subsequence which is at least about 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, or 10000 nucleobases in length. The increases or decreases in G and C content (absolute or relative) described herein can be conducted by replacing synonymous codons with low G/C content with synonymous codons having higher G/C content, or vice versa. For example, L has 6 synonymous codons: two of them have 2 G/C (CUC, CUG), 3 have a single G/C (UUG, CUU, CUA), and one has no G/C (UUA). So if the reference nucleic acid had a CUC codon in a certain position, G/C content at that position could be reduced by replacing CUC with any of the codons having a single G/C or the codon with no G/C.

See, U.S. Publ. Nos. US20140228558, US20050032730 A1; Gustafsson et al. (2012) Protein Expression and Purification 83: 37-46; all of which are incorporated herein by reference in their entireties.

c. Codon Frequency—Codon Usage Bias

Numerous codon optimization methods known in the art are based on the substitution of codons in a reference nucleic acid sequence with codons having higher frequencies. Thus, in some embodiments, a nucleic acid sequence encoding Citrin disclosed herein can be sequence optimized using methods comprising the use of modifications in the frequency of use of one or more codons relative to other synonymous codons in the sequence optimized nucleic acid with respect to the frequency of use in the non-codon optimized sequence.

As used herein, the term "codon frequency" refers to codon usage bias, i.e., the differences in the frequency of occurrence of synonymous codons in coding DNA/RNA. It is generally acknowledged that codon preferences reflect a balance between mutational biases and natural selection for translational optimization. Optimal codons help to achieve faster translation rates and high accuracy. As a result of these factors, translational selection is expected to be stronger in highly expressed genes. In the field of bioinformatics and computational biology, many statistical methods have been proposed and used to analyze codon usage bias. See, e.g., Comeron & Aguadé (1998) J. Mol. Evol. 47: 268-74. Methods such as the 'frequency of optimal codons' (Fop) (Ikemura (1981) J. Mol. Biol. 151 (3): 389-409), the Relative Codon Adaptation (RCA) (Fox & Eril (2010) DNA Res. 17 (3): 185-96) or the 'Codon Adaptation Index' (CAI) (Sharp & Li (1987) Nucleic Acids Res. 15 (3): 1281-95) are used to predict gene expression levels, while methods such as the 'effective number of codons' (Nc) and Shannon entropy from information theory are used to measure codon usage evenness. Multivariate statistical methods, such as correspondence analysis and principal component analysis, are widely used to analyze variations in codon usage among genes (Suzuki et al. (2008) DNA Res. 15 (6): 357-65; Sandhu et al., In Silico Biol. 2008; 8(2):187-92).

The nucleic acid sequence encoding a Citrin polypeptide disclosed herein (e.g., a wild type nucleic acid sequence, a mutant nucleic acid sequence, a chimeric nucleic sequence, etc. which can be, for example, an mRNA), can be codon optimized using methods comprising substituting at least one codon in the reference nucleic acid sequence with an alternative codon having a higher or lower codon frequency in the synonymous codon set; wherein the resulting sequence optimized nucleic acid has at least one optimized property with respect to the reference nucleic acid sequence.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the reference nucleic acid sequence encoding Citrin are substituted with alternative codons, each alternative codon having a codon frequency higher than the codon frequency of the substituted codon in the synonymous codon set.

In some embodiments, at least one codon in the reference nucleic acid sequence encoding Citrin is substituted with an alternative codon having a codon frequency higher than the codon frequency of the substituted codon in the synonymous codon set, and at least one codon in the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in the reference nucleic acid sequence encoding Citrin are substituted with alternative codons, each alternative codon having a codon frequency higher than the codon frequency of the substituted codon in the synonymous codon set.

In some embodiments, at least one alternative codon having a higher codon frequency has the highest codon frequency in the synonymous codon set. In other embodiments, all alternative codons having a higher codon frequency have the highest codon frequency in the synonymous codon set.

In some embodiments, at least one alternative codon having a lower codon frequency has the lowest codon frequency in the synonymous codon set. In some embodiments, all alternative codons having a higher codon frequency have the highest codon frequency in the synonymous codon set.

In some specific embodiments, at least one alternative codon has the second highest, the third highest, the fourth highest, the fifth highest or the sixth highest frequency in the synonymous codon set. In some specific embodiments, at least one alternative codon has the second lowest, the third lowest, the fourth lowest, the fifth lowest, or the sixth lowest frequency in the synonymous codon set.

Optimization based on codon frequency can be applied globally, as described above, or locally to the reference nucleic acid sequence encoding a Citrin polypeptide. In some embodiments, when applied locally, regions of the reference nucleic acid sequence can modified based on codon frequency, substituting all or a certain percentage of codons in a certain subsequence with codons that have higher or lower frequencies in their respective synonymous codon sets. Thus, in some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in a subsequence of the reference nucleic acid sequence are substituted with alternative codons, each alternative codon having a codon frequency higher than the codon frequency of the substituted codon in the synonymous codon set.

In some embodiments, at least one codon in a subsequence of the reference nucleic acid sequence encoding a Citrin polypeptide is substituted with an alternative codon having a codon frequency higher than the codon frequency of the substituted codon in the synonymous codon set, and at least one codon in a subsequence of the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in a subsequence of the reference nucleic acid sequence encoding a Citrin polypeptide are substituted with alternative codons, each alternative codon having a codon frequency higher than the codon frequency of the substituted codon in the synonymous codon set.

In some embodiments, at least one alternative codon substituted in a subsequence of the reference nucleic acid sequence encoding a Citrin polypeptide and having a higher codon frequency has the highest codon frequency in the synonymous codon set. In other embodiments, all alternative codons substituted in a subsequence of the reference nucleic acid sequence and having a lower codon frequency have the lowest codon frequency in the synonymous codon set.

In some embodiments, at least one alternative codon substituted in a subsequence of the reference nucleic acid sequence encoding a Citrin polypeptide and having a lower codon frequency has the lowest codon frequency in the synonymous codon set. In some embodiments, all alternative codons substituted in a subsequence of the reference nucleic acid sequence and having a higher codon frequency have the highest codon frequency in the synonymous codon set.

In specific embodiments, a sequence optimized nucleic acid encoding a Citrin polypeptide can comprise a subsequence having an overall codon frequency higher or lower than the overall codon frequency in the corresponding subsequence of the reference nucleic acid sequence at a specific location, for example, at the 5' end or 3' end of the sequence optimized nucleic acid, or within a predetermined distance from those region (e.g., at least 1, 2, 3, 4, 5, 6, 7, 8, 9, 10, 15, 20, 25, 30, 35, 40, 45, 50, 55, 60, 65, 70, 75, 80, 85, 90, 95 or 100 codons from the 5' end or 3' end of the sequence optimized nucleic acid). In some embodiments, an sequence optimized nucleic acid encoding a Citrin polypeptide can comprise more than one subsequence having an overall codon frequency higher or lower than the overall codon frequency in the corresponding subsequence of the reference nucleic acid sequence. A skilled artisan would understand that subsequences with overall higher or lower overall codon frequencies can be organized in innumerable patterns, depending on whether the overall codon frequency is higher or lower, the length of the subsequence, the distance between subsequences, the location of the subsequences, etc.

See, U.S. Pat. Nos. 5,082,767, 8,126,653, 7,561,973, 8,401,798; U.S. Publ. No. US 20080046192, US 20080076161; Int'l. Publ. No. WO2000018778; Welch et al. (2009) PLoS ONE 4(9): e7002; Gustafsson et al. (2012) Protein Expression and Purification 83: 37-46; Chung et al. (2012) BMC Systems Biology 6:134; all of which are incorporated herein by reference in their entireties.

d. Destabilizing Motif Substitution

There is a variety of motifs that can affect sequence optimization, which fall into various non-exclusive categories, for example:
  (i) Primary sequence based motifs: Motifs defined by a simple arrangement of nucleotides.
  (ii) Structural motifs: Motifs encoded by an arrangement of nucleotides that tends to form a certain secondary structure.
  (iii) Local motifs: Motifs encoded in one contiguous subsequence.
  (iv) Distributed motifs: Motifs encoded in two or more disjoint subsequences.
  (v) Advantageous motifs: Motifs which improve nucleotide structure or function.
  (vi) Disadvantageous motifs: Motifs with detrimental effects on nucleotide structure or function.

There are many motifs that fit into the category of disadvantageous motifs. Some examples include, for example, restriction enzyme motifs, which tend to be relatively short, exact sequences such as the restriction site motifs for Xba1 (TCTAGA), EcoRI (GAATFC), EcoRII (CCWGG, wherein W means A or T, per the IUPAC ambiguity codes), or HindIII (AAGCTT); enzyme sites, which tend to be longer and based on consensus not exact sequence, such in the T7 RNA polymerase (GnnnnWn-CRnCTCnCnnWnD, wherein n means any nucleotide, R means A or G, W means A or T, D means A or G or T but not C); structural motifs, such as GGGG repeats (Kim et al. (1991) Nature 351(6324):331-2); or other motifs such as CUG-triplet repeats (Querido et al. (2014) J. Cell Sci. 124:1703-1714).

Accordingly, the nucleic acid sequence encoding a Citrin polypeptide disclosed herein can be sequence optimized using methods comprising substituting at least one destabilizing motif in a reference nucleic acid sequence, and removing such disadvantageous motif or replacing it with an advantageous motif.

In some embodiments, the optimization process comprises identifying advantageous and/or disadvantageous motifs in the reference nucleic sequence, wherein such motifs are, e.g., specific subsequences that can cause a loss of stability in the reference nucleic acid sequence prior or during the optimization process. For example, substitution of specific bases during optimization can generate a subsequence (motif) recognized by a restriction enzyme. Accordingly, during the optimization process the appearance of disadvantageous motifs can be monitored by comparing the sequence optimized sequence with a library of motifs known to be disadvantageous. Then, the identification of disadvantageous motifs could be used as a post-hoc filter, i.e., to determine whether a certain modification which potentially could be introduced in the reference nucleic acid sequence should be actually implemented or not.

In some embodiments, the identification of disadvantageous motifs can be used prior to the application of the sequence optimization methods disclosed herein, i.e., the identification of motifs in the reference nucleic acid sequence encoding a Citrin polypeptide and their replacement with alternative nucleic acid sequences can be used as a preprocessing step, for example, before uridine reduction. In other embodiments, the identification of disadvantageous motifs and their removal is used as an additional sequence optimization technique integrated in a multiparametric nucleic acid optimization method comprising two or more of the sequence optimization methods disclosed herein. When used in this fashion, a disadvantageous motif identified during the optimization process would be removed, for example, by substituting the lowest possible number of nucleobases in order to preserve as closely as possible the original design principle(s) (e.g., low U, high frequency, etc.).

See, e.g., U.S. Publ. Nos. US20140228558, US20050032730, or US20140228558, which are herein incorporated by reference in their entireties.

e. Limited Codon Set Optimization

In some particular embodiments, sequence optimization of a reference nucleic acid sequence encoding a Citrin polypeptide can be conducted using a limited codon set, e.g., a codon set wherein less than the native number of codons is used to encode the 20 natural amino acids, a subset of the 20 natural amino acids, or an expanded set of amino acids including, for example, non-natural amino acids.

The genetic code is highly similar among all organisms and can be expressed in a simple table with 64 entries which would encode the 20 standard amino acids involved in protein translation plus start and stop codons. The genetic code is degenerate, i.e., in general, more than one codon specifies each amino acid. For example, the amino acid leucine is specified by the UUA, UUG, CUU, CUC, CUA, or CUG codons, while the amino acid serine is specified by UCA, UCG, UCC, UCU, AGU, or AGC codons (difference in the first, second, or third position). Native genetic codes comprise 62 codons encoding naturally occurring amino acids. Thus, in some embodiments of the methods disclosed herein optimized codon sets (genetic codes) comprising less than 62 codons to encode 20 amino acids can comprise 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 30, 29, 28, 27, 26, 25, 24, 23, 22, 21, or 20 codons.

In some embodiments, the limited codon set comprises less than 20 codons. For example, if a protein contains less than 20 types of amino acids, such protein could be encoded by a codon set with less than 20 codons. Accordingly, in some embodiments, an optimized codon set comprises as many codons as different types of amino acids are present in the protein encoded by the reference nucleic acid sequence. In some embodiments, the optimized codon set comprises 19, 18, 17, 16, 15, 14, 13, 12, 11, 10, 9, 8, 7, 6, 5, 4, 3, 2 or even 1 codon.

In some embodiments, at least one amino acid selected from the group consisting of Ala, Arg, Asn, Asp, Cys, Gln, Glu, Gly, His, Ile, Leu, Lys, Phe, Pro, Ser, Thr, Tyr, and Val, i.e., amino acids which are naturally encoded by more than one codon, is encoded with less codons than the naturally occurring number of synonymous codons. For example, in some embodiments, Ala can be encoded in the sequence optimized nucleic acid by 3, 2 or 1 codons; Cys can be encoded in the sequence optimized nucleic acid by 1 codon; Asp can be encoded in the sequence optimized nucleic acid by 1 codon; Glu can be encoded in the sequence optimized nucleic acid by 1 codon; Phe can be encoded in the sequence optimized nucleic acid by 1 codon; Gly can be encoded in the sequence optimized nucleic acid by 3 codons, 2 codons or 1 codon; His can be encoded in the sequence optimized nucleic acid by 1 codon; Ile can be encoded in the sequence optimized nucleic acid by 2 codons or 1 codon; Lys can be encoded in the sequence optimized nucleic acid by 1 codon; Leu can be encoded in the sequence optimized nucleic acid by 5 codons, 4 codons, 3 codons, 2 codons or 1 codon; Asn can be encoded in the sequence optimized nucleic acid by 1 codon; Pro can be encoded in the sequence optimized nucleic acid by 3 codons, 2 codons, or 1 codon; Gln can be encoded in the sequence optimized nucleic acid by 1 codon; Arg can be encoded in the sequence optimized nucleic acid by 5 codons, 4 codons, 3 codons, 2 codons, or 1 codon; Ser can be encoded in the sequence optimized nucleic acid by 5 codons, 4 codons, 3 codons, 2 codons, or 1 codon; Thr can be encoded in the sequence optimized nucleic acid by 3 codons, 2 codons, or 1 codon; Val can be encoded in the sequence optimized nucleic acid by 3 codons, 2 codons, or 1 codon; and, Tyr can be encoded in the sequence optimized nucleic acid by 1 codon.

In some embodiments, at least one amino acid selected from the group consisting of Ala, Arg, Asn, Asp, Cys, Gln, Glu, Gly, His, Ile, Leu, Lys, Phe, Pro, Ser, Thr, Tyr, and Val, i.e., amino acids which are naturally encoded by more than one codon, is encoded by a single codon in the limited codon set.

In some specific embodiments, the sequence optimized nucleic acid is a DNA and the limited codon set consists of 20 codons, wherein each codon encodes one of 20 amino acids. In some embodiments, the sequence optimized nucleic acid is a DNA and the limited codon set comprises at least one codon selected from the group consisting of GCT, GCC, GCA, and GCG; at least a codon selected from the group consisting of CGT, CGC, CGA, CGG, AGA, and AGG; at least a codon selected from AAT or ACC; at least a codon selected from GAT or GAC; at least a codon selected from TGT or TGC; at least a codon selected from CAA or CAG; at least a codon selected from GAA or GAG; at least a codon selected from the group consisting of GGT, GGC, GGA, and GGG; at least a codon selected from CAT or CAC; at least a codon selected from the group consisting of ATF, ATC, and ATA; at least a codon selected from the group consisting of TTA, TTG, CTT, CTC, CTA, and CTG; at least a codon selected from AAA or AAG; an ATG codon; at least a codon selected from TTT or TTC; at least a codon selected from the group consisting of CCT, CCC, CCA, and CCG; at least a codon selected from the group consisting of TCT, TCC, TCA, TCG, AGT, and AGC; at least a codon selected from the group consisting of ACT, ACC, ACA, and ACG; a TGG codon; at least a codon selected from TAT or TAC; and, at least a codon selected from the group consisting of GTT, GTC, GTA, and GTG.

In other embodiments, the sequence optimized nucleic acid is an RNA (e.g., an mRNA) and the limited codon set consists of 20 codons, wherein each codon encodes one of 20 amino acids. In some embodiments, the sequence optimized nucleic acid is an RNA and the limited codon set comprises at least one codon selected from the group consisting of GCU, GCC, GCA, and GCG; at least a codon selected from the group consisting of CGU, CGC, CGA, CGG, AGA, and AGG; at least a codon selected from AAU or ACC; at least a codon selected from GAU or GAC; at least a codon selected from UGU or UGC; at least a codon selected from CAA or CAG; at least a codon selected from GAA or GAG; at least a codon selected from the group consisting of GGU, GGC, GGA, and GGG; at least a codon selected from CAU or CAC; at least a codon selected from the group consisting of AUU, AUC, and AUA; at least a codon selected from the group consisting of UUA, UUG, CUU, CUC, CUA, and CUG; at least a codon selected from AAA or AAG; an AUG codon; at least a codon selected from UUU or UUC; at least a codon selected from the group consisting of CCU, CCC, CCA, and CCG; at least a codon selected from the group consisting of UCU, UCC, UCA, UCG, AGU, and AGC; at least a codon selected from the group consisting of ACU, ACC, ACA, and ACG; a UGG codon; at least a codon selected from UAU or UAC; and, at least a codon selected from the group consisting of GUU, GUC, GUA, and GUG.

In some specific embodiments, the limited codon set has been optimized for in vivo expression of a sequence optimized nucleic acid (e.g., a synthetic mRNA) following administration to a certain tissue or cell.

In some embodiments, the optimized codon set (e.g., a 20 codon set encoding 20 amino acids) complies at least with one of the following properties:
  (i) the optimized codon set has a higher average G/C content than the original or native codon set; or,
  (ii) the optimized codon set has a lower average U content than the original or native codon set; or,
  (iii) the optimized codon set is composed of codons with the highest frequency; or,
  (iv) the optimized codon set is composed of codons with the lowest frequency; or,
  (v) a combination thereof.

In some specific embodiments, at least one codon in the optimized codon set has the second highest, the third highest, the fourth highest, the fifth highest or the sixth highest frequency in the synonymous codon set. In some specific embodiments, at least one codon in the optimized codon has the second lowest, the third lowest, the fourth lowest, the fifth lowest, or the sixth lowest frequency in the synonymous codon set.

As used herein, the term "native codon set" refers to the codon set used natively by the source organism to encode the reference nucleic acid sequence. As used herein, the term "original codon set" refers to the codon set used to encode the reference nucleic acid sequence before the beginning of sequence optimization, or to a codon set used to encode an optimized variant of the reference nucleic acid sequence at the beginning of a new optimization iteration when sequence optimization is applied iteratively or recursively.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest frequency. In other embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest frequency.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest uridine content. In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest uridine content.

In some embodiments, the average G/C content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% higher than the average G/C content (absolute or relative) of the original codon set. In some embodiments, the average G/C content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% lower than the average G/C content (absolute or relative) of the original codon set.

In some embodiments, the uracil content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% higher than the average uracil content (absolute or relative) of the original codon set. In some embodiments, the uracil content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% lower than the average uracil content (absolute or relative) of the original codon set.

See also U.S. Appl. Publ. No. 2011/0082055, and Int'l. Publ. No. WO2000018778, both of which are incorporated herein by reference in their entireties.

8. Characterization of Sequence Optimized Nucleic Acids

In some embodiments of the invention, the polynucleotide (e.g., a RNA, e.g., an mRNA) comprising a sequence optimized nucleic acid disclosed herein encoding a Citrin polypeptide can be tested to determine whether at least one nucleic acid sequence property (e.g., stability when exposed to nucleases) or expression property has been improved with respect to the non-sequence optimized nucleic acid.

As used herein, "expression property" refers to a property of a nucleic acid sequence either in vivo (e.g., translation efficacy of a synthetic mRNA after administration to a subject in need thereof) or in vitro (e.g., translation efficacy of a synthetic mRNA tested in an in vitro model system). Expression properties include but are not limited to the amount of protein produced by an mRNA encoding a Citrin polypeptide after administration, and the amount of soluble or otherwise functional protein produced. In some embodiments, sequence optimized nucleic acids disclosed herein can be evaluated according to the viability of the cells expressing a protein encoded by a sequence optimized nucleic acid sequence (e.g., a RNA, e.g., an mRNA) encoding a Citrin polypeptide disclosed herein.

In a particular embodiment, a plurality of sequence optimized nucleic acids disclosed herein (e.g., a RNA, e.g., an mRNA) containing codon substitutions with respect to the non-optimized reference nucleic acid sequence can be characterized functionally to measure a property of interest, for example an expression property in an in vitro model system, or in vivo in a target tissue or cell.

a. Optimization of Nucleic Acid Sequence Intrinsic Properties

In some embodiments of the invention, the desired property of the polynucleotide is an intrinsic property of the nucleic acid sequence. For example, the nucleotide sequence (e.g., a RNA, e.g., an mRNA) can be sequence optimized for in vivo or in vitro stability. In some embodiments, the nucleotide sequence can be sequence optimized for expression in a particular target tissue or cell. In some embodiments, the nucleic acid sequence is sequence optimized to increase its plasma half life by preventing its degradation by endo and exonucleases.

In other embodiments, the nucleic acid sequence is sequence optimized to increase its resistance to hydrolysis in solution, for example, to lengthen the time that the sequence optimized nucleic acid or a pharmaceutical composition comprising the sequence optimized nucleic acid can be stored under aqueous conditions with minimal degradation.

In other embodiments, the sequence optimized nucleic acid can be optimized to increase its resistance to hydrolysis in dry storage conditions, for example, to lengthen the time that the sequence optimized nucleic acid can be stored after lyophilization with minimal degradation.

b. Nucleic Acids Sequence Optimized for Protein Expression

In some embodiments of the invention, the desired property of the polynucleotide is the level of expression of a Citrin polypeptide encoded by a sequence optimized sequence disclosed herein. Protein expression levels can be measured using one or more expression systems. In some embodiments, expression can be measured in cell culture systems, e.g., CHO cells or HEK293 cells. In some embodiments, expression can be measured using in vitro expression systems prepared from extracts of living cells, e.g., rabbit reticulocyte lysates, or in vitro expression systems prepared by assembly of purified individual components. In other embodiments, the protein expression is measured in an in vivo system, e.g., mouse, rabbit, monkey, etc.

In some embodiments, protein expression in solution form can be desirable. Accordingly, in some embodiments, a reference sequence can be sequence optimized to yield a sequence optimized nucleic acid sequence having optimized levels of expressed proteins in soluble form. Levels of protein expression and other properties such as solubility, levels of aggregation, and the presence of truncation products (i.e., fragments due to proteolysis, hydrolysis, or defective translation) can be measured according to methods known in the art, for example, using electrophoresis (e.g., native or SDS-PAGE) or chromatographic methods (e.g., HPLC, size exclusion chromatography, etc.).

c. Optimization of Target Tissue or Target Cell Viability

In some embodiments, the expression of heterologous therapeutic proteins encoded by a nucleic acid sequence can have deleterious effects in the target tissue or cell, reducing protein yield, or reducing the quality of the expressed product (e.g., due to the presence of protein fragments or precipitation of the expressed protein in inclusion bodies), or causing toxicity.

Accordingly, in some embodiments of the invention, the sequence optimization of a nucleic acid sequence disclosed herein, e.g., a nucleic acid sequence encoding a Citrin polypeptide, can be used to increase the viability of target cells expressing the protein encoded by the sequence optimized nucleic acid.

Heterologous protein expression can also be deleterious to cells transfected with a nucleic acid sequence for autologous or heterologous transplantation. Accordingly, in some embodiments of the present disclosure the sequence optimization of a nucleic acid sequence disclosed herein can be used to increase the viability of target cells expressing the protein encoded by the sequence optimized nucleic acid sequence. Changes in cell or tissue viability, toxicity, and other physiological reaction can be measured according to methods known in the art.

d. Reduction of Immune and/or Inflammatory Response

In some cases, the administration of a sequence optimized nucleic acid encoding Citrin polypeptide or a functional fragment thereof can trigger an immune response, which could be caused by (i) the therapeutic agent (e.g., an mRNA encoding a Citrin polypeptide), or (ii) the expression product of such therapeutic agent (e.g., the Citrin polypeptide encoded by the mRNA), or (iv) a combination thereof. Accordingly, in some embodiments of the present disclosure the sequence optimization of nucleic acid sequence (e.g., an mRNA) disclosed herein can be used to decrease an immune or inflammatory response triggered by the administration of a nucleic acid encoding a Citrin polypeptide or by the expression product of Citrin encoded by such nucleic acid.

In some aspects, an inflammatory response can be measured by detecting increased levels of one or more inflammatory cytokines using methods known in the art, e.g., ELISA. The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GRO$\alpha$, interferon-$\gamma$ (IFN$\gamma$), tumor necrosis factor $\alpha$ (TNF$\alpha$), interferon $\gamma$-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interferon-13 (Il-13), interferon α (IFN-α), etc.

9. Modified Nucleotide Sequences Encoding Citrin Polypeptides

In some embodiments, the polynucleotide (e.g., a RNA, e.g., an mRNA) of the invention comprises a chemically modified nucleobase, e.g., 5-methoxyuracil. In some embodiments, the mRNA is a uracil-modified sequence comprising an ORF encoding a Citrin polypeptide, wherein the mRNA comprises a chemically modified nucleobase, e.g., 5-methoxyuracil.

In certain aspects of the invention, when the 5-methoxyuracil base is connected to a ribose sugar, as it is in polynucleotides, the resulting modified nucleoside or nucleotide is referred to as 5-methoxyuridine. In some embodiments, uracil in the polynucleotide is at least about 25%, at least about 30%, at least about 40%, at least about 50%, at least about 60%, at least about 70%, at least about 80%, at least 90%, at least 95%, at least 99%, or about 100% 5-methoxyuracil. In one embodiment, uracil in the polynucleotide is at least 95% 5-methoxyuracil. In another embodiment, uracil in the polynucleotide is 100% 5-methoxyuracil.

In embodiments where uracil in the polynucleotide is at least 95% 5-methoxyuracil, overall uracil content can be adjusted such that an mRNA provides suitable protein expression levels while inducing little to no immune response. In some embodiments, the uracil content of the ORF is between about 105% and about 145%, about 105% and about 140%, about 110% and about 140%, about 110% and about 145%, about 115% and about 135%, about 105% and about 135%, about 110% and about 135%, about 115% and about 145%, or about 115% and about 140% of the theoretical minimum uracil content in the corresponding wild-type ORF (% Utm). In other embodiments, the uracil content of the ORF is between about 117% and about 134% or between 118% and 132% of the % $U_{TM}$. In some embodiments, the uracil content of the ORF encoding a Citrin polypeptide is about 115%, about 120%, about 125%, about 130%, about 135%, about 140%, about 145%, or about 150% of the % Utm. In this context, the term "uracil" can refer to 5-methoxyuracil and/or naturally occurring uracil.

In some embodiments, the uracil content in the ORF of the mRNA encoding a Citrin polypeptide of the invention is less than about 50%, about 40%, about 30%, about 20% or about 15% of the total nucleobase content in the ORF. In some embodiments, the uracil content in the ORF is between about 15% and about 25% of the total nucleobase content in the ORF. In other embodiments, the uracil content in the ORF is between about 20% and about 30% of the total nucleobase content in the ORF. In one embodiment, the uracil content in the ORF of the mRNA encoding a Citrin polypeptide is less than about 30% of the total nucleobase content in the open reading frame. In this context, the term "uracil" can refer to 5-methoxyuracil and/or naturally occurring uracil.

In further embodiments, the ORF of the mRNA encoding a Citrin polypeptide having 5-methoxyuracil and adjusted uracil content has increased Cytosine (C), Guanine (G), or Guanine/Cytosine (G/C) content (absolute or relative). In some embodiments, the overall increase in C, G, or G/C content (absolute or relative) of the ORF is at least about 2%, at least about 3%, at least about 4%, at least about 5%, at least about 6%, at least about 7%, at least about 10%, at least about 15%, at least about 20%, at least about 40%, at least about 50%, at least about 60%, at least about 70%, at least about 80%, at least about 90%, at least about 95%, or at least about 100% relative to the G/C content (absolute or relative) of the wild-type ORF. In some embodiments, the G, the C, or the G/C content in the ORF is less than about 100%, less than about 90%, less than about 85%, or less than about 80% of the theoretical maximum G, C, or G/C content of the corresponding wild type nucleotide sequence encoding the Citrin polypeptide (% $G_{TMX}$; % $C_{TMX}$, or % $G/C_{TMX}$). In other embodiments, the G, the C, or the G/C content in the ORF is between about 70% and about 80%, between about 71% and about 79%, between about 71% and about 78%, or between about 71% and about 77% of the % $G_{TMX}$, % $C_{TMX}$, or % $G/C_{TMX}$. In some embodiments, the increases in G and/or C content (absolute or relative) described herein can be conducted by replacing synonymous codons with low G, C, or G/C content with synonymous codons having higher G, C, or G/C content. In other embodiments, the increase in G and/or C content (absolute or relative) is conducted by replacing a codon ending with U with a synonymous codon ending with G or C.

In further embodiments, the ORF of the mRNA encoding a Citrin polypeptide of the invention comprises 5-methoxyuracil and has an adjusted uracil content containing less uracil pairs (UU) and/or uracil triplets (UUU) and/or uracil quadruplets (UUUU) than the corresponding wild-type nucleotide sequence encoding the Citrin polypeptide. In some embodiments, the ORF of the mRNA encoding a Citrin polypeptide of the invention contains no uracil pairs and/or uracil triplets and/or uracil quadruplets. In some embodiments, uracil pairs and/or uracil triplets and/or uracil quadruplets are reduced below a certain threshold, e.g., no more than 1, 2, 3, 4, 5, 6, 7, 8, 9, 10, 11, 12, 13, 14, 15, 16, 17, 18, 19, or 20 occurrences in the ORF of the mRNA encoding the Citrin polypeptide. In a particular embodiment, the ORF of the mRNA encoding the Citrin polypeptide of the invention contains less than 20, 19, 18, 17, 16, 15, 14, 13, 12, 11, 10, 9, 8, 7, 6, 5, 4, 3, 2, or 1 non-phenylalanine uracil pairs and/or triplets. In another embodiment, the ORF of the mRNA encoding the Citrin polypeptide contains no non-phenylalanine uracil pairs and/or triplets.

In further embodiments, the ORF of the mRNA encoding a Citrin polypeptide of the invention comprises 5-methoxyuracil and has an adjusted uracil content containing less uracil-rich clusters than the corresponding wild-type nucleotide sequence encoding the Citrin polypeptide. In some embodiments, the ORF of the mRNA encoding the Citrin polypeptide of the invention contains uracil-rich clusters that are shorter in length than corresponding uracil-rich clusters in the corresponding wild-type nucleotide sequence encoding the Citrin polypeptide.

In further embodiments, alternative lower frequency codons are employed. At least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the Citrin polypeptide-encoding ORF of the 5-methoxyuracil-comprising mRNA are substituted with alternative codons, each alternative codon having a codon frequency lower than the codon frequency of the substituted codon in the synonymous codon set. The ORF also has adjusted uracil content, as described above. In some embodiments, at least one codon in the ORF of the mRNA encoding the Citrin polypeptide is substituted with an alternative codon having a codon frequency lower than the codon frequency of the substituted codon in the synonymous codon set.

In some embodiments, the adjusted uracil content, Citrin polypeptide-encoding ORF of the 5-methoxyuracil-comprising mRNA exhibits expression levels of Citrin when administered to a mammalian cell that are higher than expression levels of Citrin from the corresponding wild-type mRNA. In other embodiments, the expression levels of Citrin when administered to a mammalian cell are increased relative to a corresponding mRNA containing at least 95% 5-methoxyuracil and having a uracil content of about 160%, about 170%, about 180%, about 190%, or about 200% of the theoretical minimum. In yet other embodiments, the expression levels of Citrin when administered to a mammalian cell are increased relative to a corresponding mRNA, wherein at least about 50%, at least about 60%, at least about 70%, at least about 80%, at least about 90%, or about 100% of uracils are 1-methylpseudouracil or pseudouracils. In some embodiments, the mammalian cell is a mouse cell, a rat cell, or a rabbit cell. In other embodiments, the mammalian cell is a monkey cell or a human cell. In some embodiments, the human cell is a HeLa cell, a BJ fibroblast cell, or a peripheral blood mononuclear cell (PBMC). In some embodiments, Citrin is expressed when the mRNA is administered to a mammalian cell in vivo. In some embodiments, the mRNA is administered to mice, rabbits, rats, monkeys, or humans. In one embodiment, mice are null mice. In some embodiments, the mRNA is administered to mice in an amount of about 0.01 mg/kg, about 0.05 mg/kg, about 0.1 mg/kg, or about 0.15 mg/kg. In some embodiments, the mRNA is administered intravenously or intramuscularly. In other embodiments, the Citrin polypeptide is expressed when the mRNA is administered to a mammalian cell in vitro. In some embodiments, the expression is increased by at least about 2-fold, at least about 5-fold, at least about 10-fold, at least about 50-fold, at least about 500-fold, at least about 1500-fold, or at least about 3000-fold. In other embodiments, the expression is increased by at least about 10%, about 20%, about 30%, about 40%, about 50%, 60%, about 70%, about 80%, about 90%, or about 100%.

In some embodiments, adjusted uracil content, Citrin polypeptide-encoding ORF of the 5-methoxyuracil-comprising mRNA exhibits increased stability. In some embodiments, the mRNA exhibits increased stability in a cell relative to the stability of a corresponding wild-type mRNA under the same conditions. In some embodiments, the mRNA exhibits increased stability including resistance to nucleases, thermal stability, and/or increased stabilization of secondary structure. In some embodiments, increased stability exhibited by the mRNA is measured by determining the half-life of the mRNA (e.g., in a plasma, cell, or tissue sample) and/or determining the area under the curve (AUC) of the protein expression by the mRNA over time (e.g., in vitro or in vivo). An mRNA is identified as having increased stability if the half-life and/or the AUC is greater than the half-life and/or the AUC of a corresponding wild-type mRNA under the same conditions.

In some embodiments, the mRNA of the present invention induces a detectably lower immune response (e.g., innate or acquired) relative to the immune response induced by a corresponding wild-type mRNA under the same conditions. In other embodiments, the mRNA of the present disclosure induces a detectably lower immune response (e.g., innate or acquired) relative to the immune response induced by an mRNA that encodes for a Citrin polypeptide but does not comprise 5-methoxyuracil under the same conditions, or relative to the immune response induced by an mRNA that encodes for a Citrin polypeptide and that comprises 5-methoxyuracil but that does not have adjusted uracil content under the same conditions. The innate immune response can be manifested by increased expression of pro-inflammatory cytokines, activation of intracellular PRRs (RIG-I, MDA5, etc), cell death, and/or termination or reduction in protein translation. In some embodiments, a reduction in the innate immune response can be measured by expression or activity level of Type 1 interferons (e.g., IFN-α, IFN-β, IFN-κ, IFN-δ, IFN-ε, IFN-τ, IFN-ω, and IFN-ζ) or the expression of interferon-regulated genes such as the toll-like receptors (e.g., TLR7 and TLR8), and/or by decreased cell death following one or more administrations of the mRNA of the invention into a cell.

In some embodiments, the expression of Type-1 interferons by a mammalian cell in response to the mRNA of the present disclosure is reduced by at least 10%, 20%, 30%, 40%, 50%, 60%, 70%, 80%, 90%, 95%, 99%, or greater than 99% relative to a corresponding wild-type mRNA, to an mRNA that encodes a Citrin polypeptide but does not comprise 5-methoxyuracil, or to an mRNA that encodes a Citrin polypeptide and that comprises 5-methoxyuracil but that does not have adjusted uracil content. In some embodiments, the interferon is IFN-β. In some embodiments, cell death frequency cased by administration of mRNA of the present disclosure to a mammalian cell is 10%, 25%, 50%, 75%, 85%, 90%, 95%, or over 95% less than the cell death frequency observed with a corresponding wild-type mRNA, an mRNA that encodes for a Citrin polypeptide but does not comprise 5-methoxyuracil, or an mRNA that encodes for a Citrin polypeptide and that comprises 5-methoxyuracil but that does not have adjusted uracil content. In some embodiments, the mammalian cell is a BJ fibroblast cell. In other embodiments, the mammalian cell is a splenocyte. In some embodiments, the mammalian cell is that of a mouse or a rat. In other embodiments, the mammalian cell is that of a human. In one embodiment, the mRNA of the present disclosure does not substantially induce an innate immune response of a mammalian cell into which the mRNA is introduced.

In some embodiments, the polynucleotide is an mRNA that comprises an ORF that encodes a Citrin polypeptide, wherein uracil in the mRNA is at least about 95% 5-methoxyuracil, wherein the uracil content of the ORF is between about 115% and about 135% of the theoretical minimum uracil content in the corresponding wild-type ORF, and wherein the uracil content in the ORF encoding the Citrin polypeptide is less than about 30% of the total nucleobase content in the ORF. In some embodiments, the ORF that encodes the Citrin polypeptide is further modified to increase G/C content of the ORF (absolute or relative) by at least about 40%, as compared to the corresponding wild-type ORF. In yet other embodiments, the ORF encoding the Citrin polypeptide contains less than 20 non-phenylalanine uracil pairs and/or triplets. In some embodiments, at least one codon in the ORF of the mRNA encoding the Citrin polypeptide is further substituted with an alternative codon having a codon frequency lower than the codon frequency of the substituted codon in the synonymous codon set. In some embodiments, the expression of the Citrin polypeptide encoded by an mRNA comprising an ORF wherein uracil in the mRNA is at least about 95% 5-methoxyuracil, and wherein the uracil content of the ORF is between about 115% and about 135% of the theoretical minimum uracil content in the corresponding wild-type ORF, is increased by at least about 10-fold when compared to expression of the Citrin polypeptide from the corresponding wild-type mRNA. In some embodiments, the mRNA comprises an open ORF wherein uracil in the mRNA is at least about 95% 5-methoxyuracil, and wherein the uracil content of the ORF is between about 115% and about 135% of the theoretical minimum uracil content in the corresponding wild-type ORF, and wherein the mRNA does not substantially induce an innate immune response of a mammalian cell into which the mRNA is introduced.

10. Methods for Modifying Polynucleotides

The invention includes modified polynucleotides comprising a polynucleotide described herein (e.g., a polynucleotide, e.g., an mRNA, comprising a nucleotide sequence encoding a Citrin polypeptide). The modified polynucleotides can be chemically modified and/or structurally modified. When the polynucleotides of the present invention are chemically and/or structurally modified the polynucleotides can be referred to as "modified polynucleotides."

The present disclosure provides for modified nucleosides and nucleotides of a polynucleotide (e.g., RNA polynucleotides, such as mRNA polynucleotides) encoding a Citrin polypeptide. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside including a phosphate group. Modified nucleotides can by synthesized by any useful method, such as, for example, chemically, enzymatically, or recombinantly, to include one or more modified or non-natural nucleosides. Polynucleotides can comprise a region or regions of linked nucleosides. Such regions can have variable backbone linkages. The linkages can be standard phosphodiester linkages, in which case the polynucleotides would comprise regions of nucleotides.

The modified polynucleotides disclosed herein can comprise various distinct modifications. In some embodiments, the modified polynucleotides contain one, two, or more (optionally different) nucleoside or nucleotide modifications. In some embodiments, a modified polynucleotide, introduced to a cell can exhibit one or more desirable properties, e.g., improved protein expression, reduced immunogenicity, or reduced degradation in the cell, as compared to an unmodified polynucleotide.

a. Structural Modifications

In some embodiments, a polynucleotide of the present invention (e.g., a polynucleotide comprising a nucleotide sequence encoding a Citrin polypeptide) is structurally modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" can be chemically modified to "AT-5meC-G". The same polynucleotide can be structurally modified from "ATCG" to "ATCCCG". Here, the dinucleotide "CC" has been inserted, resulting in a structural modification to the polynucleotide.

b. Chemical Modifications

In some embodiments, the polynucleotides of the present invention are chemically modified. As used herein in reference to a polynucleotide, the terms "chemical modification" or, as appropriate, "chemically modified" refer to modification with respect to adenosine (A), guanosine (G), uridine (U), thymidine (T) or cytidine (C) ribo- or deoxyribonucleosides in one or more of their position, pattern, percent or population. Generally, herein, these terms are not intended to refer to the ribonucleotide modifications in naturally occurring 5'-terminal mRNA cap moieties.

In some embodiments, the polynucleotides of the present invention can have a uniform chemical modification of all or any of the same nucleoside type or a population of modifications produced by mere downward titration of the same starting modification in all or any of the same nucleoside type, or a measured percent of a chemical modification of all any of the same nucleoside type but with random incorporation, such as where all uridines are replaced by a uridine analog, e.g., pseudouridine or 5-methoxyuridine. In another embodiment, the polynucleotides can have a uniform chemical modification of two, three, or four of the same nucleoside type throughout the entire polynucleotide (such as all uridines and all cytosines, etc. are modified in the same way).

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker can be incorporated into polynucleotides of the present disclosure.

The skilled artisan will appreciate that, except where otherwise noted, polynucleotide sequences set forth in the instant application will recite "T"s in a representative DNA sequence but where the sequence represents RNA, the "T"s would be substituted for "U"s.

Modifications of polynucleotides (e.g., RNA polynucleotides, such as mRNA polynucleotides) that are useful in the compositions, methods and synthetic processes of the present disclosure include, but are not limited to the following nucleotides, nucleosides, and nucleobases: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6,N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo) adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-T-b-azidoadenosine TP; 2'-Deoxy-2'-b-bromoadenosine TP; 2'-Deoxy-2'-b-chloroadenosine TP; 2'-Deoxy-T-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl) cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-T-a-mercaptocytidine TP; 2'-Deoxy-2'-α-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-α-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine;

1-ethyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine,), 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl) pseudo-UTP; 1-Methyl-pseudo-UTP; 1-Ethyl-pseudo-UTP; 2 (thio)pseudouracil; 2' deoxy uridine; 2' fluorouridine; 2-(thio)uracil; 2,4-(dithio)psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl) uracil; 4 (thio)pseudouracil; 4-(thio)pseudouracil; 4-(thio)uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio) uracil; 5 (methylaminomethyl)-4 (thio)uracil; 5 (propynyl) uracil; 5 (trifluoromethyl)uracil; 5-(2-aminopropyl)uracil; 5-(alkyl)-2-(thio)pseudouracil; 5-(alkyl)-2,4 (dithio) pseudouracil; 5-(alkyl)-4 (thio)pseudouracil; 5-(alkyl) pseudouracil; 5-(alkyl)uracil; 5-(alkynyl)uracil; 5-(allylamino)uracil; 5-(cyanoalkyl)uracil; 5-(dialkylaminoalkyl) uracil; 5-(dimethylaminoalkyl)uracil; 5-(guanidiniumalkyl) uracil; 5-(halo)uracil; 5-(1,3-diazole-1-alkyl)uracil; 5-(methoxy)uracil; 5-(methoxycarbonylmethyl)-2-(thio) uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio)uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Aminophenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonylbenzyl)pseudouridine TP; 1-(4-Methoxybenzyl)pseudouridine TP; 1-(4-Methoxy-benzyl)pseudo-UTP; 1-(4-Methoxyphenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl}pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctylpseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyan-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-T-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-T-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}]propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl; 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalthlhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl;

pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Aminopentaoxanonadecyl)adenosine TP.

In some embodiments, the polynucleotide (e.g., RNA polynucleotide, such as mRNA polynucleotide) includes a combination of at least two (e.g., 2, 3, 4 or more) of the aforementioned modified nucleobases.

In some embodiments, the mRNA comprises at least one chemically modified nucleoside. In some embodiments, the at least one chemically modified nucleoside is selected from the group consisting of pseudouridine (ψ), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 1-ethyl-pseudouridine (e1), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyl-adenosine, 2-geranylthiouridine, 2-lysidine, 2-selenouridine, 3-(3-amino-3-carboxypropyl)-5,6-dihydrouridine, 3-(3-amino-3-carboxypropyl)pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamyl-queuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQ0base, preQ1base, and two or more combinations thereof. In some embodiments, the at least one chemically modified nucleoside is selected from the group consisting of pseudouridine, 1-methyl-pseudouridine, 1-ethyl-pseudouridine, 5-methylcytosine, 5-methoxyuridine, and a combination thereof. In some embodiments, the polynucleotide (e.g., RNA polynucleotide, such as mRNA polynucleotide) includes a combination of at least two (e.g., 2, 3, 4 or more) of the aforementioned modified nucleobases.

(i) Base Modifications

In certain embodiments, the chemical modification is at nucleobases in the polynucleotides (e.g., RNA polynucleotide, such as mRNA polynucleotide). In some embodiments, modified nucleobases in the polynucleotide (e.g., RNA polynucleotide, such as mRNA polynucleotide) are selected from the group consisting of 1-methyl-pseudouridine (m1ψ), 1-ethyl-pseudouridine (e1ψ), 5-methoxy-uridine (mo5U), 5-methyl-cytidine (m5C), pseudouridine (ψ), α-thio-guanosine and α-thio-adenosine. In some embodiments, the polynucleotide includes a combination of at least two (e.g., 2, 3, 4 or more) of the aforementioned modified nucleobases.

In some embodiments, the polynucleotide (e.g., RNA polynucleotide, such as mRNA polynucleotide) comprises pseudouridine (ψ) and 5-methyl-cytidine (m5C). In some embodiments, the polynucleotide (e.g., RNA polynucleotide, such as mRNA polynucleotide) comprises 1-methyl-pseudouridine (m1ψ). In some embodiments, the polynucleotide (e.g., RNA polynucleotide, such as mRNA polynucleotide) comprises 1-ethyl-pseudouridine (e1ψ). In some embodiments, the polynucleotide (e.g., RNA polynucleotide, such as mRNA polynucleotide) comprises 1-methyl-pseudouridine (m1ψ) and 5-methyl-cytidine (m5C). In some embodiments, the polynucleotide (e.g., RNA polynucleotide, such as mRNA polynucleotide) comprises 1-ethyl-pseudouridine (e1) and 5-methyl-cytidine (m5C). In some embodiments, the polynucleotide (e.g., RNA polynucleotide, such as mRNA polynucleotide) comprises 2-thiouridine (s2U). In some embodiments, the polynucleotide (e.g., RNA polynucleotide, such as mRNA polynucleotide) comprises 2-thiouridine and 5-methyl-cytidine (m5C). In some embodiments, the polynucleotide (e.g., RNA polynucleotide, such as mRNA polynucleotide) comprises methoxy-uridine (mo5U). In some embodiments, the polynucleotide (e.g., RNA polynucleotide, such as mRNA polynucleotide) comprises 5-methoxy-uridine (mo5U) and 5-methyl-cytidine (m5C). In some embodiments, the polynucleotide (e.g., RNA polynucleotide, such as mRNA polynucleotide) comprises 2'-O-methyl uridine. In some embodiments, the polynucleotide (e.g., RNA polynucleotide, such as mRNA polynucleotide) comprises 2'-O-methyl uridine and 5-methyl-cytidine (m5C). In some embodiments, the polynucleotide (e.g., RNA polynucleotide, such as mRNA polynucleotide) comprises N6-methyl-adenosine (m6A). In some embodiments, the polynucleotide (e.g., RNA polynucleotide, such as mRNA polynucleotide) comprises N6-methyl-adenosine (m6A) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methyl-cytidine (m5C), meaning that all cytosine residues in the mRNA sequence are replaced with 5-methyl-cytidine (m5C). Similarly, a polynucleotide can be uniformly modified for any type of nucleoside residue present in the sequence by replacement with a modified residue such as any of those set forth above.

In some embodiments, the chemically modified nucleosides in the open reading frame are selected from the group consisting of uridine, adenine, cytosine, guanine, and any combination thereof.

In some embodiments, the modified nucleobase is a modified cytosine. Examples of nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine.

In some embodiments, a modified nucleobase is a modified uridine. Example nucleobases and nucleosides having a modified uridine include 5-cyano uridine or 4'-thio uridine.

In some embodiments, a modified nucleobase is a modified adenine. Example nucleobases and nucleosides having a modified adenine include 7-deaza-adenine, 1-methyl-adenosine (m1A), 2-methyl-adenine (m2A), N6-methyl-adenine (m6A), and 2,6-Diaminopurine.

In some embodiments, a modified nucleobase is a modified guanine. Example nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

In some embodiments, the nucleobase modified nucleotides in the polynucleotide (e.g., RNA polynucleotide, such as mRNA polynucleotide) are 5-methoxyuridine.

In some embodiments, the polynucleotide (e.g., RNA polynucleotide, such as mRNA polynucleotide) includes a combination of at least two (e.g., 2, 3, 4 or more) of modified nucleobases.

In some embodiments, at least 95% of a type of nucleobases (e.g., uracil) in a polynucleotide of the invention (e.g., an mRNA encoding Citrin) are modified nucleobases. In some embodiments, at least 95% of uracil in a polynucleotide of the present invention (e.g., an mRNA encoding Citrin) is 5-methoxyuracil.

In some embodiments, the polynucleotide (e.g., RNA polynucleotide, such as mRNA polynucleotide) comprises 5-methoxyuridine (5mo5U) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methoxyuridine, meaning that substantially all uridine residues in the mRNA sequence are replaced with 5-methoxyuridine. Similarly, a polynucleotide can be uniformly modified for any type of nucleoside residue present in the sequence by replacement with a modified residue such as any of those set forth above.

In some embodiments, the modified nucleobase is a modified cytosine.

In some embodiments, a modified nucleobase is a modified uracil. Example nucleobases and nucleosides having a modified uracil include 5-methoxyuracil.

In some embodiments, a modified nucleobase is a modified adenine.

In some embodiments, a modified nucleobase is a modified guanine.

In some embodiments, the nucleobases, sugar, backbone, or any combination thereof in the open reading frame encoding a Citrin polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the uridine nucleosides in the open reading frame encoding a Citrin polypeptide, e.g., a Citrin polypeptide or a functional fragment or variant thereof, are chemically modified by at least 10%, at least 20%, at least 30%, at least 40%, at least 50%, at least 60%, at least 70%, at least 80%, at least 90%, at least 95%, at least 99%, or 100%.

In some embodiments, the adenosine nucleosides in the open reading frame encoding a Citrin polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the cytidine nucleosides in the open reading frame encoding a Citrin polypeptide are chemically modified by at least at least 10%, at least 20%, at least 30%, at least 40%, at least 50%, at least 60%, at least 70%, at least 80%, at least 90%, at least 95%, at least 99%, or 100%.

In some embodiments, the guanosine nucleosides in the open reading frame encoding a Citrin polypeptide are chemically modified by at least at least 10%, at least 20%, at least 30%, at least 40%, at least 50%, at least 60%, at least 70%, at least 80%, at least 90%, at least 95%, at least 99%, or 100%.

In some embodiments, the polynucleotides can include any useful linker between the nucleosides. Such linkers, including backbone modifications, that are useful in the composition of the present disclosure include, but are not limited to the following: 3'-alkylene phosphonates, 3'-amino phosphoramidate, alkene containing backbones, aminoalkylphosphoramidates, aminoalkylphosphotriesters, boranophosphates, —$CH_2$—O—N($CH_3$)—$CH_2$—, —$CH_2$—N($CH_3$)—N($CH_3$)—$CH_2$—, —$CH_2$—NH—$CH_2$—, chiral phosphonates, chiral phosphorothioates, formacetyl and thioformacetyl backbones, methylene (methylimino), methylene formacetyl and thioformacetyl backbones, methyleneimino and methylenehydrazino backbones, morpholino linkages, —N($CH_3$)—$CH_2$—$CH_2$—, oligonucleosides with heteroatom internucleoside linkage, phosphinates, phosphoramidates, phosphorodithioates, phosphorothioate internucleoside linkages, phosphorothioates, phosphotriesters, PNA, siloxane backbones, sulfamate backbones, sulfide sulfoxide and sulfone backbones, sulfonate and sulfonamide backbones, thionoalkylphosphonates, thionoalkylphosphotriesters, and thionophosphoramidates.

(ii) Sugar Modifications

The modified nucleosides and nucleotides (e.g., building block molecules), which can be incorporated into a polynucleotide (e.g., RNA or mRNA, as described herein), can be modified on the sugar of the ribonucleic acid. For example, the 2' hydroxyl group (OH) can be modified or replaced with a number of different substituents. Exemplary substitutions at the 2'-position include, but are not limited to, H, halo, optionally substituted $C_{1-6}$ alkyl; optionally substituted $C_{1-6}$ alkoxy; optionally substituted $C_{6-10}$ aryloxy; optionally substituted $C_{3-8}$ cycloalkyl; optionally substituted $C_{3-8}$ cycloalkoxy; optionally substituted $C_{6-10}$ aryloxy; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), —O($CH_2CH_2O)_n CH_2CH_2OR$, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein Generally, RNA includes the sugar group ribose, which is a 5-membered ring having an oxygen. Exemplary, non-limiting modified nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar. Such sugar modifications are taught International Patent Publication Nos. WO2013052523 and WO2014093924, the contents of each of which are incorporated herein by reference in their entireties.

(iii) Combinations of Modifications

The polynucleotides of the invention (e.g., a polynucleotide comprising a nucleotide sequence encoding a Citrin polypeptide or a functional fragment or variant thereof) can include a combination of modifications to the sugar, the nucleobase, and/or the internucleoside linkage. These combinations can include any one or more modifications described herein.

Combinations of modified nucleotides can be used to form the polynucleotides of the invention. Unless otherwise noted, the modified nucleotides can be completely substituted for the natural nucleotides of the polynucleotides of the invention. As a non-limiting example, the natural nucleotide uridine can be substituted with a modified nucleoside described herein. In another non-limiting example, the natural nucleotide uridine can be partially substituted or replaced (e.g., about 0%, 1%, 5%, 10%, 15%, 20%, 25%, 30%, 35%, 40%, 45%, 50%, 55%, 60%, 65%, 70%, 75%, 80%, 85%, 90%, 95% or 99%) with at least one of the modified nucleoside disclosed herein. Any combination of base/sugar or linker can be incorporated into the polynucleotides of the invention and such modifications are taught in International Patent Publications WO2013052523 and WO2014093924, and U.S. Publ. Nos. US 20130115272 and US20150307542, the contents of each of which are incorporated herein by reference in its entirety.

11. Untranslated Regions (UTRs)

Untranslated regions (UTRs) are nucleic acid sections of a polynucleotide before a start codon (5'UTR) and after a stop codon (3'UTR) that are not translated. In some embodiments, a polynucleotide (e.g., a ribonucleic acid (RNA), e.g., a messenger RNA (mRNA)) of the invention comprising an open reading frame (ORF) encoding a Citrin polypeptide further comprises UTR (e.g., a 5'UTR or functional fragment thereof, a 3'UTR or functional fragment thereof, or a combination thereof).

A UTR can be homologous or heterologous to the coding region in a polynucleotide. In some embodiments, the UTR is homologous to the ORF encoding the Citrin polypeptide. In some embodiments, the UTR is heterologous to the ORF encoding the Citrin polypeptide. In some embodiments, the polynucleotide comprises two or more 5'UTRs or functional fragments thereof, each of which has the same or different nucleotide sequences. In some embodiments, the polynucleotide comprises two or more 3'UTRs or functional fragments thereof, each of which has the same or different nucleotide sequences.

In some embodiments, the 5'UTR or functional fragment thereof, 3' UTR or functional fragment thereof, or any combination thereof is sequence optimized.

In some embodiments, the 5'UTR or functional fragment thereof, 3' UTR or functional fragment thereof, or any combination thereof comprises at least one chemically modified nucleobase, e.g., 1-methylpseudouridine or 5-methoxyuracil.

UTRs can have features that provide a regulatory role, e.g., increased or decreased stability, localization and/or translation efficiency. A polynucleotide comprising a UTR can be administered to a cell, tissue, or organism, and one or more regulatory features can be measured using routine methods. In some embodiments, a functional fragment of a 5'UTR or 3'UTR comprises one or more regulatory features of a full length 5' or 3' UTR, respectively.

Natural 5'UTRs bear features that play roles in translation initiation. They harbor signatures like Kozak sequences that are commonly known to be involved in the process by which the ribosome initiates translation of many genes. Kozak sequences have the consensus CCR(A/G)CCAUGG, where R is a purine (adenine or guanine) three bases upstream of the start codon (AUG), which is followed by another 'G'. 5'UTRs also have been known to form secondary structures that are involved in elongation factor binding.

By engineering the features typically found in abundantly expressed genes of specific target organs, one can enhance the stability and protein production of a polynucleotide. For example, introduction of 5'UTR of liver-expressed mRNA, such as albumin, serum amyloid A, Apolipoprotein A/B/E, transferrin, alpha fetoprotein, erythropoietin, or Factor VIII, can enhance expression of polynucleotides in hepatic cell lines or liver. Likewise, use of 5'UTR from other tissue-specific mRNA to improve expression in that tissue is possible for muscle (e.g., MyoD, Myosin, Myoglobin, Myogenin, Herculin), for endothelial cells (e.g., Tie-1, CD36), for myeloid cells (e.g., C/EBP, AML1, G-CSF, GM-CSF, CD11b, MSR, Fr-1, i-NOS), for leukocytes (e.g., CD45, CD18), for adipose tissue (e.g., CD36, GLUT4, ACRP30, adiponectin) and for lung epithelial cells (e.g., SP-A/B/C/D).

In some embodiments, UTRs are selected from a family of transcripts whose proteins share a common function, structure, feature or property. For example, an encoded polypeptide can belong to a family of proteins (i.e., that share at least one function, structure, feature, localization, origin, or expression pattern), which are expressed in a particular cell, tissue or at some time during development. The UTRs from any of the genes or mRNA can be swapped for any other UTR of the same or different family of proteins to create a new polynucleotide.

In some embodiments, the 5'UTR and the 3'UTR can be heterologous. In some embodiments, the 5'UTR can be derived from a different species than the 3'UTR In some embodiments, the 3'UTR can be derived from a different species than the 5'UTR.

Co-owned International Patent Application No. PCT/US2014/021522 (Publ. No. WO/2014/164253, incorporated herein by reference in its entirety) provides a listing of exemplary UTRs that can be utilized in the polynucleotide of the present invention as flanking regions to an ORF.

Exemplary UTRs of the application include, but are not limited to, one or more 5'UTR and/or 3'UTR derived from the nucleic acid sequence of: a globin, such as an α- or β-globin (e.g., a *Xenopus*, mouse, rabbit, or human globin); a strong Kozak translational initiation signal; a CYBA (e.g., human cytochrome b-245 α polypeptide); an albumin (e.g., human albumin7); a HSD17B4 (hydroxysteroid (17-β) dehydrogenase); a virus (e.g., a tobacco etch virus (TEV), a Venezuelan equine encephalitis virus (VEEV), a Dengue virus, a cytomegalovirus (CMV) (e.g., CMV immediate early 1 (IE1)), a hepatitis virus (e.g., hepatitis B virus), a sindbis virus, or a PAV barley yellow dwarf virus); a heat shock protein (e.g., hsp70); a translation initiation factor (e.g., eIF4G); a glucose transporter (e.g., hGLUT1 (human glucose transporter 1)); an actin (e.g., human α or β actin); a GAPDH; a tubulin; a histone; a citric acid cycle enzyme; a topoisomerase (e.g., a 5'UTR of a TOP gene lacking the 5' TOP motif (the oligopyrimidine tract)); a ribosomal protein Large 32 (L32); a ribosomal protein (e.g., human or mouse ribosomal protein, such as, for example, rps9); an ATP synthase (e.g., ATP5A1 or the β subunit of mitochondrial H+-ATP synthase); a growth hormone e (e.g., bovine (bGH) or human (hGH)); an elongation factor (e.g., elongation factor 1 α1 (EEF1A1)); a manganese superoxide dismutase (MnSOD); a myocyte enhancer factor 2A (MEF2A); a β-F1-ATPase, a creatine kinase, a myoglobin, a granulocyte-colony stimulating factor (G-CSF); a collagen (e.g., collagen type I, alpha 2 (Col1A2), collagen type I, alpha 1 (Col1A1), collagen type VI, alpha 2 (Col6A2), collagen type VI, alpha 1 (Col6A1)); a ribophorin (e.g., ribophorin I (RPNI)); a low density lipoprotein receptor-related protein (e.g., LRP1); a cardiotrophin-like cytokine factor (e.g., Nnt1); calreticulin (Calr); a procollagen-lysine, 2-oxoglutarate 5-dioxygenase 1 (Plod 1); and a nucleobindin (e.g., Nucb1).

In some embodiments, the 5'UTR is selected from the group consisting of a β-globin 5'UTR; a 5'UTR containing a strong Kozak translational initiation signal; a cytochrome b-245 α polypeptide (CYBA) 5'UTR; a hydroxysteroid (17-β) dehydrogenase (HSD17B4) 5'UTR; a Tobacco etch virus (TEV) 5'UTR; a Venezuelen equine encephalitis virus (TEEV) 5'UTR; a 5' proximal open reading frame of rubella virus (RV) RNA encoding nonstructural proteins; a Dengue virus (DEN) 5'UTR; a heat shock protein 70 (Hsp70) 5'UTR; a eIF4G 5'UTR; a GLUT1 5'UTR; functional fragments thereof and any combination thereof.

In some embodiments, the 3'UTR is selected from the group consisting of a β-globin 3'UTR; a CYBA 3'UTR; an albumin 3'UTR; a growth hormone (GH) 3'UTR; a VEEV 3'UTR; a hepatitis B virus (HBV) 3'UTR; α-globin 3'UTR; a DEN 3'UTR; a PAV barley yellow dwarf virus (BYDV-PAV) 3'UTR; an elongation factor 1 α1 (EEF1A1) 3'UTR; a manganese superoxide dismutase (MnSOD) 3'UTR; a β subunit of mitochondrial H(+)-ATP synthase (β-mRNA) 3'UTR; a GLUT1 3'UTR; a MEF2A 3'UTR; a β-F1-ATPase 3'UTR; functional fragments thereof and combinations thereof.

Wild-type UTRs derived from any gene or mRNA can be incorporated into the polynucleotides of the invention. In some embodiments, a UTR can be altered relative to a wild type or native UTR to produce a variant UTR, e.g., by changing the orientation or location of the UTR relative to the ORF; or by inclusion of additional nucleotides, deletion of nucleotides, swapping or transposition of nucleotides. In some embodiments, variants of 5' or 3' UTRs can be utilized, for example, mutants of wild type UTRs, or variants wherein one or more nucleotides are added to or removed from a terminus of the UTR.

Additionally, one or more synthetic UTRs can be used in combination with one or more non-synthetic UTRs. See, e.g., Mandal and Rossi, Nat. Protoc. 2013 8(3):568-82, and sequences available at www.addgene.org/Derrick_Rossi/, the contents of each are incorporated herein by reference in their entirety. UTRs or portions thereof can be placed in the same orientation as in the transcript from which they were selected or can be altered in orientation or location. Hence, a 5' and/or 3' UTR can be inverted, shortened, lengthened, or combined with one or more other 5' UTRs or 3' UTRs.

In some embodiments, the polynucleotide comprises multiple UTRs, e.g., a double, a triple or a quadruple 5'UTR or 3'UTR. For example, a double UTR comprises two copies of the same UTR either in series or substantially in series. For example, a double beta-globin 3'UTR can be used (see US2010/0129877, the contents of which are incorporated herein by reference in its entirety).

In certain embodiments, the polynucleotides of the invention comprise a 5'UTR and/or a 3'UTR selected from any of the UTRs disclosed herein. In some embodiments, the 5'UTR comprises:

```
5'UTR-001 (Upstream UTR)
                                          (SEQ ID NO. 30)
(GGGAAAUAAGAGAGAAAAGAAGAGUAAGAAGAAAUAUAAGAGCCACC);

5'UTR-002 (Upstream UTR)
                                          (SEQ ID NO. 31)
(GGGAGAUCAGAGAGAAAAGAAGAGUAAGAAGAAAUAUAAGAGCCACC);

5'UTR-003 (Upstream UTR)
(SEQ ID NO. 32);

5'UTR-004 (Upstream UTR)
                                          (SEQ ID NO. 33)
(GGGAGACAAGCUUGGCAUUCCGGUACUGUUGGUAAAGCCACC);

5'UTR-005 (Upstream UTR)
                                          (SEQ ID NO. 34)
(GGGAGAUCAGAGAGAAAAGAAGAGUAAGAAGAAAUAUAAGAGCCACC);

5'UTR-006 (Upstream UTR)
(SEQ ID NO. 35);

5'UTR-007 (Upstream UTR)
                                          (SEQ ID NO. 36)
(GGGAGACAAGCUUGGCAUUCCGGUACUGUUGGUAAAGCCACC);

5'UTR-008 (Upstream UTR)
                                          (SEQ ID NO. 37)
(GGGAAUUAACAGAGAAAAGAAGAGUAAGAAGAAAUAUAAGAGCCACC);

5'UTR-009 (Upstream UTR)
                                          (SEQ ID NO. 38)
(GGGAAAUUAGACAGAAAAGAAGAGUAAGAAGAAAUAUAAGAGCCACC);

UTR 5'UTR-010, Upstream
                                          (SEQ ID NO. 39)
(GGGAAAUAAGAGAGUAAAGAACAGUAAGAAGAAAUAUAAGAGCCACC);

5'UTR-011 (Upstream UTR)
                                          (SEQ ID NO. 40)
(GGGAAAAAGAGAGAAAAGAAGACUAAGAAGAAAUAUAAGAGCCACC);
```

5'UTR-012 (Upstream UTR)
(SEQ ID NO. 41)
(GGGAAAUAAGAGAGAAAAGAAGAGUAAGAAGAUAUAUAAGAGCCACC);

5'UTR-013 (Upstream UTR)
(SEQ ID NO. 42)
(GGGAAAUAAGAGACAAAACAAGAGUAAGAAGAAAUAUAAGAGCCACC);

5'UTR-014 (Upstream UTR)
(SEQ ID NO. 43)
(GGGAAAUUAGAGAGUAAAGAACAGUAAGUAGAAUUAAAAGAGCCACC);

5'UTR-15 (Upstream UTR)
(SEQ ID NO. 44)
(GGGAAAUAAGAGAGAAUAGAAGAGUAAGAAGAAAUAUAAGAGCCACC);

5'UTR-016 (Upstream UTR)
(SEQ ID NO. 45)
(GGGAAAUAAGAGAGAAAAGAAGAGUAAGAAGAAAAUUAAGAGCCACC);

5'UTR-017 (Upstream UTR)
(SEQ ID NO. 46)
(GGGAAAUAAGAGAGAAAAGAAGAGUAAGAAGAAAUUUAAGAGCCACC);
or 5'UTR-018 (Upstream UTR)
(SEQ ID NO. 47)
(UCAAGCUUUUGGACCCUCGUACAGAAGCUAAUACGACUCACUAUAGGGA
AAUAAGAGAGAAAAGAAGAGUAAGAAGAAAUAUAAGAGCCACC).

In some embodiments, the 3'UTR comprises:

142-3p 3' UTR (UTR including miR142-3p
binding site)
(SEQ ID NO. 48)
(UGAUAAUAGUCCAUAAAGUAGGAAACACUACAGCUGGAGCCUCGGUGGC

CAUGCUUCUUGCCCCUUGGGCCUCCCCCCAGCCCCUCCUCCCCUUCCUGC

ACCCGUACCCCCGUGGUCUUUGAAUAAAGUCUGAGUGGGCGGC);

142-3p 3' UTR (UTR including miR142-3p
binding site)
(SEQ ID NO. 49)
(UGAUAAUAGGCUGGAGCCUCGGUGGCUCCAUAAAGUAGGAAACACUACA

CAUGCUUCUUGCCCCUUGGGCCUCCCCCCAGCCCCUCCUCCCCUUCCUGC

ACCCGUACCCCCGUGGUCUUUGAAUAAAGUCUGAGUGGGCGGC);

142-3p 3' UTR (UTR including miR142-3p
binding site)
(SEQ ID NO. 50)
(UGAUAAUAGGCUGGAGCCUCGGUGGCCAUGCUUCUUGCCCCUUCCAUAA

AGUAGGAAACACUACAUGGGCCUCCCCCCAGCCCCUCCUCCCCUUCCUGC

ACCCGUACCCCCGUGGUCUUUGAAUAAAGUCUGAGUGGGCGGC);

142-3p 3' UTR (UTR including miR142-3p
binding site)
(SEQ ID NO. 51)
(UGAUAAUAGGCUGGAGCCUCGGUGGCCAUGCUUCUUGCCCCUUGGGCCU

CCCCCCAGUCCAUAAAGUAGGAAACACUACACCCCUCCUCCCCUUCCUGC

ACCCGUACCCCCGUGGUCUUUGAAUAAAGUCUGAGUGGGCGGC);

142-3p 3' UTR (UTR including miR142-3p
binding site)
(SEQ ID NO. 52)
(UGAUAAUAGGCUGGAGCCUCGGUGGCCAUGCUUCUUGCCCCUUGGGCCU

CCCCCCAGCCCCUCCUCCCCUUCUCCAUAAAGUAGGAAACACUACACUGC

ACCCGUACCCCCGUGGUCUUUGAAUAAAGUCUGAGUGGGCGGC);

142-3p 3' UTR (UTR including miR142-3p
binding site)
(SEQ ID NO. 53)
(UGAUAAUAGGCUGGAGCCUCGGUGGCCAUGCUUCUUGCCCCUUGGGCCU

CCCCCCAGCCCCUCCUCCCCUUCCUGCACCCGUACCCCCUCCAUAAAGUA

GGAAACACUACAGUGGUCUUUGAAUAAAGUCUGAGUGGGCGGC);

142-3p 3' UTR (UTR including miR142-3p
binding site)
(SEQ ID NO. 54)
(UGAUAAUAGGCUGGAGCCUCGGUGGCCAUGCUUCUUGCCCCUUGGGCCU

CCCCCAGCCCCUCCUCCCCUUCCUGCACCCGUACCCCCGUGGUCUUUGA

AUAAAGUUCCAUAAAGUAGGAAACACUACACUGAGUGGGCGGC);

3'UTR (miR142 + miR126 binding sites variant 1)
(SEQ ID NO. 105)
UGAUAAUAGUCCAUAAAGUAGGAAACACUACAGCUGGAGCCUCGGUGGCC

AUGCUUCUUGCCCCUUGGGCCUCCCCCCAGCCCCUCCUCCCCUUCCUGCA

CCCGUACCCCCGCAUUAUUACUCACGGUACGAGUGGUCUUUGAAUAAAG

UCUGAGUGGGCGGC;

3'UTR (miR142 + miR126 binding sites variant 2)
(SEQ ID NO. 147)
UGAUAAUAGUCCAUAAAGUAGGAAACACUACAGCUGGAGCCUCGGUGGCC

UAGCUUCUUGCCCCUUGGGCCUCCCCCCAGCCCCUCCUCCCCUUCCUGCA

CCCGUACCCCCGCAUUAUUACUCACGGUACGAGUGGUCUUUGAAUAAAG

UCUGAGUGGGCGGC;
or

3'UTR (miR142 binding site)
(SEQ ID NO. 148)
UGAUAAUAGGCUGGAGCCUCGGUGGCCUAGCUUCUUGCCCCUUGGGCCUC

CCCCAGCCCCUCCUCCCCUUCCUGCACCCGUACCCCCUCCAUAAAGUAG

GAAACACUACAGUGGUCUUUGAAUAAAGUCUGAGUGGGCGGC.

In certain embodiments, the 5'UTR and/or 3'UTR sequence of the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5'UTR sequences comprising any of SEQ ID NOs: 30-47, 79, 120-122, 126-128 and/or 3'UTR sequences comprises any of SEQ ID NOs: 48-72, 80, 81, 102-105, 108-117, 124, 125, 147-157, and any combination thereof.

The polynucleotides of the invention can comprise combinations of features. For example, the ORF can be flanked by a 5'UTR that comprises a strong Kozak translational initiation signal and/or a 3'UTR comprising an oligo(dT) sequence for templated addition of a poly-A tail. A 5'UTR can comprise a first polynucleotide fragment and a second polynucleotide fragment from the same and/or different UTRs (see, e.g., US2010/0293625, herein incorporated by reference in its entirety).

Other non-UTR sequences can be used as regions or subregions within the polynucleotides of the invention. For example, introns or portions of intron sequences can be incorporated into the polynucleotides of the invention. Incorporation of intronic sequences can increase protein production as well as polynucleotide expression levels. In some embodiments, the polynucleotide of the invention comprises an internal ribosome entry site (IRES) instead of or in addition to a UTR (see, e.g., Yakubov et al., Biochem. Biophys. Res. Commun. 2010 394(1):189-193, the contents of which are incorporated herein by reference in their entirety). In some embodiments, the polynucleotide comprises an IRES instead of a 5'UTR sequence. In some embodiments, the polynucleotide comprises an ORF and a viral capsid sequence. In some embodiments, the polynucleotide comprises a synthetic 5'UTR in combination with a non-synthetic 3'UTR.

In some embodiments, the UTR can also include at least one translation enhancer polynucleotide, translation enhancer element, or translational enhancer elements (collectively, "TEE," which refers to nucleic acid sequences that increase the amount of polypeptide or protein produced from a polynucleotide. As a non-limiting example, the TEE can include those described in US2009/0226470, incorporated herein by reference in its entirety, and others known in the art. As a non-limiting example, the TEE can be located between the transcription promoter and the start codon. In some embodiments, the 5'UTR comprises a TEE.

In one aspect, a TEE is a conserved element in a UTR that can promote translational activity of a nucleic acid such as, but not limited to, cap-dependent or cap-independent translation.

In one non-limiting example, the TEE comprises the TEE sequence in the 5'-leader of the Gtx homeodomain protein. See Chappell et al., PNAS 2004 101:9590-9594, incorporated herein by reference in its entirety.

In some embodiments, the polynucleotide of the invention comprises one or multiple copies of a TEE. The TEE in a translational enhancer polynucleotide can be organized in one or more sequence segments. A sequence segment can harbor one or more of the TEES provided herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the TEE provided herein, identical or different number of copies of each of the TEE, and/or identical or different organization of the TEE within each sequence segment. In one embodiment, the polynucleotide of the invention comprises a translational enhancer polynucleotide sequence. Non-limiting examples of TEE sequences are described in U.S. Publication 2014/0200261, the contents of which are incorporated herein by reference in their entirety.

12. MicroRNA (miRNA) Binding Sites

Polynucleotides of the invention can include regulatory elements, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. In some embodiments, polynucleotides including such regulatory elements are referred to as including "sensor sequences". Non-limiting examples of sensor sequences are described in U.S. Publication 2014/0200261, the contents of which are incorporated herein by reference in their entirety.

In some embodiments, a polynucleotide (e.g., a ribonucleic acid (RNA), e.g., a messenger RNA (mRNA)) of the invention comprises an open reading frame (ORF) encoding a polypeptide of interest and further comprises one or more miRNA binding site(s). Inclusion or incorporation of miRNA binding site(s) provides for regulation of polynucleotides of the invention, and in turn, of the polypeptides encoded therefrom, based on tissue-specific and/or cell-type specific expression of naturally-occurring miRNAs.

The present invention also provides pharmaceutical compositions and formulations that comprise any of the polynucleotides described above. In some embodiments, the composition or formulation further comprises a delivery agent.

In some embodiments, the composition or formulation can contain a polyribonucleotide comprising a sequence optimized nucleic acid sequence disclosed herein which encodes a polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a polypeptide. In some embodiments, the polyribonucleotide further comprises a miRNA binding site, e.g., a miRNA binding site that binds miR-126, miR-142, miR-144, miR-146, miR-150, miR-155, miR-16, miR-21, miR-223, miR-24, miR-27 and miR-26a.

A miRNA, e.g., a natural-occurring miRNA, is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA. In some embodiments, a miRNA seed can comprise 7 nucleotides (e.g., nucleotides 2-8 of the mature miRNA), wherein the seed-complementary site in the corresponding miRNA binding site is flanked by an adenosine (A) opposed to miRNA position 1. In some embodiments, a miRNA seed can comprise 6 nucleotides (e.g., nucleotides 2-7 of the mature miRNA), wherein the seed-complementary site in the corresponding miRNA binding site is flanked by an adenosine (A) opposed to miRNA position 1. See, for example, Grimson A, Farh K K, Johnston W K, Garrett-Engele P. Lim L P, Bartel D P; Mol Cell. 2007 Jul. 6; 27(1):91-105. miRNA profiling of the target cells or tissues can be conducted to determine the presence or absence of miRNA in the cells or tissues. In some embodiments, a polynucleotide (e.g., a ribonucleic acid (RNA), e.g., a messenger RNA (mRNA)) of the invention comprises one or more microRNA binding sites, microRNA target sequences, microRNA complementary sequences, or microRNA seed complementary sequences. Such sequences can correspond to, e.g., have complementarity to, any known microRNA such as those taught in US Publication US2005/0261218 and US Publication US2005/0059005, the contents of each of which are incorporated herein by reference in their entirety.

microRNAs derive enzymatically from regions of RNA transcripts that fold back on themselves to form short hairpin structures often termed a pre-miRNA (precursor-miRNA). A pre-miRNA typically has a two-nucleotide overhang at its 3' end, and has 3' hydroxyl and 5' phosphate groups. This precursor-mRNA is processed in the nucleus and subsequently transported to the cytoplasm where it is further processed by DICER (a RNase III enzyme), to form a mature microRNA of approximately 22 nucleotides. The mature microRNA is then incorporated into a ribonuclear particle to form the RNA-induced silencing complex, RISC, which mediates gene silencing. Art-recognized nomenclature for mature miRNAs typically designates the arm of the pre-miRNA from which the mature miRNA derives; "5p" means the microRNA is from the 5 prime arm of the pre-miRNA hairpin and "3p" means the microRNA is from the 3 prime end of the pre-miRNA hairpin. A miR referred to by number herein can refer to either of the two mature microRNAs originating from opposite arms of the same pre-miRNA (e.g., either the 3p or 5p microRNA). All miRs referred to herein are intended to include both the 3p and 5p arms/sequences, unless particularly specified by the 3p or 5p designation.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the invention comprising an ORF encoding a polypeptide of interest and further comprises one or more miRNA binding site(s). In exemplary embodiments, a 5'UTR and/or 3'UTR of the polynucleotide (e.g., a ribonucleic acid (RNA), e.g., a messenger RNA (mRNA)) comprises the one or more miRNA binding site(s).

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the invention, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide long miRNA sequence, to a 19-23 nucleotide long miRNA sequence, or to a 22 nucleotide long miRNA sequence. A miRNA binding site can be complementary to only a portion of a miRNA, e.g., to a portion less than 1, 2, 3, or 4 nucleotides of the full length of a naturally-occurring miRNA sequence, or to a portion less than 1, 2, 3, or 4 nucleotides shorter than a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with an miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the invention, the polynucleotide can be targeted for degradation or reduced translation, provided the miRNA in question is available. This can reduce off-target effects upon delivery of the polynucleotide. For example, if a polynucleotide of the invention is not intended to be delivered to a tissue or cell but ends up is said tissue or cell, then a miRNA abundant in the tissue or cell can inhibit the expression of the gene of interest if one or multiple binding sites of the miRNA are engineered into the 5'UTR and/or 3'UTR of the polynucleotide. Thus, in some embodiments, incorporation of one or more miRNA binding sites into an mRNA of the disclosure may reduce the hazard of off-target effects upon nucleic acid molecule delivery and/or enable tissue-specific regulation of expression of a polypeptide encoded by the mRNA. In yet other embodiments, incorporation of one or more miRNA binding sites into an mRNA of the disclosure can modulate immune responses upon nucleic acid delivery in vivo. In further embodiments, incorporation of one or more miRNA binding sites into an mRNA of the disclosure can modulate accelerated blood clearance (ABC) of lipid-comprising compounds and compositions described herein.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

Regulation of expression in multiple tissues can be accomplished through introduction or removal of one or more miRNA binding sites, e.g., one or more distinct miRNA binding sites. The decision whether to remove or insert a miRNA binding site can be made based on miRNA expression patterns and/or their profilings in tissues and/or cells in development and/or disease. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

miRNAs and miRNA binding sites can correspond to any known sequence, including non-limiting examples described in U.S. Publication Nos. 2014/0200261, 2005/0261218, and 2005/0059005, each of which are incorporated herein by reference in their entirety.

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polynucleotide can be shut-off by adding miR-142 binding sites to the 3'-UTR of the polynucleotide, enabling more stable gene transfer in tissues and cells. miR-142 efficiently degrades exogenous polynucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5'UTR and/or 3'UTR of a polynucleotide of the invention can selectively repress gene expression in antigen presenting cells through miR-142 mediated degradation, limiting antigen presentation in antigen presenting cells (e.g., dendritic cells) and thereby preventing antigen-mediated immune response after the delivery of the polynucleotide. The polynucleotide is then stably expressed in target tissues or cells without triggering cytotoxic elimination.

In one embodiment, binding sites for miRNAs that are known to be expressed in immune cells, in particular, antigen presenting cells, can be engineered into a polynucleotide of the invention to suppress the expression of the polynucleotide in antigen presenting cells through miRNA mediated RNA degradation, subduing the antigen-mediated immune response. Expression of the polynucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5'UTR and/or 3'UTR of a polynucleotide of the invention.

To further drive the selective degradation and suppression in APCs and macrophage, a polynucleotide of the invention can include a further negative regulatory element in the 5'UTR and/or 3'UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. MiRNA binding sites from any liver specific miRNA can be introduced to or removed from a polynucleotide of the invention to regulate expression of the polynucleotide in the liver. Liver specific miRNA binding sites can be engineered alone or further in combination with immune cell (e.g., APC) miRNA binding sites in a polynucleotide of the invention.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. miRNA binding sites from any lung specific miRNA can be introduced to or removed from a polynucleotide of the invention to regulate expression of the polynucleotide in the lung. Lung specific miRNA binding sites can be engineered alone or further in combination with immune cell (e.g., APC) miRNA binding sites in a polynucleotide of the invention.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. mMiRNA binding sites from any heart specific microRNA can be introduced to or removed from a polynucleotide of the invention to regulate expression of the polynucleotide in the heart. Heart specific miRNA binding sites can be engineered alone or further in combination with immune cell (e.g., APC) miRNA binding sites in a polynucleotide of the invention.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p. miRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. miRNA binding sites from any CNS specific miRNA can be introduced to or removed from a polynucleotide of the invention to regulate expression of the polynucleotide in the nervous system. Nervous system specific miRNA binding sites can be engineered alone or further in combination with immune cell (e.g., APC) miRNA binding sites in a polynucleotide of the invention.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. MiRNA binding sites from any pancreas specific miRNA can be introduced to or removed from a polynucleotide of the invention to regulate expression of the polynucleotide in the pancreas. Pancreas specific miRNA binding sites can be engineered alone or further in combination with immune cell (e.g. APC) miRNA binding sites in a polynucleotide of the invention.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. miRNA binding sites from any kidney specific miRNA can be introduced to or removed from a polynucleotide of the invention to regulate expression of the polynucleotide in the kidney. Kidney specific miRNA binding sites can be engineered alone or further in combination with immune cell (e.g., APC) miRNA binding sites in a polynucleotide of the invention.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polynucleotide of the invention to regulate expression of the polynucleotide in the muscle. Muscle specific miRNA binding sites can be engineered alone or further in combination with immune cell (e.g., APC) miRNA binding sites in a polynucleotide of the invention.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA, 2012, 18, 472-484, herein incorporated by reference in its entirety). miRNA binding sites from any endothelial cell specific miRNA can be introduced to or removed from a polynucleotide of the invention to regulate expression of the polynucleotide in the endothelial cells.

miRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. miRNA binding sites from any epithelial cell specific miRNA can be introduced to or removed from a polynucleotide of the invention to regulate expression of the polynucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008,18, 610-621; Yoo J K et al., Stem Cells Dev. 2012, 21(11), 2049-2057, each of which is herein incorporated by reference in its entirety). MiRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-5481, miR-548m, miR-548n, miR-548o-3p, miR-548o-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008,18, 610-621; Goff L A et al., PLoS One, 2009, 4:e7192; Bar M et al., Stem cells, 2008, 26, 2496-2505, the content of each of which is incorporated herein by reference in its entirety).

In one embodiment, the binding sites of embryonic stem cell specific miRNAs can be included in or removed from the 3'UTR of a polynucleotide of the invention to modulate the development and/or differentiation of embryonic stem cells, to inhibit the senescence of stem cells in a degenerative condition (e.g. degenerative diseases), or to stimulate the senescence and apoptosis of stem cells in a disease condition (e.g. cancer stem cells).

In some embodiments, miRNAs are selected based on expression and abundance in immune cells of the hematopoietic lineage, such as B cells, T cells, macrophages, dendritic cells, and cells that are known to express TLR7/TLR8 and/or able to secrete cytokines such as endothelial cells and platelets. In some embodiments, the miRNA set thus includes miRs that may be responsible in part for the immunogenicity of these cells, and such that a corresponding miR-site incorporation in polynucleotides of the present invention (e.g., mRNAs) could lead to destabilization of the mRNA and/or suppression of translation from these mRNAs in the specific cell type. Non-limiting representative examples include miR-142, miR-144, miR-150, miR-155 and miR-223, which are specific for many of the hematopoietic cells; miR-142, miR150, miR-16 and miR-223, which are expressed in B cells; miR-223, miR-451, miR-26a, miR-16, which are expressed in progenitor hematopoietic cells; and miR-126, which is expressed in plasmacytoid dendritic cells, platelets and endothelial cells. For further discussion of tissue expression of miRs see e.g., Teruel-Montoya, R. et al. (2014) PLoS One 9:e102259; Landgraf, P. et al. (2007) Cell 129:1401-1414; Bissels, U. et al. (2009) RNA 15:2375-2384. Any one miR-site incorporation in the 3'UTR and/or 5' UTR may mediate such effects in multiple cell types of interest (e.g., miR-142 is abundant in both B cells and dendritic cells).

In some embodiments, it may be beneficial to target the same cell type with multiple miRs and to incorporate binding sites to each of the 3p and 5p arm if both are abundant (e.g., both miR-142-3p and miR142-5p are abundant in hematopoietic stem cells). Thus, in certain embodiments, polynucleotides of the invention contain two or more (e.g., two, three, four or more) miR bindings sites from: (i) the group consisting of miR-142, miR-144, miR-150, miR-155 and miR-223 (which are expressed in many hematopoietic cells); or (ii) the group consisting of miR-142, miR150, miR-16 and miR-223 (which are expressed in B cells); or the group consisting of miR-223, miR-451, miR-26a, miR-16 (which are expressed in progenitor hematopoietic cells).

In some embodiments, it may also be beneficial to combine various miRs such that multiple cell types of interest are targeted at the same time (e.g., miR-142 and miR-126 to target many cells of the hematopoietic lineage and endothelial cells). Thus, for example, in certain embodiments, polynucleotides of the invention comprise two or more (e.g., two, three, four or more) miRNA bindings sites, wherein: (i) at least one of the miRs targets cells of the hematopoietic lineage (e.g., miR-142, miR-144, miR-150, miR-155 or miR-223) and at least one of the miRs targets plasmacytoid dendritic cells, platelets or endothelial cells (e.g., miR-126); or (ii) at least one of the miRs targets B cells (e.g., miR-142, miR150, miR-16 or miR-223) and at least one of the miRs targets plasmacytoid dendritic cells, platelets or endothelial cells (e.g., miR-126); or (iii) at least one of the miRs targets progenitor hematopoietic cells (e.g., miR-223, miR-451, miR-26a or miR-16) and at least one of the miRs targets plasmacytoid dendritic cells, platelets or endothelial cells (e.g., miR-126); or (iv) at least one of the miRs targets cells of the hematopoietic lineage (e.g., miR-142, miR-144, miR-150, miR-155 or miR-223), at least one of the miRs targets B cells (e.g., miR-142, miR150, miR-16 or miR-223) and at least one of the miRs targets plasmacytoid dendritic cells, platelets or endothelial cells (e.g., miR-126); or any other possible combination of the foregoing four classes of miR binding sites (i.e., those targeting the hematopoietic lineage, those targeting B cells, those targeting progenitor hematopoietic cells and/or those targeting plamacytoid dendritic cells/platelets/endothelial cells).

In one embodiment, to modulate immune responses, polynucleotides of the present invention can comprise one or more miRNA binding sequences that bind to one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) reduces or inhibits immune cell activation (e.g., B cell activation, as measured by frequency of activated B cells) and/or cytokine production (e.g., production of IL-6, IFN-γ and/or TNFα). Furthermore, it has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) can reduce or inhibit an anti-drug antibody (ADA) response against a protein of interest encoded by the mRNA.

In another embodiment, to modulate accelerated blood clearance of an polynucleotide delivered in a lipid-comprising compound or composition, polynucleotides of the invention can comprise one or more miR binding sequences that bind to one or more miRNAs expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miR binding sites reduces or inhibits accelerated blood clearance (ABC) of the lipid-comprising compound or composition for use in delivering the mRNA. Furthermore, it has now been discovered that incorporation of one or more miR binding sites into an mRNA reduces serum levels of anti-PEG anti-IgM (e.g, reduces or inhibits the acute production of IgMs that recognize polyethylene glycol (PEG) by B cells) and/or reduces or inhibits proliferation and/or activation of plasmacytoid dendritic cells following administration of a lipid-comprising compound or composition comprising the mRNA.

In some embodiments, miR sequences may correspond to any known microRNA expressed in immune cells, including but not limited to those taught in US Publication US2005/0261218 and US Publication US2005/0059005, the contents of which are incorporated herein by reference in their entirety. Non-limiting examples of miRs expressed in immune cells include those expressed in spleen cells, myeloid cells, dendritic cells, plasmacytoid dendritic cells, B cells, T cells and/or macrophages. For example, miR-142-3p, miR-142-5p, miR-16, miR-21, miR-223, miR-24 and miR-27 are expressed in myeloid cells, miR-155 is expressed in dendritic cells, B cells and T cells, miR-146 is upregulated in macrophages upon TLR stimulation and miR-126 is expressed in plasmacytoid dendritic cells. In certain embodiments, the miR(s) is expressed abundantly or preferentially in immune cells. For example, miR-142 (miR-142-3p and/or miR-142-5p), miR-126 (miR-126-3p and/or miR-126-5p), miR-146 (miR-146-3p and/or miR-146-5p) and miR-155 (miR-155-3p and/or miR155-5p) are expressed abundantly in immune cells. These microRNA sequences are known in the art and, thus, one of ordinary skill in the art can readily design binding sequences or target sequences to which these microRNAs will bind based upon Watson-Crick complementarity.

Accordingly, in various embodiments, polynucleotides of the present invention comprise at least one microRNA binding site for a miR selected from the group consisting of miR-142, miR-146, miR-155, miR-126, miR-16, miR-21, miR-223, miR-24 and miR-27. In another embodiment, the mRNA comprises at least two miR binding sites for microRNAs expressed in immune cells. In various embodiments, the polynucleotide of the invention comprises 1-4, one, two, three or four miR binding sites for microRNAs expressed in immune cells. In another embodiment, the polynucleotide of the invention comprises three miR binding sites. These miR binding sites can be for microRNAs selected from the group consisting of miR-142, miR-146, miR-155, miR-126, miR-16, miR-21, miR-223, miR-24, miR-27, and combinations thereof. In one embodiment, the polynucleotide of the invention comprises two or more (e.g., two, three, four) copies of the same miR binding site expressed in immune cells, e.g., two or more copies of a miR binding site selected from the group of miRs consisting of miR-142, miR-146, miR-155, miR-126, miR-16, miR-21, miR-223, miR-24, miR-27.

In one embodiment, the polynucleotide of the invention comprises three copies of the same miR binding site. In certain embodiments, use of three copies of the same miR binding site can exhibit beneficial properties as compared to use of a single miR binding site. Non-limiting examples of sequences for 3' UTRs containing three miR bindings sites are shown in SEQ ID NO: 108 (three miR-142-3p binding sites) and SEQ ID NO: 110 (three miR-142-5p binding sites).

In another embodiment, the polynucleotide of the invention comprises two or more (e.g., two, three, four) copies of at least two different miR binding sites expressed in immune cells. Non-limiting examples of sequences of 3' UTRs containing two or more different miR binding sites are shown in SEQ ID NO: 105 (one miR-142-3p binding site and one miR-126-3p binding site), SEQ ID NO: 111 (two miR-142-5p binding sites and one miR-142-3p binding sites) and SEQ ID NO: 114 (two miR-155-5p binding sites and one miR-142-3p binding sites).

In another embodiment, the polynucleotide of the invention comprises at least two miR binding sites for microRNAs expressed in immune cells, wherein one of the miR binding sites is for miR-142-3p. In various embodiments, the polynucleotide of the invention comprises binding sites for miR-142-3p and miR-155 (miR-155-3p or miR-155-5p), miR-142-3p and miR-146 (miR-146-3 or miR-146-5p), or miR-142-3p and miR-126 (miR-126-3p or miR-126-5p).

In another embodiment, the polynucleotide of the invention comprises at least two miR binding sites for microRNAs expressed in immune cells, wherein one of the miR binding sites is for miR-126-3p. In various embodiments, the polynucleotide of the invention comprises binding sites for miR-126-3p and miR-155 (miR-155-3p or miR-155-5p), miR-126-3p and miR-146 (miR-146-3p or miR-146-5p), or miR-126-3p and miR-142 (miR-142-3p or miR-142-5p).

In another embodiment, the polynucleotide of the invention comprises at least two miR binding sites for microRNAs expressed in immune cells, wherein one of the miR binding sites is for miR-142-5p. In various embodiments, the polynucleotide of the invention comprises binding sites for miR-142-5p and miR-155 (miR-155-3p or miR-155-5p), miR-142-5p and miR-146 (miR-146-3 or miR-146-5p), or miR-142-5p and miR-126 (miR-126-3p or miR-126-5p).

In yet another embodiment, the polynucleotide of the invention comprises at least two miR binding sites for microRNAs expressed in immune cells, wherein one of the miR binding sites is for miR-155-5p. In various embodiments, the polynucleotide of the invention comprises binding sites for miR-155-5p and miR-142 (miR-142-3p or miR-142-5p), miR-155-5p and miR-146 (miR-146-3 or miR-146-5p), or miR-155-5p and miR-126 (miR-126-3p or miR-126-5p).

miRNA can also regulate complex biological processes such as angiogenesis (e.g., miR-132) (Anand and Cheresh Curr Opin Hematol 2011 18:171-176). In the polynucleotides of the invention, miRNA binding sites that are involved in such processes can be removed or introduced, in order to tailor the expression of the polynucleotides to biologically relevant cell types or relevant biological processes. In this context, the polynucleotides of the invention are defined as auxotrophic polynucleotides.

In some embodiments, a polynucleotide of the invention comprises a miRNA binding site, wherein the miRNA binding site comprises one or more nucleotide sequences selected from TABLE 3 and TABLE 4, including one or more copies of any one or more of the miRNA binding site sequences. In some embodiments, a polynucleotide of the invention further comprises at least one, two, three, four, five, six, seven, eight, nine, ten, or more of the same or different miRNA binding sites selected from TABLE 3 and TABLE 4, including any combination thereof.

In some embodiments, the miRNA binding site binds to miR-142 or is complementary to miR-142. In some embodiments, the miR-142 comprises SEQ ID NO:73. In some embodiments, the miRNA binding site binds to miR-142-3p or miR-142-5p. In some embodiments, the miR-142-3p binding site comprises SEQ ID NO:75. In some embodiments, the miR-142-5p binding site comprises SEQ ID NO:77. In some embodiments, the miRNA binding site comprises a nucleotide sequence at least 80%, at least 85%, at least 90%, at least 95%, or 100% identical to SEQ ID NO:75 or SEQ ID NO:77.

In some embodiments, the miRNA binding site binds to miR-126 or is complementary to miR-126. In some embodiments, the miR-126 comprises SEQ ID NO: 142. In some embodiments, the miRNA binding site binds to miR-126-3p or miR-126-5p. In some embodiments, the miR-126-3p binding site comprises SEQ ID NO: 144. In some embodiments, the miR-126-5p binding site comprises SEQ ID NO: 146. In some embodiments, the miRNA binding site comprises a nucleotide sequence at least 80%, at least 85%, at least 90%, at least 95%, or 100% identical to SEQ ID NO: 144 or SEQ ID NO: 146.

In one embodiment, the 3' UTR comprises two miRNA binding sites, wherein a first miRNA binding site binds to miR-142 and a second miRNA binding site binds to miR-126. In a specific embodiment, the 3' UTR binding to miR-142 and miR-126 comprises, consists, or consists essentially of the sequence of SEQ ID NO: 105 or 147.

TABLE 3 miR-142, miR-126, and
miR-142 and miR-126 binding sites

| SEQ ID NO. | Description | Sequence |
|---|---|---|
| 73 | miR-142 | GACAGUGCAGUCACCCAUAAAGUAG AAAGCACUACUAACAGCACUGGAGG GUGUAGUGUUUCCUACUUUAUGGAU GAGUGUACUGUG |
| 74 | miR-142-3p | UGUAGUGUUUCCUACUUUAUGGA |
| 75 | miR-142-3p binding site | UCCAUAAAGUAGGAAACACUACA |
| 76 | miR-142-5p | CAUAAAGUAGAAAGCACUACU |
| 77 | miR-142-5p binding site | AGUAGUGCUUUCUACUUUAUG |
| 142 | miR-126 | CGCUGGCGACGGGACAUUAUUACUU UUGGUACGCGCUGUGACACUUCAAA CUCGUACCGUGAGUAAUAAUGCGCC GUCCACGGCA |
| 143 | miR-126-3p | UCGUACCGUGAGUAAUAAUGCG |
| 144 | miR-126-3p binding site | CGCAUUAUUACUCACGGUACGA |

TABLE 3-continued miR-142, miR-126, and
miR-142 and miR-126 binding sites

| SEQ ID NO. | Description | Sequence |
|---|---|---|
| 145 | miR-126-5p | CAUUAUUACUUUUGGUACGCG |
| 146 | miR-126-5p binding site | CGCGUACCAAAAGUAAUAAUG |

In some embodiments, a miRNA binding site is inserted in the polynucleotide of the invention in any position of the polynucleotide (e.g., the 5'UTR and/or 3'UTR). In some embodiments, the 5'UTR comprises a miRNA binding site. In some embodiments, the 3'UTR comprises a miRNA binding site. In some embodiments, the 5'UTR and the 3'UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

In some embodiments, a miRNA binding site is inserted in at least about 30 nucleotides downstream from the stop codon of an ORF in a polynucleotide of the invention comprising the ORF. In some embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of an ORF in a polynucleotide of the invention. In some embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of an ORF in a polynucleotide of the invention.

In some embodiments, a miRNA binding site is inserted within the 3' UTR immediately following the stop codon of the coding region within the polynucleotide of the invention, e.g., mRNA. In some embodiments, if there are multiple copies of a stop codon in the construct, a miRNA binding site is inserted immediately following the final stop codon. In some embodiments, a miRNA binding site is inserted further downstream of the stop codon, in which case there are 3' UTR bases between the stop codon and the miR binding site(s). In some embodiments, three non-limiting examples of possible insertion sites for a miR in a 3' UTR are shown in SEQ ID NOs: 115, 116, and 117, which show a 3' UTR sequence with a miR-142-3p site inserted in one of three different possible insertion sites, respectively, within the 3' UTR.

In some embodiments, one or more miRNA binding sites can be positioned within the 5' UTR at one or more possible insertion sites. For example, three non-limiting examples of possible insertion sites for a miR in a 5' UTR are shown in SEQ ID NOs: 120, 121, and 122, which show a 5' UTR sequence with a miR-142-3p site inserted into one of three different possible insertion sites, respectively, within the 5' UTR.

In one embodiment, a codon optimized open reading frame encoding a polypeptide of interest comprises a stop codon and the at least one microRNA binding site is located within the 3' UTR 1-100 nucleotides after the stop codon. In one embodiment, the codon optimized open reading frame encoding the polypeptide of interest comprises a stop codon and the at least one microRNA binding site for a miR expressed in immune cells is located within the 3' UTR 30-50 nucleotides after the stop codon. In another embodiment, the codon optimized open reading frame encoding the polypeptide of interest comprises a stop codon and the at least one microRNA binding site for a miR expressed in immune cells is located within the 3' UTR at least 50 nucleotides after the stop codon. In other embodiments, the codon optimized open reading frame encoding the polypeptide of interest comprises a stop codon and the at least one microRNA binding site for a miR expressed in immune cells is located within the 3' UTR immediately after the stop codon, or within the 3' UTR 15-20 nucleotides after the stop codon or within the 3' UTR 70-80 nucleotides after the stop codon. In other embodiments, the 3'UTR comprises more than one miRNA binding site (e.g., 2-4 miRNA binding sites), wherein there can be a spacer region (e.g., of 10-100, 20-70 or 30-50 nucleotides in length) between each miRNA binding site. In another embodiment, the 3' UTR comprises a spacer region between the end of the miRNA binding site(s) and the poly A tail nucleotides. For example, a spacer region of 10-100, 20-70 or 30-50 nucleotides in length can be situated between the end of the miRNA binding site(s) and the beginning of the poly A tail.

In one embodiment, a codon optimized open reading frame encoding a polypeptide of interest comprises a start codon and the at least one microRNA binding site is located within the 5' UTR 1-100 nucleotides before (upstream of) the start codon. In one embodiment, the codon optimized open reading frame encoding the polypeptide of interest comprises a start codon and the at least one microRNA binding site for a miR expressed in immune cells is located within the 5' UTR 10-50 nucleotides before (upstream of) the start codon. In another embodiment, the codon optimized open reading frame encoding the polypeptide of interest comprises a start codon and the at least one microRNA binding site for a miR expressed in immune cells is located within the 5' UTR at least 25 nucleotides before (upstream of) the start codon. In other embodiments, the codon optimized open reading frame encoding the polypeptide of interest comprises a start codon and the at least one microRNA binding site for a miR expressed in immune cells is located within the 5' UTR immediately before the start codon, or within the 5' UTR 15-20 nucleotides before the start codon or within the 5' UTR 70-80 nucleotides before the start codon. In other embodiments, the 5'UTR comprises more than one miRNA binding site (e.g., 2-4 miRNA binding sites), wherein there can be a spacer region (e.g., of 10-100, 20-70 or 30-50 nucleotides in length) between each miRNA binding site.

In one embodiment, the 3' UTR comprises more than one stop codon, wherein at least one miRNA binding site is positioned downstream of the stop codons. For example, a 3' UTR can comprise 1, 2 or 3 stop codons. Non-limiting examples of triple stop codons that can be used include: UGAUAAUAG, UGAUAGUAA, UAAUGAUAG, UGAUAAUAA, UGAUAGUAG, UAAUGAUGA, UAAUAGUAG, UGAUGAUGA, UAAUAAUAA and UAGUAGUAG. Within a 3' UTR, for example, 1, 2, 3 or 4 miRNA binding sites, e.g., miR-142-3p binding sites, can be positioned immediately adjacent to the stop codon(s) or at any number of nucleotides downstream of the final stop codon. When the 3' UTR comprises multiple miRNA binding sites, these binding sites can be positioned directly next to each other in the construct (i.e., one after the other) or, alternatively, spacer nucleotides can be positioned between each binding site.

In one embodiment, the 3' UTR comprises three stop codons with a single miR-142-3p binding site located downstream of the 3rd stop codon. Non-limiting examples of sequences of 3' UTR having three stop codons and a single miR-142-3p binding site located at different positions downstream of the final stop codon are shown in SEQ ID NOs: 103 and 115-117.

TABLE 4

3'UTRs, miR sequences, and miR binding sites

| SEQ ID NO: | Sequence |
|---|---|
| 81 | GCUGGAGCCUCGGUGGCCAUGCUUCUUGCCCCUUGGGCCUCCCCCAGCCCC UCCUCCCCUUCCUGCACCCGUACCCCCUCCAUAAAGUAGGAAACACUACAGU GGUCUUUGAAUAAAGUCUGAGUGGGCGGC (3'UTR with miR 142-3p binding site) |
| 82 | UCCAUAAAGUAGGAAACACUACA (miR 142-3p binding site) |
| 83 | UGUAGUGUUUCCUACUUUAUGGA (miR 142-3p sequence) |
| 84 | CAUAAAGUAGAAAGCACUACU (miR 142-5p sequence) |
| 85 | CCUCUGAAAUUCAGUUCUUCAG (miR 146-3p sequence) |
| 86 | UGAGAACUGAAUUCCAUGGGUU (miR 146-5p sequence) |

TABLE 4-continued

3'UTRs, miR sequences, and miR binding sites

| SEQ ID NO: | Sequence |
|---|---|
| 87 | CUCCUACAUAUUAGCAUUAACA<br>(miR 155-3p sequence) |
| 88 | UUAAUGCUAAUCGUGAUAGGGGU<br>(miR 155-5p sequence) |
| 89 | UCGUACCGUGAGUAAUAAUGCG<br>(miR 126-3p sequence) |
| 90 | CAUUAUUACUUUUGGUACGCG<br>(miR 126-5p sequence) |
| 91 | CCAGUAUUAACUGUGCUGCUGA<br>(miR 16-3p sequence) |
| 92 | UAGCAGCACGUAAAUAUUGGCG<br>(miR 16-5p sequence) |
| 93 | CAACACCAGUCGAUGGGCUGU<br>(miR 21-3p sequence) |
| 94 | UAGCUUAUCAGACUGAUGUUGA<br>(miR 21-5p sequence) |
| 95 | UGUCAGUUUGUCAAAUACCCCA<br>(miR 223-3p sequence) |
| 96 | CGUGUAUUUGACAAGCUGAGUU<br>(miR 223-5p sequence) |
| 97 | UGGCUCAGUUCAGCAGGAACAG<br>(miR 24-3p sequence) |
| 98 | UGCCUACUGAGCUGAUAUCAGU<br>(miR 24-5p sequence) |
| 99 | UUCACAGUGGCUAAGUUCCGC<br>(miR 27-3p sequence) |
| 100 | AGGGCUUAGCUGCUUGUGAGCA<br>(miR 27-5p sequence) |
| 101 | CGCAUUAUUACUCACGGUACGA<br>(miR 126-3p binding site) |
| 102 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC<u>CGCAUUAUUACUCACG<br>GUACG</u>AGUGGUCUUUGAAUAAAGUCUGAGUGGGCGGC<br>(3'UTR with miR 126-3p binding site) |
| 72 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCGUGGUCUUUGAAUAAA<br>GUCUGAGUGGGCGGC<br>(3' UTR, no miR binding sites) |
| 103 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC<u>UCCAUAAAGUAGGAAA<br>CACUACAGUGGU</u>CUUUGAAUAAAGUCUGAGUGGGCGGC<br>(3' UTR with miR 142-3p binding site) |
| 104 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC<u>CGCAUUAUUACUCACG<br>GUACG</u>AGUGGUCUUUGAAUAAAGUCUGAGUGGGCGGC<br>(3' UTR with miR 126-3p binding site) |
| 105 | UGAUAAUAGU<u>CCAUAAAGUAGGAAACACUACAG</u>CUGGAGCCUCGGUGGCCAU<br>GCUUCUUGCCCCUUGGGCCUCCCCCCAGCCCCUCCUCCCCUUCCUGCACCCG<br>UACCCCC<u>CGCAUUAUUACUCACGGUACG</u>AGUGGUCUUUGAAUAAAGUCUGAG<br>UGGGCGGC<br>(3' UTR with miR 142-3p and miR 126-3p binding sites) |
| 106 | UUAAUGCUAAUUGUGAUAGGGGU<br>(miR 155-5p sequence) |
| 107 | ACCCCUAUCACAAUUAGCAUUAA<br>(miR 155-5p binding site) |

TABLE 4-continued

3'UTRs, miR sequences, and miR binding sites

| SEQ ID NO: | Sequence |
|---|---|
| 108 | UGAUAAUAGUCCAUAAAGUAGGAAACACUACAGCUGGAGCCUCGGUGGCCAU<br>GCUUCUUGCCCCUUGGGCCUCCAUAAAGUAGGAAACACUACAUCCCCCCAGC<br>CCCUCCUCCCCUUCCUGCACCCGUACCCCCUCCAUAAAGUAGGAAACACUAC<br>AGUGGUCUUUGAAUAAAGUCUGAGUGGGCGGC<br>(3' UTR with 3 miR 142-3p binding sites) |
| 109 | UGAUAAUAGGCUGGAGCCUCGGUGGCCAUGCUUCUUGCCCCUUGGGCCUCCC<br>CCCAGCCCCUCCUCCCCUUCCUGCACCCGUACCCC*AGUAGUGCUUUCUACU<br>UUAUG*GUGGUCUUUGAAUAAAGUCUGAGUGGGCGGC<br>(3'UTR with miR 142-5p binding site) |
| 110 | UGAUAAUAG*AGUAGUGCUUUCUACUUUAUG*GCUGGAGCCUCGGUGGCCAUGC<br>UUCUUGCCCCUUGGGCC*AGUAGUGCUUUCUACUUUAUG*UCCCCCCAGCCCU<br>CCUCCCCUUCCUGCACCCGUACCCCC*AGUAGUGCUUUCUACUUUAUG*GUGGU<br>CUUUGAAUAAAGUCUGAGUGGGCGGC<br>(3'UTR with 3 miR 142-5p binding sites) |
| 111 | UGAUAAUAG*AGUAGUGCUUUCUACUUUAUG*GCUGGAGCCUCGGUGGCCAUGC<br>UUCUUGCCCCUUGGGCCUCCAUAAAGUAGGAAACACUACAUCCCCCCAGCCC<br>CUCCUCCCCUUCCUGCACCCGUACCCCC*AGUAGUGCUUUCUACUUUAUG*GUG<br>GUCUUUGAAUAAAGUCUGAGUGGGCGGC<br>(3'UTR with 2 miR 142-5p binding sites and 1 miR 142-3p binding site) |
| 112 | UGAUAAUAGGCUGGAGCCUCGGUGGCCAUGCUUCUUGCCCCUUGGGCCUCCC<br>CCCAGCCCCUCCUCCCCUUCCUGCACCCGUACCCC*ACCCCUAUCACAAUUA<br>GCAUUAAG*UGGUCUUUGAAUAAAGUCUGAGUGGGCGGC<br>(3'UTR with miR 155-5p binding site) |
| 113 | UGAUAAUAG*ACCCCUAUCACAAUUAGCAUUAAG*CUGGAGCCUCGGUGGCCAU<br>GCUUCUUGCCCCUUGGGCC*ACCCCUAUCACAAUUAGCAUUAAU*CCCCCCAGC<br>CCCUCCUCCCCUUCCUGCACCCGUACCCCC*ACCCCUAUCACAAUUAGCAUUA<br>AGUGGUCUUUGAAUAAAGUCUGAGUGGGCGGC<br>(3' UTR with 3 miR 155-5p binding sites) |
| 114 | UGAUAAUAG*ACCCCUAUCACAAUUAGCAUUAAG*CUGGAGCCUCGGUGGCCAU<br>GCUUCUUGCCCCUUGGGCCUCCAUAAAGUAGGAAACACUACAUCCCCCCAGC<br>CCCUCCUCCCCUUCCUGCACCCGUACCCCC*ACCCCUAUCACAAUUAGCAUUA<br>AGUGGUCUUUGAAUAAAGUCUGAGUGGGCGGC<br>(3'UTR with 2 miR 155-5p binding sites and 1 miR 142-3p binding site) |
| 115 | UGAUAAUAGUCCAUAAAGUAGGAAACACUACAGCUGGAGCCUCGGUGGCCAU<br>GCUUCUUGCCCCUUGGGCCUCCCCCCAGCCCCUCCUCCCCUUCCUGCACCCG<br>UACCCCGUGGUCUUUGAAUAAAGUCUGAGUGGGCGGC<br>(3'UTR with miR 142-3p binding site, P1 insertion) |
| 116 | UGAUAAUAGGCUGGAGCCUCGGUGGCUCCAUAAAGUAGGAAACACUACACAU<br>GCUUCUUGCCCCUUGGGCCUCCCCCAGCCCCUCCUCCCCUUCCUGCACCCG<br>UACCCCGUGGUCUUUGAAUAAAGUCUGAGUGGGGGC<br>(3'UTR with miR 142-3p binding site, P2 insertion) |
| 50 | UGAUAAUAGGCUGGAGCCUCGGUGGCCAUGCUUCUUGCCCCUUCCAUAAAGU<br>AGGAAACACUACAUGGGCCUCCCCCCAGCCCCUCCUCCCCUUCCUGCACCCG<br>UACCCCGUGGUCUUUGAAUAAAGUCUGAGUGGGCGGC<br>(3' UTR including miR142-3p binding site) |
| 51 | UGAUAAUAGGCUGGAGCCUCGGUGGCCAUGCUUCUUGCCCCUUGGGCCUCCC<br>CCCAGUCCAUAAAGUAGGAAACACUACACCCCUCCUCCCCUUCCUGCACCCG<br>UACCCCGUGGUCUUUGAAUAAAGUCUGAGUGGGCGGC<br>(3'UTR including miR142-3p binding site) |
| 52 | UGAUAAUAGGCUGGAGCCUCGGUGGCCAUGCUUCUUGCCCCUUGGGCCUCCC<br>CCCAGCCCCUCCUCCCCUUCUCCAUAAAGUAGGAAACACUACACUGCACCCG<br>UACCCCGUGGUCUUUGAAUAAAGUCUGAGUGGGGGC<br>(3'UTR including including miR142-3p binding site) |
| 54 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCCGUGGUCUUUGAAUAAA<br>GUUCCAUAAAGUAGGAAACACUACACUGAGUGGGCGGC<br>(3'UTR including including miR142-3p binding site) |

TABLE 4-continued

3'UTRs, miR sequences, and miR binding sites

| SEQ ID NO: | Sequence |
|---|---|
| 117 | UGAUAAUAGGCUGGAGCCUCGGUGGCCAUGCUUCUUGCCCCUUGGGCCUCCA<br>UAAAGUAGGAAACACUACAUCCCCCAGCCCCUCCUCCCCUUCCUGCACCCG<br>UACCCCCGUGGUCUUUGAAUAAAGUCUGAGUGGGCGGC<br>(3'UTR with miR 142-3p binding site, P3 insertion) |
| 118 | AGUAGUGCUUUCUACUUUAUG<br>(miR-142-5p binding site) |
| 119 | GACAGUGCAGUCACCCAUAAAGUAGAAAGCACUACUAACAGCACUGGAGGGU<br>GUAGUGUUUCCUACUUUAUGGAUGAGUGUACUGUG<br>(miR-142) |
| 30 | GGGAAAUAAGAGAGAAAAGAAGAGUAAGAAGAAAUAUAAGAGCCACC<br>(5' UTR) |
| 120 | GGGAAAUAAGAGUCCAUAAAGUAGGAAACACUACAAGAAAAGAAGAGUAAGA<br>AGAAAUAUAAGAGCCACC<br>(5' UTR with miR142-3p binding site at position p1) |
| 12 | GGGAAAUAAGAGAGAAAAGAAGAGUAAUCCAUAAAGUAGGAAACACUACAGA<br>AGAAAUAUAAGAGCCACC<br>(5' UTR with miR142-3p binding site at position p2) |
| 122 | GGGAAAUAAGAGAGAAAAGAAGAGUAAGAAGAAAUAUAAUCCAUAAAGUAGG<br>AAACACUACAGAGCCACC<br>(5' UTR with miR142-3p binding site at position p3) |
| 124 | UGAUAAUAGAGUAGUGCUUUCUACUUUAUGGCUGGAGCCUCGGUGGCCAUGC<br>UUCUUGCCCCUUGGGCCAGUAGUGCUUUCUACUUUAUGUCCCCCCAGCCCCU<br>CUCCCCUUCCUGCACCCGUACCCCCAGUAGUGCUUUCUACUUUAUGGUGGUC<br>UUUGAAUAAAGUCUGAGUGGGCGGC<br>(3'UTR with 3 miR 142-5p binding sites) |
| 125 | UGAUAAUAGAGUAGUGCUUUCUACUUUAUGGCUGGAGCCUCGGUGGCCAUGC<br>UUCUUGCCCCUUGGGCCUCCAUAAAGUAGGAAACACUACAUCCCCCCAGCCC<br>CUCCUCCCCUUCCUGCACCCGUACCCCCAGUAGUGCUUUCUACUUUAUGGUG<br>GUCUUUGAAUAAAGUCUGAGUGGGCGGC<br>(3'UTR with 2 miR 142-5p binding sites and 1 miR 142-3p binding site) |
| 149 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCCGUGGUCUUUGAAUAAA<br>GUCUGAGUGGGCGGC<br>(3' UTR, no miR binding sites variant 2) |
| 148 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCCUCCAUAAAGUAGGAAA<br>CACUACAGUGGUCUUUGAAUAAAGUCUGAGUGGGCGGC<br>(3' UTR with miR 142-3p binding site variant 2) |
| 150 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCCGCAUUAUUACUCACG<br>GUACGAGUGGUCUUUGAAUAAAGUCUGAGUGGGCGGC<br>(3' UTR with miR 126-3p binding site variant 3) |
| 147 | UGAUAAUAGUCCAUAAAGUAGGAAACACUACAGCUGGAGCCUCGGUGGCCUA<br>GCUUCUUGCCCCUUGGGCCUCCCCCCAGCCCCUCCUCCCCUUCCUGCACCCG<br>UACCCCCGCAUUAUUACUCACGGUACGAGUGGUCUUUGAAUAAAGUCUGAG<br>UGGGCGGC<br>(3' UTR with miR 142-3p and miR 126-3p binding sites variant 2) |
| 151 | UGAUAAUAGUCCAUAAAGUAGGAAACACUACAGCUGGAGCCUCGGUGGCCUA<br>GCUUCUUGCCCCUUGGGCCUCCAUAAAGUAGGAAACACUACAUCCCCCAGC<br>CCCUCCUCCCCUUCCUGCACCCGUACCCCCUCCAUAAAGUAGGAAACACUAC<br>AGUGGUCUUUGAAUAAAGUCUGAGUGGGCGGC<br>(3' UTR with 3 miR 142-3p binding sites variant 2) |
| 152 | UGAUAAUAGUCCAUAAAGUAGGAAACACUACAGCUGGAGCCUCGGUGGCCUA<br>GCUUCUUGCCCCUUGGGCCUCCCCCCAGCCCCUCCUCCCCUUCCUGCACCCG<br>UACCCCCGUGGUCUUUGAAUAAAGUCUGAGUGGGCGGC<br>(3'UTR with miR 142-3p binding site, P1 insertion variant 2) |
| 153 | UGAUAAUAGGCUGGAGCCUCGGUGGCUCCAUAAAGUAGGAAACACUACACUA<br>GCUUCUUGCCCCUUGGGCCUCCCCCCAGCCCCUCCUCCCCUUCCUGCACCCG<br>UACCCCCGUGGUCUUUGAAUAAAGUCUGAGUGGGCGGC<br>(3'UTR with miR 142-3p binding site, P2 insertion variant 2) |

TABLE 4-continued

3'UTRs, miR sequences, and miR binding sites

| SEQ ID NO: | Sequence |
|---|---|
| 154 | UGAUAAUAGGCUGGAGCCUCGGUGGCCUAGCUUCUUGCCCCUUGGGCCUCCA<br>UAAAGUAGGAAACACUACAUCCCCCAGCCCCUCCUCCCCUUCCUGCACCCG<br>UACCCCCGUGGUCUUUGAAUAAAGUCUGAGUGGGCGGC<br>(3'UTR with miR 142-3p binding site, P3 insertion variant 2) |
| 155 | UGAUAAUAGGCUGGAGCCUCGGUGGCCUAGCUUCUUGCCCCUUGGGCCUCCC<br>CCCAGCCCCUCCUCCCCUUCCUGCACCCGUACCCC*ACCCCUAUCACAAUUA<br>GCAUUAAGUGGUCUUUGAAUAAAGUCUGAGUGGGCGGC*<br>(3'UTR with miR 155-5p binding site variant 2) |
| 156 | UGAUAAUAG*ACCCCUAUCACAAUUAGCAUUAAGCUGGAGCCUCGGUGGCCUA<br>GCUUCUUGCCCCUUGGGCCACCCCUAUCACAAUUAGCAUUAAUCCCCCAGC<br>CCCUCCUCCCCUUCCUGCACCCGUACCCCCACCCCUAUCACAAUUAGCAUUA<br>AGUGGUCUUUGAAUAAAGUCUGAGUGGGCGGC*<br>(3' UTR with 3 miR 155-5p binding sites variant 2) |
| 157 | UGAUAAUAG*ACCCCUAUCACAAUUAGCAUUAAGCUGGAGCCUCGGUGGCCUA<br>GCUUCUUGCCCCUUGGGCC*<u>UCCAUAAAGUAGGAAACACUACAU</u>CCCCCCAGC<br>CCCUCCUCCCCUUCCUGCACCCGUACCCCC*ACCCCUAUCACAAUUAGCAUUA<br>AGUGGUCUUUGAAUAAAGUCUGAGUGGGCGGC*<br>(3'UTR with 2 miR 155-5p binding sites and 1 miR 142-3p binding site variant 2) |

Stop codon = bold
miR 142-3p binding site = underline
miR 126-3p binding site = bold underline
miR 155-5p binding site = italicized
miR 142-5p binding site = italicized and bold underline In one embodiment, the polynucleotide of the invention comprises a 5' UTR, a codon optimized open reading frame encoding a polypeptide of interest, a 3' UTR comprising the at least one miRNA binding site for a miR expressed in immune cells, and a 3' tailing region of linked nucleosides. In various embodiments, the 3' UTR comprises 1-4, at least two, one, two, three or four miRNA binding sites for miRs expressed in immune cells, preferably abundantly or preferentially expressed in immune cells.

In one embodiment, the at least one miRNA expressed in immune cells is a miR-142-3p microRNA binding site. In one embodiment, the miR-142-3p microRNA binding site comprises the sequence shown in SEQ ID NO: 82. In one embodiment, the 3' UTR of the mRNA comprising the miR-142-3p microRNA binding site comprises the sequence shown in SEQ ID NO: 81.

In one embodiment, the at least one miRNA expressed in immune cells is a miR-126 microRNA binding site. In one embodiment, the miR-126 binding site is a miR-126-3p binding site. In one embodiment, the miR-126-3p microRNA binding site comprises the sequence shown in SEQ ID NO: 144. In one embodiment, the 3' UTR of the mRNA of the invention comprising the miR-126-3p microRNA binding site comprises the sequence shown in SEQ ID NO: 102.

Non-limiting exemplary sequences for miRs to which a microRNA binding site(s) of the disclosure can bind include the following: miR-142-3p (SEQ ID NO: 83), miR-142-5p (SEQ ID NO: 84), miR-146-3p (SEQ ID NO: 85), miR-146-5p (SEQ ID NO: 86), miR-155-3p (SEQ ID NO: 87), miR-155-5p (SEQ ID NO: 88), miR-126-3p (SEQ ID NO: 89), miR-126-5p (SEQ ID NO: 90), miR-16-3p (SEQ ID NO: 91), miR-16-5p (SEQ ID NO: 92), miR-21-3p (SEQ ID NO: 93), miR-21-5p (SEQ ID NO: 94), miR-223-3p (SEQ ID NO: 95), miR-223-5p (SEQ ID NO: 96), miR-24-3p (SEQ ID NO: 97), miR-24-5p (SEQ ID NO: 98), miR-27-3p (SEQ ID NO: 99) and miR-27-5p (SEQ ID NO: 100). Other suitable miR sequences expressed in immune cells (e.g., abundantly or preferentially expressed in immune cells) are known and available in the art, for example at the University of Manchester's microRNA database, miRBase. Sites that bind any of the aforementioned miRs can be designed based on Watson-Crick complementarity to the miR, typically 100% complementarity to the miR, and inserted into an mRNA construct of the disclosure as described herein.

In another embodiment, a polynucleotide of the present invention (e.g., and mRNA, e.g., the 3' UTR thereof) can comprise at least one miRNA binding site to thereby reduce or inhibit accelerated blood clearance, for example by reducing or inhibiting production of IgMs, e.g., against PEG, by B cells and/or reducing or inhibiting proliferation and/or activation of pDCs, and can comprise at least one miRNA binding site for modulating tissue expression of an encoded protein of interest.

miRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3'UTR of the same sequence type.

In one embodiment, other regulatory elements and/or structural elements of the 5'UTR can influence miRNA mediated gene regulation. One example of a regulatory element and/or structural element is a structured IRES (Internal Ribosome Entry Site) in the 5'UTR, which is necessary for the binding of translational elongation factors to initiate protein translation. EIF4A2 binding to this secondarily structured element in the 5'-UTR is necessary for miRNA mediated gene expression (Meijer H A et al., Science, 2013, 340, 82-85, herein incorporated by reference in its entirety). The polynucleotides of the invention can further include this structured 5'UTR in order to enhance microRNA mediated gene regulation.

At least one miRNA binding site can be engineered into the 3'UTR of a polynucleotide of the invention. In this context, at least two, at least three, at least four, at least five, at least six, at least seven, at least eight, at least nine, at least ten, or more miRNA binding sites can be engineered into a 3'UTR of a polynucleotide of the invention. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the invention. In one embodiment, miRNA binding sites incorporated into a polynucleotide of the invention can be the same or can be different miRNA sites. A combination of different miRNA binding sites incorporated into a polynucleotide of the invention can include combinations in which more than one copy of any of the different miRNA sites are incorporated. In another embodiment, miRNA binding sites incorporated into a polynucleotide of the invention can target the same or different tissues in the body. As a non-limiting example, through the introduction of tissue-, cell-type-, or disease-specific miRNA binding sites in the 3'-UTR of a polynucleotide of the invention, the degree of expression in specific cell types (e.g., myeloid cells, endothelial cells, etc.)) can be reduced.

In one embodiment, a miRNA binding site can be engineered near the 5' terminus of the 3'UTR, about halfway between the 5' terminus and 3' terminus of the 3'UTR and/or near the 3' terminus of the 3'UTR in a polynucleotide of the invention. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3'UTR. As yet another non-limiting example, a miRNA binding site can be engineered near the 5' terminus of the 3'UTR and near the 3' terminus of the 3'UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In some embodiments, the expression of a polynucleotide of the invention can be controlled by incorporating at least one sensor sequence in the polynucleotide and formulating the polynucleotide for administration. As a non-limiting example, a polynucleotide of the invention can be targeted to a tissue or cell by incorporating a miRNA binding site and formulating the polynucleotide in a lipid nanoparticle comprising an ionizable lipid, including any of the lipids described herein.

A polynucleotide of the invention can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the invention can be designed for optimal protein expression in a tissue or cell, or in the context of a biological condition.

In some embodiments, a polynucleotide of the invention can be designed to incorporate miRNA binding sites that either have 100% identity to known miRNA seed sequences or have less than 100% identity to miRNA seed sequences. In some embodiments, a polynucleotide of the invention can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment, a translation enhancer element (TEE) can be incorporated on the 5'end of the stem of a stem loop and a miRNA seed can be incorporated into the stem of the stem loop. In another embodiment, a TEE can be incorporated on the 5' end of the stem of a stem loop, a miRNA seed can be incorporated into the stem of the stem loop and a miRNA binding site can be incorporated into the 3' end of the stem or the sequence after the stem loop. The miRNA seed and the miRNA binding site can be for the same and/or different miRNA sequences.

In one embodiment, the incorporation of a miRNA sequence and/or a TEE sequence changes the shape of the stem loop region which can increase and/or decrease translation. (see e.g, Kedde et al., "A *Pumilio*-induced RNA structure switch in p27-3'UTR controls miR-221 and miR-22 accessibility." Nature Cell Biology. 2010, incorporated herein by reference in its entirety).

In one embodiment, the 5'-UTR of a polynucleotide of the invention can comprise at least one miRNA sequence. The miRNA sequence can be, but is not limited to, a 19 or 22 nucleotide sequence and/or a miRNA sequence without the seed.

In one embodiment the miRNA sequence in the 5'UTR can be used to stabilize a polynucleotide of the invention described herein.

In another embodiment, a miRNA sequence in the 5'UTR of a polynucleotide of the invention can be used to decrease the accessibility of the site of translation initiation such as, but not limited to, a start codon. See, e.g., Matsuda et al., PLoS One. 2010 11(5):e15057; incorporated herein by reference in its entirety, which used antisense locked nucleic acid (LNA) oligonucleotides and exon-junction complexes (EJCs) around a start codon (−4 to +37 where the A of the AUG colons is +1) in order to decrease the accessibility to the first start codon (AUG). Matsuda showed that altering the sequence around the start codon with an LNA or EJC affected the efficiency, length and structural stability of a polynucleotide. A polynucleotide of the invention can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site.

In some embodiments, a polynucleotide of the invention can include at least one miRNA in order to dampen the antigen presentation by antigen presenting cells. The miRNA can be the complete miRNA sequence, the miRNA seed sequence, the miRNA sequence without the seed, or a combination thereof. As a non-limiting example, a miRNA incorporated into a polynucleotide of the invention can be specific to the hematopoietic system. As another non-limiting example, a miRNA incorporated into a polynucleotide of the invention to dampen antigen presentation is miR-142-3p.

In some embodiments, a polynucleotide of the invention can include at least one miRNA in order to dampen expression of the encoded polypeptide in a tissue or cell of interest. As a non-limiting example a polynucleotide of the invention can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the invention can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the invention more unstable in antigen presenting cells. Non-limiting examples of these miRNAs include mir-142-5p, mir-142-3p, mir-146a-5p, and mir-146-3p.

In one embodiment, a polynucleotide of the invention comprises at least one miRNA sequence in a region of the polynucleotide that can interact with a RNA binding protein.

In some embodiments, the polynucleotide of the invention (e.g., a RNA, e.g., an mRNA) comprising (i) a sequence-optimized nucleotide sequence (e.g., an ORF) encoding a Citrin polypeptide (e.g., the wild-type sequence, functional fragment, or variant thereof) and (ii) a miRNA binding site (e.g., a miRNA binding site that binds to miR-142 and/or a miRNA binding site that binds to miR-126).

In some embodiments, the polynucleotide of the invention comprises a uracil-modified sequence encoding a Citrin polypeptide disclosed herein and a miRNA binding site disclosed herein, e.g., a miRNA binding site that binds to miR-142 and/or a miRNA binding site that binds to miR-126. In some embodiments, the polynucleotide of the invention comprises a uracil-modified sequence encoding a polypeptide disclosed herein and a miRNA binding site disclosed herein, e.g., a miRNA binding site that binds to miR-142miR-126, miR-142, miR-144, miR-146, miR-150, miR-155, miR-16, miR-21, miR-223, miR-24, miR-27 or miR-26a. In some embodiments, the miRNA binding site binds to miR126-3p, miR-142-3p, miR-142-5p, or miR-155. In some embodiments, the polynucleotide of the invention comprises a uracil-modified sequence encoding a polypeptide disclosed herein and at least two different microRNA binding sites, wherein the microRNA is expressed in an immune cell of hematopoietic lineage or a cell that expresses TLR7 and/or TLR8 and secretes pro-inflammatory cytokines and/or chemokines, and wherein the polynucleotide comprises one or more modified nucleobases. In some embodiments, the uracil-modified sequence encoding a Citrin polypeptide comprises at least one chemically modified nucleobase, e.g., 5-methoxyuracil. In some embodiments, at least 95% of a type of nucleobase (e.g., uricil) in a uracil-modified sequence encoding a Citrin polypeptide of the invention are modified nucleobases. In some embodiments, at least 95% of uricil in a uracil-modified sequence encoding a Citrin polypeptide is 5-methoxyuridine. In some embodiments, the polynucleotide (e.g., a RNA, e.g., an mRNA) disclosed herein, e.g., comprising an miRNA binding site, is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

13. 3'UTRs

In certain embodiments, a polynucleotide of the present invention (e.g., a polynucleotide comprising a nucleotide sequence encoding a Citrin polypeptide of the invention) further comprises a 3' UTR.

3'-UTR is the section of mRNA that immediately follows the translation termination codon and often contains regulatory regions that post-transcriptionally influence gene expression. Regulatory regions within the 3'-UTR can influence polyadenylation, translation efficiency, localization, and stability of the mRNA. In one embodiment, the 3'-UTR useful for the invention comprises a binding site for regulatory proteins or microRNAs. In certain embodiments, the 3' UTR useful for the polynucleotides of the invention comprises a 3'UTR selected from SEQ ID NOs: 48-72, 80, 81, 102-105, 108-117, 124, 125, 147-157, and any combination thereof. In some embodiments, the 3' UTR comprises a nucleic acid sequence selected from the group consisting of SEQ ID NOs: 105, 147, 148, or any combination thereof. In some embodiments, the 3' UTR comprises a nucleic acid sequence of SEQ ID NO: 147. In some embodiments, the 3' UTR comprises a nucleic acid sequence of SEQ ID NO: 148.

In certain embodiments, the 3' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 3'UTR sequences of SEQ ID NOs: 48-72, 80, 81, 102-105, 108-117, 124, 125, 147-157, and any combination thereof.

14. Regions Having a 5' Cap

The invention also includes a polynucleotide that comprises both a 5' Cap and a polynucleotide of the present invention (e.g., a polynucleotide comprising a nucleotide sequence encoding a Citrin polypeptide).

The 5' cap structure of a natural mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns during mRNA splicing.

Endogenous mRNA molecules can be 5'-end capped generating a 5'-ppp-5'-triphosphate linkage between a terminal guanosine cap residue and the 5'-terminal transcribed sense nucleotide of the mRNA molecule. This 5'-guanylate cap can then be methylated to generate an N7-methyl-guanylate residue. The ribose sugars of the terminal and/or anteterminal transcribed nucleotides of the 5' end of the mRNA can optionally also be 2'-O-methylated. 5'-decapping through hydrolysis and cleavage of the guanylate cap structure can target a nucleic acid molecule, such as an mRNA molecule, for degradation.

In some embodiments, the polynucleotides of the present invention (e.g., a polynucleotide comprising a nucleotide sequence encoding a Citrin polypeptide) incorporate a cap moiety.

In some embodiments, polynucleotides of the present invention (e.g., a polynucleotide comprising a nucleotide sequence encoding a Citrin polypeptide) comprise a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, MA) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and seleno-phosphate nucleotides.

Additional modifications include, but are not limited to, 2'-O-methylation of the ribose sugars of 5'-terminal and/or 5'-anteterminal nucleotides of the polynucleotide (as mentioned above) on the 2'-hydroxyl group of the sugar ring. Multiple distinct 5'-cap structures can be used to generate the 5'-cap of a nucleic acid molecule, such as a polynucleotide that functions as an mRNA molecule. Cap analogs, which herein are also referred to as synthetic cap analogs, chemical caps, chemical cap analogs, or structural or functional cap analogs, differ from natural (i.e., endogenous, wild-type or physiological) 5'-caps in their chemical structure, while retaining cap function. Cap analogs can be chemically (i.e., non-enzymatically) or enzymatically synthesized and/or linked to the polynucleotides of the invention.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine (m$^7$G-3'mppp-G; which can equivalently be designated 3' O-Me-m7G(5')ppp(5')G). The 3'-O atom of the other, unmodified, guanine becomes linked to the 5'-terminal nucleotide of the capped polynucleotide. The N7- and 3'-O-methylated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-5'-triphosphate-5'-guanosine, m$^7$Gm-ppp-G).

In some embodiments, the cap is a dinucleotide cap analog. As a non-limiting example, the dinucleotide cap analog can be modified at different phosphate positions with a boranophosphate group or a phosphoroselenoate group such as the dinucleotide cap analogs described in U.S. Pat. No. 8,519,110, the contents of which are herein incorporated by reference in its entirety.

In another embodiment, the cap is a cap analog is a N7-(4-chlorophenoxyethyl) substituted dinucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-m$^{3'-O}$G(5')ppp(5')G cap analog (See, e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present invention is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous 5'-cap structures of nucleic acids produced by the endogenous, cellular transcription machinery, can lead to reduced translational competency and reduced cellular stability.

Polynucleotides of the invention (e.g., a polynucleotide comprising a nucleotide sequence encoding a Citrin polypeptide) can also be capped post-manufacture (whether IVT or chemical synthesis), using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present invention are those that, among other things, have enhanced binding of cap binding proteins, increased half-life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N, pN2p (cap 0), 7mG(5')ppp(5')NlmpNp (cap 1), and 7mG(5')-ppp(5')NlmpN2mp (cap 2).

As a non-limiting example, capping chimeric polynucleotides post-manufacture can be more efficient as nearly 100% of the chimeric polynucleotides can be capped. This is in contrast to ~80% when a cap analog is linked to a chimeric polynucleotide in the course of an in vitro transcription reaction.

According to the present invention, 5' terminal caps can include endogenous caps or cap analogs. According to the present invention, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

15. Poly-A Tails

In some embodiments, the polynucleotides of the present disclosure (e.g., a polynucleotide comprising a nucleotide sequence encoding a Citrin polypeptide) further comprise a poly-A tail. In further embodiments, terminal groups on the poly-A tail can be incorporated for stabilization. In other embodiments, a poly-A tail comprises des-3' hydroxyl tails.

During RNA processing, a long chain of adenine nucleotides (poly-A tail) can be added to a polynucleotide such as an mRNA molecule in order to increase stability. Immediately after transcription, the 3' end of the transcript can be cleaved to free a 3' hydroxyl. Then poly-A polymerase adds a chain of adenine nucleotides to the RNA. The process, called polyadenylation, adds a poly-A tail that can be between, for example, approximately 80 to approximately 250 residues long, including approximately 80, 90, 100, 110, 120, 130, 140, 150, 160, 170, 180, 190, 200, 210, 220, 230, 240 or 250 residues long.

PolyA tails can also be added after the construct is exported from the nucleus.

According to the present invention, terminal groups on the poly A tail can be incorporated for stabilization. Polynucleotides of the present invention can include des-3' hydroxyl tails. They can also include structural moieties or 2'-Omethyl modifications as taught by Junjie Li, et al. (Current Biology, Vol. 15, 1501-1507, Aug. 23, 2005, the contents of which are incorporated herein by reference in its entirety).

The polynucleotides of the present invention can be designed to encode transcripts with alternative polyA tail structures including histone mRNA. According to Norbury, "Terminal uridylation has also been detected on human replication-dependent histone mRNAs. The turnover of these mRNAs is thought to be important for the prevention of potentially toxic histone accumulation following the completion or inhibition of chromosomal DNA replication. These mRNAs are distinguished by their lack of a 3' poly(A) tail, the function of which is instead assumed by a stable stem-loop structure and its cognate stem-loop binding protein (SLBP); the latter carries out the same functions as those of PABP on polyadenylated mRNAs" (Norbury, "Cytoplasmic RNA: a case of the tail wagging the dog," Nature Reviews Molecular Cell Biology; AOP, published online 29 Aug. 2013; doi:10.1038/nrm3645) the contents of which are incorporated herein by reference in its entirety.

Unique poly-A tail lengths provide certain advantages to the polynucleotides of the present invention. Generally, the length of a poly-A tail, when present, is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides).

In some embodiments, the polynucleotide or region thereof includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the polynucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present invention are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone.

16. Start Codon Region

The invention also includes a polynucleotide that comprises both a start codon region and the polynucleotide described herein (e.g., a polynucleotide comprising a nucleotide sequence encoding a Citrin polypeptide). In some embodiments, the polynucleotides of the present invention can have regions that are analogous to or function like a start codon region.

In some embodiments, the translation of a polynucleotide can initiate on a codon that is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/UUG (see Touriol et al. Biology of the Cell 95 (2003) 169-178 and Matsuda and Mauro PLoS ONE, 2010 5:11; the contents of each of which are herein incorporated by reference in its entirety).

As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. (See, e.g., Matsuda and Mauro PLoS ONE, 2010 5:11; the contents of which are herein incorporated by reference in its entirety). Masking any of the nucleotides flanking a codon that initiates translation can be used to alter the position of translation initiation, translation efficiency, length and/or structure of a polynucleotide.

In some embodiments, a masking agent can be used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon-junction complexes (EJCs) (See, e.g., Matsuda and Mauro describing masking agents LNA polynucleotides and EJCs (PLoS ONE, 2010 5:11); the contents of which are herein incorporated by reference in its entirety).

In another embodiment, a masking agent can be used to mask a start codon of a polynucleotide in order to increase the likelihood that translation will initiate on an alternative start codon. In some embodiments, a masking agent can be used to mask a first start codon or alternative start codon in order to increase the chance that translation will initiate on a start codon or alternative start codon downstream to the masked start codon or alternative start codon.

In some embodiments, a start codon or alternative start codon can be located within a perfect complement for a miRNA binding site. The perfect complement of a miRNA binding site can help control the translation, length and/or structure of the polynucleotide similar to a masking agent. As a non-limiting example, the start codon or alternative start codon can be located in the middle of a perfect complement for a miRNA binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide can be removed from the polynucleotide sequence in order to have the translation of the polynucleotide begin on a codon that is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

17. Stop Codon Region

The invention also includes a polynucleotide that comprises both a stop codon region and the polynucleotide described herein (e.g., a polynucleotide comprising a nucleotide sequence encoding a Citrin polypeptide). In some embodiments, the polynucleotides of the present invention can include at least two stop codons before the 3' untranslated region (UTR). The stop codon can be selected from TGA, TAA and TAG in the case of DNA, or from UGA, UAA and UAG in the case of RNA. In some embodiments, the polynucleotides of the present invention include the stop codon TGA in the case or DNA, or the stop codon UGA in the case of RNA, and one additional stop codon. In a further embodiment the addition stop codon can be TAA or UAA.

In another embodiment, the polynucleotides of the present invention include three consecutive stop codons, four stop codons, or more.

18. Insertions and Substitutions

The invention also includes a polynucleotide of the present disclosure that further comprises insertions and/or substitutions.

In some embodiments, the 5'UTR of the polynucleotide can be replaced by the insertion of at least one region and/or string of nucleosides of the same base. The region and/or string of nucleotides can include, but is not limited to, at least 3, at least 4, at least 5, at least 6, at least 7 or at least 8 nucleotides and the nucleotides can be natural and/or unnatural. As a non-limiting example, the group of nucleotides can include 5-8 adenine, cytosine, thymine, a string of any of the other nucleotides disclosed herein and/or combinations thereof.

In some embodiments, the 5'UTR of the polynucleotide can be replaced by the insertion of at least two regions and/or strings of nucleotides of two different bases such as, but not limited to, adenine, cytosine, thymine, any of the other nucleotides disclosed herein and/or combinations thereof. For example, the 5'UTR can be replaced by inserting 5-8 adenine bases followed by the insertion of 5-8 cytosine bases. In another example, the 5'UTR can be replaced by inserting 5-8 cytosine bases followed by the insertion of 5-8 adenine bases.

In some embodiments, the polynucleotide can include at least one substitution and/or insertion downstream of the transcription start site that can be recognized by an RNA polymerase. As a non-limiting example, at least one substitution and/or insertion can occur downstream of the transcription start site by substituting at least one nucleic acid in the region just downstream of the transcription start site (such as, but not limited to, +1 to +6). Changes to region of nucleotides just downstream of the transcription start site can affect initiation rates, increase apparent nucleotide triphosphate (NTP) reaction constant values, and increase the dissociation of short transcripts from the transcription complex curing initial transcription (Brieba et al, Biochemistry (2002) 41: 5144-5149; herein incorporated by reference in its entirety). The modification, substitution and/or insertion of at least one nucleoside can cause a silent mutation of the sequence or can cause a mutation in the amino acid sequence.

In some embodiments, the polynucleotide can include the substitution of at least 1, at least 2, at least 3, at least 4, at least 5, at least 6, at least 7, at least 8, at least 9, at least 10, at least 11, at least 12 or at least 13 guanine bases downstream of the transcription start site.

In some embodiments, the polynucleotide can include the substitution of at least 1, at least 2, at least 3, at least 4, at least 5 or at least 6 guanine bases in the region just downstream of the transcription start site. As a non-limiting example, if the nucleotides in the region are GGGAGA, the guanine bases can be substituted by at least 1, at least 2, at least 3 or at least 4 adenine nucleotides. In another non-limiting example, if the nucleotides in the region are GGGAGA the guanine bases can be substituted by at least 1, at least 2, at least 3 or at least 4 cytosine bases. In another non-limiting example, if the nucleotides in the region are GGGAGA the guanine bases can be substituted by at least 1, at least 2, at least 3 or at least 4 thymine, and/or any of the nucleotides described herein.

In some embodiments, the polynucleotide can include at least one substitution and/or insertion upstream of the start codon. For the purpose of clarity, one of skill in the art would appreciate that the start codon is the first codon of the protein coding region whereas the transcription start site is the site where transcription begins. The polynucleotide can include, but is not limited to, at least 1, at least 2, at least 3, at least 4, at least 5, at least 6, at least 7 or at least 8 substitutions and/or insertions of nucleotide bases. The nucleotide bases can be inserted or substituted at 1, at least 1, at least 2, at least 3, at least 4 or at least 5 locations upstream of the start codon. The nucleotides inserted and/or substituted can be the same base (e.g., all A or all C or all T or all G), two different bases (e.g., A and C, A and T, or C and T), three different bases (e.g., A, C and T or A, C and T) or at least four different bases.

As a non-limiting example, the guanine base upstream of the coding region in the polynucleotide can be substituted with adenine, cytosine, thymine, or any of the nucleotides described herein. In another non-limiting example the substitution of guanine bases in the polynucleotide can be designed so as to leave one guanine base in the region downstream of the transcription start site and before the start codon (see Esvelt et al. Nature (2011) 472(7344):499-503; the contents of which is herein incorporated by reference in its entirety). As a non-limiting example, at least 5 nucleotides can be inserted at 1 location downstream of the transcription start site but upstream of the start codon and the at least 5 nucleotides can be the same base type.

19. Polynucleotide Comprising an mRNA Encoding a Citrin Polypeptide

In certain embodiments, a polynucleotide of the present disclosure, for example a polynucleotide comprising an mRNA nucleotide sequence encoding a Citrin polypeptide, comprises from 5' to 3' end:
(i) a 5' cap provided above;
(ii) a 5' UTR, such as the sequences provided above;
(iii) an open reading frame encoding a Citrin polypeptide, e.g., a sequence optimized nucleic acid sequence encoding Citrin disclosed herein;
(iv) at least one stop codon;
(v) a 3' UTR, such as the sequences provided above; and
(vi) a poly-A tail provided above.

In some embodiments, the polynucleotide further comprises a miRNA binding site, e.g, a miRNA binding site that binds to miRNA-142. In some embodiments, the 5'UTR comprises the miRNA binding site.

In some embodiments, a polynucleotide of the present disclosure comprises a nucleotide sequence encoding a polypeptide sequence at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the protein sequence of a wild type Citrin (e.g, isoform 1 or 2).

In some embodiments, a polynucleotide of the present disclosure, for example a polynucleotide comprising an mRNA nucleotide sequence encoding a Citrin polypeptide, comprises (1) a 5' cap provided above, for example, CAP 1, (2) a nucleotide sequence selected form the group consisting of SEQ ID NO: 130, 133, 136, and 139, and (3) a poly-A tail provided above, for example, a poly A tail of about 100 residues, wherein
SEQ ID NO: 130 comprises from 5' to 3' end: 5' UTR of SEQ ID NO:30, CTNL2 polypeptide ORF of SEQ ID NO: 129, and 3'UTR of SEQ ID NO: 105;
SEQ ID NO: 133 comprises from 5' to 3' end: 5' UTR of SEQ ID NO:30, CTNL2 polypeptide ORF of SEQ ID NO: 132, and 3'UTR of SEQ ID NO: 105;
SEQ ID NO: 136 comprises from 5' to 3' end: 5' UTR of SEQ ID NO:30, CTNL2 polypeptide ORF of SEQ ID NO: 135, and 3'UTR of SEQ ID NO: 105;
SEQ ID NO: 139 comprises from 5' to 3' end: 5' UTR of SEQ ID NO:30, CTNL2 polypeptide ORF of SEQ ID NO: 138, and 3'UTR of SEQ ID NO: 105.

TABLE 5 mRNA Constructs

| SEQ ID | Construct no. | Sequence (5' UTR = bold underline; 3' UTR comprising a stop codon = bold italics) |
|---|---|---|
| NO. 130 | #1 | GGGAAAUAAGAGAGAAAAGAAGAGUAAGAAGAAAUAUAAGAGCCACCAUGGCCGCCGCCAAGGUCGCCCUCACCAAGAGGGCGGACCCCGCGGAGCUCAGGACCAUCUUUCUCAAGUACGCCUCCAUCGAGAAGAACGGGGAGUUCUUCAUGAGCCCGAACGAUUUCGUCACCAGGUACCUCAACAUCUUCGGCGAGAGCCAGCCCAACCCGAAGACCGUAGAGCUCCUCAGCGGCGUCGUCGACCAGACGAAGGACGGACUCAUUAGCUUCCAGGAGUUCGUCGCCUUCGAGAGCGUCCUCUGCGCGCCCGACGCCCUCUUCAUGGUCGCGUUCCAGCUGUUCGAUAAGGCCGGCAAGGGCGAGGUGACCUUUGAAGAUGUGAAGCAGGUGUUCGGUCAGACCACCAUCCACCAGCACAUCCCUUUUAACUGGGACUCAGAAUUCGUCCAGCUGCACUUCGGCAAGGAAAGGAAGCGCCAUCUGACCUACGCCGAGUUCACACAGUUUCUCCUGGAGAUCCAGCUGGAACACGCCAAACAGGCGUUCGUUCAGCGGGACAACGCCAGGACCGGCCGGGUCACCGCGAUCGACUUCCGUGAUAUCAUGGUGACCAUCAGGCCUCACGUCCUGACGCCCUUCGUGGAAGAGUGCCUGGUGGCCGCCGCGGGUGGGACCACGUCCCACCAGGUGAGCUUCUCCUAUUUUAACGGGUUCAACAGCCUCCUCAACAACAUGGAGCUGAUCCGGAAGAUCUAUAGCACCCUGGCCGGGACGCGCAAGGACGUCGAGGUGACCAAGGAAGAAUUCGUGCUGGCCGCCCAGAAGUUUGGCCAGGUGACGCCCAUGGAGGUGGACAUCCUGUUCCAACUGGCGGACCUGUACGAACCCAGGGGCCGGAUGACCCUGGCCGACAUCGAGCGCAUUGCCCCGCUCGAGGAGGGCACCCUGCCCUUCAACCUGGCGGAGGCCCAGCGCCAGAAGGCCAGCGGGGACAGCGCCAGGCCCGUCCUGCUGCAGGUGGCCGAGUCCGCGUACAGGUUCGGUCUGGGGAGCGUCGCGGGAGCCGUGGGUGCCACCGCCGUGUAUCCGAUCGACCUCGUGAAGACCCGUAUGCAGAAUCAGAGGUCCACCGGCAGCUUCGUGGGCGAGCUCAUGUACAAGAACUCCUUCGACUGUUUCAAGAAGGUUCUCCGGUACGAGGGGUUCUUCGGCCUCUACCGGGGACUGCUACCCCAGCUGCUCGGCGUGGCGCCCGAGAAGGCCA |

TABLE 5-continued mRNA Constructs

| SEQ ID | Construct no. | Sequence (5' UTR = bold underline; 3' UTR comprising a stop codon = bold italics) |
|---|---|---|
| | | UCAAGCUCACGGUCAACGACUUUGUGCGGGACAAGUUCAUGCACAAGGACG<br>GCAGCGUCCCACUGGCCGCCGAGAUUCUGGCAGGCGGCUGCGCCGGAGGC<br>AGCCAGGUCAUCUUUACCAACCCCACUGGAGAUCGUGAAGAUCAGGCUGCAA<br>GUGGCCGGGGAGAUUACCACCGGACCCCGUGUGAGCGCCCUGAGCGUGGU<br>GAGGGACCUUGGCUUCUUUGGCAUAUACAAGGGAGCCAAGGCCUGCUUUCU<br>GAGGGACAUCCCGUUUCCGCCAUAUACUUUCCCUGCUACGCCCACGUGAA<br>AGCGAGCUUCGCCAACGAGGACGGCCAGGUCAGUCCCGGCUCCCUACUGCU<br>GGCCGGAGCCAUCGCCGGGAUGCCCGCCGCCAGCCUGGUGACGCCCGCGG<br>ACGUUAUCAAGACCAGGCUGCAGGUGGCGGCCAGGGGGGCCAGACCACCU<br>ACAGCGGCGUGAUCGACUGCUUCCGCAAGAUCCUGCGGGAGGAGGGCCC<br>AAGGCCCUGUGGAAAGGCGCCGGGGCAAGGGUGUUCAGGAGCAGCCCACA<br>GUUCGGGGUGACCCUGCUUACCUACGAACUGCUGCAGCGGUGGUUCUAUAU<br>CGACUUCGGAGGAGUCAAGCCCAUGGGCUCCGAGCCUGUGCCCAAGAGCAG<br>GAUCAAUCUGCCCGCGCCCAACCCAGACCACGUGGGAGGGUACAAACUGGC<br>CGUGGCCACCUUCGCCGGAAUCGAGAACAAGUUCGGCCUGUAUCUGCCCCU<br>GUUCAAACCGUCCGUCUCCACCAGCAAGGCCAUCGGCGGAGGCCCC*UGAUA*<br>*AUAGUCCAUAAAGUAGGAAACACUACAGCUGGAGCCUCGGUGGCCAUGCU*<br>*UCUUGCCCCUUGGGCCUCCCCCCAGCCCCUCCUCCCCUUCCUGCACCCGUA*<br>*CCCCCCGCAUUAUUACUCACGGUACGAGUGGUCUUUGAAUAAAGUCUGAG*<br>*UGGGCGGC* |
| 133 | #2 | <u>GGGAAAUAAGAGAGAAAAGAAGAGUAAGAAGAAAUAUAAGAGCCACCAUG</u><br>GCCGCCGCCAAGGUCGCCCUCACCAAGAGGGCGGACCCCGCGGAGCUCAG<br>GACCAUCUUUCUCAAGUACGCCUCCAUCGAGAAGAACGGGGAGUUCUUCAU<br>GAGCCCGAACGAUUUCGUCACCAGGUACCUCAACAUCUUCGGCGAGAGCCA<br>GCCCAACCCGAAGACCGUAGAGCUCCUCAGCGGCGUCGUCGACCAGACGAA<br>GGACGGACUCAUUAGCUUCCAGGAGUUCGUCGCCUUCGAGAGCGUCCUCUG<br>CGCCCCCGACGCCCUCUUCAUGGUCGCGUUCCAGCUGUUCGAUAAGGCCG<br>GCAAGGGCGAGGUGACCUUUGAAGAUGUGAAGCAGGUGUUCGGUCAGACCA<br>CCAUCCACCAGCACAUCCCUUUUAACUGGGACUCAGAAUUCGUCCAGCUGC<br>ACUUCGGCAAGGAAAGGAAGCGCCAUCUGACCUACGCCGAGUUCACACAGU<br>UUCUCCUGGAGAUCCAGCUGGAACACGCCAAACAGGCGUUCGUUCAGCGGG<br>ACAACGCCAGGACCGGCCGGGUCACCGCGAUCGACUUCCGUGAUAUCAUGG<br>UGACCAUCAGGCCUCACGUCCUGACCCCCUUCGUGGAAGAGUGCCUGGUGG<br>CCGCCGCGGGUGGGACCACGUCCCACCAGGUGAGCUUCUCCUAUUUUAACG<br>GGUUCAACAGCCUCCUCAACAACAUGGAGCUGAUCCGGAAGAUCUAUAGCA<br>CCCUGGCCGGGACGCGCAAGGACGUCGAGGUGACCAAGGAAGAAUUCGUGC<br>UGGCCGCCCAGAAGUUUGGCCAGGUGACCCCCAUGGAGGUGGACAUCCUG<br>UUCCAACUGGCGGACCUGUACGAACCCAGGGGCCGGAUGACCCUGGCCGAC<br>AUCGAGCGCAUUGCCCCGCUCGAGGAGGGCACCCUGCCCUUCAACCUGGCG<br>GAGGCCCAGCGCCAGAAGGCCAGCGGGGACAGCGCCAGGCCCGUCCUGCU<br>GCAGGUGGCCGAGUCCGCGUACAGGUUCGGUCUGGGGAGCGUCGCGGGAG<br>CCGUGGGUGCCACCGCCGUGUAUCCGAUCGACCUCGUGAAGACCCGUAUGC<br>AGAAUCAGAGGUCCACCGGCAGCUUCGUGGGCGAGCUCAUGUACAAGAACU<br>CCUUCGACUGUUUCAAGAAGGUUCUCCGGUACGAGGGGUUCUUCGGCCUCU<br>ACCGGGGGCUGCUACCCCAGCUGCUCGGCGUGGCGCCCGAGAAGGCCAUC<br>AAGCUCACGGUCAACGACUUUGUGCGGGACAAGUUCAUGCACAAGGACGGC<br>AGCGUCCCCUGGCCGCCGAGAUUCUGGCAGGCGGCUGCGCCGGAGGCAG<br>CCAGGUCAUCUUUACCAACCCCCUGGAGAUCGUGAAGAUCAGGCUGCAAGU<br>GGCCGGGGAGAUUACCACCGGACCCCGUGUGAGCGCCCUGAGCGUGGUGA<br>GGGACCUUGGCUUCUUUGGCAUAUACAAGGGAGCCAAGGCCUGCUUUCUGA<br>GGGACAUCCCGUUUCCGCCAUAUACUUUCCCUGCUACGCCCACGUGAAAG<br>CGAGCUUCGCCAACGAGGACGGCCAGGUCAGUCCCGGCUCCCUACUGCUG<br>GCCGGAGCCAUCGCCGGGAUGCCCGCCGCCAGCCUGGUGACCCCGCGGA<br>CGUUAUCAAGACCAGGCUGCAGGUGGCGGCCAGGGCGGGCCAGACCACCUA<br>CAGCGGCGUGAUCGACUGCUUCCGCAAGAUCCUGCGGGAGGAGGGCCCA<br>AGGCCCUGUGGAAAGGCGCCGGGGCAAGGGUGUUCAGGAGCAGCCCCAG<br>UUCGGGGUGACCCUGCUUACCUACGAACUGCUGCAGCGGUGGUUCUAUAUC<br>GACUUCGGGGAGUCAAGCCCAUGGGCUCCGAGCCUGUGCCCAAGAGCAG<br>GAUCAAUCUGCCCGCCCCAACCCAGACCACGUGGGAGGGUACAAACUGGC<br>CGUGGCCACCUUCGCCGGAAUCGAGAACAAGUUCGGCCUGUAUCUGCCCCU<br>GUUCAAACCGUCCGUCUCCACCAGCAAGGCCAUCGGCGGGGCCCC*UGAUA*<br>*AUAGUCCAUAAAGUAGGAAACACUACAGCUGGAGCCUCGGUGGCCAUGCU*<br>*UCUUGCCCCUUGGGCCUCCCCCCAGCCCCUCCUCCCCUUCCUGCACCCGUA*<br>*CCCCCCGCAUUAUUACUCACGGUACGAGUGGUCUUUGAAUAAAGUCUGAG*<br>*UGGGCGGC* |
| 136 | #3 | <u>GGGAAAUAAGAGAGAAAAGAAGAGUAAGAAGAAAUAUAAGAGCCACC</u>AUG<br>GCCGCCGCCAAGGUCGCACUCACCAAACGGGCCGACCCCGCCGAGCUCAGG<br>ACCAUCUUCCUCAAGUACGCCAGCAUCGAGAAGAACGGGGAGUUCUUCAUG<br>AGCCCCAACGACUUCGUAACCAGGUACCUCAAUAUCUUCGGCGAAAGCCAG<br>CCCAACCCGAAGACCGUCGAGCUCCUCUCCGGGGUCGUCGAUCAGACCAAG<br>GACGGGCUCAUCUCCUUCCAGGAGUUCGUGGCCUUCGAGUCCGUCCUCUG<br>CGCCCCGGACGCCCUCUUCAUGGUCGCCUUCCAACUCUUCGAUAAGGCCGG<br>GAAAGGCGAGGUGACCUUCGAAGAUGUGAAGCAGGUUUUCGGCCAGACCAC |

TABLE 5-continued mRNA Constructs

| SEQ ID | Construct no. | Sequence (5' UTR = bold underline; 3' UTR comprising a stop codon = bold italics) |
|---|---|---|
| | | GAUCCACCAGCAUAUCCCCUUUAACUGGGACAGCGAGUUCGUGCAGCUGCA CUUCGGCAAAGAGAGGAAGAGGCACCUCACCUAUGCCGAAUUCACACAAUUC CUGCUCGAGAUUCAGCUGGAGCAUGCCAAACAAGCCUUUGUCCAGCGGGAC AACGCCAGGACCGGCAGGGUCACCGCGAUCGACUUUCGCGAUAUCAUGGUG ACCAUCAGGCCCCACGUGCUCACCCCCUUUGUGGAGGAGUGCCUGGUCGCC GCCGCCGGCGGGACGACCAGCCACCAGGUGUCCUUCUCAUACUUCAACGGG UUCAACAGCCUGCUGAACAACAUGGAGCUGAUCCGCAAGAUCUACUCCACCC UGGCCGGCACCAGGAAGGACGUGGAAGUGACCAAGGAGGAGUUCGUUCUC GCCGCCCAGAAAUUCGGACAGGUGACCCCGAUGGAGGUGGACAUCCUCUUC CAGCUGGCCGAUCUCUACGAGCCCCGGGGCAGGAUGACGCUCGCCGACAUC GAGCGAAUCGCCCCCUGGAGGAGGGUACCCUUCCCUUCAACCUGGCCGAG GCCCAGCGACAGAAAGCCAGCGGCGACAGUGCCAGGCCCGUGCUCCUGCAG GUGGCCGAAUCGCCUACAGAUUUGGCCUGGGCAGCGUCGCCGGCGCAGU GGGCGCCACCGCCGUGUACCCGAUCGACCUGGUCAAGACCAGGAUGCAGAA CCAGAGAAGCACCGGCUCCUUUGUGGGCGAGCUUAUGUACAAGAACAGCUU CGACUGCUUCAAGAAGGUCCUGCGUUACGAGGGCUUCUUCGGGCUGUACC GGGGCCUGCUGCCGCAGCUGCUAGGCUCGCGCCCGAGAAGGCCAUUAAG CUGACCGUGAACGACUUCGUACGGGACAAAUUCAUGCACAAGGACGGCAGU GUGCCCCUGGCCGCAGAGAUCCUGGCCGGGGGCUGUGCCGGCGGGUCCCA GGUGAUCUUUACGAACCCCCUGGAGAUAGUGAAGAUCCGCUGCAGGUGGC CGGGGAGAUCACCACCGGCCCCCGGGUGUCCGCCCUGAGCGUCGUGAGGG AUCUGGGGUUCUUUGGCAUCUAUAAGGGUGCCAAGGCCUGCUUCCUGCGU GACAUUCCCUUUAGCGCCAUCUACUUCCCCUGCUACGCCCAUGUCAAGGCC AGCUUCGCCAACGAAGACGGACAGGUGAGCCCCGGGUCCCUGCUGCUGGC CGGCGCCAUCGCAGGGAUGCCGGCCGCCUCACUGGUGACCCCGGCGGACG UGAUAAAGACGAGGCUGCAGGUGGCCGCCCGCGCAGGCCAGACCACGUACU CGGGUGUGAUAGACUGCUUCCGGAAGAUCCUGAGGGAAGAAGGCCCCAAGG CCCUGUGGAAGGGGGCCGGCGCCAGGGUGUUCCGCAGCAGCCCCCAGUUC GGGGUCACCCUGCUCACGUACGAGCUCCUGCAGAGGUGGUUCUACAUCGAC UUUGGCGGGGUCAAGCCCAUGGGCAGUGAGCCGGUGCCCAAGAGCCGGAU CAAUCUGCCCGCCCCCAACCCUGACCACGUCGGCGGGUACAAACUGGCGGU GGCCACCUUCGCCGGCAUCGAGAACAAGUUUGGCCUGUACCUGCCGCUGUU UAAGCCGUCCGUGAGCACCUCCAAGGCCAUCGGGGGGGCCCA*UGAUAAUA GUCCAUAAAGUAGGAAACACUACAGCUGGAGCCUCGGUGGCCAUGCUUCU UGCCCCUUGGGCCUCCCCCAGCCCCUCUCCCCUUCCUGCACCCGUACCC CCCGCAUUAUUACUCACGGUACGAGUGGUCUUUGAAUAAAGUCUAGUGG GCGGC* |
| 139 | #4 | <u>GGGAAAUAAGAGAGAAAAGAAGAGUAAGAAGAAAUAUAAGAGCCACC</u>AUG GCCGCCGCUAAGGUCGCCCUCACGAAGCGGGCCGAUCCCGCCGAGCUCCG GACCAUCUUUCUCAAAUACGCCAGCAUCGAGAAGAACGGCGAGUUCUUCAU GUCCCCCAACGACUUCGUCACCAGGUACCUAAACAUCUUCGGCGAGAGCCA GCCGAACCCCAAGACCGUCGAAUUGCUAUCGGGCGUCGUCGACCAGACCAA GGACGGGCUCAUCAGCUUCCAGGAGUUCGUCGCCUUCGAGUCCGUCCUCU GCGCCCCCGACGCCCUCUUCAUGGUAGCAUUCCAGUUGUUCGACAAGGCCG GAAAGGGGGAGGUGACCUUCGAGGACGUGAAGCAGGUGUUUGGUCAGACC ACCAUCCAUCAGCACAUCCCGUUUAACUGGGACUCGGAGUUCGUGCAGCUC CACUUCGGCAAGGAACGAAAGCGGCACCUCACCUACGCCGAGUUCACCCAG UUCCUGCUGGAGAUCCAGCUGGAACACGCCAAGCAGGCCUUCGUGCAGCGA GACAAUGCGAGGACCGGGCGCGUGACUGCCAUCGAUUUCAGGGACAUCAUG GUGACCAUCCGGCCCCACGUGCUGACUCCCUUCGUGGAGGAGUGCCUGGU CGCAGCCGCCGGGGGUACCACCUCCCACCAGGUGAGCUUCAGCUACUUCAA CGGCUUCAACAGCCUGCUCAACAACAUGGAACUGAUCCGCAAGAUCUAUUCC ACACUCGCCGGCACCAGGAAGGAUGUGGAGGUGACCAAGGAGGAGUUUGUG CUGGCGCCCAGAAGUUUGGGCAGGUCACCCCCAUGGAGGUGGACAUCCU CUUCCAGCUGGCCGACCUGUACGAGCCCAGGGGCAGGAUGACCCUGGCCG ACAUCGAACGAAUCGCCCCCCUGGAGGAGGGCACACUGCCCUUCAACCUGG CCGAGGCCCAGAGGCAGAAGGCCUCCGGCGACAGCGCCCAGCCCGUGCUU CUGCAAGUGGCCGAGAGCGCCUACCGCUUUGGCCUGGGAUCCGUGGCCGG CGCCGUCGGUGCCACCGCCGUGUACCCAAUCGACCUAGUGAAGACACGCAU GCAGAACCAGCGCAGCACCGGCUCCUUUGUCGGGGAGCUGAUGUAUAAGAA CAGCUUCGACUGCUUCAAGAAGGUGCUGCGCUACGAGGGCUUCUUCGGCCU GUACAGGGGCUGCUGCCCAACUGCUGGGCGUGGCCCCGAGAAGGCCA UCAAGCUGACCGUUAACGACUUCGUCGAGACAAGUUCAUGCACAAGGACG GCAGCGUGCCCUUGGCCGCAGAGAUACUGGCCGGGGGCUGCGCCGGCGGG UCGCAGGUGAUCUUCACCAACCCCCUCGAGAUCGUAAAGAUCAGGCUCCAA GUGGCCGGGGAGAUCACCACCGGCCCCAGGGUGUCCGCCCUGUCGGUGGU CAGGGACCUGGGGUUCUUCGGGAUAUACAAGGGCGCGAAGGCCUGCUUCC UGAGGGACAUCCCCUUCAGCGCCAUCUACUUUCCCUGCUACGCCCACGUCA AGGCCAGCUUCGCCAACGAGGAUGGCCAGGUGUCCCCGGGCUCCCUGCUC CUGGCCGGUGCUAUCGCGGGAAUGCCCGCCGCGAGCCUGGUGACCCCCGC CGAUGUGAUCAAGACCAGGCUGCAAGUCGCGGCGAGGGCCGGUCAGACCAC CUACUCCGGGGUCAUCGAUUGCUUUAGGAAGAUCCUCCGGGAGGAGGGGC CCAAGGCACUGUGGAAGGGGGCCGGGGCCAGGGUGUUCCGUAGCUCCCCC CAGUUUGGCGUGACCCUGCUGACCUACGAACUGCUGCAGAGGUGGUUCUAC |

TABLE 5-continued mRNA Constructs

| SEQ ID | Construct no. | Sequence (5' UTR = bold underline; 3' UTR comprising a stop codon = bold italics) |
|---|---|---|
| | | AUCGACUUCGGGGGCGUGAAGCCCAUGGGCUCCGAGCCGGUGCCUAAGAG<br>CCGGAUCAAUCUGCCCGCCCCCAACCCCGACCACGUGGGGGGCUACAAGCU<br>GGCCGUGGCUACCUUCGCCGGUAUCGAGAACAAGUUCGGCCUGUACCUGCC<br>CCUGUUCAAGCCCUCCGUGAGCACGAGCAAGGCCAUCGGGGGGGCCCC*U*<br>*GAUAAUAGUCCAUAAAGUAGGAAACACUACAGCUGGAGCCUCGGUGGCCA*<br>*UGCUUCUUGCCCCUUGGGCCUCCCCCCAGCCCCUCCUCCCCUUCCUGCACC*<br>*CGUACCCCCGCAUUAUUACUCACGGUACGAGUGGUCUUUGAAUAAAGUC*<br>*UGAGUGGGCGGC* |

20. Methods of Making Polynucleotides

The present disclosure also provides methods for making a polynucleotide of the invention (e.g., a polynucleotide comprising a nucleotide sequence encoding a Citrin polypeptide) or a complement thereof.

In some aspects, a polynucleotide (e.g., a RNA, e.g., an mRNA) disclosed herein, and encoding a Citrin polypeptide, can be constructed using in vitro transcription. In other aspects, a polynucleotide (e.g., a RNA, e.g., an mRNA) disclosed herein, and encoding a Citrin polypeptide, can be constructed by chemical synthesis using an oligonucleotide synthesizer.

In other aspects, a polynucleotide (e.g., a RNA, e.g., an mRNA) disclosed herein, and encoding a Citrin polypeptide is made by using a host cell. In certain aspects, a polynucleotide (e.g., a RNA, e.g., an mRNA) disclosed herein, and encoding a Citrin polypeptide is made by one or more combination of the IVT, chemical synthesis, host cell expression, or any other methods known in the art.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., a RNA, e.g., an mRNA) encoding a Citrin polypeptide. The resultant polynucleotides, e.g., mRNAs, can then be examined for their ability to produce protein and/or produce a therapeutic outcome.

a. In Vitro Transcription/Enzymatic Synthesis

The polynucleotides of the present invention disclosed herein (e.g., a polynucleotide comprising a nucleotide sequence encoding a Citrin polypeptide) can be transcribed using an in vitro transcription (IVT) system. The system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate polynucleotides disclosed herein. See U.S. Publ. No. US20130259923, which is herein incorporated by reference in its entirety.

Any number of RNA polymerases or variants can be used in the synthesis of the polynucleotides of the present invention. RNA polymerases can be modified by inserting or deleting amino acids of the RNA polymerase sequence. As a non-limiting example, the RNA polymerase can be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants can be obtained by evolving an RNA polymerase, optimizing the RNA polymerase amino acid and/or nucleic acid sequence and/or by using other methods known in the art. As a non-limiting example, T7 RNA polymerase variants can be evolved using the continuous directed evolution system set out by Esvelt et al. (Nature 472:499-503 (2011); herein incorporated by reference in its entirety) where clones of T7 RNA polymerase can encode at least one mutation such as, but not limited to, lysine at position 93 substituted for threonine (K93T), I4M, A7T, E63V, V64D, A65E, D66Y, T76N, C125S, S128R, A136T, N165S, G175S, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants can encode at least mutation as described in U.S. Pub. Nos. 20100120024 and 20070117112; herein incorporated by reference in their entireties. Variants of RNA polymerase can also include, but are not limited to, substitutional variants, conservative amino acid substitution, insertional variants, and/or deletional variants.

In one aspect, the polynucleotide can be designed to be recognized by the wild type or variant RNA polymerases. In doing so, the polynucleotide can be modified to contain sites or regions of sequence changes from the wild type or parent chimeric polynucleotide.

Polynucleotide or nucleic acid synthesis reactions can be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of E. coli, Bacillus DNA polymerase I, Thermus aquaticus (Taq) DNA polymerases, and the T7 RNA and DNA polymerases, is among the best studied of these families. Another large family is DNA polymerase a (pol a) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. (Cheng et al., PNAS 91:5695-5699 (1994), the contents of which are incorporated herein by reference in their entirety). RNA polymerases from bacteriophage T3, T7, and SP6 have been widely used to prepare RNAs for biochemical and biophysical studies. RNA polymerases, capping enzymes, and poly-A polymerases are disclosed in the co-pending International Publication No. WO2014028429, the contents of which are incorporated herein by reference in their entirety.

In one aspect, the RNA polymerase which can be used in the synthesis of the polynucleotides of the present invention is a Syn5 RNA polymerase. (see Zhu et al. Nucleic Acids Research 2013, doi: 10.1093/nar/gkt1193, which is herein incorporated by reference in its entirety). The Syn5 RNA polymerase was recently characterized from marine cyanophage Syn5 by Zhu et al. where they also identified the promoter sequence (see Zhu et al. Nucleic Acids Research 2013, the contents of which is herein incorporated by reference in its entirety). Zhu et al. found that Syn5 RNA polymerase catalyzed RNA synthesis over a wider range of temperatures and salinity as compared to Ti RNA polymerase. Additionally, the requirement for the initiating nucleotide at the promoter was found to be less stringent for Syn5 RNA polymerase as compared to the T7 RNA polymerase making Syn5 RNA polymerase promising for RNA synthesis.

In one aspect, a Syn5 RNA polymerase can be used in the synthesis of the polynucleotides described herein. As a non-limiting example, a Syn5 RNA polymerase can be used in the synthesis of the polynucleotide requiring a precise 3'-terminus.

In one aspect, a Syn5 promoter can be used in the synthesis of the polynucleotides. As a non-limiting example, the Syn5 promoter can be 5'-ATFGGGCACCCGTAAGGG-3' (SEQ ID NO: 78) as described by Zhu et al. (Nucleic Acids Research 2013).

In one aspect, a Syn5 RNA polymerase can be used in the synthesis of polynucleotides comprising at least one chemical modification described herein and/or known in the art (see e.g., the incorporation of pseudo-UTP and 5Me-CTP described in Zhu et al. Nucleic Acids Research 2013).

In one aspect, the polynucleotides described herein can be synthesized using a Syn5 RNA polymerase which has been purified using modified and improved purification procedure described by Zhu et al. (Nucleic Acids Research 2013).

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods can be applied in the manufacture of the polynucleotides of the invention. For example, polymerase chain reaction (PCR), strand displacement amplification (SDA), nucleic acid sequence-based amplification (NASBA), also called transcription mediated amplification (TMA), and/or rolling-circle amplification (RCA) can be utilized in the manufacture of one or more regions of the polynucleotides of the present invention.

b. Chemical Synthesis

Standard methods can be applied to synthesize an isolated polynucleotide sequence encoding an isolated polypeptide of interest, such as a polynucleotide of the invention (e.g., a polynucleotide comprising a nucleotide sequence encoding a Citrin polypeptide). For example, a single DNA or RNA oligomer containing a codon-optimized nucleotide sequence coding for the particular isolated polypeptide can be synthesized. In other aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., a RNA, e.g., an mRNA) can be chemically synthesized using chemical synthesis methods and potential nucleobase substitutions known in the art. See, for example, International Publication Nos. WO2014093924, WO2013052523; WO2013039857, WO2012135805, WO2013151671; U.S. Publ. No. US20130115272; or U.S. Pat. No. 8,999,380 or U.S. Pat. No. 8,710,200, all of which are herein incorporated by reference in their entireties.

c. Purification of Polynucleotides Encoding Citrin

Purification of the polynucleotides described herein (e.g., a polynucleotide comprising a nucleotide sequence encoding a Citrin polypeptide) can include, but is not limited to, polynucleotide clean-up, quality assurance and quality control. Clean-up can be performed by methods known in the arts such as, but not limited to, AGENCOURT® beads (Beckman Coulter Genomics, Danvers, MA), poly-T beads, LNA oligo-T capture probes (EXIQON® Inc., Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC).

The term "purified" when used in relation to a polynucleotide such as a "purified polynucleotide" refers to one that is separated from at least one contaminant. As used herein, a "contaminant" is any substance that makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

In some embodiments, purification of a polynucleotide of the invention (e.g., a polynucleotide comprising a nucleotide sequence encoding a Citrin polypeptide) removes impurities that can reduce or remove an unwanted immune response, e.g., reducing cytokine activity.

In some embodiments, the polynucleotide of the invention (e.g., a polynucleotide comprising a nucleotide sequence encoding a Citrin polypeptide) is purified prior to administration using column chromatography (e.g., strong anion exchange HPLC, weak anion exchange HPLC, reverse phase HPLC (RP-HPLC), and hydrophobic interaction HPLC (HIC-HPLC), or (LCMS)).

In some embodiments, the polynucleotide of the invention (e.g., a polynucleotide comprising a nucleotide sequence a Citrin polypeptide) purified using column chromatography (e.g., strong anion exchange HPLC, weak anion exchange HPLC, reverse phase HPLC (RP-HPLC, hydrophobic interaction HPLC (HIC-HPLC), or (LCMS)) presents increased expression of the encoded Citrin protein compared to the expression level obtained with the same polynucleotide of the present disclosure purified by a different purification method.

In some embodiments, a column chromatography (e.g., strong anion exchange HPLC, weak anion exchange HPLC, reverse phase HPLC (RP-HPLC), hydrophobic interaction HPLC (HIC-HPLC), or (LCMS)) purified polynucleotide comprises a nucleotide sequence encoding a Citrin polypeptide comprising one or more of the point mutations known in the art.

In some embodiments, the use of RP-HPLC purified polynucleotide increases Citrin protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the expression levels of Citrin protein in the cells before the RP-HPLC purified polynucleotide was introduced in the cells, or after a non-RP-HPLC purified polynucleotide was introduced in the cells.

In some embodiments, the use of RP-HPLC purified polynucleotide increases functional Citrin protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the functional expression levels of Citrin protein in the cells before the RP-HPLC purified polynucleotide was introduced in the cells, or after a non-RP-HPLC purified polynucleotide was introduced in the cells.

In some embodiments, the use of RP-HPLC purified polynucleotide increases detectable Citrin activity in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the activity levels of functional Citrin in the cells before the RP-HPLC purified polynucleotide was introduced in the cells, or after a non-RP-HPLC purified polynucleotide was introduced in the cells.

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure.

A quality assurance and/or quality control check can be conducted using methods such as, but not limited to, gel electrophoresis, UV absorbance, or analytical HPLC. In another embodiment, the polynucleotide can be sequenced by methods including, but not limited to reverse-transcriptase-PCR.

d. Quantification of Expressed Polynucleotides Encoding Citrin

In some embodiments, the polynucleotides of the present invention (e.g., a polynucleotide comprising a nucleotide sequence encoding a Citrin polypeptide), their expression products, as well as degradation products and metabolites can be quantified according to methods known in the art.

In some embodiments, the polynucleotides of the present invention can be quantified in exosomes or when derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes can be retrieved from an organ selected from the group consisting of lung, heart, pancreas, stomach, intestine, bladder, kidney, ovary, testis, skin, colon, breast, prostate, brain, esophagus, liver, and placenta.

In the exosome quantification method, a sample of not more than 2 mL is obtained from the subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of a polynucleotide can be an expression level, presence, absence, truncation or alteration of the administered construct. It is advantageous to correlate the level with one or more clinical phenotypes or with an assay for a human disease biomarker.

The assay can be performed using construct specific probes, cytometry, qRT-PCR, real-time PCR, PCR, flow cytometry, electrophoresis, mass spectrometry, or combinations thereof while the exosomes can be isolated using immunohistochemical methods such as enzyme linked immunosorbent assay (ELISA) methods. Exosomes can also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of polynucleotides remaining or delivered. This is possible because the polynucleotides of the present invention differ from the endogenous forms due to the structural or chemical modifications.

In some embodiments, the polynucleotide can be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified polynucleotide can be analyzed in order to determine if the polynucleotide can be of proper size, check that no degradation of the polynucleotide has occurred. Degradation of the polynucleotide can be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

21. Pharmaceutical Compositions and Formulations

The present invention provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a Citrin polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a Citrin polypeptide. In some embodiments, the polynucleotide further comprises a miRNA binding site, e.g., a miRNA binding site that binds miR-126, miR-142, miR-144, miR-146, miR-150, miR-155, miR-16, miR-21, miR-223, miR-24, miR-27 and miR-26a.

Pharmaceutical compositions or formulation can optionally comprise one or more additional active substances, e.g., therapeutically and/or prophylactically active substances. Pharmaceutical compositions or formulation of the present invention can be sterile and/or pyrogen-free. General considerations in the formulation and/or manufacture of pharmaceutical agents can be found, for example, in Remington: The Science and Practice of Pharmacy 21$^{st}$ ed., Lippincott Williams & Wilkins, 2005 (incorporated herein by reference in its entirety). In some embodiments, compositions are administered to humans, human patients or subjects. For the purposes of the present disclosure, the phrase "active ingredient" generally refers to polynucleotides to be delivered as described herein.

Formulations and pharmaceutical compositions described herein can be prepared by any method known or hereafter developed in the art of pharmacology. In general, such preparatory methods include the step of associating the active ingredient with an excipient and/or one or more other accessory ingredients, and then, if necessary and/or desirable, dividing, shaping and/or packaging the product into a desired single- or multi-dose unit.

A pharmaceutical composition or formulation in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the subject being treated and further depending upon the route by which the composition is to be administered.

In some embodiments, the compositions and formulations described herein can contain at least one polynucleotide of the invention. As a non-limiting example, the composition or formulation can contain 1, 2, 3, 4 or 5 polynucleotides of the invention. In some embodiments, the compositions or formulations described herein can comprise more than one type of polynucleotide. In some embodiments, the composition or formulation can comprise a polynucleotide in linear and circular form. In another embodiment, the composition or formulation can comprise a circular polynucleotide and an in vitro transcribed (IVT) polynucleotide. In yet another embodiment, the composition or formulation can comprise an NT polynucleotide, a chimeric polynucleotide and a circular polynucleotide.

Although the descriptions of pharmaceutical compositions and formulations provided herein are principally directed to pharmaceutical compositions and formulations that are suitable for administration to humans, it will be understood by the skilled artisan that such compositions are generally suitable for administration to any other animal, e.g., to non-human animals, e.g. non-human mammals. The present invention provides pharmaceutical formulations that comprise a polynucleotide described herein (e.g., a polynucleotide comprising a nucleotide sequence encoding a Citrin polypeptide). The polynucleotides described herein can be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide to specific tissues or cell types); (5) increase the translation of encoded protein in vivo; and/or (6) alter the release profile of encoded protein in vivo. In some embodiments, the pharmaceutical formulation disclosed herein further comprises a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cryoprotectants, and/or bulking agents, as suited to the particular dosage form desired. Various excipients for formulating pharmaceutical compositions and techniques for preparing the composition are known in the art (see Remington: The Science and Practice of Pharmacy, 21st Edition, A. R. Gennaro (Lippincott, Williams & Wilkins, Baltimore, MD, 2006; incorporated herein by reference in its entirety).

Exemplary diluents include, but are not limited to, calcium or sodium carbonate, calcium phosphate, calcium hydrogen phosphate, sodium phosphate, lactose, sucrose, cellulose, microcrystalline cellulose, kaolin, mannitol, sorbitol, etc., and/or combinations thereof.

Exemplary granulating and/or dispersing agents include, but are not limited to, starches, pregelatinized starches, or microcrystalline starch, alginic acid, guar gum, agar, poly (vinyl-pyrrolidone), (providone), cross-linked poly(vinyl-pyrrolidone) (crospovidone), cellulose, methylcellulose, carboxymethyl cellulose, cross-linked sodium carboxymethyl cellulose (croscarmellose), magnesium aluminum silicate (VEEGUM®), sodium lauryl sulfate, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), sorbitan fatty acid esters (e.g., polyoxyethylene sorbitan monooleate [TWEEN®80], sorbitan monopalmitate [SPAN®40], glyceryl monooleate, polyoxyethylene esters, polyethylene glycol fatty acid esters (e.g., CREMOPHOR®), polyoxyethylene ethers (e.g., polyoxyethylene lauryl ether [BRIJ®30]), PLUORINC®F 68, POLOXAMER®188, etc. and/or combinations thereof.

Exemplary binding agents include, but are not limited to, starch, gelatin, sugars (e.g., sucrose, glucose, dextrose, dextrin, molasses, lactose, lactitol, mannitol), amino acids (e.g., glycine), natural and synthetic gums (e.g., acacia, sodium alginate), ethylcellulose, hydroxyethylcellulose, hydroxypropyl methylcellulose, etc., and combinations thereof.

Oxidation is a potential degradation pathway for mRNA, especially for liquid mRNA formulations. In order to prevent oxidation, antioxidants can be added to the formulations. Exemplary antioxidants include, but are not limited to, alpha tocopherol, ascorbic acid, acorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

Exemplary chelating agents include, but are not limited to, ethylenediaminetetraacetic acid (EDTA), citric acid monohydrate, disodium edetate, fumaric acid, malic acid, phosphoric acid, sodium edetate, tartaric acid, trisodium edetate, etc., and combinations thereof.

Exemplary antimicrobial or antifungal agents include, but are not limited to, benzalkonium chloride, benzethonium chloride, methyl paraben, ethyl paraben, propyl paraben, butyl paraben, benzoic acid, hydroxybenzoic acid, potassium or sodium benzoate, potassium or sodium sorbate, sodium propionate, sorbic acid, etc., and combinations thereof.

Exemplary preservatives include, but are not limited to, vitamin A, vitamin C, vitamin E, beta-carotene, citric acid, ascorbic acid, butylated hydroxyanisol, ethylenediamine, sodium lauryl sulfate (SLS), sodium lauryl ether sulfate (SLES), etc., and combinations thereof.

In some embodiments, the pH of polynucleotide solutions are maintained between pH 5 and pH 8 to improve stability. Exemplary buffers to control pH can include, but are not limited to sodium phosphate, sodium citrate, sodium succinate, histidine (or histidine-HCl), sodium malate, sodium carbonate, etc., and/or combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium or magnesium lauryl sulfate, etc., and combinations thereof.

The pharmaceutical composition or formulation described here can contain a cryoprotectant to stabilize a polynucleotide described herein during freezing. Exemplary cryoprotectants include, but are not limited to mannitol, sucrose, trehalose, lactose, glycerol, dextrose, etc., and combinations thereof.

The pharmaceutical composition or formulation described here can contain a bulking agent in lyophilized polynucleotide formulations to yield a "pharmaceutically elegant" cake, stabilize the lyophilized polynucleotides during long term (e.g., 36 month) storage. Exemplary bulking agents of the present invention can include, but are not limited to sucrose, trehalose, mannitol, glycine, lactose, raffinose, and combinations thereof.

In some embodiments, the pharmaceutical composition or formulation further comprises a delivery agent. The delivery agent of the present disclosure can include, without limitation, liposomes, lipid nanoparticles, lipidoids, polymers, lipoplexes, microvesicles, exosomes, peptides, proteins, cells transfected with polynucleotides, hyaluronidase, nanoparticle mimics, nanotubes, conjugates, and combinations thereof.

22. Delivery Agents a. Lipid Compound

The present disclosure provides pharmaceutical compositions with advantageous properties. The lipid compositions described herein may be advantageously used in lipid nanoparticle compositions for the delivery of therapeutic and/or prophylactic agents, e.g., mRNAs, to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent, e.g., mRNA, has an increased therapeutic index as compared to a corresponding formulation which comprises a reference lipid (e.g., MC3, KC2, or DLinDMA) and the same therapeutic or prophylactic agent.

In certain embodiments, the present application provides pharmaceutical compositions comprising:
(a) a polynucleotide comprising a nucleotide sequence encoding a Citrin polypeptide; and
(b) a delivery agent.

In some embodiments, the delivery agent comprises a lipid compound having the formula (I)

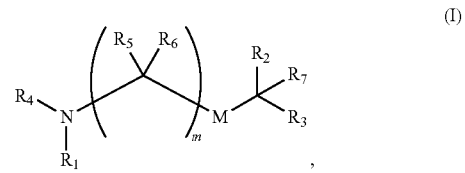

wherein
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;
each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In some embodiments, a subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof, wherein alkyl and alkenyl groups may be linear or branched.

In some embodiments, a subset of compounds of Formula (I) includes those in which when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13,
or salts or stereoisomers thereof.

In another embodiments, another subset of compounds of Formula (I) includes those in which
- $R_1$ is selected from the group consisting of $C_{5-20}$ alkyl, $C_{5-20}$ alkenyl, —R*YR", —YR", and —R"M'R';
- $R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
- $R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5;
- each $R_5$ is independently selected from the group consisting of $C_{1-3}$ alkyl, $C_{2-3}$ alkenyl, and H;
- each $R_6$ is independently selected from the group consisting of $C_{1-3}$ alkyl, $C_{2-3}$ alkenyl, and H;
- M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
- $R_7$ is selected from the group consisting of $C_{1-3}$ alkyl, $C_{2-3}$ alkenyl, and H;
- each R is independently selected from the group consisting of $C_{1-3}$ alkyl, $C_{2-3}$ alkenyl, and H;
- each R' is independently selected from the group consisting of $C_{1-18}$ alkyl, $C_{2-18}$ alkenyl, —R*YR", —YR", and H;
- each R" is independently selected from the group consisting of $C_{3-14}$ alkyl and $C_{3-14}$ alkenyl;
- each R* is independently selected from the group consisting of $C_{1-12}$ alkyl and $C_{2-12}$ alkenyl;
- each Y is independently a $C_{3-6}$ carbocycle;
- each X is independently selected from the group consisting of F, Cl, Br, and I; and
- m is selected from 5, 6, 7, 8, 9, 10, 11, 12, and 13, or salts or stereoisomers thereof.

In yet other embodiments, another subset of compounds of Formula (I) includes those in which
- $R_1$ is selected from the group consisting of $C_{5-30}$ alkyl, $C_{5-20}$ alkenyl, —R*YR", —YR", and —R"M'R';
- $R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
- $R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- to 14-membered heteroaryl or 8- to 14-membered heterocycloalkyl;
- each $R_5$ is independently selected from the group consisting of $C_{1-3}$ alkyl, $C_{2-3}$ alkenyl, and H;
- each $R_6$ is independently selected from the group consisting of $C_{1-3}$ alkyl, $C_{2-3}$ alkenyl, and H;
- M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;
- $R_7$ is selected from the group consisting of $C_{1-3}$ alkyl, $C_{2-3}$ alkenyl, and H;
- $R_8$ is selected from the group consisting of $C_{3-6}$ carbocycle and heterocycle;
- $R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;
- each R is independently selected from the group consisting of $C_{1-3}$ alkyl, $C_{2-3}$ alkenyl, and H;
- each R' is independently selected from the group consisting of $C_{1-18}$ alkyl, $C_{2-18}$ alkenyl, —R*YR", —YR", and H;
- each R" is independently selected from the group consisting of $C_{3-14}$ alkyl and $C_{3-14}$ alkenyl;
- each R* is independently selected from the group consisting of $C_{1-12}$ alkyl and $C_{2-12}$ alkenyl;
- each Y is independently a $C_{3-6}$ carbocycle;
- each X is independently selected from the group consisting of F, Cl, Br, and I; and
- m is selected from 5, 6, 7, 8, 9, 10, 11, 12, and 13, or salts or stereoisomers thereof.

In yet other embodiments, another subset of compounds of Formula (I) includes those in which
- $R_1$ is selected from the group consisting of $C_{5-20}$ alkyl, $C_{5-20}$ alkenyl, —R*YR", —YR", and —R"M'R';
- $R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
- $R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- to 14-membered heteroaryl or 8- to 14-membered heterocycloalkyl;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR'', —YR'', and H;

each R'' is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which R$_1$ is selected from the group consisting of C$_{5-30}$ alkyl, C$_{5-20}$ alkenyl, —R*YR'', —YR'', and —R''M'R';

R$_2$ and R$_3$ are independently selected from the group consisting of H, C$_{1-14}$ alkyl, C$_{2-14}$ alkenyl, —R*YR'', —YR'', and —R*OR'', or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ(R)$_2$, and unsubstituted C$_{1-6}$ alkyl, where Q is selected from a C$_{3-6}$ carbocycle, a 5- to 14-membered heteroaryl having one or more heteroatoms selected from N, O, and S. —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR'', —YR'', and H;

each R'' is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which R$_1$ is selected from the group consisting of C$_{5-20}$ alkyl, C$_{5-20}$ alkenyl, —R*YR'', —YR'', and —R''M'R';

R$_2$ and R$_3$ are independently selected from the group consisting of H, C$_{1-14}$ alkyl, C$_{2-14}$ alkenyl, —R*YR'', —YR'', and —R*OR'', or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ(R)$_2$, and unsubstituted C$_{1-6}$ alkyl, where Q is selected from a C$_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, and each n is independently selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR'', —YR'', and H;

each R'' is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which R$_1$ is selected from the group consisting of C$_{5-30}$ alkyl, C$_{5-20}$ alkenyl, —R*YR'', —YR'', and —R''M'R';

R$_2$ and R$_3$ are independently selected from the group consisting of H, C$_{2-14}$ alkyl, C$_{2-14}$ alkenyl, —R*YR'', —YR″, and —R*OR″, or $R_2$ and $R_3$, together with the atom to which they are attached, form a heterocycle or carbocycle;

$R_4$ is —(CH$_2$)$_n$Q or —(CH$_2$)$_n$CHQR, where Q is —N(R)$_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR″, —YR″, and H;

each R″ is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-20}$ alkyl, $C_{5-20}$ alkenyl, —R*YR″, —YR″, and —R″M'R';

$R_2$ and $R_3$ are independently selected from the group consisting of H, $C_{2-14}$ alkyl, $C_{2-14}$ alkenyl, —R*YR″, —YR″, and —R*OR″, or $R_2$ and $R_3$, together with the atom to which they are attached, form a heterocycle or carbocycle;

$R_4$ is —(CH$_2$)$_n$Q or —(CH$_2$)$_n$CHQR, where Q is —N(R)$_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR″, —YR″, and H;

each R″ is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still other embodiments, another subset of compounds of Formula (I) includes those in which $R_1$ is selected from the group consisting of $C_{5-30}$ alkyl, $C_{5-20}$ alkenyl, —R*YR″, —YR″, and —R″M'R';

$R_2$ and $R_3$ are independently selected from the group consisting of $C_{1-14}$ alkyl, $C_{2-14}$ alkenyl, —R*YR″, —YR″, and —R*OR″, or $R_2$ and $R_3$, together with the atom to which they are attached, form a heterocycle or carbocycle;

$R_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR″, —YR″, and H;

each R″ is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still other embodiments, another subset of compounds of Formula (I) includes those in which $R_1$ is selected from the group consisting of $C_{5-20}$ alkyl, $C_{5-20}$ alkenyl, —R*YR″, —YR″, and —R″M'R';

$R_2$ and $R_3$ are independently selected from the group consisting of $C_{1-14}$ alkyl, $C_{2-14}$ alkenyl, —R*YR″, —YR″, and —R*OR″, or $R_2$ and $R_3$, together with the atom to which they are attached, form a heterocycle or carbocycle;

$R_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR″, —YR″, and H;

each R″ is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In certain embodiments, a subset of compounds of Formula (I) includes those of Formula (IA):

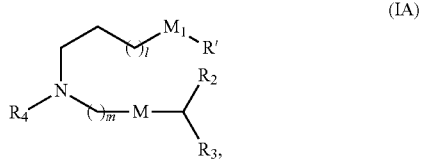

(IA)

or a salt or stereoisomer thereof, wherein l is selected from 1, 2, 3, 4, and 5;

m is selected from 5, 6, 7, 8, and 9;

$M_1$ is a bond or M';

$R_4$ is unsubstituted $C_{1-3}$ alkyl, or $-(CH_2)_nQ$, in which Q is OH, $-NHC(S)N(R)_2$, $-NHC(O)N(R)_2$, $-N(R)C(O)R$, $-N(R)S(O)_2R$, $-N(R)R_8$, $-NHC(=NR_9)N(R)_2$, $-NHC(=CHR_9)N(R)_2$, $-OC(O)N(R)_2$, $-N(R)C(O)OR$, heteroaryl or heterocycloalkyl;

M and M' are independently selected from $-C(O)O-$, $-OC(O)-$, $-C(O)N(R')-$, $-P(O)(OR')O-$, $-S-S-$, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IA), or a salt or stereoisomer thereof, wherein l is selected from 1, 2, 3, 4, and 5; m is selected from 5, 6, 7, 8, and 9;

$M_1$ is a bond or M';

$R_4$ is unsubstituted $C_{1-3}$ alkyl, or $-(CH_2)_nQ$, in which Q is OH, $-NHC(S)N(R)_2$, or $-NHC(O)N(R)_2$;

M and M' are independently selected from $-C(O)O-$, $-OC(O)-$, $-C(O)N(R')-$, $-P(O)(OR')O-$, an aryl group, and a heteroaryl group; and $R_2$ and $R_3$ are independently selected from the group consisting of H, $C_{1-14}$ alkyl, and $C_{2-14}$ alkenyl.

In certain embodiments, a subset of compounds of Formula (I) includes those of Formula (II):

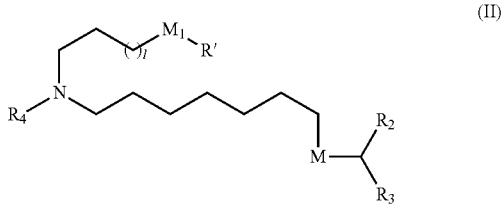

(II)

or a salt or stereoisomer thereof, wherein l is selected from 1, 2, 3, 4, and 5;

$M_1$ is a bond or M';

$R_4$ is unsubstituted $C_{1-3}$ alkyl, or $-(CH_2)_nQ$, in which n is 2, 3, or 4, and Q is OH, $-NHC(S)N(R)_2$, $-NHC(O)N(R)_2$, $-N(R)C(O)R$, $-N(R)S(O)_2R$, $-N(R)R_8$, $-NHC(=NR_9)N(R)_2$, $-NHC(=CHR_9)N(R)_2$, $-OC(O)N(R)_2$, $-N(R)C(O)OR$, heteroaryl or heterocycloalkyl;

M and M' are independently selected from $-C(O)O-$, $-OC(O)-$, $-C(O)N(R')-$, $-P(O)(OR')O-$, $-S-S-$, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II), or a salt or stereoisomer thereof, wherein l is selected from 1, 2, 3, 4, and 5;

$M_1$ is a bond or M';

$R_4$ is unsubstituted $C_{1-3}$ alkyl, or $-(CH_2)_nQ$, in which n is 2, 3, or 4, and Q is OH, $-NHC(S)N(R)_2$, or $-NHC(O)N(R)_2$;

M and M' are independently selected from $-C(O)O-$, $-OC(O)-$, $-C(O)N(R')-$, $-P(O)(OR')O-$, an aryl group, and a heteroaryl group; and $R_2$ and $R_3$ are independently selected from the group consisting of H, $C_{1-14}$ alkyl, and $C_{2-14}$ alkenyl.

In some embodiments, the compound of formula (I) is of the formula (IIa),

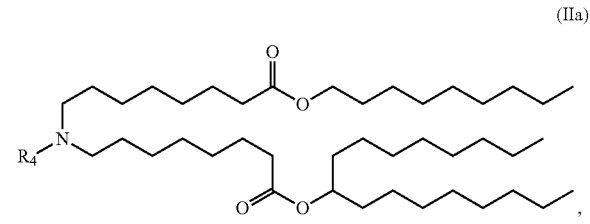

(IIa)

or a salt thereof, wherein $R_4$ is as described above.

In some embodiments, the compound of formula (I) is of the formula (IIb),

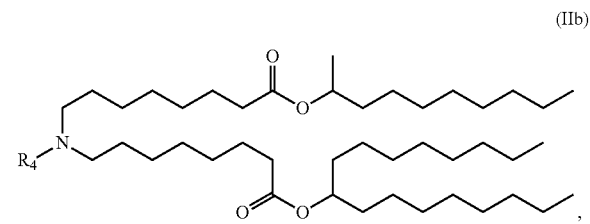

(IIb)

or a salt thereof, wherein $R_4$ is as described above.

In some embodiments, the compound of formula (I) is of the formula (IIc),

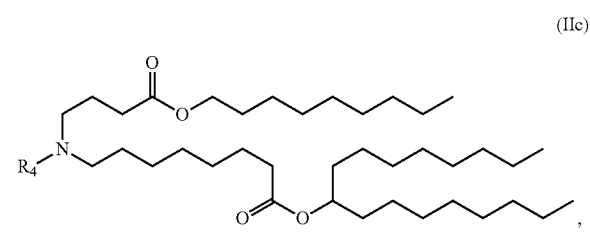

(IIc)

or a salt thereof, wherein $R_4$ is as described above.

In some embodiments, the compound of formula (I) is of the formula (IIe):

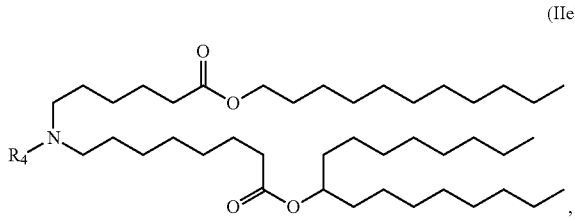
(IIe)

or a salt thereof, wherein $R_4$ is as described above.

In some embodiments, the compound of formula (IIa), (IIb), (IIc), or (IIe) comprises an $R_4$ which is selected from —$(CH_2)_nQ$ and —$(CH_2)_nCHQR$, wherein Q, R and n are as defined above.

In some embodiments, Q is selected from the group consisting of —OR, —OH, —O$(CH_2)_nN(R)_2$, —OC(O)R, —$CX_3$, —CN, —N(R)C(O)R, —N(H)C(O)R, —N(R)S(O)$_2$R, —N(H)S(O)$_2$R, —N(R)C(O)N(R)$_2$, —N(H)C(O)N (R)$_2$, —N(H)C(O)N(H)(R), —N(R)C(S)N(R)$_2$, —N(H)C (S)N(R)$_2$, —N(H)C(S)N(H)(R), and a heterocycle, wherein R is as defined above. In some aspects, n is 1 or 2. In some embodiments, Q is OH, —NHC(S)N(R)$_2$, or —NHC(O)N (R)$_2$.

In some embodiments, the compound of formula (I) is of the formula (IId),

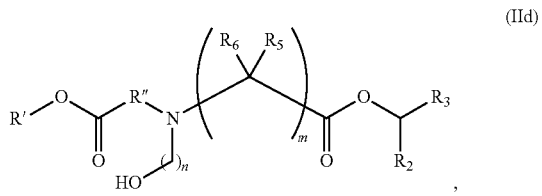
(IId)

or a salt thereof, wherein $R_2$ and $R_3$ are independently selected from the group consisting of $C_{5-14}$ alkyl and $C_{5-14}$ alkenyl, n is selected from 2, 3, and 4, and R', R'', $R_5$, $R_6$ and m are as defined above.

In some aspects of the compound of formula (IId), $R_2$ is $C_8$ alkyl. In some aspects of the compound of formula (IId), $R_3$ is $C_5$-$C_9$ alkyl. In some aspects of the compound of formula (IId), m is 5, 7, or 9. In some aspects of the compound of formula (IId), each $R_5$ is H. In some aspects of the compound of formula (IId), each $R_6$ is H.

In another aspect, the present application provides a lipid composition (e.g., a lipid nanoparticle (LNP)) comprising: (1) a compound having the formula (I); (2) optionally a helper lipid (e.g. a phospholipid); (3) optionally a structural lipid (e.g. a sterol); and (4) optionally a lipid conjugate (e.g. a PEG-lipid). In exemplary embodiments, the lipid composition (e.g., LNP) further comprises a polynucleotide encoding a Citrin polypeptide, e.g., a polynucleotide encapsulated therein.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms).

The notation "$C_{1-14}$ alkyl" means a linear or branched, saturated hydrocarbon including 1-14 carbon atoms. An alkyl group can be optionally substituted.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond.

The notation "$C_{2-14}$ alkenyl" means a linear or branched hydrocarbon including 2-14 carbon atoms and at least one double bond. An alkenyl group can include one, two, three, four, or more double bonds. For example, $C_{18}$ alkenyl can include one or more double bonds. A $C_{18}$ alkenyl group including two double bonds can be a linoleyl group. An alkenyl group can be optionally substituted.

As used herein, the term "carbocycle" or "carbocyclic group" means a mono- or multi-cyclic system including one or more rings of carbon atoms. Rings can be three, four, five, six, seven, eight, nine, ten, eleven, twelve, thirteen, fourteen, or fifteen membered rings.

The notation "$C_{3-6}$ carbocycle" means a carbocycle including a single ring having 3-6 carbon atoms. Carbocycles can include one or more double bonds and can be aromatic (e.g., aryl groups). Examples of carbocycles include cyclopropyl, cyclopentyl, cyclohexyl, phenyl, naphthyl, and 1,2-dihydronaphthyl groups. Carbocycles can be optionally substituted.

As used herein, the term "heterocycle" or "heterocyclic group" means a mono- or multi-cyclic system including one or more rings, where at least one ring includes at least one heteroatom. Heteroatoms can be, for example, nitrogen, oxygen, or sulfur atoms. Rings can be three, four, five, six, seven, eight, nine, ten, eleven, or twelve membered rings. Heterocycles can include one or more double bonds and can be aromatic (e.g., heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. Heterocycles can be optionally substituted.

As used herein, a "biodegradable group" is a group that can facilitate faster metabolism of a lipid in a subject. A biodegradable group can be, but is not limited to, —C(O) O—, —OC(O)—, —C(O)N(R')—, —N(R')C(O)—, —C(O)—, —C(S)—, —C(S)S—, —SC(S)—, —CH (OH)—, —P(O)(OR')O—, —S(O)$_2$—, an aryl group, and a heteroaryl group.

As used herein, an "aryl group" is a carbocyclic group including one or more aromatic rings. Examples of aryl groups include phenyl and naphthyl groups.

As used herein, a "heteroaryl group" is a heterocyclic group including one or more aromatic rings. Examples of heteroaryl groups include pyrrolyl, furyl, thiophenyl, imidazolyl, oxazolyl, and thiazolyl. Both aryl and heteroaryl groups can be optionally substituted. For example, M and M' can be selected from the non-limiting group consisting of optionally substituted phenyl, oxazole, and thiazole. In the formulas herein, M and M' can be independently selected from the list of biodegradable groups above.

Alkyl, alkenyl, and cyclyl (e.g., carbocyclyl and heterocyclyl) groups can be optionally substituted unless otherwise specified. Optional substituents can be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by Cam), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., —C(OR)$_2$R"", in which each OR are alkoxy groups that can be the same or different and R"" is an alkyl or alkenyl group), a phosphate (e.g., P(O)$_4^{3-}$), a thiol (e.g., —SH), a sulfoxide (e.g., —S(O)R), a sulfuric acid (e.g., —S(O)OH), a sulfonic acid (e.g., —S(O)$_{20}$H), a thial (e.g., —C(S)H), a sulfate (e.g., S(O)$_4^{2-}$), a sulfonyl (e.g., —S(O)$_2$—), an amide (e.g., —C(O)NR$_2$, or —N(R)C(O)R), an azido (e.g., —N$_3$), a nitro (e.g., —NO$_2$), a cyano (e.g., —CN), an isocyano (e.g., —NC), an acyloxy (e.g., —OC(O)R), an amino (e.g., —NR$_2$, —NRH, or —NH$_2$), a carbamoyl (e.g., —OC(O)NR$_2$, —OC(O)NRH, or —OC(O)NH$_2$), a sulfonamide (e.g., —S(O)$_2$NR$_2$, —S(O)$_2$NRH, —S(O)$_2$NH$_2$, —N(R)S(O)$_2$R, —N(H)S(O)$_2$R, —N(R)S(O)$_2$H, or —N(H)S(O)$_2$H), an alkyl group, an alkenyl group, and a cyclyl (e.g., carbocyclyl or heterocyclyl) group.

In any of the preceding, R is an alkyl or alkenyl group, as defined herein. In some embodiments, the substituent groups themselves can be further substituted with, for example, one, two, three, four, five, or six substituents as defined herein. For example, a C$_{1-6}$ alkyl group can be further substituted with one, two, three, four, five, or six substituents as described herein.

The compounds of any one of formulae (I), (IA), (II), (IIa), (IIb), (IIc), (IId), and (IIe) include one or more of the following features when applicable.

In some embodiments, R$_4$ is selected from the group consisting of a C$_{3-6}$ carbocycle, —(CH$_2$)$_n$Q, —(CH$_2$)$_n$CHQR, —CHQR, and —CQ(R)$_2$, where Q is selected from a C$_{3-6}$ carbocycle, 5- to 14-membered aromatic or non-aromatic heterocycle having one or more heteroatoms selected from N, O, S. and P. —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5.

In another embodiment, R$_4$ is selected from the group consisting of a C$_{3-6}$ carbocycle, —(CH$_2$)$_n$Q, —(CH$_2$)$_n$CHQR, —CHQR, and —CQ(R)$_2$, where Q is selected from a C$_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and a 5- to 14-membered heterocycloalkyl having one or more heteroatoms selected from N, O, and S which is substituted with one or more substituents selected from oxo (=O), OH, amino, and C$_{1-3}$ alkyl, and each n is independently selected from 1, 2, 3, 4, and 5.

In another embodiment, R$_4$ is selected from the group consisting of a C$_{3-6}$ carbocycle, —(CH$_2$)$_n$Q, —(CH$_2$)$_n$CHQR, —CHQR, and —CQ(R)$_2$, where Q is selected from a C$_{3-6}$ carbocycle, a 5- to 14-membered heterocycle having one or more heteroatoms selected from N, O, and S. —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and each n is independently selected from 1, 2, 3, 4, and 5; and when Q is a 5- to 14-membered heterocycle and (i) R$_4$ is —(CH$_2$)$_n$Q in which n is 1 or 2, or (ii) R$_4$ is —(CH$_2$)$_n$CHQR in which n is 1, or (iii) R$_4$ is —CHQR, and —CQ(R)$_2$, then Q is either a 5- to 14-membered heteroaryl or 8- to 14-membered heterocycloalkyl.

In another embodiment, R$_4$ is selected from the group consisting of a C$_{3-6}$ carbocycle, —(CH$_2$)$_n$Q, —(CH$_2$)$_n$CHQR, —CHQR, and —CQ(R)$_2$, where Q is selected from a C$_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and each n is independently selected from 1, 2, 3, 4, and 5.

In another embodiment, R$_4$ is unsubstituted C$_{1-4}$ alkyl, e.g., unsubstituted methyl.

In certain embodiments, the disclosure provides a compound having the Formula (I), wherein R$_4$ is —(CH$_2$)$_n$Q or —(CH$_2$)$_n$CHQR, where Q is —N(R)$_2$, and n is selected from 3, 4, and 5.

In certain embodiments, the disclosure provides a compound having the Formula (I), wherein R$_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5.

In certain embodiments, the disclosure provides a compound having the Formula (I), wherein R$_2$ and R$_3$ are independently selected from the group consisting of C$_{2-14}$ alkyl, C$_{2-14}$ alkenyl, —R*YR", —YR", and —R*OR", or R$_2$ and R$_3$, together with the atom to which they are attached, form a heterocycle or carbocycle, and R$_4$ is —(CH$_2$)$_n$Q or —(CH$_2$)$_n$CHQR, where Q is —N(R)$_2$, and n is selected from 3, 4, and 5.

In certain embodiments, R$_2$ and R$_3$ are independently selected from the group consisting of C$_{2-14}$ alkyl, C$_{2-14}$ alkenyl, —R*YR", —YR", and —R*OR", or R$_2$ and R$_3$, together with the atom to which they are attached, form a heterocycle or carbocycle.

In some embodiments, R$_1$ is selected from the group consisting of C$_{5-20}$ alkyl and C$_{5-20}$ alkenyl.

In other embodiments, R$_1$ is selected from the group consisting of —R*YR", —YR", and —R"M'R'.

In certain embodiments, R$_1$ is selected from —R*YR" and —YR". In some embodiments, Y is a cyclopropyl group. In some embodiments, R* is C$_8$ alkyl or C$_8$ alkenyl. In certain embodiments, R" is C$_{3-12}$ alkyl. For example, R" can be C$_3$ alkyl. For example, R" can be C$_{4-8}$ alkyl (e.g., C$_4$, C$_5$, C$_6$, C$_7$, or C$_8$ alkyl).

In some embodiments, R$_1$ is C$_{5-20}$ alkyl. In some embodiments, R$_1$ is C$_6$ alkyl. In some embodiments, R$_1$ is C$_8$ alkyl. In other embodiments, R$_1$ is C$_9$ alkyl. In certain embodiments, R$_1$ is C$_{14}$ alkyl. In other embodiments, R$_1$ is C$_{18}$ alkyl.

In some embodiments, R$_1$ is C$_{5-20}$ alkenyl. In certain embodiments, R$_1$ is C$_{18}$ alkenyl. In some embodiments, R$_1$ is linoleyl.

In certain embodiments, R$_1$ is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl, or heptadeca-9-yl). In certain embodiments, R$_1$ is

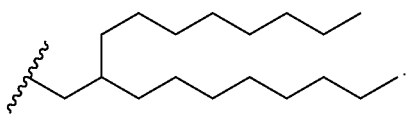 [SMILES: *CC(CCCCCCCC)CCCCCCCC ; "."]

In certain embodiments, $R_1$ is unsubstituted $C_{5-20}$ alkyl or $C_{5-20}$ alkenyl. In certain embodiments, R' is substituted $C_{5-20}$ alkyl or $C_{5-20}$ alkenyl (e.g., substituted with a $C_{3-6}$ carbocycle such as 1-cyclopropylnonyl).

In other embodiments, $R_1$ is —R"M'R'.

In some embodiments, R' is selected from —R*YR" and —YR". In some embodiments, Y is $C_{3-8}$ cycloalkyl. In some embodiments, Y is $C_{6-10}$ aryl. In some embodiments, Y is a cyclopropyl group. In some embodiments, Y is a cyclohexyl group. In certain embodiments, R* is $C_1$ alkyl.

In some embodiments, R" is selected from the group consisting of $C_{3-12}$ alkyl and $C_{3-12}$ alkenyl. In some embodiments, R" adjacent to Y is $C_1$ alkyl. In some embodiments, R" adjacent to Y is $C_4$-9 alkyl (e.g., $C_4$, $C_5$, $C_6$, $C_7$ or $C_8$ or $C_9$ alkyl).

In some embodiments, R' is selected from $C_4$ alkyl and $C_4$ alkenyl. In certain embodiments, R' is selected from $C_5$ alkyl and $C_5$ alkenyl. In some embodiments, R' is selected from $C_6$ alkyl and $C_6$ alkenyl. In some embodiments, R' is selected from $C_7$ alkyl and $C_7$ alkenyl. In some embodiments, R' is selected from $C_9$ alkyl and $C_9$ alkenyl.

In other embodiments, R' is selected from $C_{11}$ alkyl and $C_{11}$ alkenyl. In other embodiments, R' is selected from $C_{12}$ alkyl, $C_{12}$ alkenyl, $C_{13}$ alkyl, $C_{13}$ alkenyl, $C_{14}$ alkyl, $C_{14}$ alkenyl, $C_{15}$ alkyl, $C_{15}$ alkenyl, $C_{1-6}$ alkyl, $C_{16}$ alkenyl, $C_{17}$ alkyl, $C_{17}$ alkenyl, $C_{18}$ alkyl, and $C_{18}$ alkenyl. In certain embodiments, R' is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl or heptadeca-9-yl). In certain embodiments, R' is

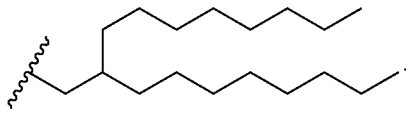 [SMILES: *CC(CCCCCCCC)CCCCCCCC ; "."]

In certain embodiments, R' is unsubstituted $C_{1-18}$ alkyl. In certain embodiments, R' is substituted $C_{1-18}$ alkyl (e.g., $C_{1-15}$ alkyl substituted with a $C_{3-6}$ carbocycle such as 1-cyclopropylnonyl).

In some embodiments, R" is selected from the group consisting of $C_{3-14}$ alkyl and $C_{3-14}$ alkenyl. In some embodiments, R" is $C_3$ alkyl, $C_4$ alkyl, $C_5$ alkyl, $C_6$ alkyl, $C_7$ alkyl, or $C_8$ alkyl. In some embodiments, R" is $C_9$ alkyl, $C_{10}$ alkyl, $C_{11}$ alkyl, $C_{12}$ alkyl, $C_{13}$ alkyl, or $C_{14}$ alkyl.

In some embodiments, M' is —C(O)O—. In some embodiments, M' is —OC(O)—.

In other embodiments, M' is an aryl group or heteroaryl group. For example, M' can be selected from the group consisting of phenyl, oxazole, and thiazole.

In some embodiments, M is —C(O)O— In some embodiments, M is —OC(O)—. In some embodiments, M is —C(O)N(R')—. In some embodiments, M is —P(O)(OR')O—.

In other embodiments, M is an aryl group or heteroaryl group. For example, M can be selected from the group consisting of phenyl, oxazole, and thiazole.

In some embodiments, M is the same as M'. In other embodiments, M is different from M'.

In some embodiments, each $R_5$ is H. In certain such embodiments, each $R_6$ is also H.

In some embodiments, $R_7$ is H. In other embodiments, $R_7$ is $C_{1-3}$ alkyl (e.g., methyl, ethyl, propyl, or i-propyl).

In some embodiments, $R_2$ and $R_3$ are independently $C_{5-14}$ alkyl or $C_{5-14}$ alkenyl.

In some embodiments, $R_2$ and $R_3$ are the same. In some embodiments, $R_2$ and $R_3$ are $C_8$ alkyl. In certain embodiments, $R_2$ and $R_3$ are $C_2$ alkyl. In other embodiments, $R_2$ and $R_3$ are $C_3$ alkyl. In some embodiments, $R_2$ and $R_3$ are $C_4$ alkyl. In certain embodiments, $R_2$ and $R_3$ are $C_5$ alkyl. In other embodiments, $R_2$ and $R_3$ are $C_6$ alkyl. In some embodiments, $R_2$ and $R_3$ are $C_7$ alkyl.

In other embodiments, $R_2$ and $R_3$ are different. In certain embodiments, $R_2$ is $C_8$ alkyl. In some embodiments, $R_3$ is Cia (e.g., $C_1$, $C_2$, $C_3$, $C_4$, $C_5$, $C_6$, or $C_7$ alkyl) or $C_9$ alkyl.

In some embodiments, $R_7$ and $R_3$ are H.

In certain embodiments, $R_2$ is H.

In some embodiments, m is 5, 7, or 9.

In some embodiments, $R_4$ is selected from —$(CH_2)_nQ$ and —$(CH_2)_n$CHQR.

In some embodiments, Q is selected from the group consisting of —OR, —OH, —O$(CH_2)_n$N$(R)_2$, —OC(O)R, —$CX_3$, —CN, —N(R)C(O)R, —N(H)C(O)R, —N(R)S(O)$_2$R, —N(H)S(O)$_2$R, —N(R)C(O)N$(R)_2$, —N(H)C(O)N$(R)_2$, —N(H)C(O)N(H)(R), —N(R)C(S)N$(R)_2$, —N(H)C(S)N$(R)_2$, —N(H)C(S)N(H)(R), —C(R)N$(R)_2$C(O)OR, a carbocycle, and a heterocycle.

In certain embodiments, Q is —OH.

In certain embodiments, Q is a substituted or unsubstituted 5- to 10-membered heteroaryl, e.g., Q is an imidazole, a pyrimidine, a purine, 2-amino-1,9-dihydro-6H-purin-6-one-9-yl (or guanin-9-yl), adenin-9-yl, cytosin-1-yl, or uracil-1-yl. In certain embodiments, Q is a substituted 5- to 14-membered heterocycloalkyl, e.g., substituted with one or more substituents selected from oxo (=O), OH, amino, and $C_{1-3}$ alkyl. For example, Q is 4-methylpiperazinyl, 4-(4-methoxybenzyl)piperazinyl, or isoindolin-2-yl-1,3-dione.

In certain embodiments, Q is an unsubstituted or substituted $C_{6-10}$ aryl (such as phenyl) or $C_{3-6}$ cycloalkyl.

In some embodiments, n is 1. In other embodiments, n is 2. In further embodiments, n is 3. In certain other embodiments, n is 4. For example, $R_4$ can be —$(CH_2)_2$OH. For example, $R_4$ can be —$(CH_2)_3$OH. For example, $R_4$ can be —$(CH_2)_4$OH. For example, $R_4$ can be benzyl. For example, $R_4$ can be 4-methoxybenzyl.

In some embodiments, $R_4$ is a $C_{3-6}$ carbocycle. In some embodiments, $R_4$ is a $C_{3-6}$ cycloalkyl. For example, $R_4$ can be cyclohexyl optionally substituted with e.g., OH, halo, $C_{1-6}$ alkyl, etc. For example, $R_4$ can be 2-hydroxycyclohexyl.

In some embodiments, R is H.

In some embodiments, R is unsubstituted $C_{1-3}$ alkyl or unsubstituted $C_{2-3}$ alkenyl. For example, $R_4$ can be —$CH_2CH(OH)CH_3$ or —$CH_2CH(OH)CH_2CH_3$.

In some embodiments, R is substituted $C_{1-3}$ alkyl, e.g., $CH_2OH$. For example, $R_4$ can be —$CH_2CH(OH)CH_2OH$.

In some embodiments, $R_2$ and $R_3$, together with the atom to which they are attached, form a heterocycle or carbocycle. In some embodiments, $R_2$ and $R_3$, together with the atom to which they are attached, form a 5- to 14-membered aromatic or non-aromatic heterocycle having one or more heteroatoms selected from N, O, S. and P. In some embodiments, $R_2$ and $R_3$, together with the atom to which they are attached, form an optionally substituted $C_{3-20}$ carbocycle (e.g., $C_{3-18}$ carbocycle, $C_{3-15}$ carbocycle, $C_{3-12}$ carbocycle, or $C_{3-10}$ carbocycle), either aromatic or non-aromatic. In some embodiments, $R_2$ and $R_3$, together with the atom to which they are attached, form a $C_{3-6}$ carbocycle. In other embodiments, $R_2$ and $R_3$, together with the atom to which they are attached, form a $C_6$ carbocycle, such as a cyclohexyl or phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, can form a cyclohexyl or phenyl group bearing one or more $C_5$ alkyl substitutions. In certain embodiments, the heterocycle or $C_{3-6}$ carbocycle formed by $R_2$ and $R_3$, is substituted with a carbocycle groups. For example, $R_2$ and $R_3$, together with the atom to which they are attached, can form a cyclohexyl or phenyl group that is substituted with cyclohexyl. In some embodiments, $R_2$ and $R_3$, together with the atom to which they are attached, form a $C_7$-15 carbocycle, such as a cycloheptyl, cyclopentadecanyl, or naphthyl group.

In some embodiments, $R_4$ is selected from —$(CH_2)_nQ$ and —$(CH_2)_nCHQR$ In some embodiments, Q is selected from the group consisting of —OR, —OH, —O$(CH_2)_nN(R)_2$, —OC(O)R, —CX$_3$, —CN, —N(R)C(O)R, —N(H)C(O)R, —N(R)S(O)$_2$R, —N(H)S(O)$_2$R, —N(R)C(O)N(R)$_2$, —N(H)C(O)N(R)$_2$, —N(H)C(O)N(H)(R), —N(R)C(S)N(R)$_2$, —N(H)C(S)N(R)$_2$, —N(H)C(S)N(H)(R), and a heterocycle. In other embodiments, Q is selected from the group consisting of an imidazole, a pyrimidine, and a purine.

In some embodiments, $R_2$ and $R_3$, together with the atom to which they are attached, form a heterocycle or carbocycle. In some embodiments, $R_2$ and $R_3$, together with the atom to which they are attached, form a $C_{3-6}$ carbocycle, such as a phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, can form a phenyl group bearing one or more $C_5$ alkyl substitutions.

In some embodiments, the pharmaceutical compositions of the present disclosure, the compound of formula (I) is selected from the group consisting of:

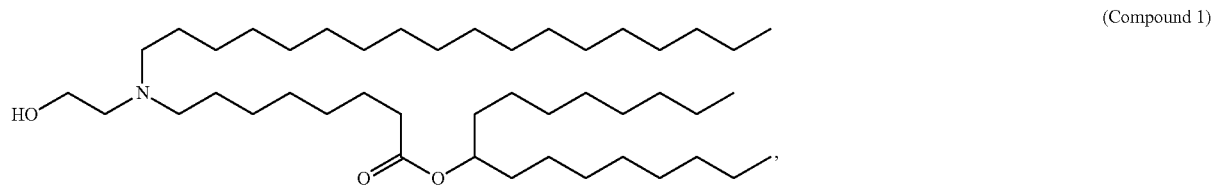

(Compound 1)

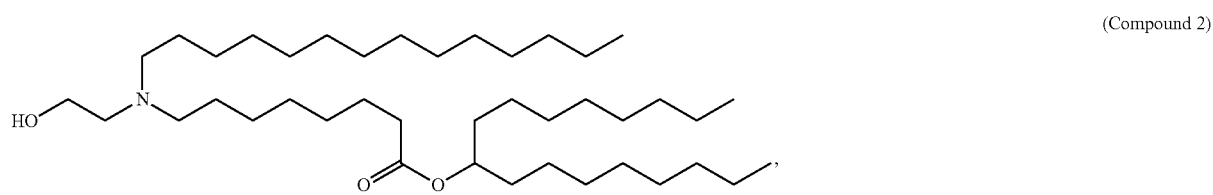

(Compound 2)

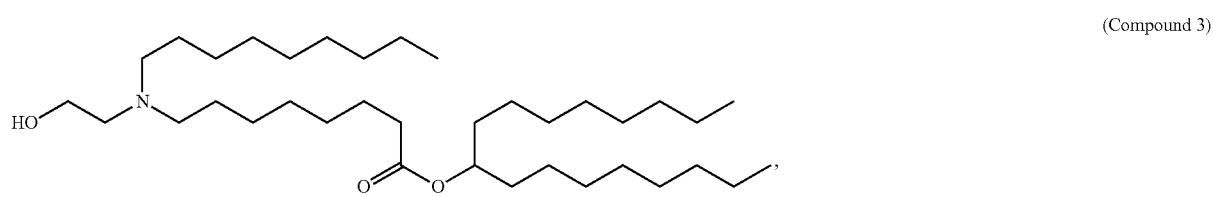

(Compound 3)

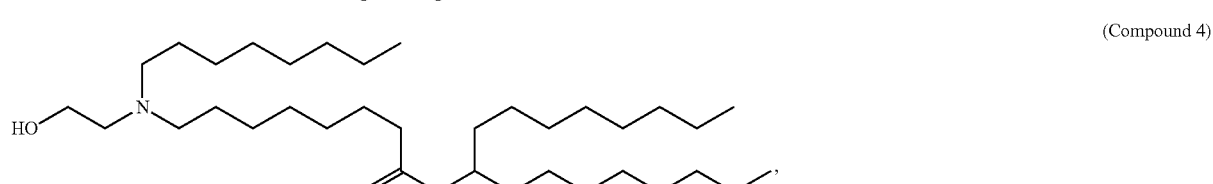

(Compound 4)

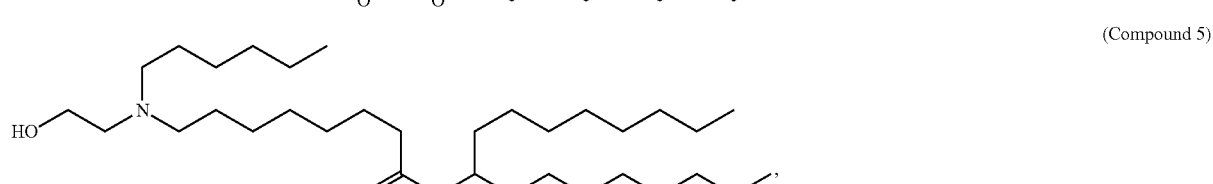

(Compound 5)

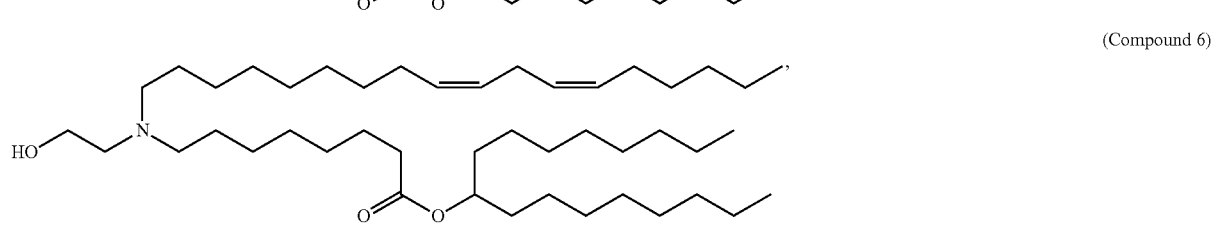

(Compound 6)

(Compound 7)
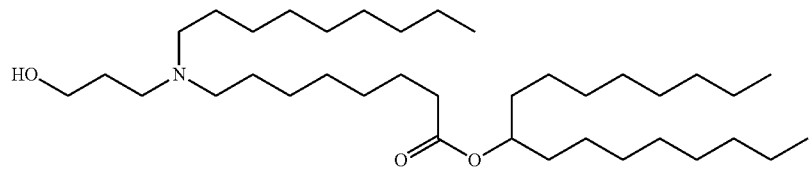
(Compound 8)
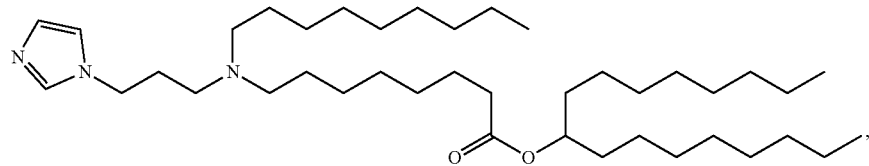
(Compound 9)
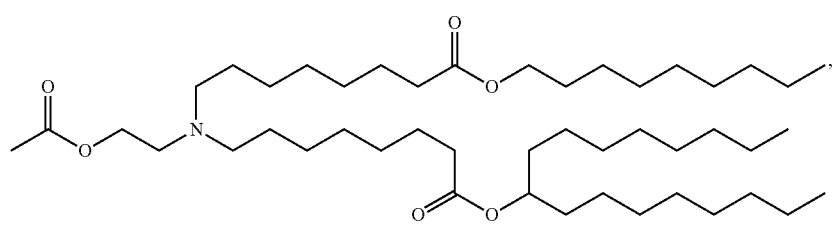
(Compound 10)
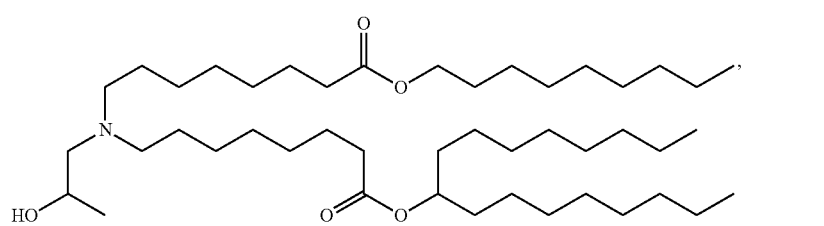
(Compound 11)
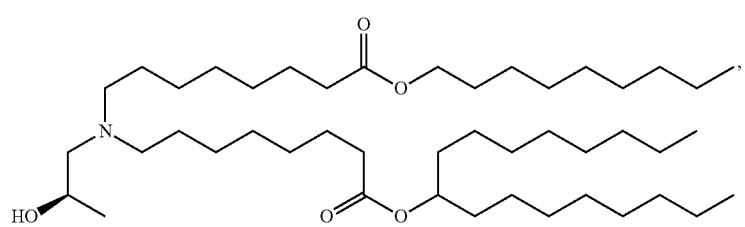
(Compound 12)
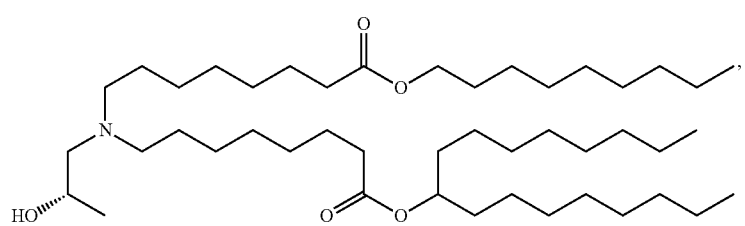
(Compound 13)
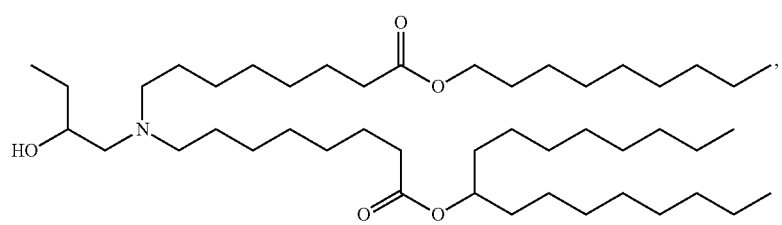

-continued
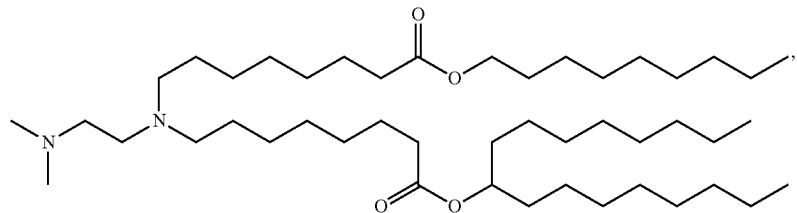
(Compound 14)
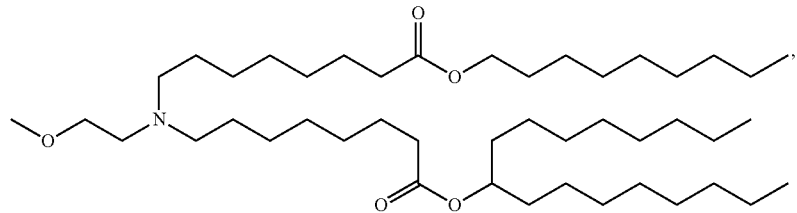
(Compound 15)
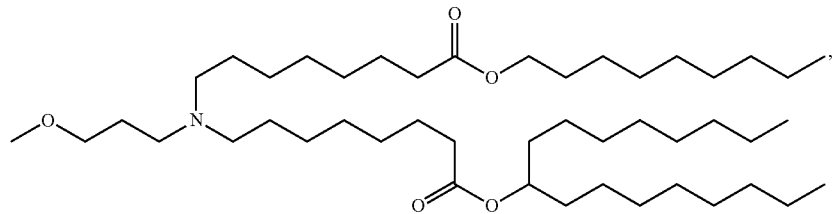
(Compound 16)
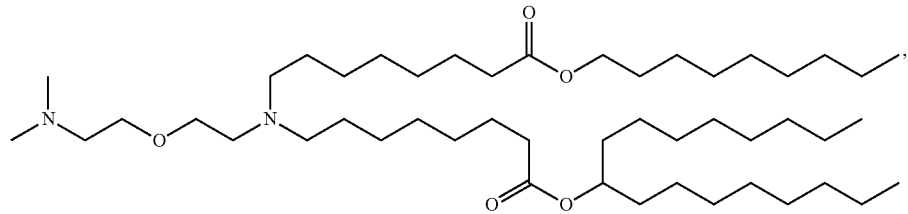
(Compound 17)
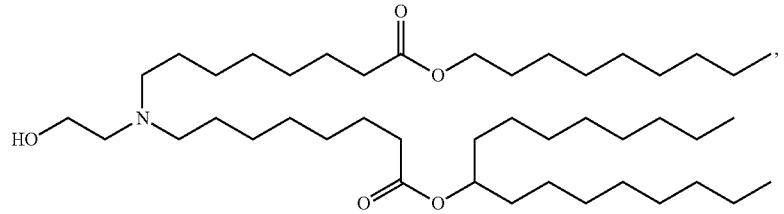
(Compound 18)
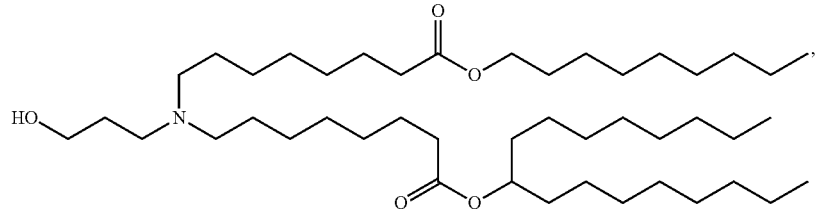
(Compound 19)
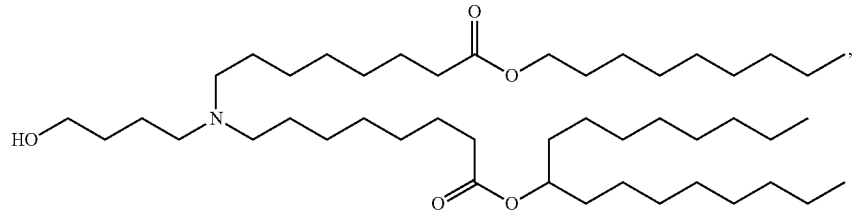
(Compound 20)

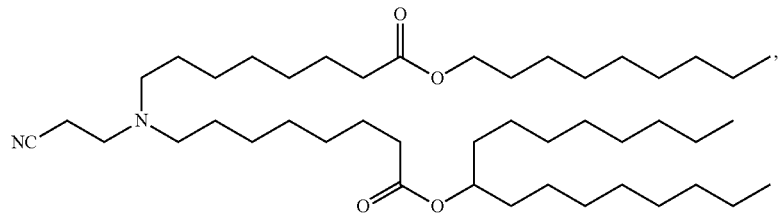
(Compound 21)
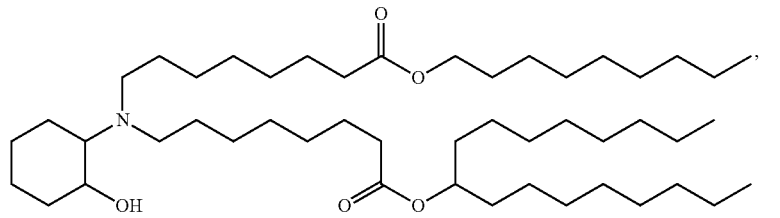
(Compound 22)
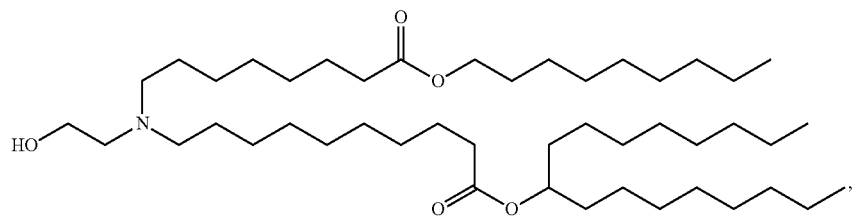
(Compound 23)
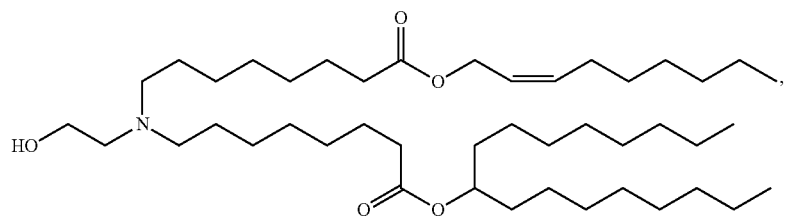
(Compound 24)
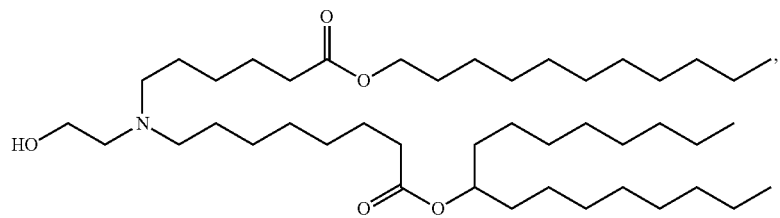
(Compound 25)
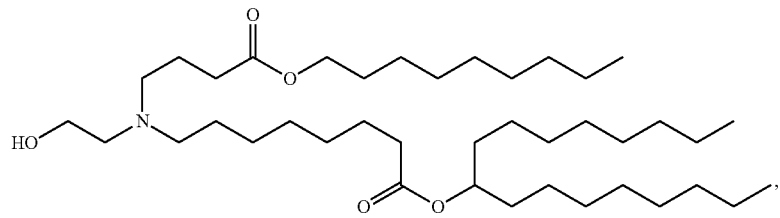
(Compound 26)
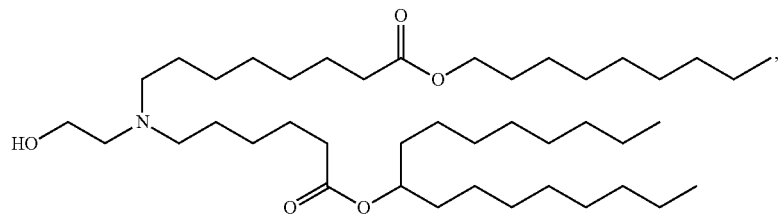
(Compound 27)

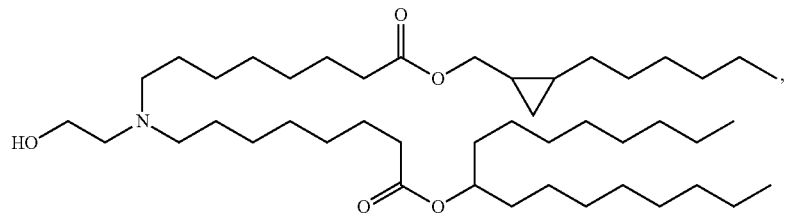
(Compound 28)
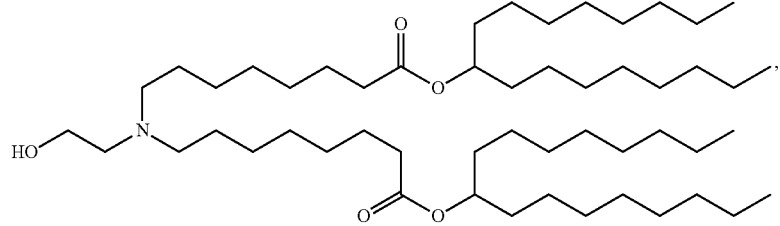
(Compound 29)
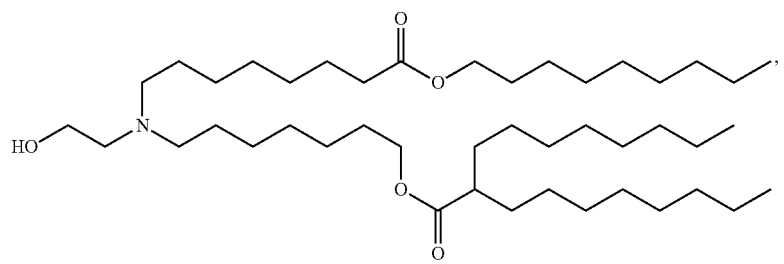
(Compound 30)
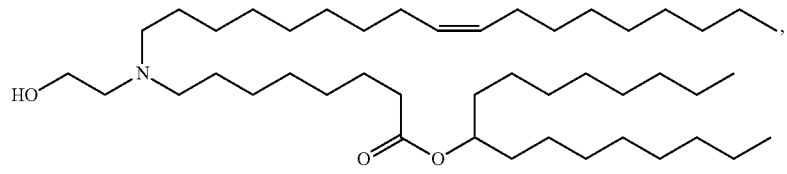
(Compound 31)
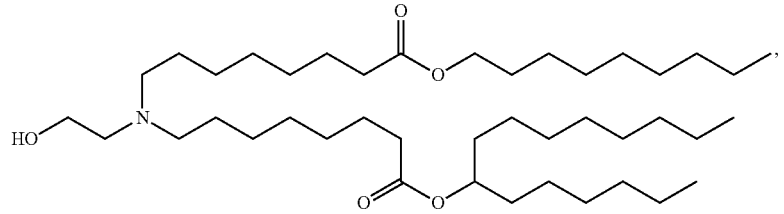
(Compound 32)
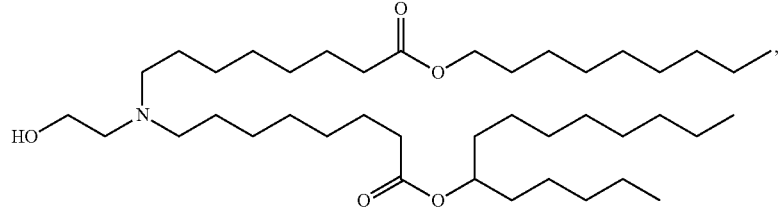
(Compound 33)
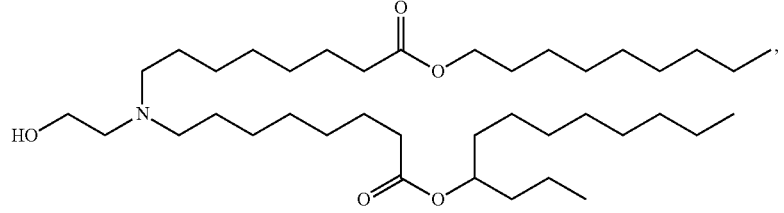
(Compound 34)

-continued
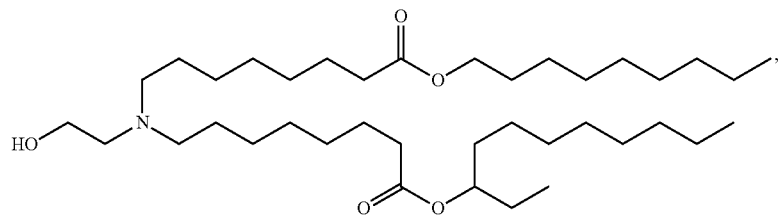
(Compound 35)
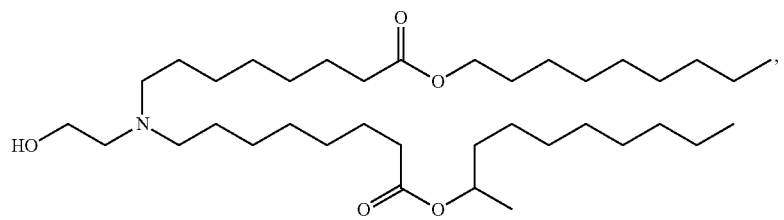
(Compound 36)
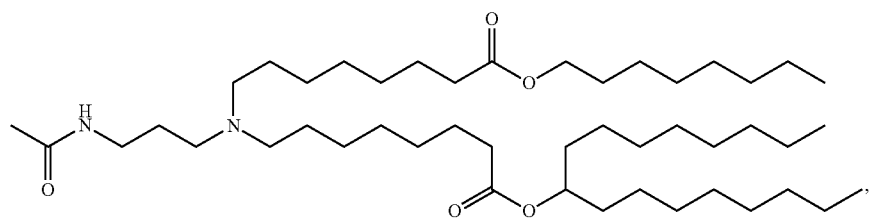
(Compound 37)
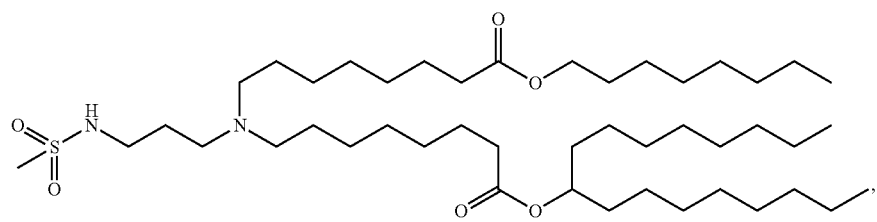
(Compound 38)
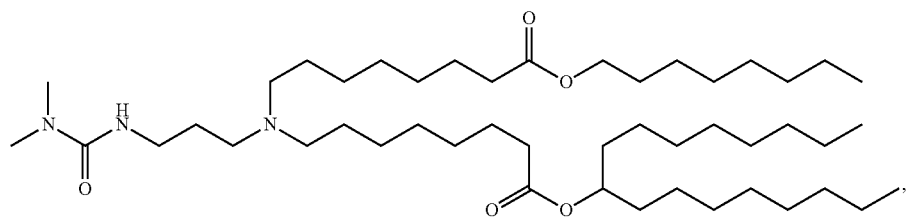
(Compound 39)
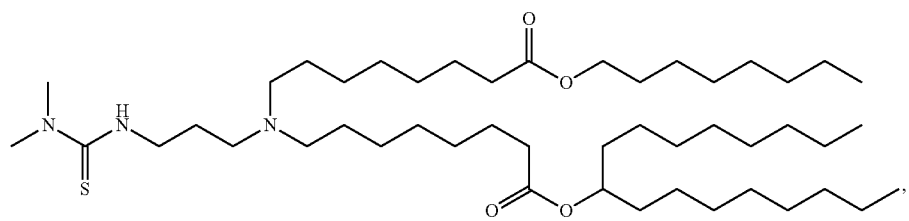
(Compound 40)
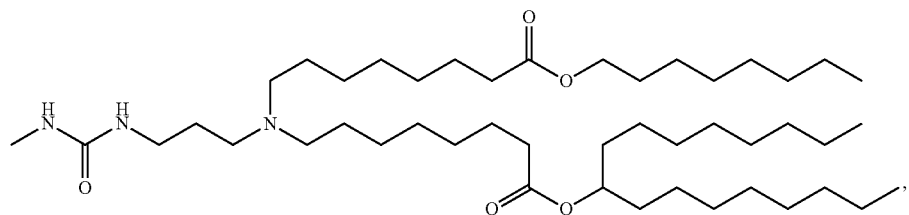
(Compound 41)

(Compound 42)
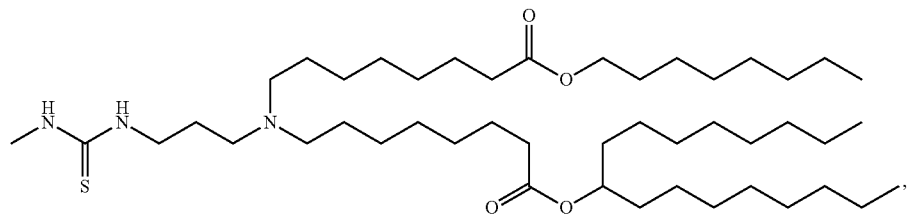
(Compound 43)
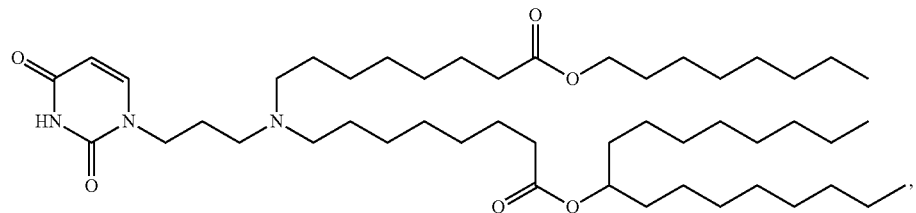
(Compound 44)
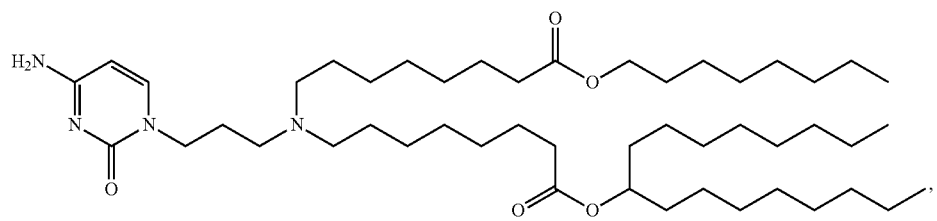
(Compound 45)
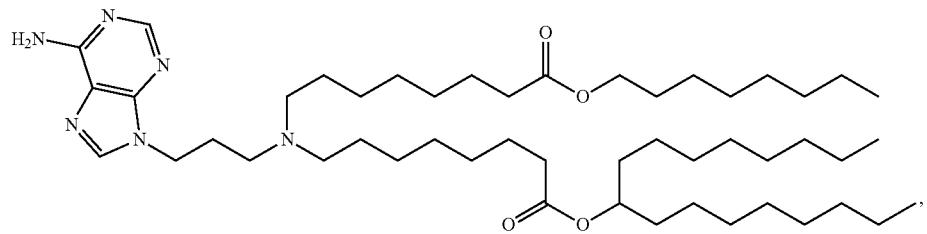
(Compound 46)
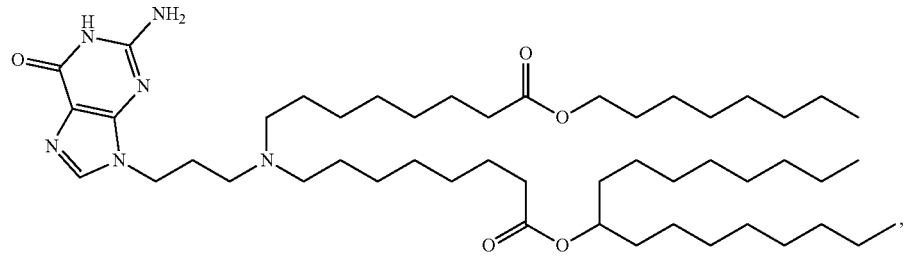
(Compound 47)
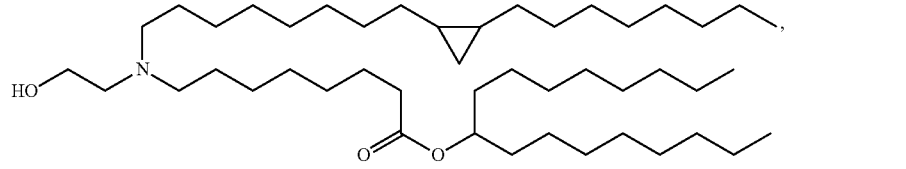
(Compound 48)
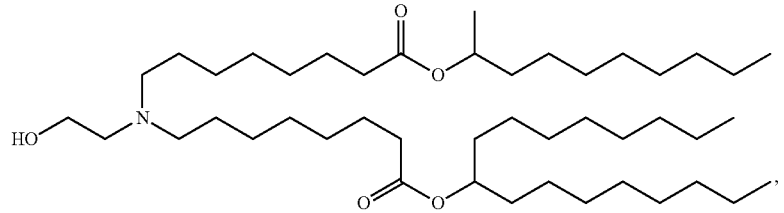

-continued
(Compound 49)
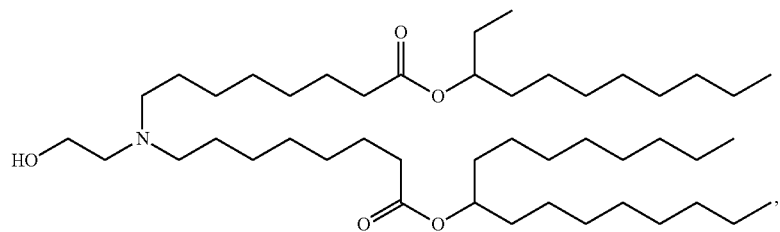
(Compound 50)
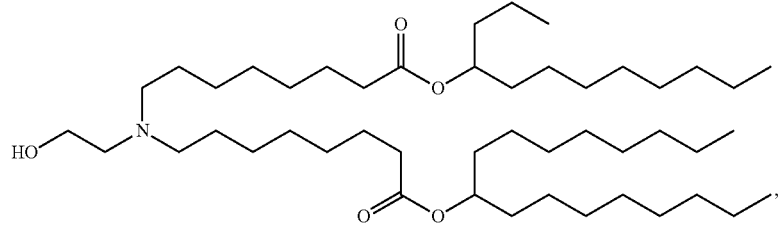
(Compound 51)
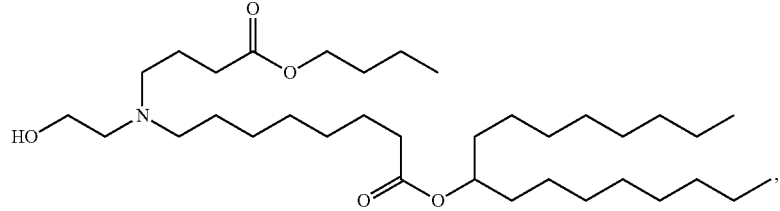
(Compound 52)
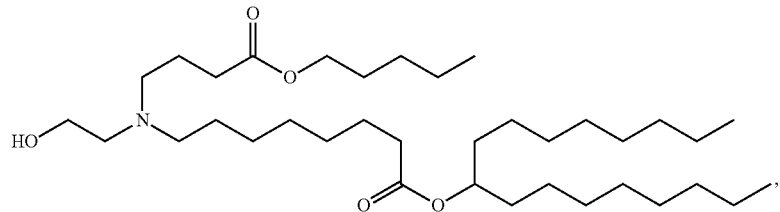
(Compound 53)
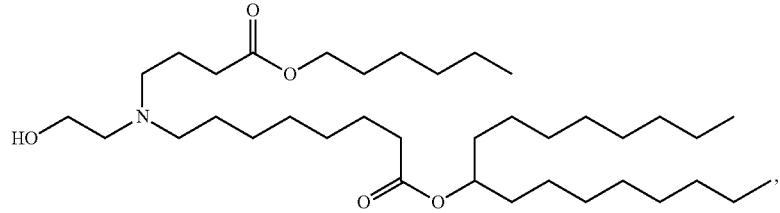
(Compound 54)
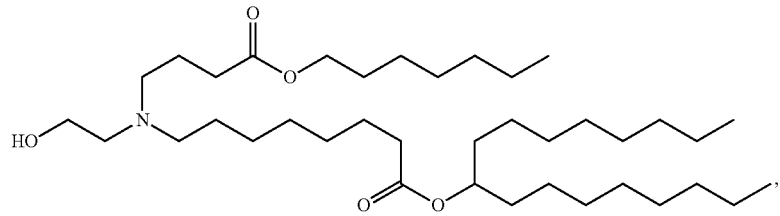
(Compound 55)
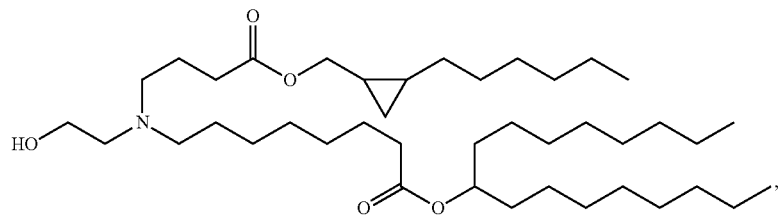

-continued
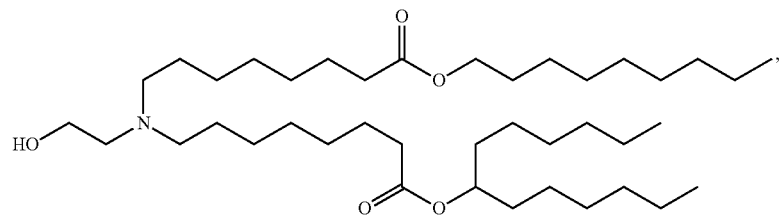
(Compound 56)
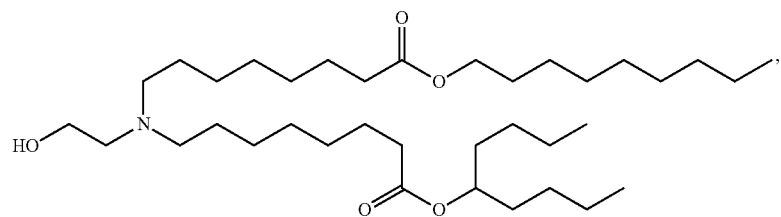
(Compound 57)
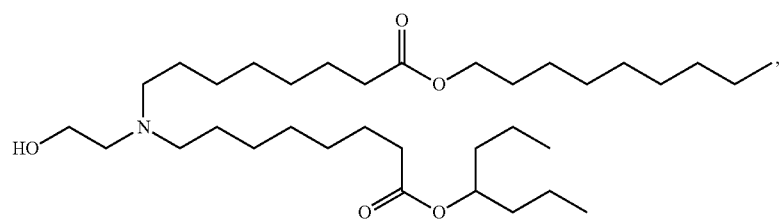
(Compound 58)
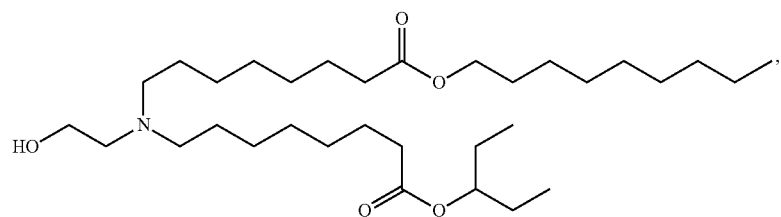
(Compound 59)
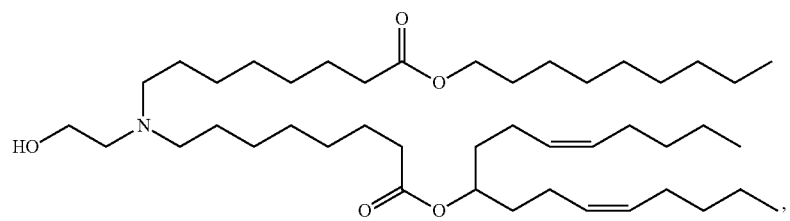
(Compound 60)
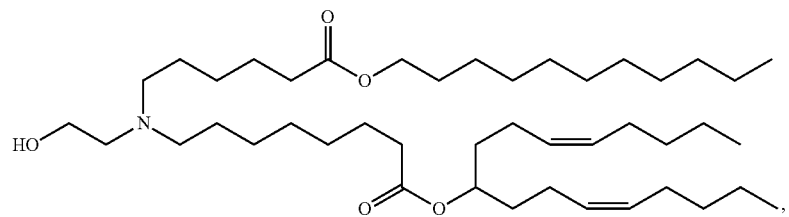
(Compound 61)
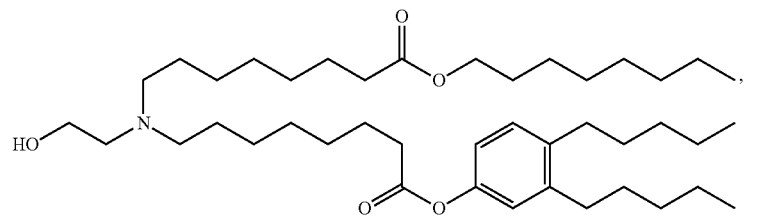
(Compound 62)

-continued
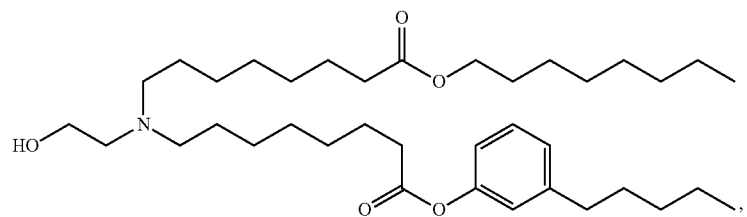
(Compound 63)
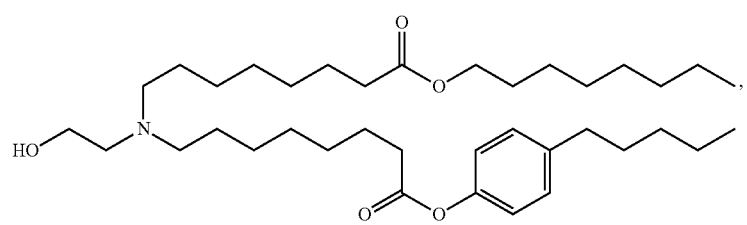
(Compound 64)
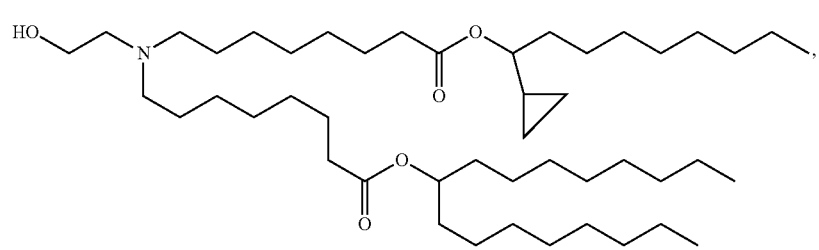
(Compound 65)
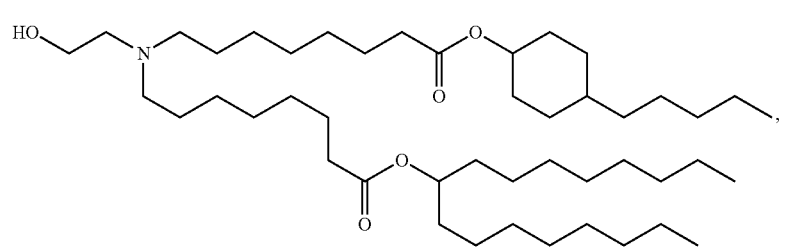
(Compound 66)
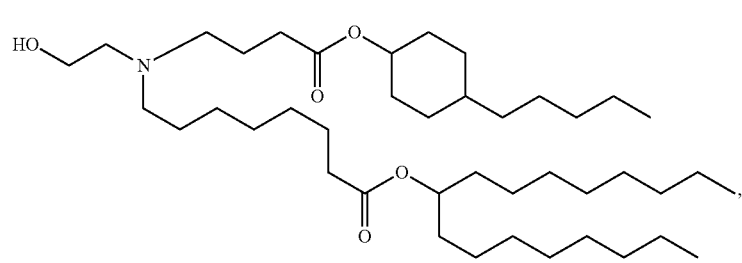
(Compound 67)
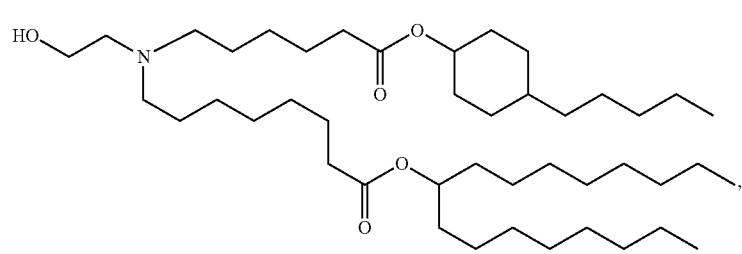
(Compound 68)

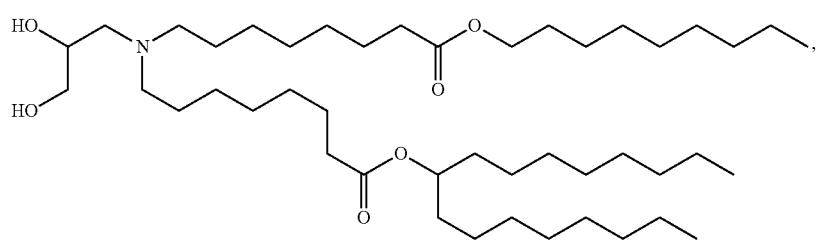
(Compound 69)
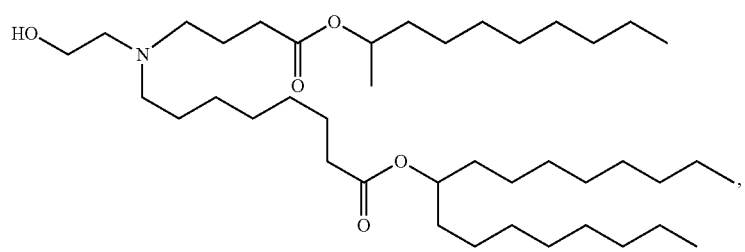
(Compound 70)
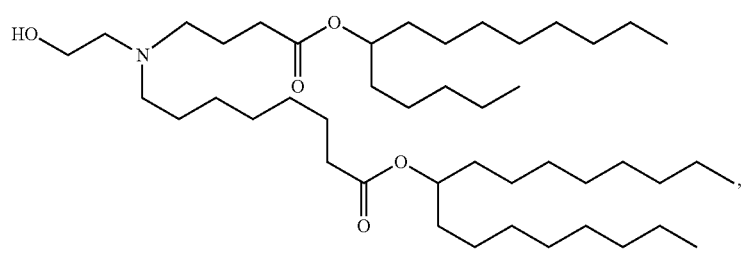
(Compound 71)
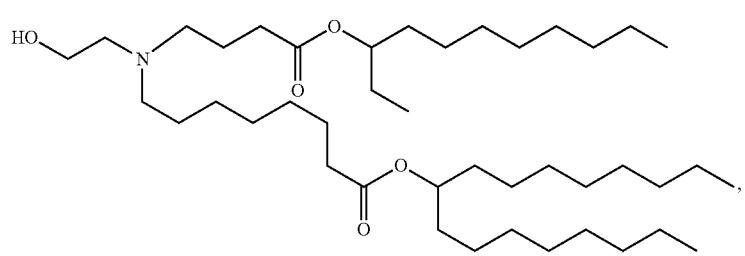
(Compound 72)
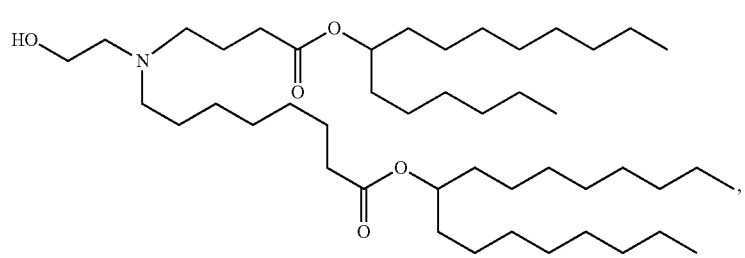
(Compound 73)
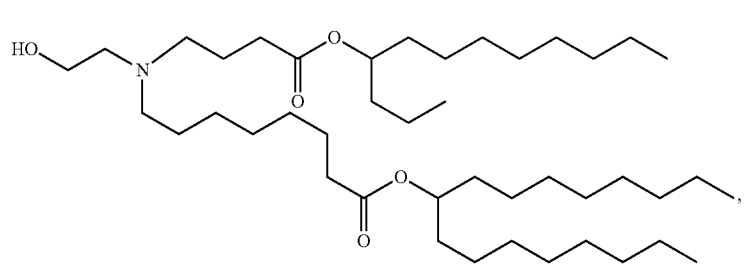
(Compound 74)

-continued
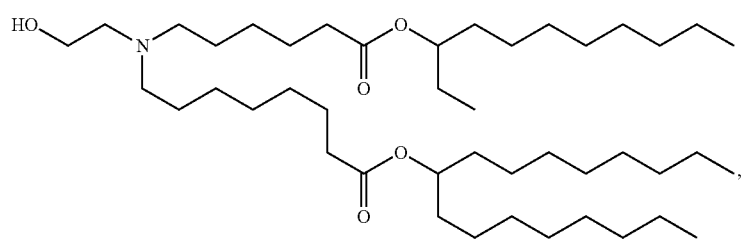
(Compound 75)
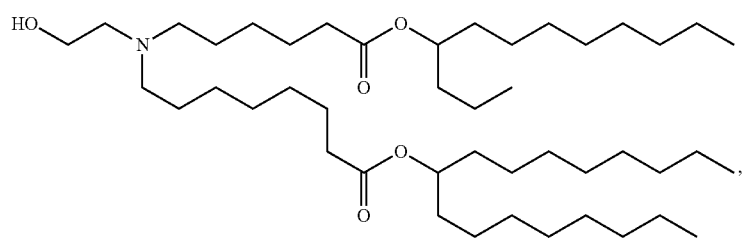
(Compound 76)
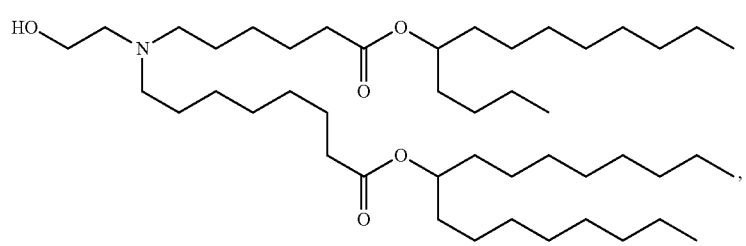
(Compound 77)
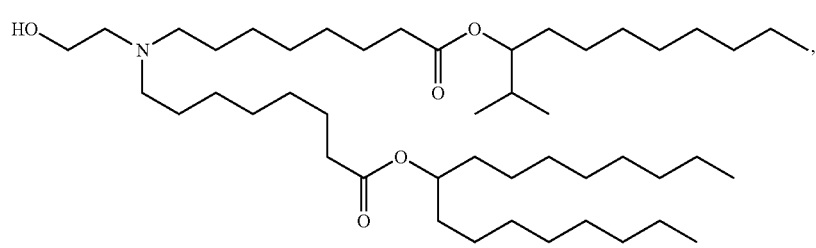
(Compound 78)
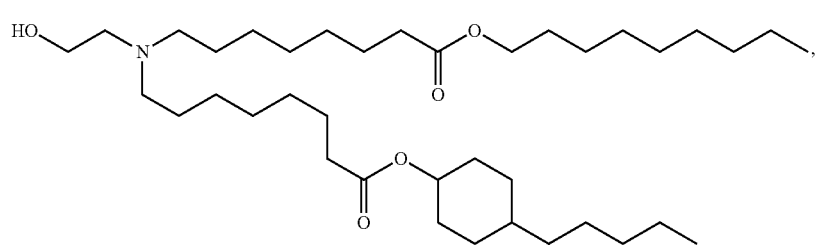
(Compound 79)
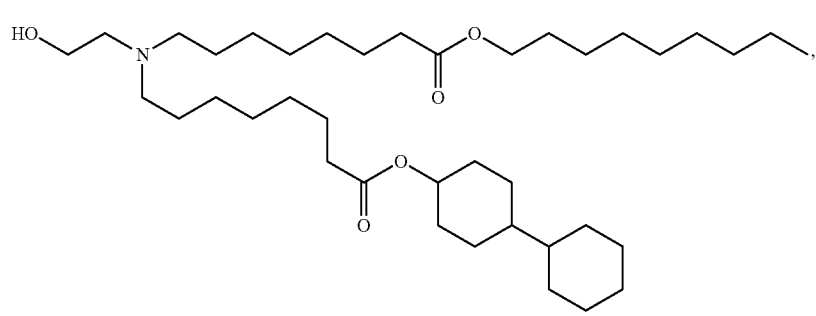
(Compound 80)

-continued
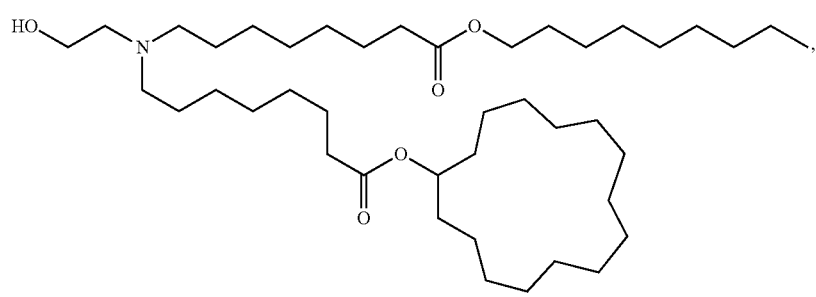
(Compound 81)
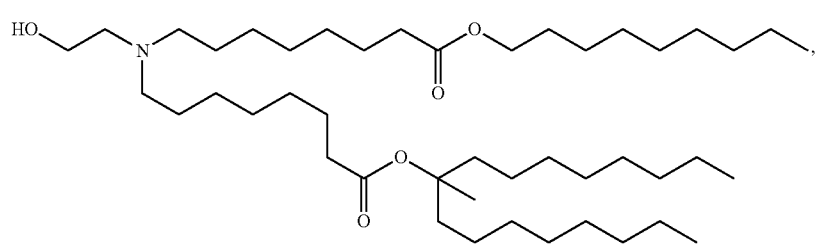
(Compound 82)
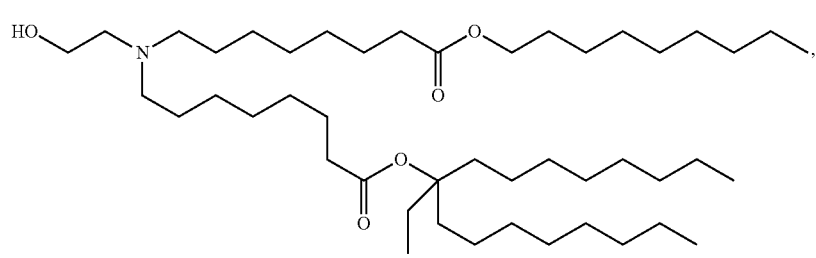
(Compound 83)
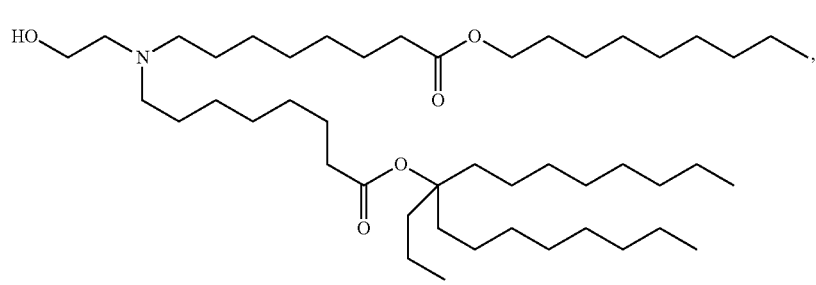
(Compound 84)
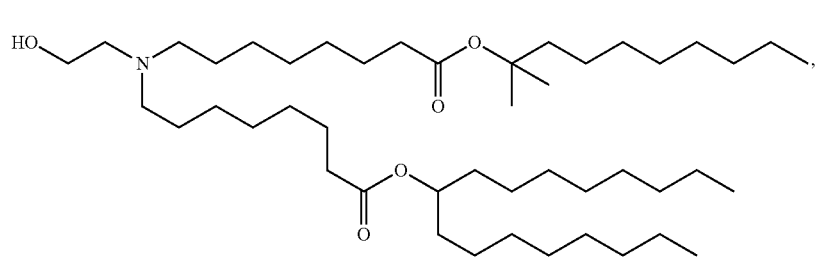
(Compound 85)
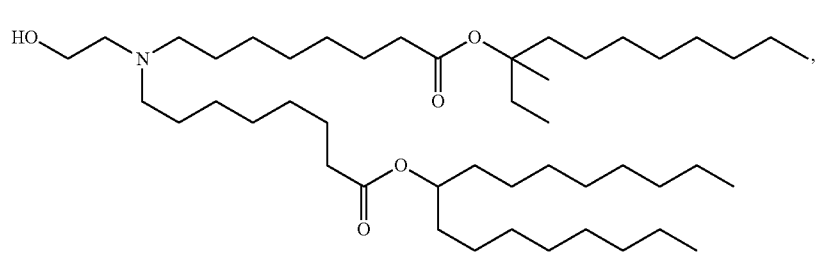
(Compound 86)

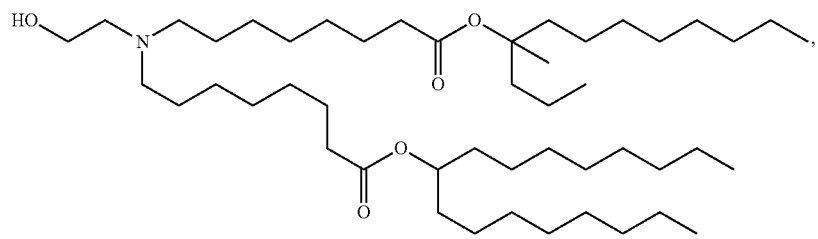
(Compound 87)
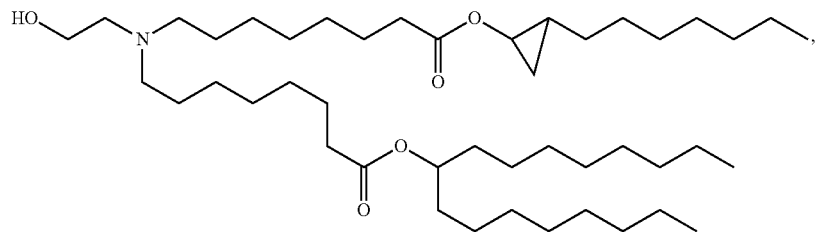
(Compound 88)
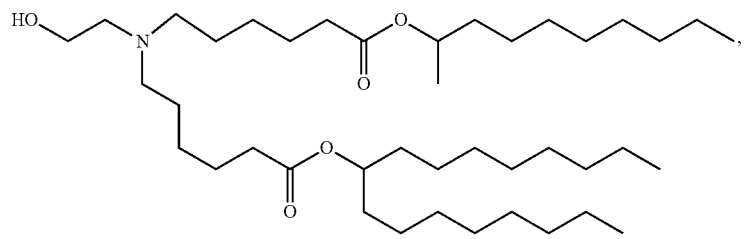
(Compound 89)
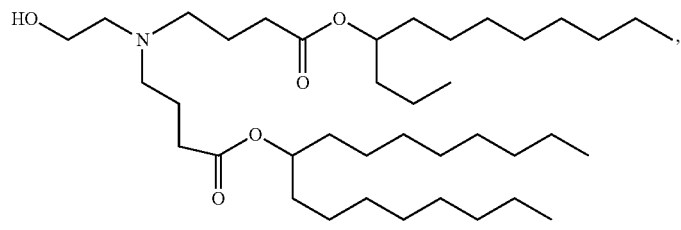
(Compound 90)
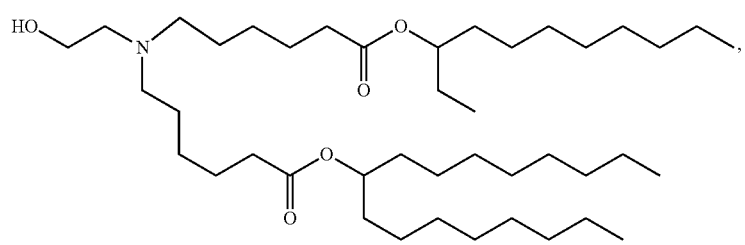
(Compound 91)
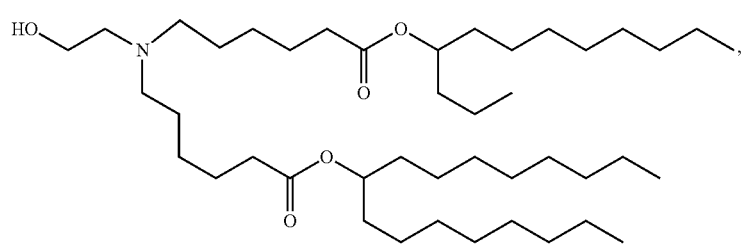
(Compound 92)

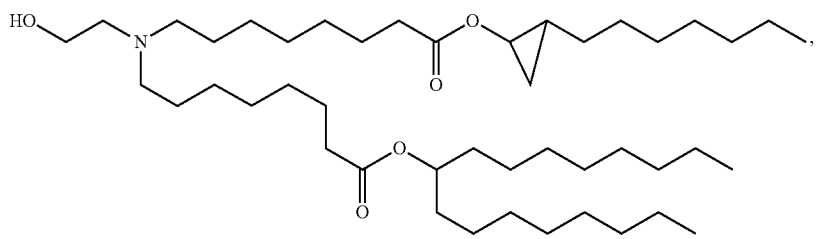
(Compound 93)
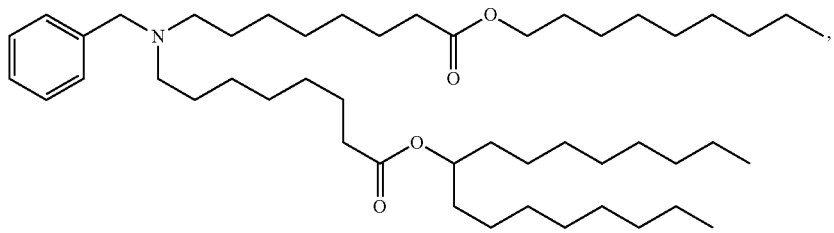
(Compound 94)
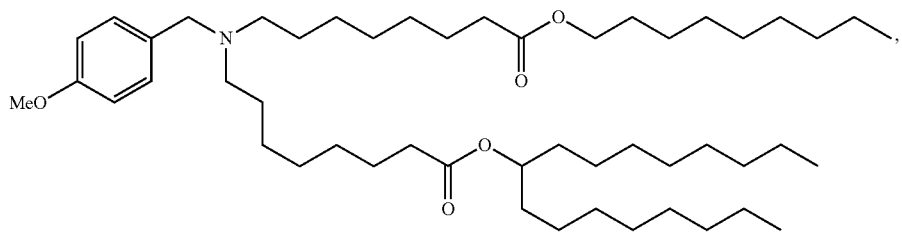
(Compound 95)
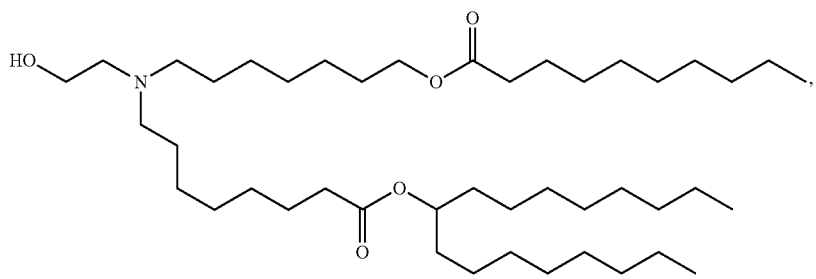
(Compound 96)
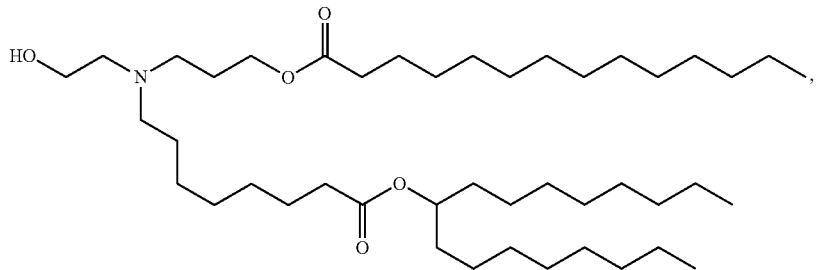
(Compound 97)
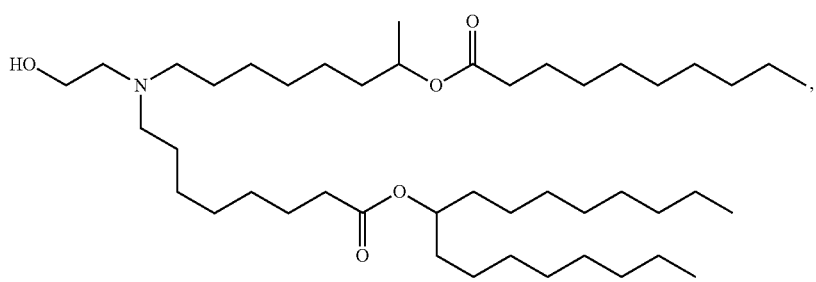
(Compound 98)

-continued
(Compound 99)
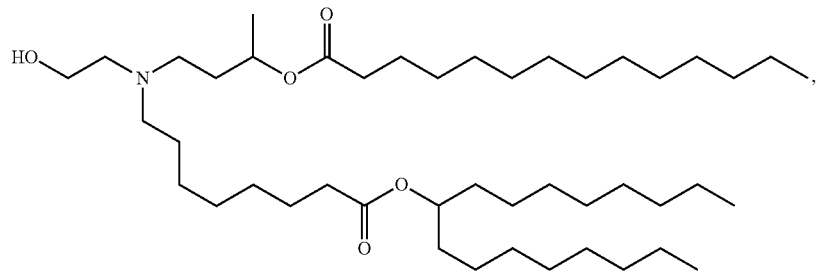
(Compound 100)
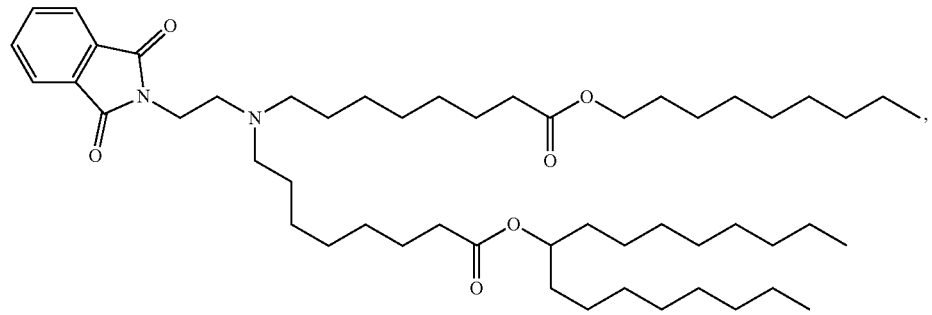
(Compound 101)
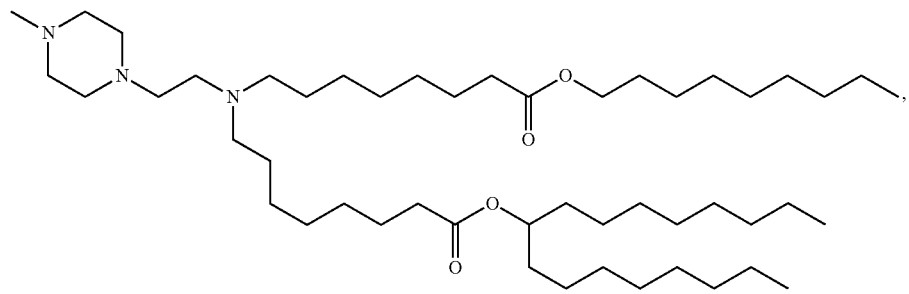
(Compound 102)
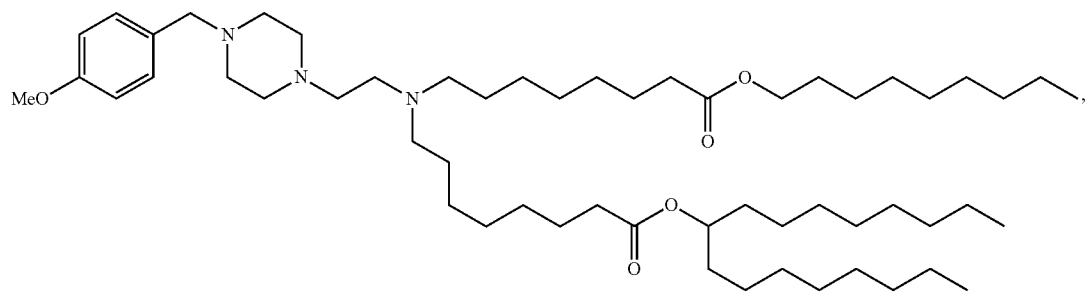
(Compound 103)
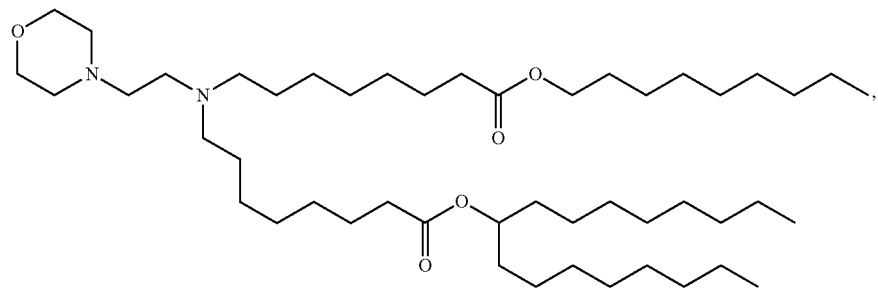

-continued
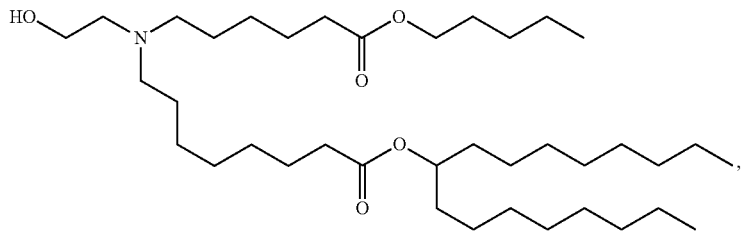
(Compound 104)
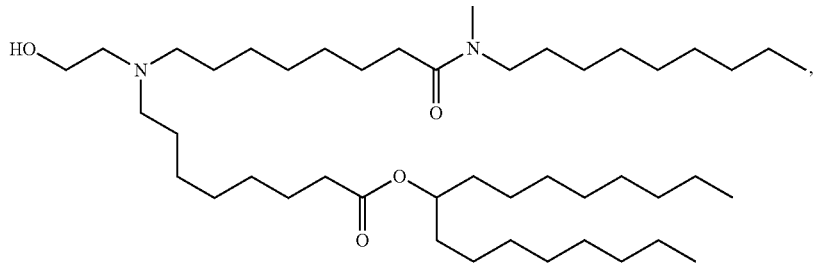
(Compound 105)
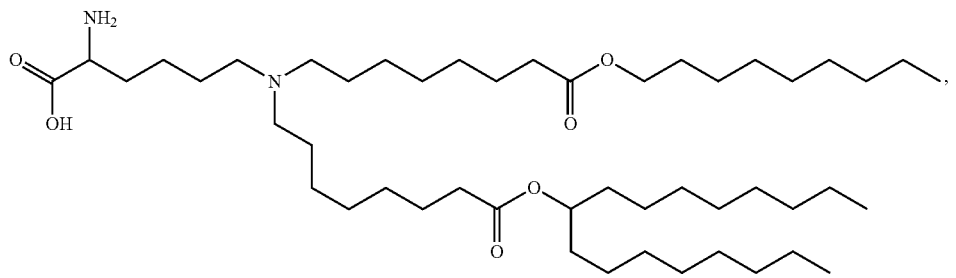
(Compound 106)
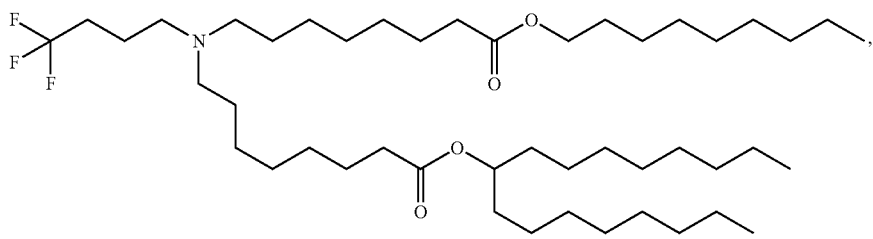
(Compound 107)
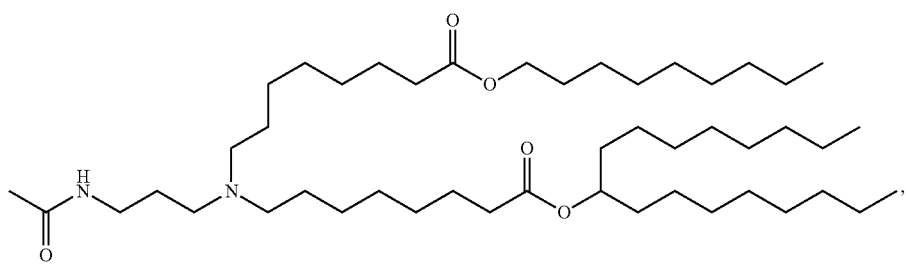
(Compound 108)
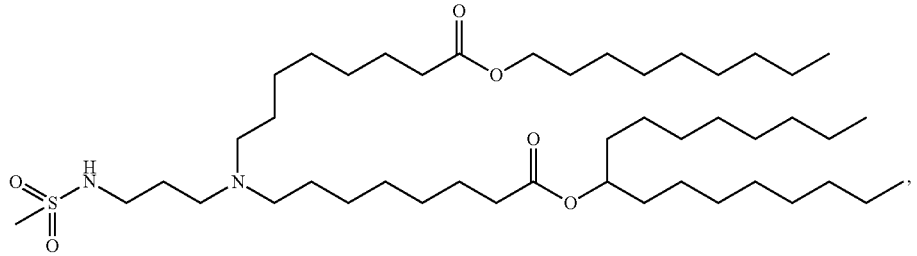
(Compound 109)

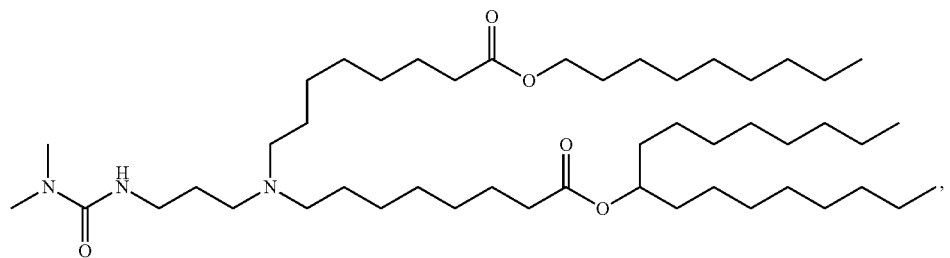
(Compound 110)
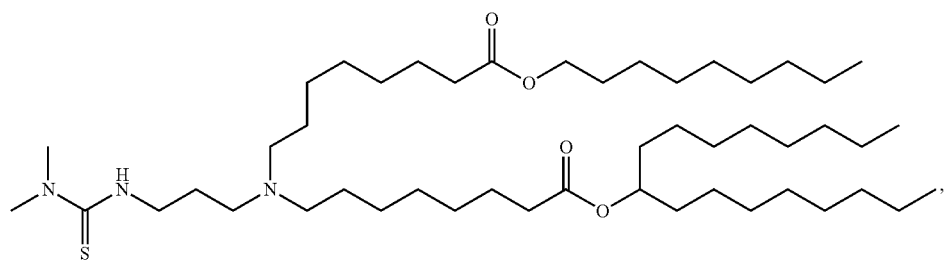
(Compound 111)
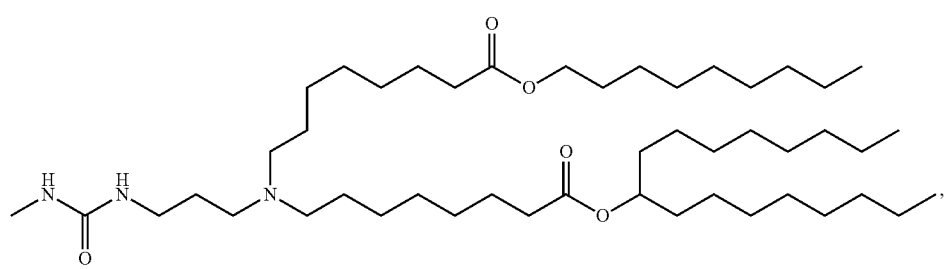
(Compound 112)
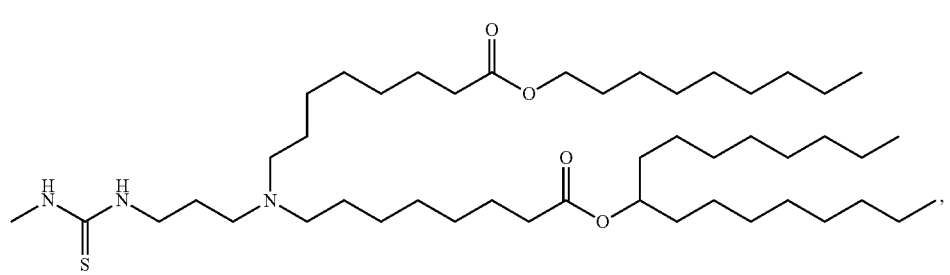
(Compound 113)
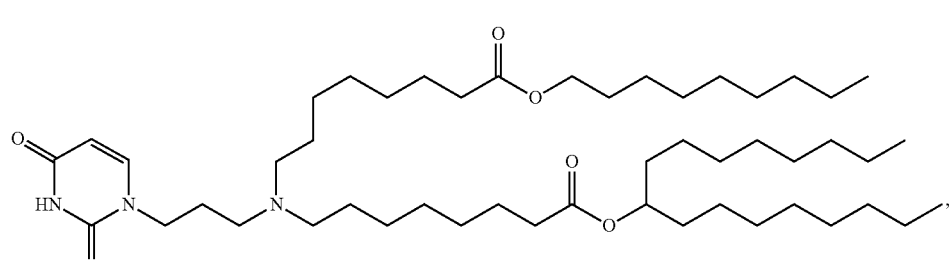
(Compound 114)
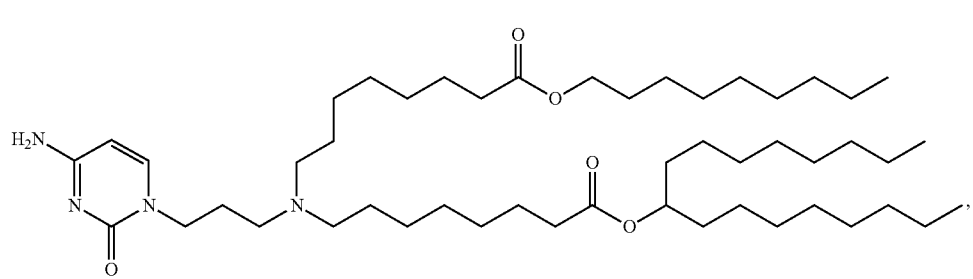
(Compound 115)

-continued
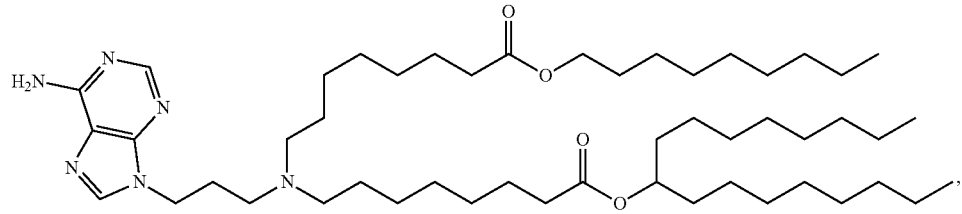
(Compound 116)
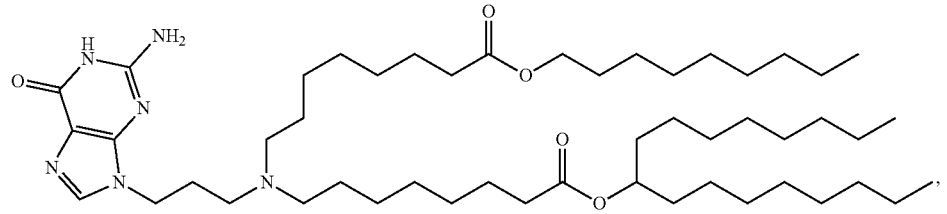
(Compound 117)
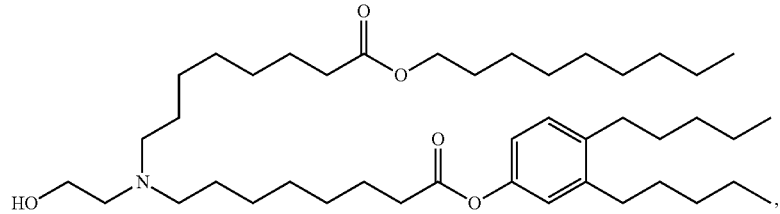
(Compound 118)
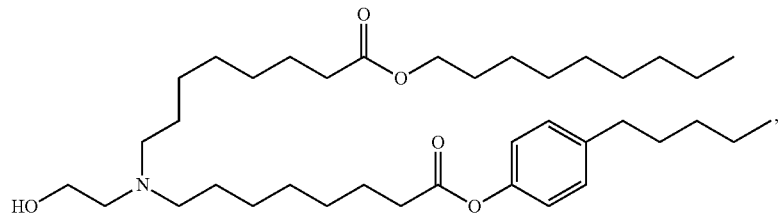
(Compound 119)
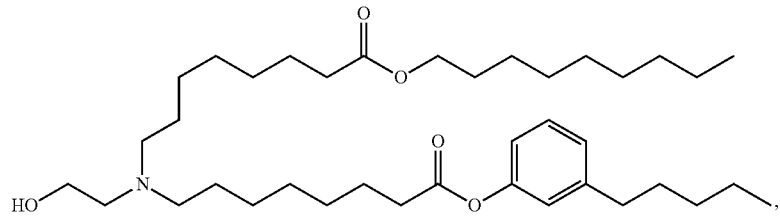
(Compound 120)
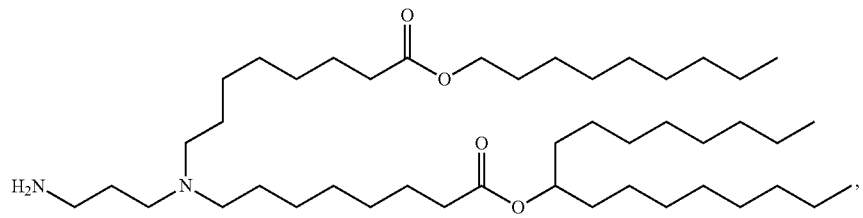
(Compound 121)
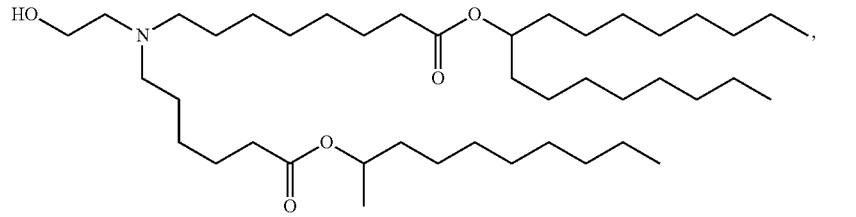
(Compound 122)

-continued
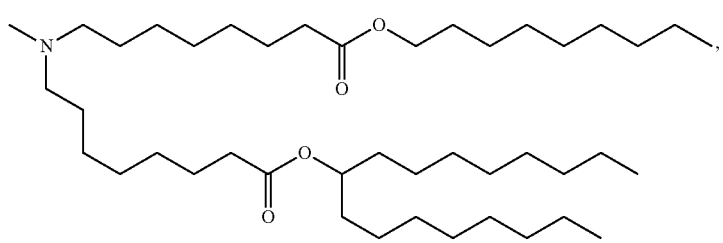
(Compound 123)
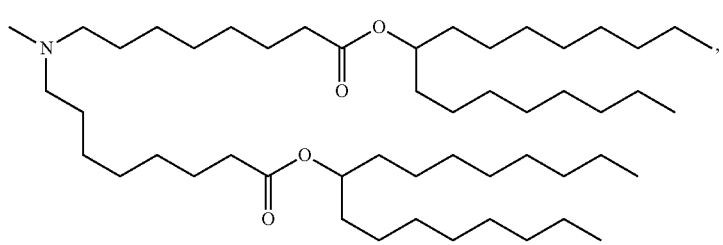
(Compound 124)
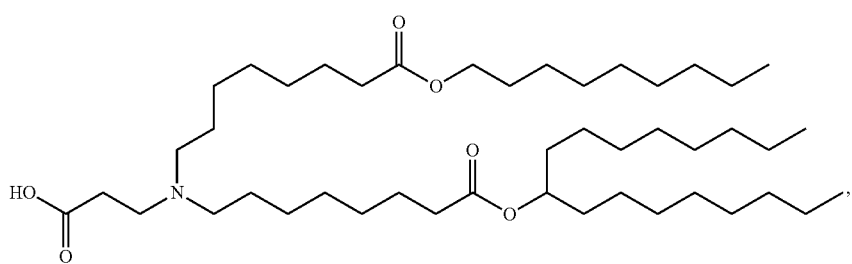
(Compound 125)
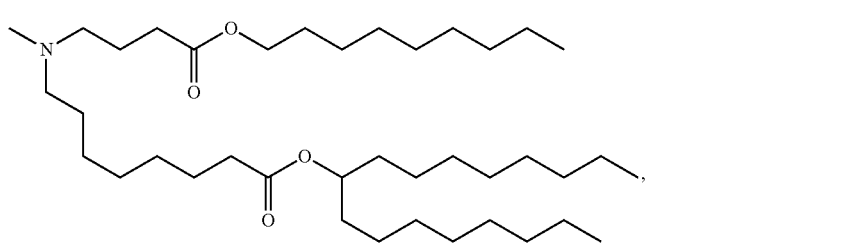
(Compound 126)
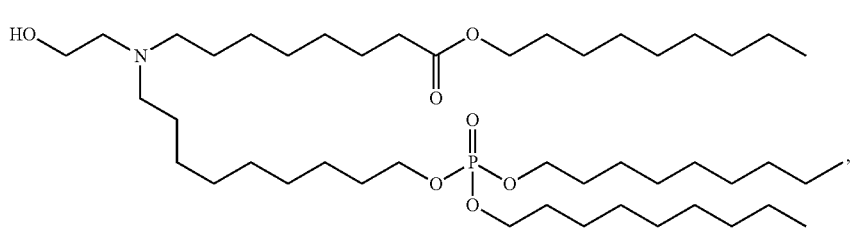
(Compound 127)
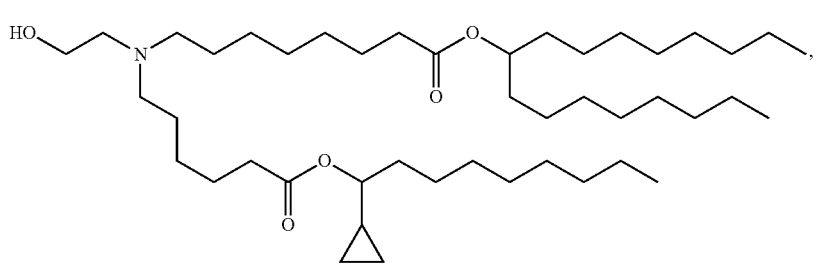
(Compound 128)

-continued
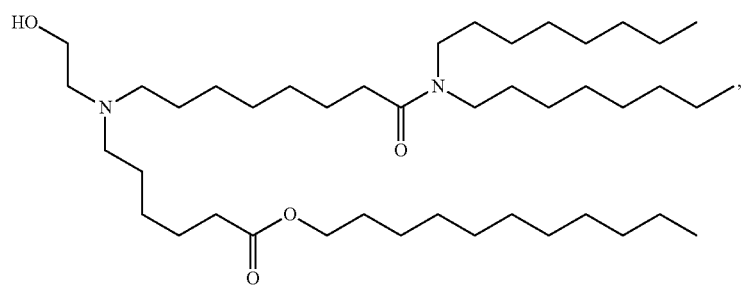
(Compound 129)
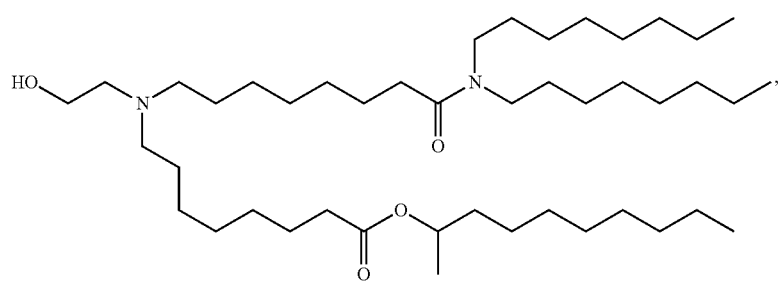
(Compound 130)
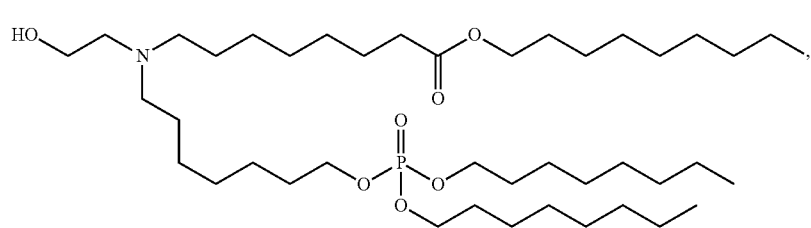
(Compound 131)
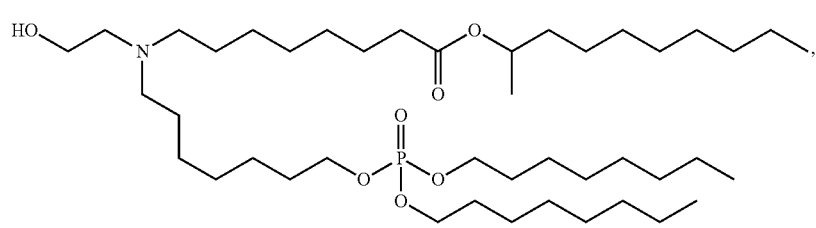
(Compound 132)
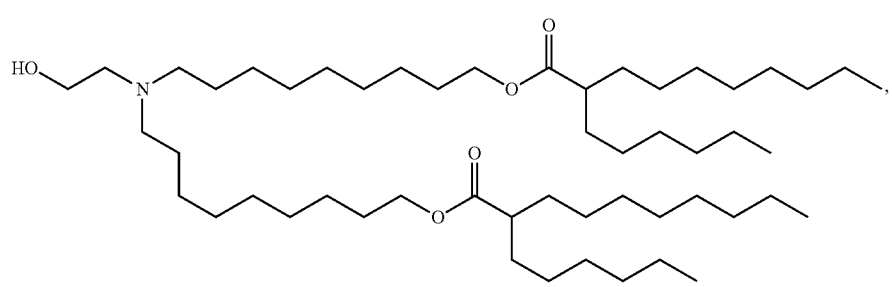
(Compound 133)
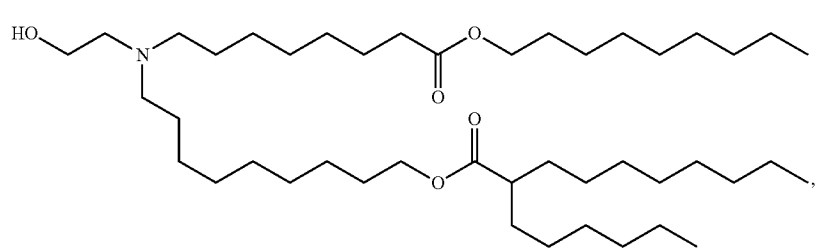
(Compound 134)

-continued
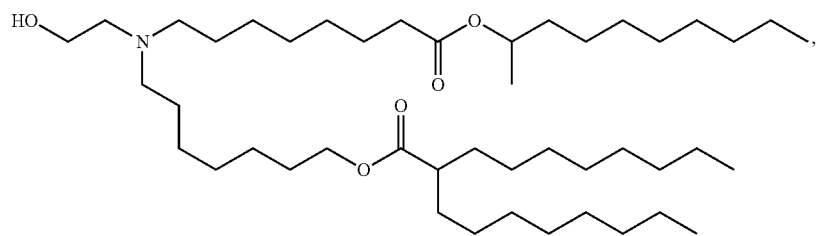
(Compound 135)
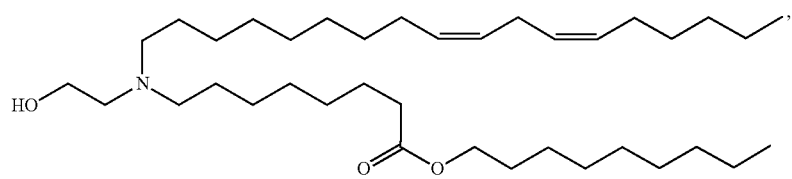
(Compound 136)
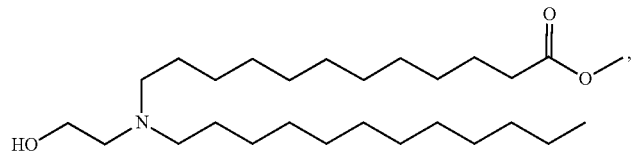
(Compound 137)
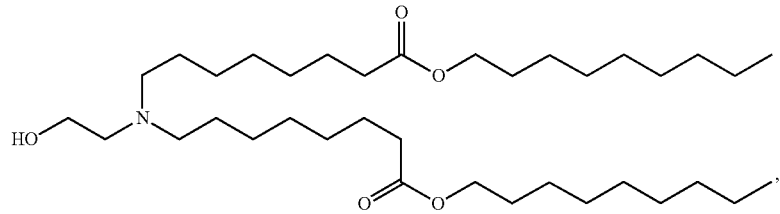
(Compound 138)
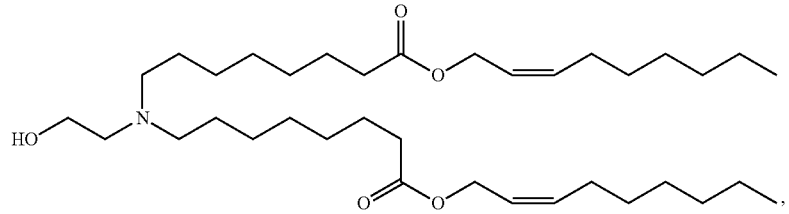
(Compound 139)
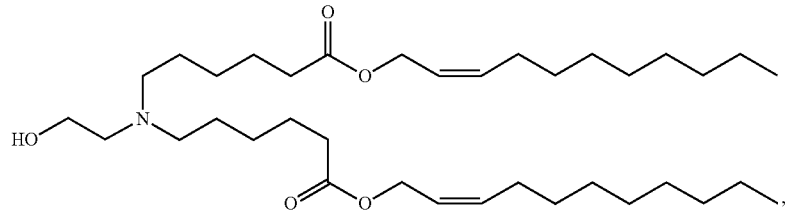
(Compound 140)
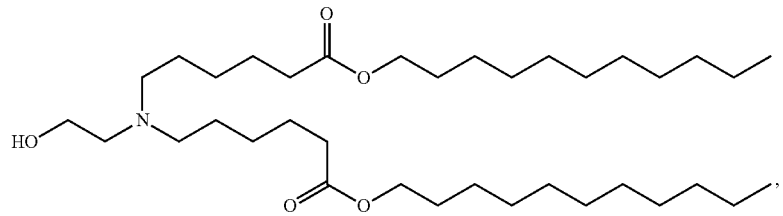
(Compound 141)

-continued
(Compound 142)
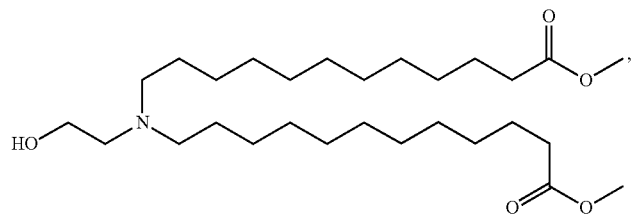
(Compound 143)
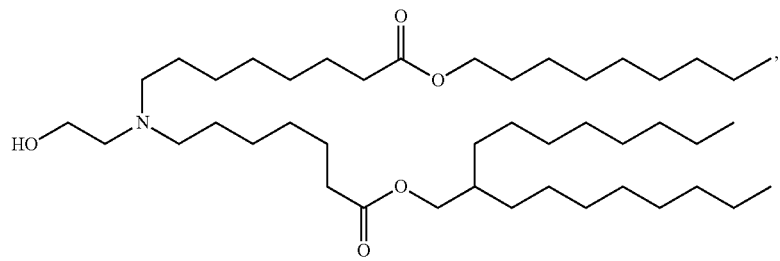
(Compound 144)
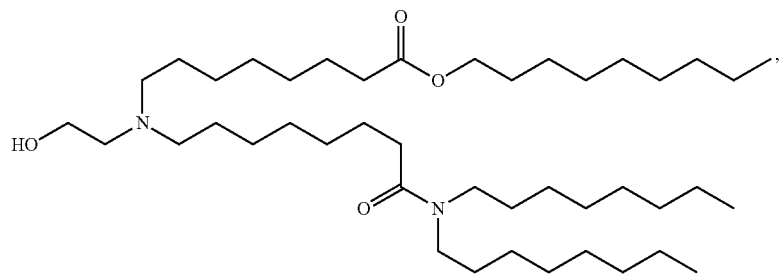
(Compound 145)
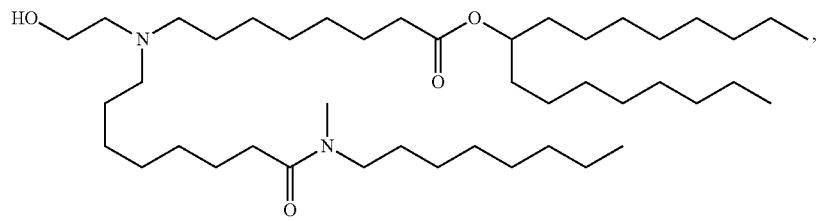
(Compound 146)
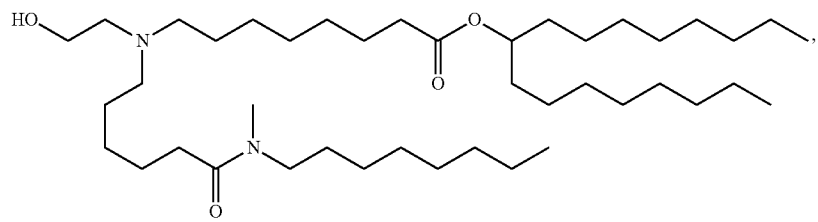
(Compound 147)
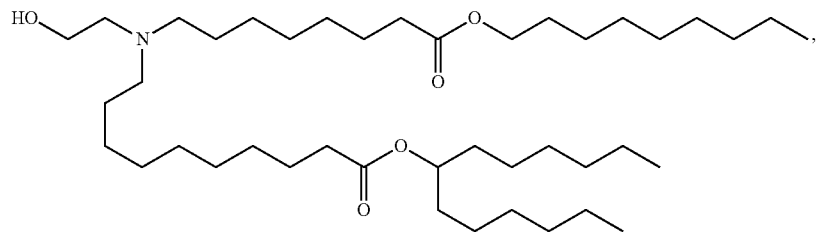

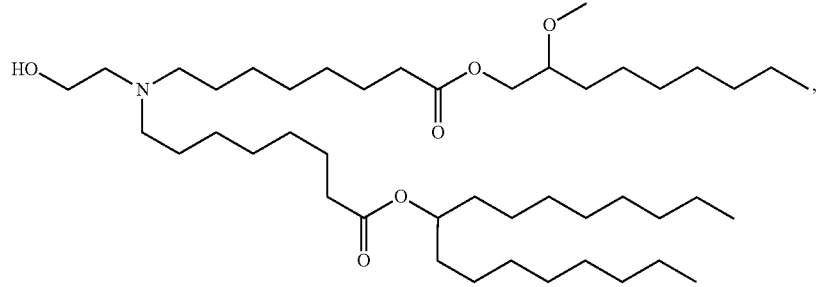
(Compound 148)
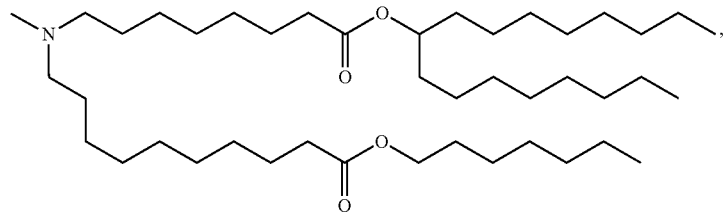
(Compound 149)
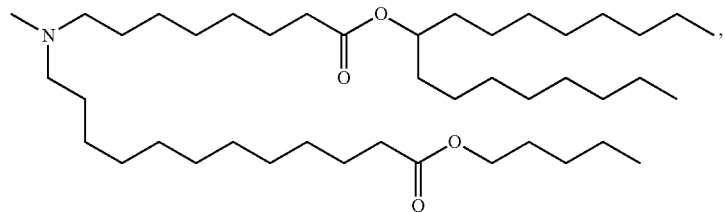
(Compound 150)
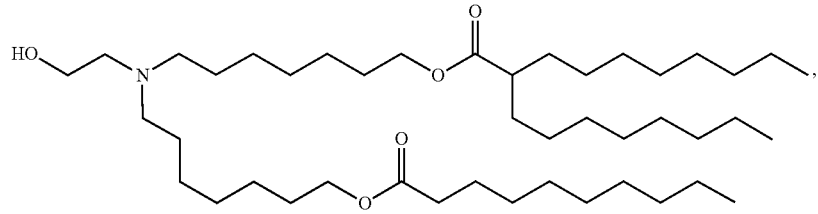
(Compound 151)
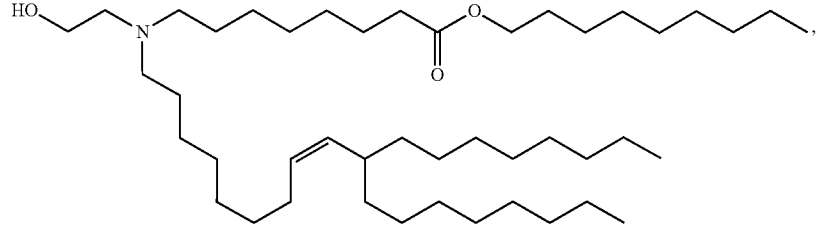
(Compound 152)
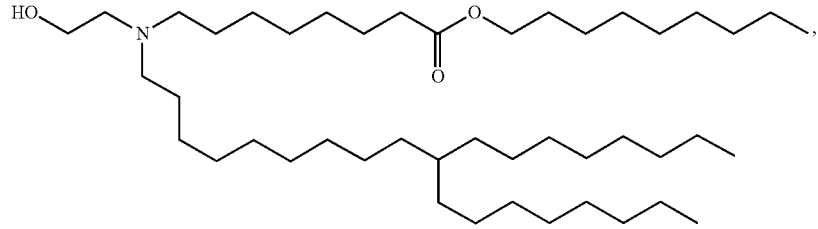
(Compound 153)

-continued
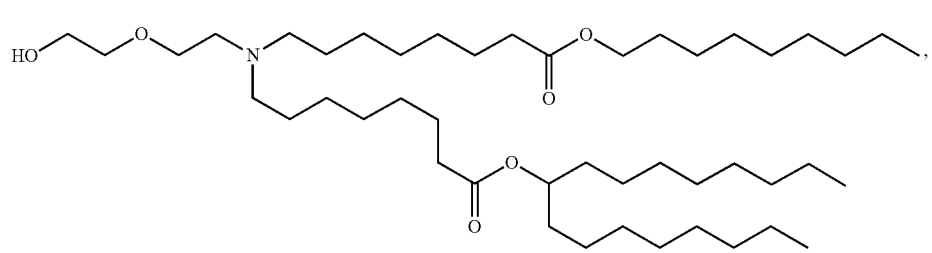
(Compound 154)
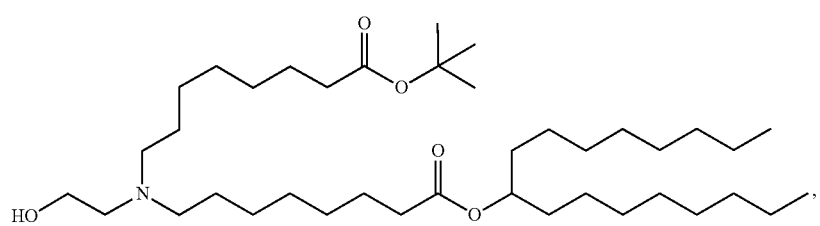
(Compound 155)
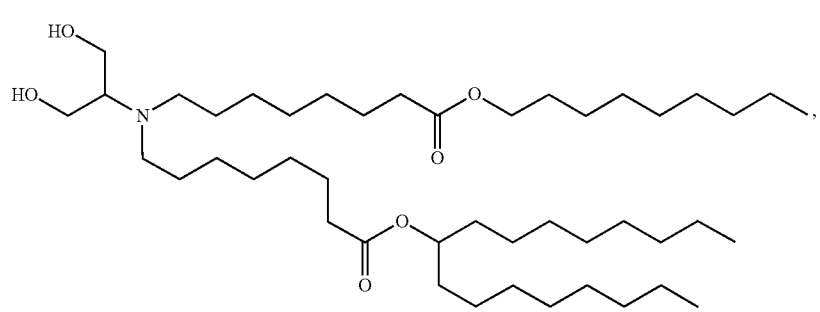
(Compound 156)
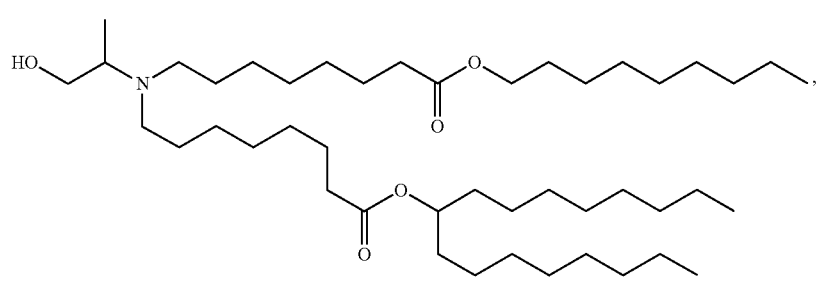
(Compound 157)
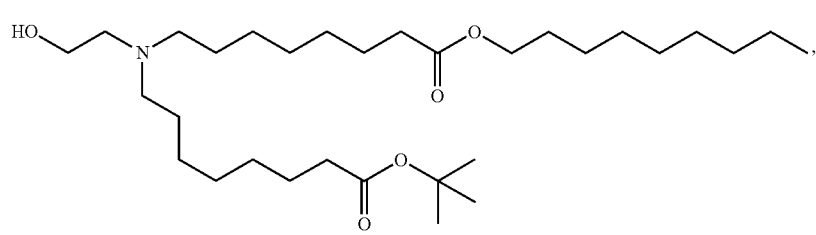
(Compound 158)
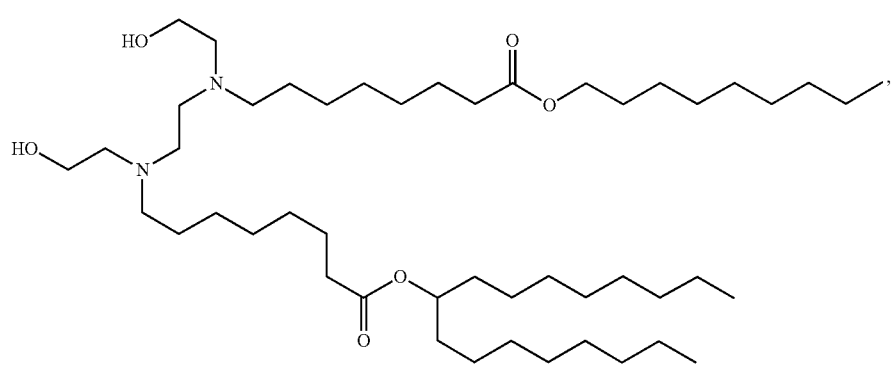
(Compound 159)

(Compound 160)
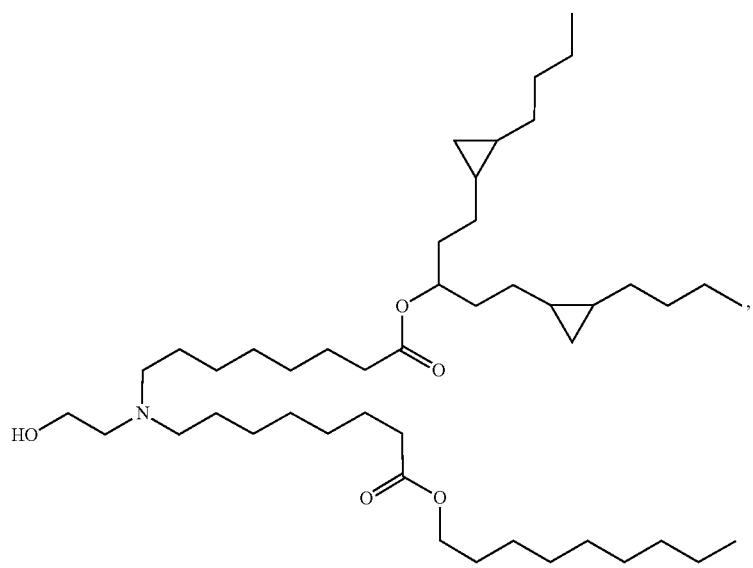
(Compound 161)
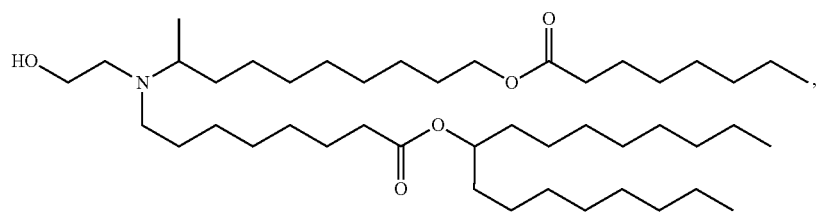
(Compound 162)
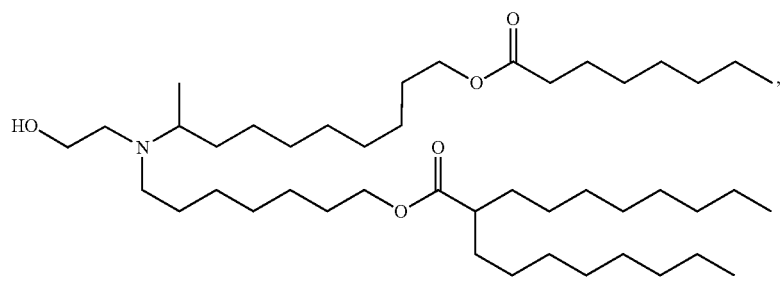
(Compound 163)
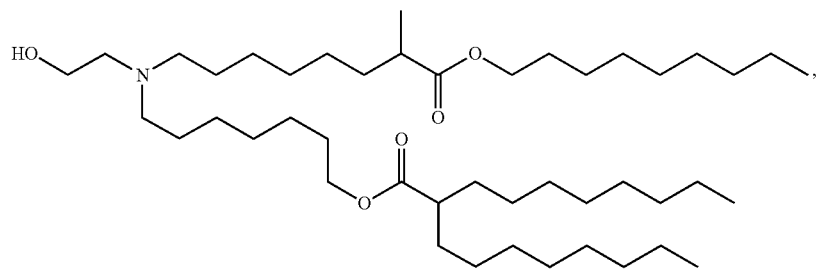
(Compound 164)
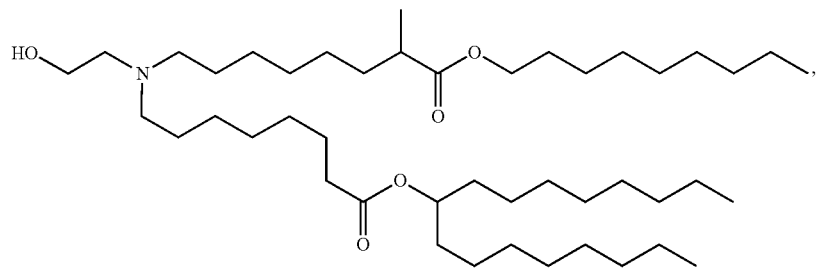

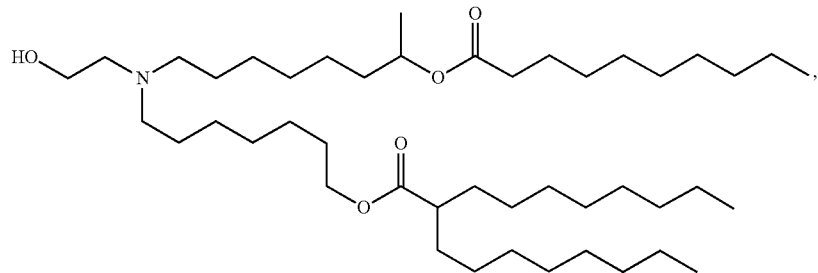
(Compound 165)
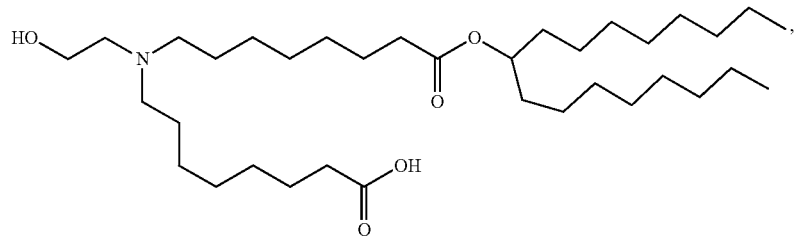
(Compound 166)
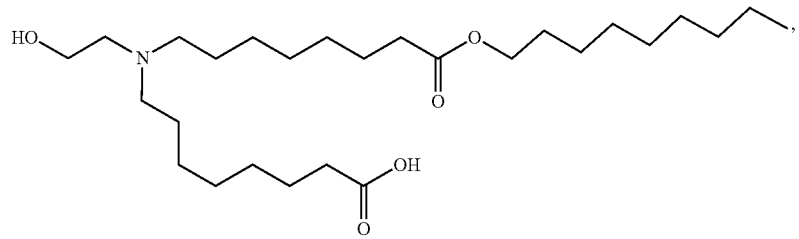
(Compound 167)
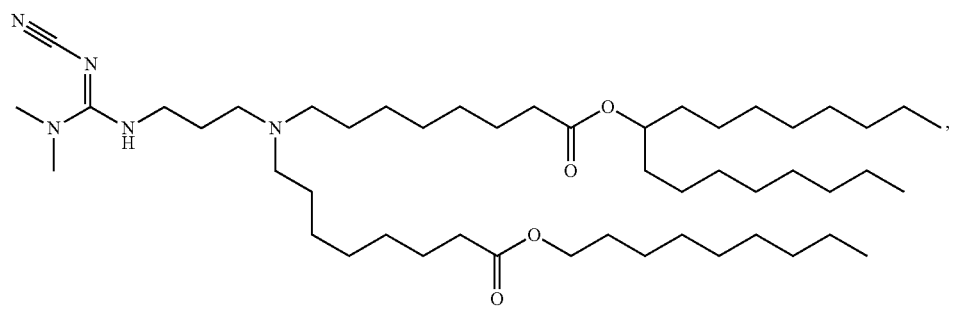
(Compound 168)
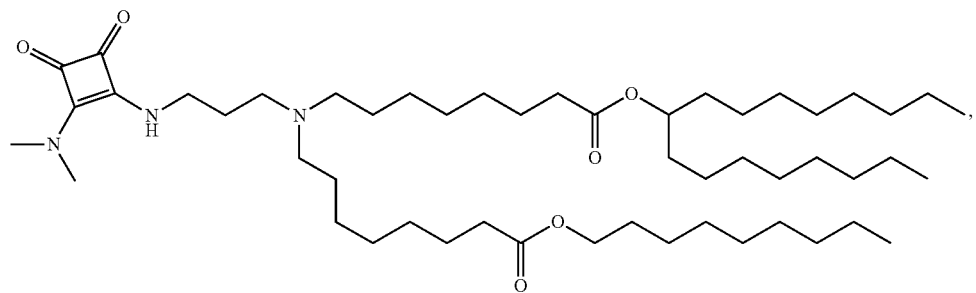
(Compound 169)

-continued
(Compound 170)
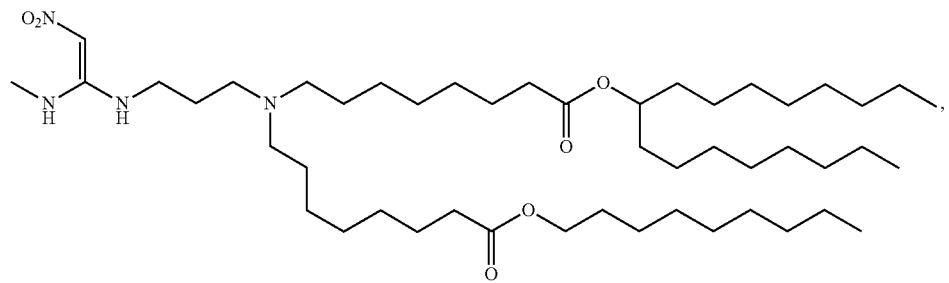
(Compound 171)
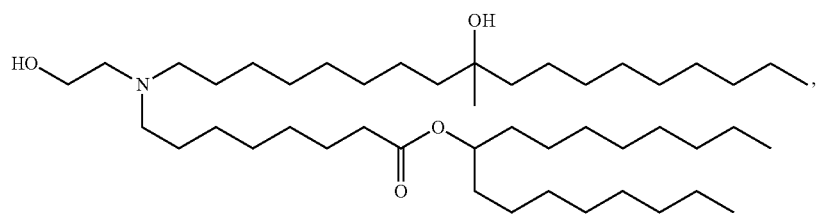
(Compound 172)
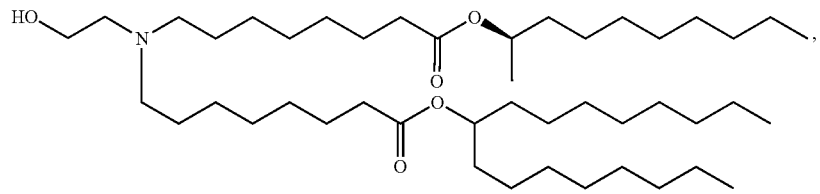
(Compound 173)
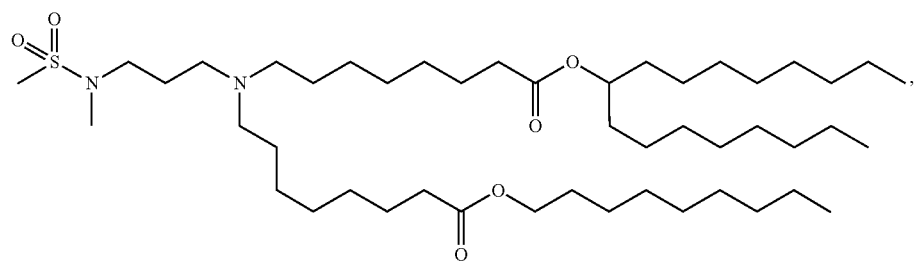
(Compound 174)
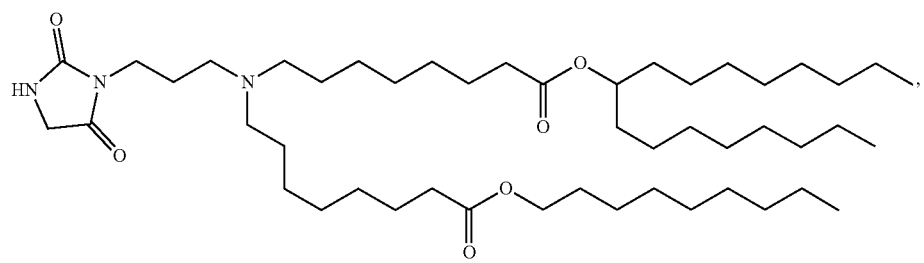
(Compound 175)
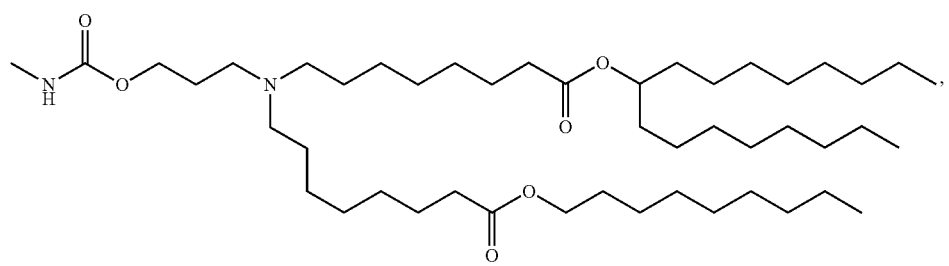

-continued
(Compound 176)
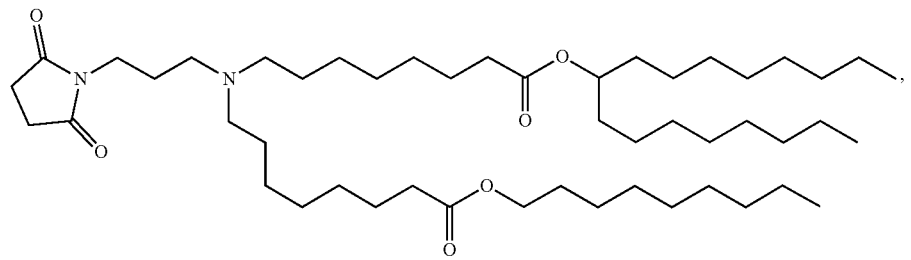
(Compound 177)
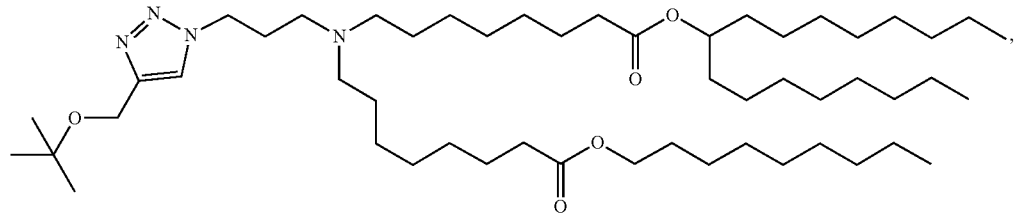
(Compound 178)
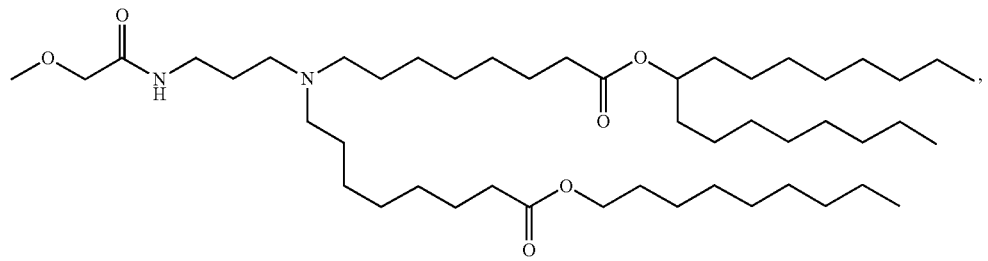
(Compound 179)
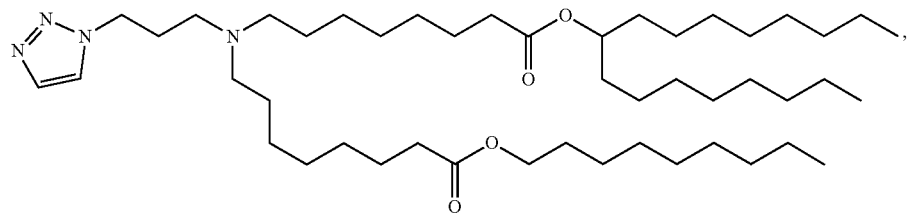
(Compound 180)
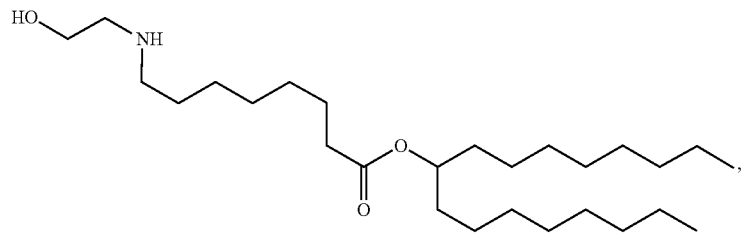
(Compound 181)
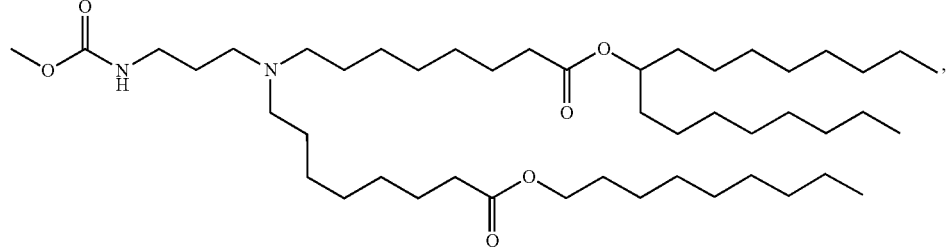

(Compound 182)
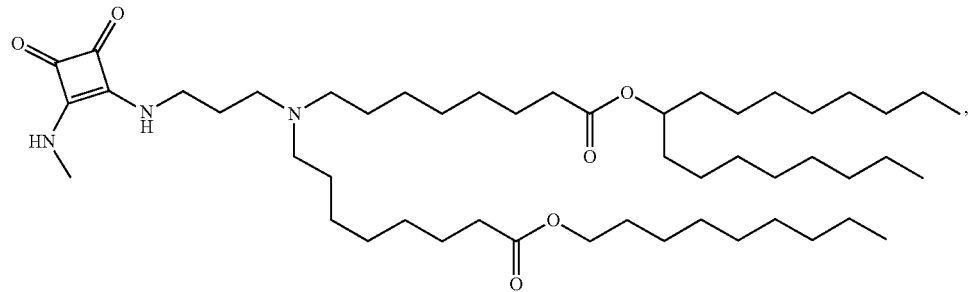
(Compound 183)
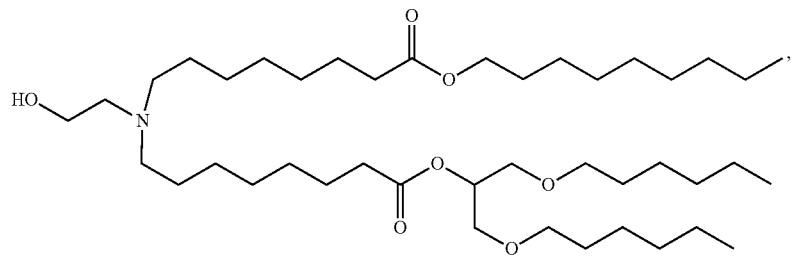
(Compound 184)
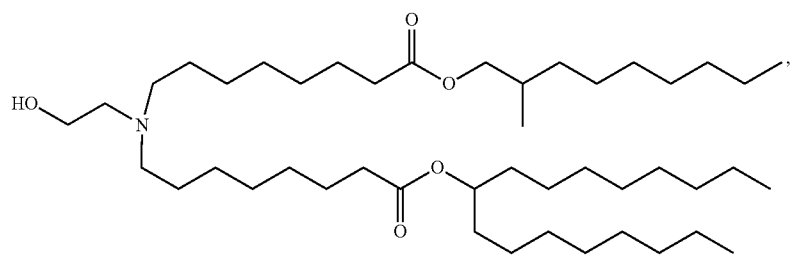
(Compound 185)
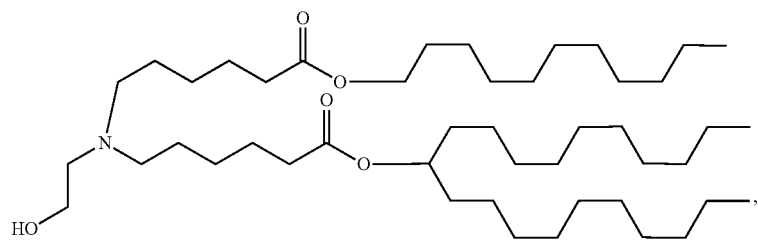
(Compound 186)
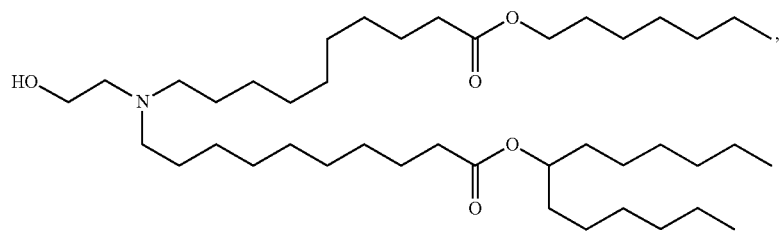
(Compound 187)
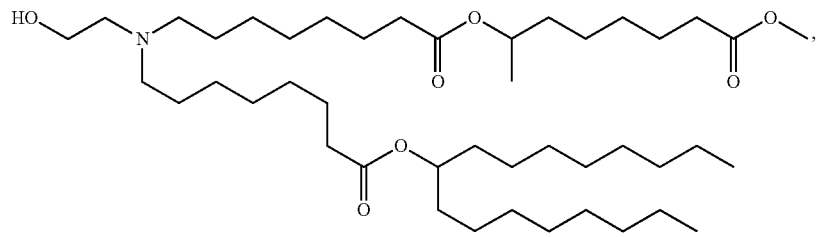

-continued
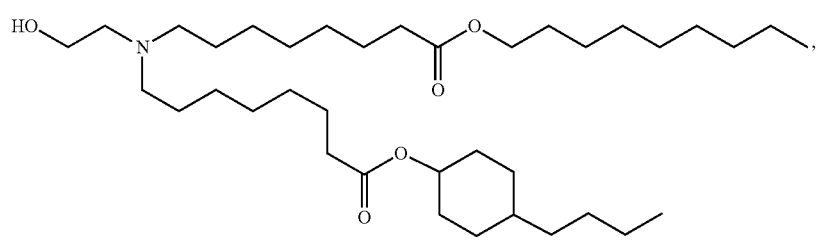
(Compound 188)
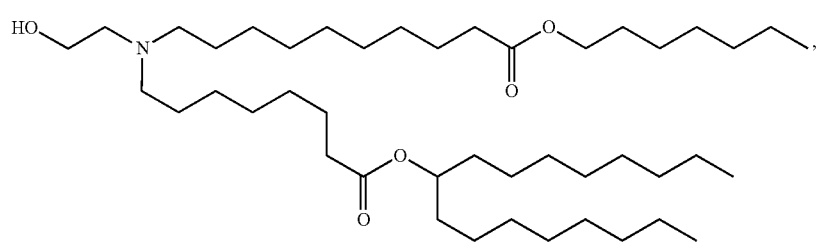
(Compound 189)
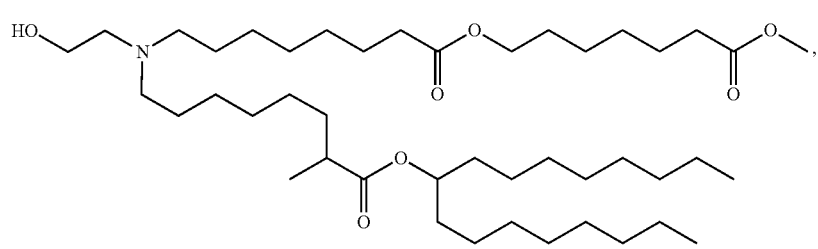
(Compound 190)
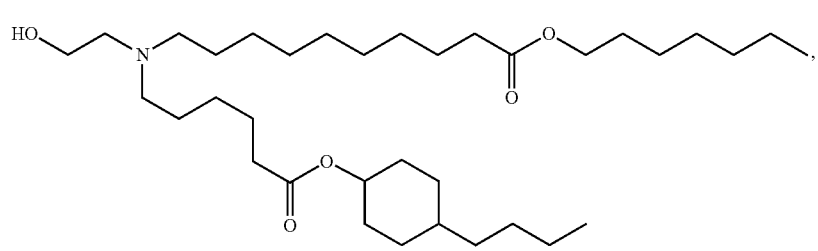
(Compound 191)
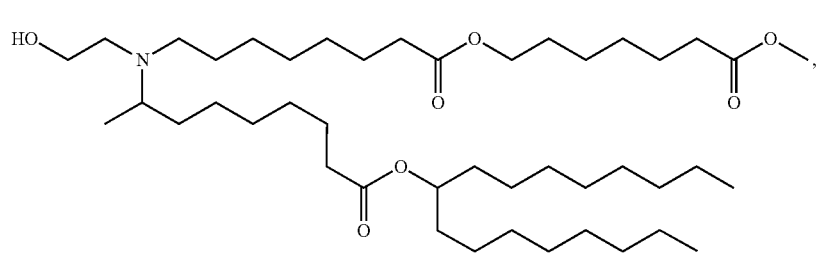
(Compound 192)
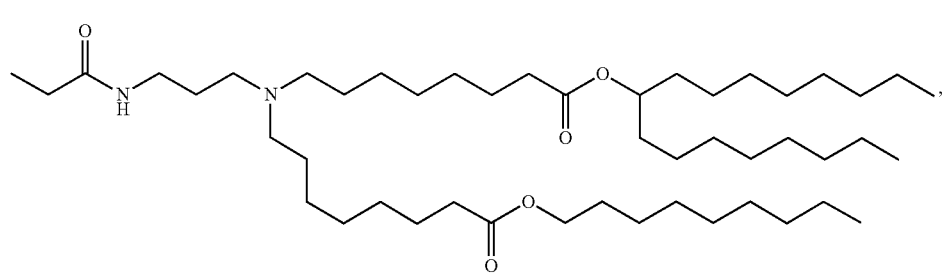
(Compound 193)

-continued
(Compound 194)
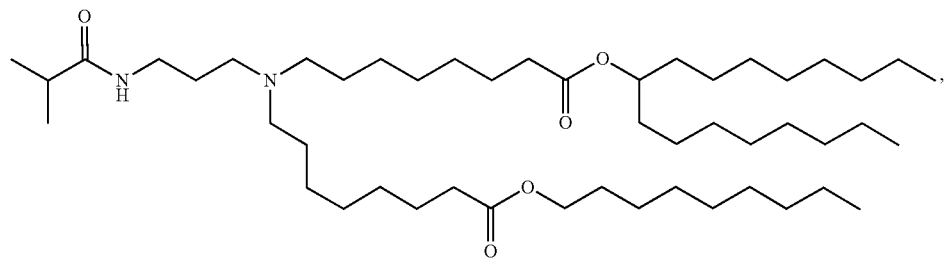
(Compound 195)
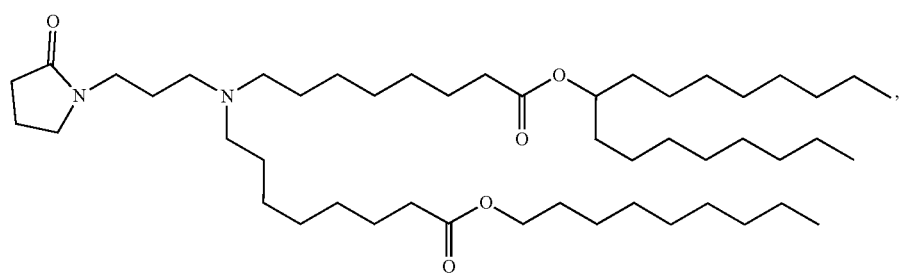
(Compound 196)
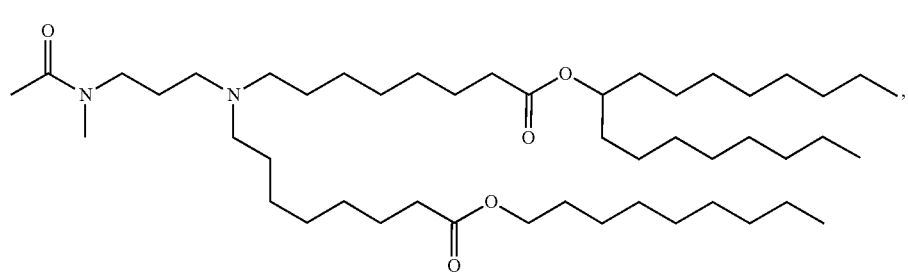
(Compound 197)
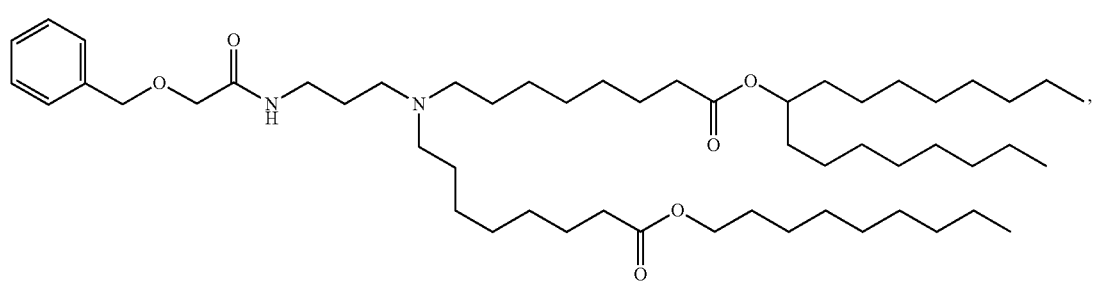
(Compound 198)
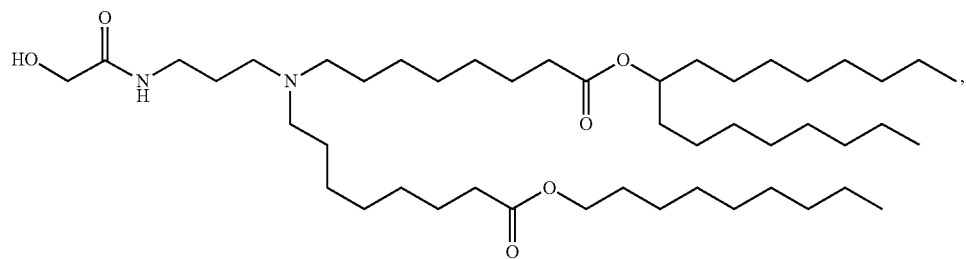
(Compound 199)
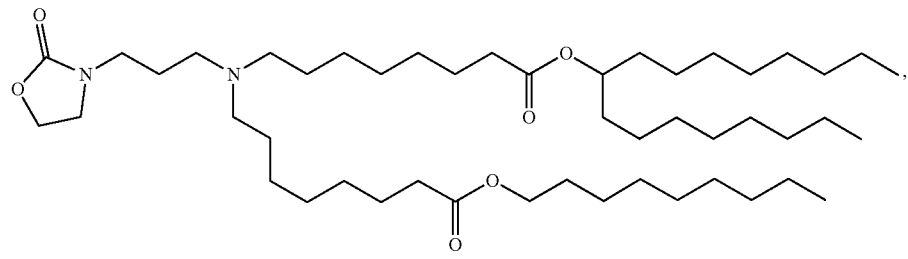

-continued
(Compound 200)
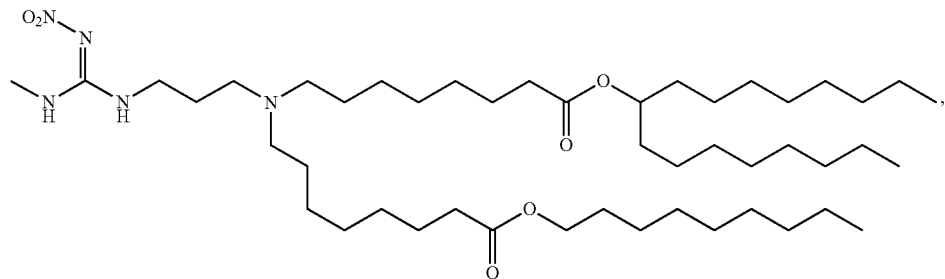
(Compound 201)
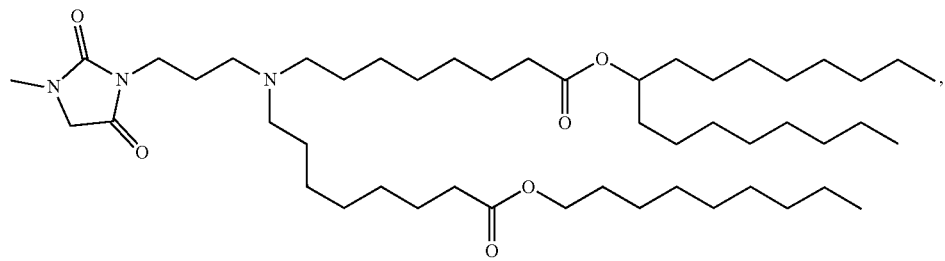
(Compound 202)
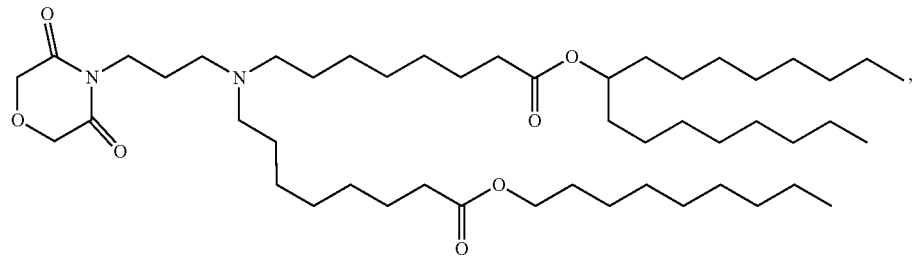
(Compound 203)
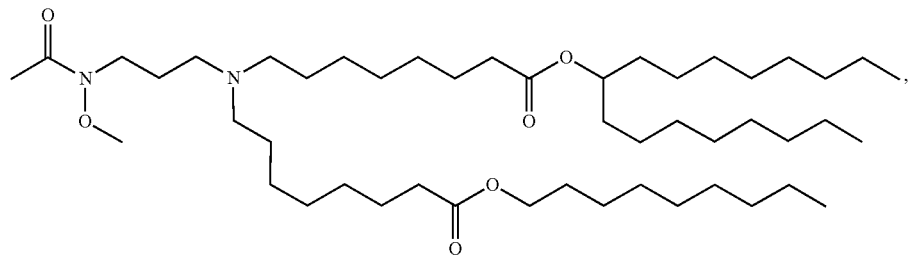
(Compound 204)
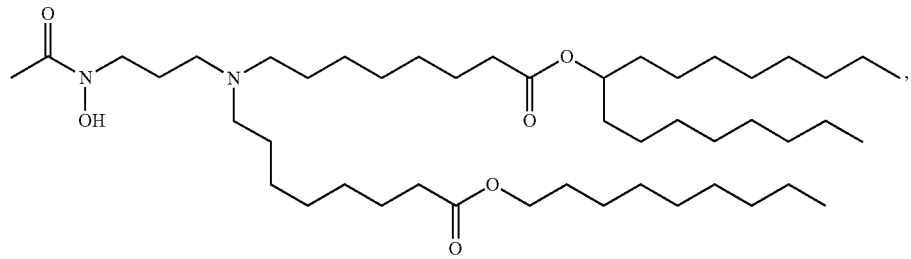
(Compound 205)
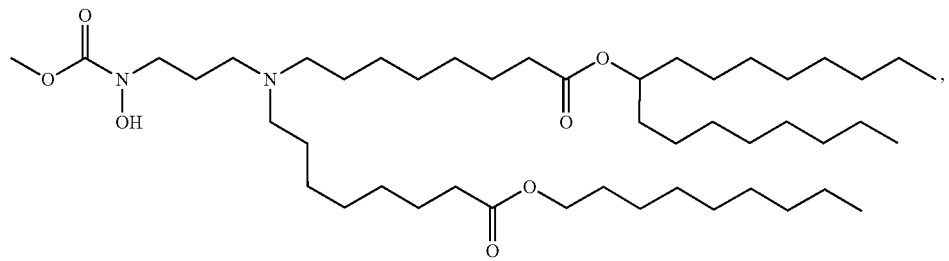

(Compound 206)
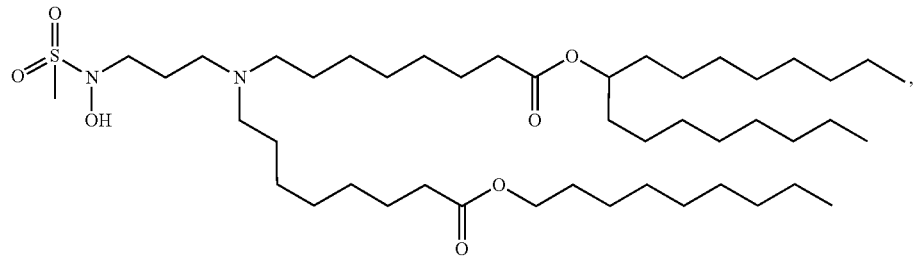
(Compound 207)
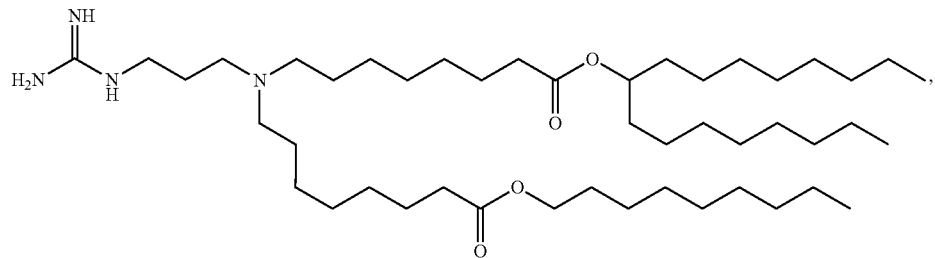
(Compound 208)
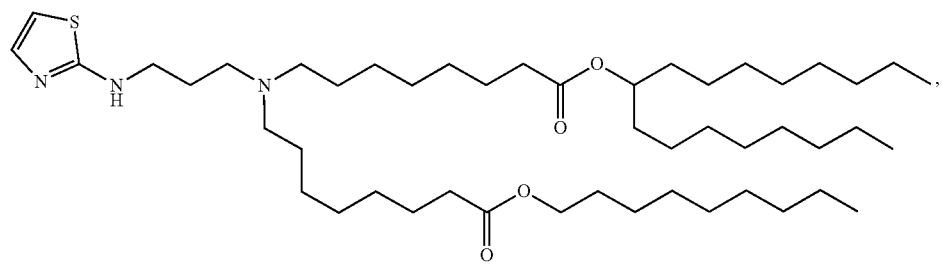
(Compound 209)
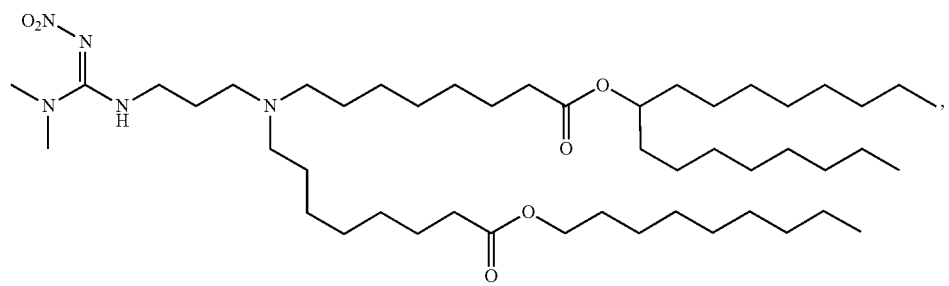
(Compound 210)
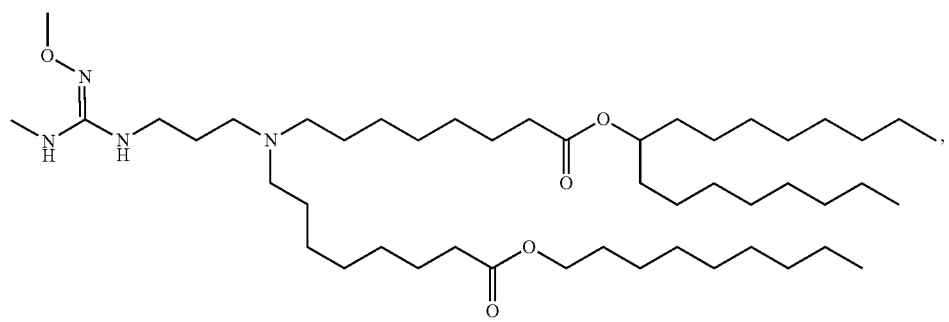

-continued
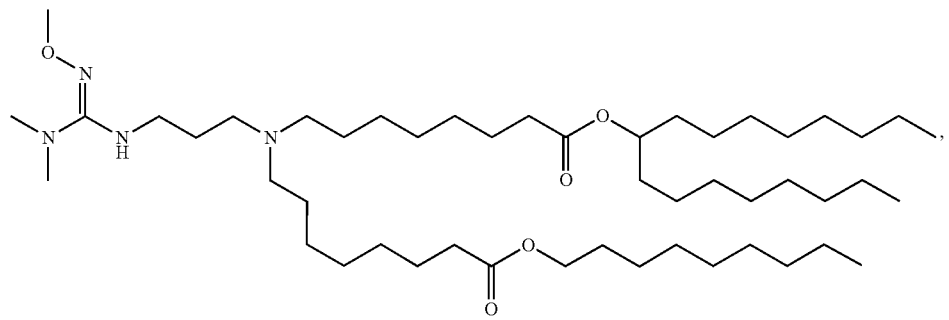
(Compound 211)
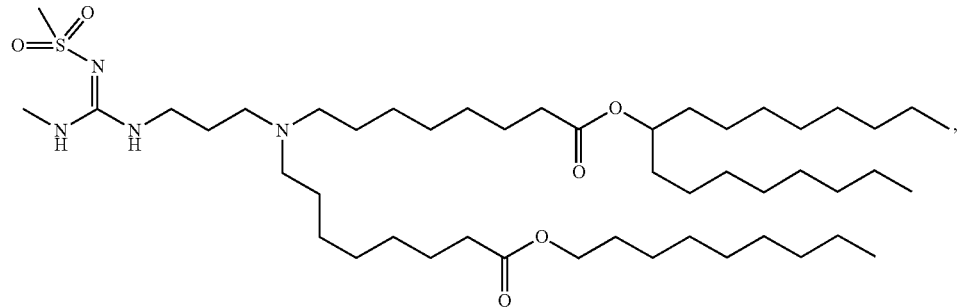
(Compound 212)
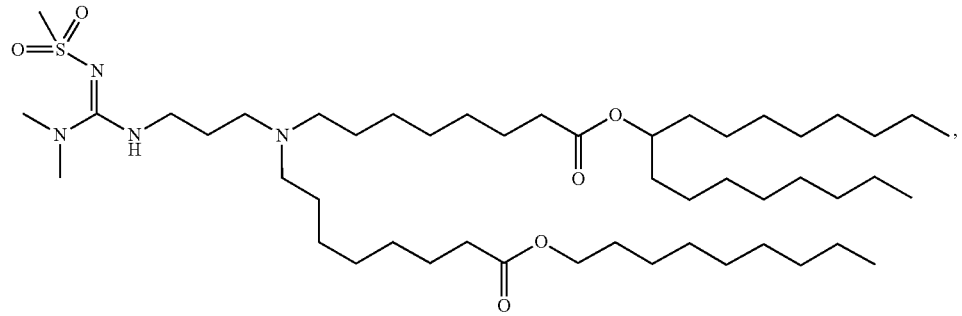
(Compound 213)
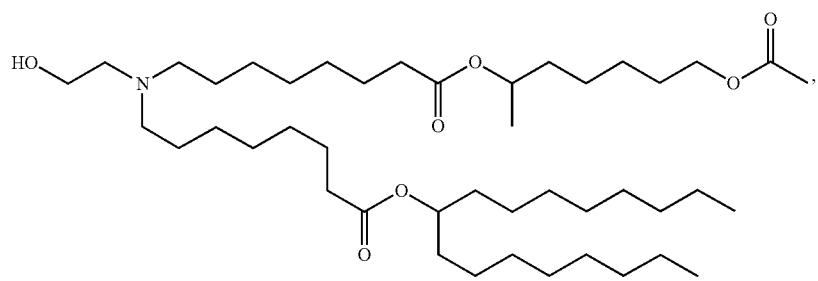
(Compound 214)
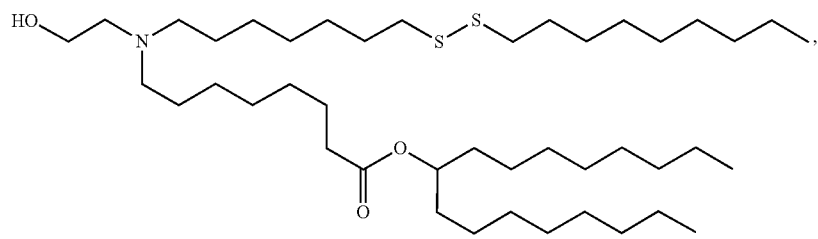
(Compound 215)

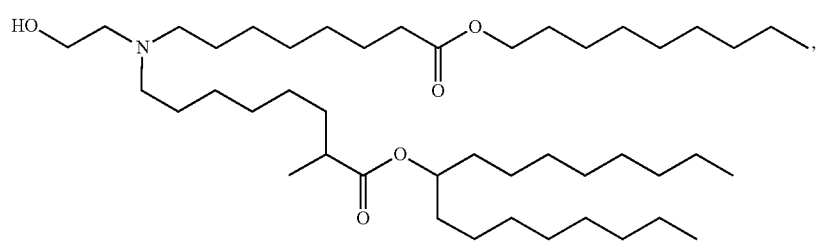
(Compound 216)
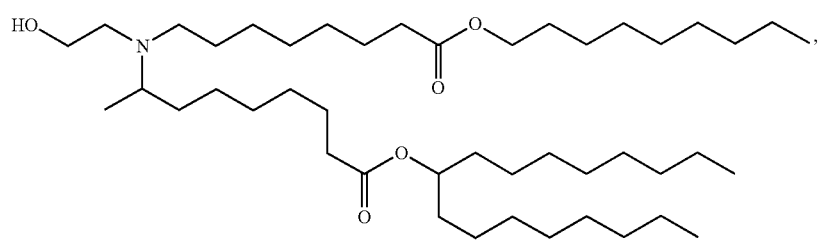
(Compound 217)
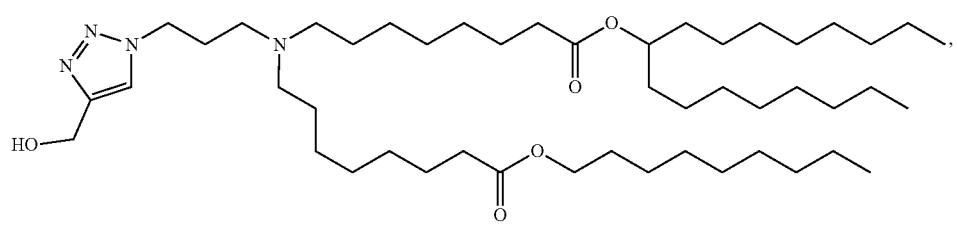
(Compound 218)
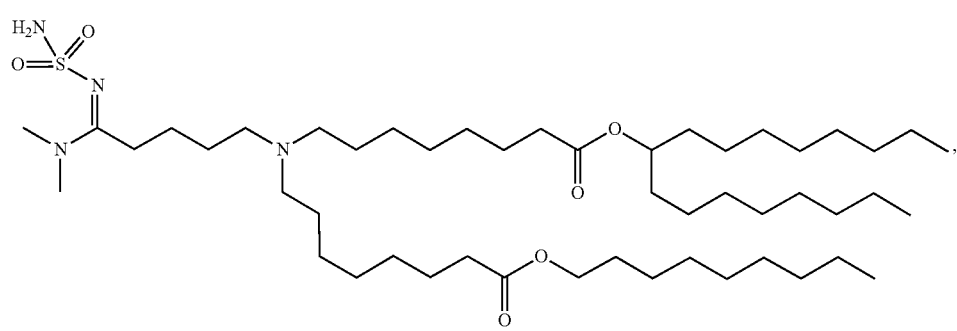
(Compound 219)
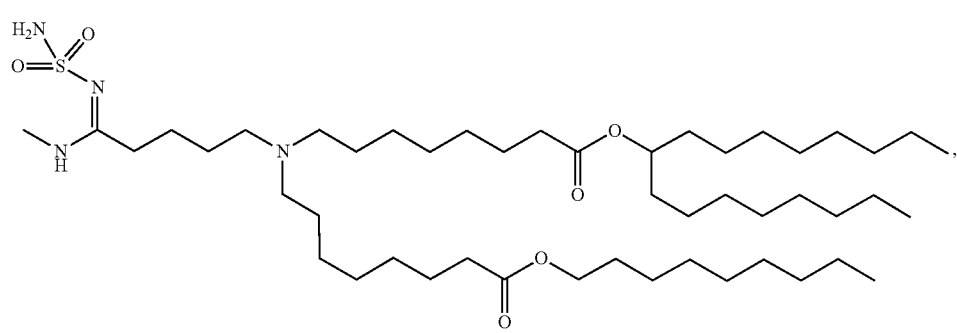
(Compound 220)

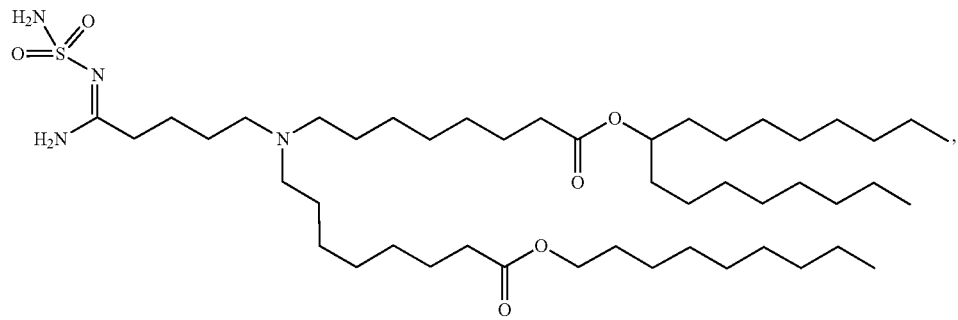
(Compound 221)
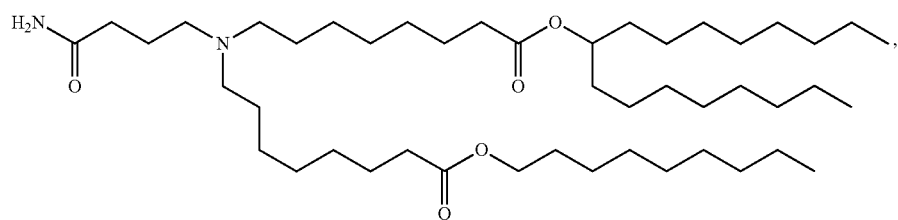
(Compound 222)
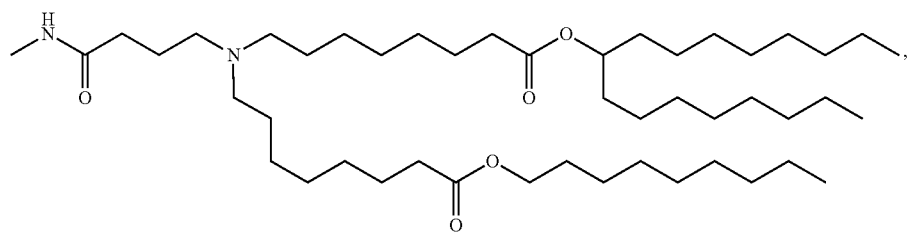
(Compound 223)
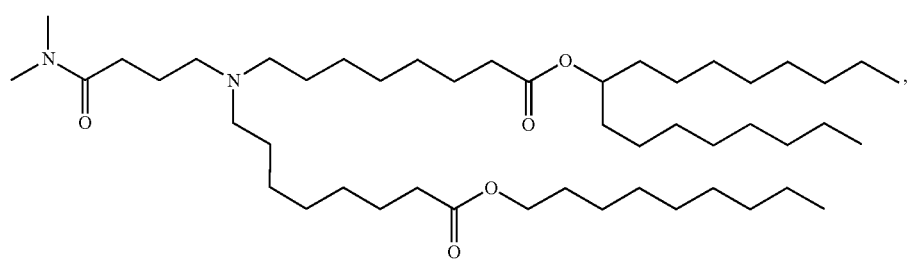
(Compound 224)
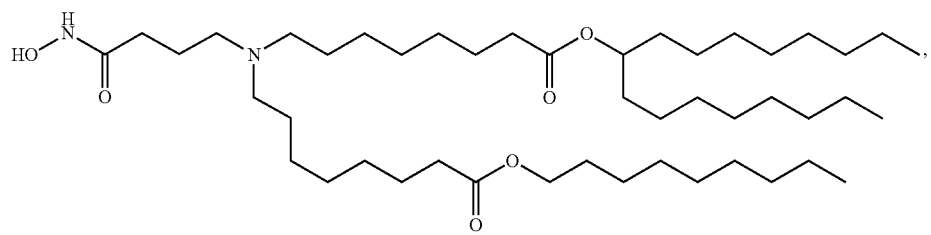
(Compound 225)
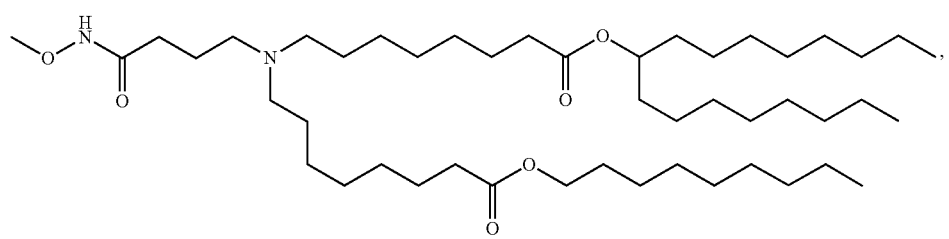
(Compound 226)

-continued

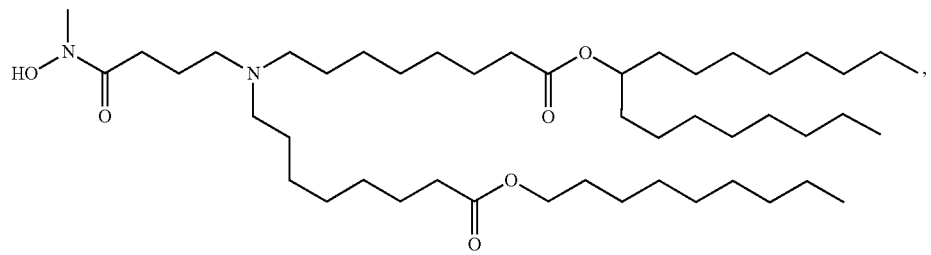
(Compound 227)

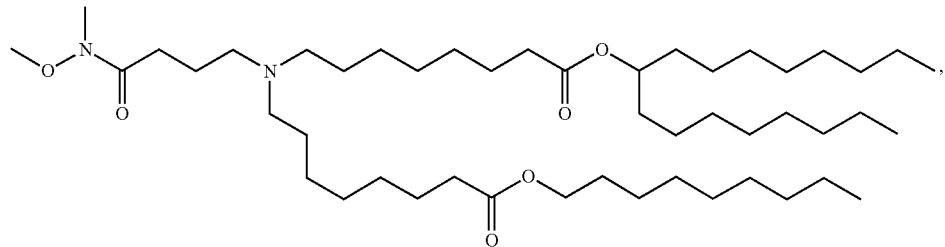
(Compound 228)

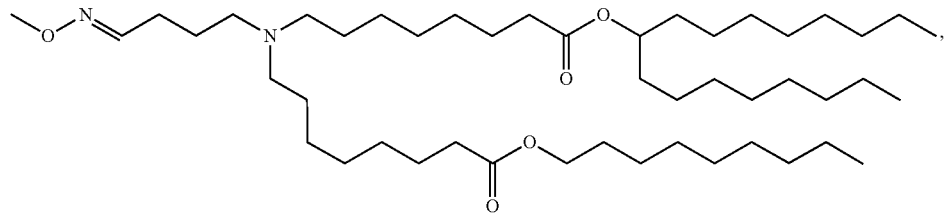
(Compound 229)

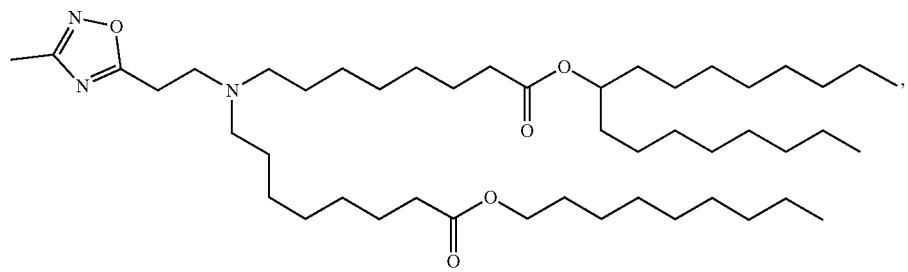
(Compound 230)

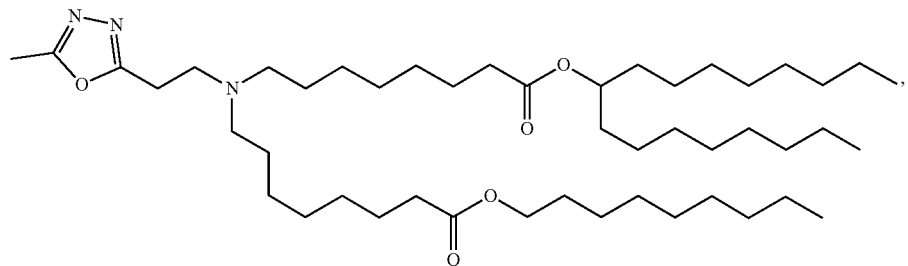
(Compound 231)

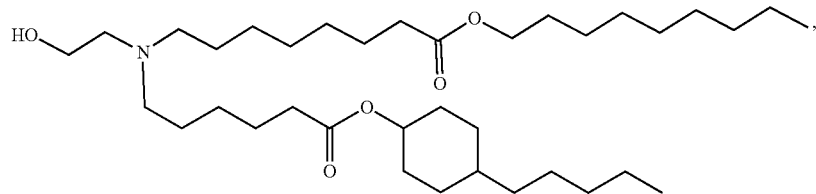
(Compound 232)

and salts or stereoisomers thereof.

In other embodiments, the compound of Formula (I) is selected from the group consisting of Compound 1-Compound 147, or salt or stereoisomers thereof.

In some embodiments ionizable lipids including a central piperazine moiety are provided.

In some embodiments, the delivery agent comprises a lipid compound having the formula (III)

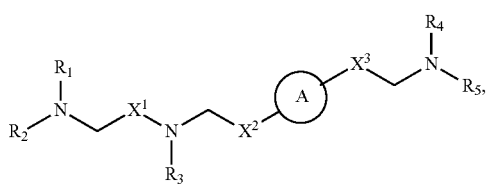

(III)

or salts or stereoisomers thereof, wherein
ring A

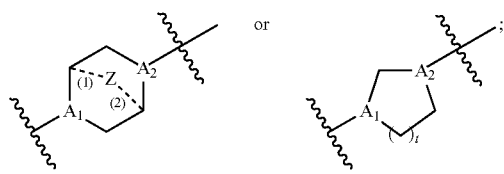

t is 1 or 2;
  $A_1$ and $A_2$ are each independently selected from CH or N;
  Z is $CH_2$ or absent wherein when Z is $CH_2$, the dashed lines (1) and (2) each represent a single bond; and when Z is absent, the dashed lines (1) and (2) are both absent;
  $R_1, R_2, R_3, R_4,$ and $R_5$ are independently selected from the group consisting of $C_{5-20}$ alkyl, $C_{5-20}$ alkenyl, —R"MR', —R*YR", —YR", and —R*OR";
  each M is independently selected from the group consisting of —C(O)O—, —OC(O)—, —OC(O)O—, —C(O)N(R')—, —N(R')C(O)—, —C(O)—, —C(S)—, —C(S)S—, —S C(S)—, —CH(OH)—, —P(O)(OR')O—, —S(O)$_2$—, an aryl group, and a heteroaryl group;
  $X^1, X^2,$ and $X^3$ are independently selected from the group consisting of a bond, —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;
  each Y is independently a $C_{3-6}$ carbocycle;
  each R* is independently selected from the group consisting of $C_{1-12}$ alkyl and $C_{2-12}$ alkenyl;
  each R is independently selected from the group consisting of $C_{1-3}$ alkyl and a $C_{3-6}$ carbocycle;
  each R' is independently selected from the group consisting of $C_{1-12}$ alkyl, $C_{2-12}$ alkenyl, and H; and
  each R" is independently selected from the group consisting of $C_{3-12}$ alkyl and $C_3$-12 alkenyl,
wherein when ring A is

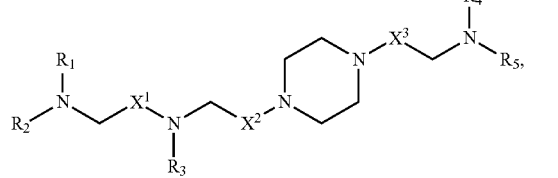

then
  i) at least one of $X^1, X^2,$ and $X^3$ is not —CH$_2$—; and/or
  ii) at least one of $R_1, R_2, R_3, R_4,$ and $R_5$ is —R"MR'.

In some embodiments, the compound is of any of formulae (IIIa1)-(IIIa6):

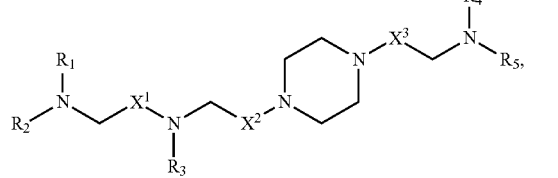

(IIIa1)

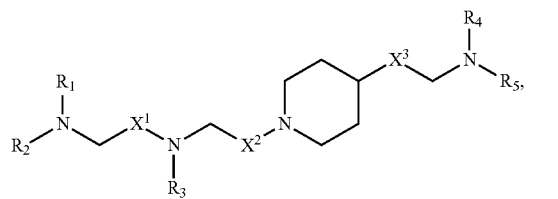

(IIIa2)

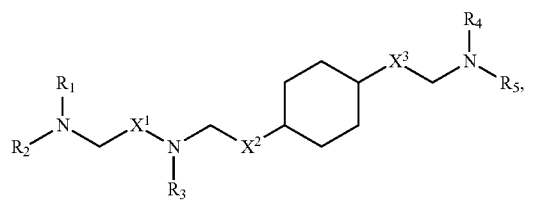

(IIIa3)

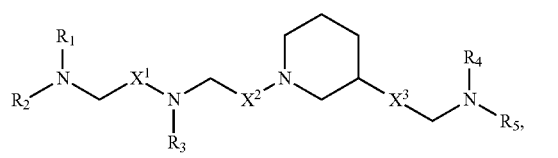

(IIIa4)

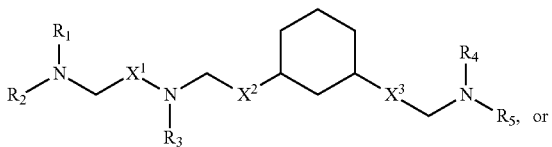

(IIIa5)

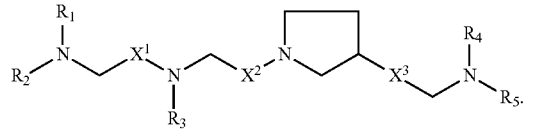

(IIIa6)

The compounds of Formula (III) or any of (IIIa1)-(IIIa6) include one or more of the following features when applicable.

In some embodiments, ring A is

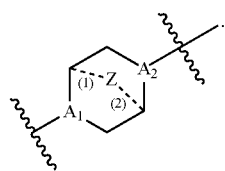

In some embodiments, ring A is

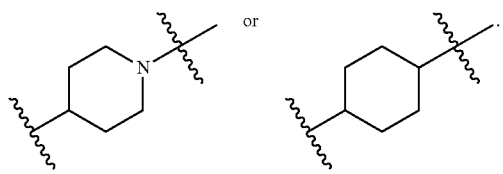 [SMILES: *C1CCN(*)CC1 ; *C1CCC(*)CC1]

In some embodiments, ring A is

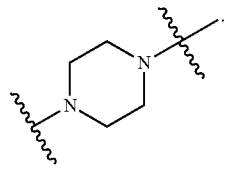 [SMILES: *N1CCN(*)CC1]

In some embodiments, ring A is

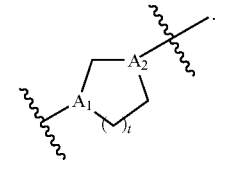

In some embodiments, ring A is

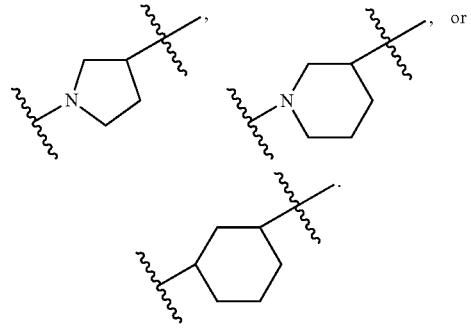

In some embodiments, ring A is

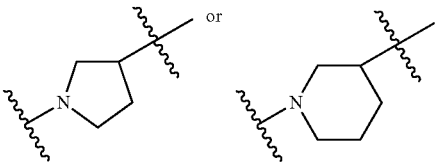 [SMILES: *C1CCN(*)C1 ; *C1CCCN(*)C1]

wherein ring, in which the N atom is connected with $X^2$.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, at least one of $X^1$, $X^2$, and $X^3$ is not —$CH_2$—. For example, in certain embodiments, $X^1$ is not —$CH_2$—. In some embodiments, at least one of $X^1$, $X^2$, and $X^3$ is —C(O)—.

In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.

In some embodiments, $X^3$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—. In other embodiments, $X^3$ is —$CH_2$—.

In some embodiments, $X^3$ is a bond or —$(CH_2)_2$—.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is —R"MR'. In some embodiments, at most one of $R_1$, $R_2$, $R_3$, $R_4$, and $R_5$ is —R"MR'. For example, at least one of $R_1$, $R_2$, and $R_3$ may be —R"MR', and/or at least one of $R_4$ and $R_5$ is —R"MR'. In certain embodiments, at least one M is —C(O)O—. In some embodiments, each M is —C(O)O—. In some embodiments, at least one M is —OC(O)—. In some embodiments, each M is —OC(O)—. In some embodiments, at least one M is —OC(O)O—. In some embodiments, each M is —OC(O)O—. In some embodiments, at least one R" is $C_3$ alkyl. In certain embodiments, each R" is $C_3$ alkyl. In some embodiments, at least one R" is $C_5$ alkyl. In certain embodiments, each R" is $C_5$ alkyl. In some embodiments, at least one R" is $C_6$ alkyl. In certain embodiments, each R" is $C_6$ alkyl. In some embodiments, at least one R" is $C_7$ alkyl. In certain embodiments, each R" is $C_7$ alkyl. In some embodiments, at least one R' is $C_5$ alkyl. In certain embodiments, each R' is $C_5$ alkyl. In other embodiments, at least one R' is $C_1$ alkyl. In certain embodiments, each R' is $C_1$ alkyl. In some embodiments, at least one R' is $C_2$ alkyl. In certain embodiments, each R' is $C_2$ alkyl.

In some embodiments, at least one of $R_1$, $R_2$, $R_3$, $R_4$, and $R_5$ is $C_{12}$ alkyl. In certain embodiments, each of $R_1$, $R_2$, $R_3$, $R_4$, and $R_5$ are $C_{12}$ alkyl.

In certain embodiments, the compound is selected from the group consisting of:
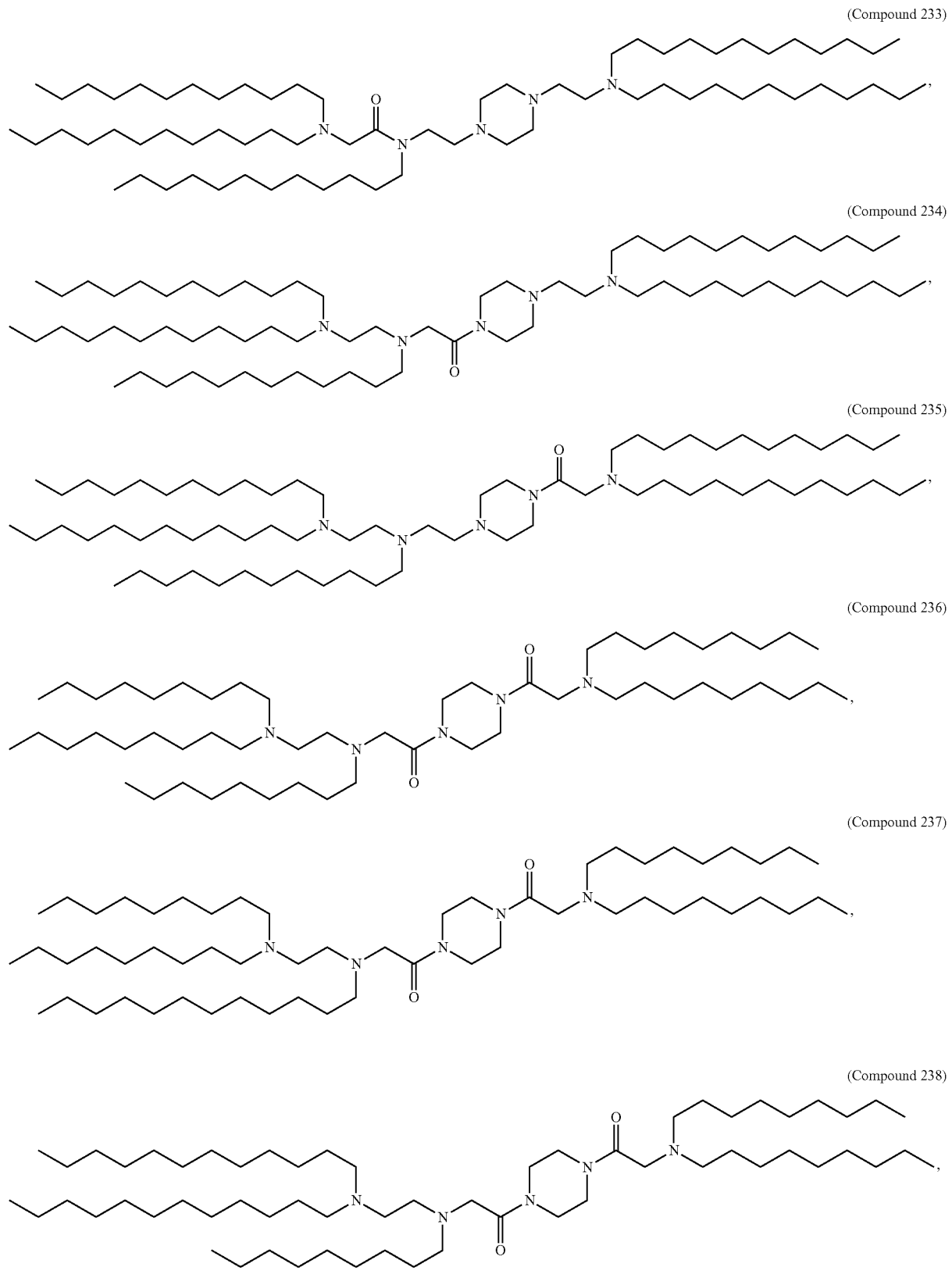

-continued
(Compound 239)
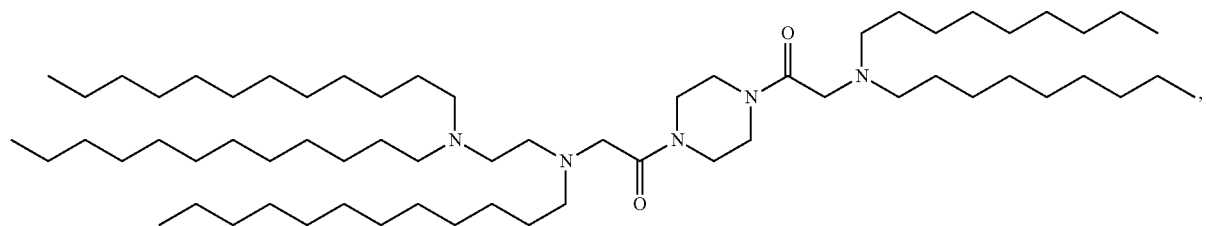
(Compound 240)
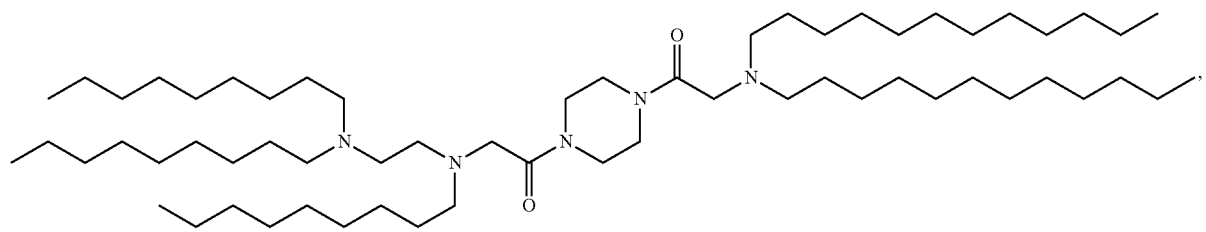
(Compound 241)
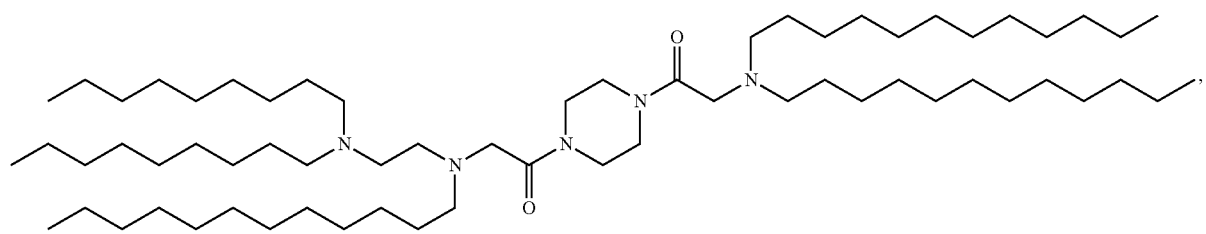
(Compound 242)
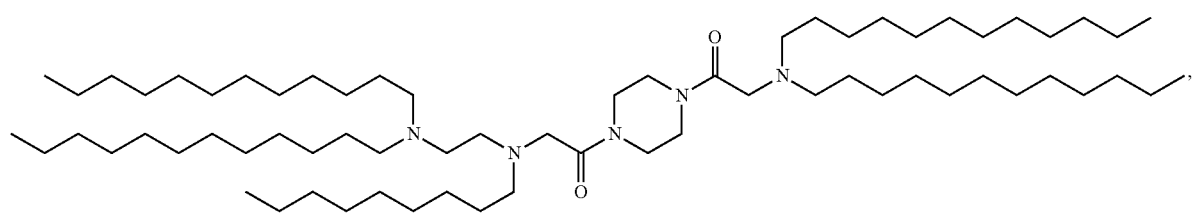
(Compound 243)
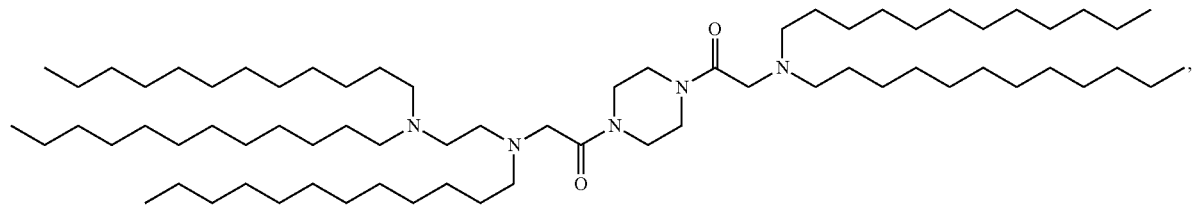
(Compound 244)
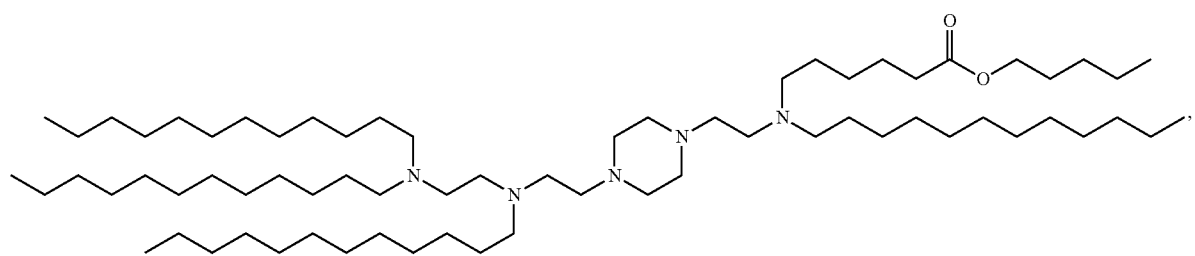

-continued
(Compound 245)
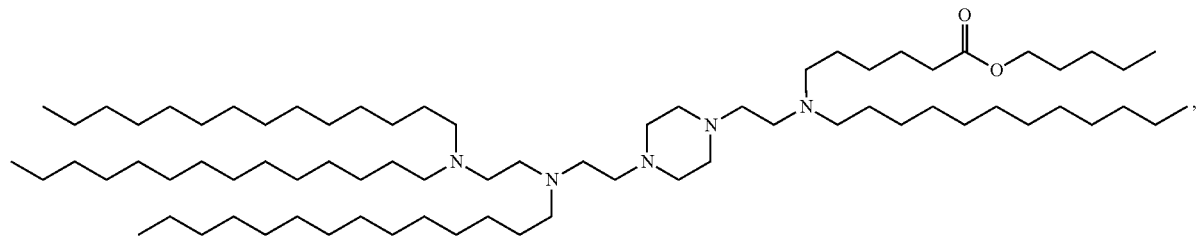
(Compound 246)
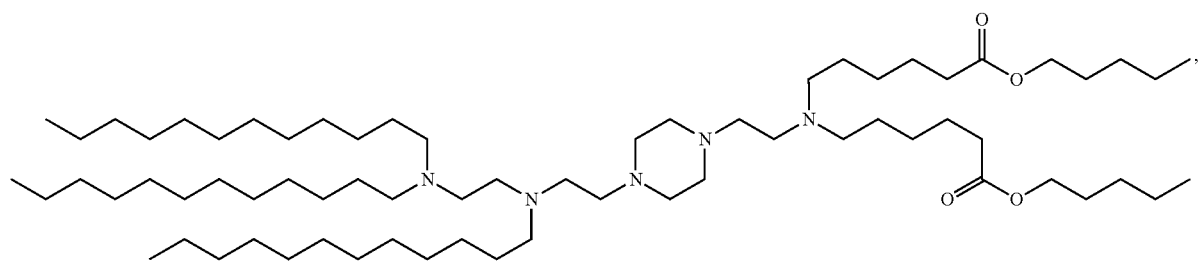
(Compound 247)
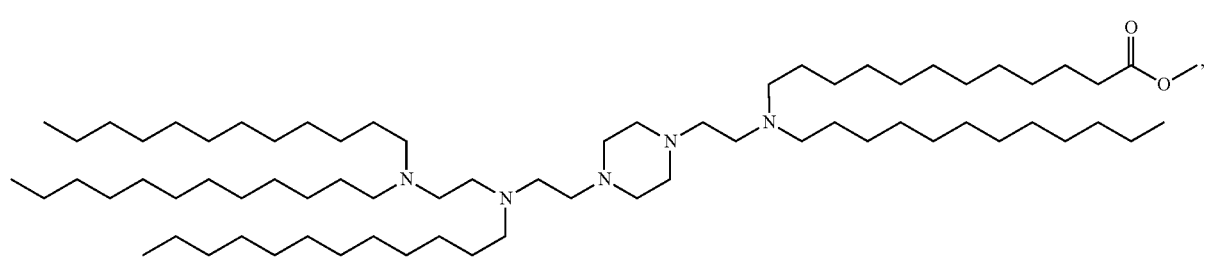
(Compound 248)
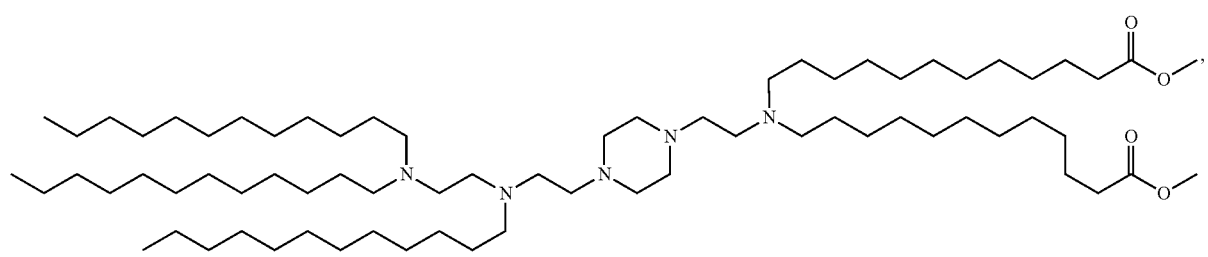
(Compound 274)
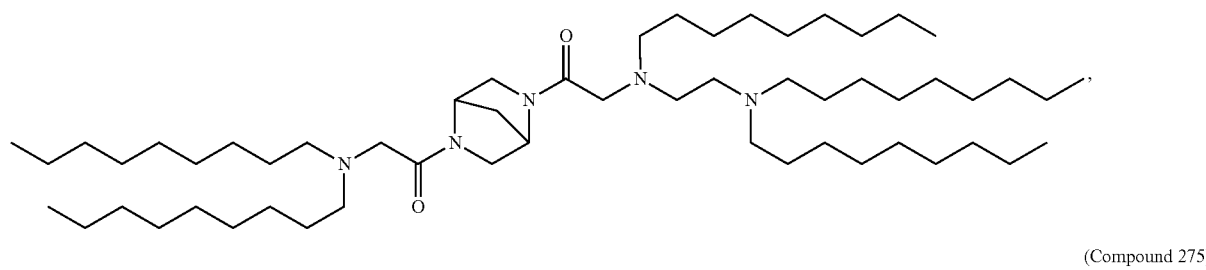
(Compound 275)
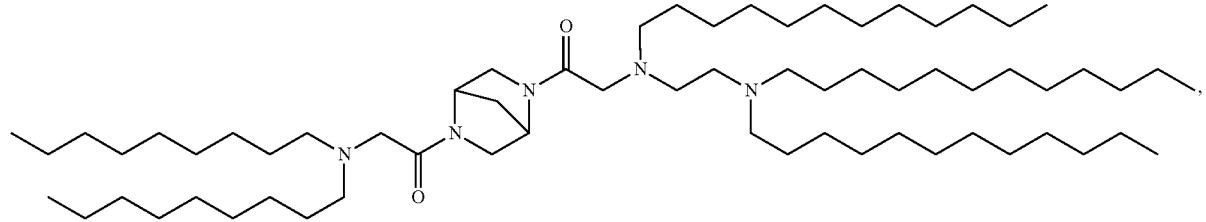

(Compound 276)
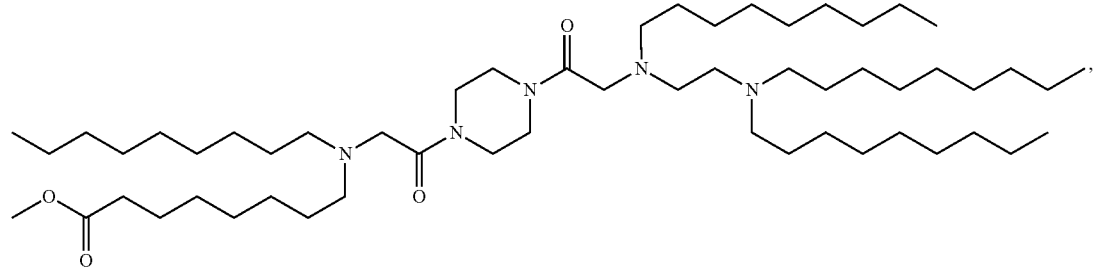
(Compound 277)
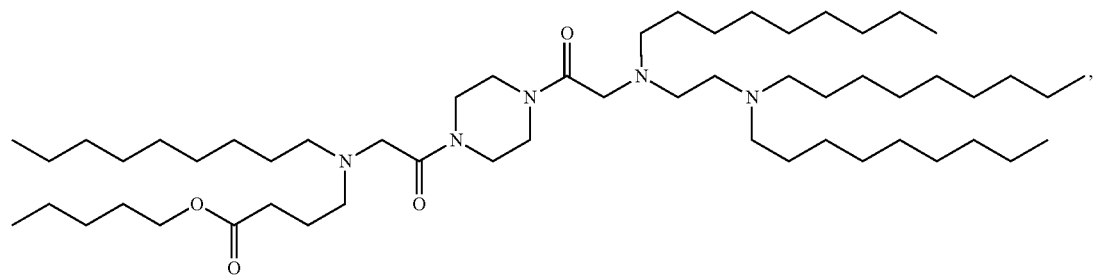
(Compound 278)
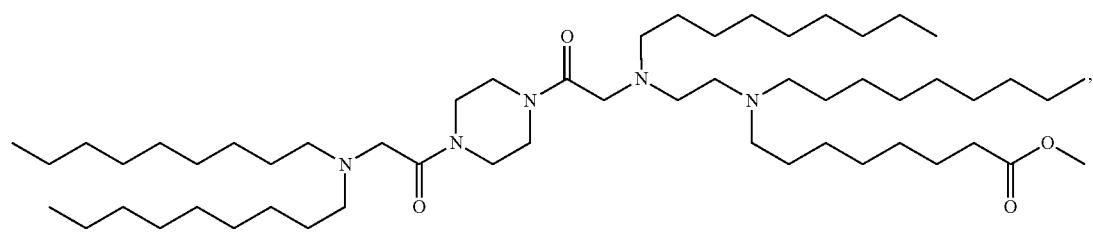
(Compound 279)
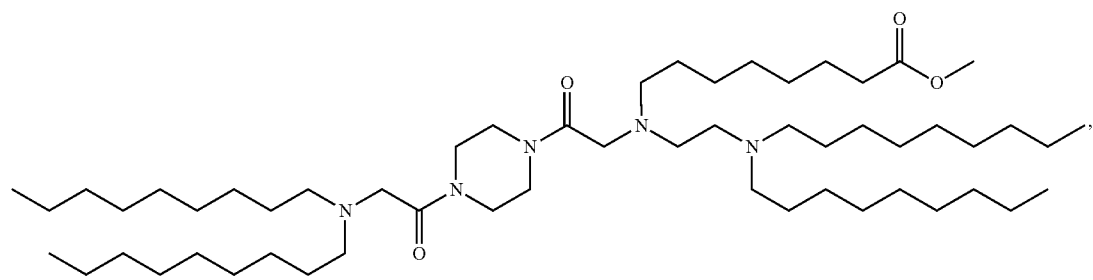
(Compound 280)
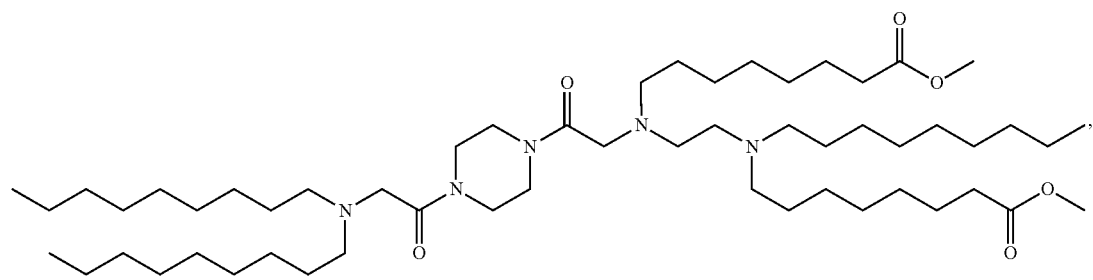

-continued
(Compound 281)
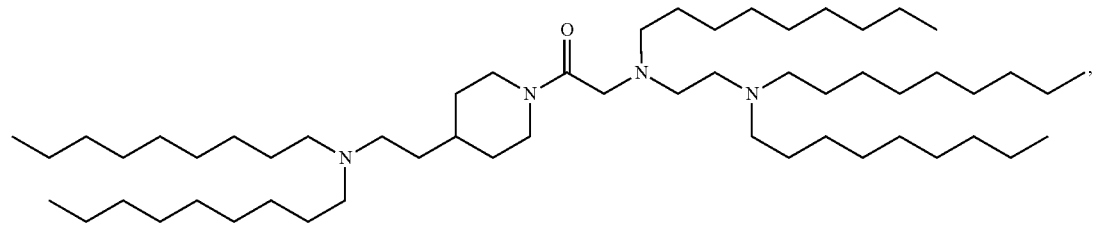
(Compound 282)
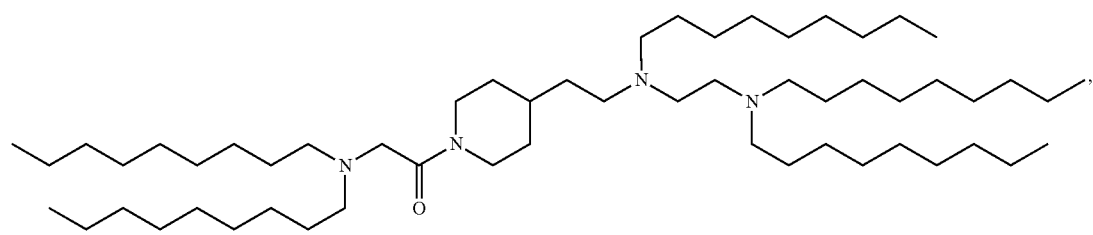
(Compound 283)
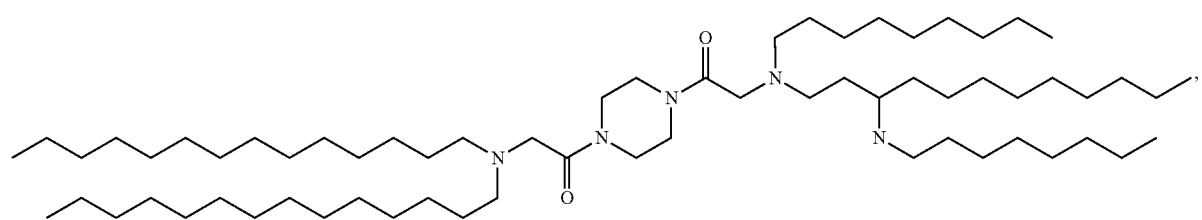
(Compound 284)
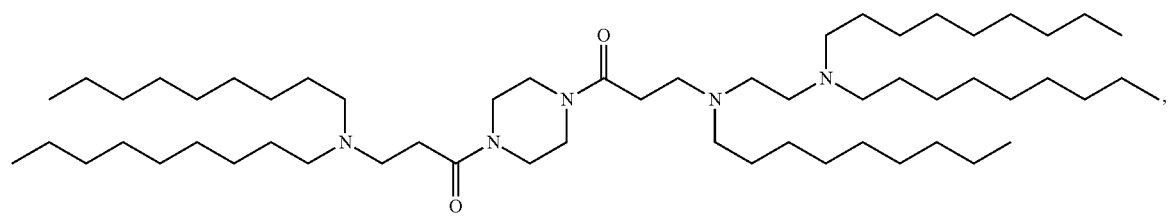
(Compound 285)
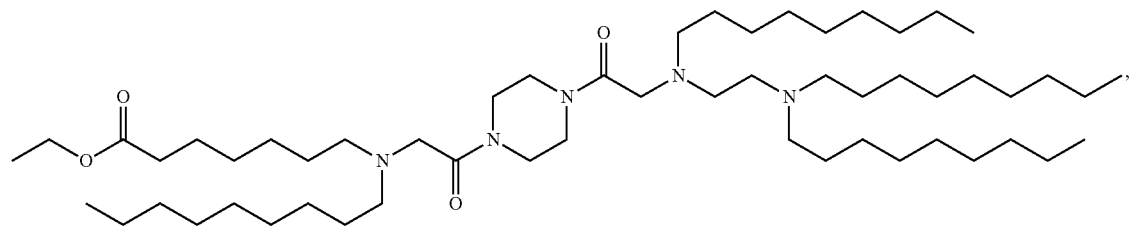
(Compound 286)
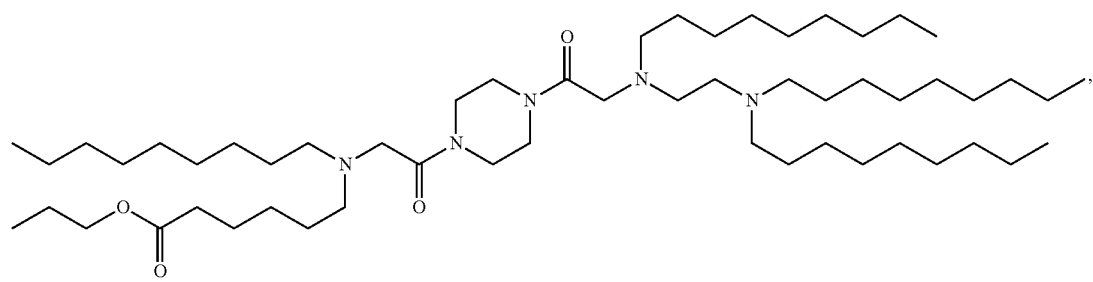

-continued
(Compound 287)
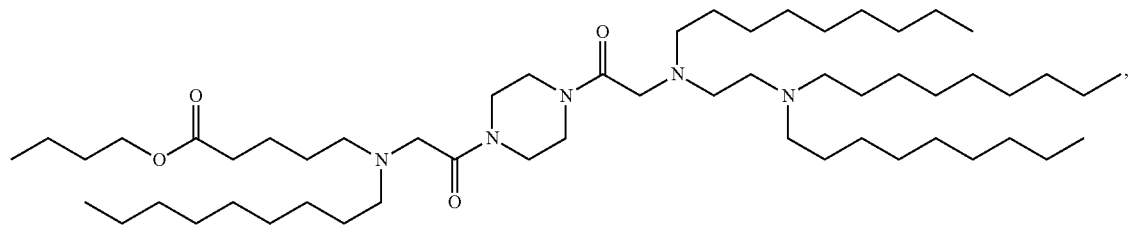
(Compound 288)
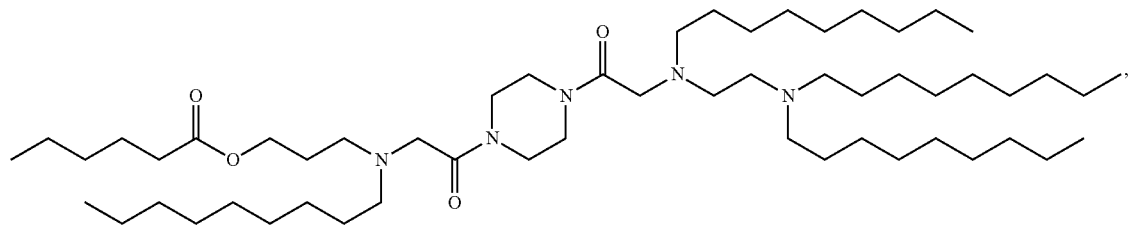
(Compound 289)
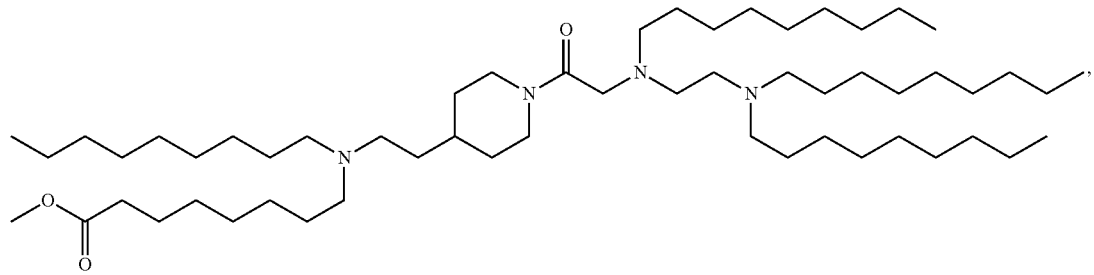
(Compound 290)
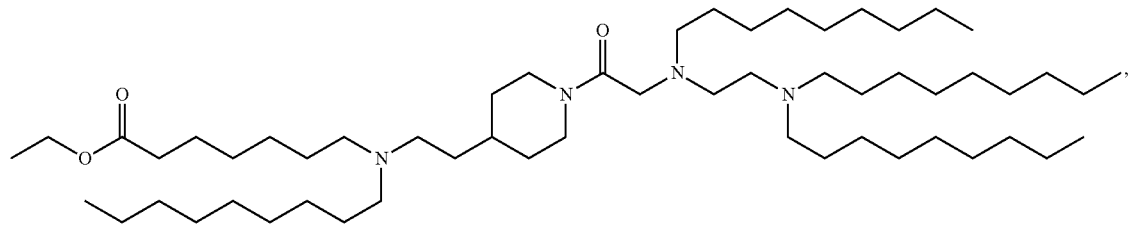
(Compound 291)
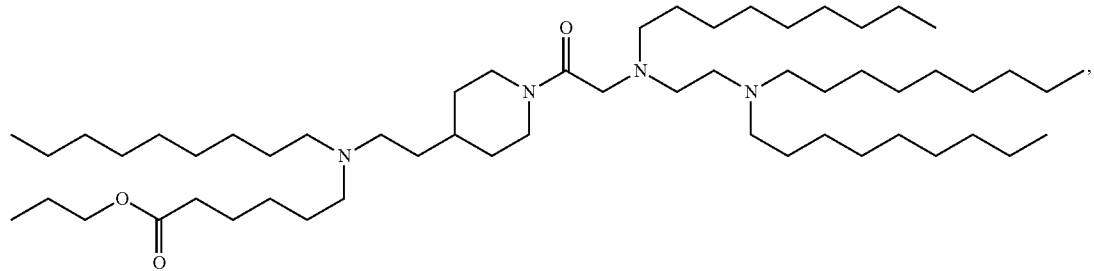
(Compound 292)
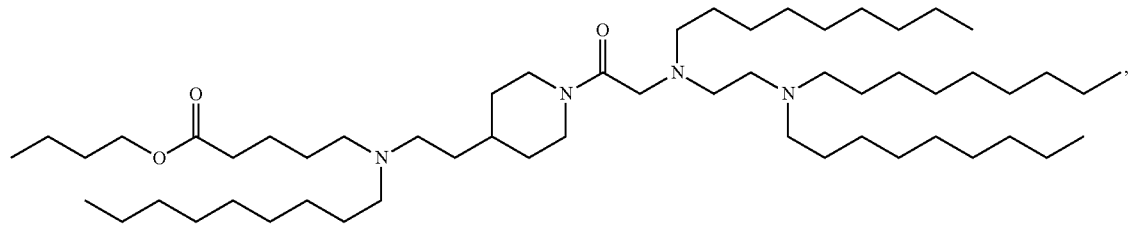

(Compound 293)
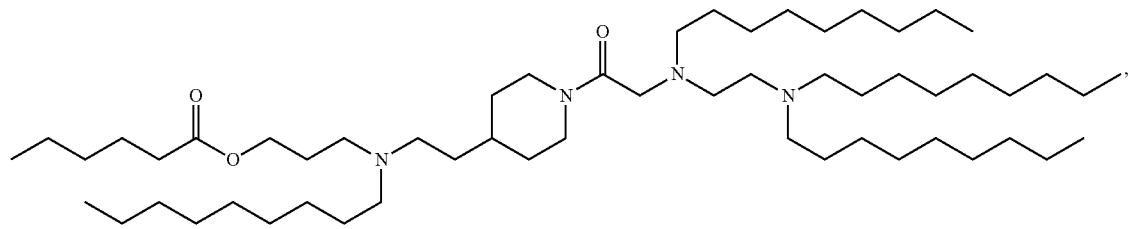
(Compound 294)
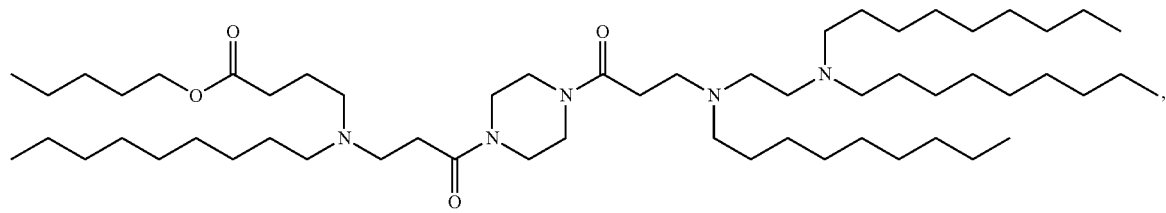
(Compound 295)
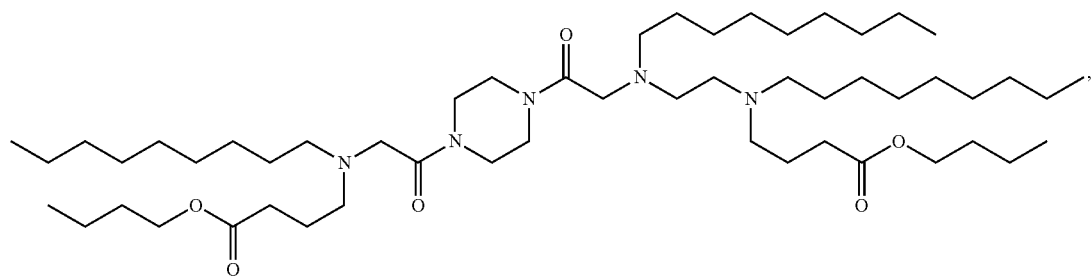
(Compound 296)
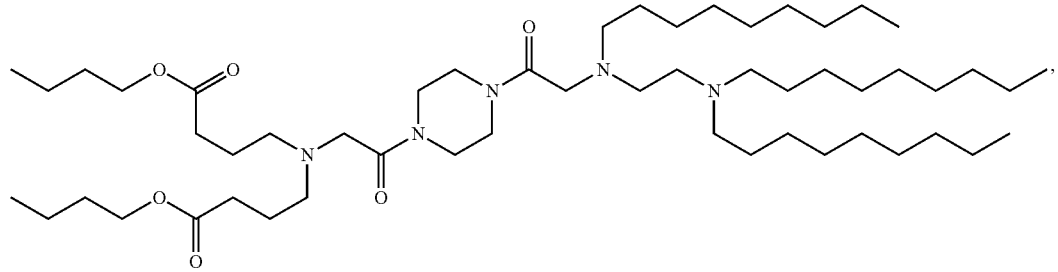
(Compound 297)
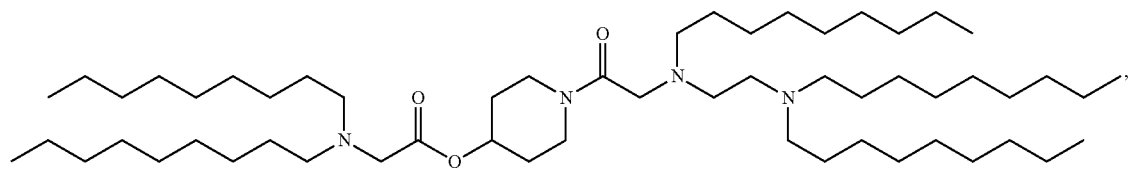
(Compound 298)
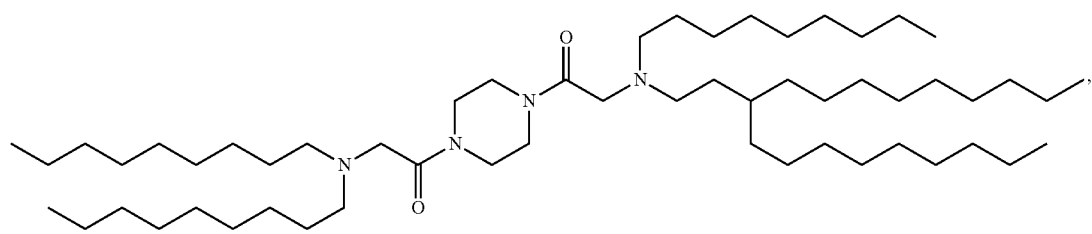

-continued
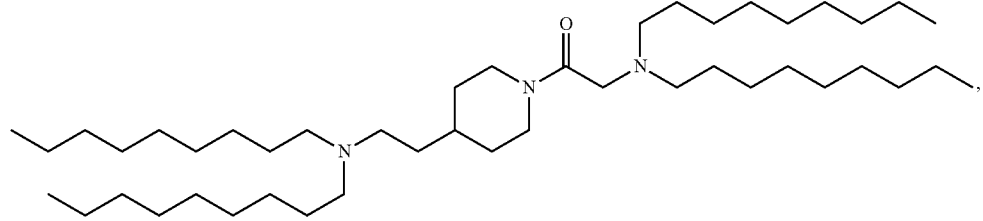
(Compound 300)
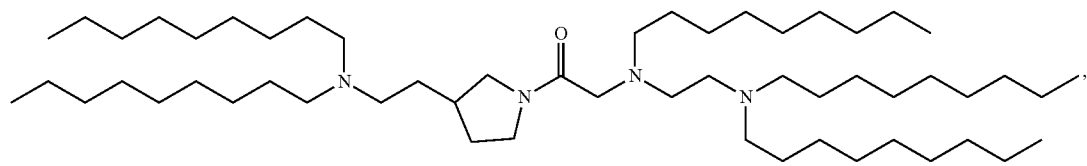
(Compound 301)
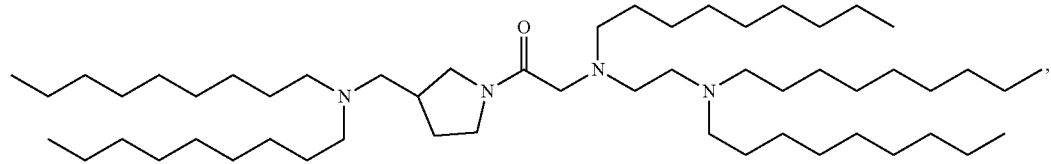
(Compound 302)
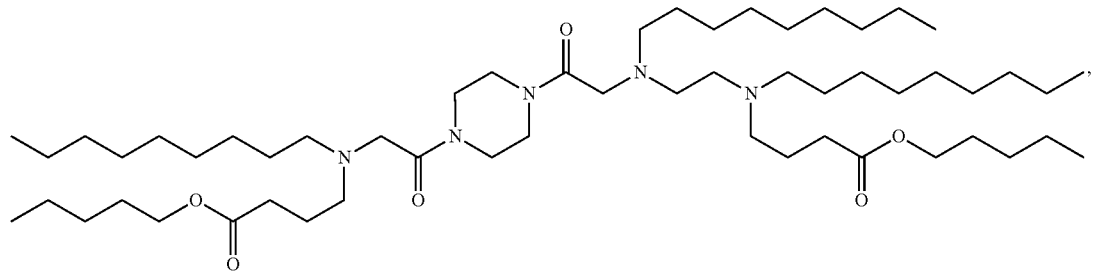
(Compound 303)
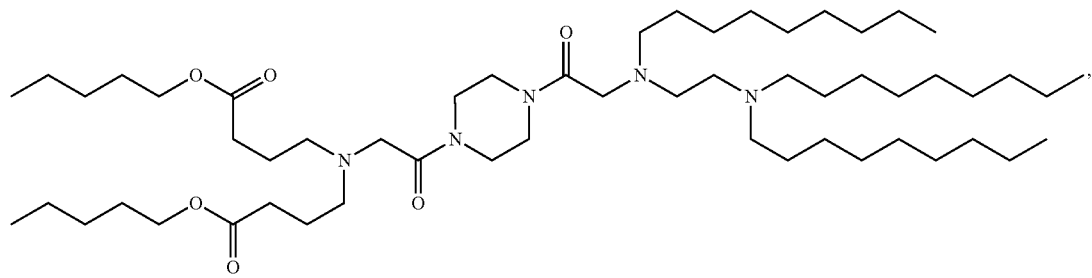
(Compound 304)
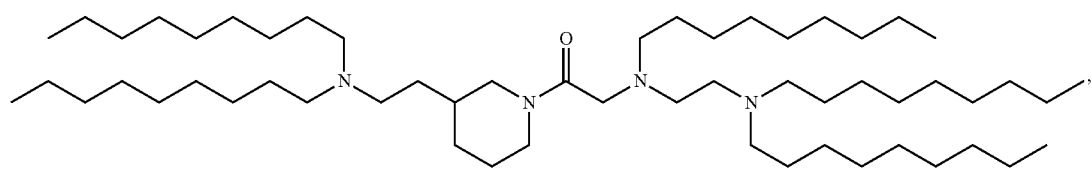
(Compound 305)
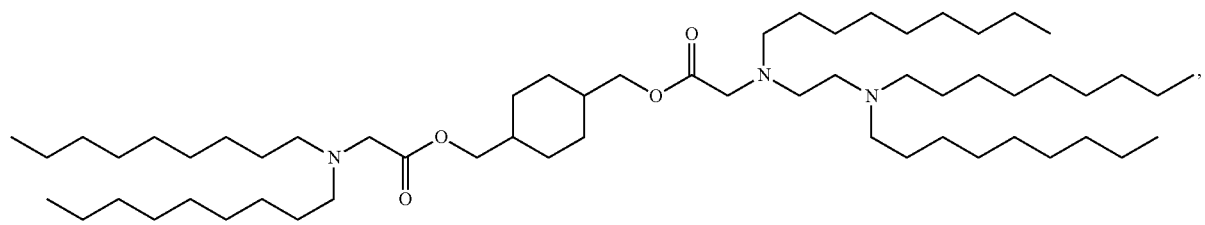
(Compound 306)

(Compound 307)
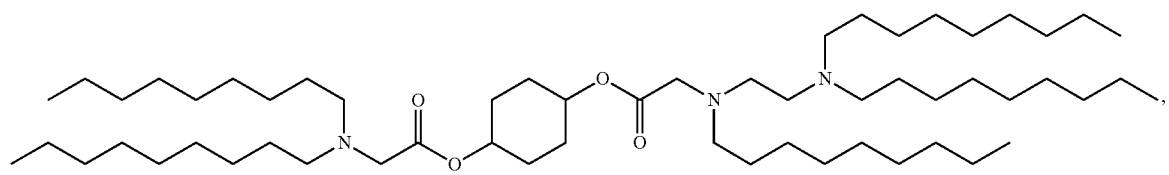
(Compound 308)
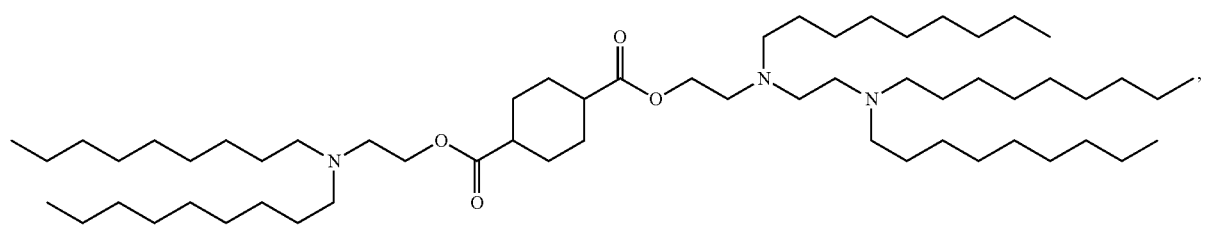
(Compound 310)
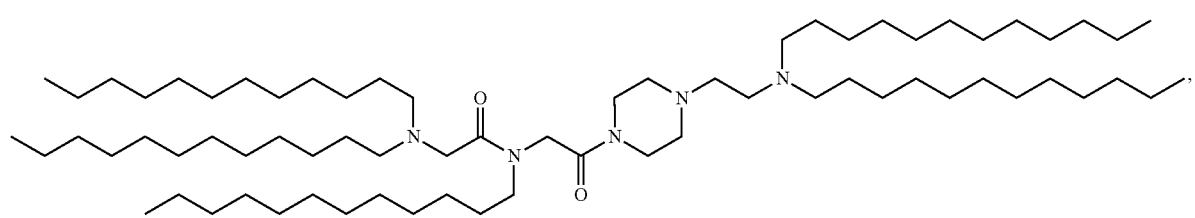
(Compound 311)
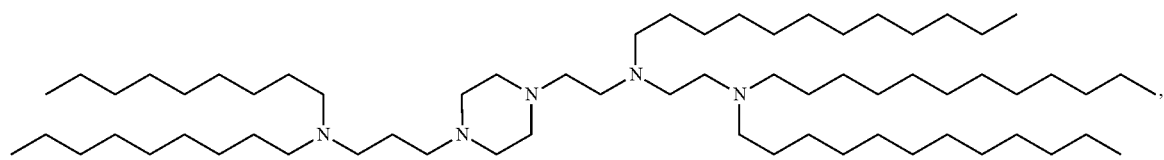
(Compound 312)
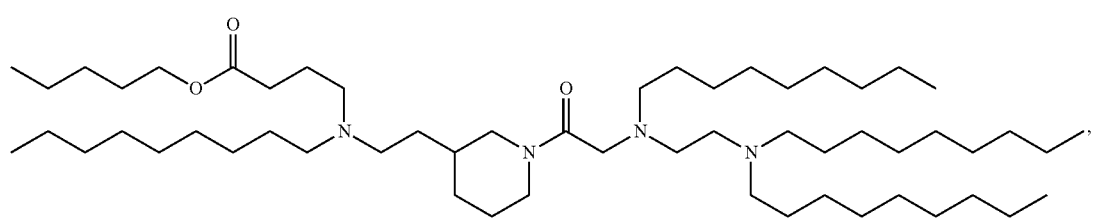
(Compound 313)
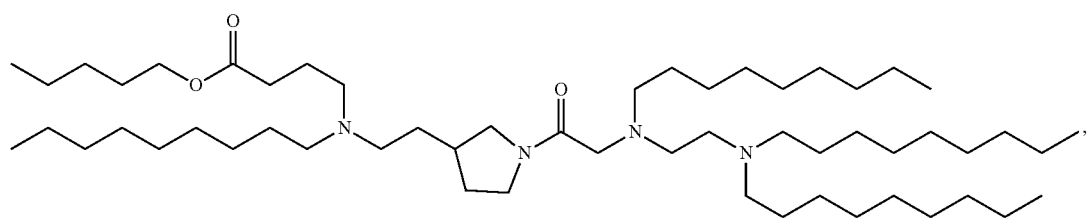
(Compound 314)
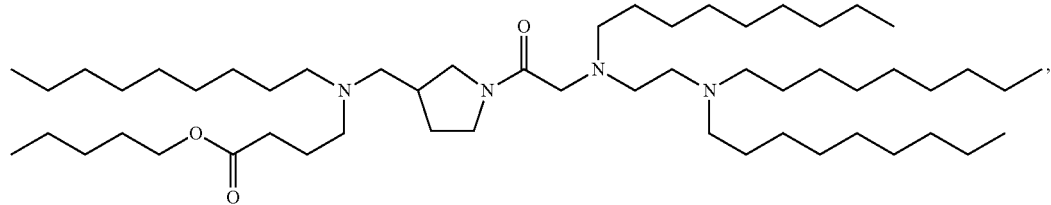

(Compound 315)
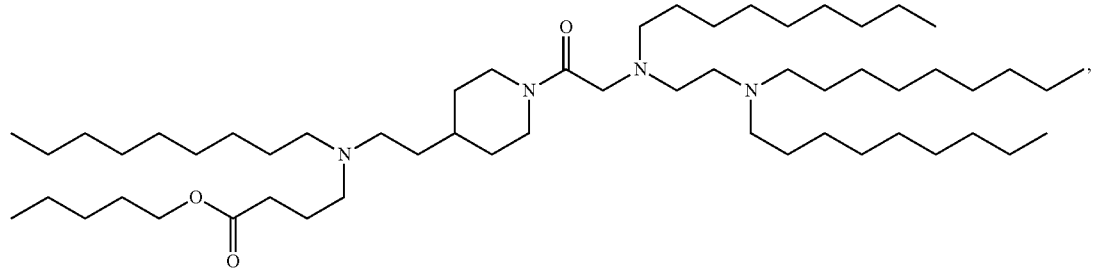
(Compound 316)
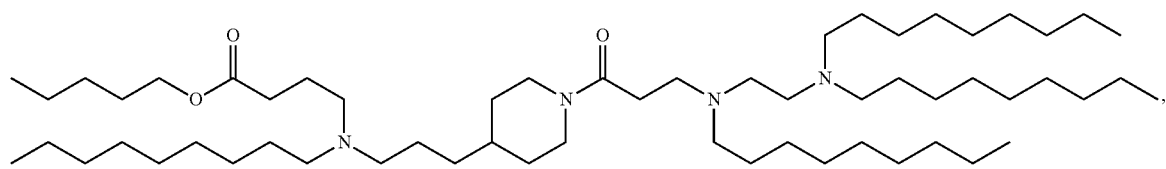
(Compound 317)
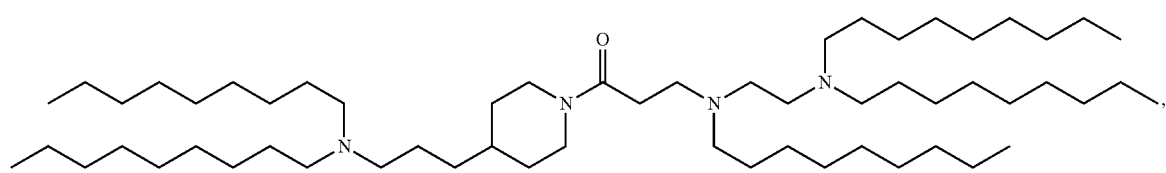
(Compound 318)
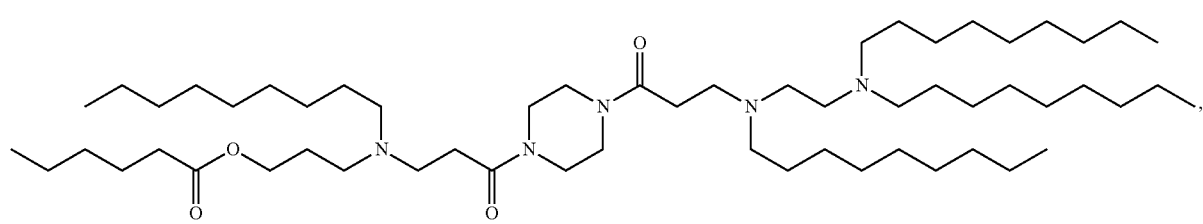
(Compound 319)
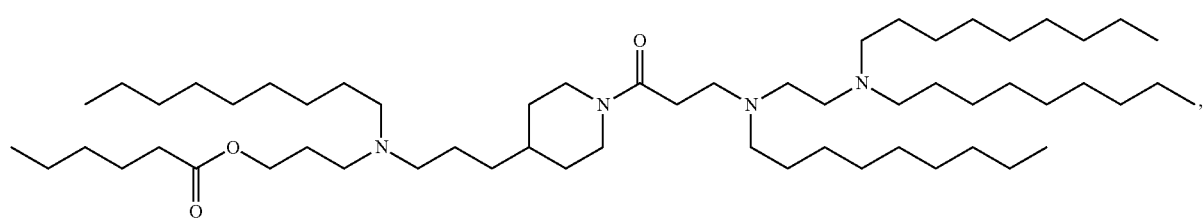
(Compound 320)
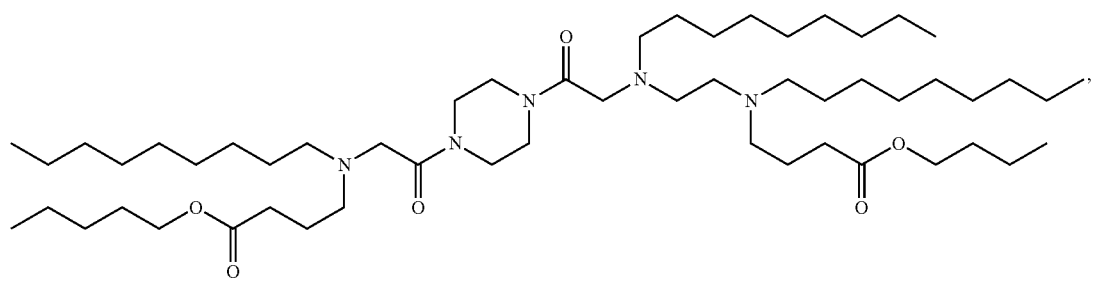

-continued
(Compound 321)
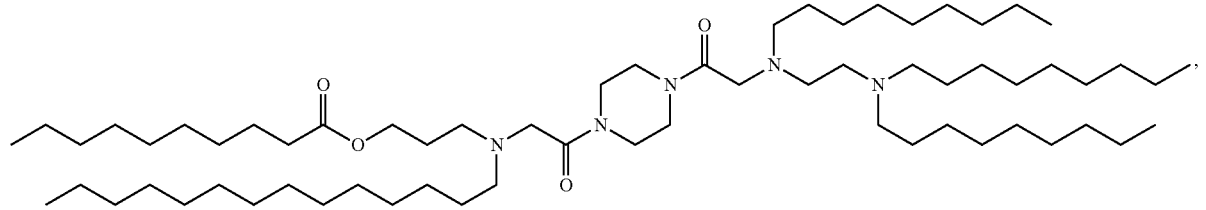
(Compound 322)
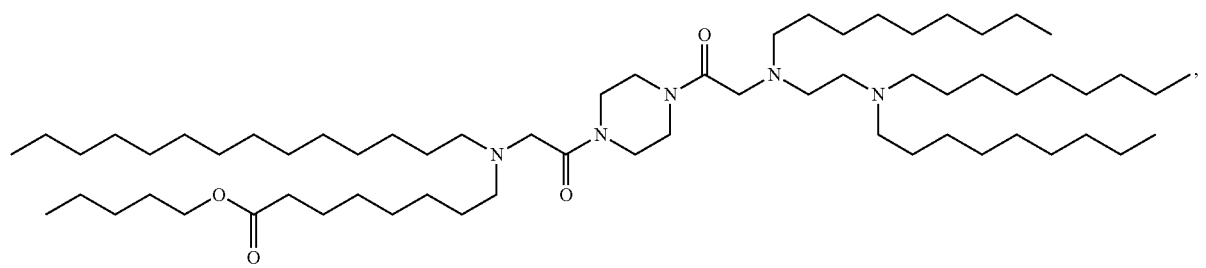
(Compound 323)
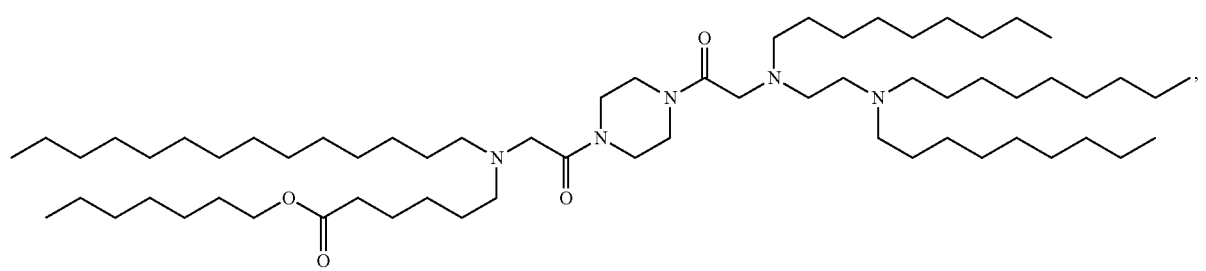
(Compound 324)
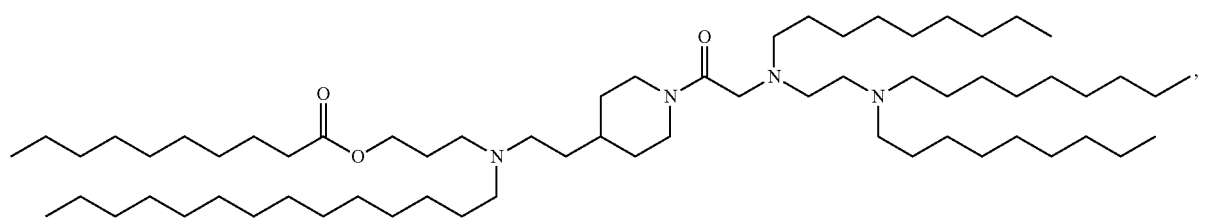
(Compound 325)
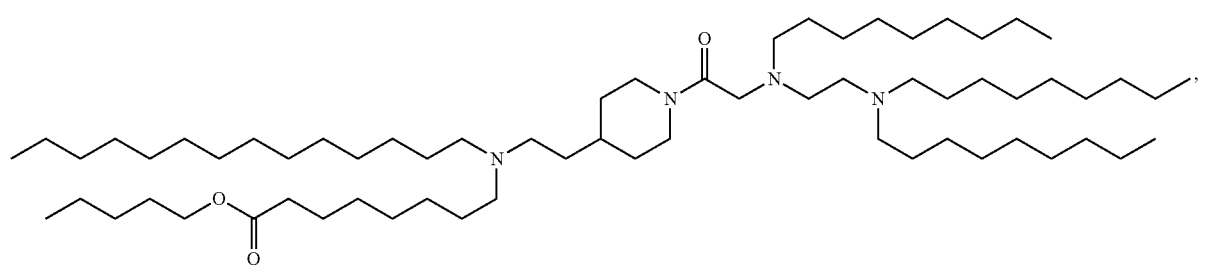
(Compound 326)
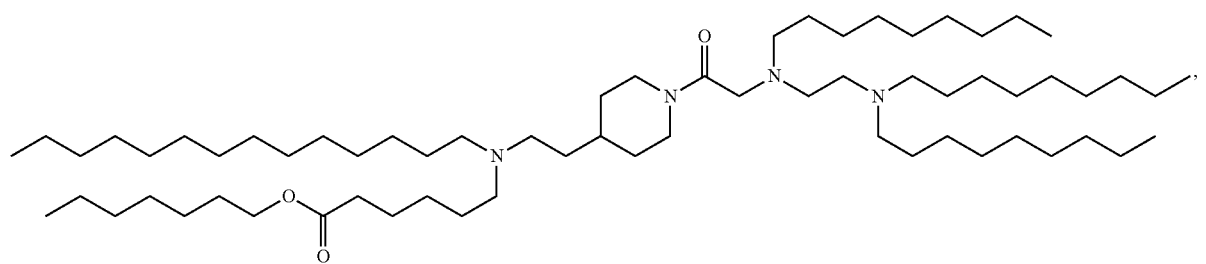

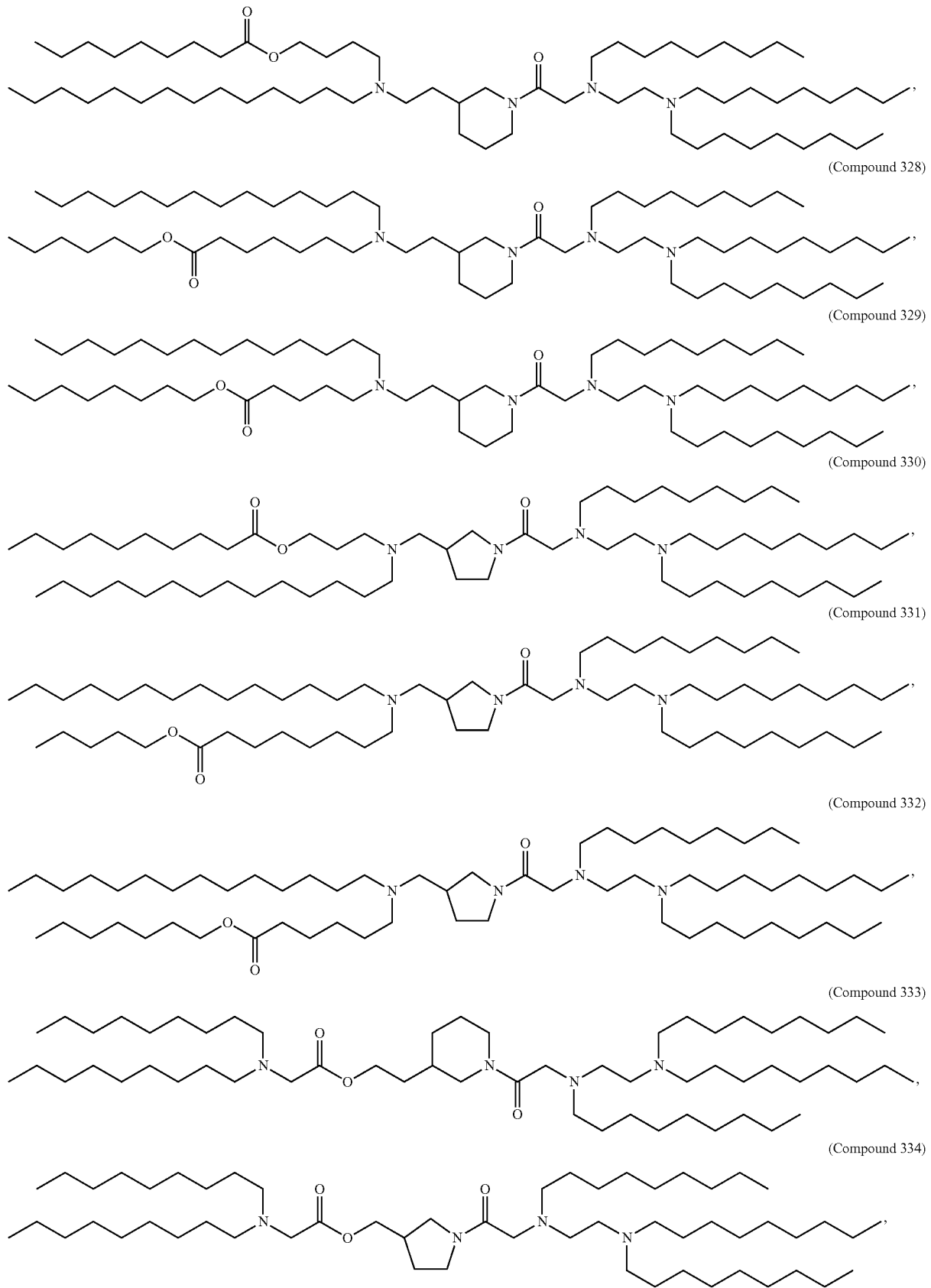

(Compound 335)
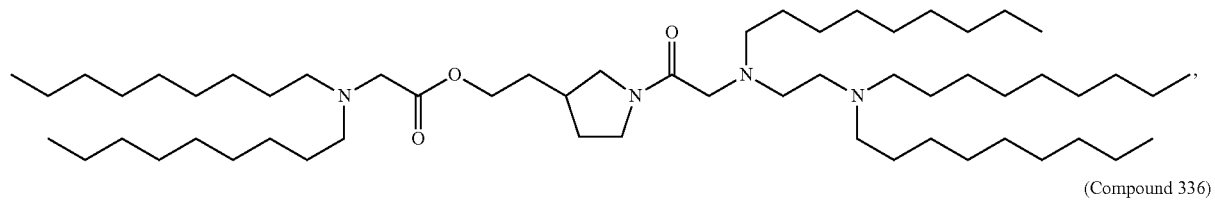
(Compound 336)
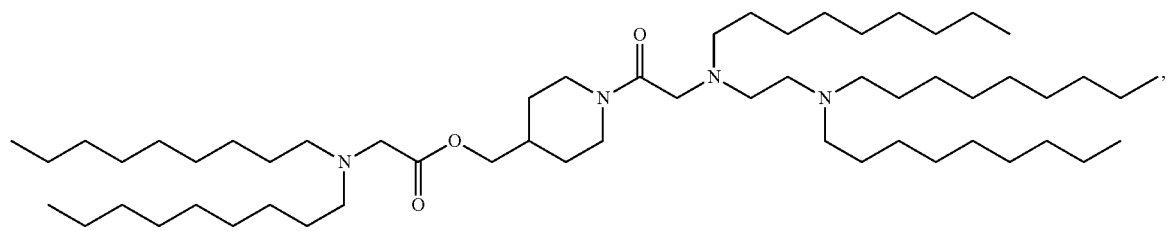
(Compound 337)
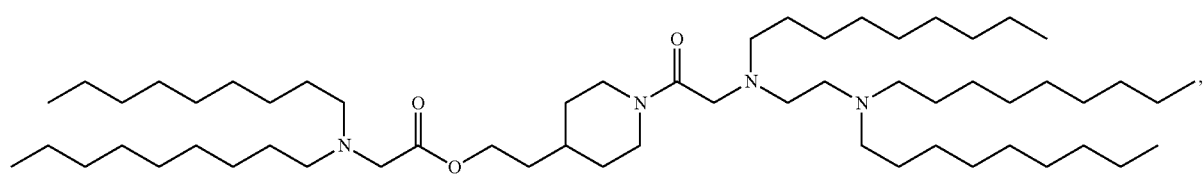
(Compound 338)
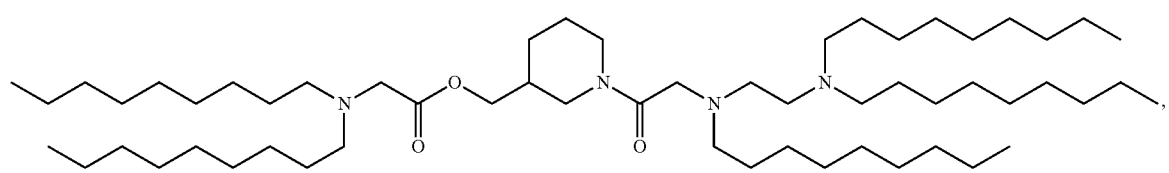
(Compound 339)
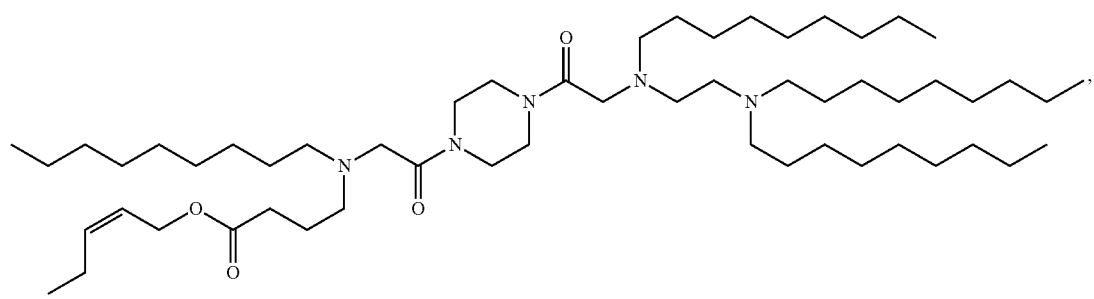
(Compound 340)
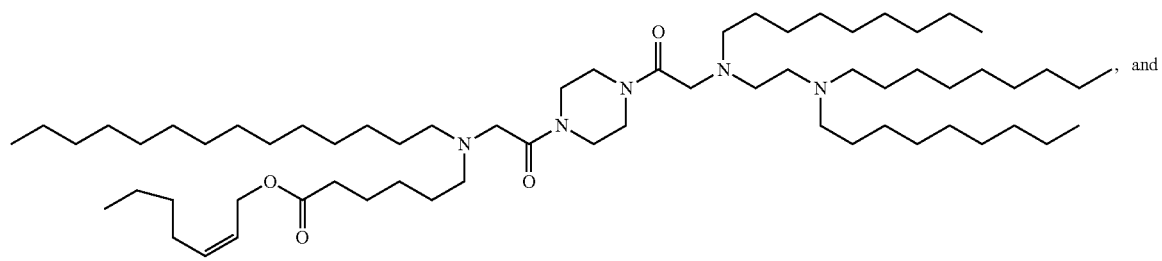
, and -continued

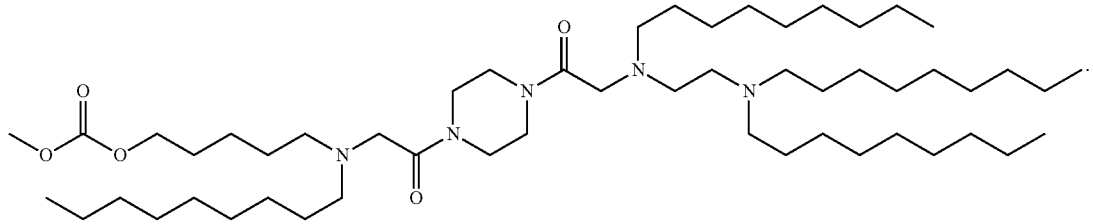

(Compound 341)

In some embodiments, the delivery agent comprises Compound 236.

In some embodiments, the delivery agent comprises a compound having the formula (IV)

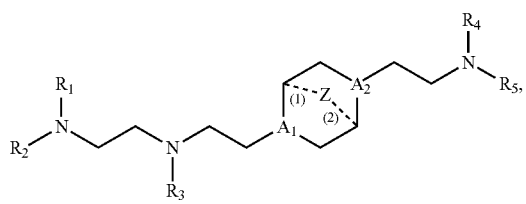

(IV)

or salts or stereoisomer thereof, wherein $A_1$ and $A_2$ are each independently selected from CH or N and at least one of $A_1$ and $A_2$ is N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{6-20}$ alkyl and $C_{6-20}$ alkenyl;

wherein when ring A is

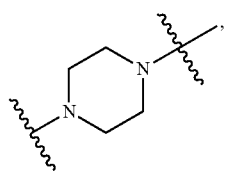 [SMILES: *N1CCN(*)CC1]

then i) $R_1$, $R_2$, $R_3$, $R_4$, and $R_5$ are the same, wherein $R_1$ is not $C_{12}$ alkyl, $C_{18}$ alkyl, or $C_{18}$ alkenyl;

ii) only one of $R_1$, $R_2$, $R_3$, $R_4$, and $R_5$ is selected from $C_{6-20}$ alkenyl;

iii) at least one of $R_1$, $R_2$, $R_3$, $R_4$, and $R_5$ have a different number of carbon atoms than at least one other of $R_1$, $R_2$, $R_3$, $R_4$, and $R_5$;

iv) $R_1$, $R_2$, and $R_3$ are selected from $C_{6-20}$ alkenyl, and $R_4$ and $R_5$ are selected from $C_{6-20}$ alkyl; or v) $R_1$, $R_2$, and $R_3$ are selected from $C_{6-20}$ alkyl, and $R_4$ and $R_5$ are selected from $C_{6-20}$ alkenyl.

In some embodiments, the compound is of formula (IVa):

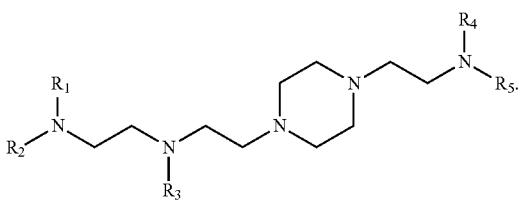

(IVa)

The compounds of Formula (IV) or (IVa) include one or more of the following features when applicable.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, $R_1$, $R_2$, $R_3$, $R_4$, and $R_5$ are the same, and are not $C_{12}$ alkyl, $C_{18}$ alkyl, or $C_{18}$ alkenyl. In some embodiments, $R_1$, $R_2$, $R_3$, $R_4$, and $R_5$ are the same and are $C_9$ alkyl or $C_{14}$ alkyl.

In some embodiments, only one of $R_1$, $R_2$, $R_3$, $R_4$, and $R_5$ is selected from $C_6$-20 alkenyl. In certain such embodiments, $R_1$, $R_2$, $R_3$, $R_4$, and $R_5$ have the same number of carbon atoms. In some embodiments, $R_4$ is selected from $C_{5-20}$ alkenyl. For example, $R_4$ may be $C_{12}$ alkenyl or $C_{18}$ alkenyl.

In some embodiments, at least one of $R_1$, $R_2$, $R_3$, $R_4$, and $R_5$ have a different number of carbon atoms than at least one other of $R_1$, $R_2$, $R_3$, $R_4$, and $R_5$.

In certain embodiments, $R_1$, $R_2$, and $R_3$ are selected from $C_{6-20}$ alkenyl, and $R_4$ and $R_5$ are selected from $C_{6-20}$ alkyl. In other embodiments, $R_1$, $R_2$, and $R_3$ are selected from $C_{6-20}$ alkyl, and $R_4$ and $R_5$ are selected from $C_{6-20}$ alkenyl.

In some embodiments, $R_1$, $R_2$, and $R_3$ have the same number of carbon atoms, and/or $R_4$ and $R_5$ have the same number of carbon atoms. For example, $R_1$, $R_2$, and $R_3$, or $R_4$ and $R_5$, may have 6, 8, 9, 12, 14, or 18 carbon atoms. In some embodiments, $R_1$, $R_2$, and $R_3$, or $R_4$ and $R_5$, are $C_{18}$ alkenyl (e.g., linoleyl). In some embodiments, $R_1$, $R_2$, and $R_3$, or $R_4$ and $R_5$, are alkyl groups including 6, 8, 9, 12, or 14 carbon atoms.

In some embodiments, $R_1$ has a different number of carbon atoms than $R_2$, $R_3$, $R_4$, and $R_5$. In other embodiments, $R_3$ has a different number of carbon atoms than $R_1$, $R_2$, $R_4$, and $R_5$. In further embodiments, $R_4$ has a different number of carbon atoms than $R_1$, $R_2$, $R_3$, and $R_5$.

In some embodiments, the compound is selected from the group consisting of:
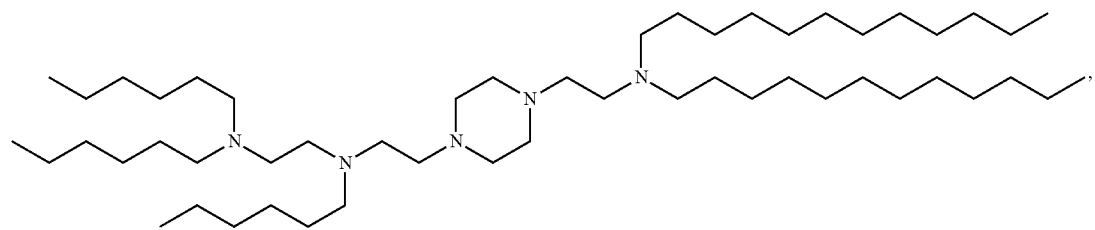
(Compound 249)
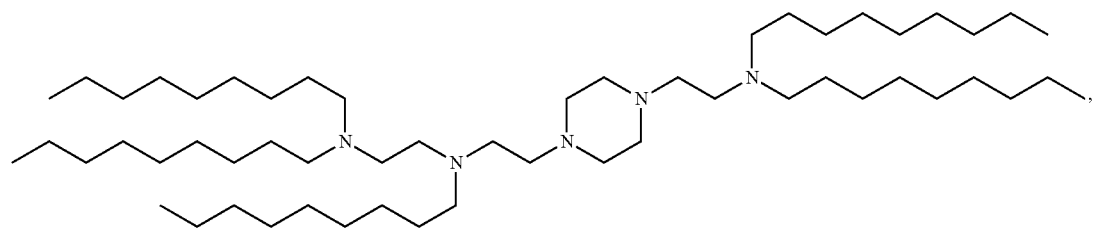
(Compound 250)
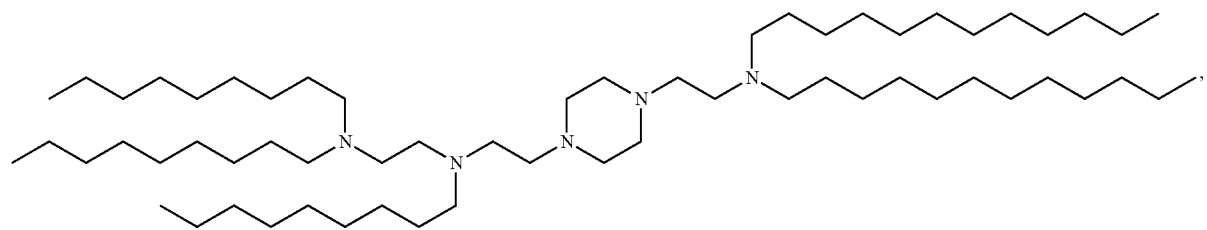
(Compound 251)
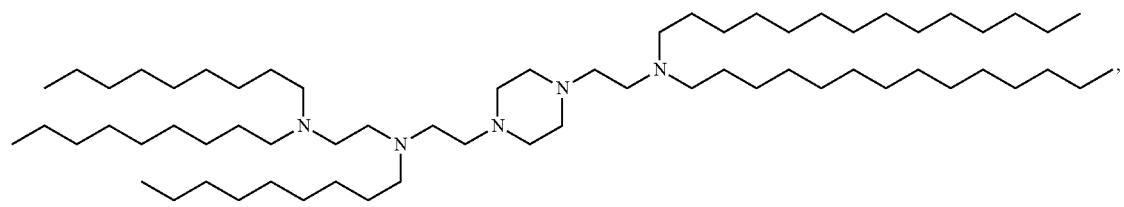
(Compound 252)
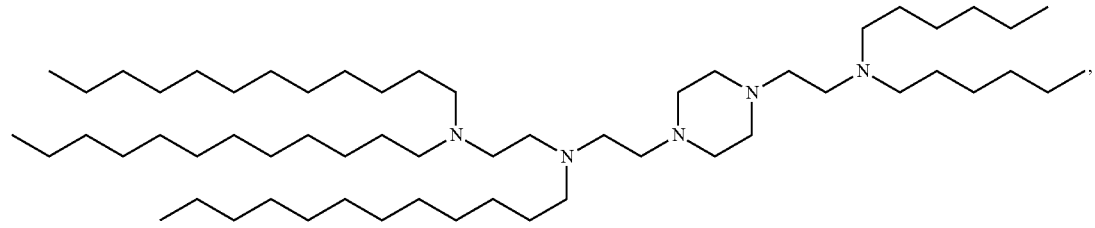
(Compound 253)
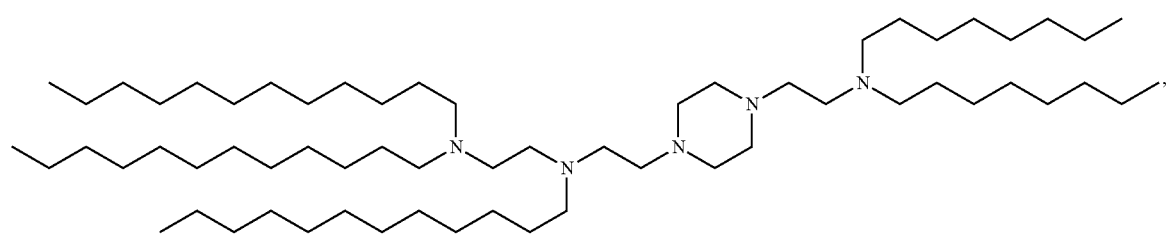
(Compound 254)

(Compound 255)
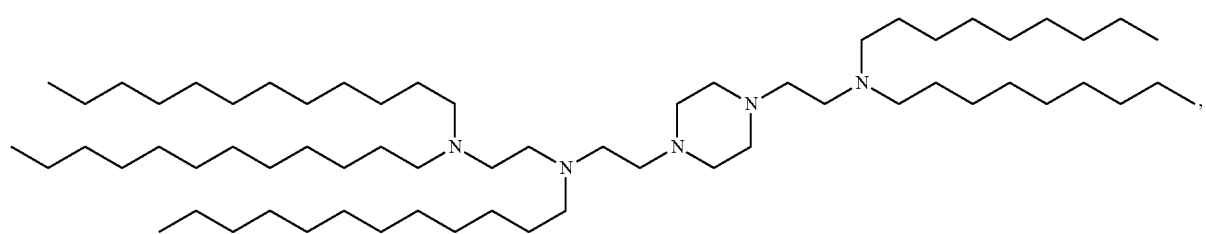
(Compound 256)
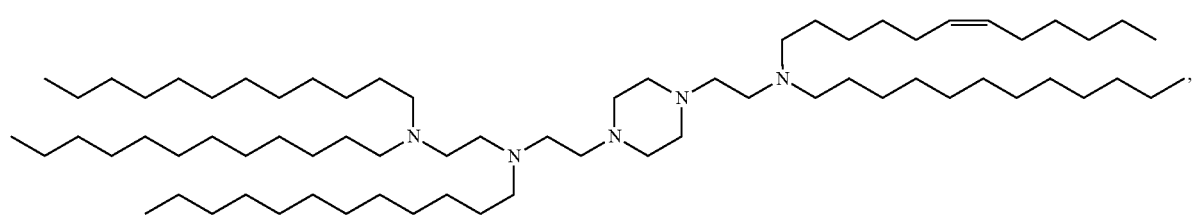
(Compound 257)
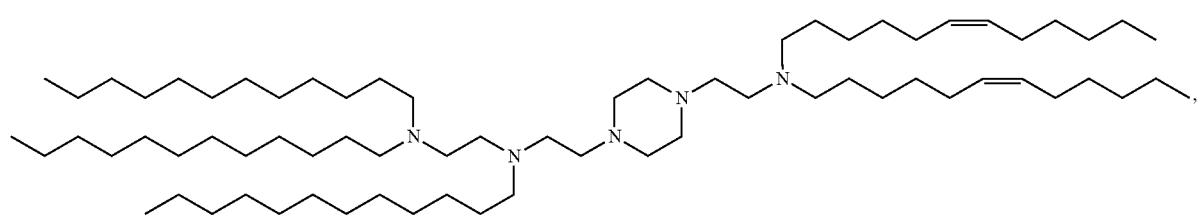
(Compound 258)
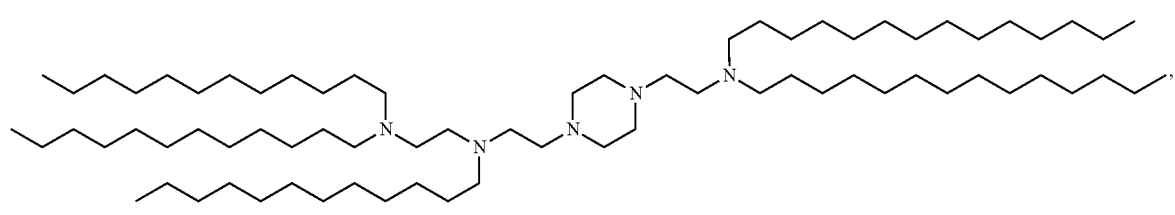
(Compound 259)
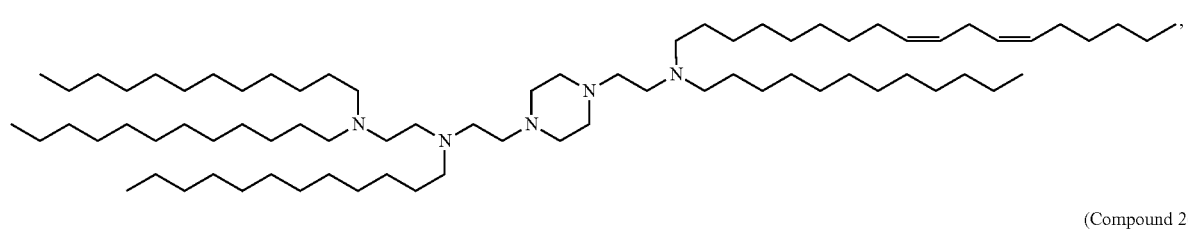
(Compound 260)
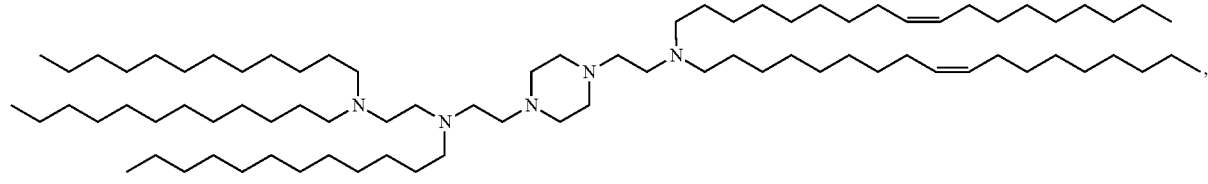
(Compound 261)
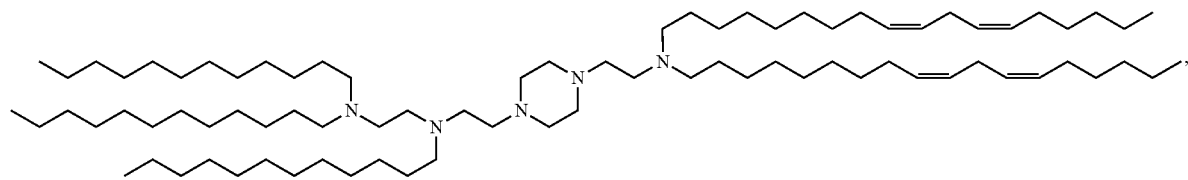

(Compound 262)

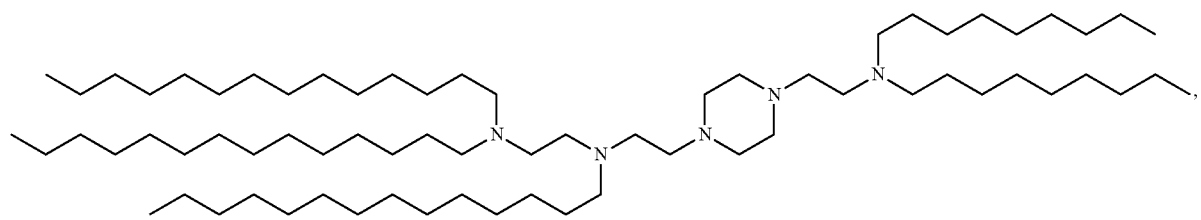

(Compound 263)

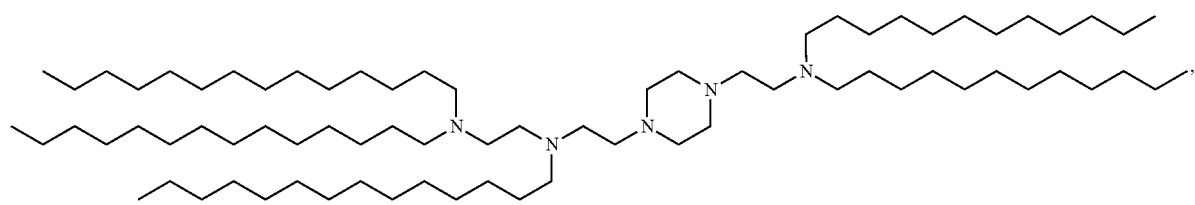

(Compound 264)

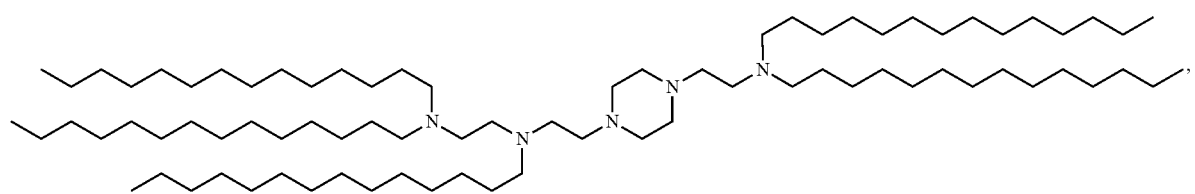

(Compound 265)

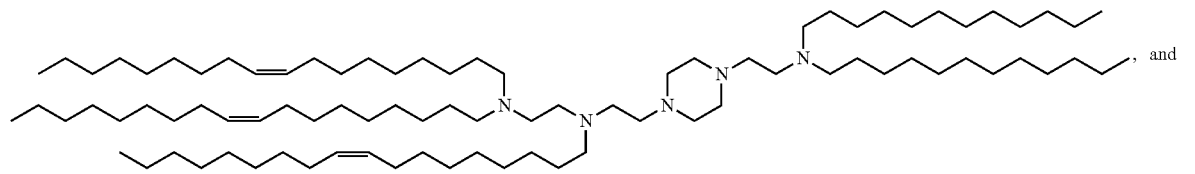, and (Compound 266)

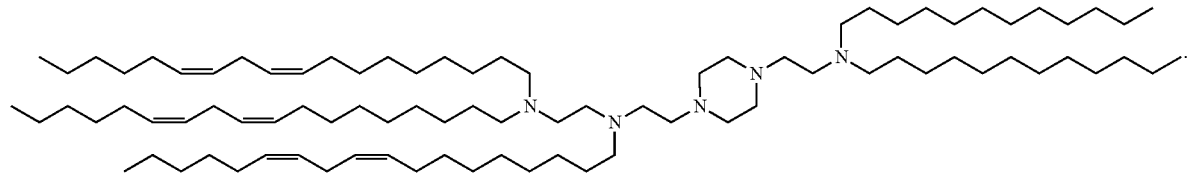.

In other embodiments, the delivery agent comprises a compound having the formula (V)

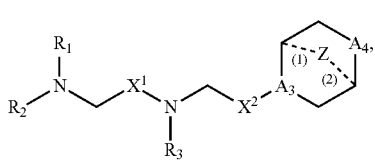

or salts or stereoisomers thereof, in which $A_3$ is CH or N;

$A_4$ is $CH_2$ or NH; and at least one of $A_3$ and $A_4$ is N or NH;

Z is $CH_2$ or absent wherein when Z is $CH_2$, the dashed lines (1) and (2) each represent a single bond; and when Z is absent, the dashed lines (1) and (2) are both absent;

$R_1$, $R_2$, and $R_3$ are independently selected from the group consisting of $C_{5-20}$ alkyl, $C_{5-20}$ alkenyl, —R"MR', —R*YR", —YR", and —R*OR";

each M is independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$X^1$ and $X^2$ are independently selected from the group consisting of —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;
each R' is independently selected from the group consisting of $C_{1-12}$ alkyl, $C_{2-12}$ alkenyl, and H; and
each R'' is independently selected from the group consisting of $C_{3-12}$ alkyl and $C_{3-12}$ alkenyl.

In some embodiments, the compound is of formula (Va):

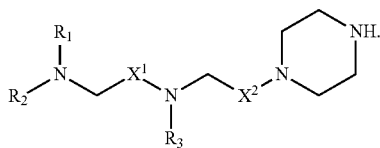

(Va)

The compounds of Formula (V) or (Va) include one or more of the following features when applicable.

In some embodiments, Z is $CH_2$.
In some embodiments, Z is absent.

In some embodiments, at least one of $A_3$ and $A_4$ is N or NH.
In some embodiments, $A_3$ is N and $A_4$ is NH.
In some embodiments, $A_3$ is N and $A_4$ is $CH_2$.
In some embodiments, $A_3$ is CH and $A_4$ is NH.
In some embodiments, at least one of $X^1$ and $X^2$ is not —$CH_2$—. For example, in certain embodiments, $X^1$ is not —$CH_2$—. In some embodiments, at least one of $X^1$ and $X^2$ is —C(O)—.

In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.

In some embodiments, $R_1$, $R_2$, and $R_3$ are independently selected from the group consisting of $C_{5-20}$ alkyl and $C_{5-20}$ alkenyl. In some embodiments, $R_1$, $R_2$, and $R_3$ are the same. In certain embodiments, $R_1$, $R_2$, and $R_3$ are $C_6$, $C_9$, $C_{12}$, or $C_{14}$ alkyl. In other embodiments, $R_1$, $R_2$, and $R_3$ are $C_{18}$ alkenyl. For example, $R_1$, $R_2$, and $R_3$ may be linoleyl.

In some embodiments, the compound is selected from the group consisting of:

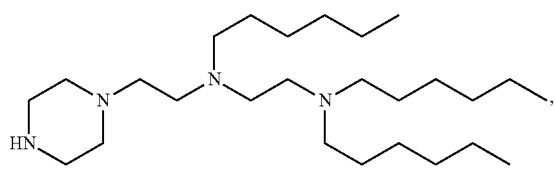

(Compound 267)

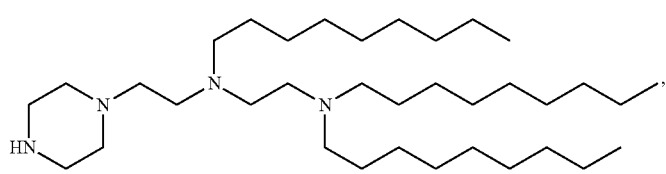

(Compound 268)

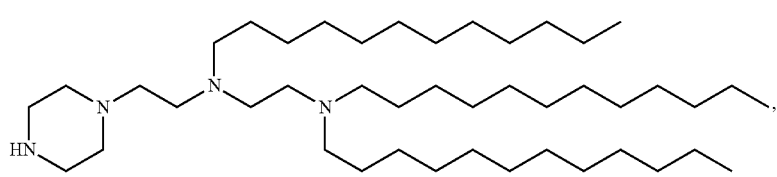

(Compound 269)

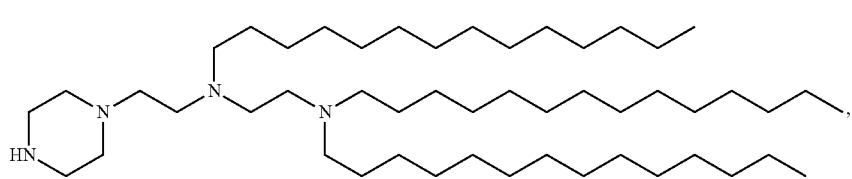

(Compound 270)

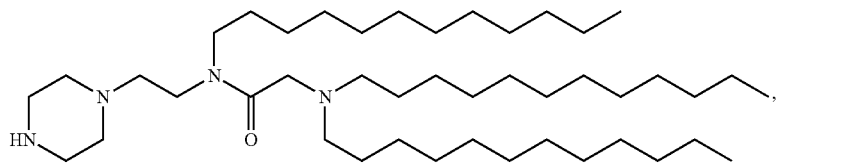

(Compound 271)

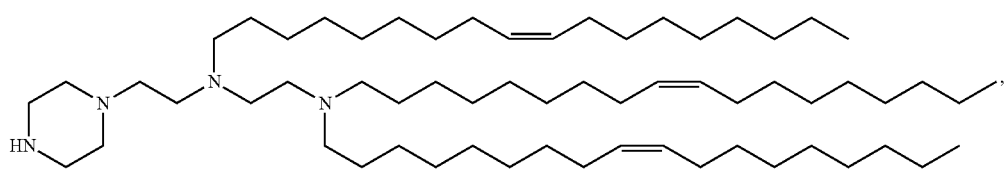

(Compound 272)

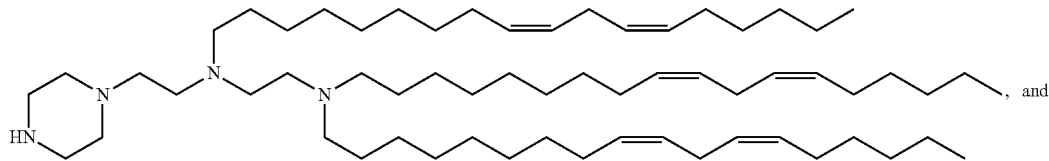

(Compound 273)

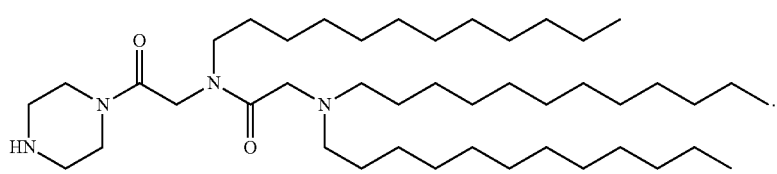

, and (Compound 309)

In other embodiments, the delivery agent comprises a compound having the formula (VI):

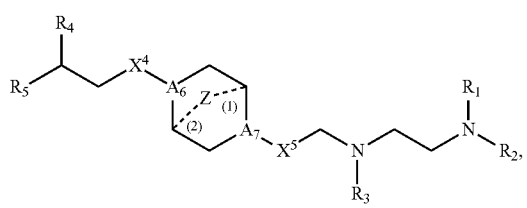

(VI)

or salts or stereoisomers thereof, in which
- $A_6$ and $A_7$ are each independently selected from CH or N, wherein at least one of $A_6$ and $A_7$ is N;
- Z is $CH_2$ or absent wherein when Z is $CH_2$, the dashed lines (1) and (2) each represent a single bond; and when Z is absent, the dashed lines (1) and (2) are both absent;
- $X^4$ and $X^5$ are independently selected from the group consisting of —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;
- $R_1$, $R_2$, $R_3$, $R_4$, and $R_5$ each are independently selected from the group consisting of $C_{5-20}$ alkyl, $C_{5-20}$ alkenyl, —R"MR', —R*YR", —YR", and —R*OR";
- each M is independently selected from the group consisting of —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;
- each Y is independently a $C_{3-6}$ carbocycle;
- each R* is independently selected from the group consisting of $C_{1-12}$ alkyl and $C_{2-12}$ alkenyl;
- each R is independently selected from the group consisting of $C_{1-3}$ alkyl and a $C_{3-6}$ carbocycle;
- each R' is independently selected from the group consisting of $C_{1-12}$ alkyl, $C_{2-12}$ alkenyl, and H; and
- each R" is independently selected from the group consisting of $C_{3-12}$ alkyl and $C_{3-12}$ alkenyl.

In some embodiments, $R_1$, $R_2$, $R_3$, $R_4$, and $R_5$ each are independently selected from the group consisting of $C_{6-20}$ alkyl and $C_{6-20}$ alkenyl.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is $C_{9-12}$ alkyl. In certain embodiments, each of $R_1$, $R_2$, $R_3$, $R_4$, and $R_5$ independently is $C_9$, $C_{12}$ or $C_{14}$ alkyl. In certain embodiments, each of $R_1$, $R_2$, $R_3$, $R_4$, and $R_5$ is $C_9$ alkyl.

In some embodiments, $A_6$ is N and $A_7$ is N. In some embodiments, $A_6$ is CH and $A_7$ is N.

In some embodiments, $X^4$ is —$CH_2$— and $X^5$ is —C(O)—. In some embodiments, $X^4$ and $X^5$ are —C(O)—.

In some embodiments, when $A_6$ is N and $A_7$ is N, at least one of $X^4$ and $X^5$ is not —$CH_2$—, e.g., at least one of $X^4$ and $X^5$ is —C(O)—. In some embodiments, when A6 is N and $A_7$ is N, at least one of $R_1$, $R_2$, $R_3$, $R_4$, and $R_5$ is —R"MR'.

In some embodiments, at least one of $R_1$, $R_2$, $R_3$, $R_4$, and $R_5$ is not —R"MR'.

In some embodiments, the compound is (Compound 299)

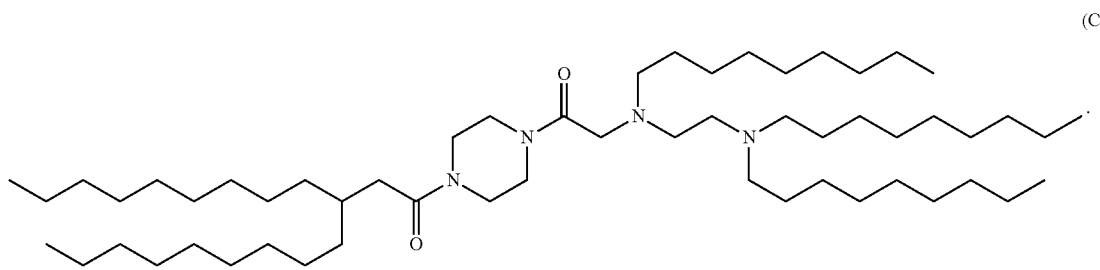

In other embodiments, the delivery agent comprises a compound having the formula:

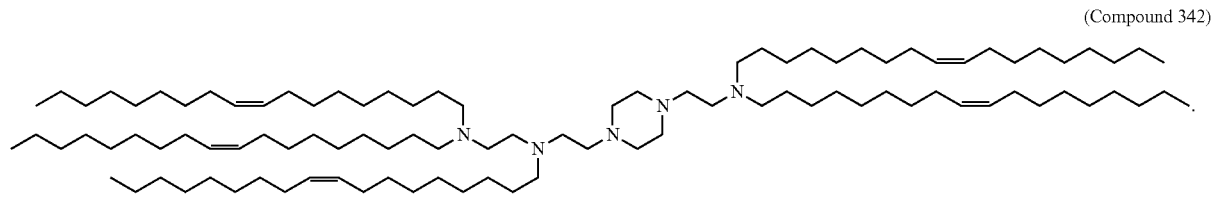 [SMILES: CCCCCCCC/C=C\CCCCCCCCN(CCCCCCCC/C=C\CCCCCCCC)CCN(CCCCCCCC/C=C\CCCCCCCC)CCN1CCN(CCN(CCCCCCCC/C=C\CCCCCCCC)CCCCCCCC/C=C\CCCCCCCC)CC1 ; "."]

(Compound 342)

Amine moieties of the lipid compounds disclosed herein can be protonated under certain conditions. For example, the central amine moiety of a lipid according to formula (I) is typically protonated (i.e., positively charged) at a pH below the pKa of the amino moiety and is substantially not charged at a pH above the pKa. Such lipids can be referred to as ionizable amino lipids.

In one specific embodiment, the ionizable amino lipid is Compound 18. In another embodiment, the ionizable amino lipid is Compound 236.

In some embodiments, the amount the ionizable amino lipid, e.g., compound of formula (I) ranges from about 1 mol % to 99 mol % in the lipid composition.

In one embodiment, the amount of the ionizable amino lipid, e.g., compound of formula (I), is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 mol % in the lipid composition.

In one embodiment, the amount of the ionizable amino lipid, e.g., the compound of formula (I), ranges from about 30 mol % to about 70 mol %, from about 35 mol % to about 65 mol %, from about 40 mol % to about 60 mol %, and from about 45 mol % to about 55 mol % in the lipid composition.

In one specific embodiment, the amount of the ionizable amino lipid, e.g., compound of formula (I), is about 50 mol % in the lipid composition.

In addition to the ionizable amino lipid disclosed herein, e.g., compound of formula (I), the lipid composition of the pharmaceutical compositions disclosed herein can comprise additional components such as phospholipids, structural lipids, PEG-lipids, and any combination thereof.

b. Additional Components in the Lipid Composition
(i) Phospholipids

The lipid composition of the pharmaceutical composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

Examples of phospholipids include, but are not limited to, the following:
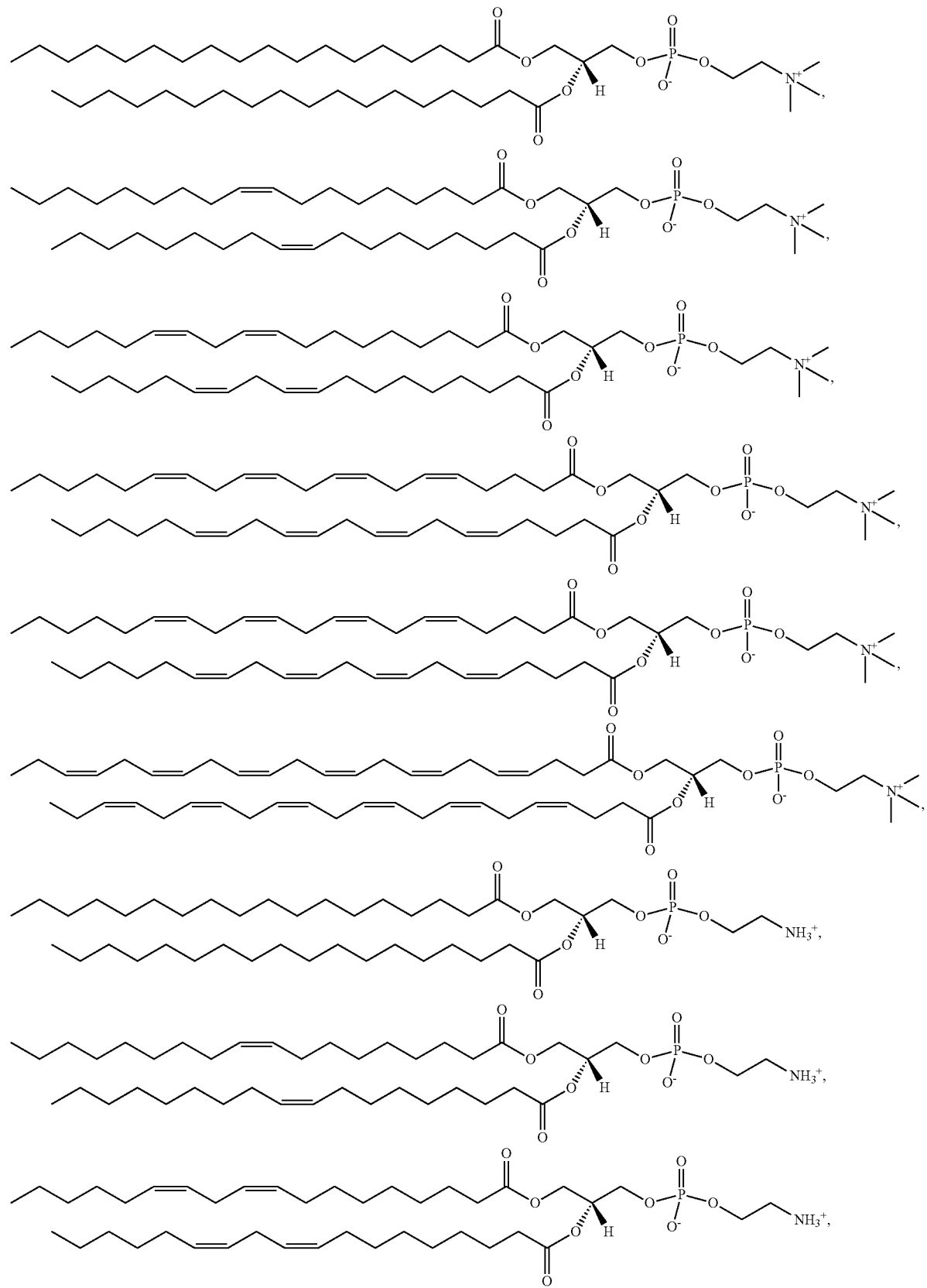

-continued

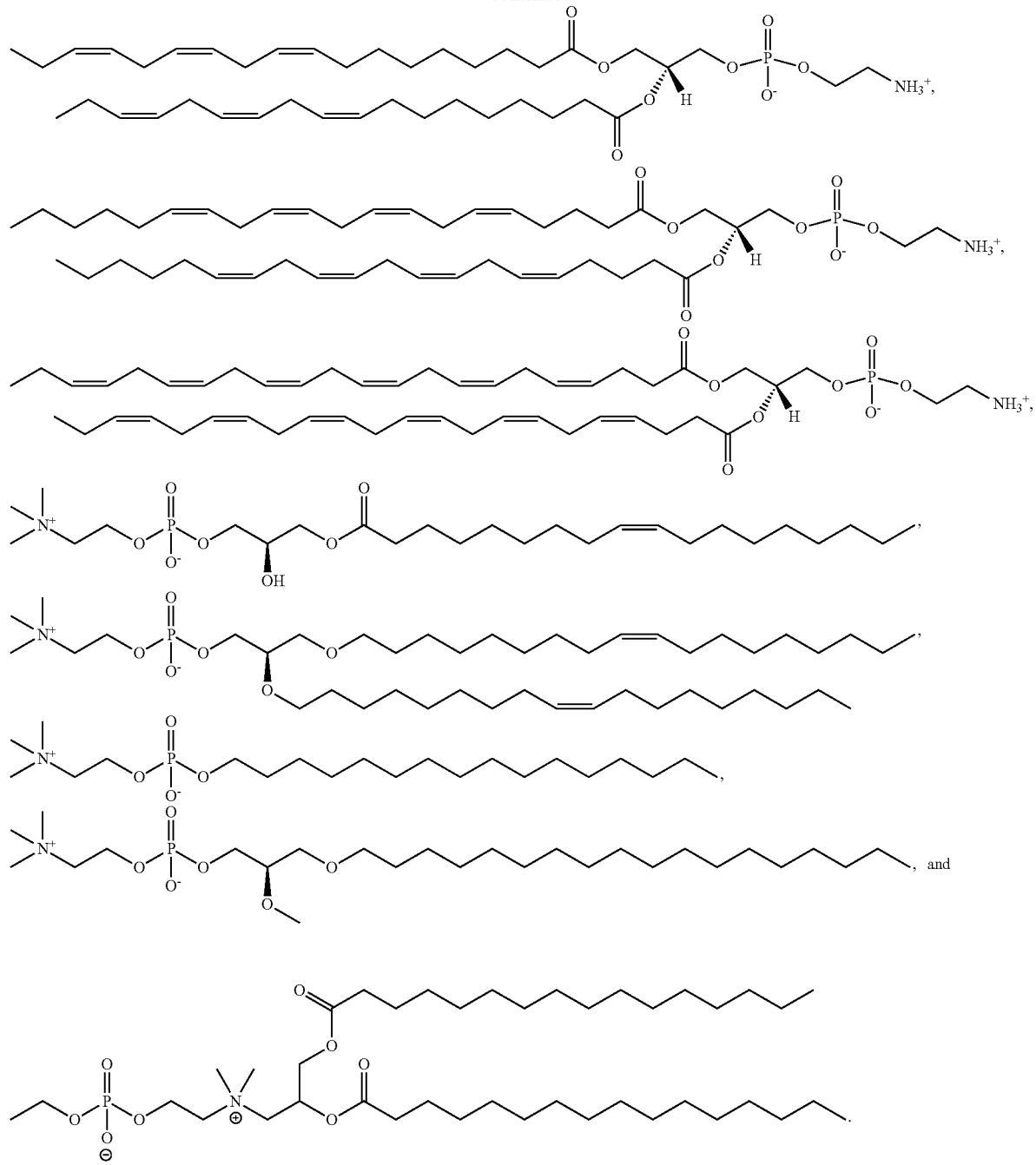

In certain embodiments, a phospholipid useful or potentially useful in the present invention is an analog or variant of DSPC. In certain embodiments, a phospholipid useful or potentially useful in the present invention is a compound of Formula (IX):

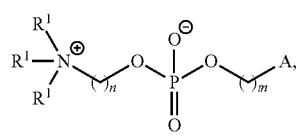

or a salt thereof, wherein:

each $R_1$ is independently optionally substituted alkyl; or optionally two $R_1$ are joined together with the intervening atoms to form optionally substituted monocyclic carbocyclyl or optionally substituted monocyclic heterocyclyl; or optionally three R' are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2,3,4, 5, 6, 7, 8, 9, or 10;

A is of the formula:

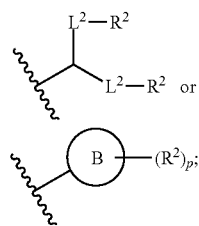

each instance of L² is independently a bond or optionally substituted C$_{1-6}$ alkylene, wherein one methylene unit of the optionally substituted C$_{1-6}$ alkylene is optionally replaced with —O—, —N(R$^N$)—, —S—, —C(O)—, —C(O)N(R$^N$)—, —NR$^N$C(O)—, —C(O)O—, —OC(O)—, —OC(O)O—, —OC(O)N(R$^N$)—, —NR$^N$C(O)O—, or —NR$^N$C(O)N(R$^N$)—;

each instance of R² is independently optionally substituted C$_{1-30}$ alkyl, optionally substituted C$_{1-30}$ alkenyl, or optionally substituted C$_{1-30}$ alkynyl; optionally wherein one or more methylene units of R² are independently replaced with optionally substituted carbocyclylene, optionally substituted heterocyclylene, optionally substituted arylene, optionally substituted heteroarylene, —N(R$^N$)—, —O—, —S—, —C(O)—, —C(O)N(R$^N$)—, —NR$^N$C(O)—, —NR$^N$C(O)N(R$^N$)—, —C(O)O—, —OC(O)—, —OC(O)O—, —OC(O)N(R$^N$)—, —NR$^N$C(O)O—, —C(O)S—, —SC(O)—, —C(=NR$^N$)—, —C(=NR$^N$)N(R$^N$)—, —NR$^N$C(=NR$^N$)—, —NR$^N$C(=NR$^N$)N(R$^N$)—, —C(S)—, —C(S)N(R$^N$)—, —NR$^N$C(S)—, —NR$^N$C(S)N(R$^N$)—, —S(O)—, —OS(O)—, —S(O)O—, —OS(O)O—, —OS(O)$_2$—, —S(O)$_2$O—, —OS(O)$_2$O—, —N(R$^N$)S(O)—, —S(O)N(R$^N$)—, —N(R$^N$)S(O)N(R$^N$)—, —OS(O)N(R$^N$)—, —N(R$^N$)S(O)O—, —S(O)$_2$—, —N(R$^1$)S(O)$_2$—, —S(O)$_2$N(R$^N$)—, —N(R$^N$)S(O)$_2$N(R$^N$)—, —OS(O)$_2$N(R$^N$)—, or —N(R$^N$)S(O)$_2$O—;

each instance of R$^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

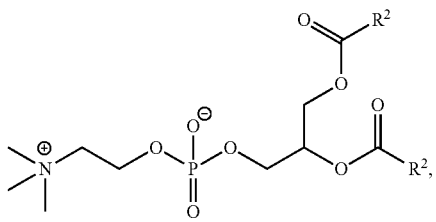

wherein each instance of R² is independently unsubstituted alkyl, unsubstituted alkenyl, or unsubstituted alkynyl.

Phospholipid Head Modifications

In certain embodiments, a phospholipid useful or potentially useful in the present invention comprises a modified phospholipid head (e.g., a modified choline group). In certain embodiments, a phospholipid with a modified head is DSPC, or analog thereof, with a modified quaternary amine. For example, in embodiments of Formula (IX), at least one of R' is not methyl. In certain embodiments, at least one of R' is not hydrogen or methyl. In certain embodiments, the compound of Formula (IX) is of one of the following formulae:

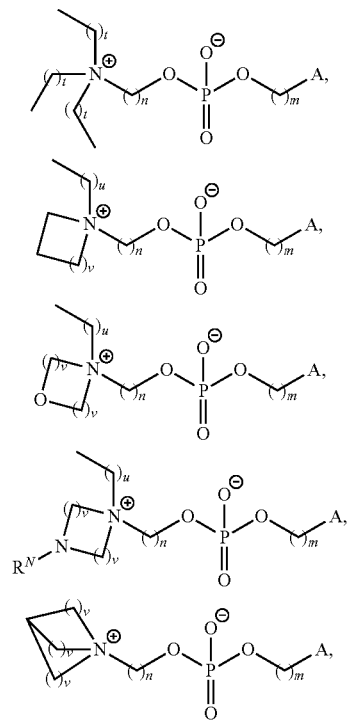

or a salt thereof, wherein:

each t is independently 1, 2, 3, 4, 5, 6, 7, 8, 9, or 10;

each u is independently 0, 1, 2, 3, 4, 5, 6, 7, 8, 9, or 10; and each v is independently 1, 2, or 3.

In certain embodiments, the compound of Formula (IX) is of one of the following formulae:

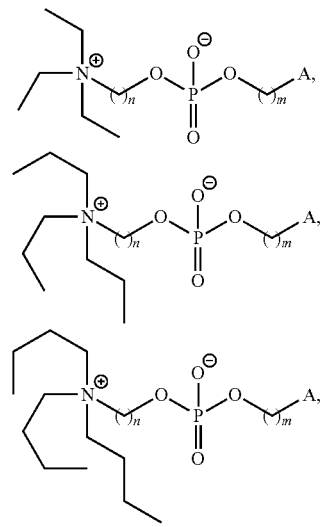

281
-continued
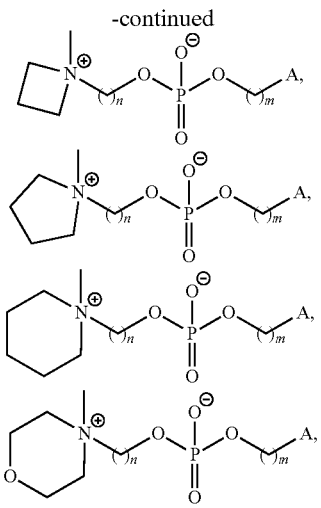
282
-continued
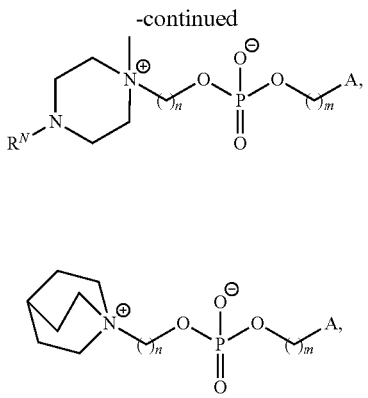
or a salt thereof.
In certain embodiments, a compound of Formula (IX) is one of the following:
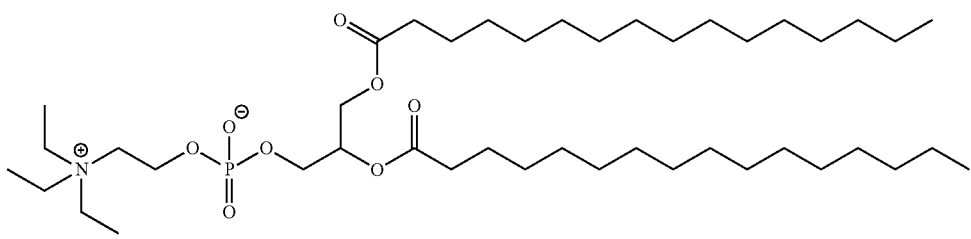
(Compound 400)
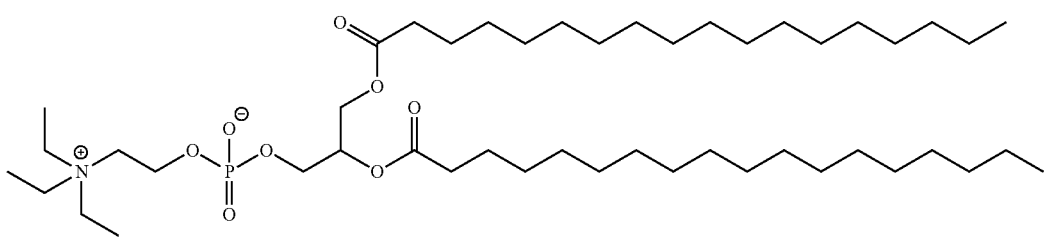
(Compound 401)
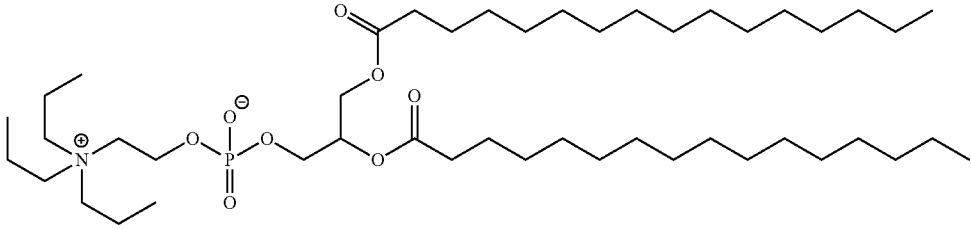
(Compound 402)
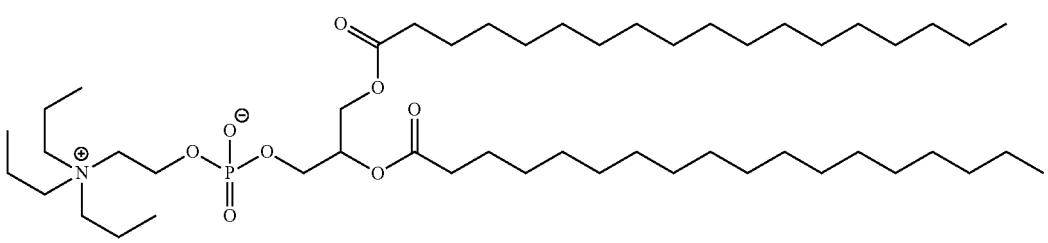
(Compound 403)

-continued
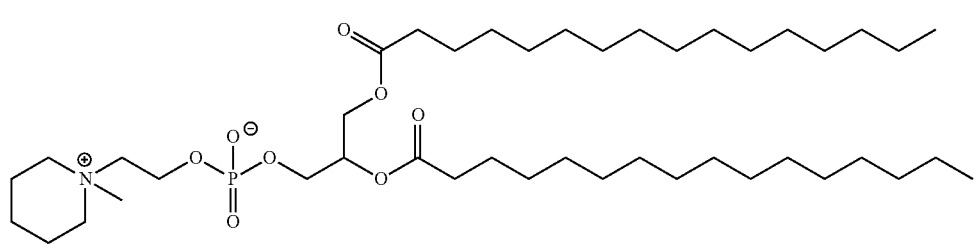
(Compound 404)
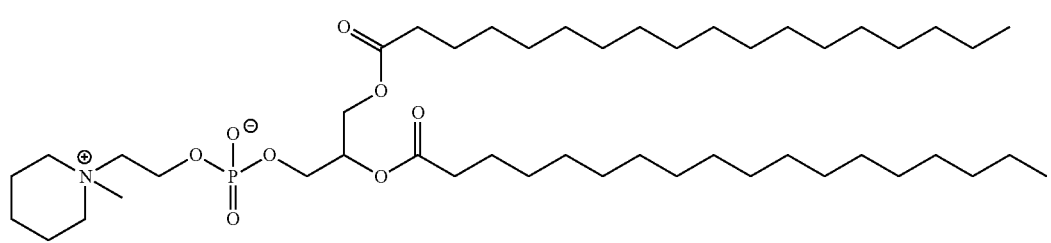
(Compound 405)
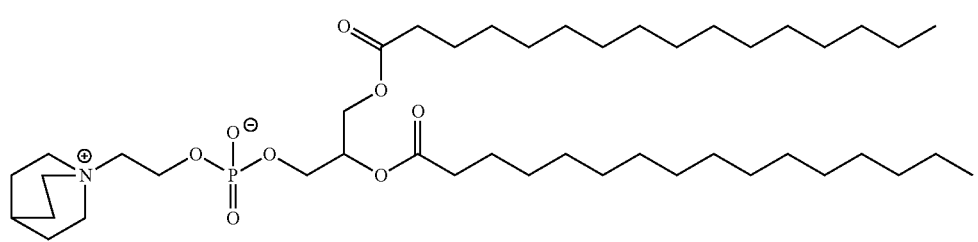
(Compound 406)
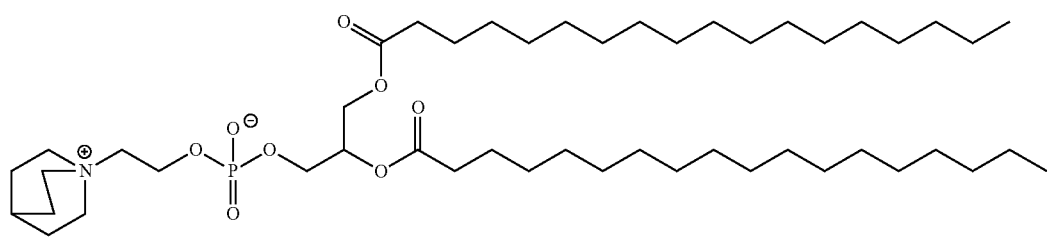
(Compound 407)
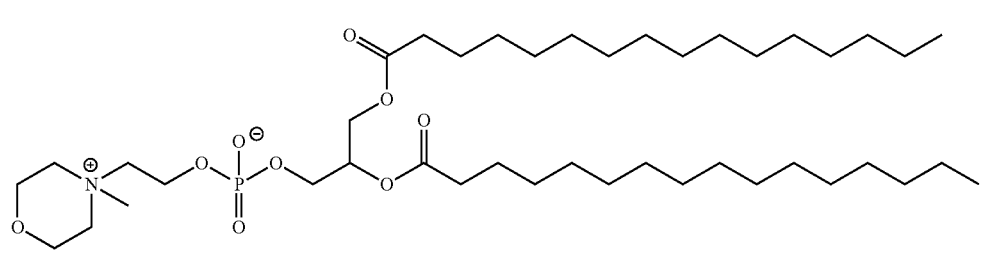
(Compound 408)
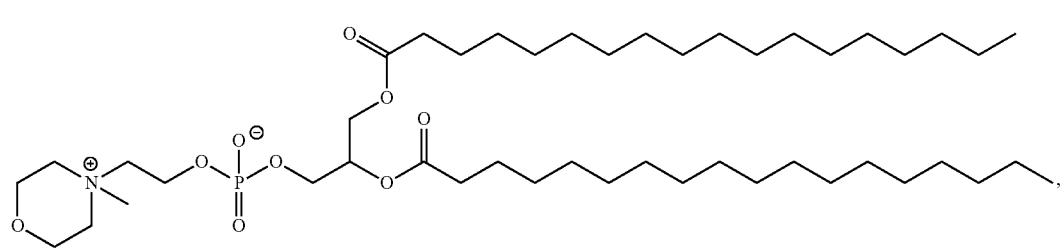
(Compound 409)
or a salt thereof.

In certain embodiments, a compound of Formula (IX) is of Formula (IX-a):

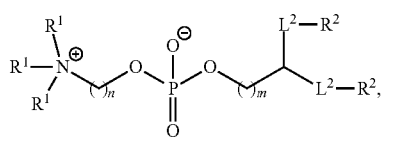
(IX-a)

or a salt thereof.

In certain embodiments, phospholipids useful or potentially useful in the present invention comprise a modified core. In certain embodiments, a phospholipid with a modified core described herein is DSPC, or analog thereof, with a modified core structure. For example, in certain embodiments of Formula (IX-a), group A is not of the following formula:

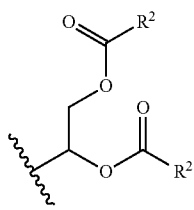

In certain embodiments, the compound of Formula (IX-a) is of one of the following formulae:

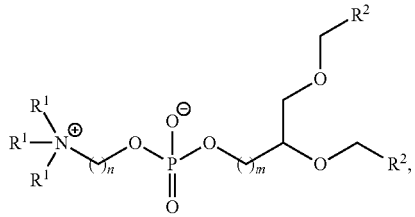

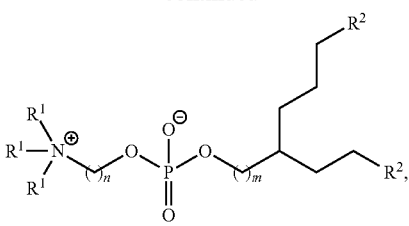

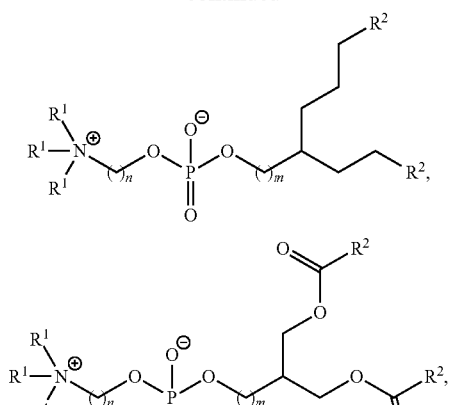

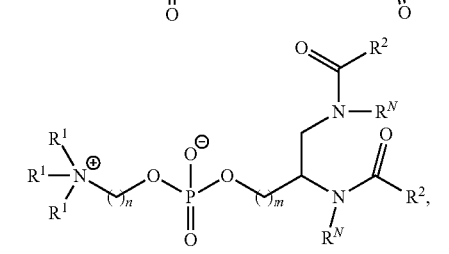

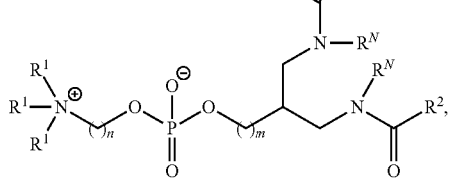

or a salt thereof.

In certain embodiments, a compound of Formula (IX) is one of the following:

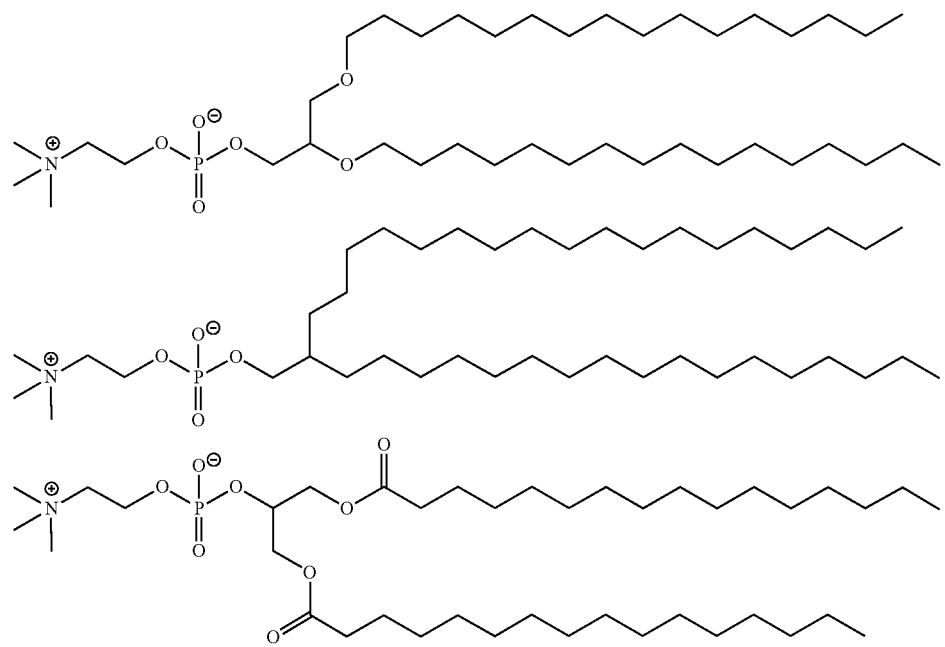

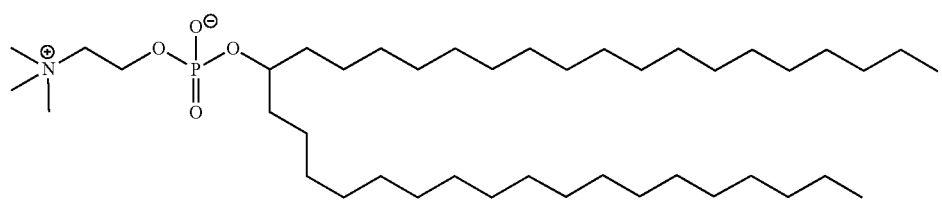

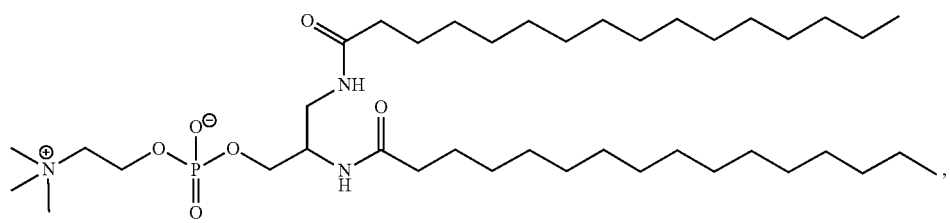

or salts thereof.

In certain embodiments, a phospholipid useful or potentially useful in the present invention comprises a cyclic moiety in place of the glyceride moiety. In certain embodiments, a phospholipid useful in the present invention is DSPC, or analog thereof, with a cyclic moiety in place of the glyceride moiety. In certain embodiments, the compound of Formula (IX) is of Formula (IX-b):

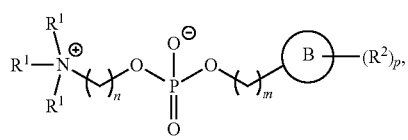

(IX-b)

or a salt thereof.

In certain embodiments, the compound of Formula (IX-b) is of Formula (IX-b-1):

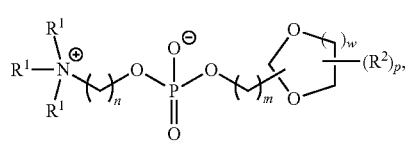

(IX-b-1)

or a salt thereof, wherein:
w is 0, 1, 2, or 3.

In certain embodiments, the compound of Formula (IX-b) is of Formula (IX-b-2):

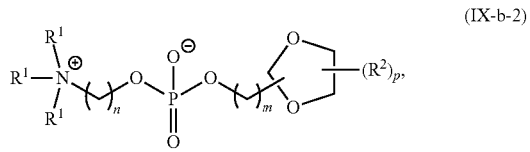

(IX-b-2)

or a salt thereof.

In certain embodiments, the compound of Formula (IX-b) is of Formula (IX-b-3):

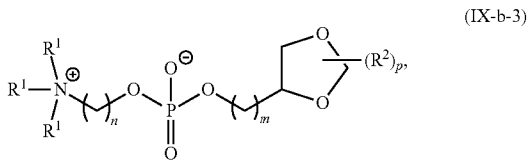

(IX-b-3)

or a salt thereof.

In certain embodiments, the compound of Formula (IX-b) is of Formula (IX-b-4):

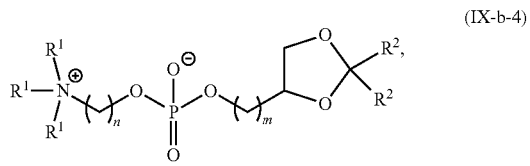

(IX-b-4)

or a salt thereof.

In certain embodiments, the compound of Formula (IX-b) is one of the following:

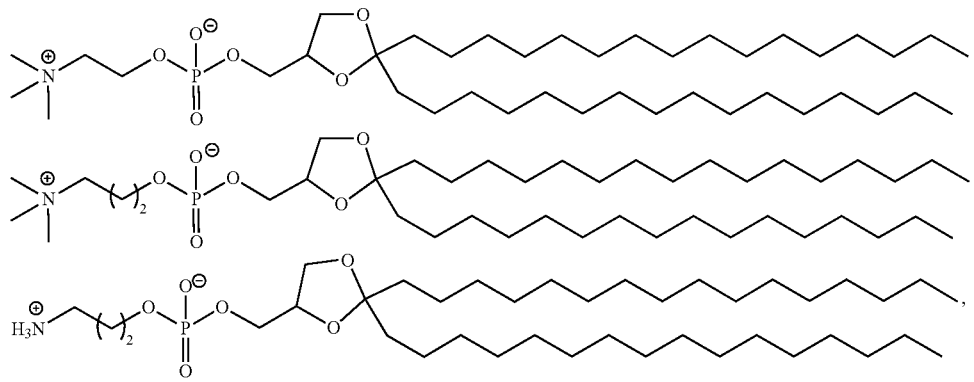

or salts thereof.

Phospholipid Tail Modifications

In certain embodiments, a phospholipid useful or potentially useful in the present invention comprises a modified tail. In certain embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IX) is of Formula (IX-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—.

In certain embodiments, the compound of Formula (IX) is of Formula (IX-c):

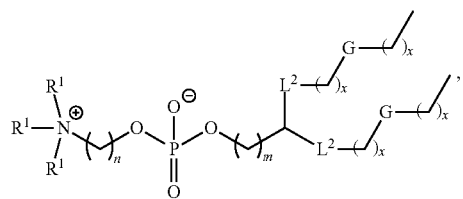

(IX-c)

or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N ($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C (S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S (O)O—, —S(O)$_2$—, —N($R^N$)S(O)$_2$—, —S(O)$_2$N ($R^N$)—, —N($R^N$)S(O)$_2$N($R^N$)—, —OS(O)$_2$N($R^N$)—, or —N($R^N$)S(O)$_2$O—. Each possibility represents a separate embodiment of the present invention.

In certain embodiments, the compound of Formula (IX-c) is of Formula (IX-c-1):

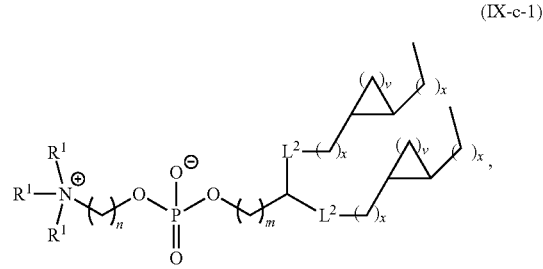

(IX-c-1)

or salt thereof, wherein:

each instance of v is independently 1, 2, or 3.

In certain embodiments, the compound of Formula (IX-c) is of Formula (IX-c-2):

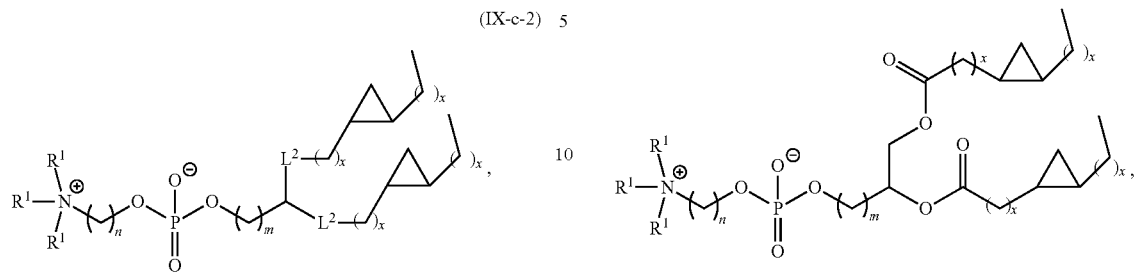
(IX-c-2)

or a salt thereof.

In certain embodiments, the compound of Formula (IX-c) is of the following formula:

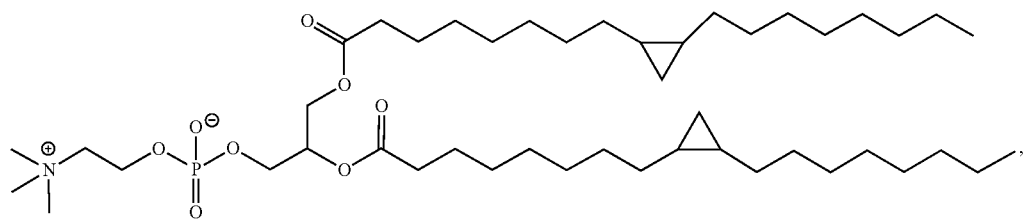 [SMILES: CCCCCCCCC1CC1CCCCCCCC(=O)OCC(COP(=O)([O-])OCC[N+](C)(C)C)OC(=O)CCCCCCCC1CC1CCCCCCCC]

or a salt thereof.

In certain embodiments, the compound of Formula (IX-c) is the following:

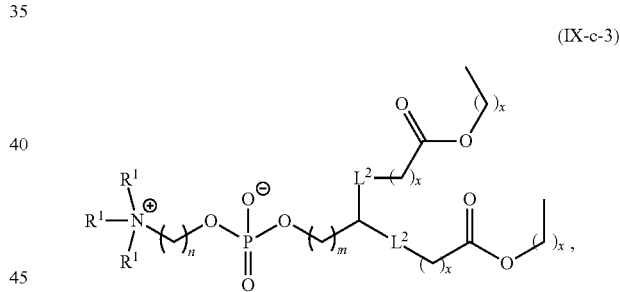

or a salt thereof.

In certain embodiments, the compound of Formula (IX-c) is of Formula (IX-c-3):

(IX-c-3)

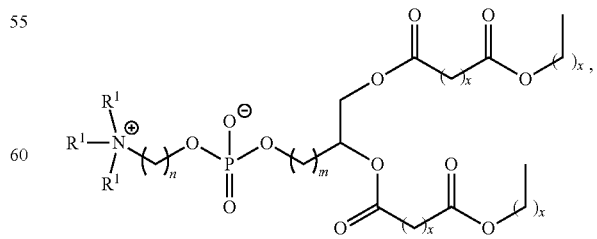

or a salt thereof.

In certain embodiments, the compound of Formula (IX-c) is of the following formulae:

or a salt thereof.

In certain embodiments, the compound of Formula (IX-c) is the following:

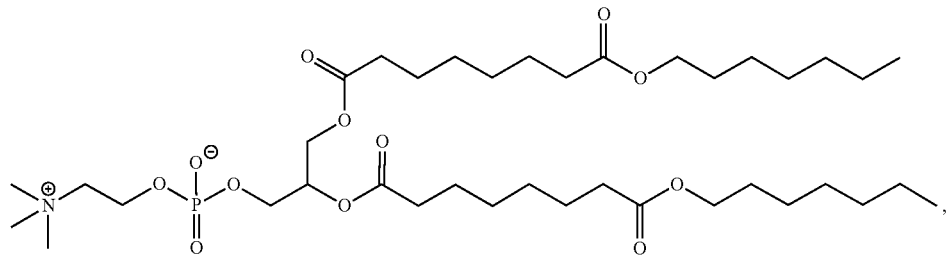 [SMILES: CCCCCCCOC(=O)CCCCCCC(=O)OCC(COP(=O)([O-])OCC[N+](C)(C)C)OC(=O)CCCCCCC(=O)OCCCCCCC]

or a salt thereof.

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IX), wherein n is 1, 3, 4, 5, 6, 7, 8, 9, or 10. For example, in certain embodiments, a compound of Formula (IX) is of one of the following formulae:

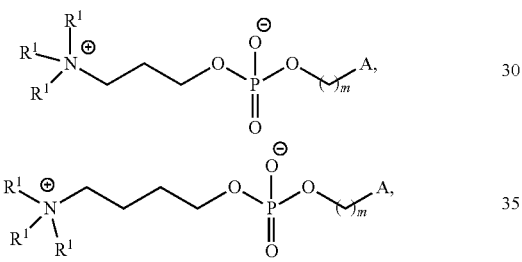

or a salt thereof.

In certain embodiments, a compound of Formula (IX) is one of the following:

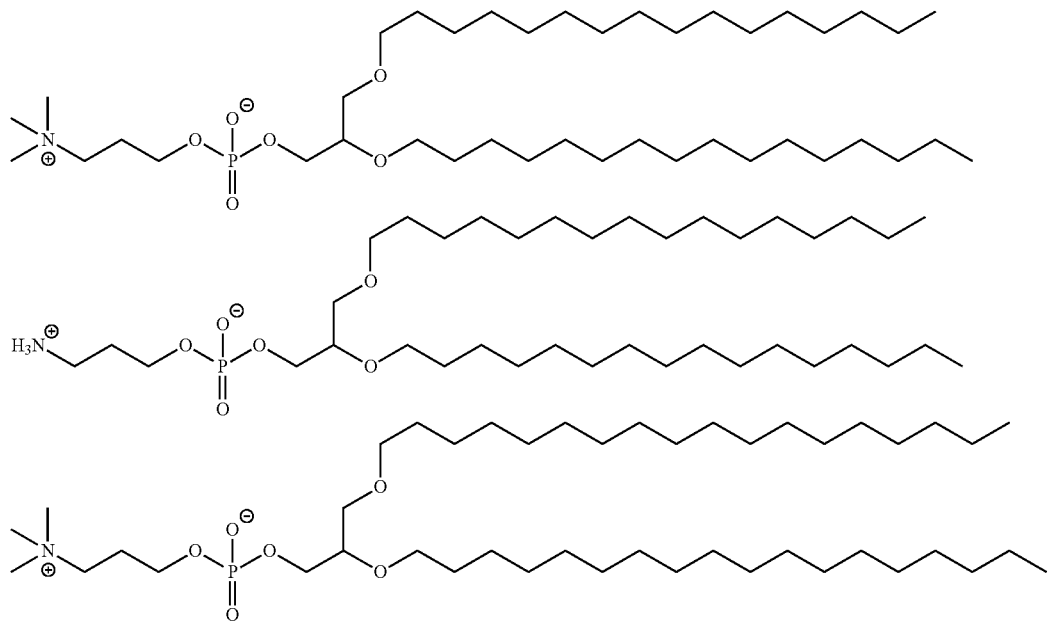

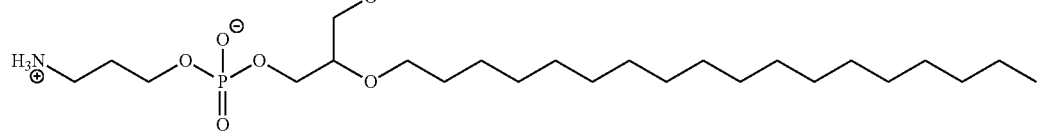
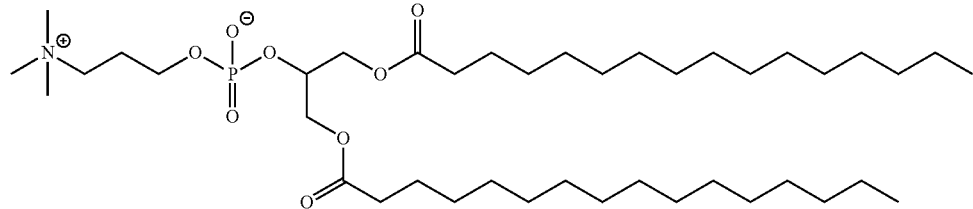
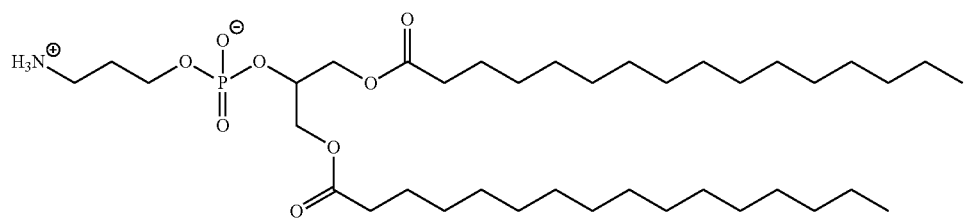
(Compound 411)
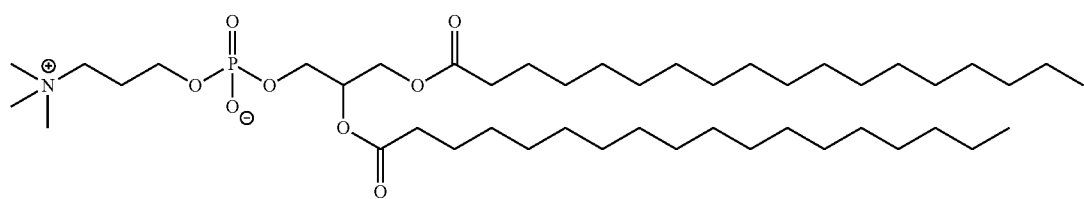
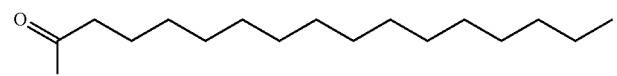
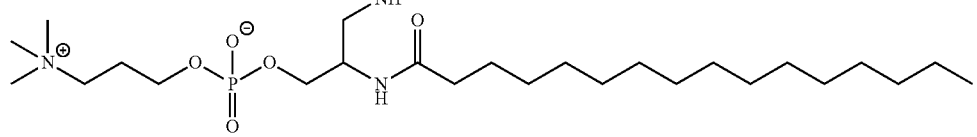
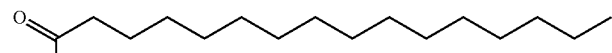
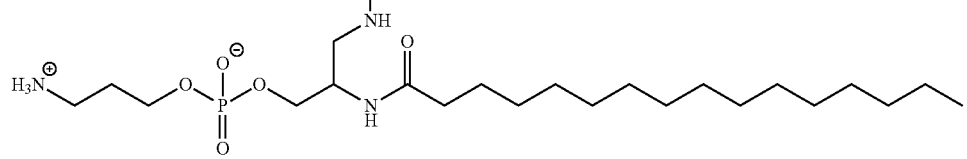
(Compound 412)
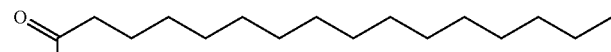
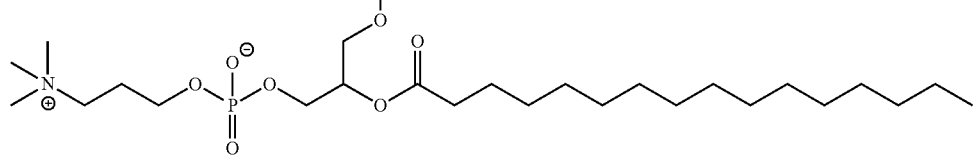

-continued
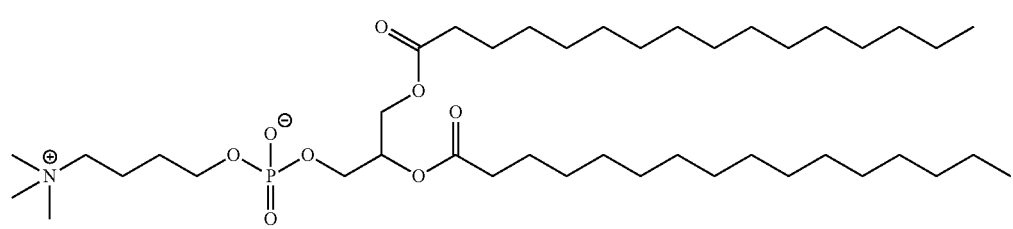
(Compound 413)
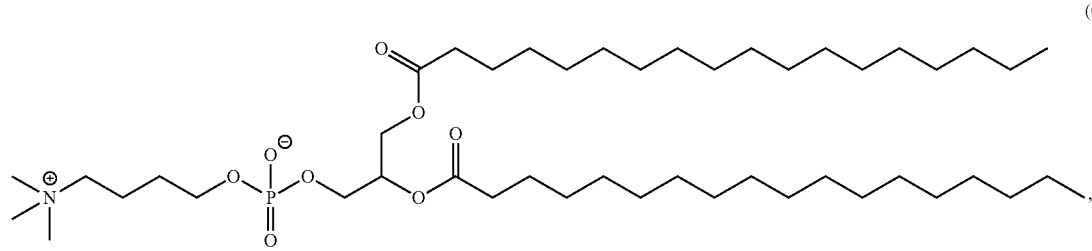
(Compound 414)
or salts thereof.
(ii) Alternative Lipids
In certain embodiments, an alternative lipid is used in place of a phospholipid of the invention. Non-limiting examples of such alternative lipids include the following:
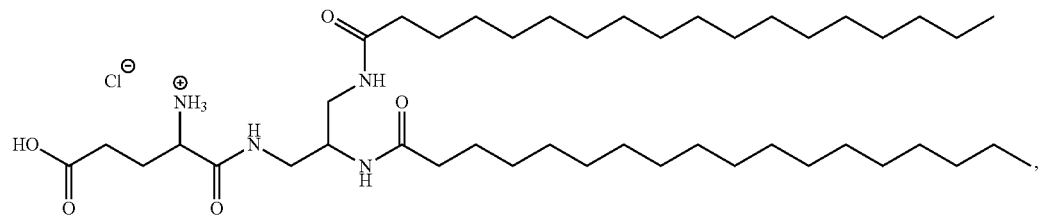
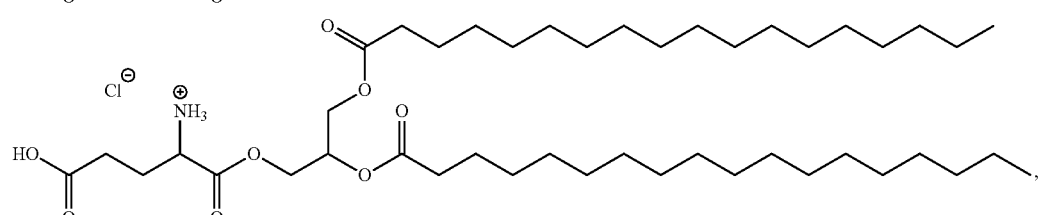
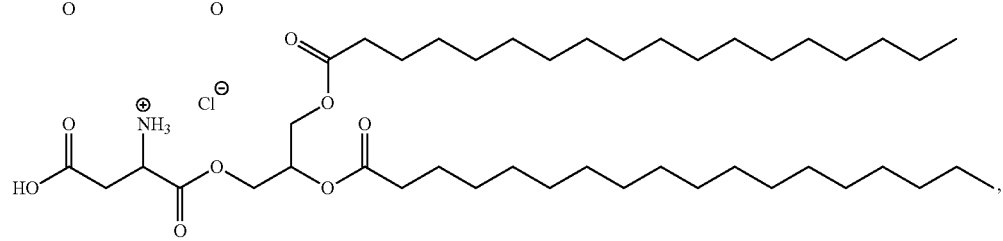
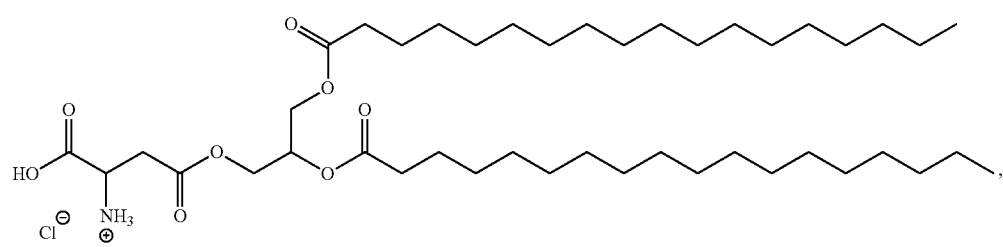

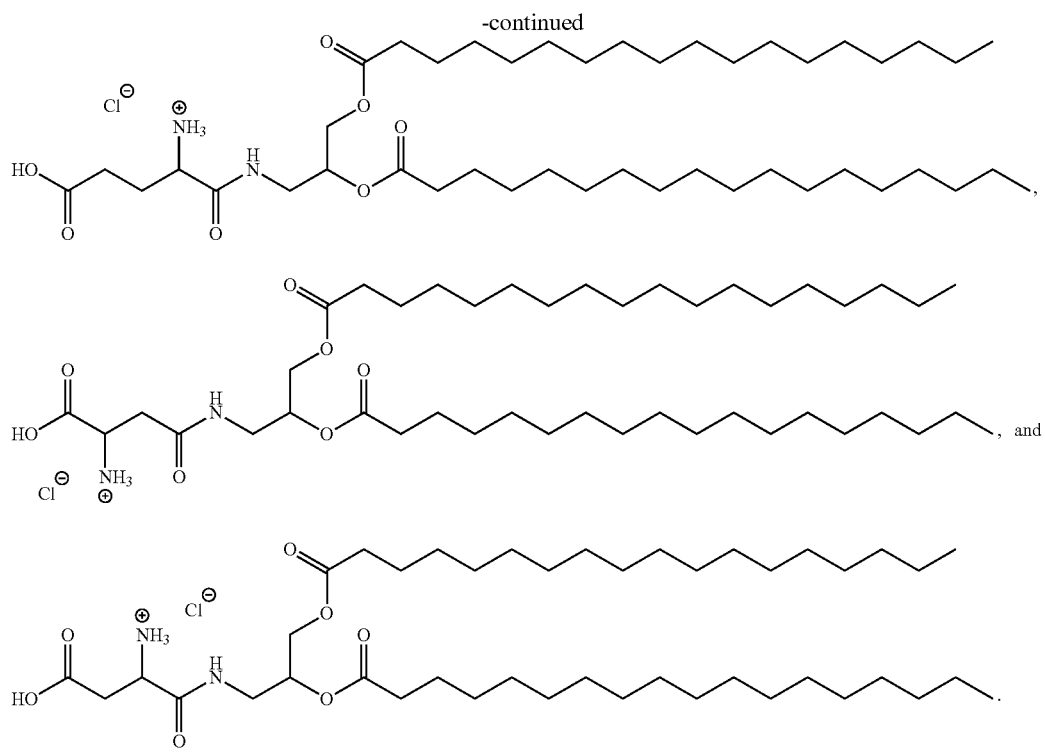

(iii) Structural Lipids

The lipid composition of a pharmaceutical composition disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol. Examples of structural lipids include, but are not limited to, the following:

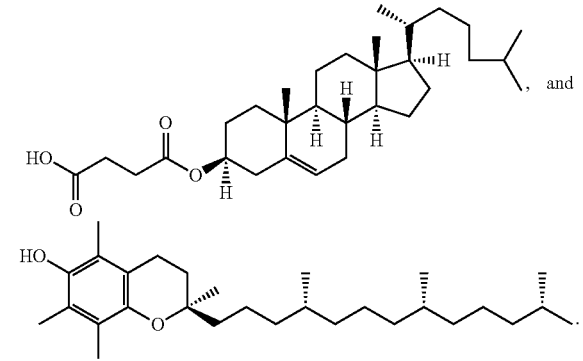

In one embodiment, the amount of the structural lipid (e.g., an sterol such as cholesterol) in the lipid composition of a pharmaceutical composition disclosed herein ranges from about 20 mol % to about 60 mol %, from about 25 mol % to about 55 mol %, from about 30 mol % to about 50 mol %, or from about 35 mol % to about 45 mol %.

In one embodiment, the amount of the structural lipid (e.g., an sterol such as cholesterol) in the lipid composition disclosed herein ranges from about 25 mol % to about 30 mol %, from about 30 mol % to about 35 mol %, or from about 35 mol % to about 40 mol %.

In one embodiment, the amount of the structural lipid (e.g., a sterol such as cholesterol) in the lipid composition disclosed herein is about 24 mol %, about 29 mol %, about 34 mol %, or about 39 mol %.

In some embodiments, the amount of the structural lipid (e.g., an sterol such as cholesterol) in the lipid composition disclosed herein is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol %.

(iv) Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-NH$_2$, has a size of about 1000, 2000, 5000, 10,000, 15,000 or 20,000 daltons. In one embodiment, the PEG-lipid is PEG$_{2k}$-DMG.

In one embodiment, the lipid nanoparticles described herein can comprise a PEG lipid which is a non-diffusible PEG. Non-limiting examples of non-diffusible PEGS include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

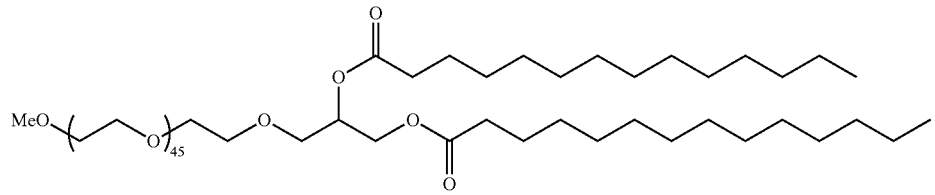

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In certain embodiments, a PEG lipid useful in the present invention is a compound of Formula (VII). Provided herein are compounds of Formula (VII):

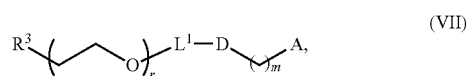

(VII)

or salts thereof, wherein:

$R^3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, —O—, —N($R^N$)—, —S—, —C(O)—, —C(O)N($R^N$)—, —$NR^N$C(O)—, —C(O)O—, —OC(O)—, —OC(O)O—, —OC(O)N($R^N$)—, —$NR^N$C(O)O—, or —$NR^N$C(O)N($R^N$)—;

D is a moiety obtained by click chemistry or a moiety cleavable under physiological conditions;

m is 0, 1, 2, 3, 4, 5, 6, 7, 8, 9, or 10;

A is of the formula:

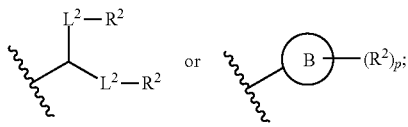

each instance of L² is independently a bond or optionally substituted C₁₋₆ alkylene, wherein one methylene unit of the optionally substituted C₁₋₆ alkylene is optionally replaced with —O—, —N(R$^N$)—, —S—, —C(O)—, —C(O)N(R$^N$)—, —NR$^N$C(O)—, —C(O)O—, —OC(O)—, —OC(O)O—, —OC(O)N(R$^N$)—, —NR$^N$C(O)O—, or —NR$^N$C(O)N(R$^N$)—; each instance of R² is independently optionally substituted C₁₋₃₀ alkyl, optionally substituted C₁₋₃₀ alkenyl, or optionally substituted C₁₋₃₀ alkynyl; optionally wherein one or more methylene units of R² are independently replaced with optionally substituted carbocyclylene, optionally substituted heterocyclylene, optionally substituted arylene, optionally substituted heteroarylene, —N(R$^N$)—, —O—, —S—, —C(O)—, —C(O)N(R$^N$)—, —NR$^N$C(O)—, —NR$^N$C(O)N(R$^N$)—, —C(O)O—, —OC(O)—, —OC(O)O—, —OC(O)N(R$^N$)—, —NR$^N$C(O)O—, —C(O)S—, —SC(O)—, —C(=NR$^N$)—, —C(=NR$^N$)N(R$^N$)—, —NR$^N$C(=NR$^N$)—, —NR$^N$C(=NR$^N$)N(R$^N$)—, —C(S)—, —C(S)N(R$^N$)—, —NR$^N$C(S)—, —NR$^N$C(S)N(R$^N$)—, —S(O)—, —OS(O)—, —S(O)O—, —OS(O)O—, —OS(O)₂—, —S(O)₂O—, —OS(O)₂O—, —N(R$^N$)S(O)—, —S(O)N(R$^N$)—, —N(R$^N$)S(O)N(R$^N$)—, —OS(O)N(R$^N$)—, —N(R$^N$)S(O)O—, —S(O)₂—, —N(R¹)S(O)₂—, —S(O)₂N(R$^N$)—, —N(R$^N$)S(O)₂N(R$^N$)—, —OS(O)₂N(R$^N$)—, or —N(R$^N$)S(O)₂O—;

each instance of R$^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (VII) is a PEG-OH lipid (i.e., R³ is —OR$^O$, and R$^O$ is hydrogen). In certain embodiments, the compound of Formula (VII) is of Formula (VII-OH):

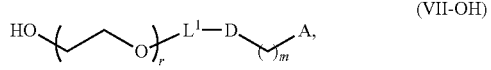

(VII-OH)

or a salt thereof.

In certain embodiments, D is a moiety obtained by click chemistry (e.g., triazole). In certain embodiments, the compound of Formula (VII) is of Formula (VII-a-1) or (VII-a-2):

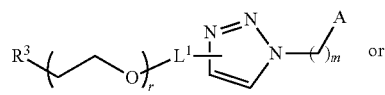

(VII-a-1)

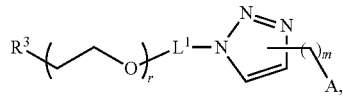

(VII-a-2)

or a salt thereof.

In certain embodiments, the compound of Formula (VII) is of one of the following formulae:

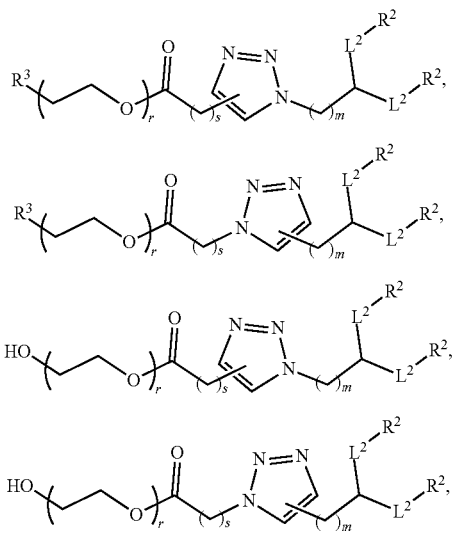

or a salt thereof, wherein
s is 0, 1, 2, 3, 4, 5, 6, 7, 8, 9, or 10.

In certain embodiments, the compound of Formula (VII) is of one of the following formulae:

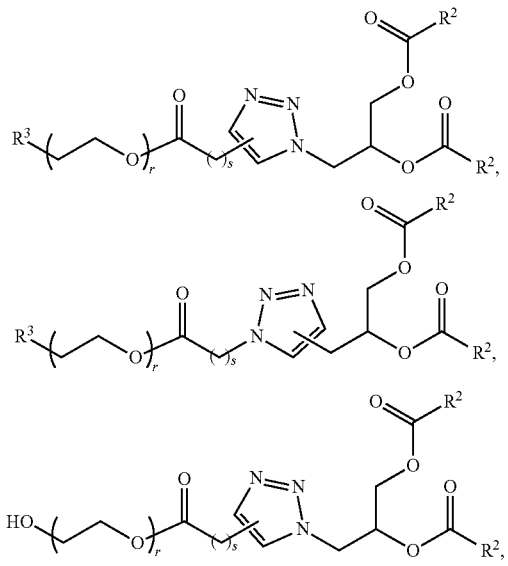

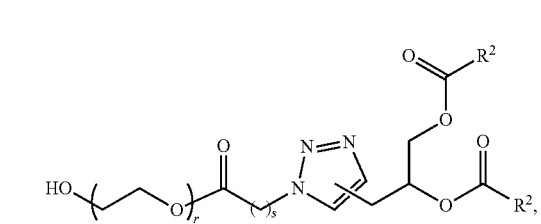

or a salt thereof.

In certain embodiments, a compound of Formula (VII) is of one of the following formulae:
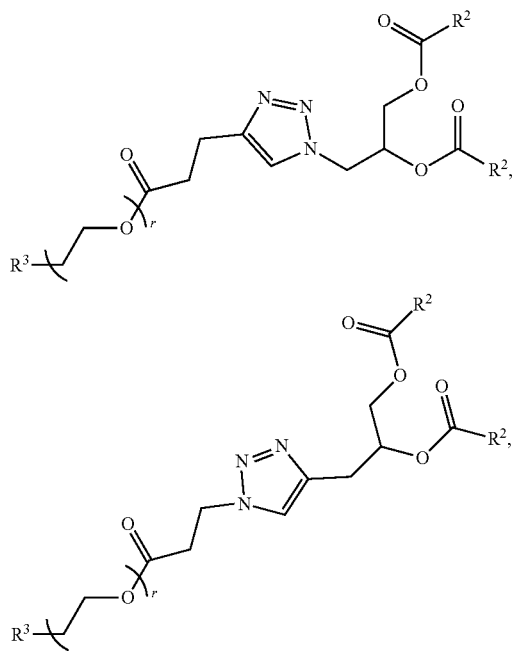
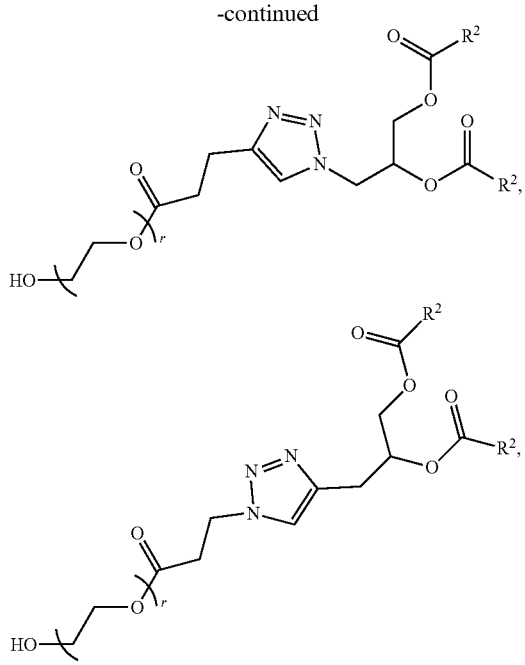
or a salt thereof.
In certain embodiments, a compound of Formula (VII) is of one of the following formulae:
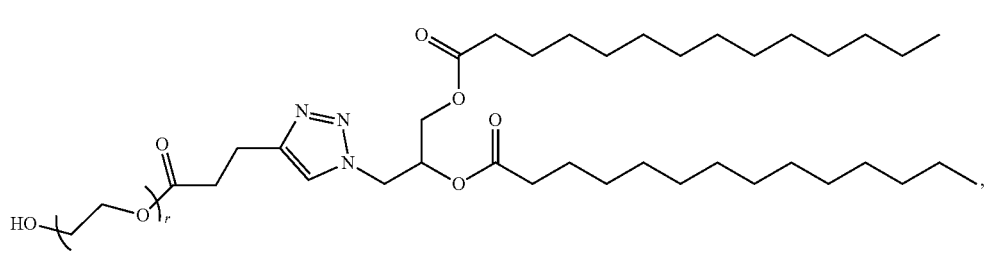
(Compound 415)
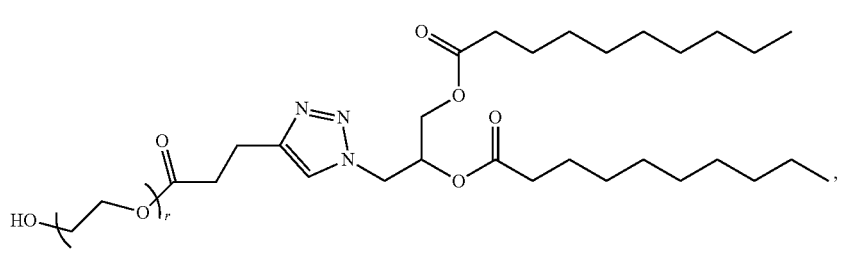
(Compound 416)
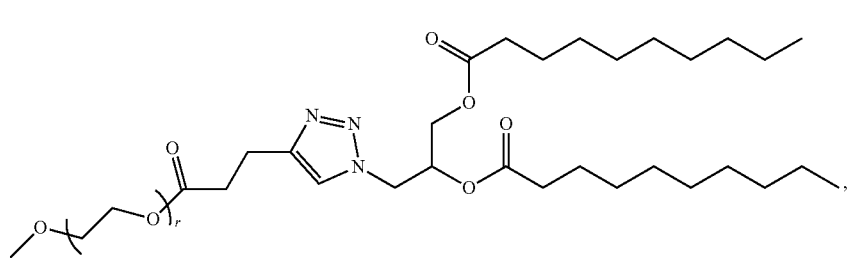
(Compound 417)

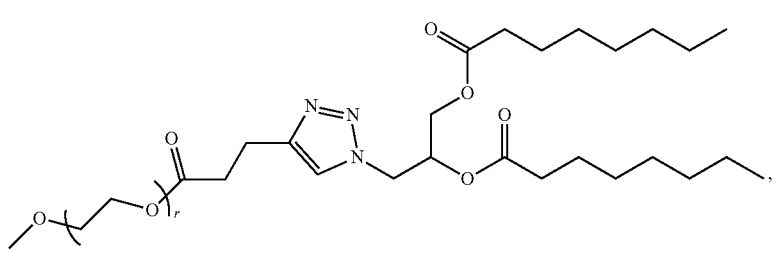

(Compound 418)

or a salt thereof.

In certain embodiments, D is a moiety cleavable under physiological conditions (e.g., ester, amide, carbonate, carbamate, urea). In certain embodiments, a compound of Formula (VII) is of Formula (VII-b-1) or (VII-b-2):

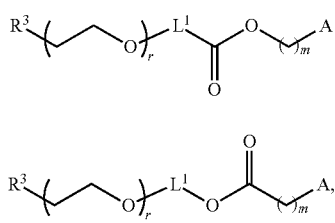

(VII-b-1)

(VII-b-2)

or a salt thereof.

In certain embodiments, a compound of Formula (VII) is of Formula (VII-b-1-OH) or (VII-b-2-OH):

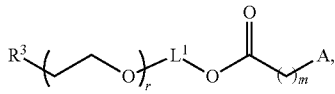

(VII-b-1-OH)

(VII-b-2-OH)

or a salt thereof.

In certain embodiments, the compound of Formula (VII) is of one of the following formulae:

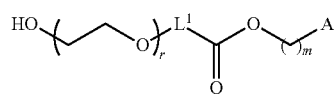

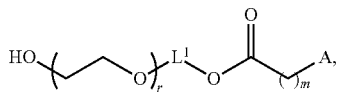

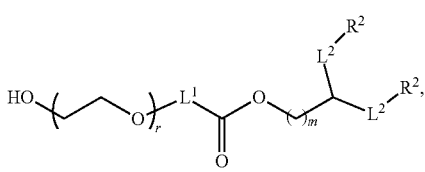

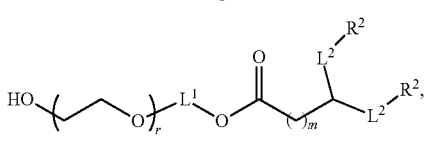

or a salt thereof.

In certain embodiments, a compound of Formula (VII) is of one of the following formulae:

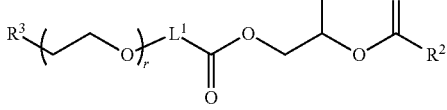

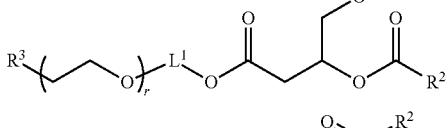

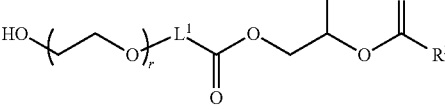

or a salt thereof.

In certain embodiments, a compound of Formula (VII) is of one of the following formulae:

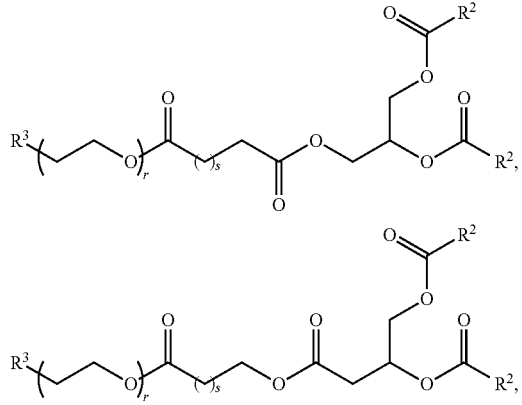

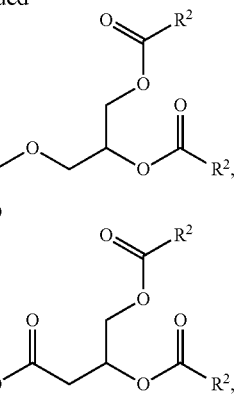

-continued or a salt thereof.

In certain embodiments, a compound of Formula (VII) is of one of the following formulae:

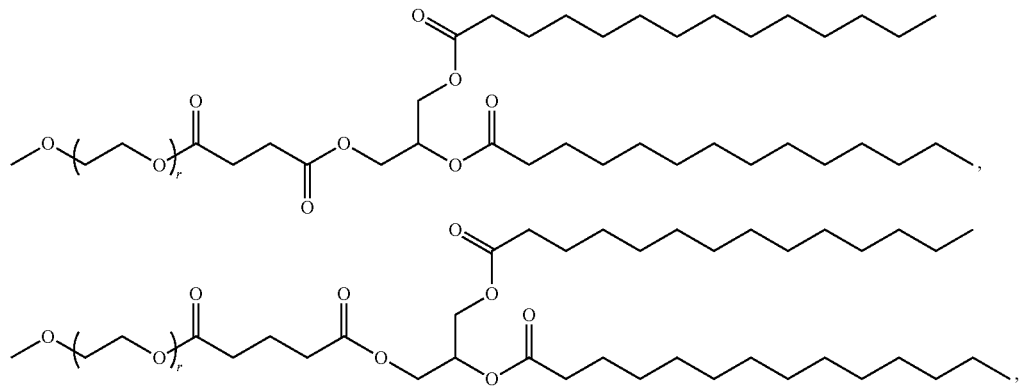

or salts thereof.

In certain embodiments, a PEG lipid useful in the present invention is a PEGylated fatty acid. In certain embodiments, a PEG lipid useful in the present invention is a compound of Formula (VIII). Provided herein are compounds of Formula (VIII):

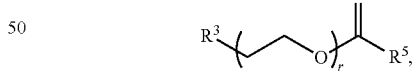

(VIII)

or a salts thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N(R$^N$)—, —NR$^N$C(O)O—, —C(O)S—, —SC(O)—, —C(=NR$^N$)—, —C(=NR$^N$)N(R$^N$)—, —NR$^N$C(=NR$^N$)—, —NR$^N$C(=NR$^N$)N(R$^N$)—, —C(S)—, —C(S)N(R$^N$)—, —NR$^N$C(S)—, —NR$^N$C(S)N(R$^N$)—, —S(O)—, —OS(O)—, —S(O)O—, —OS(O)O—, —OS(O)$_2$—, —S(O)$_2$O—, —OS(O)$_2$O—, —N(R$^N$)S(O)—, —S(O)N(R$^N$)—, —N(R$^N$)S(O)N(R$^N$)—, —OS(O)N(R$^N$)—, —N(R$^N$)S(O)O—, —S(O)$_2$—, —N(R$^N$)S(O)$_2$—, —S(O)$_2$N(R$^N$)—, —N(R$^N$)S(O)$_2$N(R$^N$)—, —OS(O)$_2$N(R$^N$)—, or —N(R$^N$)S(O)$_2$O—; and each instance of R$^N$ is independently hydrogen, optionally substituted alkyl, or a nitrogen protecting group.

In certain embodiments, the compound of Formula (VIII) is of Formula (VIII-OH):

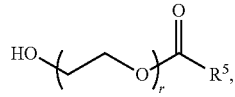

(VIII-OH)

or a salt thereof. In some embodiments, r is 45.

In certain embodiments, a compound of Formula (VIII) is of one of the following formulae:

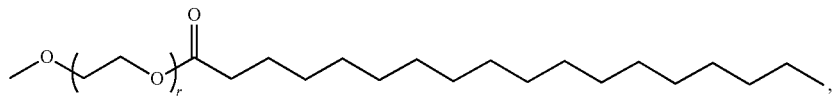

(Compound 419)

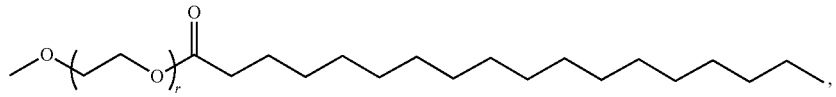

(Compound 420)

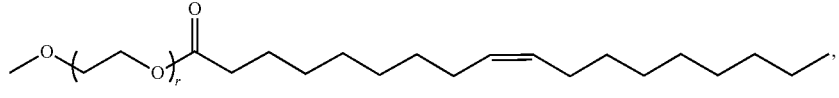

(Compound 421)

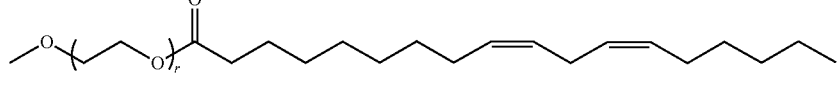

(Compound 422)

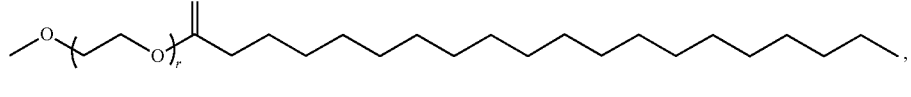

(Compound 423)

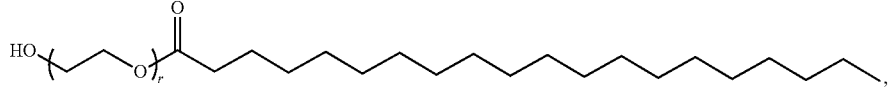

(Compound 424)

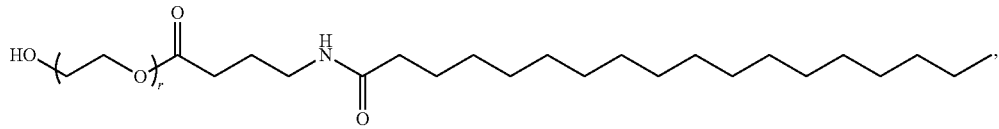

(Compound 425)

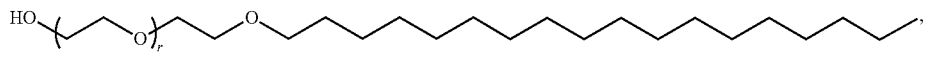

(Compound 426)

or a salt thereof. In some embodiments, r is 45.

In yet other embodiments the compound of Formula (VIII) is:

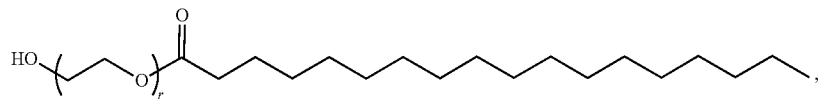

(Compound 427)

or a salt thereof.

In one embodiment, the compound of Formula (VIII) is

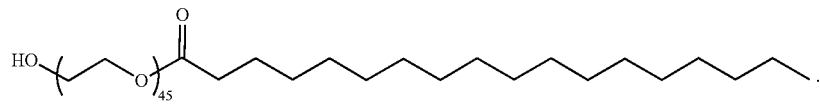

(Compound 428)

In one embodiment, the amount of PEG-lipid in the lipid composition of a pharmaceutical composition disclosed herein ranges from about 0 mol % to about 5 mol %, from about 1 mol % to about 5 mol %, from about 2 mol % to about 5 mol %, from about 0 mol % to about 4 mol %, from about 1 mol % to about 4 mol %, from about 2 mol % to about 4 mol %, from about 0 mol % to about 3 mol %, from about 1 mol % to about 3 mol %, from about 2 mol % to about 3 mol %, from about 0 mol % to about 2 mol %, or from about 1 mol % to about 2 mol %.

In one embodiment, the amount of PEG-lipid in the lipid composition disclosed herein is about 2 mol %. In one embodiment, the amount of PEG-lipid in the lipid composition disclosed herein is about 1.5 mol %.

In one embodiment, the amount of PEG-lipid in the lipid composition disclosed herein is at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mol %.

In some aspects, the lipid composition of the pharmaceutical compositions disclosed herein does not comprise a PEG-lipid.

(v) Other Ionizable Amino Lipids

The lipid composition of the pharmaceutical composition disclosed herein can comprise one or more ionizable amino lipids in addition to a lipid according to formula (I), (III), (IV), (V), or (VI).

Ionizable lipids can be selected from the non-limiting group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraazaoctatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), (13Z,16SZ)—N,N-dimethyl-3-nonydocosa-13-16-dien-1-amine (L608), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). In addition to these, an ionizable amino lipid can also be a lipid including a cyclic amine group.

Ionizable lipids can also be the compounds disclosed in International Publication No. WO 2017/075531 A1, hereby incorporated by reference in its entirety. For example, the ionizable amino lipids include, but not limited to:

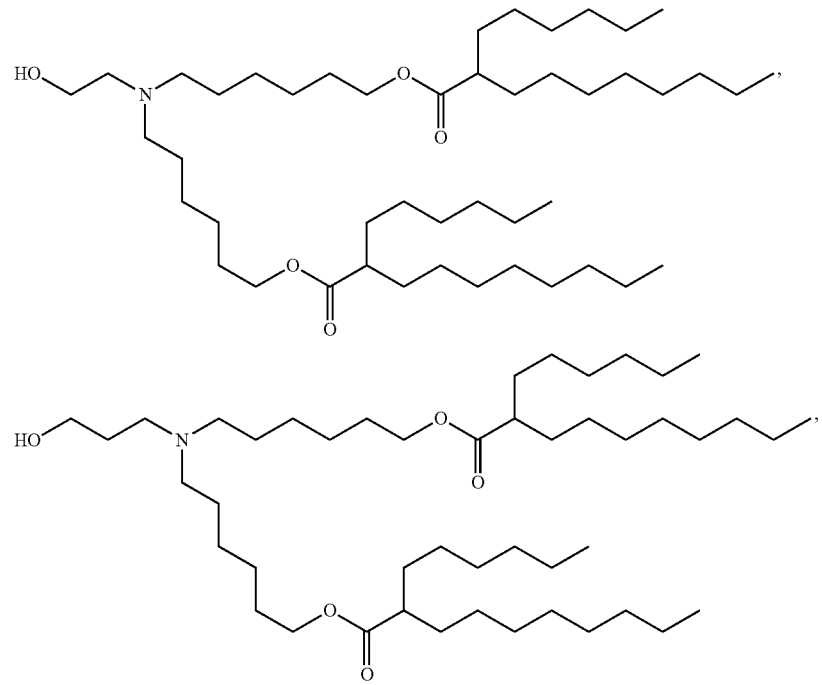

-continued
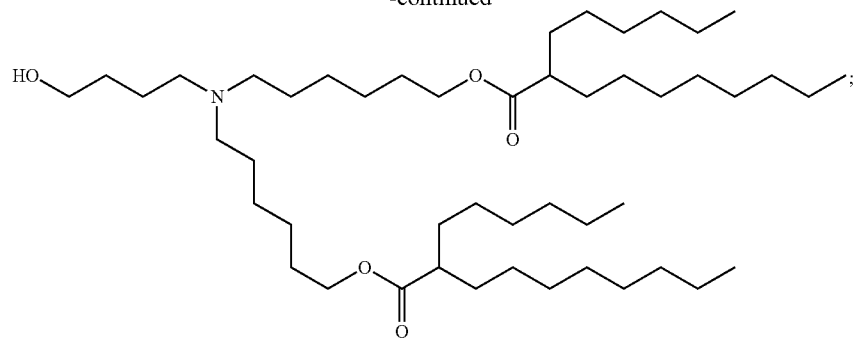
and any combination thereof.
Ionizable lipids can also be the compounds disclosed in International Publication No. WO 2015/199952 A1, hereby incorporated by reference in its entirety. For example, the ionizable amino lipids include, but not limited to:
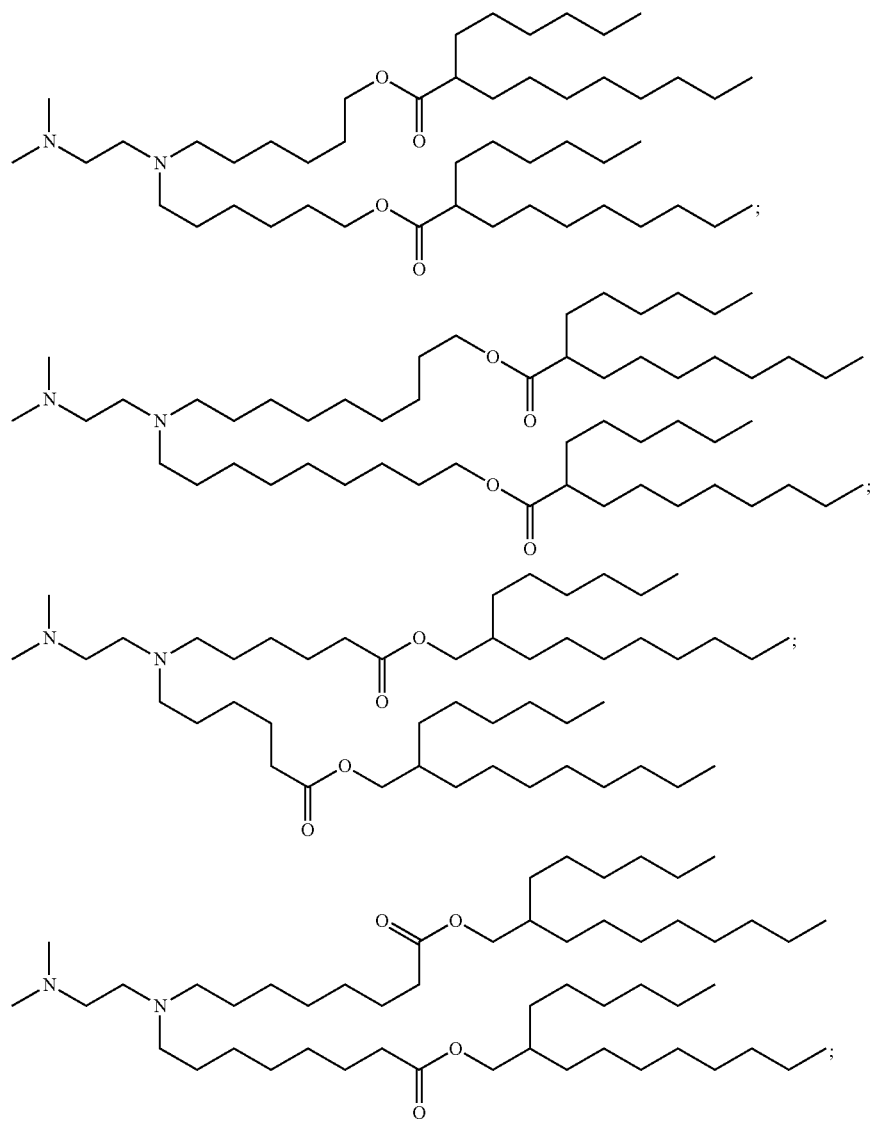

-continued
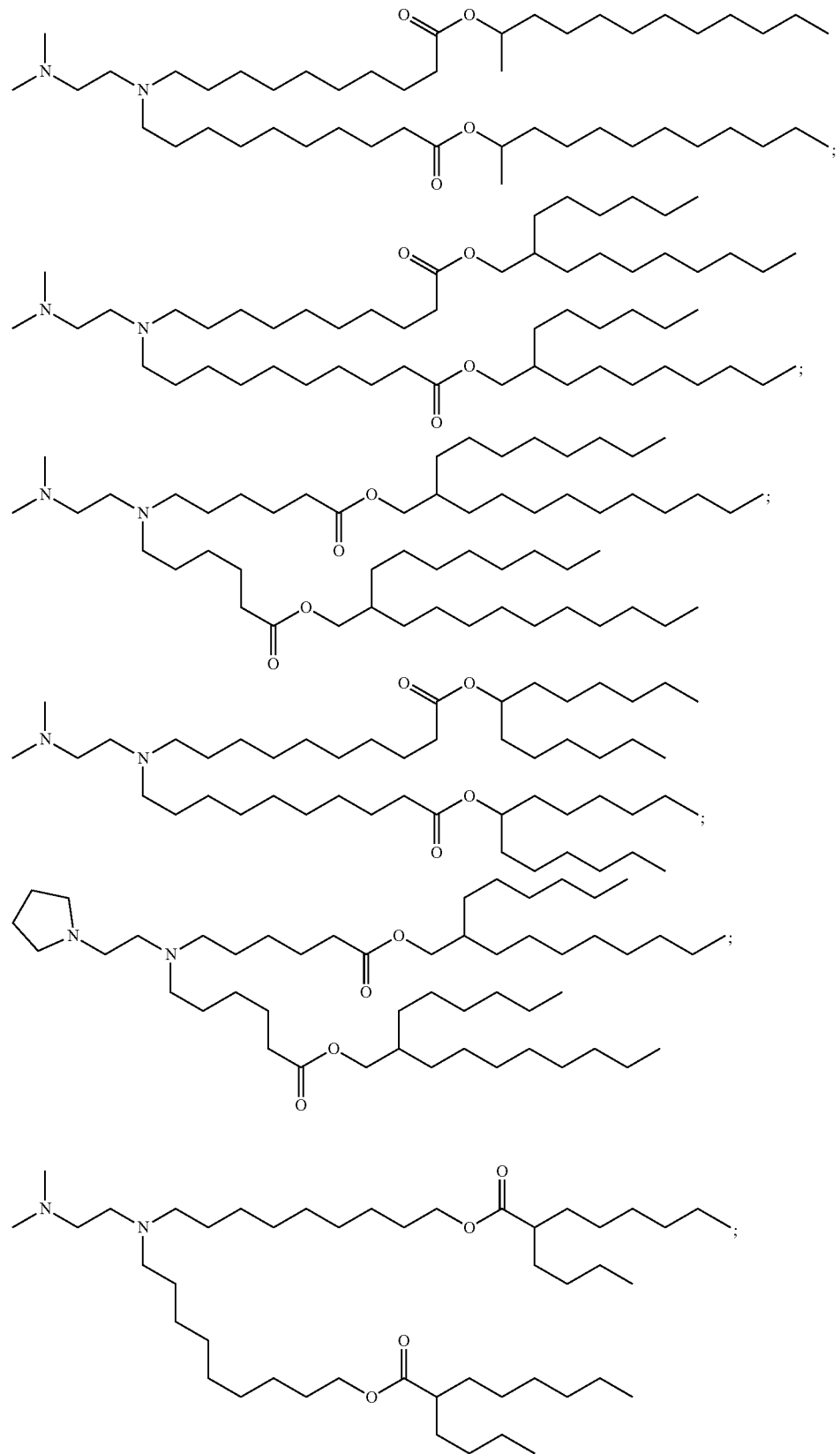
and any combination thereof.

Ionizable lipids can further include, but are not limited to:

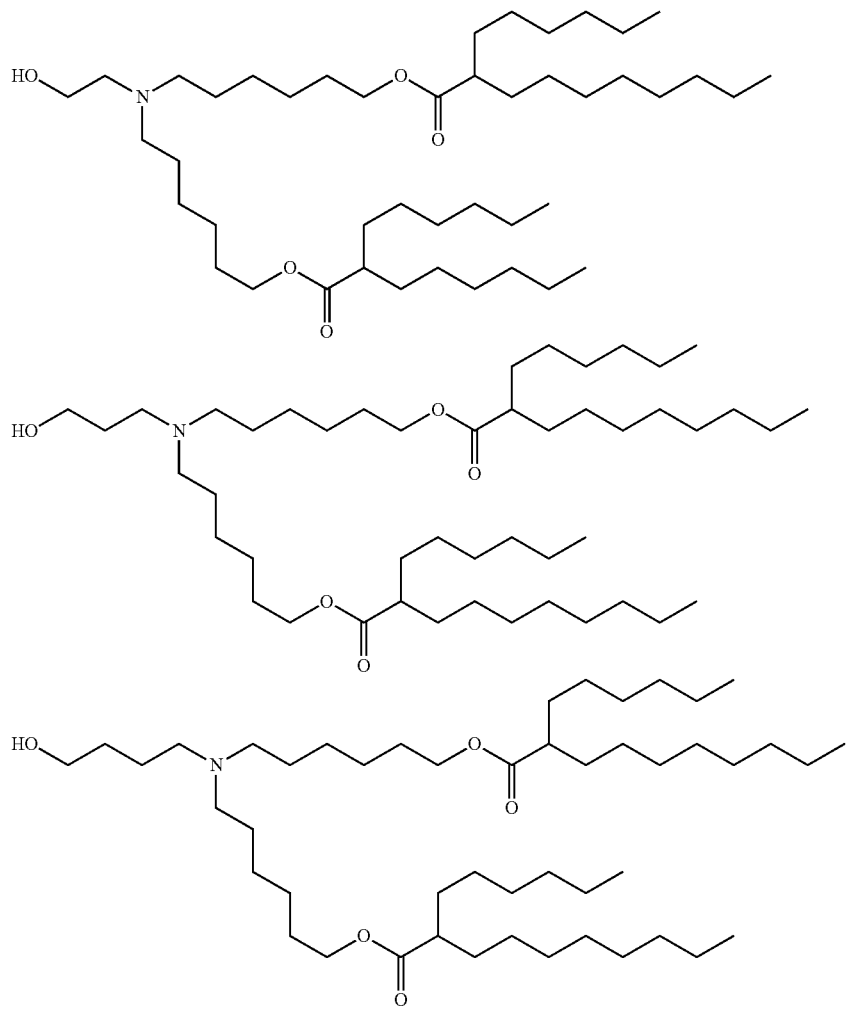

and any combination thereof.

(vi) Other Lipid Composition Components

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1,11:1, 12:1, 13:1, 14:1, 15:1, 16:1, 17:1, 18:1, 19:1, 20:1,21:1,22: 1,23:1,24:1,25:1,26:1,27:1,28:1,29:1,30:1,31:1, 32:1, 33:1, 34:1, 35:1, 36:1, 37:1, 38:1, 39:1, 40:1,41:1,42:1,43:1,44:1, 45:1,46:1,47:1,48:1,49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In some embodiments, the pharmaceutical composition disclosed herein can contain more than one polypeptides. For example, a pharmaceutical composition disclosed herein can contain two or more polynucleotides (e.g., RNA, e.g., mRNA).

In one embodiment, the lipid nanoparticles described herein can comprise polynucleotides (e.g., mRNA) in a lipid:polynucleotide weight ratio of 5:1, 10:1, 15:1, 20:1, 25:1,30:1,35:1,40:1,45:1,50:1,55:1,60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

(vii) Nanoparticle Compositions

In some embodiments, the pharmaceutical compositions disclosed herein are formulated as lipid nanoparticles (LNP). Accordingly, the present disclosure also provides nanoparticle compositions comprising (i) a lipid composition comprising a delivery agent such as a compound of formula (I) or (III) as described herein, and (ii) a polynucleotide encoding a Citrin polypeptide. In such nanoparticle composition, the lipid composition disclosed herein can encapsulate the polynucleotide encoding a Citrin polypeptide.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In some embodiments, the nanoparticle compositions of the present disclosure comprise at least one compound according to formula (I), (III), (IV), (V), or (VI). For example, the nanoparticle composition can include one or more of Compounds 1-147, or one or more of Compounds 1-342. Nanoparticle compositions can also include a variety of other components. For example, the nanoparticle composition can include one or more other lipids in addition to a lipid according to formula (I), (III), (IV), (V), or (VI), such as (i) at least one phospholipid, (ii) at least one structural lipid, (iii) at least one PEG-lipid, or (iv) any combination thereof. Inclusion of structural lipid can be optional, for example when lipids according to formula III are used in the lipid nanoparticle compositions of the invention.

In some embodiments, the nanoparticle composition comprises a compound of formula (I) (e.g., Compounds 18, 25, 26 or 48). In some embodiments, the nanoparticle composition comprises a compound of formula (I) (e.g., Compounds 18, 25, 26 or 48) and a phospholipid (e.g., DSPC)

In some embodiments, the nanoparticle composition comprises a compound of formula (III) (e.g., Compound 236). In some embodiments, the nanoparticle composition comprises a compound of formula (III) (e.g., Compound 236) and a phospholipid (e.g., DOPE or DSPC).

In some embodiments, the nanoparticle composition comprises a lipid composition consisting or consisting essentially of compound of formula (I) (e.g., Compounds 18, 25, 26 or 48). In some embodiments, the nanoparticle composition comprises a lipid composition consisting or consisting essentially of a compound of formula (I) (e.g., Compounds 18, 25, 26 or 48) and a phospholipid (e.g., DSPC).

In some embodiments, the nanoparticle composition comprises a lipid composition consisting or consisting essentially of compound of formula (III) (e.g., Compound 236). In some embodiments, the nanoparticle composition comprises a lipid composition consisting or consisting essentially of a compound of formula (III) (e.g., Compound 236) and a phospholipid (e.g., DOPE or DSPC).

In one embodiment, a lipid nanoparticle comprises an ionizable lipid, a structural lipid, a phospholipid, and mRNA. In some embodiments, the LNP comprises an ionizable lipid, a PEG-modified lipid, a sterol and a structural lipid. In some embodiments, the LNP has a molar ratio of about 20-60% ionizable lipid:about 5-25% structural lipid: about 25-55% sterol; and about 0.5-15% PEG-modified lipid. In some embodiments, the LNP comprises a molar ratio of about 50% ionizable lipid, about 1.5% PEG-modified lipid, about 38.5% cholesterol and about 10% structural lipid. In some embodiments, the LNP comprises a molar ratio of about 55% ionizable lipid, about 2.5% PEG lipid, about 32.5% cholesterol and about 10% structural lipid. In some embodiments, the ionizable lipid is an ionizable amino lipid and the structural lipid is a neutral lipid, and the sterol is a cholesterol. In some embodiments, the LNP has a molar ratio of 50:38.5:10:1.5 of ionizable lipid:cholesterol:DSPC: PEG lipid. In some embodiments, the ionizable lipid is Compound 18 or Compound 236, and the PEG lipid is Compound 428.

In some embodiments, the LNP has a molar ratio of 50:38.5:10:1.5 of Compound 18:Cholesterol:Phospholipid: Compound 428. In some embodiments, the LNP has a molar ratio of 50:38.5:10:1.5 of Compound 18:Cholesterol:DSPC: Compound 428.

In some embodiments, the LNP has a molar ratio of 50:38.5:10:1.5 of Compound 236:Cholesterol:Phospholipid: Compound 428. In some embodiments, the LNP has a molar ratio of 50:38.5:10:1.5 of Compound 236:Cholesterol:D-SPC:Compound 428.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". In certain embodiments, an ionizable lipid molecule may comprise an amine group, and can be referred to as an ionizable amino lipid. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidazolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

In addition to these, an ionizable lipid may also be a lipid including a cyclic amine group.

In one embodiment, the ionizable lipid may be selected from, but not limited to, a ionizable lipid described in International Publication Nos. WO2013086354 and WO2013116126; the contents of each of which are herein incorporated by reference in their entirety.

In yet another embodiment, the ionizable lipid may be selected from, but not limited to, formula CLI-CLXXXXII of U.S. Pat. No. 7,404,969; each of which is herein incorporated by reference in their entirety.

In one embodiment, the lipid may be a cleavable lipid such as those described in International Publication No. WO2012170889, herein incorporated by reference in its entirety. In one embodiment, the lipid may be synthesized by methods known in the art and/or as described in International Publication Nos. WO2013086354; the contents of each of which are herein incorporated by reference in their entirety.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide encoding a Citrin polypeptide are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition can depend on the size (expressed as length, or molecular mass), sequence, and other characteristics of the mRNA. The relative amounts of a polynucleotide in a nanoparticle composition can also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

23. Other Delivery Agents a. Liposomes, Lipoplexes, and Lipid Nanoparticles

In some embodiments, the compositions or formulations of the present disclosure comprise a delivery agent, e.g., a liposome, a lioplexes, a lipid nanoparticle, or any combination thereof. The polynucleotides described herein (e.g., a polynucleotide comprising a nucleotide sequence encoding a Citrin polypeptide) can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that can primarily be composed of a lipid bilayer and can be used as a delivery vehicle for the administration of pharmaceutical formulations. Liposomes can be of different sizes. A multilamellar vesicle (MLV) can be hundreds of nanometers in diameter, and can contain a series of concentric bilayers separated by narrow aqueous compartments. A small unicellular vesicle (SUV) can be smaller than 50 nm in diameter, and a large unilamellar vesicle (LUV) can be between 50 and 500 nm in diameter. Liposome design can include, but is not limited to, opsonins or ligands to improve the attachment of liposomes to unhealthy tissue or to activate events such as, but not limited to, endocytosis. Liposomes can contain a low or a high pH value in order to improve the delivery of the pharmaceutical formulations.

The formation of liposomes can depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

As a non-limiting example, liposomes such as synthetic membrane vesicles can be prepared by the methods, apparatus and devices described in U.S. Pub. Nos. US20130177638, US20130177637, US20130177636, US20130177635, US20130177634, US20130177633, US20130183375, US20130183373, and US20130183372. In some embodiments, the polynucleotides described herein can be encapsulated by the liposome and/or it can be contained in an aqueous core that can then be encapsulated by the liposome as described in, e.g., Intl. Pub. Nos. WO2012031046, WO2012031043, WO2012030901, WO2012006378, and WO2013086526; and U.S. Pub. Nos. US20130189351, US20130195969 and US20130202684. Each of the references in herein incorporated by reference in its entirety.

In some embodiments, the polynucleotides described herein can be formulated in a cationic oil-in-water emulsion where the emulsion particle comprises an oil core and a cationic lipid that can interact with the polynucleotide anchoring the molecule to the emulsion particle. In some embodiments, the polynucleotides described herein can be formulated in a water-in-oil emulsion comprising a continuous hydrophobic phase in which the hydrophilic phase is dispersed. Exemplary emulsions can be made by the methods described in Intl. Pub. Nos. WO2012006380 and WO201087791, each of which is herein incorporated by reference in its entirety.

In some embodiments, the polynucleotides described herein can be formulated in a lipid-polycation complex. The formation of the lipid-polycation complex can be accomplished by methods as described in, e.g., U.S. Pub. No. US20120178702. As a non-limiting example, the polycation can include a cationic peptide or a polypeptide such as, but not limited to, polylysine, polyomithine and/or polyarginine and the cationic peptides described in Intl. Pub. No. WO2012013326 or U.S. Pub. No. US20130142818. Each of the references is herein incorporated by reference in its entirety.

In some embodiments, the polynucleotides described herein can be formulated in a lipid nanoparticle (LNP) such as those described in Intl. Pub. Nos. WO2013123523, WO2012170930, WO2011127255 and WO2008103276; and U.S. Pub. No. US20130171646, each of which is herein incorporated by reference in its entirety.

Lipid nanoparticle formulations typically comprise one or more lipids. In some embodiments, the lipid is a cationic or an ionizable lipid. In some embodiments, the lipid is an ionizable lipid (e.g., an ionizable amino lipid), sometimes referred to in the art as an "ionizable cationic lipid". In some embodiments, lipid nanoparticle formulations further comprise other components, including a phospholipid, a structural lipid and a molecule capable of reducing particle aggregation, for example a PEG or PEG-modified lipid.

Exemplary ionizable lipids include, but not limited to, any one of Compounds 1-342 disclosed herein, DLin-MC3-DMA (MC3), DLin-DMA, DLenDMA, DLin-D-DMA, DLin-K-DMA, DLin-M-$C_2$-DMA, DLin-K-DMA, DLin-KC2-DMA, DLin-KC3-DMA, DLin-KC4-DMA, DLin-$C_2$K-DMA, DLin-MP-DMA, DODMA, 98N12-5, C12-200, DLin-C-DAP, DLin-DAC, DLinDAP, DLinAP, DLin-EG-DMA, DLin-2-DMAP, KL10, KL22, KL25, Octyl-CLinDMA, Octyl-CLinDMA (2R), Octyl-CLinDMA (2S), and any combination thereof. Other exemplary ionizable lipids include, (13Z,16Z)—N,N-dimethyl-3-nonyldocosa-13,16-dien-1-amine (L608), (20Z,23Z)—N,N-dimethylnonacosa-20,23-dien-10-amine, (17Z,20Z)—N,N-dimemyl-hexacosa-17,20-dien-9-amine, (16Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-1 O-amine, (15Z)—N,N-dimethyleptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, N,N-dimethyl-1-[(1S,2R)-2-octylcyclopropyl]eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]

methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2 [(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-Bien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine, and (11E,20Z,23Z)—N,N-dimethylnonacosa-11,20,2-trien-10-amine, and any combination thereof.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. In some embodiments, the phospholipids are DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof. In some embodiments, the phospholipids are MPPC, MSPC, PMPC, PSPC, SMPC, SPPC, DHAPE, DOPG, and any combination thereof. In some embodiments, the amount of phospholipids (e.g., DSPC) in the lipid composition ranges from about 1 mol % to about 20 mol %.

The structural lipids include sterols and lipids containing sterol moieties. In some embodiments, the structural lipids include cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the amount of the structural lipids (e.g., cholesterol) in the lipid composition ranges from about 20 mol % to about 60 mol %.

The PEG-modified lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG DMPE, PEG-DPPC, or a PEG-DSPE lipid. In some embodiments, the PEG-lipid are 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG moiety has a size of about 1000, 2000, 5000, 10,000, 15,000 or 20,000 daltons. In some embodiments, the amount of PEG-lipid in the lipid composition ranges from about 0 mol % to about 5 mol %.

In some embodiments, the LNP formulations described herein can additionally comprise a permeability enhancer molecule. Non-limiting permeability enhancer molecules are described in U.S. Pub. No. US20050222064, herein incorporated by reference in its entirety.

The LNP formulations can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP formulation can also contain a polymer conjugate (e.g., a water soluble conjugate) as described in, e.g., U.S. Pub. Nos. US20130059360, US20130196948, and US20130072709. Each of the references is herein incorporated by reference in its entirety.

The LNP formulations can comprise a conjugate to enhance the delivery of nanoparticles of the present invention in a subject. Further, the conjugate can inhibit phagocytic clearance of the nanoparticles in a subject. In some embodiments, the conjugate can be a "self" peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNP formulations can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNP formulations can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Pub. No. US20130183244, herein incorporated by reference in its entirety.

The LNP formulations can be engineered to alter the surface properties of particles so that the lipid nanoparticles can penetrate the mucosal barrier as described in U.S. Pat.

No. 8,241,670 or Intl. Pub. No. WO2013110028, each of which is herein incorporated by reference in its entirety.

The LNP engineered to penetrate mucus can comprise a polymeric material (i.e., a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates.

LNP engineered to penetrate mucus can also include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 domase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., Intl. Pub. No. WO2013110028, herein incorporated by reference in its entirety.

In some embodiments, the polynucleotide described herein is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, MA), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments, the polynucleotides described herein are formulated as a solid lipid nanoparticle (SLN), which can be spherical with an average diameter between 10 to 1000 nm. SLN possess a solid lipid core matrix that can solubilize lipophilic molecules and can be stabilized with surfactants and/or emulsifiers. Exemplary SLN can be those as described in Intl. Pub. No. WO2013105101, herein incorporated by reference in its entirety.

In some embodiments, the polynucleotides described herein can be formulated for controlled release and/or targeted delivery. As used herein, "controlled release" refers to a pharmaceutical composition or compound release profile that conforms to a particular pattern of release to effect a therapeutic outcome. In one embodiment, the polynucleotides can be encapsulated into a delivery agent described herein and/or known in the art for controlled release and/or targeted delivery. As used herein, the term "encapsulate" means to enclose, surround or encase. As it relates to the formulation of the compounds of the invention, encapsulation can be substantial, complete or partial. The term "substantially encapsulated" means that at least greater than 50, 60, 70, 80, 85, 90, 95, 96, 97, 98, 99, or greater than 99% of the pharmaceutical composition or compound of the invention can be enclosed, surrounded or encased within the delivery agent. "Partially encapsulation" means that less than 10, 10, 20, 30, 40 50 or less of the pharmaceutical composition or compound of the invention can be enclosed, surrounded or encased within the delivery agent.

Advantageously, encapsulation can be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, or greater than 99% of the pharmaceutical composition or compound of the invention are encapsulated in the delivery agent.

In some embodiments, the polynucleotide controlled release formulation can include at least one controlled release coating (e.g., OPADRY®, EUDRAGIT RL®, EUDRAGIT RS® and cellulose derivatives such as ethylcellulose aqueous dispersions (AQUACOAT® and SURELEASE®)). In some embodiments, the polynucleotide controlled release formulation can comprise a polymer system as described in U.S. Pub. No. US20130130348, or a PEG and/or PEG related polymer derivative as described in U.S. Pat. No. 8,404,222, each of which is incorporated by reference in its entirety.

In some embodiments, the polynucleotides described herein can be encapsulated in a therapeutic nanoparticle, referred to herein as "therapeutic nanoparticle polynucleotides." Therapeutic nanoparticles can be formulated by methods described in, e.g., Intl. Pub. Nos. WO2010005740, WO2010030763, WO2010005721, WO2010005723, and WO2012054923; and U.S. Pub. Nos. US20110262491, US20100104645, US20100087337, US20100068285, US20110274759, US20100068286, US20120288541, US20120140790, US20130123351 and US20130230567; and U.S. Pat. Nos. 8,206,747, 8,293,276, 8,318,208 and 8,318,211, each of which is herein incorporated by reference in its entirety.

In some embodiments, the therapeutic nanoparticle polynucleotide can be formulated for sustained release. As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle of the polynucleotides described herein can be formulated as disclosed in Intl. Pub. No. WO2010075072 and U.S. Pub. Nos. US20100216804, US20110217377, US20120201859 and US20130150295, each of which is herein incorporated by reference in their entirety.

In some embodiments, the therapeutic nanoparticle polynucleotide can be formulated to be target specific, such as those described in Intl. Pub. Nos. WO2008121949, WO2010005726, WO2010005725, WO2011084521 and WO2011084518; and U.S. Pub. Nos. US20100069426, US20120004293 and US20100104655, each of which is herein incorporated by reference in its entirety.

The LNPs can be prepared using microfluidic mixers or micromixers. Exemplary microfluidic mixers can include, but are not limited to, a slit interdigitial micromixer including, but not limited to those manufactured by Microinnova (Allerheiligen bei Wildon, Austria) and/or a staggered herringbone micromixer (SHM) (see Zhigaltsev et al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging jet (IJMM,) from the Institut für Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos. US20040262223 and US20120276209, each of which is incorporated herein by reference in their entirety.

In some embodiments, the polynucleotides described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the polynucleotides can be formulated in lipid nanoparticles using a micromixer chip such as, but not limited to, those from Harvard Apparatus (Holliston, MA) or Dolomite Microfluidics (Royston, UK). A micromixer chip can be used for rapid mixing of two or more fluid streams with a split and recombine mechanism.

In some embodiments, the polynucleotides described herein can be formulated in lipid nanoparticles having a diameter from about 1 nm to about 100 nm such as, but not limited to, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles can have a diameter from about 10 to 500 nm. In one embodiment, the lipid nanoparticle can have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the polynucleotides can be delivered using smaller LNPs. Such particles can comprise a diameter from below 0.1 μm up to 100 nm such as, but not limited to, less than 0.1 μm, less than 1.0 μm, less than 5 μm, less than 10 μm, less than 15 μm, less than 20 μm, less than 25 μm, less than 30 μm, less than 35 μm, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

The nanoparticles and microparticles described herein can be geometrically engineered to modulate macrophage and/or the immune response. The geometrically engineered particles can have varied shapes, sizes and/or surface charges to incorporate the polynucleotides described herein for targeted delivery such as, but not limited to, pulmonary delivery (see, e.g., Intl. Pub. No. WO2013082111, herein incorporated by reference in its entirety). Other physical features the geometrically engineering particles can include, but are not limited to, fenestrations, angled arms, asymmetry and surface roughness, charge that can alter the interactions with cells and tissues.

In some embodiment, the nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

b. Lipidoids

In some embodiments, the compositions or formulations of the present disclosure comprise a delivery agent, e.g., a lipidoid. The polynucleotides described herein (e.g., a polynucleotide comprising a nucleotide sequence encoding a Citrin polypeptide) can be formulated with lipidoids. Complexes, micelles, liposomes or particles can be prepared containing these lipidoids and therefore to achieve an effective delivery of the polynucleotide, as judged by the production of an encoded protein, following the injection of a lipidoid formulation via localized and/or systemic routes of administration. Lipidoid complexes of polynucleotides can be administered by various means including, but not limited to, intravenous, intramuscular, or subcutaneous routes.

The synthesis of lipidoids is described in literature (see Mahon et al., Bioconjug. Chem. 2010 21:1448-1454; Schroeder et al., J Intern Med. 2010 267:9-21; Akinc et al., Nat Biotechnol. 2008 26:561-569; Love et al., Proc Natl Acad Sci US A. 2010 107:1864-1869; Siegwart et al., Proc Natl Acad Sci USA. 2011 108:12996-3001; all of which are incorporated herein in their entireties).

Formulations with the different lipidoids, including, but not limited to penta[3-(1-laurylaminopropionyl)]-triethylenetetramine hydrochloride (TETA-SLAP; also known as 98N12-5, see Murugaiah et al., Analytical Biochemistry, 401:61 (2010)), C12-200 (including derivatives and variants), and MD1, can be tested for in vivo activity. The lipidoid "98N12-5" is disclosed by Akinc et al., Mol Ther. 2009 17:872-879. The lipidoid "C12-200" is disclosed by Love et al., Proc Natl Acad Sci US A. 2010 107:1864-1869 and Liu and Huang, Molecular Therapy. 2010 669-670. Each of the references is herein incorporated by reference in its entirety.

In one embodiment, the polynucleotides described herein can be formulated in an aminoalcohol lipidoid. Aminoalcohol lipidoids can be prepared by the methods described in U.S. Pat. No. 8,450,298 (herein incorporated by reference in its entirety).

The lipidoid formulations can include particles comprising either 3 or 4 or more components in addition to polynucleotides. Lipidoids and polynucleotide formulations comprising lipidoids are described in Intl. Pub. No. WO 2015051214 (herein incorporated by reference in its entirety.

c. Hyaluronidase

In some embodiments, the polynucleotides described herein (e.g., a polynucleotide comprising a nucleotide sequence encoding a Citrin polypeptide) and hyaluronidase for injection (e.g., intramuscular or subcutaneous injection). Hyaluronidase catalyzes the hydrolysis of hyaluronan, which is a constituent of the interstitial barrier. Hyaluronidase lowers the viscosity of hyaluronan, thereby increases tissue permeability (Frost, Expert Opin. Drug Deliv. (2007) 4:427-440). Alternatively, the hyaluronidase can be used to increase the number of cells exposed to the polynucleotides administered intramuscularly or subcutaneously.

d. Nanoparticle Mimics

In some embodiments, the polynucleotides described herein (e.g., a polynucleotide comprising a nucleotide sequence encoding a Citrin polypeptide) is encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example, the polynucleotides described herein can be encapsulated in a non-viron particle that can mimic the delivery function of a virus (see e.g., Intl. Pub. No. WO2012006376 and U.S. Pub. Nos. US20130171241 and US20130195968, each of which is herein incorporated by reference in its entirety).

e. Nanotubes

In some embodiments, the compositions or formulations of the present disclosure comprise the polynucleotides described herein (e.g., a polynucleotide comprising a nucleotide sequence encoding a Citrin polypeptide) attached or otherwise bound to (e.g., through steric, ionic, covalent and/or other forces) at least one nanotube, such as, but not limited to, rosette nanotubes, rosette nanotubes having twin bases with a linker, carbon nanotubes and/or single-walled carbon nanotubes. Nanotubes and nanotube formulations comprising a polynucleotide are described in, e.g., Intl. Pub. No. WO2014152211, herein incorporated by reference in its entirety.

f. Self-Assembled Nanoparticles, or Self-Assembled Macromolecules

In some embodiments, the compositions or formulations of the present disclosure comprise the polynucleotides described herein (e.g., a polynucleotide comprising a nucleotide sequence encoding a Citrin polypeptide) in self-assembled nanoparticles, or amphiphilic macromolecules (AMs) for delivery. AMs comprise biocompatible amphiphilic polymers that have an alkylated sugar backbone covalently linked to poly(ethylene glycol). In aqueous solution, the AMs self-assemble to form micelles. Nucleic acid self-assembled nanoparticles are described in Intl. Appl. No. PCT/US2014/027077, and AMs and methods of forming AMs are described in U.S. Pub. No. US20130217753, each of which is herein incorporated by reference in its entirety.

g. Inorganic Nanoparticles, Semi-Conductive and Metallic Nanoparticles

In some embodiments, the compositions or formulations of the present disclosure comprise the polynucleotides described herein (e.g., a polynucleotide comprising a nucleotide sequence encoding a Citrin polypeptide) in inorganic nanoparticles, or water-dispersible nanoparticles comprising a semiconductive or metallic material. The inorganic nanoparticles can include, but are not limited to, clay substances that are water swellable. The water-dispersible nanoparticles can be hydrophobic or hydrophilic nanoparticles. As a non-limiting example, the inorganic, semi-conductive and metallic nanoparticles are described in, e.g., U.S. Pat. Nos. 5,585,108 and 8,257,745; and U.S. Pub. Nos. US20120228565, US 20120265001 and US 20120283503, each of which is herein incorporated by reference in their entirety.

h. Surgical Sealants: Gels and Hydrogels

In some embodiments, the compositions or formulations of the present disclosure comprise the polynucleotides described herein (e.g., a polynucleotide comprising a nucleotide sequence encoding a Citrin polypeptide) in a surgical sealant. Surgical sealants such as gels and hydrogels are described in Intl. Appl. No. PCT/US2014/027077, herein incorporated by reference in its entirety.

i. Suspension Formulations

In some embodiments, the compositions or formulations of the present disclosure comprise the polynucleotides described herein (e.g., a polynucleotide comprising a nucleotide sequence encoding a Citrin polypeptide) in suspensions. In some embodiments, suspensions comprise a polynucleotide, water immiscible oil depots, surfactants and/or co-surfactants and/or co-solvents. Suspensions can be formed by first preparing an aqueous solution of a polynucleotide and an oil-based phase comprising one or more surfactants, and then mixing the two phases (aqueous and oil-based).

Exemplary oils for suspension formulations can include, but are not limited to, sesame oil and Miglyol (comprising esters of saturated coconut and palmkernel oil-derived caprylic and capric fatty acids and glycerin or propylene glycol), corn oil, soybean oil, peanut oil, beeswax and/or palm seed oil. Exemplary surfactants can include, but are not limited to Cremophor, polysorbate 20, polysorbate 80, polyethylene glycol, transcutol, Capmul®, labrasol, isopropyl myristate, and/or Span 80. In some embodiments, suspensions can comprise co-solvents including, but not limited to ethanol, glycerol and/or propylene glycol.

In some embodiments, suspensions can provide modulation of the release of the polynucleotides into the surrounding environment by diffusion from a water immiscible depot followed by resolubilization into a surrounding environment (e.g., an aqueous environment).

In some embodiments, the polynucleotides can be formulated such that upon injection, an emulsion forms spontaneously (e.g., when delivered to an aqueous phase), which can provide a high surface area to volume ratio for release of polynucleotides from an oil phase to an aqueous phase. In some embodiments, the polynucleotide is formulated in a nanoemulsion, which can comprise a liquid hydrophobic core surrounded by or coated with a lipid or surfactant layer. Exemplary nanoemulsions and their preparations are described in, e.g., U.S. Pat. No. 8,496,945, herein incorporated by reference in its entirety.

Cations and Anions

In some embodiments, the compositions or formulations of the present disclosure comprise the polynucleotides described herein (e.g., a polynucleotide comprising a nucleotide sequence encoding a Citrin polypeptide) and a cation or anion, such as $Zn^{2+}$, $Ca^{2+}$, $Cu^{2+}$, $Mg^{2+}$ and combinations thereof. Exemplary formulations can include polymers and a polynucleotide complexed with a metal cation as described in, e.g., U.S. Pat. Nos. 6,265,389 and 6,555,525, each of which is herein incorporated by reference in its entirety. In some embodiments, cationic nanoparticles can contain a combination of divalent and monovalent cations. The delivery of polynucleotides in cationic nanoparticles or in one or more depot comprising cationic nanoparticles can improve polynucleotide bioavailability by acting as a long-acting depot and/or reducing the rate of degradation by nucleases.

k. Molded Nanoparticles and Microparticles

In some embodiments, the compositions or formulations of the present disclosure comprise the polynucleotides described herein (e.g., a polynucleotide comprising a nucleotide sequence encoding a Citrin polypeptide) in molded nanoparticles in various sizes, shapes and chemistry. For example, the nanoparticles and/or microparticles can be made using the PRINT® technology by LIQUIDA TECHNOLOGIES® (Morrisville, NC) (e.g., International Pub. No. WO2007024323, herein incorporated by reference in its entirety).

In some embodiments, the polynucleotides described herein (e.g., a polynucleotide comprising a nucleotide sequence encoding a Citrin polypeptide) is formulated in microparticles. The microparticles can contain a core of the polynucleotide and a cortex of a biocompatible and/or biodegradable polymer, including but not limited to, poly (a-hydroxy acid), a polyhydroxy butyric acid, a polycaprolactone, a polyorthoester and a polyanhydride. The microparticle can have adsorbent surfaces to adsorb polynucleotides. The microparticles can have a diameter of from at least 1 micron to at least 100 microns (e.g., at least 1 micron, at least 10 micron, at least 20 micron, at least 30 micron, at least 50 micron, at least 75 micron, at least 95 micron, and at least 100 micron). In some embodiment, the compositions or formulations of the present disclosure are microemulsions comprising microparticles and polynucleotides. Exemplary microparticles, microemulsions and their preparations are described in, e.g., U.S. Pat. Nos. 8,460,709, 8,309,139 and 8,206,749; U.S. Pub. Nos. US20130129830, US2013195923 and US20130195898; and Intl. Pub. No. WO2013075068, each of which is herein incorporated by reference in its entirety.

l. NanoJackets and NanoLiposomes

In some embodiments, the compositions or formulations of the present disclosure comprise the polynucleotides described herein (e.g., a polynucleotide comprising a nucleotide sequence encoding a Citrin polypeptide) in NanoJackets and NanoLiposomes by Keystone Nano (State College, PA). NanoJackets are made of materials that are naturally found in the body including calcium, phosphate and can also include a small amount of silicates. Nanojackets can have a size ranging from 5 to 50 nm.

NanoLiposomes are made of lipids such as, but not limited to, lipids that naturally occur in the body. NanoLiposomes can have a size ranging from 60-80 nm. In some embodiments, the polynucleotides disclosed herein are formulated in a NanoLiposome such as, but not limited to, Ceramide NanoLiposomes.

m. Cells or Minicells

In some embodiments, the compositions or formulations of the present disclosure comprise the polynucleotides described herein (e.g., a polynucleotide comprising a nucleotide sequence encoding a Citrin polypeptide) that is transfected ex vivo into cells, which are subsequently transplanted into a subject. Cell-based formulations of the polynucleotide disclosed herein can be used to ensure cell transfection (e.g., in the cellular carrier), alter the biodistribution of the polynucleotide (e.g., by targeting the cell carrier to specific tissues or cell types), and/or increase the translation of encoded protein.

Exemplary cells include, but are not limited to, red blood cells, virosomes, and electroporated cells (see e.g., Godfrin et al., Expert Opin Biol Ther. 2012 12:127-133; Fang et al., Expert Opin Biol Ther. 2012 12:385-389; Hu et al., Proc Natl Acad Sci USA. 2011 108:10980-10985; Lund et al., Pharm Res. 2010 27:400-420; Huckriede et al., J Liposome Res. 2007; 17:39-47; Cusi, Hum Vaccin. 2006 2:1-7; de Jonge et al., Gene Ther. 2006 13:400-411; all of which are herein incorporated by reference in its entirety).

A variety of methods are known in the art and are suitable for introduction of nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

In some embodiments, the polynucleotides described herein can be delivered in synthetic virus-like particles (VLPs) synthesized by the methods as described in Intl. Pub Nos. WO2011085231 and WO2013116656; and U.S. Pub. No. 20110171248, each of which is herein incorporated by reference in its entirety.

The technique of sonoporation, or cellular sonication, is the use of sound (e.g., ultrasonic frequencies) for modifying the permeability of the cell plasma membrane. Sonoporation methods are known to deliver nucleic acids in vivo (Yoon and Park, Expert Opin Drug Deliv. 2010 7:321-330; Postema and Gilja, Curr Pharm Biotechnol. 2007 8:355-361; Newman and Bettinger, Gene Ther. 2007 14:465-475; U.S. Pub. Nos. US20100196983 and US20100009424; all herein incorporated by reference in their entirety).

In some embodiments, the polynucleotides described herein can be delivered by electroporation. Electroporation techniques are known to deliver nucleic acids in vivo and clinically (Andre et al., Curr Gene Ther. 2010 10:267-280; Chiarella et al., Curr Gene Ther. 2010 10:281-286; Hojman, Curr Gene Ther. 2010 10:128-138; all herein incorporated by reference in their entirety). Electroporation devices are sold by many companies worldwide including, but not limited to BTX® Instruments (Holliston, MA) (e.g., the AgilePulse In Vivo System) and Inovio (Blue Bell, PA) (e.g., Inovio SP-5P intramuscular delivery device or the CEL-LECTRA® 3000 intradermal delivery device).

In some embodiments, the cells are selected from the group consisting of mammalian cells, bacterial cells, plant, microbial, algal and fungal cells. In some embodiments, the cells are mammalian cells, such as, but not limited to, human, mouse, rat, goat, horse, rabbit, hamster or cow cells. In a further embodiment, the cells can be from an established cell line, including, but not limited to, HeLa, NS0, SP2/0, KEK 293T, Vero, Caco, Caco-2, MDCK, COS-1, COS-7, K562, Jurkat, CHO-K1, DG44, CHOK1SV, CHO-S, Huvec, CV-1, Huh-7, NIH3T3, HEK293, 293, A549, HepG2, IMR-90, MCF-7, U-20S, Per.C$_6$, SF9, SF21 or Chinese Hamster Ovary (CHO) cells.

In certain embodiments, the cells are fungal cells, such as, but not limited to, *Chrysosporium* cells, *Aspergillus* cells, *Trichoderma* cells, *Dictyostelium* cells, *Candida* cells, *Saccharomyces* cells, *Schizosaccharomyces* cells, and *Penicillium* cells.

In certain embodiments, the cells are bacterial cells such as, but not limited to, *E. coli*, *B. subtilis*, or BL21 cells. Primary and secondary cells to be transfected by the methods of the invention can be obtained from a variety of tissues and include, but are not limited to, all cell types that can be maintained in culture. The primary and secondary cells include, but are not limited to, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Primary cells can also be obtained from a donor of the same species or from another species (e.g., mouse, rat, rabbit, cat, dog, pig, cow, bird, sheep, goat, horse).

In some embodiments, the compositions or formulations of the present disclosure comprise the polynucleotides described herein in bacterial minicells. As a non-limiting example, bacterial minicells can be those described in Intl. Pub. No. WO2013088250 or U.S. Pub. No. US20130177499, each of which is herein incorporated by reference in its entirety.

n. Semi-Solid Compositions

In some embodiments, the compositions or formulations of the present disclosure comprise the polynucleotides described herein (e.g., a polynucleotide comprising a nucleotide sequence encoding a Citrin polypeptide) in a hydrophobic matrix to form a semi-solid or paste-like composition. As a non-limiting example, the semi-solid or paste-like composition can be made by the methods described in Intl. Pub. No. WO201307604, herein incorporated by reference in its entirety.

o. Exosomes

In some embodiments, the compositions or formulations of the present disclosure comprise the polynucleotides described herein (e.g., a polynucleotide comprising a nucleotide sequence encoding a Citrin polypeptide) in exosomes, which can be loaded with at least one polynucleotide and delivered to cells, tissues and/or organisms. As a non-limiting example, the polynucleotides can be loaded in the exosomes as described in Intl. Pub. No. WO2013084000, herein incorporated by reference in its entirety.

p. Silk-Based Delivery

In some embodiments, the compositions or formulations of the present disclosure comprise the polynucleotides described herein (e.g., a polynucleotide comprising a nucleotide sequence encoding a Citrin polypeptide) that is formulated for silk-based delivery. The silk-based delivery system can be formed by contacting a silk fibroin solution with a polynucleotide described herein. As a non-limiting example, a sustained release silk-based delivery system and methods of making such system are described in U.S. Pub. No. US20130177611, herein incorporated by reference in its entirety.

q. Amino Acid Lipids

In some embodiments, the compositions or formulations of the present disclosure comprise the polynucleotides described herein (e.g., a polynucleotide comprising a nucleotide sequence encoding a Citrin polypeptide) that is formulation with an amino acid lipid. Amino acid lipids are lipophilic compounds comprising an amino acid residue and one or more lipophilic tails. Non-limiting examples of amino acid lipids and methods of making amino acid lipids are described in U.S. Pat. No. 8,501,824. The amino acid lipid formulations can deliver a polynucleotide in releasable form that comprises an amino acid lipid that binds and releases the polynucleotides. As a non-limiting example, the release of the polynucleotides described herein can be provided by an acid-labile linker as described in, e.g., U.S. Pat. Nos. 7,098,032, 6,897,196, 6,426,086, 7,138,382, 5,563,250, and 5,505,931, each of which is herein incorporated by reference in its entirety.

r. Microvesicles

In some embodiments, the compositions or formulations of the present disclosure comprise the polynucleotides described herein (e.g., a polynucleotide comprising a nucleotide sequence encoding a Citrin polypeptide) in a microvesicle formulation. Exemplary microvesicles include those described in U.S. Pub. No. US20130209544 (herein incorporated by reference in its entirety). In some embodiments, the microvesicle is an ARRDC1-mediated microvesicles (ARMMs) as described in Intl. Pub. No. WO2013119602 (herein incorporated by reference in its entirety).

s. Interpolyelectrolyte Complexes

In some embodiments, the compositions or formulations of the present disclosure comprise the polynucleotides described herein (e.g., a polynucleotide comprising a nucleotide sequence encoding a Citrin polypeptide) in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368, herein incorporated by reference in its entirety.

t. Crystalline Polymeric Systems

In some embodiments, the compositions or formulations of the present disclosure comprise the polynucleotides described herein (e.g., a polynucleotide comprising a nucleotide sequence encoding a Citrin polypeptide) in crystalline polymeric systems. Crystalline polymeric systems are polymers with crystalline moieties and/or terminal units comprising crystalline moieties. Exemplary polymers are described in U.S. Pat. No. 8,524,259 (herein incorporated by reference in its entirety).

u. Polymers, Biodegradable Nanoparticles, and Core-Shell Nanoparticles

In some embodiments, the compositions or formulations of the present disclosure comprise the polynucleotides described herein (e.g., a polynucleotide comprising a nucleotide sequence encoding a Citrin polypeptide) and a natural and/or synthetic polymer. The polymers include, but not limited to, polyethenes, polyethylene glycol (PEG), poly(1-lysine) (PLL), PEG grafted to PLL, cationic lipopolymer, biodegradable cationic lipopolymer, polyethyleneimine (PEI), cross-linked branched poly(alkylene imines), a polyamine derivative, a modified poloxamer, elastic biodegradable polymer, biodegradable copolymer, biodegradable polyester copolymer, biodegradable polyester copolymer, multiblock copolymers, poly[α-(4-aminobutyl)-L-glycolic acid) (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyureas, polystyrenes, polyamines, polylysine, poly(ethylene imine), poly(serine ester), poly(L-lactide-co-L-lysine), poly(4-hydroxy-L-proline ester), amine-containing polymers, dextran polymers, dextran polymer derivatives or combinations thereof.

Exemplary polymers include, DYNAMIC POLYCONJUGATE® (Arrowhead Research Corp., Pasadena, CA) formulations from MIRUS® Bio (Madison, WI) and Roche Madison (Madison, WI), PHASERX™ polymer formulations such as, without limitation, SMARTT POLYMER TECHNOLOGY™ (PHASERX®, Seattle, WA), DMRU-DOPE, poloxamer, VAXFECTIN® adjuvant from Vical (San Diego, CA), chitosan, cyclodextrin from Calando Pharmaceuticals (Pasadena, CA), dendrimers and poly(lactic-co-glycolic acid) (PLGA) polymers. RONDEL™ (RNAi/Oligonucleotide Nanoparticle Delivery) polymers (Arrowhead Research Corporation, Pasadena, CA) and pH responsive co-block polymers such as PHASERX® (Seattle, WA).

The polymer formulations allow a sustained or delayed release of the polynucleotide (e.g., following intramuscular or subcutaneous injection). The altered release profile for the polynucleotide can result in, for example, translation of an encoded protein over an extended period of time. The polymer formulation can also be used to increase the stability of the polynucleotide. Sustained release formulations can include, but are not limited to, PLGA microspheres, ethylene vinyl acetate (EVAc), poloxamer, GELSITE® (Nanotherapeutics, Inc. Alachua, FL), HYLENEX® (Halozyme Therapeutics, San Diego CA), surgical sealants such as fibrinogen polymers (Ethicon Inc. Cornelia, GA), TISSELL® (Baxter International, Inc. Deerfield, IL), PEG-based sealants, and COSEAL® (Baxter International, Inc. Deerfield, IL).

As a non-limiting example modified mRNA can be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradable, biocompatible polymers that are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C.

As a non-limiting example, the polynucleotides described herein can be formulated with the polymeric compound of PEG grafted with PLL as described in U.S. Pat. No. 6,177,274. As another non-limiting example, the polynucleotides described herein can be formulated with a block copolymer such as a PLGA-PEG block copolymer (see e.g., U.S. Pub. No. US20120004293 and U.S. Pat. Nos. 8,236,330 and 8,246,968), or a PLGA-PEG-PLGA block copolymer (see e.g., U.S. Pat. No. 6,004,573). Each of the references is herein incorporated by reference in its entirety.

In some embodiments, the polynucleotides described herein can be formulated with at least one amine-containing polymer such as, but not limited to polylysine, polyethylene imine, poly(amidoamine) dendrimers, poly(amine-co-esters) or combinations thereof. Exemplary polyamine polymers and their use as delivery agents are described in, e.g., U.S. Pat. Nos. 8,460,696, 8,236,280, each of which is herein incorporated by reference in its entirety.

In some embodiments, the polynucleotides described herein can be formulated in a biodegradable cationic lipopolymer, a biodegradable polymer, or a biodegradable copolymer, a biodegradable polyester copolymer, a biodegradable polyester polymer, a linear biodegradable copolymer, PAGA, a biodegradable cross-linked cationic multi-block copolymer or combinations thereof as described in, e.g., U.S. Pat. Nos. 6,696,038, 6,517,869, 6,267,987, 6,217,912, 6,652,886, 8,057,821, and 8,444,992; U.S. Pub. Nos. US20030073619, US20040142474, US20100004315, US2012009145 and US20130195920; and Intl Pub. Nos. WO2006063249 and WO2013086322, each of which is herein incorporated by reference in its entirety.

In some embodiments, the polynucleotides described herein can be formulated in or with at least one cyclodextrin polymer as described in U.S. Pub. No. US20130184453. In some embodiments, the polynucleotides described herein can be formulated in or with at least one crosslinked cation-binding polymers as described in Intl. Pub. Nos. WO2013106072, WO2013106073 and WO2013106086. In some embodiments, the polynucleotides described herein can be formulated in or with at least PEGylated albumin polymer as described in U.S. Pub. No. US20130231287. Each of the references is herein incorporated by reference in its entirety.

In some embodiments, the polynucleotides disclosed herein can be formulated as a nanoparticle using a combination of polymers, lipids, and/or other biodegradable agents, such as, but not limited to, calcium phosphate. Components can be combined in a core-shell, hybrid, and/or layer-by-layer architecture, to allow for fine-tuning of the nanoparticle for delivery (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in their entireties). As a non-limiting example, the nanoparticle can comprise a plurality of polymers such as, but not limited to hydrophilic-hydrophobic polymers (e.g., PEG-PLGA), hydrophobic polymers (e.g., PEG) and/or hydrophilic polymers (Intl. Pub. No. WO20120225129, herein incorporated by reference in its entirety).

The use of core-shell nanoparticles has additionally focused on a high-throughput approach to synthesize cationic cross-linked nanogel cores and various shells (Siegwart et al., Proc Natl Acad Sci US A. 2011 108:12996-13001; herein incorporated by reference in its entirety). The complexation, delivery, and internalization of the polymeric nanoparticles can be precisely controlled by altering the chemical composition in both the core and shell components of the nanoparticle. For example, the core-shell nanoparticles can efficiently deliver siRNA to mouse hepatocytes after they covalently attach cholesterol to the nanoparticle.

In some embodiments, a hollow lipid core comprising a middle PLGA layer and an outer neutral lipid layer containing PEG can be used to delivery of the polynucleotides as described herein. In some embodiments, the lipid nanoparticles can comprise a core of the polynucleotides disclosed herein and a polymer shell, which is used to protect the polynucleotides in the core. The polymer shell can be any of the polymers described herein and are known in the art., the polymer shell can be used to protect the polynucleotides in the core.

Core-shell nanoparticles for use with the polynucleotides described herein are described in U.S. Pat. No. 8,313,777 or Intl. Pub. No. WO2013124867, each of which is herein incorporated by reference in their entirety.

v. Peptides and Proteins

In some embodiments, the compositions or formulations of the present disclosure comprise the polynucleotides described herein (e.g., a polynucleotide comprising a nucleotide sequence encoding a Citrin polypeptide) that is formulated with peptides and/or proteins to increase transfection of cells by the polynucleotide, and/or to alter the biodistribution of the polynucleotide (e.g., by targeting specific tissues or cell types), and/or increase the translation of encoded protein (e.g., Intl. Pub. Nos. WO2012110636 and WO2013123298. In some embodiments, the peptides can be those described in U.S. Pub. Nos. US20130129726, US20130137644 and US20130164219. Each of the references is herein incorporated by reference in its entirety.

w. Conjugates

In some embodiments, the compositions or formulations of the present disclosure comprise the polynucleotides described herein (e.g., a polynucleotide comprising a nucleotide sequence encoding a Citrin polypeptide) that is covalently linked to a carrier or targeting group, or including two encoding regions that together produce a fusion protein (e.g., bearing a targeting group and therapeutic protein or peptide) as a conjugate. The conjugate can be a peptide that selectively directs the nanoparticle to neurons in a tissue or organism, or assists in crossing the blood-brain barrier.

The conjugates include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In some embodiments, the conjugate can function as a carrier for the polynucleotide disclosed herein. The conjugate can comprise a cationic polymer such as, but not limited to, polyamine, polylysine, polyalkylenimine, and polyethylenimine that can be grafted to with poly(ethylene glycol). Exemplary conjugates and their preparations are described in U.S. Pat. No. 6,586,524 and U.S. Pub. No. US20130211249, each of which herein is incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as an endothelial cell or bone cell. Targeting groups can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent frucose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein. As a non-limiting example, the targeting group can be a glutathione receptor (GR)-binding conjugate for targeted delivery across the blood-central nervous system barrier as described in, e.g., U.S. Pub. No. US2013021661012 (herein incorporated by reference in its entirety).

In some embodiments, the conjugate can be a synergistic biomolecule-polymer conjugate, which comprises a long-acting continuous-release system to provide a greater therapeutic efficacy. The synergistic biomolecule-polymer conjugate can be those described in U.S. Pub. No. US20130195799. In some embodiments, the conjugate can be an aptamer conjugate as described in Intl. Pat. Pub. No. WO2012040524. In some embodiments, the conjugate can be an amine containing polymer conjugate as described in U.S. Pat. No. 8,507,653. Each of the references is herein incorporated by reference in its entirety. In some embodiments, the polynucleotides can be conjugated to SMARTT POLYMER TECHNOLOGY® (PHASERX®, Inc. Seattle, WA).

In some embodiments, the polynucleotides described herein are covalently conjugated to a cell penetrating polypeptide, which can also include a signal sequence or a targeting sequence. The conjugates can be designed to have increased stability, and/or increased cell transfection; and/or altered the biodistribution (e.g., targeted to specific tissues or cell types).

In some embodiments, the polynucleotides described herein can be conjugated to an agent to enhance delivery. In some embodiments, the agent can be a monomer or polymer such as a targeting monomer or a polymer having targeting blocks as described in Intl. Pub. No. WO2011062965. In some embodiments, the agent can be a transport agent covalently coupled to a polynucleotide as described in, e.g., U.S. Pat. Nos. 6,835.393 and 7,374,778. In some embodiments, the agent can be a membrane barrier transport enhancing agent such as those described in U.S. Pat. Nos. 7,737,108 and 8,003,129. Each of the references is herein incorporated by reference in its entirety.

x. Micro-Organs

In some embodiments, the compositions or formulations of the present disclosure comprise the polynucleotides described herein (e.g., a polynucleotide comprising a nucleotide sequence encoding a Citrin polypeptide) in a micro-organ that can then express an encoded polypeptide of interest in a long-lasting therapeutic formulation. Exemplary micro-organs and formulations are described in Intl. Pub. No. WO2014152211 (herein incorporated by reference in its entirety).

y. Pseudovirions

In some embodiments, the compositions or formulations of the present disclosure comprise the polynucleotides described herein (e.g., a polynucleotide comprising a nucleotide sequence encoding a Citrin polypeptide) in pseudovirions (e.g., pseudovirions developed by Aura Biosciences, Cambridge, MA).

The pseudovirion used for delivering the polynucleotides can be derived from viruses such as, but not limited to, herpes and papillomaviruses as described in, e.g., U.S. Pub. Nos. US20130012450, US20130012566, US21030012426 and US20120207840; and Intl. Pub. No. WO2013009717, each of which is herein incorporated by reference in its entirety.

The pseudovirion can be a virus-like particle (VLP) prepared by the methods described in U.S. Pub. Nos. US20120015899 and US20130177587, and Intl. Pub. Nos. WO2010047839, WO2013116656, WO2013106525 and WO2013122262. In one aspect, the VLP can be bacteriophages MS, Qβ, R17, fr, GA, Sp, MI, I, MXI, NL95, AP205, f2, PP7, and the plant viruses Turnip crinkle virus (TCV), Tomato bushy stunt virus (TBSV), Southern bean mosaic virus (SBMV) and members of the genus *Bromovirus* including Broad bean mottle virus, Brome mosaic virus, *Cassia* yellow blotch virus, Cowpea chlorotic mottle virus (CCMV), Melandrilun yellow fleck virus, and Spring beauty latent virus. In another aspect, the VLP can be derived from the influenza virus as described in U.S. Pub. No. US20130177587 and U.S. Pat. No. 8,506,967. In one aspect, the VLP can comprise a B7-1 and/or B7-2 molecule anchored to a lipid membrane or the exterior of the particle such as described in Intl. Pub. No. WO2013116656. In one aspect, the VLP can be derived from norovirus, rotavirus recombinant VP6 protein or double layered VP2/VP6 such as the VLP as described in Intl. Pub. No. WO2012049366. Each of the references is herein incorporated by reference in its entirety.

In some embodiments, the pseudovirion can be a human papilloma virus-like particle as described in Intl. Pub. No. WO2010120266 and U.S. Pub. No. US20120171290. In some embodiments, the virus-like particle (VLP) can be a self-assembled particle. In one aspect, the pseudovirions can be virion derived nanoparticles as described in U.S. Pub. Nos. US20130116408 and US20130115247; and Intl. Pub. No. WO2013119877. Each of the references is herein incorporated by reference in their entirety.

Non-limiting examples of formulations and methods for formulating the polynucleotides described herein are also provided in Intl. Pub No WO2013090648 (incorporated herein by reference in their entirety).

24. Accelerated Blood Clearance

The invention provides compounds, compositions and methods of use thereof for reducing the effect of ABC on a repeatedly administered active agent such as a biologically active agent. As will be readily apparent, reducing or eliminating altogether the effect of ABC on an administered active agent effectively increases its half-life and thus its efficacy.

In some embodiments the term reducing ABC refers to any reduction in ABC in comparison to a positive reference control ABC inducing LNP such as an MC3 LNP. ABC inducing LNPs cause a reduction in circulating levels of an active agent upon a second or subsequent administration within a given time frame. Thus a reduction in ABC refers to less clearance of circulating agent upon a second or subsequent dose of agent, relative to a standard LNP. The reduction may be, for instance, at least 10%, 15%, 20%, 25%, 30%, 35%, 40%, 45%, 50%, 55%, 60%, 65%, 70%, 75%, 80%, 85%, 90%, 95%, 98%, or 100%. In some embodiments the reduction is 10-100%, 10-50%, 20-100%, 20-50%, 30-100%, 30-50%, 40%-100%, 40-80%, 50-90%, or 50-100%. Alternatively the reduction in ABC may be characterized as at least a detectable level of circulating agent following a second or subsequent administration or at least a 2 fold, 3 fold, 4 fold, 5 fold increase in circulating agent relative to circulating agent following administration of a standard LNP. In some embodiments the reduction is a 2-100 fold, 2-50 fold, 3-100 fold, 3-50 fold, 3-20 fold, 4-100 fold, 4-50 fold, 4-40 fold, 4-30 fold, 4-25 fold, 4-20 fold, 4-15 fold, 4-10 fold, 4-5 fold, 5-100 fold, 5-50 fold, 5-40 fold, 5-30 fold, 5-25 fold, 5-20 fold, 5-15 fold, 5-10 fold, 6-100 fold, 6-50 fold, 6-40 fold, 6-30 fold, 6-25 fold, 6-20 fold, 6-15 fold, 6-10 fold, 8-100 fold, 8-50 fold, 8-40 fold, 8-30 fold, 8-25 fold, 8-20 fold, 8-15 fold, 8-10 fold, 10-100 fold, 10-50 fold, 10-40 fold, 10-30 fold, 10-25 fold, 10-20 fold, 10-15 fold, 20-100 fold, 20-50 fold, 20-40 fold, 20-30 fold, or 20-25 fold.

The disclosure provides lipid-comprising compounds and compositions that are less susceptible to clearance and thus have a longer half-life in vivo. This is particularly the case where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which certain exogenously administered agents are rapidly cleared from the blood upon second and subsequent administrations. This phenomenon has been observed, in part, for a variety of lipid-containing compositions including but not limited to lipidated agents, liposomes or other lipid-based delivery vehicles, and lipid-encapsulated agents. Heretofore, the basis of ABC has been poorly understood and in some cases attributed to a humoral immune response and accordingly strategies for limiting its impact in vivo particularly in a clinical setting have remained elusive.

This disclosure provides compounds and compositions that are less susceptible, if at all susceptible, to ABC. In some important aspects, such compounds and compositions are lipid-comprising compounds or compositions. The lipid-containing compounds or compositions of this disclosure, surprisingly, do not experience ABC upon second and subsequent administration in vivo. This resistance to ABC renders these compounds and compositions particularly suitable for repeated use in vivo, including for repeated use within short periods of time, including days or 1-2 weeks. This enhanced stability and/or half-life is due, in part, to the inability of these compositions to activate B1a and/or B1b cells and/or conventional B cells, pDCs and/or platelets.

This disclosure therefore provides an elucidation of the mechanism underlying accelerated blood clearance (ABC). It has been found, in accordance with this disclosure and the inventions provided herein, that the ABC phenomenon at least as it relates to lipids and lipid nanoparticles is mediated, at least in part an innate immune response involving B1a and/or B1b cells, pDC and/or platelets. B1a cells are normally responsible for secreting natural antibody, in the form of circulating IgM. This IgM is poly-reactive, meaning that it is able to bind to a variety of antigens, albeit with a relatively low affinity for each.

It has been found in accordance with the invention that some lipidated agents or lipid-comprising formulations such as lipid nanoparticles administered in vivo trigger and are subject to ABC. It has now been found in accordance with the invention that upon administration of a first dose of the LNP, one or more cells involved in generating an innate immune response (referred to herein as sensors) bind such agent, are activated, and then initiate a cascade of immune factors (referred to herein as effectors) that promote ABC and toxicity. For instance, B1a and B1b cells may bind to LNP, become activated (alone or in the presence of other sensors such as pDC and/or effectors such as IL6) and secrete natural IgM that binds to the LNP. Pre-existing natural IgM in the subject may also recognize and bind to the LNP, thereby triggering complement fixation. After administration of the first dose, the production of natural IgM begins within 1-2 hours of administration of the LNP. Typically by about 2-3 weeks the natural IgM is cleared from the system due to the natural half-life of IgM. Natural IgG is produced beginning around 96 hours after administration of the LNP. The agent, when administered in a naïve setting, can exert its biological effects relatively unencumbered by the natural IgM produced post-activation of the B1a cells or B1b cells or natural IgG. The natural IgM and natural IgG are non-specific and thus are distinct from anti-PEG IgM and anti-PEG IgG.

Although Applicant is not bound by mechanism, it is proposed that LNPs trigger ABC and/or toxicity through the following mechanisms. It is believed that when an LNP is administered to a subject the LNP is rapidly transported through the blood to the spleen. The LNPs may encounter immune cells in the blood and/or the spleen. A rapid innate immune response is triggered in response to the presence of the LNP within the blood and/or spleen. Applicant has shown herein that within hours of administration of an LNP several immune sensors have reacted to the presence of the LNP. These sensors include but are not limited to immune cells involved in generating an immune response, such as B cells, pDC, and platelets. The sensors may be present in the spleen, such as in the marginal zone of the spleen and/or in the blood. The LNP may physically interact with one or more sensors, which may interact with other sensors. In such a case the LNP is directly or indirectly interacting with the sensors. The sensors may interact directly with one another in response to recognition of the LNP. For instance many sensors are located in the spleen and can easily interact with one another. Alternatively one or more of the sensors may interact with LNP in the blood and become activated. The activated sensor may then interact directly with other sensors or indirectly (e.g., through the stimulation or production of a messenger such as a cytokine e.g., IL6).

In some embodiments the LNP may interact directly with and activate each of the following sensors: pDC, B1a cells, B1b cells, and platelets. These cells may then interact directly or indirectly with one another to initiate the production of effectors which ultimately lead to the ABC and/or toxicity associated with repeated doses of LNP. For instance, Applicant has shown that LNP administration leads to pDC activation, platelet aggregation and activation and B cell activation. In response to LNP platelets also aggregate and are activated and aggregate with B cells. pDC cells are activated. LNP has been found to interact with the surface of platelets and B cells relatively quickly. Blocking the activation of any one or combination of these sensors in response to LNP is useful for dampening the immune response that would ordinarily occur. This dampening of the immune response results in the avoidance of ABC and/or toxicity.

The sensors once activated produce effectors. An effector, as used herein, is an immune molecule produced by an immune cell, such as a B cell. Effectors include but are not limited to immunoglobulin such as natural IgM and natural IgG and cytokines such as IL6. B1a and B1b cells stimulate the production of natural IgMs within 2-6 hours following administration of an LNP. Natural IgG can be detected within 96 hours. IL6 levels are increased within several hours. The natural IgM and IgG circulate in the body for several days to several weeks. During this time the circulating effectors can interact with newly administered LNPs, triggering those LNPs for clearance by the body. For instance, an effector may recognize and bind to an LNP. The Fc region of the effector may be recognized by and trigger uptake of the decorated LNP by macrophage. The macrophage are then transported to the spleen. The production of effectors by immune sensors is a transient response that correlates with the timing observed for ABC.

If the administered dose is the second or subsequent administered dose, and if such second or subsequent dose is administered before the previously induced natural IgM and/or IgG is cleared from the system (e.g., before the 2-3 window time period), then such second or subsequent dose is targeted by the circulating natural IgM and/or natural IgG or Fc which trigger alternative complement pathway activation and is itself rapidly cleared. When LNP are administered after the effectors have cleared from the body or are reduced in number, ABC is not observed.

Thus, it is useful according to aspects of the invention to inhibit the interaction between LNP and one or more sensors, to inhibit the activation of one or more sensors by LNP (direct or indirect), to inhibit the production of one or more effectors, and/or to inhibit the activity of one or more effectors. In some embodiments the LNP is designed to limit or block interaction of the LNP with a sensor. For instance the LNP may have an altered PC and/or PEG to prevent interactions with sensors. Alternatively or additionally an agent that inhibits immune responses induced by LNPs may be used to achieve any one or more of these effects.

It has also been determined that conventional B cells are also implicated in ABC. Specifically, upon first administration of an agent, conventional B cells, referred to herein as CD19(+), bind to and react against the agent. Unlike B1a and B1b cells though, conventional B cells are able to mount first an IgM response (beginning around 96 hours after administration of the LNPs) followed by an IgG response (beginning around 14 days after administration of the LNPs) concomitant with a memory response. Thus, conventional B cells react against the administered agent and contribute to IgM (and eventually IgG) that mediates ABC. The IgM and IgG are typically anti-PEG IgM and anti-PEG IgG.

It is contemplated that in some instances, the majority of the ABC response is mediated through B1a cells and B1a-mediated immune responses. It is further contemplated that in some instances, the ABC response is mediated by both IgM and IgG, with both conventional B cells and B1a cells mediating such effects. In yet still other instances, the ABC response is mediated by natural IgM molecules, some of which are capable of binding to natural IgM, which may be produced by activated B1a cells. The natural IgMs may bind to one or more components of the LNPs, e.g., binding to a phospholipid component of the LNPs (such as binding to the PC moiety of the phospholipid) and/or binding to a PEG-lipid component of the LNPs (such as binding to PEG-DMG, in particular, binding to the PEG moiety of PEG-DMG). Since B1a expresses CD36, to which phosphatidylcholine is a ligand, it is contemplated that the CD36 receptor may mediate the activation of B1a cells and thus production of natural IgM. In yet still other instances, the ABC response is mediated primarily by conventional B cells.

It has been found in accordance with the invention that the ABC phenomenon can be reduced or abrogated, at least in part, through the use of compounds and compositions (such as agents, delivery vehicles, and formulations) that do not activate B1a cells. Compounds and compositions that do not activate B1a cells may be referred to herein as B1a inert compounds and compositions. It has been further found in accordance with the invention that the ABC phenomenon can be reduced or abrogated, at least in part, through the use of compounds and compositions that do not activate conventional B cells. Compounds and compositions that do not activate conventional B cells may in some embodiments be referred to herein as CD19-inert compounds and compositions. Thus, in some embodiments provided herein, the compounds and compositions do not activate B1a cells and they do not activate conventional B cells. Compounds and compositions that do not activate B1a cells and conventional B cells may in some embodiments be referred to herein as B1a/CD19-inert compounds and compositions.

These underlying mechanisms were not heretofore understood, and the role of B1a and B1b cells and their interplay with conventional B cells in this phenomenon was also not appreciated.

Accordingly, this disclosure provides compounds and compositions that do not promote ABC. These may be further characterized as not capable of activating B1a and/or B1b cells, platelets and/or pDC, and optionally conventional B cells also. These compounds (e.g., agents, including biologically active agents such as prophylactic agents, therapeutic agents and diagnostic agents, delivery vehicles, including liposomes, lipid nanoparticles, and other lipid-based encapsulating structures, etc.) and compositions (e.g., formulations, etc.) are particularly desirable for applications requiring repeated administration, and in particular repeated administrations that occur within with short periods of time (e.g., within 1-2 weeks). This is the case, for example, if the agent is a nucleic acid based therapeutic that is provided to a subject at regular, closely-spaced intervals. The findings provided herein may be applied to these and other agents that are similarly administered and/or that are subject to ABC.

Of particular interest are lipid-comprising compounds, lipid-comprising particles, and lipid-comprising compositions as these are known to be susceptible to ABC. Such lipid-comprising compounds particles, and compositions have been used extensively as biologically active agents or as delivery vehicles for such agents. Thus, the ability to improve their efficacy of such agents, whether by reducing the effect of ABC on the agent itself or on its delivery vehicle, is beneficial for a wide variety of active agents.

Also provided herein are compositions that do not stimulate or boost an acute phase response (ARP) associated with repeat dose administration of one or more biologically active agents.

The composition, in some instances, may not bind to IgM, including but not limited to natural IgM.

The composition, in some instances, may not bind to an acute phase protein such as but not limited to C-reactive protein.

The composition, in some instances, may not trigger a CD5(+) mediated immune response. As used herein, a CD5(+) mediated immune response is an immune response that is mediated by B1a and/or B1b cells. Such a response may include an ABC response, an acute phase response, induction of natural IgM and/or IgG, and the like.

The composition, in some instances, may not trigger a CD19(+) mediated immune response. As used herein, a CD19(+) mediated immune response is an immune response that is mediated by conventional CD19(+), CD5(−) B cells. Such a response may include induction of IgM, induction of IgG, induction of memory B cells, an ABC response, an anti-drug antibody (ADA) response including an anti-protein response where the protein may be encapsulated within an LNP, and the like.

B1a cells area subset of B cells involved in innate immunity. These cells are the source of circulating IgM, referred to as natural antibody or natural serum antibody. Natural IgM antibodies are characterized as having weak affinity for a number of antigens, and therefore they are referred to as "poly-specific" or "poly-reactive", indicating their ability to bind to more than one antigen. B1a cells are not able to produce IgG. Additionally, they do not develop into memory cells and thus do not contribute to an adaptive immune response. However, they are able to secrete IgM upon activation. The secreted IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In humans, B1a cells are CD19(+), CD20(+), CD27(+), CD43(+), CD70(−) and CD5(+). In mice, B1a cells are CD19(+), CD5(+), and CD45 B cell isoform B220(+). It is the expression of CD5 which typically distinguishes B1a cells from other convention B cells. B1a cells may express high levels of CD5, and on this basis may be distinguished from other B-1 cells such as B-1b cells which express low or undetectable levels of CD5. CD5 is a pan-T cell surface glycoprotein. B1a cells also express CD36, also known as fatty acid translocase. CD36 is a member of the class B scavenger receptor family. CD36 can bind many ligands, including oxidized low density lipoproteins, native lipoproteins, oxidized phospholipids, and long-chain fatty acids.

B1b cells are another subset of B cells involved in innate immunity. These cells are another source of circulating natural IgM. Several antigens, including PS, are capable of inducing T cell independent immunity through B1b activation. CD27 is typically upregulated on B1b cells in response to antigen activation. Similar to B1a cells, the Bib cells are typically located in specific body locations such as the spleen and peritoneal cavity and are in very low abundance in the blood. The B1b secreted natural IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In some embodiments it is desirable to block B1a and/or B1b cell activation. One strategy for blocking B1a and/or B1b cell activation involves determining which components of a lipid nanoparticle promote B cell activation and neutralizing those components. It has been discovered herein that at least PEG and phosphatidylcholine (PC) contribute to B1a and B1b cell interaction with other cells and/or activation. PEG may play a role in promoting aggregation between B1 cells and platelets, which may lead to activation. PC (a helper lipid in LNPs) is also involved in activating the B1 cells, likely through interaction with the CD36 receptor on the B cell surface. Numerous particles have PEG-lipid alternatives, PEG-less, and/or PC replacement lipids (e.g. oleic acid or analogs thereof) have been designed and tested. Applicant has established that replacement of one or more of these components within an LNP that otherwise would promote ABC upon repeat administration, is useful in preventing ABC by reducing the production of natural IgM and/or B cell activation. Thus, the invention encompasses LNPs that have reduced ABC as a result of a design which eliminates the inclusion of B cell triggers.

Another strategy for blocking B1a and/or B1b cell activation involves using an agent that inhibits immune responses induced by LNPs. These types of agents are discussed in more detail below. In some embodiments these agents block the interaction between B1a/B1b cells and the LNP or platelets or pDC. For instance the agent may be an antibody or other binding agent that physically blocks the interaction. An example of this is an antibody that binds to CD36 or CD6. The agent may also be a compound that prevents or disables the B1a/B1b cell from signaling once activated or prior to activation. For instance, it is possible to block one or more components in the B1a/B1b signaling cascade the results from B cell interaction with LNP or other immune cells. In other embodiments the agent may act one or more effectors produced by the B1a/B1b cells following activation. These effectors include for instance, natural IgM and cytokines.

It has been demonstrated according to aspects of the invention that when activation of pDC cells is blocked, B cell activation in response to LNP is decreased. Thus, in order to avoid ABC and/or toxicity, it may be desirable to prevent pDC activation. Similar to the strategies discussed above, pDC cell activation may be blocked by agents that interfere with the interaction between pDC and LNP and/or B cells/platelets. Alternatively agents that act on the pDC to block its ability to get activated or on its effectors can be used together with the LNP to avoid ABC.

Platelets may also play an important role in ABC and toxicity. Very quickly after a first dose of LNP is administered to a subject platelets associate with the LNP, aggregate and are activated. In some embodiments it is desirable to block platelet aggregation and/or activation. One strategy for blocking platelet aggregation and/or activation involves determining which components of a lipid nanoparticle promote platelet aggregation and/or activation and neutralizing those components. It has been discovered herein that at least PEG contribute to platelet aggregation, activation and/or interaction with other cells. Numerous particles have PEG-lipid alternatives and PEG-less have been designed and tested. Applicant has established that replacement of one or more of these components within an LNP that otherwise would promote ABC upon repeat administration, is useful in preventing ABC by reducing the production of natural IgM and/or platelet aggregation. Thus, the invention encompasses LNPs that have reduced ABC as a result of a design which eliminates the inclusion of platelet triggers. Alternatively agents that act on the platelets to block its activity once it is activated or on its effectors can be used together with the LNP to avoid ABC.

(i) Measuring ABC Activity and Related Activities

Various compounds and compositions provided herein, including LNPs, do not promote ABC activity upon administration in vivo. These LNPs may be characterized and/or identified through any of a number of assays, such as but not limited to those described below, as well as any of the assays disclosed in the Examples section, include the methods subsection of the Examples.

In some embodiments the methods involve administering an LNP without producing an immune response that promotes ABC. An immune response that promotes ABC involves activation of one or more sensors, such as B1 cells, pDC, or platelets, and one or more effectors, such as natural IgM, natural IgG or cytokines such as IL6. Thus administration of an LNP without producing an immune response that promotes ABC, at a minimum involves administration of an LNP without significant activation of one or more sensors and significant production of one or more effectors. Significant used in this context refers to an amount that would lead to the physiological consequence of accelerated blood clearance of all or part of a second dose with respect to the level of blood clearance expected for a second dose of an ABC triggering LNP. For instance, the immune response should be dampened such that the ABC observed after the second dose is lower than would have been expected for an ABC triggering LNP.

(ii) B1a or B1b Activation Assay

Certain compositions provided in this disclosure do not activate B cells, such as B1a or B1b cells (CD19+CD5+) and/or conventional B cells (CD19+CD5−). Activation of B1a cells, B1b cells, or conventional B cells may be determined in a number of ways, some of which are provided below. B cell population may be provided as fractionated B cell populations or unfractionated populations of splenocytes or peripheral blood mononuclear cells (PBMC). If the latter, the cell population may be incubated with the LNP of choice for a period of time, and then harvested for further analysis. Alternatively, the supernatant may be harvested and analyzed.

(iii) Upregulation of Activation Marker Cell Surface Expression

Activation of B1a cells, B1b cells, or conventional B cells may be demonstrated as increased expression of B cell activation markers including late activation markers such as CD86. In an exemplary non-limiting assay, unfractionated B cells are provided as a splenocyte population or as a PBMC population, incubated with an LNP of choice for a particular period of time, and then stained for a standard B cell marker such as CD19 and for an activation marker such as CD86, and analyzed using for example flow cytometry. A suitable negative control involves incubating the same population with medium, and then performing the same staining and visualization steps. An increase in CD86 expression in the test population compared to the negative control indicates B cell activation.

(iv) Pro-Inflammatory Cytokine Release

B cell activation may also be assessed by cytokine release assay. For example, activation may be assessed through the production and/or secretion of cytokines such as IL-6 and/or TNF-alpha upon exposure with LNPs of interest.

Such assays may be performed using routine cytokine secretion assays well known in the art. An increase in cytokine secretion is indicative of B cell activation.

(v) LNP Binding/Association to and/or Uptake by B Cells

LNP association or binding to B cells may also be used to assess an LNP of interest and to further characterize such LNP. Association/binding and/or uptake/internalization may be assessed using a detectably labeled, such as fluorescently labeled, LNP and tracking the location of such LNP in or on B cells following various periods of incubation.

The invention further contemplates that the compositions provided herein may be capable of evading recognition or detection and optionally binding by downstream mediators of ABC such as circulating IgM and/or acute phase response mediators such as acute phase proteins (e.g., C-reactive protein (CRP).

(vi) Methods of Use for Reducing ABC

Also provided herein are methods for delivering LNPs, which may encapsulate an agent such as a therapeutic agent, to a subject without promoting ABC.

In some embodiments, the method comprises administering any of the LNPs described herein, which do not promote ABC, for example, do not induce production of natural IgM binding to the LNPs, do not activate B1a and/or B1b cells. As used herein, an LNP that "does not promote ABC" refers to an LNP that induces no immune responses that would lead to substantial ABC or a substantially low level of immune responses that is not sufficient to lead to substantial ABC. An LNP that does not induce the production of natural IgMs binding to the LNP refers to LNPs that induce either no natural IgM binding to the LNPs or a substantially low level of the natural IgM molecules, which is insufficient to lead to substantial ABC. An LNP that does not activate B1a and/or B1b cells refer to LNPs that induce no response of B1a and/or B1b cells to produce natural IgM binding to the LNPs or a substantially low level of B1a and/or B1b responses, which is insufficient to lead to substantial ABC.

In some embodiments the terms do not activate and do not induce production are a relative reduction to a reference value or condition. In some embodiments the reference value or condition is the amount of activation or induction of production of a molecule such as IgM by a standard LNP such as an MC3 LNP. In some embodiments the relative reduction is a reduction of at least 30%, for example at least 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%. In other embodiments the terms do not activate cells such as B cells and do not induce production of a protein such as IgM may refer to an undetectable amount of the active cells or the specific protein.

(vii) Platelet Effects and Toxicity

The invention is further premised in part on the elucidation of the mechanism underlying dose-limiting toxicity associated with LNP administration. Such toxicity may involve coagulopathy, disseminated intravascular coagulation (DIC, also referred to as consumptive coagulopathy), whether acute or chronic, and/or vascular thrombosis. In some instances, the dose-limiting toxicity associated with LNPs is acute phase response (APR) or complement activation-related psudoallergy (CARPA).

As used herein, coagulopathy refers to increased coagulation (blood clotting) in vivo. The findings reported in this disclosure are consistent with such increased coagulation and significantly provide insight on the underlying mechanism. Coagulation is a process that involves a number of different factors and cell types, and heretofore the relationship between and interaction of LNPs and platelets has not been understood in this regard. This disclosure provides evidence of such interaction and also provides compounds and compositions that are modified to have reduced platelet effect, including reduced platelet association, reduced platelet aggregation, and/or reduced platelet aggregation. The ability to modulate, including preferably down-modulate, such platelet effects can reduce the incidence and/or severity of coagulopathy post-LNP administration. This in turn will reduce toxicity relating to such LNP, thereby allowing higher doses of LNPs and importantly their cargo to be administered to patients in need thereof.

CARPA is a class of acute immune toxicity manifested in hypersensitivity reactions (HSRs), which may be triggered by nanomedicines and biologicals. Unlike allergic reactions, CARPA typically does not involve IgE but arises as a consequence of activation of the complement system, which is part of the innate immune system that enhances the body's abilities to clear pathogens. One or more of the following pathways, the classical complement pathway (CP), the alternative pathway (AP), and the lectin pathway (LP), may be involved in CARPA. Szebeni, Molecular Immunology, 61:163-173 (2014).

The classical pathway is triggered by activation of the C1-complex, which contains. C1q, C1r, C1s, or C1gr2s2. Activation of the C1-complex occurs when C1q binds to IgM or IgG complexed with antigens, or when C1q binds directly to the surface of the pathogen. Such binding leads to conformational changes in the C1q molecule, which leads to the activation of C1r, which in turn, cleave C1s. The C1r2s2 component now splits C4 and then C2, producing C4a, C4b, C2a, and C2b. C4b and C2b bind to form the classical pathway C3-convertase (C4b2b complex), which promotes cleavage of C3 into C3a and C3b. C3b then binds the C3 convertase to from the C5 convertase (C4b2b3b complex). The alternative pathway is continuously activated as a result of spontaneous C3 hydrolysis. Factor P (properdin) is a positive regulator of the alternative pathway. Oligomerization of properdin stabilizes the C3 convertase, which can then cleave much more C3. The C3 molecules can bind to surfaces and recruit more B, D, and P activity, leading to amplification of the complement activation.

Acute phase response (APR) is a complex systemic innate immune responses for preventing infection and clearing potential pathogens. Numerous proteins are involved in APR and C-reactive protein is a well-characterized one.

It has been found, in accordance with the invention, that certain LNP are able to associate physically with platelets almost immediately after administration in vivo, while other LNP do not associate with platelets at all or only at background levels. Significantly, those LNPs that associate with platelets also apparently stabilize the platelet aggregates that are formed thereafter. Physical contact of the platelets with certain LNPs correlates with the ability of such platelets to remain aggregated or to form aggregates continuously for an extended period of time after administration. Such aggregates comprise activated platelets and also innate immune cells such as macrophages and B cells.

25. Methods of Use

The polynucleotides, pharmaceutical compositions and formulations described herein are used in the preparation, manufacture and therapeutic use of to treat and/or prevent Citrin-related diseases, disorders or conditions. In some embodiments, the polynucleotides, compositions and formulations of the invention are used to treat and/or prevent CTLN2.

In some embodiments, the polynucleotides, pharmaceutical compositions and formulations of the invention are used in methods for reducing ammonia levels and/or reducing triglyceride levels in a subject in need thereof. For instance, one aspect of the invention provides a method of alleviating the signs and symptoms of CTLN2 in a subject comprising the administration of a composition or formulation comprising a polynucleotide encoding Citrin to that subject (e.g, an mRNA encoding a Citrin polypeptide).

In some embodiments, the polynucleotides, pharmaceutical compositions and formulations of the invention are used to reduce the level of a metabolite associated with CTLN2 (e.g., the substrate or product, i.e., glutamate, aspartate, or ammonia), the method comprising administering to the subject an effective amount of a polynucleotide encoding a Citrin polypeptide.

In some embodiments, the administration of an effective amount of a polynucleotide, pharmaceutical composition or formulation of the invention reduces the levels of a biomarker of CTLN2, e.g., glutamate, aspartate, or ammonia. In some embodiments, the administration of the polynucleotide, pharmaceutical composition or formulation of the invention results in reduction in the level of one or more biomarkers of CTLN2, e.g., ammonia, triglycerides, glutamate, aspartate, citrulline, pyruvate and lactate, within a short period of time after administration of the polynucleotide, pharmaceutical composition or formulation of the invention.

In some embodiments, the level of one or more biomarkers of CTLN2, e.g., ammonia, triglycerides, glutamate, aspartate, citrulline, pyruvate and lactate, is measured in blood. In some embodiments, the level of one of more biomarkers is measured in a component of blood, for example in plasma or serum. Methods of obtaining blood and components of blood and for measuring the level of biomarkers in blood or a component of blood are known in the art. In some embodiments, the level of one or more biomarkers of CTLN2, e.g., ammonia, glutamate, aspartate, citrulline, pyruvate and lactate, is measured in urine. Methods of obtaining urine and for measuring the level of biomarkers in urine are known in the art. In some embodiments, the level of one or more biomarkers of CTLN2, e.g., ammonia, triglycerides, glutamate, aspartate, citrulline, pyruvate and lactate, is measured in liver tissue. Methods of obtaining liver tissue, e.g. biopsy, and for measuring the level of biomarkers in liver tissue are known in the art.

In some embodiments, the level of one or more biomarkers of CTLN2, e.g., ammonia, triglycerides, glutamate, aspartate, citrulline, pyruvate and lactate, is measured in a subject to determine the change in level of the biomarker after administration of a pharmaceutical composition or polynucleotide as described herein. In some embodiments, the level of the biomarker may be reduced at least 1.5-fold, at least 2-fold, at least 3-fold, at least 4-fold, at least 5-fold, at least 10-fold, at least 15 fold, at least 20-fold, at least 25-fold, at least 30-fold, at least 35-fold, at least 40-fold, at least 45-fold or at least 50-fold compared to a reference biomarker level in a subject having CTLN2.

In some embodiments, the blood, plasma or serum level of ammonia is reduced at least 2-fold, at least 3-fold, at least 5-fold, at least 10-fold, at least 15 fold, at least 20-fold, at least 20%, at least 30%, at least 40%, at least 50%, at least 60%, at least 70%, at least 80%, at least 90%, at least 95% or at least 98%, at least 99%, or 100% compared to a reference ammonia blood, plasma or serum level in a subject having CTLN2, for at least 24 hours, at least 48 hours, at least 72 hours, at least 96 hours, or at least 120 hours post-administration of a pharmaceutical composition or polynucleotide as described herein. Reference levels of ammonia in the blood, plasma or serum or subjects having CTLN2 and in subjects that do not have CTLN2 can be found in the art, for example, in Kobayashi et al., Citrin Deficiency, GeneReviews 2005 and in Wong et al., Arch Neurol 64(7):1034-1037 (2007), both of which are hereby incorporated by reference herein.

Replacement therapy is a potential treatment for CTLN2. Thus, in certain aspects of the invention, the polynucleotides, e.g., mRNA, disclosed herein comprise one or more sequences encoding a Citrin polypeptide that is suitable for use in gene replacement therapy for CTLN2. In some embodiments, the present disclosure treats a lack of or reduced Citrin expression and/or Citrin activity, or decreased or abnormal Citrin activity in a subject by providing a polynucleotide, e.g., mRNA, that encodes a Citrin polypeptide to the subject. In some embodiments, the polynucleotide is sequence-optimized. In some embodiments, the polynucleotide (e.g., an mRNA) comprises a nucleic acid sequence (e.g., an ORF) encoding a Citrin polypeptide, wherein the nucleic acid is sequence-optimized, e.g., by modifying its G/C, uridine, or thymidine content, and/or the polynucleotide comprises at least one chemically modified nucleoside. In some embodiments, the polynucleotide comprises a miRNA binding site, e.g., a miRNA binding site that binds miRNA-142, miRNA-126, or a combination thereof.

In some embodiments, the administration of a composition or formulation comprising polynucleotide, pharmaceutical composition or formulation of the invention to a subject results in an increase in mitochondrial uptake of glutamate, increase in mitochondrial export of aspartate and/or decrease in ammonia to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% lower than the level observed prior to the administration of the composition or formulation.

In some embodiments, the administration of the polynucleotide, pharmaceutical composition or formulation of the invention results in expression of Citrin in cells of the subject. In some embodiments, administering the polynucleotide, pharmaceutical composition or formulation of the invention results in an increase of Citrin expression and/or activity in the subject. For example, in some embodiments, the polynucleotides of the present invention are used in methods of administering a composition or formulation comprising an mRNA encoding a Citrin polypeptide to a subject, wherein the method results in an increase of Citrin expression and/or activity in at least some cells of a subject.

In some embodiments, the administration of a composition or formulation comprising an mRNA encoding a Citrin polypeptide to a subject results in an increase of Citrin expression and/or activity in cells subject to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% or more of the expression and/or activity level expected in a normal subject, e.g., a human not suffering from CTLN2.

In some embodiments, the administration of the polynucleotide, pharmaceutical composition or formulation of the invention results in expression of Citrin protein in at least some of the cells of a subject that persists for a period of time sufficient to allow reduction of ammonia to occur.

In some embodiments, the expression and/or activity of the encoded polypeptide is increased. In some embodiments, the polynucleotide increases Citrin expression levels in cells when introduced into those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% with respect to the Citrin expression and/or activity level in the cells before the polypeptide is introduced in the cells.

In some embodiments, the method or use comprises administering a polynucleotide, e.g., mRNA, comprising a nucleotide sequence having sequence similarity to a polynucleotide selected from the group of SEQ ID NOs: 5-29, 129, 132, 135, and 138 (See TABLE 2), or a polynucleotide selected from the group of SEQ ID NOs: 130, 133, 136, and 139 (See TABLE 5), wherein the polynucleotide encodes an Citrin polypeptide.

Other aspects of the present disclosure relate to transplantation of cells containing polynucleotides to a mammalian subject. Administration of cells to mammalian subjects is known to those of ordinary skill in the art, and includes, but is not limited to, local implantation (e.g., topical or subcutaneous administration), organ delivery or systemic injection (e.g., intravenous injection or inhalation), and the formulation of cells in pharmaceutically acceptable carriers.

Also provided is a method to increase survival an CTLN2 patient comprising administering to the subject a therapeutically effective amount of a composition or formulation comprising mRNA encoding a Citrin polypeptide disclosed herein.

In some aspects, the dose of mRNA encoding a Citrin polypeptide disclosed herein is at least about 0.1 nmol/kg, at least about 0.2 nmol/kg, at least about 0.3 nmol/kg, at least about 0.4 nmol/kg, at least about 0.5 nmol/kg, at least about 0.6 nmol/kg, at least about 0.7 nmol/kg, at least about 0.8 nmol/kg, at least about 0.9 nmol/kg, at least about 1 nmol/kg, at least about 1.1 nmol/kg, at least about 1.2 nmol/kg, at least about 1.3 nmol/kg, at least about 1.4 nmol/kg, at least about 1.5 nmol/kg, at least about 1.6 nmol/kg, at least about 1.7 nmol/kg, at least about 1.8 nmol/kg, at least about 1.9 nmol/kg, at least about 2 nmol/kg, at least about 2.5 nmol/kg, at least about 3 nmol/kg, at least about 3.5 nmol/kg, at least about 4 nmol/kg, at least about 4.5 nmol/kg, or at least about 5 nmol/kg. In some aspects, the dose of mRNA encoding a Citrin polypeptide disclosed herein is at least about 0.05 mg/kg, at least about 0.1 mg/kg, at least about 0.15 mg/kg, at least about 0.2 mg/kg, at least about 0.25 mg/kg, at least about 0.3 mg/kg, at least about 0.35 mg/kg, at least about 0.4 mg/kg, at least about 0.45 mg/kg, at least about 0.5 mg/kg, at least about 0.55 mg/kg, at least about 0.6 mg/kg, at least about 0.7 mg/kg, at least about 0.75 mg/kg, at least about 0.8 mg/kg, at least about 0.85 mg/kg, at least about 0.9 mg/kg, at least about 0.95 mg/kg, or at least about 1 mg/kg.

In some aspects of the method disclosed herein, the CTLN2 patient is an asymptomatic patient.

In some embodiments, the polynucleotides (e.g., mRNA), pharmaceutical compositions and formulations used in the methods of the invention comprise a uracil-modified sequence encoding a Citrin polypeptide disclosed herein and a miRNA binding site disclosed herein, e.g., a miRNA binding site that binds to miR-142 and/or a miRNA binding site that binds to miR-126. In some embodiments, the uracil-modified sequence encoding a Citrin polypeptide comprises at least one chemically modified nucleobase, e.g., 5-methoxyuracil. In some embodiments, at least 95% of a type of nucleobase (e.g., uracil) in a uracil-modified sequence encoding a Citrin polypeptide of the invention are modified nucleobases. In some embodiments, at least 95% of uricil in a uracil-modified sequence encoding a Citrin polypeptide is 5-methoxyuridine. In some embodiments, the polynucleotide (e.g., a RNA, e.g., an mRNA) disclosed herein is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

The skilled artisan will appreciate that the therapeutic effectiveness of a drug or a treatment of the instant invention can be characterized or determined by measuring the level of expression of an encoded protein (e.g., enzyme) in a sample or in samples taken from a subject (e.g., from a preclinical test subject (rodent, primate, etc.) or from a clinical subject (human). Likewise, the therapeutic effectiveness of a drug or a treatment of the instant invention can be characterized or determined by measuring the level of activity of an encoded protein (e.g., enzyme) in a sample or in samples taken from a subject (e.g., from a preclinical test subject (rodent, primate, etc.) or from a clinical subject (human). Furthermore, the therapeutic effectiveness of a drug or a treatment of the instant invention can be characterized or determined by measuring the level of an appropriate biomarker in sample(s) taken from a subject. Levels of protein and/or biomarkers can be determined post-administration with a single dose of an mRNA therapeutic of the invention or can be determined and/or monitored at several time points following administration with a single dose or can be determined and/or monitored throughout a course of treatment, e.g., a multi-dose treatment.

26. Compositions and Formulations for Use

Certain aspects of the invention are directed to compositions or formulations comprising any of the polynucleotides disclosed above.

In some embodiments, the composition or formulation comprises:
(i) a polynucleotide (e.g., a RNA, e.g., an mRNA) comprising a sequence-optimized nucleotide sequence (e.g., an ORF) encoding a Citrin polypeptide (e.g., the wild-type sequence, functional fragment, or variant thereof), wherein the polynucleotide comprises at least one chemically modified nucleobase, e.g., 5-methoxyuracil (e.g., wherein at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils), and wherein the polynucleotide further comprises a miRNA binding site, e.g., a miRNA binding site that binds to miR-142 (e.g., a miR-142-3p or miR-142-5p binding site); and (ii) a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

In some embodiments, the uracil or thymine content of the ORF relative to the theoretical minimum uracil or thymine content of a nucleotide sequence encoding the Citrin polypeptide (% $U_{TM}$ or % $T_{TM}$), is between about 100% and about 150%.

In some embodiments, the polynucleotides, compositions or formulations above are used to treat and/or prevent a Citrin-related diseases, disorders or conditions, e.g., CTLN2.

27. Forms of Administration

The polynucleotides, pharmaceutical compositions and formulations of the invention described above can be administered by any route that results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insulation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intraperi-cardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration that is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal. In specific embodiments, compositions can be administered in a way that allows them cross the blood-brain barrier, vascular barrier, or other epithelial barrier. In some embodiments, a formulation for a route of administration can include at least one inactive ingredient.

The polynucleotides of the present invention (e.g., a polynucleotide comprising a nucleotide sequence encoding a Citrin polypeptide or a functional fragment or variant thereof) can be delivered to a cell naked. As used herein in, "naked" refers to delivering polynucleotides free from agents that promote transfection. The naked polynucleotides can be delivered to the cell using routes of administration known in the art and described herein.

The polynucleotides of the present invention (e.g., a polynucleotide comprising a nucleotide sequence encoding a Citrin polypeptide or a functional fragment or variant thereof) can be formulated, using the methods described herein. The formulations can contain polynucleotides that can be modified and/or unmodified. The formulations can further include, but are not limited to, cell penetration agents, a pharmaceutically acceptable carrier, a delivery agent, a bioerodible or biocompatible polymer, a solvent, and a sustained-release delivery depot. The formulated polynucleotides can be delivered to the cell using routes of administration known in the art and described herein.

A pharmaceutical composition for parenteral administration can comprise at least one inactive ingredient. Any or none of the inactive ingredients used can have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. The sterile formulation can also comprise adjuvants such as local anesthetics, preservatives and buffering agents.

Injectable formulations can be sterilized, for example, by filtration through a bacterial-retaining filter, and/or by incorporating sterilizing agents in the form of sterile solid compositions that can be dissolved or dispersed in sterile water or other sterile injectable medium prior to use.

Injectable formulations can be for direct injection into a region of a tissue, organ and/or subject. As a non-limiting example, a tissue, organ and/or subject can be directly injected a formulation by intramyocardial injection into the ischemic region. (See, e.g., Zangi et al. Nature Biotechnology 2013; the contents of which are herein incorporated by reference in its entirety).

In order to prolong the effect of an active ingredient, it is often desirable to slow the absorption of the active ingredient from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions that are compatible with body tissues.

28. Kits and Devices a. Kits

The invention provides a variety of kits for conveniently and/or effectively using the claimed nucleotides of the present invention. Typically kits will comprise sufficient amounts and/or numbers of components to allow a user to perform multiple treatments of a subject(s) and/or to perform multiple experiments.

In one aspect, the present invention provides kits comprising the molecules (polynucleotides) of the invention.

Said kits can be for protein production, comprising a first polynucleotides comprising a translatable region. The kit can further comprise packaging and instructions and/or a delivery agent to form a formulation composition. The delivery agent can comprise a saline, a buffered solution, a lipidoid or any delivery agent disclosed herein.

In some embodiments, the buffer solution can include sodium chloride, calcium chloride, phosphate and/or EDTA. In another embodiment, the buffer solution can include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See, e.g., U.S. Pub. No. 20120258046; herein incorporated by reference in its entirety). In a further embodiment, the buffer solutions can be precipitated or it can be lyophilized. The amount of each component can be varied to enable consistent, reproducible higher concentration saline or simple buffer formulations. The components can also be varied in order to increase the stability of modified RNA in the buffer solution over a period of time and/or under a variety of conditions. In one aspect, the present invention provides kits for protein production, comprising: a polynucleotide comprising a translatable region, provided in an amount effective to produce a desired amount of a protein encoded by the translatable region when introduced into a target cell; a second polynucleotide comprising an inhibitory nucleic acid, provided in an amount effective to substantially inhibit the innate immune response of the cell; and packaging and instructions.

In one aspect, the present invention provides kits for protein production, comprising a polynucleotide comprising a translatable region, wherein the polynucleotide exhibits reduced degradation by a cellular nuclease, and packaging and instructions.

In one aspect, the present invention provides kits for protein production, comprising a polynucleotide comprising a translatable region, wherein the polynucleotide exhibits reduced degradation by a cellular nuclease, and a mammalian cell suitable for translation of the translatable region of the first nucleic acid.

b. Devices

The present invention provides for devices that can incorporate polynucleotides that encode polypeptides of interest. These devices contain in a stable formulation the reagents to synthesize a polynucleotide in a formulation available to be immediately delivered to a subject in need thereof, such as a human patient Devices for administration can be employed to deliver the polynucleotides of the present invention according to single, multi- or split-dosing regimens taught herein. Such devices are taught in, for example, International Application Publ.

No. WO2013151666, the contents of which are incorporated herein by reference in their entirety.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

According to the present invention, these multi-administration devices can be utilized to deliver the single, multi- or split doses contemplated herein. Such devices are taught for example in, International Application Publ. No. WO2013151666, the contents of which are incorporated herein by reference in their entirety.

In some embodiments, the polynucleotide is administered subcutaneously or intramuscularly via at least 3 needles to three different, optionally adjacent, sites simultaneously, or within a 60 minutes period (e.g., administration to 4, 5, 6, 7, 8, 9, or 10 sites simultaneously or within a 60 minute period).

c. Methods and Devices Utilizing Catheters and/or Lumens

Methods and devices using catheters and lumens can be employed to administer the polynucleotides of the present invention on a single, multi- or split dosing schedule. Such methods and devices are described in International Application Publication No. WO2013151666, the contents of which are incorporated herein by reference in their entirety.

d. Methods and Devices Utilizing Electrical Current

Methods and devices utilizing electric current can be employed to deliver the polynucleotides of the present invention according to the single, multi- or split dosing regimens taught herein. Such methods and devices are described in International Application Publication No. WO2013151666, the contents of which are incorporated herein by reference in their entirety.

29. Definitions

In order that the present disclosure can be more readily understood, certain terms are first defined. As used in this application, except as otherwise expressly provided herein, each of the following terms shall have the meaning set forth below. Additional definitions are set forth throughout the application.

The invention includes embodiments in which exactly one member of the group is present in, employed in, or otherwise relevant to a given product or process. The invention includes embodiments in which more than one, or all of the group members are present in, employed in, or otherwise relevant to a given product or process.

In this specification and the appended claims, the singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language "comprising," otherwise analogous aspects described in terms of "consisting of" and/or "consisting essentially of" are also provided.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleobases are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

About: The term "about" as used in connection with a numerical value throughout the specification and the claims denotes an interval of accuracy, familiar and acceptable to a person skilled in the art. Such interval of accuracy is ±10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Administered in combination: As used herein, the term "administered in combination" or "combined administration" means that two or more agents are administered to a subject at the same time or within an interval such that there can be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amino acid substitution: The term "amino acid substitution" refers to replacing an amino acid residue present in a parent or reference sequence (e.g., a wild type Citrin sequence) with another amino acid residue. An amino acid can be substituted in a parent or reference sequence (e.g., a wild type Citrin polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In other aspects, substitution patterns can be described according to the schema An(YZ), wherein A is the single letter code corresponding to the amino acid residue substituting the amino acid naturally or originally present at position X, and Y and Z are alternative substituting amino acid residues.

In the context of the present disclosure, substitutions (even when they referred to as amino acid substitution) are conducted at the nucleic acid level, i.e., substituting an amino acid residue with an alternative amino acid residue is conducted by substituting the codon encoding the first amino acid with a codon encoding the second amino acid.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately," as applied to one or more values of interest, refers to a value that is similar to a stated reference value. In certain embodiments, the term "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein with respect to a disease, the term "associated with" means that the symptom, measurement, characteristic, or status in question is linked to the diagnosis, development, presence, or progression of that disease. As association can, but need not, be causatively linked to the disease. For example, signs, symptoms, sequelae, or any effects causing a decrease in the quality of life of a patient of CTLN2 are considered associated with CTLN2 and in some embodiments of the present invention can be treated, ameliorated, or prevented by administering the polynucleotides of the present invention to a subject in need thereof.

When used with respect to two or more moieties, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It can also suggest ionic or hydrogen bonding or a hybridization based connectivity sufficiently stable such that the "associated" entities remain physically associated.

Bifunctional: As used herein, the term "bifunctional" refers to any substance, molecule or moiety that is capable of or maintains at least two functions. The functions can affect the same outcome or a different outcome. The structure that produces the function can be the same or different. For example, bifunctional modified RNAs of the present invention can encode a Citrin peptide (a first function) while those nucleosides that comprise the encoding RNA are, in and of themselves, capable of extending the half-life of the RNA (second function). In this example, delivery of the bifunctional modified RNA to a subject suffering from a protein deficiency would produce not only a peptide or protein molecule that can ameliorate or treat a disease or conditions, but would also maintain a population modified RNA present in the subject for a prolonged period of time. In other aspects, a bifunction modified mRNA can be a quimeric molecule comprising, for example, an RNA encoding a Citrin peptide (a first function) and a second protein either fused to first protein or co-expressed with the first protein.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present invention can be considered biologically active if even a portion of the polynucleotide is biologically active or mimics an activity considered biologically relevant.

Chimera: As used herein, "chimera" is an entity having two or more incongruous or heterogeneous parts or regions. For example, a chimeric molecule can comprise a first part comprising a Citrin polypeptide, and a second part (e.g., genetically fused to the first part) comprising a second therapeutic protein (e.g., a protein with a distinct enzymatic activity, an antigen binding moiety, or a moiety capable of extending the plasma half life of Citrin, for example, an Fc region of an antibody).

Sequence Optimization: The term "sequence optimization" refers to a process or series of processes by which nucleobases in a reference nucleic acid sequence are replaced with alternative nucleobases, resulting in a nucleic acid sequence with improved properties, e.g., improved protein expression or decreased immunogenicity.

In general, the goal in sequence optimization is to produce a synonymous nucleotide sequence than encodes the same polypeptide sequence encoded by the reference nucleotide sequence. Thus, there are no amino acid substitutions (as a result of codon optimization) in the polypeptide encoded by the codon optimized nucleotide sequence with respect to the polypeptide encoded by the reference nucleotide sequence.

Codon substitution: The terms "codon substitution" or "codon replacement" in the context of sequence optimization refer to replacing a codon present in a reference nucleic acid sequence with another codon. A codon can be substituted in a reference nucleic acid sequence, for example, via chemical peptide synthesis or through recombinant methods known in the art. Accordingly, references to a "substitution" or "replacement" at a certain location in a nucleic acid sequence (e.g., an mRNA) or within a certain region or subsequence of a nucleic acid sequence (e.g., an mRNA) refer to the substitution of a codon at such location or region with an alternative codon.

As used herein, the terms "coding region" and "region encoding" and grammatical variants thereof, refer to an Open Reading Frame (ORF) in a polynucleotide that upon expression yields a polypeptide or protein.

Compound: As used herein, the term "compound," is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal can be performed by varied routes of administration (e.g., intravenous, intramuscular, intradermal, and subcutaneous) and can involve varied amounts of nanoparticle compositions. Moreover, more than one mammalian cell can be contacted by a nanoparticle composition.

Conservative amino acid substitution: A "conservative amino acid substitution" is one in which the amino acid residue in a protein sequence is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitution: Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence can apply to the entire length of an polynucleotide or polypeptide or can apply to a portion, region or feature thereof.

Controlled Release: As used herein, the term "controlled release" refers to a pharmaceutical composition or compound release profile that conforms to a particular pattern of release to effect a therapeutic outcome.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA of the present invention can be single units or multimers or comprise one or more components of a complex or higher order structure.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivering: As used herein, the term "delivering" means providing an entity to a destination. For example, delivering a polynucleotide to a subject can involve administering a nanoparticle composition including the polynucleotide to the subject (e.g., by an intravenous, intramuscular, intradermal, or subcutaneous route). Administration of a nanoparticle composition to a mammal or mammalian cell can involve contacting one or more cells with the nanoparticle composition.

Delivery Agent: As used herein, "delivery agent" refers to any substance that facilitates, at least in part, the in vivo, in vitro, or ex vivo delivery of a polynucleotide to targeted cells.

Destabilized: As used herein, the term "destable," "destabilize," or "destabilizing region" means a region or molecule that is less stable than a starting, wild-type or native form of the same region or molecule.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Domain: As used herein, when referring to polypeptides, the term "domain" refers to a motif of a polypeptide having one or more identifiable structural or functional characteristics or properties (e.g., binding capacity, serving as a site for protein-protein interactions).

Dosing regimen: As used herein, a "dosing regimen" or a "dosing regimen" is a schedule of administration or physician determined regimen of treatment, prophylaxis, or palliative care.

Effective Amount. As used herein, the term "effective amount" of an agent is that amount sufficient to effect beneficial or desired results, for example, clinical results, and, as such, an "effective amount" depends upon the context in which it is being applied. For example, in the context of administering an agent that treats a protein deficiency (e.g., a Citrin deficiency), an effective amount of an agent is, for example, an amount of mRNA expressing sufficient Citrin to ameliorate, reduce, eliminate, or prevent the signs and symptoms associated with the Citrin deficiency, as compared to the severity of the symptom observed without administration of the agent. The term "effective amount" can be used interchangeably with "effective dose," "therapeutically effective amount," or "therapeutically effective dose."

Enantiomer: As used herein, the term "enantiomer" means each individual optically active form of a compound of the invention, having an optical purity or enantiomeric excess (as determined by methods standard in the art) of at least 80% (i.e., at least 90% of one enantiomer and at most 10% of the other enantiomer), at least 90%, or at least 98%.

Encapsulate: As used herein, the term "encapsulate" means to enclose, surround or encase.

Encapsulation Efficiency: As used herein, "encapsulation efficiency" refers to the amount of a polynucleotide that becomes part of a nanoparticle composition, relative to the initial total amount of polynucleotide used in the preparation of a nanoparticle composition. For example, if 97 mg of polynucleotide are encapsulated in a nanoparticle composition out of a total 100 mg of polynucleotide initially provided to the composition, the encapsulation efficiency can be given as 97%. As used herein, "encapsulation" can refer to complete, substantial, or partial enclosure, confinement, surrounding, or encasement.

Encoded protein cleavage signal: As used herein, "encoded protein cleavage signal" refers to the nucleotide sequence that encodes a protein cleavage signal.

Engineered: As used herein, embodiments of the invention are "engineered" when they are designed to have a feature or property, whether structural or chemical, that varies from a starting point, wild type or native molecule.

Enhanced Delivery: As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to the level of delivery of a polynucleotide by a control nanoparticle to a target tissue of interest (e.g., MC3, KC2, or DLinDMA). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. It will be understood that the enhanced delivery of a nanoparticle to a target tissue need not be determined in a subject being treated, it can be determined in a surrogate such as an animal model (e.g., a rat model).

Exosome: As used herein, "exosome" is a vesicle secreted by mammalian cells or a complex involved in RNA degradation.

Expression: As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end processing); (3) translation of an mRNA into a polypeptide or protein; and (4) post-translational modification of a polypeptide or protein.

Ex Vivo: As used herein, the term "ex vivo" refers to events that occur outside of an organism (e.g., animal, plant, or microbe or cell or tissue thereof). Ex vivo events can take place in an environment minimally altered from a natural (e.g., in vivo) environment.

Feature: As used herein, a "feature" refers to a characteristic, a property, or a distinctive element. When referring to polypeptides, "features" are defined as distinct amino acid sequence-based components of a molecule. Features of the polypeptides encoded by the polynucleotides of the present invention include surface manifestations, local conformational shape, folds, loops, half-loops, domains, half-domains, sites, termini or any combination thereof.

Formulation: As used herein, a "formulation" includes at least a polynucleotide and one or more of a carrier, an excipient, and a delivery agent.

Fragment: A "fragment," as used herein, refers to a portion. For example, fragments of proteins can comprise polypeptides obtained by digesting full-length protein isolated from cultured cells. In some embodiments, a fragment is a subsequences of a full length protein (e.g., Citrin) wherein N-terminal, and/or C-terminal, and/or internal subsequences have been deleted. In some preferred aspects of the present invention, the fragments of a protein of the present invention are functional fragments.

Functional: As used herein, a "functional" biological molecule is a biological molecule in a form in which it exhibits a property and/or activity by which it is characterized. Thus, a functional fragment of a polynucleotide of the present invention is a polynucleotide capable of expressing a functional Citrin fragment. As used herein, a functional fragment of Citrin refers to a fragment of wild type Citrin (i.e., a fragment of any of its naturally occurring isoforms), or a mutant or variant thereof, wherein the fragment retains a least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the biological activity of the corresponding fill length protein.

Helper Lipid: As used herein, the term "helper lipid" refers to a compound or molecule that includes a lipidic moiety (for insertion into a lipid layer, e.g., lipid bilayer) and a polar moiety (for interaction with physiologic solution at the surface of the lipid layer). Typically the helper lipid is a phospholipid. A function of the helper lipid is to "complement" the amino lipid and increase the fusogenicity of the bilayer and/or to help facilitate endosomal escape, e.g., of nucleic acid delivered to cells. Helper lipids are also believed to be a key structural component to the surface of the LNP.

Homology: As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present invention, the term homology encompasses both to identity and similarity.

In some embodiments, polymeric molecules are considered to be "homologous" to one another if at least 25%, 30%, 35%, 40%, 45%, 50%, 55%, 60%, 65%, 70%, 75%, 80%, 85%, 90%, 95%, or 99% of the monomers in the molecule are identical (exactly the same monomer) or are similar (conservative substitutions). The term "homologous" necessarily refers to a comparison between at least two sequences (polynucleotide or polypeptide sequences).

Identity: As used herein, the term "identity" refers to the overall monomer conservation between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. When comparing DNA and RNA, thymine (T) and uracil (U) can be considered equivalent.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "% ID" of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues. In some cases, the administration of a nanoparticle comprising a lipid component and an encapsulated therapeutic agent can trigger an immune response, which can be caused by (i) the encapsulated therapeutic agent (e.g., an mRNA), (ii) the expression product of such encapsulated therapeutic agent (e.g., a polypeptide encoded by the mRNA), (iii) the lipid component of the nanoparticle, or (iv) a combination thereof.

Inflammatory response: "Inflammatory response" refers to immune responses involving specific and non-specific defense systems. A specific defense system reaction is a specific immune system reaction to an antigen. Examples of specific defense system reactions include antibody responses. A non-specific defense system reaction is an inflammatory response mediated by leukocytes generally incapable of immunological memory, e.g., macrophages, eosinophils and neutrophils. In some aspects, an immune response includes the secretion of inflammatory cytokines, resulting in elevated inflammatory cytokine levels.

Inflammatory cytokines: The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (Il-13), interferon α (IFN-α), etc.

In Vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In Vivo: As used herein, the term "in vivo" refers to events that occur within an organism (e.g., animal, plant, or microbe or cell or tissue thereof).

Insertional and deletional variants: "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid. "Deletional variants" when referring to polypeptides are those with one or more amino acids in the native or starting amino acid sequence removed. Ordinarily, deletional variants will have one or more amino acids deleted in a particular region of the molecule.

Intact: As used herein, in the context of a polypeptide, the term "intact" means retaining an amino acid corresponding to the wild type protein, e.g., not mutating or substituting the wild type amino acid. Conversely, in the context of a nucleic acid, the term "intact" means retaining a nucleobase corresponding to the wild type nucleic acid, e.g., not mutating or substituting the wild type nucleobase.

Ionizable amino lipid: The term "ionizable amino lipid" includes those lipids having one, two, three, or more fatty acid or fatty alkyl chains and a pH-titratable amino head group (e.g., an alkylamino or dialkylamino head group). An ionizable amino lipid is typically protonated (i.e., positively charged) at a pH below the pKa of the amino head group and is substantially not charged at a pH above the pKa. Such ionizable amino lipids include, but are not limited to DLin-MC3-DMA (MC3) and (13Z,16SZ)—N,N-dimethyl-3-nonydocosa-13-16-dien-1-amine (L608).

Isolated: As used herein, the term "isolated" refers to a substance or entity that has been separated from at least some of the components with which it was associated (whether in nature or in an experimental setting). Isolated substances (e.g., polynucleotides or polypeptides) can have varying levels of purity in reference to the substances from which they have been isolated. Isolated substances and/or entities can be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Isomer: As used herein, the term "isomer" means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

Linker: As used herein, a "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof., Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Methods of Administration: As used herein, "methods of administration" can include intravenous, intramuscular, intradermal, subcutaneous, or other methods of delivering a composition to a subject. A method of administration can be selected to target delivery (e.g., to specifically deliver) to a specific region or system of a body.

Modified: As used herein "modified" refers to a changed state or structure of a molecule of the invention. Molecules can be modified in many ways including chemically, structurally, and functionally. In some embodiments, the mRNA molecules of the present invention are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Mucus: As used herein, "mucus" refers to the natural substance that is viscous and comprises mucin glycoproteins.

Nanoparticle Composition: As used herein, a "nanoparticle composition" is a composition comprising one or more lipids. Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Naturally occurring: As used herein, "naturally occurring" means existing in nature without artificial aid.

Non-human vertebrate: As used herein, a "non-human vertebrate" includes all vertebrates except Homo sapiens, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid sequence: The terms "nucleic acid sequence," "nucleotide sequence," or "polynucleotide sequence" are used interchangeably and refer to a contiguous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides. Exemplary nucleic acids or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an a-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

The phrase "nucleotide sequence encoding" refers to the nucleic acid (e.g., an mRNA or DNA molecule) coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional.

Part: As used herein, a "part" or "region" of a polynucleotide is defined as any portion of the polynucleotide that is less than the entire length of the polynucleotide.

Patient: As used herein, "patient" refers to a subject who can seek or be in need of treatment, requires treatment, is receiving treatment, will receive treatment, or a subject who is under care by a trained professional for a particular disease or condition. In some embodiments, the treatment is needed, required, or received to prevent or decrease the risk of developing acute disease, i.e., it is a prophylactic treatment.

Citrin Associated Disease: As use herein the terms "Citrin-associated disease" or "Citrin-associated disorder" refer to diseases or disorders, respectively, which result from aberrant Citrin activity (e.g., decreased activity or increased activity). As a non-limiting example, Citrullinemia is a Citrin associated disease.

The terms "Citrin enzymatic activity" or "Citrin activity" are used interchangeably in the present disclosure and refer to Citrin's ability to catalyze mitochondrial uptake of glutamate and/or export of aspartate and/or decrease ammonia. Accordingly, a fragment or variant retaining or having Citrin enzymatic activity or Citrin activity refers to a fragment or variant that has measurable enzymatic catalyzing the uptake of glutamate, export of aspartate or decrease of ammonia.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates can be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A (adenosine), G (guanosine), C (cytidine), and T (thymidine) in the case of a synthetic DNA, or A, C, G, and U (uridine) in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding mRNA sequences (comprising U) are considered codon-optimized nucleotide sequence of the present invention. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a ΨΨC codon (RNA map in which U has been replaced with pseudouridine).

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32:10489-10496 and references cited therein; 2'-deoxy-5-methyl-isocytidine can be prepared by the method of Tor et al., 1993, J. Am. Chem. Soc. 115:4461-4467 and references cited therein; and isoguanine nucleotides can be prepared using the method described by Switzer et al., 1993, supra, and Mantsch et al., 1993, Biochem. 14:5593-5601, or by the method described in U.S. Pat. No. 5,780,610 to Collins et al. Other nonnatural base pairs can be synthesized by the method described in Piccirilli et al., 1990, Nature 343:33-37, for the synthesis of 2,6-diaminopyrimidine and its complement (1-methylpyrazolo-[4,3]pyrimidine-5,7-(4H,6H)-dione. Other such modified nucleotide units which form unique base pairs are known, such as those described in Leach et al. (1992) J. Am. Chem. Soc. 114:3675-3683 and Switzer et al., supra.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

Polypeptide variant: As used herein, the term "polypeptide variant" refers to molecules that differ in their amino acid sequence from a native or reference sequence. The amino acid sequence variants can possess substitutions, deletions, and/or insertions at certain positions within the amino acid sequence, as compared to a native or reference sequence. Ordinarily, variants will possess at least about 50% identity, at least about 60% identity, at least about 70% identity, at least about 80% identity, at least about 90% identity, at least about 95% identity, at least about 99% identity to a native or reference sequence. In some embodiments, they will be at least about 80%, or at least about 90% identical to a native or reference sequence.

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc. divided by the measure in the body fluid.

Preventing: As used herein, the term "preventing" refers to partially or completely delaying onset of an infection, disease, disorder and/or condition; partially or completely delaying onset of one or more signs, symptoms, features, or clinical manifestations of a particular infection, disease, disorder, and/or condition; partially or completely delaying onset of one or more signs, symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease. An "immune prophylaxis" refers to a measure to produce active or passive immunity to prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine ($\psi$) refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 1-methyl-3-(3-amino-3-carboxypropyl)pseudouridine ($acp^3 \psi$), and 2'-O-methyl-pseudouridine ($\psi m$).

Purified: As used herein, "purify," "purified," "purification" means to make substantially pure or clear from unwanted components, material defilement, admixture or imperfection.

Reference Nucleic Acid Sequence: The term "reference nucleic acid sequence" or "reference nucleic acid" or "reference nucleotide sequence" or "reference sequence" refers to a starting nucleic acid sequence (e.g., a RNA, e.g., an mRNA sequence) that can be sequence optimized. In some embodiments, the reference nucleic acid sequence is a wild type nucleic acid sequence, a fragment or a variant thereof. In some embodiments, the reference nucleic acid sequence is a previously sequence optimized nucleic acid sequence.

Salts: In some aspects, the pharmaceutical composition for delivery disclosed herein and comprises salts of some of their lipid constituents. The term "salt" includes any anionic and cationic complex. Non-limiting examples of anions include inorganic and organic anions, e.g., fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof.

Sample: As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further can include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, or organs. A sample further refers to a medium, such as a nutrient broth or gel, which can contain cellular components, such as proteins or nucleic acid molecule.

Signal Sequence: As used herein, the phrases "signal sequence," "signal peptide," and "transit peptide" are used interchangeably and refer to a sequence that can direct the transport or localization of a protein to a certain organelle, cell compartment, or extracellular export. The term encompasses both the signal sequence polypeptide and the nucleic acid sequence encoding the signal sequence. Thus, references to a signal sequence in the context of a nucleic acid refer in fact to the nucleic acid sequence encoding the signal sequence polypeptide.

Signal transduction pathway: A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell.

Similarity. As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Single unit dose: As used herein, a "single unit dose" is a dose of any therapeutic administered in one dose/at one time/single route/single point of contact, i.e., single administration event.

Split dose: As used herein, a "split dose" is the division of single unit dose or total daily dose into two or more doses.

Specific delivery: As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to an off-target tissue (e.g., mammalian spleen). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. For example, for renovascular targeting, a polynucleotide is specifically provided to a mammalian kidney as compared to the liver and spleen if 1.5, 2-fold, 3-fold, 5-fold, 10-fold, 15 fold, or 20 fold more polynucleotide per 1 g of tissue is delivered to a kidney compared to that delivered to the liver or spleen following systemic administration of the polynucleotide. It will be understood that the ability of a nanoparticle to specifically deliver to a target tissue need not be determined in a subject being treated, it can be determined in a surrogate such as an animal model (e.g., a rat model).

Stable: As used herein "stable" refers to a compound that is sufficiently robust to survive isolation to a useful degree of purity from a reaction mixture, and in some cases capable of formulation into an efficacious therapeutic agent.

Stabilized: As used herein, the term "stabilize," "stabilized," "stabilized region" means to make or become stable.

Stereoisomer: As used herein, the term "stereoisomer" refers to all possible different isomeric as well as conformational forms that a compound can possess (e.g., a compound of any formula described herein), in particular all possible stenochemically and conformationally isomeric forms, all diastereomers, enantiomers and/or conformers of the basic molecular structure. Some compounds of the present invention can exist in different tautomeric forms, all of the latter being included within the scope of the present invention.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of treatment.

Substantially: As used herein, the term "substantially" refers to the qualitative condition of exhibiting total or near-total extent or degree of a characteristic or property of interest. One of ordinary skill in the biological arts will understand that biological and chemical characteristics rarely, if ever, go to completion and/or proceed to completeness or achieve or avoid an absolute result. The term "substantially" is therefore used herein to capture the potential lack of completeness inherent in many biological and chemical characteristics.

Substantially equal: As used herein as it relates to time differences between doses, the term means plus/minus 2%.

Substantially simultaneous: As used herein and as it relates to plurality of doses, the term means within 2 seconds.

Suffering from: An individual who is "suffering from" a disease, disorder, and/or condition has been diagnosed with or displays one or more signs and symptoms of the disease, disorder, and/or condition.

Susceptible to: An individual who is "susceptible to" a disease, disorder, and/or condition has not been diagnosed with and/or can not exhibit signs and symptoms of the disease, disorder, and/or condition but harbors a propensity to develop a disease or its signs and symptoms. In some embodiments, an individual who is susceptible to a disease, disorder, and/or condition (for example, CTLN2) can be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or other molecules of the present invention can be chemical or enzymatic.

Targeted Cells: As used herein, "targeted cells" refers to any one or more cells of interest. The cells can be found in vitro, in vivo, in situ or in the tissue or organ of an organism. The organism can be an animal, for example a mammal, a human, a subject or a patient.

Target tissue: As used herein "target tissue" refers to any one or more tissue types of interest in which the delivery of a polynucleotide would result in a desired biological and/or pharmacological effect. Examples of target tissues of interest include specific tissues, organs, and systems or groups thereof. In particular applications, a target tissue can be a kidney, a lung, a spleen or vascular endothelium in vessels (e.g., intra-coronary or intra-femoral). An "off-target tissue"

refers to any one or more tissue types in which the expression of the encoded protein does not result in a desired biological and/or pharmacological effect.

The presence of a therapeutic agent in an off-target issue can be the result of: (i) leakage of a polynucleotide from the administration site to peripheral tissue or distant off-target tissue via diffusion or through the bloodstream (e.g., a polynucleotide intended to express a polypeptide in a certain tissue would reach the off-target tissue and the polypeptide would be expressed in the off-target tissue); or (ii) leakage of an polypeptide after administration of a polynucleotide encoding such polypeptide to peripheral tissue or distant off-target tissue via diffusion or through the bloodstream (e.g., a polynucleotide would expressed a polypeptide in the target tissue, and the polypeptide would diffuse to peripheral tissue).

Targeting sequence: As used herein, the phrase "targeting sequence" refers to a sequence that can direct the transport or localization of a protein or polypeptide.

Terminus: As used herein the terms "termini" or "terminus," when referring to polypeptides, refers to an extremity of a peptide or polypeptide. Such extremity is not limited only to the first or final site of the peptide or polypeptide but can include additional amino acids in the terminal regions. The polypeptide based molecules of the invention can be characterized as having both an N-terminus (terminated by an amino acid with a free amino group ($NH_2$)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides can be modified such that they begin or end, as the case can be, with a non-polypeptide based moiety such as an organic conjugate.

Therapeutic Agent: The term "therapeutic agent" refers to an agent that, when administered to a subject, has a therapeutic, diagnostic, and/or prophylactic effect and/or elicits a desired biological and/or pharmacological effect. For example, in some embodiments, an mRNA encoding a Citrin polypeptide can be a therapeutic agent.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve signs and symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve signs and symptoms of, diagnose, prevent, and/or delay the onset of the infection, disease, disorder, and/or condition.

Total daily dose: As used herein, a "total daily dose" is an amount given or prescribed in 24 hr. period. The total daily dose can be administered as a single unit dose or a split dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors can regulate transcription of a target gene alone or in a complex with other molecules.

Transcription: As used herein, the term "transcription" refers to methods to produce mRNA (e.g., an mRNA sequence or template) from DNA (e.g., a DNA template or sequence).

Transfection: As used herein, "transfection" refers to the introduction of a polynucleotide (e.g., exogenous nucleic acids) into a cell wherein a polypeptide encoded by the polynucleotide is expressed (e.g., mRNA) or the polypeptide modulates a cellular function (e.g., siRNA, miRNA). As used herein, "expression" of a nucleic acid sequence refers to translation of a polynucleotide (e.g., an mRNA) into a polypeptide or protein and/or post-translational modification of a polypeptide or protein. Methods of transfection include, but are not limited to, chemical methods, physical treatments and cationic lipids or mixtures.

Treating, treatment, therapy: As used herein, the term "treating" or "treatment" or "therapy" refers to partially or completely alleviating, ameliorating, improving, relieving, delaying onset of, inhibiting progression of, reducing severity of, and/or reducing incidence of one or more signs and symptoms or features of a disease, e.g., Citrullinemia (e.g., CTLN2). For example, "treating" Citrullinemia (e.g., CTLN2) can refer to diminishing signs and symptoms associated with the disease, prolong the lifespan (increase the survival rate) of patients, reducing the severity of the disease, preventing or delaying the onset of the disease, etc. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in some way. Unmodified can, but does not always, refer to the wild type or native form of a biomolecule. Molecules can undergo a series of modifications whereby each modified molecule can serve as the "unmodified" starting molecule for a subsequent modification.

Uracil: Uracil is one of the four nucleobases in the nucleic acid of RNA, and it is represented by the letter U. Uracil can be attached to a ribose ring, or more specifically, a ribofuranose via a $\beta$-$N_1$-glycosidic bond to yield the nucleoside uridine. The nucleoside uridine is also commonly abbreviated according to the one letter code of its nucleobase, i.e., U. Thus, in the context of the present disclosure, when a monomer in a polynucleotide sequence is U, such U is designated interchangeably as a "uracil" or a "uridine."

Uridine Content: The terms "uridine content" or "uracil content" are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine Modified Sequence: The terms "uridine-modified sequence" refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms "uridine-modified sequence" and "uracil-modified sequence" are considered equivalent and interchangeable.

A "high uridine codon" is defined as a codon comprising two or three uridines, a "low uridine codon" is defined as a codon comprising one uridine, and a "no uridine codon" is a codon without any uridines. In some embodiments, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some embodiments, a high uridine codon can be replaced with another high uridine codon. In some embodiments, a low uridine codon can be replaced with another low uridine codon. In some embodiments, a no uridine codon can be replaced with another no uridine codon. A uridine-modified sequence can be uridine enriched or uridine rarefied.

Uridine Enriched: As used herein, the terms "uridine enriched" and grammatical variants refer to the increase in uridine content (expressed in absolute value or as a percentage value) in an sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases. Uridine enrichment can be global (i.e., relative to the entire length of a candidate nucleic acid sequence) or local (i.e., relative to a subsequence or region of a candidate nucleic acid sequence).

Uridine Rarefied: As used herein, the terms "uridine rarefied" and grammatical variants refer to a decrease in uridine content (expressed in absolute value or as a percentage value) in an sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

Variant: The term variant as used in present disclosure refers to both natural variants (e.g, polymorphisms, isoforms, etc) and artificial variants in which at least one amino acid residue in a native or starting sequence (e.g., a wild type sequence) has been removed and a different amino acid inserted in its place at the same position. These variants can de described as "substitutional variants." The substitutions can be single, where only one amino acid in the molecule has been substituted, or they can be multiple, where two or more amino acids have been substituted in the same molecule. If amino acids are inserted or deleted, the resulting variant would be an "insertional variant" or a "deletional variant" respectively.

30. Embodiments

Throughout this section, the term embodiment is abbreviated as 'E' followed by an ordinal. For example, E1 is equivalent to Embodiment 1.

E1. A polynucleotide comprising an open reading frame (ORF) encoding a Citrin polypeptide, wherein the uracil or thymine content of the ORF relative to the theoretical minimum uracil or thymine content of a nucleotide sequence encoding the Citrin polypeptide (% UTM or % TTM), is between about 100% and about 150%.

E2. The polynucleotide of E1, wherein the % UTM or % TTM is between about 105% and about 145%, about 105% and about 140%, about 110% and about 140%, about 110% and about 145%, about 115% and about 135%, about 105% and about 135%, about 110% and about 135%, about 115% and about 145%, about 115% and about 140%, about 115% and about 135%, about 115% and about 130%, or about 117% and about 126%.

E3. The polynucleotide of E2, wherein the % UTM or % TTM is between (i) 110%, 111%, 112%, 113%, 114%, 115%, 116%, or 117%, and (ii) 126%, 127%, 128%, 129%, 130%, 131%, 132%, 133%, 134%, 135%, 136%, 137%, 138%, 139%, or 140%.

E4. The polynucleotide of any one of E1 to E3, wherein the uracil or thymine content of the ORF relative to the uracil or thymine content of the corresponding wild-type ORF (% $U_{WT}$ or % $T_{WT}$) is less than 100%.

E5. The polynucleotide of E4, wherein the % $U_{WT}$ or % $T_{WT}$ is less than about 95%, less than about 90%, less than about 85%, less than about 80%, less than about 75%, less than about 70%, less than 69%, less than 68%, less than 67%, less than 66%, or less than 65%.

E6. The polynucleotide of E4, wherein the % UWT or % TWT is between 60% and 65%.

E7. The polynucleotide of any one of E1 to E6, wherein the uracil or thymine content in the ORF relative to the total nucleotide content in the ORF (% UTL or % TTL) is less than about 50%, less than about 40%, less than about 30%, or less than about 20%.

E8. The polynucleotide of E7, wherein the % UTL or % TTL is less than about 18%.

E9. The polynucleotide of any one of E1 to E8, wherein the % UTL or % TTL is between about 15% and about 18%.

E10. The polynucleotide of any one of E1 to E9, wherein the guanine content of the ORF with respect to the theoretical maximum guanine content of a nucleotide sequence encoding the Citrin polypeptide (% GTMX) is at least 69%, at least 70%, at least 75%, at least about 80%, at least about 85%, at least about 90%, at least about 95%, or about 100%.

E11. The polynucleotide of E10, wherein the % GTMX is between about 68% and about 80%, between about 70% and about 80%, between about 70% and about 79%, between about 70% and about 78%, between about 70% and about 77%, or between about 70% and about 76%.

E12. The polynucleotide of any one of E1 to E11, wherein the cytosine content of the ORF relative to the theoretical maximum cytosine content of a nucleotide sequence encoding the Citrin polypeptide (% CTMX) is at least 60%, at least 65%, at least about 70%, at least about 75%, at least about 80%, at least about 85%, at least about 90%, at least about 95%, or about 100%.

E13. The polynucleotide of E12, wherein the % CTMX is between about 60% and about 80%, between about 65% and about 80%, between about 65% and about 75%, or between about 69% and about 75%.

E14. The polynucleotide of any one of E1 to E13, wherein the guanine and cytosine content (G/C) of the ORF relative to the theoretical maximum G/C content of a nucleotide sequence encoding the Citrin polypeptide (% G/CTMX) is at least about 81%, at least about 85%, at least about 90%, at least about 95%, or about 100%.

E15. The polynucleotide of any one of E1 to E13, wherein the % G/CTMX is between about 80% and about 100%, between about 80% and about 95%, between about 85% and about 95%, between about 90% and about 95%, between about 91% and about 95%, or between about 91% and about 94%.

E16. The polynucleotide of any one of E1 to E15, wherein the G/C content in the ORF relative to the G/C content in the corresponding wild-type ORF (% G/CWT) is at least 102%, at least 103%, at least 104%, at least 105%, at least 106%, at least 107%, at least 110%, at least 115%, at least 120%, at least 125%, at least 130%, at least 131%, at least 132%, at least 133%, or at least 134%.

E17. The polynucleotide of any one of E1 to E15, wherein the average G/C content in the 3rd codon position in the ORF is at least 30%, at least 35%, at least 40%, at least 41%, at least 42%, at least 43%, at least 44%, at least 45%, at least 46%, at least 47%, at least 48%, or at least 49% higher than the average G/C content in the 3rd codon position in the corresponding wild-type ORF.

E18. The polynucleotide of any one of E1 to E17, wherein the ORF further comprises at least one low-frequency codon.

E19. The polynucleotide of any one of E1 to E18,
(i) wherein the ORF is at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to CITRIN-CO6, CITRIN-CO12, CITRIN-CO23, CITRIN-CO11, or CITRIN-CO25,
(ii) wherein the ORF is at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to CITRIN-CO2, CITRIN-CO16, CITRIN-CO20, CITRIN-CO17, CITRIN-CO4, or CITRIN-CO1,
(iii) wherein the ORF is at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to CITRIN-CO9, CITRIN-CO18, CITRIN-CO5, CITRIN-CO10, CITRIN-CO13, or CITRIN-CO7,
(iv) wherein the ORF is at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to CITRIN-CO15, CITRIN-CO14, CITRIN-CO3, CITRIN-CO22, or CITRIN-CO19, or
(v) wherein the ORF is at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 91%, at least 92%, at least 93%, at least 94%, at least 95%, at least 96%, at least 97%, at least 98%, at least 99%, or 100% identical to CITRIN-CO24, CITRIN-CO8, or CITRIN-CO21.

E20. A polynucleotide comprising an ORF,
(i) wherein the ORF is at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to CITRIN-CO6, CITRIN-CO12, CITRIN-CO23, CITRIN-CO11, or CITRIN-CO25,
(ii) wherein the ORF is at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to CITRIN-CO2, CITRIN-CO16, CITRIN-CO20, CITRIN-CO17, CITRIN-CO4, or CITRIN-CO1,
(iii) wherein the ORF is at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to CITRIN-CO9, CITRIN-CO18, CITRIN-CO5, CITRIN-CO10, CITRIN-CO13, or CITRIN-CO7,
(iv) wherein the ORF is at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to CITRIN-CO15, CITRIN-CO14, CITRIN-CO3, CITRIN-CO22, or CITRIN-CO19, or
(v) wherein the ORF is at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 91%, at least 92%, at least 93%, at least 94%, at least 95%, at least 96%, at least 97%, at least 98%, at least 99%, or 100% identical to CITRIN-CO24, CITRIN-CO8, or CITRIN-CO21.

E21. The polynucleotide of any one of E1 to E20, wherein the ORF has at least 74%, at least 75%, at least 76%, at least 77%, at least 78%, at least 79%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NOs: 5-29.

E22. The polynucleotide of any one of E1 to E21, wherein the Citrin polypeptide comprises an amino acid sequence at least about 95%, at least about 96%, at least about 97%, at least about 98%, at least about 99%, or about 100% identical to (i) the polypeptide sequence of wild type Citrin, isoform 1 (SEQ ID NO: 1), or (ii) the polypeptide sequence of wild type Citrin, isoform 2 (SEQ ID NO: 3), and wherein the Citrin polypeptide has aspartate or glutamate transport activity.

E23. The polynucleotide of E22, wherein the Citrin polypeptide is a variant, derivative, or mutant having aspartate or glutamate transport activity.

E24. The polynucleotide of any one of E1 to E23, wherein the polynucleotide sequence further comprises a nucleotide sequence encoding a transit peptide.

E25. The polynucleotide of any one of E1 to E24, wherein the polynucleotide is single stranded.

E26. The polynucleotide of any one of E1 to E24, wherein the polynucleotide is double stranded.

E27. The polynucleotide of any one of E1 to E26, wherein the polynucleotide is DNA.

E28. The polynucleotide of any one of E1 to E26, wherein the polynucleotide is RNA.

E29. The polynucleotide of E28, wherein the polynucleotide is mRNA.

E30. The polynucleotide of any one of E1 to E29, wherein the polynucleotide comprises at least one chemically modified nucleobase, sugar, backbone, or any combination thereof.

E31. The polynucleotide of E30, wherein the at least one chemically modified nucleobase is selected from the group consisting of pseudouracil (ψ), N1-methylpseudouracil (m1ψ), 2-thiouracil (s2U), 4'-thiouracil, 5-methylcytosine, 5-methyluracil, and any combination thereof.

E32. The polynucleotide of E30, wherein the at least one chemically modified nucleobase is 5-methoxyuracil.

E33. The polynucleotide of E32, wherein at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils.

E34. The polynucleotide of any one of E1 to E33, wherein the polynucleotide further comprises a miRNA binding site.

E35. The polynucleotide of E34, wherein the miRNA binding site comprises one or more nucleotide sequences selected from Table 3.

E36. The polynucleotide of E34, wherein the miRNA binding site binds to miR-142.

E37. The polynucleotide of E35 or E36, wherein the miRNA binding site binds to miR-142-3p or miR-142-5p.

E38. The polynucleotide of E36 or E37, wherein the miR142 comprises SEQ ID NO: 73.

E39. The polynucleotide of any one of E1 to E38, wherein the polynucleotide further comprises a 5' UTR.

E40. The polynucleotide of E39, wherein the 5' UTR comprises a nucleic acid sequence at least about 90%, at least about 95%, at least about 96%, at least about 97%, at least about 98%, at least about 99%, or about 100% identical to a sequence listed in SEQ ID NOs: 30-47.

E41. The polynucleotide of any one of E1 to E40, wherein the polynucleotide further comprises a 3' UTR.

E42. The polynucleotide of E41, wherein the 3' UTR comprises a nucleic acid sequence at least about 90%, at least about 95%, at least about 96%, at least about 97%, at least about 98%, at least about 99%, or about 100% identical to a sequence listed in SEQ ID NOs: 48-72.

E43. The polynucleotide of E41 or E42, wherein the miRNA binding site is located within the 3' UTR.

E44. The polynucleotide of any one of E1 to E43, wherein the polynucleotide further comprises a 5' terminal cap.

E45. The polynucleotide of E44, wherein the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

E46. The polynucleotide of any one of E1 to E45, wherein the polynucleotide further comprises a poly-A region.

E47. The polynucleotide of E46, wherein the poly-A region is at least about 10, at least about 20, at least about 30, at least about 40, at least about 50, at least about 60, at least about 70, at least about 80, or at least about 90 nucleotides in length.

E48. The polynucleotide of E47, wherein the poly-A region has about 10 to about 200, about 20 to about 180, about 50 to about 160, about 70 to about 140, or about 80 to about 120 nucleotides in length.

E49. The polynucleotide of any one of E1 to E48, wherein the polynucleotide encodes a Citrin polypeptide that is fused to one or more heterologous polypeptides.

E50. The polynucleotide of E49, wherein the one or more heterologous polypeptides increase a pharmacokinetic property of the Citrin polypeptide.

E51. The polynucleotide of any one of E1 to E50, wherein upon administration to a subject, the polynucleotide has:
  (i) a longer plasma half-life;
  (ii) increased expression of a Citrin polypeptide encoded by the ORF;
  (iii) a lower frequency of arrested translation resulting in an expression fragment;
  (iv) greater structural stability; or
  (v) any combination thereof,
  relative to a corresponding polynucleotide comprising SEQ ID NO: 2 or 4.

E52. The polynucleotide of any one of E1 to E51, wherein the polynucleotide comprises:
  (i) a 5'-terminal cap;
  (ii) a 5'-UTR;
  (iii) an ORF encoding a Citrin polypeptide;
  (iv) a 3'-UTR; and
  (v) a poly-A region.

E53. The polynucleotide of E52, wherein the 3'-UTR comprises a miRNA binding site.

E54. A method of producing the polynucleotide of any one of E1 to E53, the method comprising modifying an ORF encoding a Citrin polypeptide by substituting at least one uracil nucleobase with an adenine, guanine, or cytosine nucleobase, or by substituting at least one adenine, guanine, or cytosine nucleobase with a uracil nucleobase, wherein all the substitutions are synonymous substitutions.

E55. The method of E54, wherein the method further comprises replacing at least about 90%, at least about 95%, at least about 99%, or about 100% of uracils with 5-methoxyuracils.

E56. A composition comprising
  (a) the polynucleotide of any one of E1 to E53; and
  (b) a delivery agent.

E57. The composition of E56, wherein the delivery agent comprises a lipidoid, a liposome, a lipoplex, a lipid nanoparticle, a polymeric compound, a peptide, a protein, a cell, a nanoparticle mimic, a nanotube, or a conjugate.

E58. The composition of E56, wherein the delivery agent comprises a lipid nanoparticle.

E59. The composition of E58, wherein the lipid nanoparticle comprises a lipid selected from the group consisting of DLin-DMA, DLin-K-DMA, 98N12-5, C12-200, DLin-MC3-DMA, DLin-KC2-DMA, DODMA, PLGA, PEG, PEG-DMG, PEGylated lipids, amino alcohol lipids, KL22, and any combinations thereof.

E60. The composition of any one of E56 to E59, wherein the delivery agent comprises a compound having the formula (I)

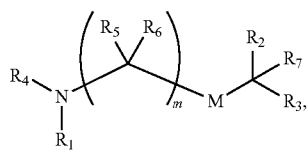

(I)

or a salt or stereoisomer thereof, wherein
  R₁ is selected from the group consisting of $C_{5-20}$ alkyl, $C_{5-20}$ alkenyl, —R*YR″, —YR″, and —R″M′R′;
  R₂ and R₃ are independently selected from the group consisting of H, $C_{1-14}$ alkyl, $C_{2-14}$ alkenyl, —R*YR″, —YR″, and —R*OR″, or R₂ and R₃, together with the atom to which they are attached, form a heterocycle or carbocycle;
  R₄ is selected from the group consisting of a $C_{3-6}$ carbocycle, —(CH₂)ₙQ, —(CH₂)ₙCHQR, —CHQR, —CQ(R)₂, and unsubstituted $C_{1-6}$ alkyl, where Q is selected from a carbocycle, heterocycle, —OR, —O(CH₂)ₙN(R)₂, —C(O)OR, —OC(O)R, —CX₃, —CX₂H, —CXH₂, —CN, —N(R)₂, —C(O)N(R)₂, —N(R)C(O)R, —N(R)S(O)₂R, —N(R)C(O)N(R)₂, —N(R)C(S)N(R)₂, and —C(R)N(R)₂C(O)OR, and each n is independently selected from 1, 2, 3, 4, and 5;
  each R₅ is independently selected from the group consisting of $C_{1-3}$ alkyl, $C_{2-3}$ alkenyl, and H;
  each R₆ is independently selected from the group consisting of $C_{1-3}$ alkyl, $C_{2-3}$ alkenyl, and H;
  M and M′ are independently selected from —C(O)O—, —OC(O)—, —C(O)N(R′)—, —N(R′)C(O)—, —C(O)—, —C(S)—, —C(S)S—, —SC(S)—, —CH(OH)—, —P(O)(OR′)O—, —S(O)₂—, an aryl group, and a heteroaryl group;
  R₇ is selected from the group consisting of $C_{1-3}$ alkyl, $C_{2-3}$ alkenyl, and H;
  each R is independently selected from the group consisting of $C_{1-3}$ alkyl, $C_{2-3}$ alkenyl, and H;
  each R′ is independently selected from the group consisting of $C_{1-18}$ alkyl, $C_{2-18}$ alkenyl, —R*YR″, —YR″, and H;
  each R″ is independently selected from the group consisting of $C_{3-14}$ alkyl and $C_{3-14}$ alkenyl;
  each R* is independently selected from the group consisting of $C_{1-12}$ alkyl and $C_{2-12}$ alkenyl;
  each Y is independently a $C_{3-6}$ carbocycle;
  each X is independently selected from the group consisting of F, Cl, Br, and I; and
  m is selected from 5, 6, 7, 8, 9, 10, 11, 12, and 13; and
  provided when R₄ is —(CH₂)ₙQ, —(CH₂)ₙCHQR, —CHQR, or —CQ(R)₂, then (i) Q is not —N(R)₂ when n is 1, 2, 3, 4 or 5, or (ii) Q is not 5, 6, or 7-membered heterocycloalkyl when n is 1 or 2.

E61. A composition comprising a nucleotide sequence encoding a Citrin polypeptide and a delivery agent, wherein the delivery agent comprises a compound having the formula (I)

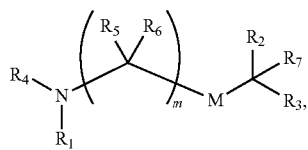

(I)

or a salt or stereoisomer thereof, wherein
  R₁ is selected from the group consisting of $C_{5-20}$ alkyl, $C_{5-20}$ alkenyl, —R*YR″, —YR″, and —R″M′R′;
  R₂ and R₃ are independently selected from the group consisting of H, $C_{1-14}$ alkyl, $C_{2-14}$ alkenyl, —R*YR″, —YR″, and —R*OR″, or R₂ and R₃, together with the atom to which they are attached, form a heterocycle or carbocycle;
  R₄ is selected from the group consisting of a $C_{3-6}$ carbocycle, —(CH₂)ₙQ, —(CH₂)ₙCHQR, —CHQR, —CQ(R)₂, and unsubstituted $C_{1-6}$ alkyl, where Q is selected from a carbocycle, heterocycle, —OR, —O(CH₂)ₙN(R)₂, —C(O)OR, —OC(O)R, —CX₃, —CX₂H, —CXH₂, —CN, —N(R)₂, —C(O)N(R)₂, —N(R)C(O)R, —N(R)S(O)₂R, —N(R)C(O)N(R)₂, —N(R)C(S)N(R)₂, and —C(R)N(R)₂C(O)OR, and each n is independently selected from 1, 2, 3, 4, and 5;
  each R₅ is independently selected from the group consisting of $C_{1-3}$ alkyl, $C_{2-3}$ alkenyl, and H;
  each R₆ is independently selected from the group consisting of $C_{1-3}$ alkyl, $C_{2-3}$ alkenyl, and H;
  M and M′ are independently selected from —C(O)O—, —OC(O)—, —C(O)N(R′)—, —N(R′)C(O)—, —C(O)—, —C(S)—, —C(S)S—, —SC(S)—, —CH(OH)—, —P(O)(OR′)O—, —S(O)₂—, an aryl group, and a heteroaryl group;
  R₇ is selected from the group consisting of $C_{1-3}$ alkyl, $C_{2-3}$ alkenyl, and H;
  each R is independently selected from the group consisting of $C_{1-3}$ alkyl, $C_{2-3}$ alkenyl, and H;
  each R′ is independently selected from the group consisting of $C_{1-18}$ alkyl, $C_{2-18}$ alkenyl, —R*YR″, —YR″, and H;
  each R″ is independently selected from the group consisting of $C_{3-14}$ alkyl and $C_{3-14}$ alkenyl;
  C3-14 alkenyl;
  each R* is independently selected from the group consisting of $C_{1-12}$ alkyl and $C_{2-12}$ alkenyl;
  each Y is independently a $C_{3-6}$ carbocycle;
  each X is independently selected from the group consisting of F, Cl, Br, and I; and
  m is selected from 5, 6, 7, 8, 9, 10, 11, 12, and 13; and
  provided when R₄ is —(CH₂)ₙQ, —(CH₂)ₙCHQR, —CHQR, or —CQ(R)₂, then (i) Q is not —N(R)₂ when n is 1, 2, 3, 4 or 5, or (ii) Q is not 5, 6, or 7-membered heterocycloalkyl when n is 1 or 2.

E62. The composition of E60 or E61, wherein the compound is of Formula (IA):

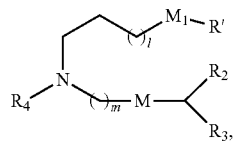

(IA)

or a salt or stereoisomer thereof, wherein
  l is selected from 1, 2, 3, 4, and 5;
  m is selected from 5, 6, 7, 8, and 9;
  M₁ is a bond or M′;
  R₄ is unsubstituted $C_{1-3}$ alkyl, or —(CH₂)ₙQ, in which n is 1, 2, 3, 4, or 5 and Q is OH, —NHC(S)N(R)₂, or —NHC(O)N(R)₂;

M and M' are independently selected from —C(O)O—, —OC(O)—, —C(O)N(R')—, —P(O)(OR')O—, an aryl group, and a heteroaryl group; and R$_2$ and R$_3$ are independently selected from the group consisting of H, C$_{1-14}$ alkyl, and C$_{2-14}$ alkenyl.

E63. The composition of any one of E60 to E62, wherein m is 5, 7, or 9.

E64. The composition of any one of E60 to E63, wherein the compound is of Formula (II):

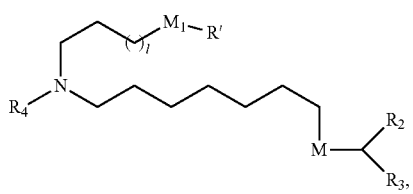

(II)

or a salt or stereoisomer thereof, wherein l is selected from 1, 2, 3, 4, and 5;

M$_1$ is a bond or M';

R$_4$ is unsubstituted C$_{1-3}$ alkyl, or —(CH$_2$)$_n$Q, in which n is 2, 3, or 4 and Q is OH, —NHC(S)N(R)$_2$, or —NHC(O)N(R)$_2$;

M and M' are independently selected from —C(O)O—, —OC(O)—, —C(O)N(R')—, —P(O)(OR')O—, an aryl group, and a heteroalyl group; and R$_2$ and R$_3$ are independently selected from the group consisting of H, C$_{1-14}$ alkyl, and C$_{2-14}$ alkenyl.

E65. The composition of any one of E62 to E64, wherein M1 is M'.

E66. The composition of E65, wherein M and M' are independently —C(O)O— or —OC(O)—.

E67. The composition of any one of E62 to E66, wherein l is 1, 3, or 5.

E68. The composition of E60 or E61, wherein the compound is selected from the group consisting of Compound 1 to Compound 147, salts and stereoisomers thereof, and any combination thereof.

E69. The composition of E60 or E61, wherein the compound is of the Formula (IIa),

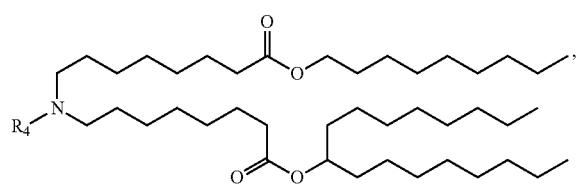

(IIa)

or a salt or stereoisomer thereof.

E70. The composition of E60 or E61, wherein the compound is of the Formula (IIb),

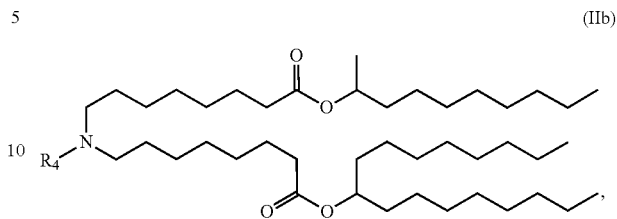

(IIb)

or a salt or stereoisomer thereof.

E71. The composition of E60 or E61, wherein the compound is of the Formula (IIc) or (IIe),

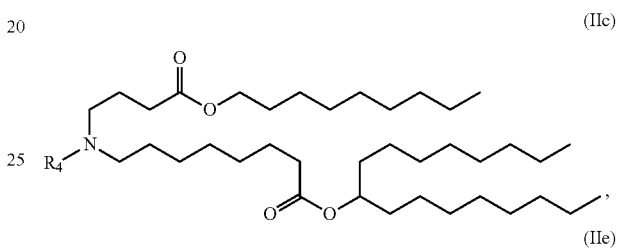

(IIc)

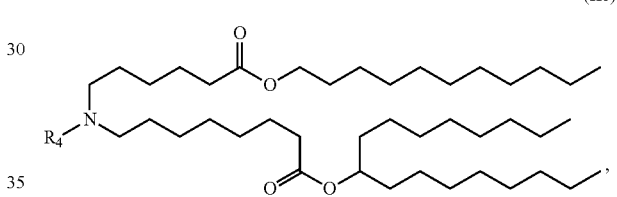

(IIe)

or a salt or stereoisomer thereof.

E72. The composition of any one of E69 to E71, wherein R$_4$ is selected from —(CH$_2$)$_n$Q and —(CH$_2$)$_n$CHQR.

E73. The composition of E60 or E61, wherein the compound is of the Formula (IId),

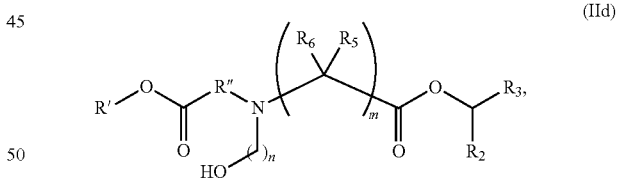

(IId)

or a salt or stereoisomer thereof, wherein R$_2$ and R$_3$ are independently selected from the group consisting of C$_{5-14}$ alkyl and C$_{5-14}$ alkenyl, n is selected from 2, 3, and 4, and R', R", R$_5$, R$_6$ and m are as defined in E60 or E61.

E74. The composition of E73, wherein R$_2$ is C$_8$ alkyl.

E75. The composition of E74, wherein R$_3$ is C$_5$ alkyl, C$_6$ alkyl, C$_7$ alkyl, C$_8$ alkyl, or C$_9$ alkyl.

E76. The composition of any one of E73 to E75, wherein m is 5, 7, or 9.

E77. The composition of any one of E73 to E76, wherein each R$_5$ is H.

E78. The composition of E77, wherein each R$_6$ is H.

E79. The composition of any one of E60 to E78, which is a nanoparticle composition.

E80. The composition of E79, wherein the delivery agent further comprises a phospholipid.

E81. The composition of E80, wherein the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16:0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and any mixtures thereof.

E82. The composition of any one of E60 to E81, wherein the delivery agent further comprises a structural lipid.

E83. The composition of E82, wherein the structural lipid is selected from the group consisting of cholesterol, fecosterol, sitosterol, ergosterol, campesterol, stigmasterol, brassicasterol, tomatidine, ursolic acid, alpha-tocopherol, and any mixtures thereof.

E84. The composition of any one of E60 to E83, wherein the delivery agent further comprises a PEG lipid.

E85. The composition of E84, wherein the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and any mixtures thereof.

E86. The composition of any one of E60 to E85, wherein the delivery agent further comprises an ionizable lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2S)).

E87. The composition of any one of E60 to E86, wherein the delivery agent further comprises a phospholipid, a structural lipid, a PEG lipid, or any combination thereof.

E88. The composition of any one of E60 to E87, wherein the composition is formulated for in vivo delivery.

E89. The composition according any one of E60 to E88, which is formulated for intramuscular, subcutaneous, or intradermal delivery.

E90. A host cell comprising the polynucleotide of any one of E1 to E53.

E91. The host cell of E90, wherein the host cell is a eukaryotic cell.

E92. A vector comprising the polynucleotide of any one of E1 to E53.

E93. A method of making a polynucleotide comprising enzymatically or chemically synthesizing the polynucleotide of any one of E1 to E53.

E94. A polypeptide encoded by the polynucleotide of any one of E1 to E53, the composition of any one of E56 to E89, the host cell of E90 or E91, or the vector of E92 or produced by the method of E93.

E95. A method of expressing in vivo an active Citrin polypeptide in a subject in need thereof comprising administering to the subject an effective amount of the polynucleotide of any one of E1 to E53, the composition of any one of E56 to E89, the host cell of E90 or E91, or the vector of E92.

E96. A method of treating citrullinemia type 2 (CTLN2) in a subject in need thereof comprising administering to the subject a therapeutically effective amount of the polynucleotide of any one of E1 to E53, the composition of any one of E56 to E89, the host cell of E90 or E91, or the vector of E92, wherein the administration alleviates the signs or symptoms of CTLN2 in the subject.

E97. A method to prevent or delay the onset of CTLN2 signs or symptoms in a subject in need thereof comprising administering to the subject a prophylactically effective amount of the polynucleotide of any one of E1 to E53, the composition of any one of E56 to E89, the host cell of E90 or E91, or the vector of E92 before CTLN2 signs or symptoms manifest, wherein the administration prevents or delays the onset of CTLN2 signs or symptoms in the subject.

E98. A method to ameliorate the signs or symptoms of CTLN2 in a subject in need thereof comprising administering to the subject a therapeutically effective amount of the polynucleotide of any one of E1 to E53, the composition of any one of E56 to E89, the host cell of E90 or E91, or the vector of E92 before CTLN2 signs or symptoms manifest, wherein the administration ameliorates CTLN2 signs or symptoms in the subject.

31. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" can mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1

Chimeric Polynucleotide Synthesis

A. Triphosphate Route

Two regions or parts of a chimeric polynucleotide can be joined or ligated using triphosphate chemistry. According to this method, a first region or part of 100 nucleotides or less can be chemically synthesized with a 5' monophosphate and terminal 3'desOH or blocked OH. If the region is longer than 80 nucleotides, it can be synthesized as two strands for ligation.

If the first region or part is synthesized as a non-positionally modified region or part using in vitro transcription (IVT), conversion the 5'monophosphate with subsequent capping of the 3' terminus can follow. Monophosphate protecting groups can be selected from any of those known in the art.

The second region or part of the chimeric polynucleotide can be synthesized using either chemical synthesis or IVT methods. NT methods can include an RNA polymerase that can utilize a primer with a modified cap. Alternatively, a cap of up to 80 nucleotides can be chemically synthesized and coupled to the NT region or part.

It is noted that for ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then such region or part can comprise a phosphate-sugar backbone.

Ligation can then be performed using any known click chemistry, orthoclick chemistry, solulink, or other bioconjugate chemistries known to those in the art.

B. Synthetic Route

The chimeric polynucleotide can be made using a series of starting segments. Such segments include:
(a) Capped and protected 5' segment comprising a normal 3'OH (SEG. 1)
(b) 5' triphosphate segment which can include the coding region of a polypeptide and comprising a normal 3'OH (SEG. 2)
(c) 5' monophosphate segment for the 3' end of the chimeric polynucleotide (e.g., the tail) comprising cordycepin or no 3'OH (SEG. 3)

After synthesis (chemical or NT), segment 3 (SEG. 3) can be treated with cordycepin and then with pyrophosphatase to create the 5'monophosphate.

Segment 2 (SEG. 2) can then be ligated to SEG. 3 using RNA ligase. The ligated polynucleotide can then be purified and treated with pyrophosphatase to cleave the diphosphate. The treated SEG.2-SEG. 3 construct is then purified and SEG. 1 is ligated to the 5' terminus. A further purification step of the chimeric polynucleotide can be performed.

Where the chimeric polynucleotide encodes a polypeptide, the ligated or joined segments can be represented as: 5'UTR (SEG. 1), open reading frame or ORF (SEG. 2) and 3'UTR+PolyA (SEG. 3).

The yields of each step can be as much as 90-95%.

Example 2

PCR for cDNA Production

PCR procedures for the preparation of cDNA can be performed using 2×KAPA HIFI™ HotStart ReadyMix by Kapa Biosystems (Woburn, MA). This system includes 2x KAPA ReadyMix 12.5 µl; Forward Primer (10 µM) 0.75 µl; Reverse Primer (10 µM) 0.75 µl; Template cDNA-100 ng; and dH$_2$O diluted to 25.0 µl. The PCR reaction conditions can be: at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention can incorporate a poly-T$_{120}$ for a poly-A$_{120}$ in the mRNA. Other reverse primers with longer or shorter poly(T) tracts can be used to adjust the length of the poly(A) tail in the polynucleotide mRNA.

The reaction can be cleaned up using Invitrogen's PURELINK™ PCR Micro Kit (Carlsbad, CA) per manufacturer's instructions (up to 5 µg). Larger reactions will require a cleanup using a product with a larger capacity. Following the cleanup, the cDNA can be quantified using the NANODROP™ and analyzed by agarose gel electrophoresis to confirm the cDNA is the expected size. The cDNA can then be submitted for sequencing analysis before proceeding to the in vitro transcription reaction.

Example 3

In Vitro Transcription (IVT)

The in vitro transcription reactions can generate polynucleotides containing uniformly modified polynucleotides. Such uniformly modified polynucleotides can comprise a region or part of the polynucleotides of the invention. The input nucleotide triphosphate (NTP) mix can be made using natural and tm-natural NTPs.

A typical in vitro transcription reaction can include the following:
1 Template cDNA—1.0 µg
2 10× transcription buffer (400 mM Tris-HCl pH 8.0, 190 mM MgCl$_2$, 50 mM DTT, 10 mM Spermidine)—2.0 µl
3 Custom NTPs (25 mM each)—7.2 µl
4 RNase Inhibitor—20 U
5 T7 RNA polymerase—3000 U
6 dH$_2$O—Up to 20.0 µl. and
7 Incubation at 37° C. for 3 hr-5 hrs.

The crude IVT mix can be stored at 4° C. overnight for cleanup the next day. 1 U of RNase-free DNase can then be used to digest the original template. After 15 minutes of incubation at 37° C., the mRNA can be purified using Ambion's MEGACLEAR™ Kit (Austin, TX) following the manufacturer's instructions. This kit can purify up to 500 µg of RNA. Following the cleanup, the RNA can be quantified using the NanoDrop and analyzed by agarose gel electrophoresis to confirm the RNA is the proper size and that no degradation of the RNA has occurred.

Example 4

Enzymatic Capping

Capping of a polynucleotide can be performed with a mixture includes: IVT RNA 60 µg-180 µg and dH$_2$O up to 72 µl. The mixture can be incubated at 65° C. for 5 minutes to denature RNA, and then can be transferred immediately to ice.

The protocol can then involve the mixing of 10× Capping Buffer (0.5 M Tris-HCl (pH 8.0), 60 mM KCl, 12.5 mM MgCl$_2$) (10.0 µl); 20 mM GTP (5.0 µl); 20 mM S-Adenosyl Methionine (2.5 µl); RNase Inhibitor (100 U); 2'-O-Methyltransferase (400U); Vaccinia capping enzyme (Guanylyl transferase) (40 U); dH$_2$O (Up to 28 µl); and incubation at 37° C. for 30 minutes for 60 µg RNA or up to 2 hours for 180 µg of RNA.

The polynucleotide can then be purified using Ambion's MEGACLEAR™ Kit (Austin, TX) following the manufacturer's instructions. Following the cleanup, the RNA can be quantified using the NANODROP™ (ThermoFisher, Waltham, MA) and analyzed by agarose gel electrophoresis to confirm the RNA is the proper size and that no degradation of the RNA has occurred. The RNA product can also be sequenced by running a reverse-transcription-PCR to generate the cDNA for sequencing.

Example 5

PolyA Tailing Reaction

Without a poly-T in the cDNA, a poly-A tailing reaction must be performed before cleaning the final product. This can be done by mixing Capped IVT RNA (100 µl); RNase Inhibitor (20 U); 10× Tailing Buffer (0.5 M Tris-HCl (pH 8.0), 2.5 M NaCl, 100 mM MgCl$_2$) (12.0 µl); 20 mM ATP (6.0 µl); Poly-A Polymerase (20 U); dH$_2$O up to 123.5 µl and incubating at 37° C. for 30 min. If the poly-A tail is already in the transcript, then the tailing reaction can be skipped and proceed directly to cleanup with Ambion's MEGA-CLEAR™ kit (Austin, TX) (up to 500 µg). Poly-A Polymerase is, in some cases, a recombinant enzyme expressed in yeast.

It should be understood that the processivity or integrity of the polyA tailing reaction does not always result in an exact size polyA tail. Hence polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the invention.

Example 6

Natural 5' Caps and 5' Cap Analogues

5'-capping of polynucleotides can be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, MA). 5'-capping of modified RNA can be completed post-transcriptionally using a Vaccinia Virus Capping Enzyme to generate the "Cap 0" structure: m7G(5')ppp(5')G (New England BioLabs, Ipswich, MA). Cap 1 structure can be generated using both Vaccinia Virus Capping Enzyme and a 2'-O methyltransferase to generate: m7G(5')ppp(5')G-2'-O-methyl. Cap 2 structure can be generated from the Cap 1 structure followed by the 2'-O-methylation of the 5'-antepenultimate nucleotide using a 2'-O methyl-transferase. Cap 3 structure can be generated from the Cap 2 structure followed by the 2'-O-methylation of the 5'-preantepenultimate nucleotide using a 2'-0 methyl-transferase. Enzymes can be derived from a recombinant source.

When transfected into mammalian cells, the modified mRNAs can have a stability of between 12-18 hours or more than 18 hours, e.g., 24, 36, 48, 60, 72 or greater than 72 hours.

Example 7

Capping Assays

A. Protein Expression Assay

Polynucleotides encoding a polypeptide, containing any of the caps taught herein, can be transfected into cells at equal concentrations. After 6, 12, 24 and 36 hours post-transfection, the amount of protein secreted into the culture medium can be assayed by ELISA. Synthetic polynucleotides that secrete higher levels of protein into the medium would correspond to a synthetic polynucleotide with a higher translationally-competent Cap structure.

B. Purity Analysis Synthesis

Polynucleotides encoding a polypeptide, containing any of the caps taught herein, can be compared for purity using denaturing Agarose-Urea gel electrophoresis or HPLC analysis. Polynucleotides with a single, consolidated band by electrophoresis correspond to the higher purity product compared to polynucleotides with multiple bands or streaking bands. Synthetic polynucleotides with a single HPLC peak would also correspond to a higher purity product. The capping reaction with a higher efficiency would provide a more pure polynucleotide population.

C. Cytokine Analysis

Polynucleotides encoding a polypeptide, containing any of the caps taught herein, can be transfected into cells at multiple concentrations. After 6, 12, 24 and 36 hours post-transfection the amount of pro-inflammatory cytokines such as TNF-alpha and IFN-beta secreted into the culture medium can be assayed by ELISA. Polynucleotides resulting in the secretion of higher levels of pro-inflammatory cytokines into the medium would correspond to polynucleotides containing an immune-activating cap structure.

D. Capping Reaction Efficiency

Polynucleotides encoding a polypeptide, containing any of the caps taught herein, can be analyzed for capping reaction efficiency by LC-MS after nuclease treatment. Nuclease treatment of capped polynucleotides would yield a mixture of free nucleotides and the capped 5'-5-triphosphate cap structure detectable by LC-MS. The amount of capped product on the LC-MS spectra can be expressed as a percent of total polynucleotide from the reaction and would correspond to capping reaction efficiency. The cap structure with higher capping reaction efficiency would have a higher amount of capped product by LC-MS.

Example 8

Agarose Gel Electrophoresis of Modified RNA or RT PCR Products

Individual polynucleotides (200-400 ng in a 20 μl volume) or reverse transcribed PCR products (200-400 ng) can be loaded into a well on a non-denaturing 1.2% Agarose E-Gel (Invitrogen, Carlsbad, CA) and run for 12-15 minutes according to the manufacturer protocol.

Example 9

Nanodrop Modified RNA Quantification and UV Spectral Data

Modified polynucleotides in TE buffer (1 μl) can be used for Nanodrop UV absorbance readings to quantitate the yield of each polynucleotide from an chemical synthesis or in vitro transcription reaction.

Example 10

Formulation of Modified mRNA Using Lipidoids

Polynucleotides can be formulated for in vitro experiments by mixing the polynucleotides with the lipidoid at a set ratio prior to addition to cells. In vivo formulation can require the addition of extra ingredients to facilitate circulation throughout the body. To test the ability of these lipidoids to form particles suitable for in vivo work, a standard formulation process used for siRNA-lipidoid formulations can be used as a starting point. After formation of the particle, polynucleotide can be added and allowed to integrate with the complex. The encapsulation efficiency can be determined using a standard dye exclusion assays.

Example 11

Method of Screening for Protein Expression

A. Electrospray Ionization

A biological sample that can contain proteins encoded by a polynucleotide administered to the subject can be prepared and analyzed according to the manufacturer protocol for electrospray ionization (ESI) using 1, 2, 3 or 4 mass analyzers. A biologic sample can also be analyzed using a tandem ESI mass spectrometry system.

Patterns of protein fragments, or whole proteins, can be compared to known controls for a given protein and identity can be determined by comparison.

B. Matrix-Assisted Laser Desorption/Ionization

A biological sample that can contain proteins encoded by one or more polynucleotides administered to the subject can be prepared and analyzed according to the manufacturer protocol for matrix-assisted laser desorption/ionization (MALDI).

Patterns of protein fragments, or whole proteins, can be compared to known controls for a given protein and identity can be determined by comparison.

C. Liquid Chromatography-Mass Spectrometry-Mass Spectrometry

A biological sample, which can contain proteins encoded by one or more polynucleotides, can be treated with a trypsin enzyme to digest the proteins contained within. The resulting peptides can be analyzed by liquid chromatography-mass spectrometry-mass spectrometry (LC/MS/MS). The peptides can be fragmented in the mass spectrometer to yield diagnostic patterns that can be matched to protein sequence databases via computer algorithms. The digested sample can be diluted to achieve 1 ng or less starting material for a given protein. Biological samples containing a simple buffer background (e.g., water or volatile salts) are amenable to direct in-solution digest; more complex backgrounds (e.g., detergent, non-volatile salts, glycerol) require an additional clean-up step to facilitate the sample analysis.

Patterns of protein fragments, or whole proteins, can be compared to known controls for a given protein and identity can be determined by comparison.

Example 12

Synthesis of mRNA Encoding Citrin

Sequence optimized polynucleotides encoding Citrin polypeptides, i.e., SEQ ID NOs: 1 and 3, are synthesized and characterized as described in Examples 1 to 11. mRNA's encoding both human Citrin are prepared for Examples 13-19 described below, and are synthesized and characterized as described in Examples 1 to 11.

An mRNA encoding human Citrin is constructed, e.g., by using the ORF sequence provided in SEQ ID NO: 2 or 4. The mRNA sequence includes both 5' and 3' UTR regions (see, e.g., SEQ ID NOs: 79 and 80, respectively). In a construct, the 5'UTR and 3'UTR sequences are:

```
5' UTR
                                      (SEQ ID NO: 79)
UCAAGCUUUUGGACCCUCGUACAGAAGCUAAUACGACUCACUAUAGGGA
AAUAAGAGAGAAAAGAAGAGUAAGAAGAAAUAUAAGAGCCACC

3' UTR
                                      (SEQ ID NO: 80)
UGAUAAUAGGCUGGAGCCUCGGUGGCCAUGCUUCUUGCCCCUUGGGCCU
CCCCCCAGCCCCUCCUCCCCUUCCUGCACCCGUACCCCCGUGGUCUUUG
AAUAAAGUCUGAGUGGGGGC
```

The Citrin mRNA sequence is prepared as modified mRNA. Specifically, during in vitro translation, modified mRNA is generated using 5-methoxy-UTP to ensure that the mRNAs contain 100% 5-methoxy-uridine instead of uridine. Further, Citrin-mRNA is synthesized with a primer that introduces a polyA-tail, and a Cap 1 structure is generated on both mRNAs using Vaccinia Virus Capping Enzyme and a 2'-O methyl-transferase to generate: m7G(5')ppp(5')G-2'-O-methyl.

Example 13

Detecting Endogenous Citrin Expression In Vitro

Citrin expression is characterized in a variety of cell lines derived from both mice and human sources. Cell are cultured in standard conditions and cell extracts are obtained by placing the cells in lysis buffer. For comparison purposes, appropriate controls are also prepared. To analyze Citrin expression, lysate samples are prepared from the tested cells and mixed with lithium dodecyl sulfate sample loading buffer and subjected to standard Western blot analysis. For detection of Citrin, the antibody used is a commercial anti-Citrin antibody. For detection of a load control, the antibody used is anti-citrase synthase (rabbit polyclonal; PA5-22126; Thermo-Fisher Scientific®). To examine the localization of endogenous Citrin, immunofluorescence analysis is performed on cells. Citrin expression is detected using a commercial anti-Citrin. The location of specific organelles can be detected with existing commercial products. For example, mitochondria can be detected using Mitotracker, and the nucleus can be stained with DAPI. Image analysis is performed on a Zeiss ELYRA imaging system.

Endogenous Citrin expression can be used as a base line to determine changes in Citrin expression resulting from transfection with mRNAs comprising nucleic acids encoding Citrin.

Example 14

In Vitro Expression of Citrin in HeLa Cells

To measure in vitro expression of human Citrin in HeLa cells, those cells are seeded on 12-well plates (BD Biosciences, San Jose, USA) one day prior to transfection. mRNA formulations comprising human Citrin or a GFP control are transfected using 800 ng mRNA and 2 µL Lipofectamin 2000 in 60 µL OPTI-MEM per well and incubated.

After 24 hours, the cells in each well are lysed using a consistent amount of lysis buffer. Appropriate controls are used. Protein concentrations of each are determined using a BCA assay according to manufacturer's instructions. To analyze Citrin expression, equal loads of each lysate (24 µg) are prepared in a loading buffer and subjected to standard Western blot analysis. For detection of Citrin, a commercial anti-Citrin antibody is used according to the manufacturer's instructions.

Example 15

In Vitro Citrin Activity in HeLa Cells

An in vitro Citrin activity assay is performed to determine whether Citrin exogenously-expressed after introduction of mRNA comprising a Citrin sequence is active.
A. Expression Assay
HeLa cells are transfected with mRNA formulations comprising human Citrin or a GFP control. Cells are transfected with Lipofectamin 2000 and lysed as described in Example 14 above. Appropriate controls are also prepared.
B. Activity Assay
To assess whether exogenous Citrin can function, an in vitro activity assay is performed using transfected HeLa cell lysates as the source of enzymatic activity. To begin, lysate is mixed Citrin substrate. The reaction is stopped by adding 100 g/L TCA and vortexing. The reaction tubes are then centrifuged at 13,000 g for 1 min, and the supernatant is analyzed for the presence of labeled enzymatic products resulting from the activity of Citrin using HPLC-based separation and quantification. Specifically, 20 µL of each activity reaction supernatant are analyzed using a HPLC system equipped with a Quatrnary-Pump, a Multi-sampler, a Thermostated Column-Compartment, a Poroshell EC-C18 120 HPLC-column and a Radiometric Detector controlled by OpenLAB Chromatography Data System, all used according to the manufacturers' recommendations.

Example 16

Measuring In Vitro Expression of Citrin in Cells

Cells from normal subjects and Citrullinemia patients are examined for their capacity to express exogenous Citrin. Cells are transfected with mRNA formulations comprising human Citrin, mouse Citrin, or a GFP control via electroporation using a standard protocol. Each construct is tested separately. After incubation, cells are lysed and protein concentration in each lysate is measured using a suitable assay, e.g., by BCA assay. To analyze Citrin expression, equal loads of each lysate are prepared in a loading buffer and subjected to standard Western blot analysis. For detection of Citrin, an anti-Citrin is used. For detection of a load control, the antibody used is anti-citrase synthase (rabbit polyclonal; MA5-17625; Pierce®).

Example 17

Measuring In Vitro Citrin Activity in Lysates

A. Expression
Cells from normal human subjects and Citrullinemia patients are cultured. Cells are transfected with mRNA formulations comprising human Citrin, mouse Citrin, or a GFP control via electroporation using a standard protocol.
B. Activity Assay
To assess whether exogenous Citrin function, an in vitro activity assay is performed using transfected cell lysates as the source of enzymatic activity. Lysate containing expressed Citrin protein is incubated with labeled Citrin substrate, and the activity of Citrin is quantified by measuring the levels of labeled products resulting from the enzymatic activity of Citrin.

Example 18

In Vivo Citrin Expression in Animal Models

To assess the ability of Citrin-containing mRNA's to facilitate Citrin expression in vivo, mRNA encoding human Citrin is introduced into C57B/L6 mice. C57B/L6 mice are injected intravenously with either control mRNA (NT-FIX) or human Citrin mRNA. The mRNA is formulated in lipid nanoparticles for delivery into the mice. Mice are sacrificed after 24 or 48 hrs. and Citrin protein levels in liver lysates are determined by capillary electrophoresis (CE). Citrate synthase expression is examined for use as a load control. For control NT-FIX injections, 4 mice are tested for each time point. For human Citrin mRNA injections, 6 mice are tested for each time point. Treatment with mRNA encoding Citrin is expected to reliably induce expression of Citrin.

Example 19

Human Citrin Mutant and Chimeric Constructs

A polynucleotide of the present invention can comprise at least a first region of linked nucleosides encoding human Citrin, which can be constructed, expressed, and characterized according to the examples above. Similarly, the polynucleotide sequence can contain one or more mutations that results in the expression of a Citrin with increased or decreased activity. Furthermore, the polynucleotide sequence encoding Citrin can be part of a construct encoding a chimeric fusion protein.

Example 20

Production of Nanoparticle Compositions

A. Production of Nanoparticle Compositions

Nanoparticles can be made with mixing processes such as microfluidics and T-junction mixing of two fluid streams, one of which contains the polynucleotide and the other has the lipid components.

Lipid compositions are prepared by combining an ionizable amino lipid disclosed herein, e.g., a lipid according to Formula (I) such as Compound 18, or a lipid according to Formula (III) such as Compound 236, a phospholipid (such as DOPE or DSPC, obtainable from Avanti Polar Lipids, Alabaster, AL), a PEG lipid (such as 1,2-dimyristoyl-sn-glycerol methoxypolyethylene glycol, also known as PEG-DMG, obtainable from Avanti Polar Lipids, Alabaster, AL or Compound 428), and a structural lipid (such as cholesterol, obtainable from Sigma-Aldrich, Taufkirchen, Germany, or a corticosteroid (such as prednisolone, dexamethasone, prednisone, and hydrocortisone), or a combination thereof) at concentrations of about 50 mM in ethanol. Solutions should be refrigerated for storage at, for example, −20° C. Lipids are combined to yield desired molar ratios and diluted with water and ethanol to a final lipid concentration of between about 5.5 mM and about 25 mM.

Nanoparticle compositions including a polynucleotide and a lipid composition are prepared by combining the lipid solution with a solution including the a polynucleotide at lipid composition to polynucleotide wt:wt ratios between about 5:1 and about 50:1. The lipid solution is rapidly injected using a NanoAssemblr microfluidic based system at flow rates between about 10 ml/min and about 18 ml/min into the polynucleotide solution to produce a suspension with a water to ethanol ratio between about 1:1 and about 4:1.

For nanoparticle compositions including an RNA, solutions of the RNA at concentrations of 0.1 mg/ml in deionized water are diluted in 50 mM sodium citrate buffer at a pH between 3 and 4 to form a stock solution.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, IL) with a molecular weight cutoff of 10 kD. The first dialysis is carried out at room temperature for 3 hours. The formulations are then dialyzed overnight at 4° C. The resulting nanoparticle suspension is filtered through 0.2 μm sterile filters (Sarstedt, Nümbrecht, Germany) into glass vials and sealed with crimp closures. Nanoparticle composition solutions of 0.01 mg/ml to 0.10 mg/ml are generally obtained.

The method described above induces nano-precipitation and particle formation. Alternative processes including, but not limited to, T-junction and direct injection, can be used to achieve the same nano-precipitation.

B. Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of a polynucleotide (e.g., RNA) in nanoparticle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of polynucleotide in the nanoparticle composition can be calculated based on the extinction coefficient of the polynucleotide used in the composition and on the difference between the absorbance at a wavelength of, for example, 260 nm and the baseline value at a wavelength of, for example, 330 nm.

For nanoparticle compositions including an RNA, a QUANT-IT™ RIBOGREEN® RNA assay (Invitrogen Corporation Carlsbad, CA) can be used to evaluate the encapsulation of an RNA by the nanoparticle composition. The samples are diluted to a concentration of approximately 5 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2% Triton X-100 solution is added to the wells. The plate is incubated at a temperature of 37° C. for 15 minutes. The RIBOGREEN® reagent is diluted 1:100 in TE buffer, and 100 μL of this solution is added to each well. The fluorescence intensity can be measured using a fluorescence plate reader (Wallac Victor 1420 Multilablel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Exemplary formulations of the nanoparticle compositions are presented in the TABLE 6 below. The term "Compound" refers to an ionizable lipid such as MC3, Compound 18, or Compound 236. "Phospholipid" can be DSPC or DOPE. "PEG-lipid" can be PEG-DMG or Compound 428.

TABLE 6

Exemplary Formulations of Nanoparticles

| Composition (mol %) | Components |
|---|---|
| 40:20:38.5:1.5 | Compound:Phospholipid:Chol:PEG-Lipid |
| 45:15:38.5:1.5 | Compound:Phospholipid:Chol:PEG-Lipid |
| 50:10:38.5:1.5 | Compound:Phospholipid:Chol:PEG-Lipid |
| 55:5:38.5:1.5 | Compound:Phospholipid:Chol:PEG-Lipid |
| 60:5:33.5:1.5 | Compound:Phospholipid:Chol:PEG-Lipid |
| 45:20:33.5:1.5 | Compound:Phospholipid:Chol:PEG-Lipid |
| 50:20:28.5:1.5 | Compound:Phospholipid:Chol:PEG-Lipid |
| 55:20:23.5:1.5 | Compound:Phospholipid:Chol:PEG-Lipid |
| 60:20:18.5:1.5 | Compound:Phospholipid:Chol:PEG-Lipid |
| 40:15:43.5:1.5 | Compound:Phospholipid:Chol:PEG-Lipid |
| 50:15:33.5:1.5 | Compound:Phospholipid:Chol:PEG-Lipid |
| 55:15:28.5:1.5 | Compound:Phospholipid:Chol:PEG-Lipid |
| 60:15:23.5:1.5 | Compound:Phospholipid:Chol:PEG-Lipid |
| 40:10:48.5:1.5 | Compound:Phospholipid:Chol:PEG-Lipid |
| 45:10:43.5:1.5 | Compound:Phospholipid:Chol:PEG-Lipid |
| 55:10:33.5:1.5 | Compound:Phospholipid:Chol:PEG-Lipid |
| 60:10:28.5:1.5 | Compound:Phospholipid:Chol:PEG-Lipid |
| 40:5:53.5:1.5 | Compound:Phospholipid:Chol:PEG-Lipid |
| 45:5:48.5:1.5 | Compound:Phospholipid:Chol:PEG-Lipid |
| 50:5:43.5:1.5 | Compound:Phospholipid:Chol:PEG-Lipid |
| 40:20:40:0 | Compound:Phospholipid:Chol:PEG-Lipid |

TABLE 6-continued

Exemplary Formulations of Nanoparticles

| Composition (mol %) | Components |
|---|---|
| 45:20:35:0 | Compound:Phospholipid:Chol:PEG-Lipid |
| 50:20:30:0 | Compound:Phospholipid:Chol:PEG-Lipid |
| 55:20:25:0 | Compound:Phospholipid:Chol:PEG-Lipid |
| 60:20:20:0 | Compound:Phospholipid:Chol:PEG-Lipid |
| 40:15:45:0 | Compound:Phospholipid:Chol:PEG-Lipid |
| 45:15:40:0 | Compound:Phospholipid:Chol:PEG-Lipid |
| 50:15:35:0 | Compound:Phospholipid:Chol:PEG-Lipid |
| 55:15:30:0 | Compound:Phospholipid:Chol:PEG-Lipid |
| 60:15:25:0 | Compound:Phospholipid:Chol:PEG-Lipid |
| 40:10:50:0 | Compound:Phospholipid:Chol:PEG-Lipid |
| 45:10:45:0 | Compound:Phospholipid:Chol:PEG-Lipid |
| 50:10:40:0 | Compound:Phospholipid:Chol:PEG-Lipid |
| 55:10:35:0 | Compound:Phospholipid:Chol:PEG-Lipid |
| 60:10:30:0 | Compound:Phospholipid:Chol:PEG-Lipid |

Example 21

Evaluation of mRNA Encoding Citrin in a Citrin Deficiency Mouse Model

Modified mRNA constructs including sequence optimized ORFs encoding human Citrin (SLC25A13) isoform 1 are shown in TABLE 7. These constructs were used in Examples 21-24 as indicated. Each of constructs #1-#4 comprises a Cap1 5' terminal cap and a 3' terminal poly-A region. Each of constructs #144 comprises a 5-methoxyuridine modified sequence.

TABLE 7

Modified mRNA constructs including optimized ORFs encoding human Citrin.

| Citrin mRNA construct | 5'UTR Q SE ID NO | Citrin ORF SEQ ID NO | 3'UTR SEQ ID NO | Full construct SEQ ID NO |
|---|---|---|---|---|
| #1 | 30 | 129 | 105 | 130 |
| #2 | 30 | 132 | 105 | 133 |
| #3 | 30 | 135 | 105 | 136 |
| #4 | 30 | 138 | 105 | 139 |

Blood ammonium level, aversion to sucrose (preference index), and body weight were assessed in double knockout mice lacking functional citrin and mitochondrial glycerol 3-phosphate dehydrogenase (mGPD) genes and citrin knock-out mice after administration of Citrin mRNA or control mRNA according to the study design shown in FIG. 7. Citrin knock-out mice do not display features of human citrin deficiency. However, mGPD/CTRN knockout mice used in this study display citrin deficiency phenotypes, such as sucrose aversion and growth retardation, and several aberrations in plasma biomarkers relative to wild-type mice, including for example, hypoinsulinemia under fed conditions; an increase in plasma triglyceride; an increase in plasma free fatty acids (FFA), aspartate aminotransferase (AST), alanine aminotransferase (ALT) and glycerol under fasted conditions; plasma hyperammonemia under fed conditions; an increase in hepatic lactate and pyruvate; an increase in hepatic triglyceride levels at 16 hours post fasting; and an increase in hepatic citrulline and glyceraldehyde 3-phosphate (G3P). Knock out mice were generated as described in Saheki et al., JBC 282(34):25041-25052 (2007); Saheki et al., Mol. Genetics and Metabolism 120: 306-316 (2017) and Moriyama et al., Biochimica et Biophysica Acta 1852:1787-1795 (2015).

Mice injected (IV) with 0.5 mg/kg mRNA encoding human Citrin (Construct #1, formulated in lipid nanoparticle Compound 18) or control mRNA (NTFIX) were sacrificed according to the schedule provided in FIG. 7. In short, WT-NtFix (n=4), Ctrn KO-NtFix (n=2), Ctrn KO-hCitrin (n=2), Double KO-NtFix (n=5), and Double KO-hCitrin (n=5) mice were bled on days −7, 2, 9, and 16, and administered 0.5 mg/kg mRNA on days 1, 8, and 15. Blood ammonium ($NH_4^+$) was measured on days 2, 9, and 16. Aversion to a 20% sucrose solution was assessed after the second injection of mRNA according to the method described in Saheki et al., Mol. Genetics and Metabolism 120:306-316 (2017). Mice were challenged with a 50% sucrose solution on day 16, and blood samples were collected one hour post-challenge. In this terminal study, mice were sacrificed on day 16, body weight was determined, and plasma, liver, and spleen samples were collected.

Blood ammonium levels are shown in FIG. 8. IV administration of mRNA encoding Citrin resulted in a 62% decrease in the blood ammonium level in double knockout mice compared blood ammonium levels in double knockout mice administered control mRNA (NTFIX). Ammonium levels in WT-NtFix, Ctrn KO-NtFix, and Ctrn KO-hCitrin are shown here for comparison.

The oral aversion of mGPD/CTRN knockout mice to sucrose was determined before and after administration of mRNA via the method described in Saheki et al. Mol Genet Metab. 120(4):306-316 (2017). Briefly, mice were provided two drinking bottles following the second injection of mRNA (see study design in FIG. 7), one bottle containing water and the other containing a 50% sucrose solution. The preference index for sucrose solution was calculated as (g of sucrose solution)/[(g of sucrose solution)+(g of water)]. Wild-type mice and Citrin knockout mice exhibited an almost 100% preference for the sucrose solution (data not shown). mGPD/CTRN knockout mice administered NtFIX mRNA exhibited a decreased preference for the sucrose solution. Administration of mRNA encoding Citrin reversed the oral aversion of mGPD/CTRN knockout mice to sucrose (FIGS. 9A-9B).

Example 22

Determination of In Vivo Citrin Protein Expression in Mice Administered mRNA Encoding Citrin Citrin protein expression in isolated liver mitochondria was measured by Western blot following mRNA administration according to the schedule in FIG. 7. Briefly, wild-type, CTRN knockout, and mGPD/CTRN knockout mice were administered control mRNA (NTFIX) or mRNA encoding Citrin (Construct #1, formulated in lipid nanoparticle Compound 18). Mice were sacrificed on day 16 and liver extracts were prepared. Citrin was detected by Western blot using an anti-Citrin antibody provided by Dr. Takeyori Saheki from the Kagoshima University Graduate School of Medical and Dental Sciences (rabbit polyclonal antibody raised against the N-terminal half of human Citrin, as described in Yasuda et al., Human Genetics 107:537-545 (2000)) (FIG. 10, top panel). mGPD protein expression was also monitored to ensure the complete deletion of the gene in mGPD/CTRN knockout mice (FIG. 10, middle panel). Citrate Synthase was detected in all samples as a control to normalize the protein expression level of Citrin (FIG. 10, lower panel). Antibodies for detection of mGPD and Citrate were purchased from Novus Biologicals (NBP1-86121) and Thermo Fisher Scientific (MA5-17265), respectively. Administration of mRNA encoding human Citrin to CTRN knockout mice and mGPD/CTRN knockout mice resulted in increased Citrin protein expression compared to control mRNA NTFIX.

Semi-quantitative analysis of Citrin expression was performed on Western blot signals from isolated liver michondria. Administration of mGPD/CTRN double knockout mice with mRNA encoding Citrin increased the relative expression of Citrin compared to control mRNA (NTFIX) (FIG. 11). An increase in Citrin expression was detected for mGPD/CTRN knockout mice administered mRNA encoding Citrin.

Example 23

Multiple Dosing of mRNA Encoding Citrin in mGPD/CTRN Double Knockout Mice

The effect of multiple doses of mRNA encoding Citrin on plasma ammonia was assessed in mGPD/CTRN knockout mice. Mice administered mRNA encoding human Citrin (Construct #1, formulated in lipid nanoparticle Compound 18) or control mRNA (NTFIX) were injected and challenged according to the timing schedule shown in FIG. 12. In short, WT mice were injected with 0.5 mg/kg NTFIX mRNA (n=4); mGPD/CTRN double KO mice were injected with 0.5 mg/kg NTFIX mRNA (n=5); mGPD/CTRN double KO mice were injected with 0.5 mg/kg Citrin mRNA (Construct #1) (n=5); and mGPD/CTRN double KO mice were injected with 0.2 mg/kg Citrin mRNA (Construct #1) (n=5). Following injections, mice were challenged with a solution containing 50% sucrose. Blood plasma was obtained from the mice 24 hours after the first and final injections and plasma levels of ammonia were determined.

Prior to injection, there was no difference in plasma ammonia levels in different groups of mice (FIG. 13A). As expected, in response to the sucrose challenge, there was a significant increase in blood ammonia levels of the mGPD/CTRN double knockout mice treated with ntFIX (FIG. 13A). However, as shown in FIG. 13A, plasma ammonia levels decreased in a dose-dependent manner following a single initial injection of Citrin mRNA, with a significant ($P<0.05$) reduction in plasma ammonia levels observed in double knockout mice receiving 0.5 mg/kg Citrin mRNA compared to control mRNA (NTFIX). After the final injection, Citrin mRNA treatment also led to a numerical decrease in plasma ammonia after the sucrose challenge (FIG. 13B).

Example 24

Determination of In Vivo Citrin Protein Expression and Activity

The in vive Citrin protein expression and activity was evaluated in wild-type mice. Mice were injected (IV) with 0.5 mg/kg mRNA encoding human Citrin (Constructs #1,2, 3 or 4) formulated in lipid nanoparticle Compound 18 or 0.5 mg/kg control mRNA (NTFIX). Liver mitochondria were isolated 24 hours following injection, and Citrin protein expression was detected by Western blot using an anti-Citrin antibody from Novus Biologicals (NBP1-33380), as shown in FIG. 14A. Expression of α-tubulin was detected in all samples as a control. A quantitative analysis of the Western blot is shown in FIG. 14B. Citrin protein expression was measured as a ratio of the Citrin band intensity from mice administered mRNA encoding Citrin to the band intensity from mice administered control mRNA (NTFIX). Constructs #1 and #2 showed the highest protein expression levels.

It is to be appreciated that the Detailed Description section, and not the Summary and Abstract sections, is intended to be used to interpret the claims. The Summary and Abstract sections can set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An mRNA comprising an open reading frame (ORF) encoding the human Citrin polypeptide of SEQ ID NO: 1, wherein the ORF is 100% identical to the nucleotide sequence of SEQ ID NO:129.

2. A lipid nanoparticle comprising the mRNA of claim 1, and a compound having the formula:

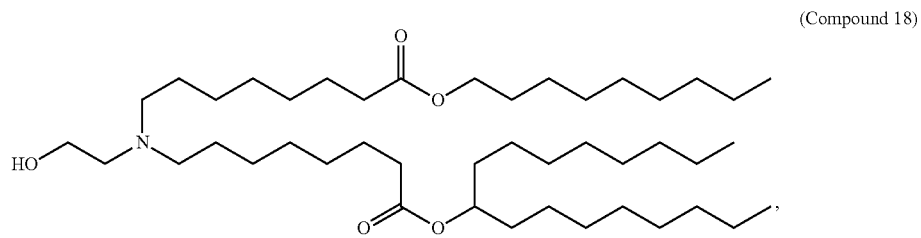 [SMILES: CCCCCCCCCOC(=O)CCCCCCCN(CCO)CCCCCCCC(=O)OC(CCCCCCCC)CCCCCCCC]

(Compound 18)

or a salt thereof.

3. A method of treating citrullinemia type 2 (CTLN2) in a human subject in need thereof, comprising administering to the human subject an effective amount of the lipid nanoparticle of claim 2.

* * * * *

SEQUENCE LISTING

```
<160> NUMBER OF SEQ ID NOS: 157

<210> SEQ ID NO 1
<211> LENGTH: 675
<212> TYPE: PRT
<213> ORGANISM: Artificial Sequence
<220> FEATURE:
<223> OTHER INFORMATION: wild type Citrin, isoform 1 peptide

<400> SEQUENCE: 1
```

-continued

```
Met Ala Ala Ala Lys Val Ala Leu Thr Lys Arg Ala Asp Pro Ala Glu
1               5                   10                  15

Leu Arg Thr Ile Phe Leu Lys Tyr Ala Ser Ile Glu Lys Asn Gly Glu
            20                  25                  30

Phe Phe Met Ser Pro Asn Asp Phe Val Thr Arg Tyr Leu Asn Ile Phe
        35                  40                  45

Gly Glu Ser Gln Pro Asn Pro Lys Thr Val Glu Leu Leu Ser Gly Val
    50                  55                  60

Val Asp Gln Thr Lys Asp Gly Leu Ile Ser Phe Gln Glu Phe Val Ala
65                  70                  75                  80

Phe Glu Ser Val Leu Cys Ala Pro Asp Ala Leu Phe Met Val Ala Phe
                85                  90                  95

Gln Leu Phe Asp Lys Ala Gly Lys Gly Glu Val Thr Phe Glu Asp Val
            100                 105                 110

Lys Gln Val Phe Gly Gln Thr Thr Ile His Gln His Ile Pro Phe Asn
        115                 120                 125

Trp Asp Ser Glu Phe Val Gln Leu His Phe Gly Lys Glu Arg Lys Arg
    130                 135                 140

His Leu Thr Tyr Ala Glu Phe Thr Gln Phe Leu Leu Glu Ile Gln Leu
145                 150                 155                 160

Glu His Ala Lys Gln Ala Phe Val Gln Arg Asp Asn Ala Arg Thr Gly
                165                 170                 175

Arg Val Thr Ala Ile Asp Phe Arg Asp Ile Met Val Thr Ile Arg Pro
            180                 185                 190

His Val Leu Thr Pro Phe Val Glu Glu Cys Leu Val Ala Ala Ala Gly
        195                 200                 205

Gly Thr Thr Ser His Gln Val Ser Phe Ser Tyr Phe Asn Gly Phe Asn
    210                 215                 220

Ser Leu Leu Asn Asn Met Glu Leu Ile Arg Lys Ile Tyr Ser Thr Leu
225                 230                 235                 240

Ala Gly Thr Arg Lys Asp Val Glu Val Thr Lys Glu Phe Val Leu
                245                 250                 255

Ala Ala Gln Lys Phe Gly Gln Val Thr Pro Met Glu Val Asp Ile Leu
            260                 265                 270

Phe Gln Leu Ala Asp Leu Tyr Glu Pro Arg Gly Arg Met Thr Leu Ala
        275                 280                 285

Asp Ile Glu Arg Ile Ala Pro Leu Glu Glu Gly Thr Leu Pro Phe Asn
    290                 295                 300

Leu Ala Glu Ala Gln Arg Gln Lys Ala Ser Gly Asp Ser Ala Arg Pro
305                 310                 315                 320

Val Leu Leu Gln Val Ala Glu Ser Ala Tyr Arg Phe Gly Leu Gly Ser
                325                 330                 335

Val Ala Gly Ala Val Gly Ala Thr Ala Val Tyr Pro Ile Asp Leu Val
            340                 345                 350

Lys Thr Arg Met Gln Asn Gln Arg Ser Thr Gly Ser Phe Val Gly Glu
        355                 360                 365

Leu Met Tyr Lys Asn Ser Phe Asp Cys Phe Lys Lys Val Leu Arg Tyr
    370                 375                 380

Glu Gly Phe Phe Gly Leu Tyr Arg Gly Leu Leu Pro Gln Leu Leu Gly
385                 390                 395                 400

Val Ala Pro Glu Lys Ala Ile Lys Leu Thr Val Asn Asp Phe Val Arg
                405                 410                 415
```

Asp Lys Phe Met His Lys Asp Gly Ser Val Pro Leu Ala Ala Glu Ile
            420                 425                 430

Leu Ala Gly Gly Cys Ala Gly Gly Ser Gln Val Ile Phe Thr Asn Pro
        435                 440                 445

Leu Glu Ile Val Lys Ile Arg Leu Gln Val Ala Gly Glu Ile Thr Thr
    450                 455                 460

Gly Pro Arg Val Ser Ala Leu Ser Val Val Arg Asp Leu Gly Phe Phe
465                 470                 475                 480

Gly Ile Tyr Lys Gly Ala Lys Ala Cys Phe Leu Arg Asp Ile Pro Phe
                485                 490                 495

Ser Ala Ile Tyr Phe Pro Cys Tyr Ala His Val Lys Ser Phe Ala
                500                 505                 510

Asn Glu Asp Gly Gln Val Ser Pro Gly Ser Leu Leu Ala Gly Ala
            515                 520                 525

Ile Ala Gly Met Pro Ala Ala Ser Leu Val Thr Pro Ala Asp Val Ile
        530                 535                 540

Lys Thr Arg Leu Gln Val Ala Ala Arg Ala Gly Gln Thr Thr Tyr Ser
545                 550                 555                 560

Gly Val Ile Asp Cys Phe Arg Lys Ile Leu Arg Glu Glu Gly Pro Lys
                565                 570                 575

Ala Leu Trp Lys Gly Ala Gly Ala Arg Val Phe Arg Ser Ser Pro Gln
            580                 585                 590

Phe Gly Val Thr Leu Leu Thr Tyr Glu Leu Leu Gln Arg Trp Phe Tyr
        595                 600                 605

Ile Asp Phe Gly Gly Val Lys Pro Met Gly Ser Glu Pro Val Pro Lys
610                 615                 620

Ser Arg Ile Asn Leu Pro Ala Pro Asn Pro Asp His Val Gly Gly Tyr
625                 630                 635                 640

Lys Leu Ala Val Ala Thr Phe Ala Gly Ile Glu Asn Lys Phe Gly Leu
                645                 650                 655

Tyr Leu Pro Leu Phe Lys Pro Ser Val Ser Thr Ser Lys Ala Ile Gly
            660                 665                 670

Gly Gly Pro
        675

<210> SEQ ID NO 2
<211> LENGTH: 2025
<212> TYPE: DNA
<213> ORGANISM: Artificial Sequence
<220> FEATURE:
<223> OTHER INFORMATION: wild type Citrin, isoform 1 NA

<400> SEQUENCE: 2
atggcggccg ccaaggtggc tttaaccaag agagcagatc cagctgagct tagaacaata     60 ttttttgaagt atgcaagcat tgagaaaaac ggtgaatttt tcatgtcccc caatgacttt    120
gtcactcgat acttgaacat ttttggagaa agccagccta atccaaagac tgtgaacttt    180
ttaagtggag tggtggatca gaccaaagat ggattaatat ctttcaaga atttgttgcc     240 tttgaatctg tcctgtgtgc ccctgatgct tgtttatgg tagccttca gctgtttgac     300 aaagctggca aggagaagt aactttgag gatgttaagc aagttttgg acagaccaca      360 attcatcaac atattccatt taactgggat tcagaatttg tgcaactaca ttttggaaaa    420
gaaagaaaaa gacacctgac atatgcggaa tttactcagt tttttattgga atacaactg    480 gagcacgcaa agcaagcctt tgtgcaacgg gacaatgcta ggactgggag agtcacagcc    540

-continued

| | |
|---|---|
| atcgacttcc gagacatcat ggtcaccatc cgcccccatg tcttgactcc ttttgtagaa | 600 |
| gaatgtctag tagctgctgc tggaggtacc acatcccatc aagttagttt ctcctatttt | 660 |
| aatggattta attcgctcct taacaacatg gaactcatta gaaagatcta tagcactctg | 720 |
| gctggcacca ggaaagatgt tgaagtgact aaggaggagt tgttctggc agctcagaaa | 780 |
| tttggtcagg ttacacccat ggaagttgac atcttgtttc agttagcaga tttatatgag | 840 |
| ccaaggggac gtatgacctt agcagacatt gaacggattg ctcctctgga gagggaact | 900 |
| ctgcccttta acttggctga ggcccagagg cagaaggcct caggtgattc agctcgacca | 960 |
| gttcttctac aagttgcaga gtcggcctac aggtttggtc tgggttctgt tgctggagct | 1020 |
| gttggagcca ctgctgtgta tcctatcgat cttgtaaaaa ctcgaatgca gaaccaacga | 1080 |
| tcaactggct cttttgtggg agaactcatg tataaaaaca gctttgactg ttttaagaaa | 1140 |
| gtgctacgct atgaaggctt cttggactg tatagaggtc tgttgccaca gttattggga | 1200 |
| gttgccccag agaaggccat aaaacttaca gtgaacgatt ttgtgaggga taaatttatg | 1260 |
| cacaaagatg gttcggtccc acttgcagca gaaattcttg ctggaggctg cgctggaggc | 1320 |
| tcccaggtga ttttcacaaa tcctttagaa atcgtcaaga tccgtttgca agtggcagga | 1380 |
| gaaatcacca ctggtcctcg agtcagtgct ctgtctgtcg tgcgggacct gggtttttt | 1440 |
| gggatctaca agggtgccaa agcatgcttt ctgcgggaca ttccttctc ggccatctac | 1500 |
| tttccgtgct atgctcatgt gaaggcttcc tttgcaaatg aagatgggca ggttagccca | 1560 |
| ggaagcctgc tcttagctgg tgccatagct ggtatgcctg cagcatcttt agtgacccct | 1620 |
| gctgatgtta tcaagacgag attacaggtg gctgcccggg ctggccaaac cacttacagc | 1680 |
| ggagtgatag actgctttag aaagatactg cgtgaagaag gaccaaaagc tctgtggaag | 1740 |
| ggagctggtc tcgtgtatt tcgatcctca ccccagtttg gtgtaacttt gctgacttac | 1800 |
| gaattgctac agcgatggtt ctacattgat tttggaggag taaaacccat gggatcagag | 1860 |
| ccagttccta atccaggat caacctgcct gccccgaatc ctgatcacgt tggggctac | 1920 |
| aaactggcag ttgctacatt tgcagggatt gaaaacaaat ttggactta cctacctctc | 1980 |
| ttcaagccat cagtatctac ctcaaaggct attggtggag gccca | 2025 |

<210> SEQ ID NO 3
<211> LENGTH: 676
<212> TYPE: PRT
<213> ORGANISM: Artificial Sequence
<220> FEATURE:
<223> OTHER INFORMATION: wild type Citrin, isoform 2 peptide

<400> SEQUENCE: 3

Met Ala Ala Ala Lys Val Ala Leu Thr Lys Arg Ala Asp Pro Ala Glu
1               5                   10                  15

Leu Arg Thr Ile Phe Leu Lys Tyr Ala Ser Ile Glu Lys Asn Gly Glu
                20                  25                  30

Phe Phe Met Ser Pro Asn Asp Phe Val Thr Arg Tyr Leu Asn Ile Phe
            35                  40                  45

Gly Glu Ser Gln Pro Asn Pro Lys Thr Val Glu Leu Leu Ser Gly Val
        50                  55                  60

Val Asp Gln Thr Lys Asp Gly Leu Ile Ser Phe Gln Glu Phe Val Ala
65                  70                  75                  80

Phe Glu Ser Val Leu Cys Ala Pro Asp Ala Leu Phe Met Val Ala Phe
                85                  90                  95

Gln Leu Phe Asp Lys Ala Gly Lys Gly Glu Val Thr Phe Glu Asp Val

```
                100                 105                 110
Lys Gln Val Phe Gly Gln Thr Thr Ile His Gln His Ile Pro Phe Asn
            115                 120                 125
Trp Asp Ser Glu Phe Val Gln Leu His Phe Gly Lys Glu Arg Lys Arg
        130                 135                 140
His Leu Thr Tyr Ala Glu Phe Thr Gln Phe Leu Leu Glu Ile Gln Leu
145                 150                 155                 160
Glu His Ala Lys Gln Ala Phe Val Gln Arg Asp Asn Ala Arg Thr Gly
                165                 170                 175
Arg Val Thr Ala Ile Asp Phe Arg Asp Ile Met Val Thr Ile Arg Pro
            180                 185                 190
His Val Leu Thr Pro Phe Val Glu Glu Cys Leu Val Ala Ala Ala Gly
        195                 200                 205
Gly Thr Thr Ser His Gln Val Ser Phe Ser Tyr Phe Asn Gly Phe Asn
    210                 215                 220
Ser Leu Leu Asn Asn Met Glu Leu Ile Arg Lys Ile Tyr Ser Thr Leu
225                 230                 235                 240
Ala Gly Thr Arg Lys Asp Val Glu Val Thr Lys Glu Glu Phe Val Leu
                245                 250                 255
Ala Ala Gln Lys Phe Gly Gln Val Thr Pro Met Glu Val Asp Ile Leu
            260                 265                 270
Phe Gln Leu Ala Asp Leu Tyr Glu Pro Arg Gly Arg Met Thr Leu Ala
        275                 280                 285
Asp Ile Glu Arg Ile Ala Pro Leu Glu Glu Gly Thr Leu Pro Phe Asn
    290                 295                 300
Leu Ala Glu Ala Gln Arg Gln Lys Ala Ser Gly Asp Ser Ala Arg
305                 310                 315                 320
Pro Val Leu Leu Gln Val Ala Glu Ser Ala Tyr Arg Phe Gly Leu Gly
                325                 330                 335
Ser Val Ala Gly Ala Val Gly Ala Thr Ala Val Tyr Pro Ile Asp Leu
            340                 345                 350
Val Lys Thr Arg Met Gln Asn Gln Arg Ser Thr Gly Ser Phe Val Gly
        355                 360                 365
Glu Leu Met Tyr Lys Asn Ser Phe Asp Cys Phe Lys Lys Val Leu Arg
    370                 375                 380
Tyr Glu Gly Phe Phe Gly Leu Tyr Arg Gly Leu Leu Pro Gln Leu Leu
385                 390                 395                 400
Gly Val Ala Pro Glu Lys Ala Ile Lys Leu Thr Val Asn Asp Phe Val
                405                 410                 415
Arg Asp Lys Phe Met His Lys Asp Gly Ser Val Pro Leu Ala Ala Glu
            420                 425                 430
Ile Leu Ala Gly Gly Cys Ala Gly Gly Ser Gln Val Ile Phe Thr Asn
        435                 440                 445
Pro Leu Glu Ile Val Lys Ile Arg Leu Gln Val Ala Gly Glu Ile Thr
    450                 455                 460
Thr Gly Pro Arg Val Ser Ala Leu Ser Val Val Arg Asp Leu Gly Phe
465                 470                 475                 480
Phe Gly Ile Tyr Lys Gly Ala Lys Ala Cys Phe Leu Arg Asp Ile Pro
                485                 490                 495
Phe Ser Ala Ile Tyr Phe Pro Cys Tyr Ala His Val Lys Ala Ser Phe
            500                 505                 510
Ala Asn Glu Asp Gly Gln Val Ser Pro Gly Ser Leu Leu Leu Ala Gly
        515                 520                 525
```

```
Ala Ile Ala Gly Met Pro Ala Ala Ser Leu Val Thr Pro Ala Asp Val
            530                 535                 540

Ile Lys Thr Arg Leu Gln Val Ala Ala Arg Ala Gly Gln Thr Thr Tyr
545                 550                 555                 560

Ser Gly Val Ile Asp Cys Phe Arg Lys Ile Leu Arg Glu Glu Gly Pro
                565                 570                 575

Lys Ala Leu Trp Lys Gly Ala Gly Ala Arg Val Phe Arg Ser Ser Pro
            580                 585                 590

Gln Phe Gly Val Thr Leu Leu Thr Tyr Glu Leu Leu Gln Arg Trp Phe
            595                 600                 605

Tyr Ile Asp Phe Gly Gly Val Lys Pro Met Gly Ser Glu Pro Val Pro
            610                 615                 620

Lys Ser Arg Ile Asn Leu Pro Ala Pro Asn Pro Asp His Val Gly Gly
625                 630                 635                 640

Tyr Lys Leu Ala Val Ala Thr Phe Ala Gly Ile Glu Asn Lys Phe Gly
                645                 650                 655

Leu Tyr Leu Pro Leu Phe Lys Pro Ser Val Ser Thr Ser Lys Ala Ile
            660                 665                 670

Gly Gly Gly Pro
            675

<210> SEQ ID NO 4
<211> LENGTH: 2028
<212> TYPE: DNA
<213> ORGANISM: Artificial Sequence
<220> FEATURE:
<223> OTHER INFORMATION: wild type Citrin, isoform 2 NA

<400> SEQUENCE: 4
atggcggccg ccaaggtggc tttaaccaag agagcagatc cagctgagct tagaacaata      60
tttttgaagt atgcaagcat tgagaaaaac ggtgaatttt tcatgtcccc caatgacttt     120
gtcactcgat acttgaacat ttttggagaa agccagccta atccaaagac tgtggaactt     180
ttaagtggag tggtggatca gaccaaagat ggattaatat cttttcaaga atttgttgcc     240
tttgaatctg tcctgtgtgc ccctgatgct ttgtttatgg tagcctttca gctgtttgac     300
aaagctggca aggagaagt aacttttgag gatgttaagc aagttttttgg acagaccaca     360 attcatcaac atattccatt taactgggat tcagaatttg tgcaactaca ttttggaaaa     420
gaaagaaaaa gacacctgac atatgcggaa tttactcagt ttttattgga aatacaactg     480
gagcacgcaa agcaagcctt tgtgcaacgg acaatgcta ggactgggag agtcacagcc     540
atcgacttcc gagacatcat ggtcaccatc cgcccccatg tcttgactcc ttttgtagaa     600
gaatgtctag tagctgctgc tggaggtacc acatcccatc aagttagttt ctcctatttt     660
aatggattta attcgctcct taacaacatg gaactcatta gaaagatcta tagcactctg     720
gctggcacca ggaaagatgt tgaagtgact aaggaggagt ttgttctggc agctcagaaa     780
tttggtcagg ttacacccat ggaagttgac atcttgtttc agttagcaga tttatatgag     840 ccaagggggac gtatgacctt agcagacatt gaacggattg ctcctctgga gagggaact      900 ctgcccttta acttggctga ggcccagagg cagcagaagg cctcaggtga ttcagctcga     960
ccagttcttc tacaagttgc agagtcggcc tacaggtttg gtctgggttc tgttgctgga    1020
gctgttggag ccactgctgt gtatcctatc gatcttgtaa aaactcgaat gcagaaccaa    1080
cgatcaactg gctcttttgt gggagaactc atgtataaaa acagctttga ctgttttaag    1140
```

-continued

```
aaagtgctac gctatgaagg cttctttgga ctgtatagag gtctgttgcc acagttattg      1200
ggagttgccc cagagaaggc cataaaactt acagtgaacg attttgtgag ggataaattt      1260
atgcacaaag atggttcggt cccacttgca gcagaaattc ttgctggagg ctgcgctgga      1320
ggctcccagg tgattttcac aaatccttta gaaatcgtca agatccgttt gcaagtggca      1380
ggagaaatca ccactggtcc tcgagtcagt gctctgtctg tcgtgcggga cctggggttt      1440
tttgggatct acaagggtgc caaagcatgc tttctgcggg acattccttt ctcggccatc      1500
tactttccgt gctatgctca tgtgaaggct tcctttgcaa atgaagatgg gcaggttagc      1560
ccaggaagcc tgctcttagc tggtgccata gctggtatgc ctgcagcatc tttagtgacc      1620
cctgctgatg ttatcaagac gagattacag gtggctgccc gggctggcca aaccacttac      1680
agcggagtga tagactgctt tagaaagata ctgcgtgaag aaggaccaaa agctctgtgg      1740
aagggagctg gtgctcgtgt atttcgatcc tcacccccagt ttggtgtaac tttgctgact      1800
tacgaattgc tacagcgatg gttctacatt gattttggag gagtaaaacc catgggatca      1860
gagccagttc ctaaatccag gatcaacctg cctgccccga atcctgatca cgttgggggc      1920
tacaaactgg cagttgctac atttgcaggg attgaaaaca aatttggact ttacctacct      1980
ctcttcaagc catcagtatc tacctcaaag gctattggtg gaggccca              2028
```

<210> SEQ ID NO 5
<211> LENGTH: 2025
<212> TYPE: RNA
<213> ORGANISM: Artificial Sequence
<220> FEATURE:
<223> OTHER INFORMATION: Citrin-CO01

<400> SEQUENCE: 5

```
auggccgccg ccaaggugge gcugaccaag agggccgacc cggccgagcu gcggaccauc      60
uuucugaagu acgccuccau cgagaagaac ggagaguucu caugagcccc caacgauuuc      120
gugaccaggu accugaacau uuucggggag agccagccca acccgaagac cguggagcug      180
cucuccggcg uggugaccca ccaaggacgg gacugauua gcuucagga guucgucgcg      240 uucgaaagcg ugcugugcgc ccccgacgcc cuguucaugg uggccuucca acuguucgac      300
aaggccggga aaggcgaggu cacuuuugag gacgugaagc aggugucgg ccaaaccacc      360 auccaccagc acaucccuu caacugggac agcgaguucg ugcagcugca cuuugguaaa      420
gagaggaagc gccaucugac cuacgccgaa uuuacccagu ccugcuggga gauccagcug      480
gagcacgcca gcaggccuu cguccagcgc gauaacgccc ggaccggccg ggugaccgcc      540
aucgauuuca gggacaucau ggugaccauc cggccccaug ugcugacccc cuucguggag      600
gagugccugg uggccgccgc cgggggcacg acgucccacc aggugccuu cuccuacuuc      660 aauggauuca cucccuccuu gaacaacaug gagcugauca ggaagaucua cagcacccug      720
gccggcacca ggaaagaugu ggaagugacg aaggaggagu cgugcugge cgcccagaag      780 uucggccagg ugacccccau ggagguggac auccucuucc agcuggccga ccuguacgag      840
cccaggggcc gcaugacccu ggcagauaua gagcgaauug cgcccuggga ggagggcacc      900
cugcccuuca accuagccga agcccagcga cagaaggccu ccggggacuc cgccggccg      960 guacugcugc aggugggccga gagcgccuac cgguucgggc uggggagcgu ggccggggcc      1020
gugggggcua ccgccguguca ccccauugac cuggugaaga ccaggaugca gaaccagcgg      1080
agcacaggcu ccuucguggg cgagcugaug uacaagaaca gcuucgacug cuucaagaag      1140
gugcugcgcu acgagggcuu cuuuggccug uacaggggcc ugcugccgca acugcucggg      1200
```

```
gucgccccg agaaggccau caagcugacc gugaaugacu cugugcggga caaguucaug    1260
cacaaggacg ggagcgugcc ccuggcagcc gagauccugg cgggcggaug cgccggcggc    1320
agccagguaa ucuucaccaa cccccuggag aucgugaaga ccgucugca gguggcgggc    1380 gagaucacca cggguccag ggucagcgcc ugagcgugg ugcgggaccu ggggguucuuc    1440 ggcaucuaca agggcgccaa ggccugcuuc cugagggaca uccccuucag cgccaucuac    1500
uuccccugcu acgccacgu gaaagccucc uuugcaaacg aggacgggca agucagcccc    1560
ggcagccugc ugcuggccgg ggccauugcc ggcaugcccg ccgccagccu ggugacccc    1620 gccgacguga ucaaaacccg gcugcagguc gccgcccgag cgggccagac gaccuacucc    1680
ggagucauug acugcuuccg uaagauccug cgggaggagg ggcccaaagc ccuguggaaa    1740
ggugccggcg cuagggguguu uaggagcucc ccccaguuug gggucacccu gcucaccuac    1800
gagcuccucc agaggugguu uuacaucgac uucgggggcg ugaaacccau gggcagcgag    1860
cccgugccga agagcaggau caaccugccc gcgcccaauc ccgaccaugu ggggggcuac    1920
aaacuggccg uggccaccuu cgccggcauc gaaaacaagu ucggccucua ccugcccug    1980 uucaagccca gcgugaguac cagcaaggcc aucggcggcg ccccc               2025
```

<210> SEQ ID NO 6
<211> LENGTH: 2025
<212> TYPE: RNA
<213> ORGANISM: Artificial Sequence
<220> FEATURE:
<223> OTHER INFORMATION: Citrin-CO02

<400> SEQUENCE: 6

```
auggccgccg ccaaggucgc ccugaccaag cgggccgacc ccgccgagcu gaggaccauc      60
uuccucaagu acgccagcau cgaaaagaac ggcgaauucu caugucccc aaacgacuuc    120 gugacccguu accugaauau cuucgggaaa agccagccca ucccaaaac cgucgaacug    180 cugagcggcg uggugaccca gaccaaagau ggacugauca gcuuucagga guugguggcg    240
uucgaguccg ugcugugcgc ccccgacgcc cuguucaugg uggcguucca gcuguucgau    300
aaggcgggga aaggcgaagu gaccuucgag gacgugaaac aaguguucgg gcagaccacc    360
auccaccagc acauccccuu caacugggac agcgaauuug uccaacugca cuucggcaag    420
gagcggaaga ggcaucugac cuacgccgag uucacccagu uccugcugga gauccagcuu    480
gaacaugcua gcaggccuu cgugcagagg gauaacgccc ggacuggcag ggugaccgcc    540
aucgacuucc gggacaucau ggugaccauc cgucgcaug ugcuaccccc cuucgucgag    600
gagugccucg uggccgccgc cggcggaacc accagccacc agguagcuu uagcuacuuc    660 aacgcuuua cagccugcu caacaacaug gagcugaucc guaagaucua cagcacccug    720
gccggcacaa ggaaggacgu cgagguggacc aaggagagu cgugcuggc cgcccagaag    780 uucggucagg ucacccccau ggaggugga uccuguucc agcucgcgga ccuguacgag    840
cccgggggca ggaugacccu ggccgacauc gagcggaucg ccccccugga gagggcaca    900 cucccccuuca accuggccga ggccagcga cagaaggccu ccggcgauag cgccggccc    960 guccuucugc agguggccga aagccccuac agguucgggc uggcagcgu cgccggcgcc   1020 guaggcgcca ccgccguguga cccuaucgac cucgugaaaa ccaggaugca gaaucagcgg   1080
ucgaccggcu cuuuugucgg cgagcugaug uacaagaaca gcuucgacug cuucaagaaa   1140
gugcugaggu augagggcuu cuucggccug uaugggggcc ugcugcccca gcugcuggga   1200
```

```
guggcccccg agaaggccau caagcugaca gucaacgacu cgugaggga caaguucaug      1260 cacaaagaug ggagcgugcc ucuggccgcg gagauccugg ccggcgguug cgccggcgga     1320 agccaggugua ucuucaccaa cccgcuggag aucgugaaaa uaaggcugca aguggccggg    1380
gaaaucacca ccggcccacg cguaagcgcc cugucggugg ugagggaccu gggcuucuuc    1440
ggcaucuaua agggcgccaa ggccugcuuc cugcgcgaca uccccuucuc cgccauauac    1500
uuccccugcu acgccacgu gaaggccagc uucgccaacg aggacgguca ggugagcccc     1560
gggagccugc ugcuggcagg cgccaucgcc gggaugcccg ccgccagccu cgugacuccc    1620
gccgacguca ucaagaccag gcugcagguc gcggccaggg ccggccaaac gaccuacucc    1680
ggcgugaucg acugcuuuag gaagauccuc cgggaagaag gccccaaggc ccugugugaaa   1740 ggagcgggcg ccaggguauu ccggagcagc ccacaguucg gcgugacccu ccucacuuac    1800
gaacugcugc agcgguggu cuacaucgac uucgcggag ugaaaccgau ggggagcgag      1860
cccgugccca agagcaggau caaucugccc gcccccaacc ccgaccacgu gggcggguac    1920
aaacuggccg uggccacccuu ucgccggcauc gagaacaagu ucggccugua ccugcccccuc 1980 uucaaacccca gcgucuccac cagcaaggcg aucggcggug ccccc                   2025
```

<210> SEQ ID NO 7
<211> LENGTH: 2025
<212> TYPE: RNA
<213> ORGANISM: Artificial Sequence
<220> FEATURE:
<223> OTHER INFORMATION: Citrin-CO03

<400> SEQUENCE: 7

```
auggccgccg ccaaagucgc ccugacaaag agggccgacc ccgccgagcu ccgcaccauc      60
uuucugaagu acgccuccau cgagaagaac ggggaguucu uuaugagccc caacgauuuc    120
gugacccggu accugaacau cuucggcgag agccagccca ccccaagac uguggagcug     180 cugauccggcg ugguggacca gaccaaggau ggcuugauuu cauuccagga guucguggcc    240
uuugaaagcg uccugugcgc ccccgacgcc cguucaaugg uggccuucca gcuguucgau    300
aaggccggca aggagaggu gaccuucgag gauguaaagc agguguucgg gcagaccacc     360
auccaccagc acaucccccuu caacugggau agcgaauuug ugcagcugca cuucggcaaa    420
gagcggaaga ggcaccugac cuaugccgag uucacccagu ccugcuga gauccagcug     480 gaacacgcaa acaggccuu ugugcagcgg acaacgcca ggaccggcag ggugaccgcg     540
aucgacuuca gggauaucau ggugaccauu aggccgcacg ucugacacc cuucguggag    600 gagugccugg uggccgccgc gggcggcacc accuccccauc agguguccuu cagcuacuuc   660
aacggcuuca auagucugcu gaacaacaug gagcugaucc ggaagaucua uagcaccucug   720 gcgggcacca ggaaagacgu ggaagugacc aaggaggagu cgugcuggc cgcccaaaaa    780 uucgggcagg ugacccccau ggagguggac auccucuuuc agcucgccga ccuguacgag    840 cccagggca ggaugacccu ggcggacauc gagaggaucc ccccccucga ggagggcacc    900 cugccuca aucuggccga ggccagagg cagaaggccu ccggcgacag cgcccgcccc       960
gugcucuugc aggucgccga guccgccuau agguucgggc ugggccccgu ggccggagca   1020
gugggggcca ccgccgugua ccccaucgac cucgugaaga cgaggaugca gaaccagagg   1080
agcaccggga gcuucgugg ugagcugaug uacaaaaaua gcuucgauug cuucaagaag   1140
gugcugaggu acgagggcuu cuucggccug uacagaggcc ugcugccaca gcugcugggc    1200
guggcccccg agaaagccau caagcucacc gucaaugacu cgucaggga caaauuuaug    1260
```

```
cacaaggacg gcagcgugcc ccuggcugcc gagauccugg cuggggggug cgccggggggg    1320 agccagguga ucuucaccaa cccccucgag aucgucaaaa ucaggcugca gguggccgga    1380
gaaauaacca cuggcccag aguguccgcc cugagcgugg ugcgggaucu gggcuucuuc    1440
ggcaucuaua agggcgccaa ggccugcuuc cugagggaca uccccuucag cgccaucuau    1500
uuccccugcu acgccacgu caaggcuagc uucgccaacg aggacggaca ggugucccc    1560 ggcucccugc ugcucgcggg cgccaucgcc gggaugcccg ccgccagccu ggugaccccc    1620
gccgacguca ucaaaaccag gcugcaagug gccgcaaggg ccggccagac caccuacucc    1680
ggcgucaucg acugcuuucg gaagauccug cgugaggagg ccccaaggc ccugugggaaa    1740 ggggccggcg cccgugguguu uaggagcucc ccccaguucg gcgugacacu gcugacauau    1800
gagcugcugc aaagguggu cuacauagac uuuggcggcg ugaagcccau gggcagcgag    1860 ccuguccca agagcaggau caaccucccc cgcgccgaacc ccgaccacgu gggcggcuac    1920
aagcucgcag uggcgaccuu cgcgggaauc gagaacaagu ucggacugua ccuccccug    1980 uucaagcccu ccgucagcac cagcaaagcg aucggaggcg ccca              2025
```

<210> SEQ ID NO 8
<211> LENGTH: 2025
<212> TYPE: RNA
<213> ORGANISM: Artificial Sequence
<220> FEATURE:
<223> OTHER INFORMATION: Citrin-CO04

<400> SEQUENCE: 8

```
auggccgccg ccaaaguggc ccugaccaaa cgugccgacc ccgccgagcu gcgcaccauc    60
uuccugaagu acgccuccau cgagaagaac ggcgaguucu uuaugucccc caacgacuuu    120
gucacccggu aucugaacau cuucggggag agccagccca ccccaagac cgucgagcuc    180 cucuccggcg ugguggacca gaccaaagac ggccugauca gcuuucagga guucguggcc    240
uucgaaagcg ugcugugcgc gcccgacgcc cuguucaugg ucgccuucca gcucuucgac    300
aaagccggca agggcgaggu gaccuuuugag gacgugaagc aggucuucgg ccaaaccacc    360
auucaucagc acauccccuu caacugggac ucugaguucu gcagcuccca cuucgggaaa    420
gagaggaagc ucaccucac guacgccgag uuccccagu uucugcugga gauccagcug    480
gagcacgcca agcaagccuu guacagcggg acaacgcgc gcaccggccg ggugacggcc    540
aucgacuuca gggacaucau ggucaccauc cggccccacg ugcugacccc guucguggag    600
gagugucugg uggccgccgc cggcgggacc accagccacc aggugaguuu cccuacuuc    660 aacggauuca acucccuccu gaacaacaug gagcugaucc ggaagaucua cagcacccug    720
gccggcacca ggaaggacgu ggagguga cc aaggaagaau uugugcugc cgcccaaaaa    780 uucggccaag ugaccccau ggaggucgau auucuguucc agcuagccga ccucuacgag    840
ccuagggggc ggaugacccu ggccgacauc gagaggaucg cccccuugga gaggggcacc    900
cugccuuuca accuggccga ggcgcagcgg cagaaggccu caggcgacuc ugcccgaccc    960
gugcuucugc aaguggccga ucggccuac agguucggac ugggcagcgu ggccggcgcc    1020
gugggcgcca ccgccgucua ccccaucgac cuggucaaaa ccaggaugca gaaccagagg    1080
agcacuggcu ccuucguugg cgagcugaug uacaagaaca gcuucgacug cuucaagaag    1140
guccucaggu acgagggcuu cuucggccug uacagggggc uccugccca gcuucucggg    1200 gucgccccg agaaggcgau caagcucacc gugaacgacu ucgugaggga uaaguucaug    1260
```

-continued

| | |
|---|---|
| cacaaggacg gcuccgugcc ccuggccgcc gagauacuag ccggcggcug cgccggcggu | 1320 |
| ucccagguga uuuucaccaa cccccuggaa aucguaaaaa uccggcugca gguggccggg | 1380 |
| gagauaacca ccgggccgcg cgugagcgcc cugagcgugg uccgggaccu gggcuucuuc | 1440 |
| ggcaucuaca agggcgccaa ggccugcuuc cugagggaua uccccuucuc cgccaucuac | 1500 |
| uucccgugcu augcccacgu gaaagcgagc uucgccaacg aggauggcca agugagcccc | 1560 |
| gggagccucc ugcucgccgg ggccauagcc ggcaugcccg ccgccucccu cgugacgccc | 1620 |
| gccgauguga ucaagacccg gcugcaggua gcagcgcggg ccggccagac gaccuacagc | 1680 |
| ggcgugaucg acugcuuccg gaaaauccug agagaggagg gcccgaaggc ccucuggaag | 1740 |
| ggggcaggcg cacgcguguu caggagcagc ccccaguucg gcgugacccu gcucaccuac | 1800 |
| gagcugcugc agaggugguu cuauaucgac uucggcggcg ugaagcccau gggcagcgaa | 1860 |
| ccggugccca aaucuaggau caacuugccc gcacccaacc ccgaccacgu gggcggguac | 1920 |
| aaacuggcgg uggccaccuu cgccggaauc gaaaacaagu uggccuguac ccugccccug | 1980 |
| uuuaaacccu ccgugagcac cagcaaggcc aucgggggcg gcccc | 2025 |

<210> SEQ ID NO 9
<211> LENGTH: 2025
<212> TYPE: RNA
<213> ORGANISM: Artificial Sequence
<220> FEATURE:
<223> OTHER INFORMATION: Citrin-CO05

<400> SEQUENCE: 9

| | |
|---|---|
| auggcugccg ccaaggugge ccugaccaag agggccgauc ccgccgagcu gcgcacgauc | 60 |
| uuccugaagu acgccagcau cgagaagaac ggugaguuuu caugagcccc caacgacuuc | 120 |
| gucaccaggu aucugaauau cuucggcgag ucccaaccca accccaagac cguggaacug | 180 |
| uugagcggcg ugguggacca gaccaaggac gggcucaucu cguuccagga guucguggcc | 240 |
| uucgagaucg uccugugcgc ccccgacgcc cucuuuaugg ucgccuuuca gcuguucgac | 300 |
| aaggccggca agggcgaggu gacguucgag gacgugaagc aggucuucgg ccagaccacc | 360 |
| auccaccagc acauccccuu caacugggac agcgaguuca uacagcugca uucggaaag | 420 |
| gagcggaaga ggcaccugac cuacgccgag uucacccagu uccugcugga gauccagcug | 480 |
| gagcacgcca agcaggccuu cgugcagcgu gacaacgcgc ggacgggcag ggucaccgcc | 540 |
| aucgacuucc gggacauaau ggugacgauc cgcccccacg ugcugacgcc cuucguggag | 600 |
| gagugccugg uggccgccgc cggcggaaca accagccauc aggucagcuu cagcuauuuc | 660 |
| aacggcuuca acucgcugcu caacaacaug gaacucauca ggaagauaua cagcacccug | 720 |
| gccggcacca ggaaggacgu ggaggugacc aaggaagagu cguccuggc cgcccagaaa | 780 |
| uuuggacagg ucaccccgau ggaggucgac auccuguucc agcuggccga ccucuacgag | 840 |
| cccaggggcc gcaugacccu ggccgacauc gagcgcaucg cccccccugga agagggcacg | 900 |
| cugcccuuca accuggccga ggcccaacgg cagaaggccu ccggcgauag cgcccggccc | 960 |
| guccugcucc aaguggcaga guccgccuac cguuucggcc ugggcuccgu ggccggggcc | 1020 |
| gugggcgcga cugcggugua ccccaucgac cugguuaaga ccaggaugca gaaucagagg | 1080 |
| agcaccggau ccuuugucgg ggagcugaug uauaagaacu ccuucgacug cuucaagaag | 1140 |
| gugcugcgcu acgagggguu uucggccgu auaggggcc uccgcccca gcugcugggg | 1200 |
| gucgcccccg agaaggccau caaacugacc gucaacgauu cguccggga caaguucaug | 1260 |
| cacaaggacg gcagcgugcc ccuggcggcc gaaauccugg ccggcgguug cgccggaggc | 1320 |

-continued

| | |
|---|---|
| ucccaaguga ucuucacgaa ccccccucgaa auugugaaga uccggcugca ggugggccggc | 1380 |
| gagaucacca cgggcccag ggugagcgcc cugagcguag uccgcgaccu gggcuucuuc | 1440 |
| ggcaucuaca aggggggcuaa agccugcuuc cucagggaca uccccuucuc cgccaucuac | 1500 |
| uuccccuguu acgcccacgu gaaggccagc uuugccaacg aggacggcca ggugagcccc | 1560 |
| gguagccugc uccuggccgg cgccaucgcu gggaugcccg ccgccagccu ggugaccccc | 1620 |
| gccgacguca ucaagaccag guucagguc cgccaggg ccggcagac caccuacagc | 1680 |
| ggcgugauag acugcuucag gaagauccuu agggaggagg ggcccaaggc gcucuggaag | 1740 |
| ggggccggcg cccgcguguu ccgcuccagc ccccaguucg gcgugacccu gcugaccuau | 1800 |
| gagcuccugc agcggugguu cuacaucgau uucggcggcg ugaaacccau gggcagcgag | 1860 |
| cccgugccca agagcaggau caaccugcca gcccccaacc ccgaccacgu gggcgggguac | 1920 |
| aaacuggcgg uggccacuuu cgccggcaua gagaacaagu ucgggcuuua ccucccccug | 1980 |
| uuuaaaccua gcgugucaac cagcaaggcc aucggcggcg gcccc | 2025 |

<210> SEQ ID NO 10
<211> LENGTH: 2025
<212> TYPE: RNA
<213> ORGANISM: Artificial Sequence
<220> FEATURE:
<223> OTHER INFORMATION: Citrin-CO06

<400> SEQUENCE: 10

| | |
|---|---|
| auggccgccg caaagguugc ccucacaaag cgggccgacc ccgcggagcu gcgaaccauc | 60 |
| uuccugaagu acgccuccau cgagaagaac ggcgaguuuu ucaugagccc caacgacuuu | 120 |
| gugacccgau accucaauau cuucggcgag agccagccca accccaagac cgucgagcuc | 180 |
| cucuccggcg uggugaccca gaccaaagac gggcucauca gcuuccagga guucguggcc | 240 |
| uucgaaagcg ugcugugcgc ccccgacgcc cuguucaugg uggccuucca guuguucgau | 300 |
| aaagccggca agggcgaggu cacguucgaa gacgugaagc agguguucgg acagaccacc | 360 |
| auccaucagc acauccccuu caacuggggac uccgaguucg ugcagcugca cuuuggcaag | 420 |
| gagaggaaaa ggcaucugac cuacgccgag uucacccaau uucugcugga aauccagcuc | 480 |
| gaacacgcca agcaagccuu cguccaacga gauaacgcca ggacaggccg cgugaccgcc | 540 |
| aucgacuuca gggacaucau ggugaccauc aggcccaug cgcucacccc cuucgucgag | 600 |
| gagugccuag uggcggccgc cgggggaacc accagccacc aggucuccuu cagcuauuuc | 660 |
| aacggcuuca cagccugcu gaacaauaug gagcugauca ggaagaucua cagcaccccug | 720 |
| gccggcaccc ggaaggacgu ggaggucacg aaggaggagu uguccuggc cgcccagaag | 780 |
| uuugggcagg ugacccgau ggaaguggac auccuguucc agcuggccga ucuguacgag | 840 |
| cccgggggcc ggaugacccu ggccgauauc gagcggaucg cccccuugga ggaaggcacc | 900 |
| cugcccuuca aucuggcgga ggcccagaga cagaaggcca cgcgcgacag cgccaggccc | 960 |
| gugcucuuac agguggcaga gagcgccuau agguucggcc ucggcuccgu ggccggcgcc | 1020 |
| gugggggcca ccgccguagua cccgaucgac cuggugaaga cgaggaugca gaaccagcga | 1080 |
| aguacgggca guucguggg cgagcugaug uacaagaacu ccuucgacug cuucaagaag | 1140 |
| gugcugaggu acgaggggu cuucggccug uacaggggcc uccugcccca gcucuugggc | 1200 |
| gucgccccgg agaaggccau caagcugacg gugaaugacu uugugaggga caaauucaug | 1260 |
| cauaaggacg gcucugucc ccuggccgcc gaaauccugg ccggcggcug cgcuggcggc | 1320 |

| | |
|---|---|
| agccaaguga uuuucaccaa ccccuucgag aucgugaaaa uuaggcugca ggucgccggg | 1380 |
| gagaucacca ccgguccgcg ggugagcgcc cuguccgucg uccgggaucu ggcuucuuc | 1440 |
| ggcaucuaca agggagccaa ggccugcuuc ucucagggaca ucccguucag cgccaucuac | 1500 |
| uuccccugcu augcccacgu gaaagccagc uucgccaacg aggacggcca agucagcccg | 1560 |
| ggcucccugc ugcuggccgg cgccaucgcc ggcaugcccg ccgccagccu ggugacccc | 1620 |
| gccgacguga uaaaaaccag gcugcaggug gccgccaggg ccggccagac caccuacagc | 1680 |
| ggggucaucg acugcuuccg caagauccuc cgggaggagg ggcccaaggc ucuguggaag | 1740 |
| ggcgccgggg ccagggucuu caggucgagc ccccaguucg gggugacgcu gcugacauac | 1800 |
| gagcugcugc aaaggugguu cuacaucgau uucgguggag ucaaacccau gggaagcgag | 1860 |
| ccgguccca agagcaggau caaucugccc gcccccaacc ccgaccaugu gggcggcuac | 1920 |
| aagcuggccg uggccaccuu cgccgggauc gaaaacaagu ucggacugua ccugcccccug | 1980 |
| uuuaaacccu cagugccac cuccaaggcc aucggcggcg ccccc | 2025 |

<210> SEQ ID NO 11
<211> LENGTH: 2025
<212> TYPE: RNA
<213> ORGANISM: Artificial Sequence
<220> FEATURE:
<223> OTHER INFORMATION: Citrin-C007

<400> SEQUENCE: 11

| | |
|---|---|
| auggccgcug ccaagguggc ccugaccaag cgggcugacc ccgccgagcu gaggacaauc | 60 |
| uuccugaaau acgcgucgau cgagaagaac ggcgaguucu ucaugagccc uaacgacuuc | 120 |
| gugacccgcu accugaacau cuucggagag agccagccca cccgaagac cguggaacug | 180 |
| cucagcggcg ugguggacca aaccaaggac ggccugaucu ccuuccagga guucguggcc | 240 |
| uucgagagcg ugcugugcgc gcccgacgcc cuguuuaugg uggccuucca gcuguucgau | 300 |
| aaagcgggga aggggggagu gacguucgag gaugugaagc aggugucgg ccagacgacc | 360 |
| auacaccagc acaucccccu caacugggac uccgaguuug ucagcugca cuucggcaag | 420 |
| gagcggaaaa ggcauuugac guacgccgag uucacccagu uccugcugga gauccaacug | 480 |
| gagcacgcca agcaggccuu cgugcagcga caacgccca ggaccgggag ggugacggcg | 540 |
| auagacuucc gggacaucau ggugaccauc aggcccacg uccugacccc cuucguagag | 600 |
| gaaugucugg ucgccgccgc cggcggcacc accagccacc aagugagcuu uagcuacuuc | 660 |
| aacggcuuca acagccugcu caacaacaug aacugaucc gcaagaucua cagcaccuc | 720 |
| gccggaaccc gcaaggacgu ggaggugacg aaggaagaau ucguccuggc cgcacagaag | 780 |
| uucggccagg ugaccccuau ggagguggau auccucuucc agcugccga ccucuacgag | 840 |
| ccccggggca ggaugacccu ggccgauauc gaaaggaucg cccccuggac ggagggguacc | 900 |
| cugcccuuca accuggccga ggccagcgg caaaaggccu ccggcgacag cgcccgaccc | 960 |
| gucugcucc aaguggccga gucagcguac agguugggcc uggcagcgu ggccggcgcc | 1020 |
| gucggcgcca ccgccgugua ccccauagac cuggugaaga ccaggaugca gaaccagagg | 1080 |
| agcaccggca gcuucgucgg ggagcugaug uauaaaaacu ccuuugacug uuucaagaag | 1140 |
| gugcugcgcu augaaggcuu cuucggacug uacaggggcc uccugcccca gcugcugggg | 1200 |
| gucgcccccc agaaggccau caagcugacc gugaacgacu uugugaggga caaguuuaug | 1260 |
| cacaaggaug gcagcgugcc ccuggccgcc gagauccugg cgggcggcug ugcgggggc | 1320 |
| ucgcaggcca ucuucacgaa uccccucgaa aucgucaaaa uucgccugca aguggccggg | 1380 |

| | | | |
|---|---|---|---|
| gaaaucacca | ccggaccccg cgugagcgcc cucagcgugg ugagggaccu | aggguucuuc | 1440 |
| ggcauuuaca | agggcgccaa ggccugcuuc cugagggaca uccccuuuuc | cgccaucuac | 1500 |
| uuccccuguu | acgccacugu gaaggccagc uucgccaacg aggacgggca | gguuagcccc | 1560 |
| gggucgcugc | ugcuggccgg cgccaucgca gggaugccgg ccgccagccu | ggucacccc | 1620 |
| gccgacguca | ucaaaacccg gcugcaggug gccgccaggg caggccagac | caccuauagc | 1680 |
| ggggugauag | acugcuuucg uaagauucuc agggaggagg gccccaaggc | gcuguggaag | 1740 |
| ggggccgggg | ccagggucuu ccgguccagc ccccaguucg gggugacacu | ccugaccuau | 1800 |
| gaacugcugc | agaggugguu cuacaucgau uccggcggcg ugaagccuau | ggggagcgag | 1860 |
| cccgugccca | aaagcaggau caaccugccc gccccgaacc ccgaucacgu | gggcggauau | 1920 |
| aagcuggccg | uggccacccu ucgccgguau cgaaaacaagu ucggacugua | ccugccccug | 1980 |
| uucaagccca | gcgucagcac cucgaaggcg aucggaggcg guccg | | 2025 |

<210> SEQ ID NO 12
<211> LENGTH: 2025
<212> TYPE: RNA
<213> ORGANISM: Artificial Sequence
<220> FEATURE:
<223> OTHER INFORMATION: Citrin-CO08

<400> SEQUENCE: 12

| | | | |
|---|---|---|---|
| auggccgccg | ccaaggugge ccugaccaag cgggccgauc cgccgagcu | gcguaccauc | 60 |
| uuucugaagu | acgccuccau cgagaagaac ggcgaguucu ucaugagccc | caacgacuuc | 120 |
| gugacccggu | accucaacau cuucggugag ucgcagccga ccccaagac | cguggaacuc | 180 |
| cugagcgggg | ugguggacca gaccaaggac ggcucacauaa gcuucaaga | guucguggcc | 240 |
| uuugaguccg | ugcuuugcgc ccccgacgcc cuguucaugg uagccuucca | gcuguucgac | 300 |
| aaggccggca | aggcgaggu gaccuucgaa gaugugaagc aggucuuugg | ucagaccacc | 360 |
| auacaucagc | acauccccuu caacugggac agcgaguuug ugcagcugca | uuucggaaag | 420 |
| gagaggaaac | ggcaccugac cuacgccgag uucacccagu uccugcugga | gauccagcug | 480 |
| gagcacgcca | acaggccuu cgugcagcgc gacaacgcgc ggaccggccg | ggugacugcc | 540 |
| aucgacuucc | gggacaucau ggugacgauc aggccccacg uguugacccc | cuucguggag | 600 |
| gagugucugg | uggccgccgc cggcgggacc accucccauc aggucuccuu | uagcuacuuc | 660 |
| aaugggguuca | acagccugcu gaacaacaug gagcugaucc gaaagaucua | uagcacgcuc | 720 |
| gccggcaccc | ggaaggaugu ggaggugacc aaggaagagu cguccuggc | ugcccagaag | 780 |
| uucggacagg | ugaccccau ggaggugau auacuguucc agcucgccga | ccuguacgag | 840 |
| cccaggggac | guaugacccu ggcggauauc gagaggaucc cccccuugga | ggagggcacc | 900 |
| cugcccuuca | accuggcaga ggcgcagagg cagaaggcca gcgggacag | cgcccgaccu | 960 |
| guccugcugc | aggugggccga auccgccuac cgguucggcc ugggcagcgu | agccggcgcc | 1020 |
| gucggugcca | ccgccgugua ccccauugac cucgugaaga cccggaugca | gaaccagcga | 1080 |
| agcaccggua | gcuucgucgg cgagcugaug uacaagaaua gcuugacug | cuucaagaag | 1140 |
| guccugaggu | acgaaggcuu uuucggucug uaucggggcc ugcugcccca | acugcugggg | 1200 |
| gucgcccccg | agaaggcuau caagcugacg gugaacgacu ucgugcgcga | uaaauucaug | 1260 |
| cacaaggacg | gcuccgucc ccucgccgcc gagauccugg ccggaggcug | cgccggggc | 1320 |
| ucccaaguua | ucuucaccaa ccccuggaa aucguuaaga uccggcugca | ggucgcgggc | 1380 |

```
gagaucacca ccggccccg cgugccgcc cugccgugg ugagggaccu gggcuucuuc    1440
ggcauauaca aaggugccaa ggccugcuuc cugagggaua uccccuucag cgccaucuac    1500
uuccccugcu acgcccacgu gaaggccagc uucgccaacg aggauggcca ggucuccccc    1560
ggcucucugc ugcucgcggg cgccaucgcc ggcaugcccg ccgcgucccu ggugaccccc    1620
gccgacguga uaaagaccag gcugcaggug ccgccaggg caggccagac caccuacagc    1680
ggggucaucg acugcuucag gaagauccug agggaggag gccgaaggc ccucuggaag    1740 ggcgccgggg ccagggguguu uaggucaagc ccccaguucg gggucacccu ccugaccuac    1800
gagcugcugc agaggugguu cuauaucgac uucggggcg ugaagcccau ggcuccgag     1860 ccggugccaa aguccgcau caaccugccc gccccgaacc ccgaucacgu cggcggcuac    1920
aagcucgccg uggccaccuu ugccgguauc gagaacaagu ucggacugua ucugccccug    1980
uucaagccga gcgugagcac cagcaaggcc aucggcgggg gcccg                   2025
```

<210> SEQ ID NO 13
<211> LENGTH: 2025
<212> TYPE: RNA
<213> ORGANISM: Artificial Sequence
<220> FEATURE:
<223> OTHER INFORMATION: Citrin-CO09

<400> SEQUENCE: 13

```
auggccgccg ccaaggucgc ccugaccaag cgggcggacc ccgccgagcu gaggacaauc    60
uuccugaagu acgccuccau ugagaagaac ggcgaauuuu ucaugagccc caacgacuuu    120
gugacgcgcu accugaauau cuucgggga ucccagccca ccccaagac gguggagcuc    180 cugagcggcg uggucgacca aaccaaggac ggacugauca gcuucagga guucguggcc    240 uucgagucag ugcugugcgc ccccgaugcc cguucaugg uugccuucca gcuguucgau    300
aaggccggua aggggaggu gaccuucgaa gaugugaagc agguguuugg gcagaccacc    360
auccaccagc auauaccguu caauuggac agcgaguuug cgcagcugca cuucggcaag    420
gagaggaaga ggcaucugac cuacgccgag uucacccaau uccugcucga gauccagcuc    480
gagcacgcca gcaggccuu cguacagagg gacaacgccc ggaccgggag ggugaccgcc    540
aucgacuucc gggacaucau ggugaccauc cguccgcacg uccugacccc uuuguggag    600 gagugccugg ucgccgcggc cggcggcacc accagccacc aggugagcuu cagcuacuuc    660
aacggguuca acagccugcu caacaacaug gagcugauca ggaagaucua cagcacccug    720
gccggcacca ggaaagacgu ggaggugacc aaggaggagu cgugcuggc cgcccagaag    780 uucgggcagg ugaccccau ggaaguggac auccuguucc aacucgccga ccuguacgag    840
ccccgaggua ggaugacccu ggccgacaua gagcgaaucg ccccgcucga ggagggaaca    900
cuccccuuua aucuggcgga agcccaaagg caaaaagcca gcggcgacag cgcccgcccc    960
gugcugcugc aggugggcgga gagcgccuau cguuuuggc ucgggagcgu ggccggcgcg    1020
guaggagcca ccgccgucua ccccaucgac cuggugaaga ccaggaugca gaaucagcga    1080
agcaccgggu ccuucguggg cgagcugaug uacaagaaua gcuucgacug cuucaagaag    1140
guacugcgcu acgagggcuu cuucggccug uacaggggc uccugccca gcuccuggc     1200 guugccccg agaaggccau caaacucacc gucaacgacu ucgugaggga caaguucaug    1260
cauaaggacg gcucgguggcc ccuggccgcc gaaauccugg cgggggcugu cgccggagga    1320
agccagguga ucuucacuaa cccccucgag auagugaaga ucaggcugca ggucgccggc    1380
gagaucacca ccggccccag ggugagcgcc cucuccgugg ugagggaucu gggcuucuuc    1440
```

| | | | |
|---|---|---|---|
| ggcaucuaca | agggcgccaa | ggccugcuuc cuccgggaua ucccguucuc cgccaucuau | 1500 |
| uuccccugcu | augcucacgu | gaaggccagc uuugccaacg aggauggaca ggugagcccc | 1560 |
| ggcucccugc | ugcuggccgg | cgccaucgca gguaugcccg cugccucccu cgugaccccc | 1620 |
| gccgacguga | ucaagacucg | ccuccaggug gccgccaggg ccggccagac caccuacucc | 1680 |
| ggcgucaucg | auugcuuccg | gaagauccuc cgugaagagg ucccaaggcc ccucuggaaa | 1740 |
| ggcgccggug | cgcgagguguu | uaggagcagc ccccaguucg gggugacucu gcugaccuac | 1800 |
| gagcugcucc | agaggugguu | cuacaucgac uucggcggag uaaagcccau gggcagcgag | 1860 |
| cccgucccca | agucgcgcau | caaccucccc gccccgaacc ccgaccacgu cggcgguuac | 1920 |
| aagcuggccg | uggccaccuu | ugccggcauc gagaacaagu ucggccugua ccucccccug | 1980 |
| uucaaaccca | gcgugaguac | cucgaaggcg aucggcggcg ggccc | 2025 |

<210> SEQ ID NO 14
<211> LENGTH: 2025
<212> TYPE: RNA
<213> ORGANISM: Artificial Sequence
<220> FEATURE:
<223> OTHER INFORMATION: Citrin-CO10

<400> SEQUENCE: 14

| | | | |
|---|---|---|---|
| auggcagccg | ccaaggucgc | ccuuaccaaa cgugccgauc ccgcggagcu gaggaccauc | 60 |
| uuccugaagu | acgcaagcau | cgagaagaac ggcgaguucu caugucccc caacgacuuc | 120 |
| gugaccaggu | aucgaauau | cuucggggaa ucccaaccca aucccaagac cgucgagcuc | 180 |
| cugagcggcg | uaguggauca | aaccaaggac ggccugaucu cguuccagga guuugucgcc | 240 |
| uuugagagcg | ugcucugcgc | ccccgacgcc cguuuauggu cgccuucca gcuguucgau | 300 |
| aaggccggga | agggcgaagu | gaccuucgaa gacgugaagc aggucuucgg ccagaccacc | 360 |
| auacaccagc | auaucccuuu | uaacgggac agcgaauucg ugcagcugca cuucggaaag | 420 |
| gagaggaaga | ggcaccugac | guaugccgag uucacgcaau ucugcugga gauccagcuc | 480 |
| gaacacgcga | agcaggccuu | cguccagagg gacaacgccc gcaccgggag ggugaccgcc | 540 |
| aucgacuucc | gcgauaucau | ggugaccauc cgaccccacg ugcugacccc cuucgucgag | 600 |
| gagugccucg | uggcagcagc | cggcggcacc acgucgcacc aggugagcuu uccuacuuc | 660 |
| aacggguuca | acagccugcu | gaacaauaug gagcugauca ggaagauaua cagcacccuc | 720 |
| gcggguaccc | ggaaggacgu | ggaggugacc aaggaggagu ucugcugggc cgcccagaag | 780 |
| uuugggcagg | ugacccccau | ggaggugac auccuguucc agcugccga ccuguacgag | 840 |
| ccccggggcc | gcaugacccu | ggccgacauc gagaggaucg ccccccugga gagggcaca | 900 |
| cugccuuuca | accuggcgga | ggcgcagagg cagaaggcca cggggacag cgccaggccc | 960 |
| guacugcugc | aggucgccga | gagcgccuac cgauuuggcc uggggagcgu ggcuggcgca | 1020 |
| gugggcgcca | ccgcggugua | ccccaucgac cucgugaaga cccggaugca aaaccagagg | 1080 |
| agcacaggga | gcuucguggg | ggagcugaug uacaagaaca gcuucgacug uuucaaaaag | 1140 |
| gugcugaggu | augagggcuu | uucgggcug uacagggggc ugcuccccca gcugcucggc | 1200 |
| guggccccgg | agaaggccau | aaagcugacc gugaacgacu cguccggga caaguucaug | 1260 |
| cacaaagacg | gcagcgcccc | ccuggccgcc gagauccugg ccggcggcug cgccggcggc | 1320 |
| ucccagguga | ucuuuacaaa | uccccucgaa auugugaaga ucagguugca aguggccggc | 1380 |
| gagaucacca | ccggccccag | ggugagcgcc cugagcgugg ugagggaccu cggcuuuuuc | 1440 |

```
ggcaucuaca agggcgccaa ggccugcuuu cugcgugaca ucccauucag cgccaucuau    1500
uuccccugcu acgcccacgu gaaagccucg uuugccaacg aggacggcca ggugucgccc    1560
ggcagucugc ugcuggccgg ugccaucgcc ggcaugcccg ccgcgucccu ggugaccccc    1620
gccgacguga ucaaaacuag gcugcaggug ccgcccgcg ccggccagac cacguacagc     1680
ggcgugaucg acugcuuccg aaagauccug agggaggagg gccccaaggc ccuguggaag    1740
ggugcaggcg ccaggguguu ccgcccuccc ccccaguucg gcgugacgcu ccugaccuac    1800
gagcugcugc agcgcugguu cuauaucgau uuggcggcg ucaagcccau gggcucggag     1860
cccgugccca aguccaggau caaccucccc gcgcccaacc ccgaccaugu gggcggauac    1920
aaacucgcgg uggccaccuu cgcaggcauc gagaacaagu cggccucua ccugccacuu     1980 uucaagcccu ccguguccac cuccaaggcc aucgggggcg ccccc                    2025
```

<210> SEQ ID NO 15
<211> LENGTH: 2025
<212> TYPE: RNA
<213> ORGANISM: Artificial Sequence
<220> FEATURE:
<223> OTHER INFORMATION: Citrin-CO11

<400> SEQUENCE: 15

```
auggccgccg ccaaggtggc ccugaccaag agggccgacc ccgcggagcu gaggaccauu    60
uuccugaaau acgccagcau cgagaagaac ggcgaguucu ucaugagccc caacgacuuc    120
gucacccggu accucaacau cuucggagag agccagccca ccccaaaaac uguggagcug    180
cugagcggcg ucguggacca gacgaaggac ggccucauca gcuuccagga auucgucgcc    240
uucgaauccg ugcucugcgc gcccgacgcc cguucauggu ggccuuuca gcuguucgac    300 aaggcaggga aggggaagu caccuucgag gaugugaagc aaguguuugg ccagacgacg    360
auccaccagc acaucccuu uaacugggac agcgaauucg ugcaacucca cuucggaaag    420
gagcgcaaga ggcaccugac cuacgcgag uucacccaau ccugcuggga auacagcug    480 gagcacgcca gcaggcguu ugugcagcgg acaacgcca ggaccggcag ggucaccgcc    540
aucgacuucc gggacauaau ggugaccauc cgccccacg ugcugacacc guucugagaa    600
gagugccugg uggccgcggc cggggcacg accucccacc aggugagcuu ucgacuuc     660 aacggcuuca cagccugcu caauaacaug gagcugaucc ggaagaucua uagcacccug    720
gccggcacca ggaaggacgu ggaggugacc aaggaggaau cgugcucgc ggcccagaag    780 uucgccagg ugaccccau ggagguggac auccuguuuc agcuggcaga ccuguacgag     840 cccagggga cguaugaccu ggccgauauc gagcguaucg cgcccuggga ggagguacc     900 cuccccuuca accuagccga ggcccagcga cagaaggcca cgggggacu ggcaaggccc    960 gugcugcugc aggucgccga gagcgccuac agguuugggc uggggagcgu ugccggcgcc    1020
guggggccca cggccguguua ccccaucgac cuggucaaga cccgaaugca aaaccaacgc    1080
agcaccggcu ccuucgugg ggagcugaug uacaaaaacu ccuucgacug cuucaaaaag    1140
gugcugaggu acgaggggu uuucgggcug uacaggggcc ugcuccccca gcugcugggc    1200
guggcccccg aaaagccau caagcugacc gugaaugacu cgugcgcga uaaguucaug    1260 cacaaggaug gguccgugcc ccucgcggcc gagauccugg ccgcggggug ugccggcggc    1320 ucccaggugua ucuucaccaa ccccuggag aucgugaaaa ucaggcugca agucgccggc    1380 gagaucaacca cggcccccg cgugccgcc cugagcgugg ucagagaccu cggcuucuuc    1440
ggcauauaca agggcgccaa ggccugcuuc cugcgggaca ucccccuucag cgccaucuac    1500
```

| | | | | |
|---|---|---|---|---|
| uuccccugcu | acgcacaugu | gaaggcgucc | uucgccaaug | aggacggcca | ggucagcccc | 1560 |
| ggcagccugc | ugcuggccgg | cgccaucgcc | ggcaugcccg | cagccucccu | cgucacccccc | 1620 |
| gccgauguga | ucaagaccag | gcugcaggug | gccgcgaggg | cuggccagac | caccuacagc | 1680 |
| ggcgugaucg | acugcuucag | gaagauacug | agggaggaag | ccccaaggc | ccugugggaaa | 1740 |
| ggggccggcg | cccgcguguu | caggagcagc | ccccaguucg | gugugacccu | gcugacguac | 1800 |
| gagcugcugc | agcggugguu | uuacauagau | uccggcggug | ugaagcccau | gggcucugag | 1860 |
| cccgucccca | aauccaggau | caaccugccc | gcccccaacc | ccgaccacgu | gggcggcuac | 1920 |
| aagcuggccg | ucgccaccuu | cgccggcauc | gagaacaagu | cgggcugua | ccugcccccug | 1980 |
| uucaaaccga | gcgugucgac | aagcaaggcc | aucgggggcg | ggcccc | | 2025 |

<210> SEQ ID NO 16
<211> LENGTH: 2025
<212> TYPE: RNA
<213> ORGANISM: Artificial Sequence
<220> FEATURE:
<223> OTHER INFORMATION: Citrin-CO12

<400> SEQUENCE: 16

| | | | | | | |
|---|---|---|---|---|---|---|
| auggcggccg | ccaaggugc | gcugacgaag | cgggccgacc | ccgccgagcu | gaggaccauc | 60 |
| uuucugaagu | acgccagcau | cgaaaagaac | ggcgaguucu | ucaugccccc | caacgacuuc | 120 |
| gucacgaggu | accugaacau | cuucggagag | ucccaaccca | auccgaagac | cgucgaacug | 180 |
| cuguccggug | uggucgacca | gaccaaggac | ggccuaaucu | ccuuccagga | auucguggcc | 240 |
| uucgagagcg | ugcugugcgc | ccccgaugcc | cuguucaugg | uggccuucca | gcuguuugac | 300 |
| aaagccggca | agggcgaggu | gacuuucgaa | gaugugaagc | aggguguuugg | acagaccacc | 360 |
| auccaccagc | acaucccccuu | caacugggac | agcgaguucg | ugcagcugca | cuucgggaaa | 420 |
| gaacggaaga | ggcaucugac | cuacgccgag | uucacgcagu | uccugcugga | auccagcug | 480 |
| gagcacgcca | agcaagcguu | cgugcagagg | gacaacgccc | ggaccggcag | gguuaccgcc | 540 |
| auugacuuca | gggauaucau | ggucacuauc | cggccccacg | uccugacgcc | cuucguggag | 600 |
| gagugccugg | uggccgcggc | cggcgggacg | acccccccauc | aggugucuuu | uagcuacuuu | 660 |
| aacggccuuca | auagccugcu | gaauaauaug | gagcugauca | ggaagaucua | cuccacccug | 720 |
| gccgggaccc | ggaaggacgu | ggaagugacc | aaagaggagu | uugugcuggc | cgcccagaaa | 780 |
| uucggccagg | ugaccccgau | ggagguggac | aucuuguucc | agcuggcgga | ucucuaugag | 840 |
| ccccgaggcc | ggaugacccu | ggccgauauu | gaaaggaucg | ccccccugga | ggagggaacc | 900 |
| cugccauuca | accucgccga | agcccagagg | cagaaggcga | gcgggggauuc | cgccaggcca | 960 |
| gugcuccugc | aggugcagga | guccgcguac | cgcuucggcc | uugggccgu | ggccggcgcc | 1020 |
| gugggcgcca | cggcagucua | ccccaucgac | cugguccaaga | cccggaugca | gaaccagcgc | 1080 |
| agcaccggga | gcuucguggg | cgagcugaug | uacaagaaca | gcuucgacug | cuucaagaag | 1140 |
| gugcugaggu | acgagggguu | cuucgggcuc | uaccgggggc | ugcugcccca | gcuccugggg | 1200 |
| guggcccccgg | agaaagccau | caagcucacc | gugaaugauu | uugugaggga | caaguucaug | 1260 |
| cacaaggacg | gcagcgugcc | ccuggccgcc | gagauccugg | caggcggcug | cgccggcggc | 1320 |
| ucccagguga | ucuucaccaa | uccccuggag | aucguuaaga | ucaggcucca | gguggccggc | 1380 |
| gagauuacca | ccggccccccg | cguguccgcc | cugagcgugg | ugcgcgaucu | ggggguucuuc | 1440 |
| ggcaucuaca | agggcgccaa | ggccugcuuc | cugcgggaua | ucccccuucag | cgccaucuac | 1500 |

| | | |
|---|---|---|
| uuucccugcu augcccaugu gaaggccagc uucgcaaaug aagaugggca ggugucgccc | 1560 |
| ggguccugc ugcuugccgg ugccaucgcg ggcaugccgg ccgccagccu ggugaccccu | 1620 |
| gccgauguga ucaaaaccag gcugcaggug ccgccaggg ccggccagac caccuacagc | 1680 |
| ggugugaucg auugcuucag gaagauccuc cgggaggagg cccccaaggc ccuguggaag | 1740 |
| ggggccggcg cccgcguguu ccgcagcucg ccgcaauucg gugucacccu ccugaccuac | 1800 |
| gagcugcugc aaaggugguu cuauaucgac uucggcggcg ucaagcccau ggcagcgag | 1860 |
| cccgugccca aaucuaggau caaccucccc gccccgaacc cugaccaugu cggcggcuac | 1920 |
| aagcuggccg uggccaccuu cgccgguauc gagaacaagu cgggcucua ccugcccug | 1980 |
| uucaagccca gcgucagcac cagcaaggcc aucggcggcg gcccg | 2025 |

<210> SEQ ID NO 17
<211> LENGTH: 2025
<212> TYPE: RNA
<213> ORGANISM: Artificial Sequence
<220> FEATURE:
<223> OTHER INFORMATION: Citrin-CO13

<400> SEQUENCE: 17

| | | |
|---|---|---|
| auggccgccg ccaaagugc ccugaccaaa agggccgacc cugcggagcu gaggaccauc | 60 |
| uuccugaagu acgccagcau cgagaaaaac ggggaguuuu ucaugagccc caacgacuuc | 120 |
| gugacgcggu accgaacau auucggcgag agccagcca accccaagac cguggagcuc | 180 |
| cugagcggcg uugucgauca gaccaaagau ggucugaucu ccuucagga guuguggcc | 240 |
| uuugagagcg ugcugugcgc ccccgacgcc cguucaugg ucgccuuuca gcuguucgac | 300 |
| aaggcuggca agggcgaggu gaccuucgag gacguuaagc aggguucgg gcaaaccacc | 360 |
| auccaccagc auauccccuu caacugggac agcgaguucg ugcagcucca cuucggcaag | 420 |
| gaaaggaagc ggcaccugac cuacgcagag uucacgcagu uccugcugga aauccaacug | 480 |
| gaacacgcca aacaggccuu cguccagagg gacaacgccc ggacggggag ggucaccgcc | 540 |
| auagacuuca gggacaucau ggugacgaua cggccgcacg ugcugacgcc cuuuguggag | 600 |
| gagugccugg uggccgccgc cggggcacc accucccauc aggugagcuu cagcuauuuc | 660 |
| aauggcuuca acagccuccu gaauaacaug gagcuaauca ggaagauaua cagcacccug | 720 |
| gccggcacca ggaaggacgu ggaggugacc aaggaggagu cgugcuggc cgcccaaaag | 780 |
| uucggccagg ugaccccau ggaagucgau auccuguucc agcucgccga ccuguacgaa | 840 |
| ccccguggcc ggaugacccu ggccgacauc gagcggaucg ccccacugga ggagggcacu | 900 |
| cugccguuca ccuggccga ggcccaaagg cagaaagccu ccggggacuc cgcgaggccg | 960 |
| guccugcugc aggucgccga gagcgccuau cgauucgggc ugggcuccgu ggccggcgcc | 1020 |
| gugggggcga ccgccgugua ucccaucgac cuggugaaga ccaggaugca gaaccagagg | 1080 |
| ucaaccggcu ccuucguggg ggagcugaug uauaagaaua gcuucgacug uuucaagaag | 1140 |
| gugcugcggu augagggguu cuucggccug uacagaggcc ugcugcccca gcuguugggg | 1200 |
| guggccccg agaaagcaau caagcugacc gugaacgacu ucgugaggga caaguucaug | 1260 |
| cacaaagacg gaagcgugcc ccuggccgcc gagauccugg ccggcgguug cgcgggagga | 1320 |
| ucccagguca ucuucaccaa cccgcuggag aucgucaaaa uccgccugca gguggccggc | 1380 |
| gagaucacca ccggccccag ggugagcgcg cugucccgugg ucggggaccu cggguucuuc | 1440 |
| ggcaucuaca aaggagccaa agccugcuuc cugaggauua ucccuucuc cgcuaucuac | 1500 |
| ucccccuguu augcccacgu gaaggcgucg uucgcuaaug aagacgggca agugucccca | 1560 |

```
gggucccugc ugcucgccgg cgccaucgcc gguaugccag ccgccagccu ggugaccccc    1620
gcagacguca uaaagacgcg ccugcagguc gcggccaggg ccgggcagac aacguacagc    1680
ggaguuaucg acugcuuccg gaagauccuc cgggaggagg ccccaaggc ccuguggaag     1740 ggcgccggcg cucggguguu ucggagcucc ccgcaguucg gugugacgcu gcugaccuac    1800
gagcuccucc agaggugguu cuacaucgac uucggcgggg ugaagcccau gggcuccgag    1860
cccgucccca gagccgaauu aaaucugccc gcccccaacc ccgaucacgu ggggggauac    1920
aaacuggcgg uggcgaccuu cgccgggauc gagaauaagu uggggcugua ccucccccua    1980
uucaagccca gcgucagcac cagcaaggcc aucgggggag ggccg                    2025
```

<210> SEQ ID NO 18
<211> LENGTH: 2025
<212> TYPE: RNA
<213> ORGANISM: Artificial Sequence
<220> FEATURE:
<223> OTHER INFORMATION: Citrin-CO14

<400> SEQUENCE: 18

```
auggccgcag ccaaggugge ccugaccaag cgggcugacc ccgccgagcu gcgcaccauc    60
uuccugaaau acgccagcau cgaaaagaac ggcgaguucu cauguccccc gaacgacuuc    120
gugaccaggu aucuaaacau cuuccggcgaa agccaaccca accccaagac ggugagcug   180 cucagcggcg ucguggauca gaccaaagac ggccugaucu ccuuccagga guucgucgcc    240
uucgagagcg ugcugugugc ccccgacgcc cuguucaugg uggccuucca gcuguucgau    300
aaggccggca aggggaggu gaccuucgaa gacgugaagc agguuuucgg ucaaacgacg    360
auccaccagc auauaccguu caauugggac uccgaguucg ugcaacugca cuucgggaag    420
gaacggaagc ggcaucucac cuacgccgag uucacccagu uucugcugga aaccagcug    480 gaacacgcca gcaggccuu cguccagagg gacaacgcca ggaccgggag ggugaccgcc    540
aucgauuuca gggacaucau ggugacgauc aggccucacg ugcugacgcc cuucguggag    600
gagugccuug uggccgccgc cgguggcacc acuagccacc aggugagcuu cagcuacuuc    660 aacgggguuca acagccugcu gaauaauaug gagcugauaa ggaagaucua uagcacccug    720
gccggcaccc ggaaggaugu ggaggugacc aaggaggagu cgugcuggc cgcccagaag    780 uucggccagg ugacacccau ggaggucgac auccuguuuc agcucgccga ccuguacgag    840
cccaggggcc ggaugacccu ggccgauauc gagaggaucg cgccccugga ggagggacc    900 cugcccuuca accuggcgga agcgcagcgc cagaaggcaa gcggagacuc cgcaaggccc    960
gugcuccugc aggugccga agcgcguac cgcuucggcc uggguccgu ggccggcgcg    1020 gugggcgcca ccgccgucua ccccaucgac cuugcaaga ccaggaugca aaaccagcgc    1080
ucgaccggca gcuucguggg cgagcucaug uacaagaaca gcuugacug uuucaagaag    1140 gugcugagau augaagggguu cucggccug uacagggggcc uccugccca acugcugggc    1200 guggcgcccg aaaaggccau caagcucacc gugaacgacu ucgugaggga caaauucaug    1260
cacaaggacg gguccgucc ccuggccgcc gagauccugg ccggcgguug cgccggcggc    1320
ucccagguga ucuucaccaa uccgcuggag aucgugaga ccggcugca gguggcgggc    1380 gaaaucacca ccgggccaag gguauccgcc cugagcgugg ucgggaccu cgggguucuuc    1440 gggaucuaca aaggcgccaa ggccugcuuc uccgcgaca uccccuuuag cgcgaucuac    1500 uucccugcu acgccacgu gaaggccucc uucgccaacg aggacggcca agugagcccc    1560
```

| | |
|---|---|
| ggcucccugc ugcuggcagg cgcgaucgcc ggaaugcccg ccgccagccu cgucacgccc | 1620 |
| gccgacguga ucaagacccg gcugcaaguc gccgcgaggg ccggccagac caccuacagc | 1680 |
| ggggucaucg auugcuuccg aaagauccug agggaggaag ggcccaaggc gcuguggaag | 1740 |
| ggggccgggg ccaggguguu cagaagcagc ccccaguucg gcugacccu gcugaccuac | 1800 |
| gagcuccugc agcggugguu cuacaucgac uucggaggcg uaaagccgau gggcagcgaa | 1860 |
| cccgugccua aguccgauau caaccugccc gcccccaauc cggaccacgu gggcggauac | 1920 |
| aagcuggcgg uggccaccuu cgccggcauc gagaacaagu cggccucua ccucccgcug | 1980 |
| uuuaagccca gcgugagcac cagcaaagcc aucguggug gcccg | 2025 |

<210> SEQ ID NO 19
<211> LENGTH: 2025
<212> TYPE: RNA
<213> ORGANISM: Artificial Sequence
<220> FEATURE:
<223> OTHER INFORMATION: Citrin-CO15

<400> SEQUENCE: 19

| | |
|---|---|
| auggcugccg ccaaagucgc ccugaccaag cgugcggacc ccgccagcu caggacgauc | 60 |
| uuccugaagu acgcgagcau cgagaagaac ggggaguuuu ucaugucccc caacgacuuc | 120 |
| gucacgaggu accugaacau cuucggcgag agccagccca ucccaagac cguggaacug | 180 |
| cuguccggcg uguggacca gaccaaggac gggcucaucu ccuuccagga guucguggcc | 240 |
| uucgaaagcg ugcugugugc ccccgaugcc cuguucaugg uggccuucca gcuguucgac | 300 |
| aaggccggca agggcgaggu gaccuucgag gacgugaagc aguguucgg ccagaccacg | 360 |
| auccaccagc acaucccguu caacugggac agugaguucg ugcagcugca cuucggcaaa | 420 |
| gagcggaagc gccaccugac cuacgccgag uucacccagu uccuccucga gauccaacug | 480 |
| gaacacgcca gcaggccuu cgugcagcgu gacaacgcca ggaccggccg ggugaccgcc | 540 |
| aucgauuuua gggacauaau ggugaccauc cgccccacg ugcugacccc cuucguggag | 600 |
| gagugccucg ucgccgcggc cggcggcacc accagccacc aggugagcuu cagcuacuuc | 660 |
| aacggcuuca auagccugcu gaacaacaug gagcugauac gaaaaaucua cagcaccug | 720 |
| gccgggacca ggaaggacgu ggaagugacc aaggaggagu cguccuggc cgcccagaag | 780 |
| uucggccaag ucaccccau ggaaguggac auccuuuucc agcuggccga ccuuacgag | 840 |
| ccccgaggcc ggaugacccu ggccgacauc gaacgcaucg cccccucga ggagggcacc | 900 |
| cugcccuuua accuggccga ggcgcagagg cagaaggccu caggagacag cgccaggccg | 960 |
| guguugcugc aggugccga aagcgccuac agguucggac ugggcuccgu ggccggcgcu | 1020 |
| gucgcgccca ccgccgugua ucccaucgau cuggugaaaa cccgaaugca gaaccaaagg | 1080 |
| uccaccggua gcuucguggg cgagcugaug uacaaaaaca gcuucgacug cuucaagaag | 1140 |
| gugcugcggu acgaaggcuu cuucggccug uaccggggcc ugcugcccca gcuccugggc | 1200 |
| gucgcccccg aaaaggcaau caagcugacc gugaacgacu cgugcgcga caaguucaug | 1260 |
| cacaaggacg gcuccgugcc ccucgccgcc gagauucugg ccgggggug cgccggcggc | 1320 |
| agccagguga ucuucaccaa cccccucgag aucgugaaaa ucaggcugca aguggccggc | 1380 |
| gagauaacca ccgggcccag ggugucccgc cugagcgucg ugcgagaccu gggguuuuc | 1440 |
| ggcauauaca agggcgccaa ggcgugcuuc cugagagaua uaccauucuc agccaucuac | 1500 |
| uuccccugcu acgccacgu aaaggccagc uucgccaacg aggauggcca ggugccccc | 1560 |
| ggcagccugc ugcucgccgg cgcuauagcc ggcaugcccg ccgccucccu gguuacccc | 1620 |

```
gccgacguca ucaaaaccag gcugcaaguu gccgcccggg ccggccagac cacguacagc    1680
ggcgugauug auugcuuccg caagauccug agggaagaag gcccaaagc ccuguggaag     1740 ggcgccgggg caagguguu ccgcagcucc ccccaguucg gcugacccu gcugaccuac      1800 gagcuccugc agcgcugguu uuacaucgac uucggcggcg ugaagcccau gggaagcgaa    1860
cccgugccca agagcaggau caaucugccg gcccccaacc ccgaccacgu gggggggua     1920 aagcuggcgc uggccaccuu cgccgggauc gagaacaagu ucggucucua ccuccccug     1980 uucaagcccu cggugagcac cagcaaggcg aucgggggcg gcccg                    2025
```

<210> SEQ ID NO 20
<211> LENGTH: 2025
<212> TYPE: RNA
<213> ORGANISM: Artificial Sequence
<220> FEATURE:
<223> OTHER INFORMATION: Citrin-CO16

<400> SEQUENCE: 20

```
auggccgccg ccaaggugc ccugaccaag agggccgauc ccgccgagcu gaggaccauc     60
uuccugaagu acgcuagcau cgagaagaac ggggaguucu ucaugagccc aaacgacuuu    120
guuacgaggu accuuaauau cuucggcgag agccaaccca aucccaagac cguggagcuc    180
cucagcgggg uggucgauca gacgaaggac ggccugauca gcuuucaaga guucgucgcc    240
uuugagagcg uccugugcgc ccccgacgcc cuauucaugg uggccuucca gcuguucgac    300
aaggccggca agggagaggu gaccuucgag gacgugaaac agguguuugg ucagaccacg    360
auccaccagc acaucccguu caacugggau uccgaguucg ugcagcugca cuucggcaag    420
gagaggaaga ggcaucugac guacgcugag uucacucaau uccugcugga gauccaacug    480
gagcacgcua agcaggccuu cgugcagcgc gacaacgccc gcaccgggcg cgugaccgcu    540
aucgacuucc gagacaucau ggugaccauc aggccgcacg ugcugacccc cuucgucgaa    600
gagugcuugg uggccgccgc cggcggaacc accagccauc aagugccuu cagcuacuuc     660 aacggcuuua acuccugcu caauaacaug gagcugauca ggaagaucua uccacccug      720 gccggcacga ggaaagaugu agaggugacc aaggaggagu cgugcucgc ggcccagaag     780 uuugggcagg ugacacccau ggaaguggac auccuguuuc aacuggccga ccuuacgag     840 cccaggggga ggaugacccu ggccgacauc gagaggaucc ccccccugga ggaggcacc     900 cugccguuca aucuggccga ggcacagagg cagaaggccu ccggcgauag cgccaggccc    960
guccugcugc aggugggccga gagcgcuuau agguucgggc uggggagcgu ggccggagcc   1020
gucggcgcca ccgccgugua ccccaucgac cuggucaaga ccaggaugca gaaccagagg    1080
agcaccggcu ccuuugugggg cgagcucaug uacaagaaca gcuucgacug cuucaagaag   1140
guacugcgcu acgagggcuu cuucggccug uacaggggc ugcuccccca gcugcugggg    1200
guggcgcccc agaaagccau caaacugacc gugaacgauu cgucaggga caaguucaug    1260 cacaaggacg ggagcgugcc acuggccgcc gagauucugg ccggcgguug cgccggggc   1320 ucccaaguga ucuucaccaa uccccuggag aucgucaaga uaaggcugca gguggccggc    1380
gaaauaacca cugggcccag ggugagcgcc cuguccgugg ugagggaccu gggcuucuuc   1440
ggcaucuaua agggcgccaa ggccugcuuc cugagggaca uccccuucag cgccaucuac    1500
uuccccugcu augcucacgu caaggcaagc uucgccaacg aagacgggca ggugagcccc   1560
gggagccucc uucuggccgg ggccaucgcc ggcaugcccg ccgccagccu ggucaccccg    1620
```

| | |
|---|---|
| gcggauguga ucaagaccag gcugcagguu gccgcccgag ccggccagac caccuacagc | 1680 |
| ggcgugaucg auuguuuucg gaagauccug agggaggagg gaccgaaggc acuguggaaa | 1740 |
| ggggccggug ccagagaguguu ccgauccagc ccgcaguuug gagugacccu gcucaccuac | 1800 |
| gagcugcuuc aacggugguu cuacaucgac uucggcggug ugaagccaau gggcagcgag | 1860 |
| cccgugccca agagccgcau uaaccugccc gccccaaacc ccgaccacgu gggcggcuac | 1920 |
| aaacuggccg uggccaccuu ugccggcauc gagaacaagu ucggccucua ucugccccug | 1980 |
| uucaagccca gcgugucgac cagcaaggcc aucggcggcg guccc | 2025 |

<210> SEQ ID NO 21
<211> LENGTH: 2025
<212> TYPE: RNA
<213> ORGANISM: Artificial Sequence
<220> FEATURE:
<223> OTHER INFORMATION: Citrin-CO17

<400> SEQUENCE: 21

| | |
|---|---|
| auggccgccg ccaaggaggc ccugacgaag agggccgacc ccgccgaacu ccggaccauc | 60 |
| uuucugaagu acgccagcau cgagaagaac ggagaguucu ucaugagccc caacgauuuu | 120 |
| gugacccggu aucugaauau cuucggcgaa ucccaaccca cccgaagac gguggagcug | 180 |
| cugagcggcg uggugaccac gaccaaagac gggcugaucu ccuuccagga guucguggcg | 240 |
| uuugagagcu acugugugc cccggacgcc cuguucaugg uggccuucca gcuguucgau | 300 |
| aaagccggca aaggcgaggu gacguucgaa gacgugaaac agguguucgg ccagaccacc | 360 |
| auucaccagc acauccccuu caacugggac agcgaguucu ccagcugca uuuuggcaag | 420 |
| gagcgcaaga ggcaccugac cuacgccgag uucacacaau uucuccugga gauccaacug | 480 |
| gagcacgcca agcaagccuu cgugcagagg gauaacgccc gaacaggccg ggugaccgcc | 540 |
| aucgauuuca gggacauaau ggugacaaua cgcccccacg ugcucacccc cuucguggag | 600 |
| gagugccuag uggccgccgc cggcgggacg accucccacc aagugagcuu cagcuacuuu | 660 |
| aacggcuuca cucccugcu gaauaacaug gaacugauaa ggaagaucua cagcacccua | 720 |
| gccggcaccc guaaggacgu ggaggugacc aaggaggagu cgugcuggc ugcccagaag | 780 |
| uucggccaag ugaccccccau ggaggugac auccuguucc agcucgcgga ucucuacgag | 840 |
| cccccggggcc ggaugacccu ggcggacauc gaaaggaucg cccauuaga ggagggcacc | 900 |
| cugcccuuca aucucgccga agcccagcgg cagaaggccu ccggcgacag cgcgcgcccu | 960 |
| gugcuguugc aggugccga gagccgccua gguucggcc ucgguccggu ggccggagcu | 1020 |
| gugggcgcca ccgccgucua cccaaucgac cuggugaaga ccaggaugca aaaucaaagg | 1080 |
| ucaaccggcu ccuuugugg gcgagcugau gucaagaacu ccuucgacug cuucaagaag | 1140 |
| gugcugaggu acgaaggauu cuucggccug uaccgcgggc ugcugcccca acugcucggc | 1200 |
| guggccccg agaaggccau caagcugacc gucaacgauu ucgugaggga caaguucaug | 1260 |
| cacaaggacg gcagcgugcc ccucgccgcc gagauacugg ccggcgguug cgccggcggc | 1320 |
| agccagguga ucuucaccaa cccccuggag aucgugaaga ucaggcugca aguggccggc | 1380 |
| gagaucacca ccggacccg cguguccgcc cugucagucg ugagggaccu ggggguucuuc | 1440 |
| ggaaucuaca agggcgcaaaa ggccugcuuc cugagggaca ucccguucag cgccaucuac | 1500 |
| uucccccugcu acgccacgu caaggccagc uucgccaaug aagacggcca ggucucgccc | 1560 |
| ggcagccugc ugcucgccgg cgccauagcc ggaaugccag ccgccucccu ggugaccccg | 1620 |
| gccgacguca ucaagaccag gcuccaggug gccgccagag ccggccagac caccuacagc | 1680 |

```
gggguguaucg acugcuucag gaagauccug cgggaggaag gccccaaggc ccucuggaag    1740
ggggccgggg cccggguguu caggagcagc ccacaguucg gcugacccu gcugaccuac     1800 gagcugcuac agcgguggu cuacaucgac uucggguggcg ugaagcccau gggcagcgag    1860
cccgugccca agagcaggau caaccugccc gcccccaauc cugaccaugu gggcggcuac    1920
aagcuggcag uggcuaccuu ugccggcauc gagaauaagu ucggccugua ucugccacug    1980
uucaagcccu ccgugagcac cucgaaggcc auaggcggcg guccc                    2025
```

<210> SEQ ID NO 22
<211> LENGTH: 2025
<212> TYPE: RNA
<213> ORGANISM: Artificial Sequence
<220> FEATURE:
<223> OTHER INFORMATION: Citrin-CO18

<400> SEQUENCE: 22

```
auggccgccg ccaaggugg ccugaccaag agagccgauc ccgccgagcu gcgcaccauc     60
uuccugaagu acgcaucaau cgagaagaac ggcgaguuuu caugagccc caacgacuuu    120 gugacgcgcu accugaacau cuucggcgag agucagccca ccccaaaaac gguggagcug    180
cugucaggcg ugguggacca gaccaaggac ggccugauca gcuuccagga guuuguggcc    240
uuugagagcg ugcuguguge ccccgacgcc cuguucaugg uggccuucca gcuguucgac    300
aaggcaggga agggcgaggu gaccuucgag gacgugaagc aggugucgg gcagaccacc    360 auccaccagc acaucccuu caacugggac uccgaguucg uccagcugca cuuuggcaag    420
gagaggaagc gccaccugac guacgccgag uuuacccagu uccugcugga gauccaacug    480
gagcacgcca gcaggccuu cgugcagagg gacaacgcca ggacaggccg ggugaccgcc    540
aucgacuuca gggacaucau ggugaccauc aggccccaug ugcugacccc guucgucgag    600
gagugccucg uggccgcugc cggggggacc accagccacc aggugagcu uaguuacuuc    660 aauggcuuua acucgcugcu gaacaacaug gagcugaucc ggaagauaua cagcacccug    720
gccggaaccc ggaaggacgu ggaagucacc aaagaggagu cgugcuggc cgcccagaag    780 uuuggccaag ugacgcccau ggaggucgac auccuguuuc agcuggccga ccauacgag    840 ccccgaggcc ggaugacccu ggccgacaua gaaaggauag cccccugga ggagggggacc    900 cuucccuuca aucuggccga ggcccagagg cagaaggcca cgcgcgauag cgccaggccc    960
gugcuacugc aggugccga gagugccuac cgguucggcc ugggcuccgu ggcaggcgcc    1020
gugggcgcca ccgccguguac cccgaucgac cuggugaaga ccaggaugca gaaccagcgg    1080
agcaccgggu ccuucguggg ggagcugaug uacaagaacu ccuucgacug uuuaagaaa    1140 gugcugcgcu acgagggggu uuucgggcug uaccgaggcc ugcugcccca gcuucucggc    1200
guggccccgg agaagcuau aaagcugacc gugaaugauu cgugaggga caaguucaug    1260 cacaaggacg gcagcguacc cucucgcgcc gagauccucg ccggcggcug ugcgggcggg    1320 agccaggugac ucuuuaccaa cccgcuggag auugugaaga uucggcugca ggugcggcc    1380 gaaauuacca ccggccccag gguauccggcc cugucccgugg ugagggaccu gggcuucuu    1440 ggcaucuaca aggggggccaa ggccugucuc ucagggauua ucccccucag cgccaucuac    1500 uucccccuccu acgccacgu gaaggccucc uuugccaacg aggacggcca ggugagcccc    1560
ggcagccugc uucuggccgg cgccaucgcc ggcaugccg ccgccagccu ggugacccccg    1620 gcggacguga ucaagacgcg ccugcaggug gcagcaaggg ccgggcagac caccuacagc    1680
```

| | |
|---|---|
| gggguugaucg auugcuucag gaagauccug agggaggaag gccccaaggc ccucuggaag | 1740 |
| ggggccggag ccagggguguu ccggagcucc ccgcaguucg gcugacccu gcugaccuau | 1800 |
| gagcuccugc agcggugguu cuacauagac uucggcggag ugaagccuau gggcagcgag | 1860 |
| cccgugccga aaagcaggau caaccugccc gccccgaacc ccgaccaugu cggcggcuac | 1920 |
| aagcuggcgg uggccaccuu cgcagggaua gagaauaagu uggccugua ccugcccc uc | 1980 |
| uucaagccca gcgugagcac cagcaaggcc auaggcggcg ggccc | 2025 |

<210> SEQ ID NO 23
<211> LENGTH: 2025
<212> TYPE: RNA
<213> ORGANISM: Artificial Sequence
<220> FEATURE:
<223> OTHER INFORMATION: Citrin-CO19

<400> SEQUENCE: 23

| | |
|---|---|
| auggccgccg ccaaggugc ucugaccaag agggcggacc ccgccgagcu gaggaccauc | 60 |
| uuccugaagu acgccucuau cgagaagaac ggcgaauucu caugucacc caacgacuuc | 120 |
| gugaccaggu accugaacau cuucggcgag agccaaccca accccaagac cguggagcug | 180 |
| cugagcggcg uggguggacca gacgaaggac ggccugauca gcuuccagga guucguggcc | 240 |
| uucgagagcg ugcucugcgc ccccgacgcc cuguucaugg uggccuucca gcuguucgac | 300 |
| aaggccggca agggcgaagu gaccuucgaa gacgugaagc agguguuugg ccagaccacc | 360 |
| auccaccagc acauccccuu caacugggac agcgaauucg uccagcugca cuucggcaag | 420 |
| gagcggaagc ggcaccucac cuacgccgag uucacccagu uccugcucga gauccagcug | 480 |
| gaacacgcca agcaagccuu cgugcaaagg gauaacgcca ggaccggcag ggucaccgcc | 540 |
| aucgacuucc gugacaucau ggucaccaua cgaccccacg ugcugacccc cuucgucgag | 600 |
| gagugucugg uggccgccgc agggggggacg accagccacc aaguaagcuu cagcuacuuc | 660 |
| aacggcuuca cagccugcu gaacaacaug gagcucauca gaaaaaucua cucuacccug | 720 |
| gccgggacca ggaaagacgu cgaagugacg aaggaggagu ucguccuggc cgcccagaag | 780 |
| uucggccagg ucaccccccau ggaggucgac auacuguucc agcuggccga ccucuaugaa | 840 |
| cccagggcca ggaugacccu ggccgauauc gaacgcaucg ccccccuagga ggagggggacc | 900 |
| uugccauuca aucuggccga ggccagcgg cagaaggcca cggcgacag cgccagaccc | 960 |
| gugcugcugc aggucgcgga gagcgccuac cguuucggcc ugggagcgu agcgggcgcc | 1020 |
| gugggggcca ccgccgugua ccccaucgau cuggugaaga ccaggaugca gaaccagcga | 1080 |
| uccaccggca gcuucugggg cgagcugaug uauaagaacu cauuugacug cuucaagaag | 1140 |
| gugcuucgau acgagggguu cuucggccug uaccgaggac ugcugcccca acugcugggc | 1200 |
| guggcccccgg agaaggcgau uaagcugacc gugaaugau ucgugcgcga caaauucaug | 1260 |
| cacaaggacg gcuccgugcc ccuggccgcc gaaauccugg ccggcgggug cgccgguggc | 1320 |
| ucccagguga uauucaccaa uccccucgaa ucguaaaaaa ucaggcugca gguggcgggg | 1380 |
| gagaucacca ccgggccgag ggugagcgcc cugucagugg uaagggaccu ggggguucuuc | 1440 |
| ggcaucuaca agggagccaa ggccugcuuc cugcgggaua ucccauucag cgccauuuau | 1500 |
| uucccccugcu acgccaugu gaaggccucc uucgccaacg aggacggcca agugagcccc | 1560 |
| ggcagccugc ucuggccgg ggccaucgcc ggcaugccg ccgccucgcu agugaccccc | 1620 |
| gccgauguca ucaagacccg gcugcaggug ccgccagggg ccggucagac gaccuacuca | 1680 |
| ggcgugaucg acugcuuuag gaaaauccug agggaggagg gccccaaagc gcuguggaag | 1740 |

```
ggcgcugggg cccgugucuu caggaccucc ccccaguucg gagugacccu gcucacguac    1800
gaacugcugc agaggugguu uuacaucgac uucggcggcg ugaagcccau ggcagcgag     1860 cccgugccca aaagcaggau caaccucccg gcgcccaacc ccgaccaugu gggggcuac     1920 aaacuggcgu uggccacguu cgcgggcauc gagaacaagu cgggcugua ccugcccug      1980 uucaaaccca gcgugagcac cagcaaggcc aucggcggcg gucca                   2025
```

<210> SEQ ID NO 24
<211> LENGTH: 2025
<212> TYPE: RNA
<213> ORGANISM: Artificial Sequence
<220> FEATURE:
<223> OTHER INFORMATION: Citrin-CO20

<400> SEQUENCE: 24

```
auggccgccg ccaaggucgc ccucaccaaa agggccgacc cggccgagcu ccggaccauu     60
uuccucaagu acgccagcau cgaaaagaac ggcgaguucu ucaugagccc caacgacuuc    120
guaacaaggu accucaacau cuucggugag agccagccca accccaagac cguggagcuc    180
cucagcggcg uggucgauca gaccaaggau ggccugauca gcuuucaaga guucguggcc    240
uucgagagcg uauugugcgc ccccgacgcg cuguuuaugg uggccuuuca gcuguucgac    300
aaagccggca aggcgaggu gacauucgag gacgugaagc aaguguucgg ccaaaccacc    360
auccaccaac acauccccuu caacugggac uccgaguucg ugcagcugca cuucgguaag    420
gagcggaagc gccaucugac uuacgccgag uucacgcaau uccuccgga gauccagcug     480 gagcacgcca agcaggccuu ugugcaacga gacaacgcca ggaccgguag ggucaccgcc    540
aucgauuucc gggacaucau gguaacgaua cggccccacg ugcugacgcc guuuguggaa    600
gaguguuaua aagccgcggc cggcggcacc accucgcacc aggucagcuu cagcuacuuc    660 aauggccuuca uagccugcu caacaacaug gagcugauca ggaagaucua uagcacccuc    720
gccggcacca ggaaggacgu ggaagugacc aaggaagagu cgugcuggc cgcgcagaag    780 uucggccagg ugaccccau ggaagucgac auccuguucc agcuggccga ccuuacagag    840
cccccgggga ggaugacccu ggcggacauc gagagguac ccccccugg ggagggacc     900 cugccguuca accuggcaga ggcccagagg caaaaggcca gcgggacag cgcccggccc   960 gugcugcugc aagguggcga gagcgccuac cgauucggcc uugggagcgu cgccggccgc  1020
gugggggcga ccgccgugua ucccaucgac cuggugaaaa cccgaaugca gaaccagcgg   1080
agcaccggau ccuuuguggg cgagcugaug uacaagaaca gcuucgacug cuucaagaag   1140
guccugcgcu augagggcuu cuucggccug uacagagggc ugcugcccca gcuccggggg   1200
guggcccccg aaaagccau caagcugacc gucaacgacu uugugaggga uaaguuuaug   1260
cacaaagacg gcagcgugcc ccucgccgcc gagauccugg ccggaggcug cgccggaggu    1320 agccaggua ucuuccaccaa uccccuggag auagugaaaaa uccggcugca gguggccggc   1380
gaaaucacca ccgccccag ggugucgcc cugucccgggg ugcgcgaccu gggcuucuuc    1440
ggcaucuaua agggcccaa ggcgugcuuc cucaggaca uccauucag cgccauauau     1500 ucccccugcu acgccacgu gaaggccucc uucgccaaacg aggacggcca ggugagcccc    1560
ggcucgcugc ugcuggccgg agccaucgcc ggcaugccg ccgcucacu ggugacccc      1620 gcggacguga uaagacccg gcugcaggug ccgcgaggg ccggacagac caccuacucc     1680
ggggucaucg acugcuucag gaagauccuc cggggaggagg gccccaaggc ccugugggaaa 1740
```

| | |
|---|---|
| ggagcgggcg ccagggguguu ucgaagcagc ccccaguucg gcgugacccu ccugaccuac | 1800 |
| gagcugcucc agaggugguu cuacaucgac uucgggggcg ugaagcccau gggcuccgag | 1860 |
| cccgugccca agagcaggau uaaccugccg gcccccaacc cagaccacgu cggcggcuac | 1920 |
| aagcuggccg uggccaccuu ugcaggcauc gaaaacaagu uggccucua ccuucccccug | 1980 |
| uuuaaaccca gcgugagcac aagcaaggcc auugggggggg gaccg | 2025 |

<210> SEQ ID NO 25
<211> LENGTH: 2025
<212> TYPE: RNA
<213> ORGANISM: Artificial Sequence
<220> FEATURE:
<223> OTHER INFORMATION: Citrin-CO21

<400> SEQUENCE: 25

| | |
|---|---|
| auggccgccg ccaaagugg ccugacgaag agggcagacc ccgccgagcu gaggaccauc | 60 |
| uuucugaagu acgcaagcau cgagaagaac ggcgaguucu ucaugagccc caacgacuuc | 120 |
| gugaccaggu accuuaauau cuucggcgag agccagccca accccaaaac gguggagcug | 180 |
| cucagcgggg uggucgacca gaccaaagac ggacugauca gcuuccagga guucguggcc | 240 |
| uucgagucccg ugcugugcgc cccagaugcc cuguucaugg uggccuucca acucuucgac | 300 |
| aaggccggga agggcgaagu gaccuucgaa gacgugaagc aggguucgg gcaaacaacg | 360 |
| auccaccagc auauccccuu caacuggac ucggaguucu gcagcugca uucggcaaa | 420 |
| gagaggaagc gccaucuaac uuacgccgag uucacccagu uccugcugga aauccagcug | 480 |
| gagcaugcca agcaggccuu cguccagcgc gauaacgccc gaaccggccg cgugaccgcc | 540 |
| auugacuuca gggacaucau ggugaccauc cgccccacg ugcugacccc cuuugucgag | 600 |
| gagugccugg uggccgccgc cgggggggacg accucccacc aggucagcuu uccuauuuc | 660 |
| aacggcuuca acagccugcu gaacaauaug gagcugauca ggaagaucua cagcacccuc | 720 |
| gccggcaccc gcaaggaugu ggaggugaca aaggaggagu cgugcuggc cgcccaaaag | 780 |
| uucggucagg ugaccccgau ggaggggaac auccucuucc aacuggccga ccuguacgag | 840 |
| ccccgugggcc gcaugacccu cgccgauauc gagaggaucg ccccccugga ggaggcacc | 900 |
| cugcccuuca aucuggccga ggccagcgg cagaaggcgu ccggcgauag cgcgcgccca | 960 |
| guccuccucc aggucgccga gucggcauac cguuucggcc ucggaagcgu ggccggcgcc | 1020 |
| gugggguccaa ccgccgugua ccccaucgac cuggugaaga ccaggaugca gaaccagagg | 1080 |
| agcaccggaa gcuucuggg ggagcugaug uacaagaaca gcuuugacug cuucaaaaag | 1140 |
| gugcugcgau acgagggauu uuuggccuc uacagggggcc ugcugcccca gcugcuggga | 1200 |
| gucgccccg agaaggccau caagcugacc gugaacgacu cgugaggga caaguucaug | 1260 |
| cauaaggacg gcuccgucccc ccuggccgcc gagauccugg cagggggggug cgccggcggc | 1320 |
| ucccaggucaa ucuuuaccaa ccccuggag aucgugaaga uaaggcugca gguggccggc | 1380 |
| gaaaucacca ccgggcccag ggucagcgcc cugagcgugg ugcgggaccu gggcuuuuu | 1440 |
| ggcaucuaca aaggcgccaa ggccugcuuc cugcgagaca uccccuucuc agccaucuac | 1500 |
| uuccccugcu acgccaugu gaaggccagu uucgccaaug aggacggcca ggugucccca | 1560 |
| ggcagccuuc ugcucgccgg cgccaucgcc ggcaugcccg ccgcucccu ggugacccccg | 1620 |
| gcggacguga ucaagaccag gcugcaggug gccgccaggg cuggucagac gaccuacagc | 1680 |
| ggcgugaucg acugcuucag gaagauccuc agggaggagg ccccaaaagc ccuguggaag | 1740 |
| ggcgcaggcg ccagagugu caggagcagc ccccaguucg ggugacccu gcucaccuac | 1800 |

```
gagcugcugc agaggugguu cuacaucgac uucggcggug ugaaacccau gggcagcgaa   1860
cccguaccca aaagccggau caaccugccc gcccccaauc ccgaccacgu gggggggguac   1920 aagcucgccg uggccacauu cgcggggauc gagaacaagu cgggcucua ccugccccug   1980 uuuaaaccga gcgugagcac gagcaaggcc aucggcgggg ggccc                    2025

<210> SEQ ID NO 26
<211> LENGTH: 2025
<212> TYPE: RNA
<213> ORGANISM: Artificial Sequence
<220> FEATURE:
<223> OTHER INFORMATION: Citrin-CO22

<400> SEQUENCE: 26
auggccgccg ccaaagucgc ccugacgaag agggcggauc ccgccgagcu caggacaauc     60
uuccugaagu acgcguccau cgagaagaac ggggaguucu caugucccc caacgacuuc    120 gugaccaggu accuaaacau cuuccggcga guccagccca accccaagac cguggagcug    180
cuguccggag ugguggacca gaccaaggac ggccugauca gcuuccaaga auucgucgcc    240
uuugagagcg ugcugugcgc cccggacgcc cguucauggu ggccuucca gcuguucgac    300 aaagccggua agggcgaggu gaccuucgag gaugugaagc aggugu ucgg gcagaccaca   360 auccaccaac acaucccguu caauuggac agcgaguuug cgcagcugca cuucgguaag    420
gagcggaagc gucaucugac guacgcggag uucacccagu ccugcugga gauccagcug    480 gagcaugcca agcaggccuu cgugcagagg acaacgccc ggacaggcag ggugacugcg    540
auugacuucc gagauaucau ggugaccauc aggccacacg uccugacccc cuucguggag    600
gagugucucg ucgccgccgc ggguggcacg accagccacc aggucagcuu cagcuacuuc    660
aacggcuuca acucacugcu gaacaacaug gaguugauuc ggaaaaucua cagcacccug    720
gccggcacca ggaaggaugu cgaagucacc aaggaggagu cgucgcuggc cgcccagaag    780
uucggccagg ugaccccaau ggagguggau auccuguucc agcuggccga ccucuacgag    840 ccccgggaa ggaugacccu ggccgauauc gagcgcaucg cccccggga gagggcacc     900 cugccauuca accuggccga ggccagcgu cagaaggcca gcgggauuc agccaggccc     960 guacugcugc aggugccga gagcgccuac cgguucggcc ugggcuccgu ggccggcgcc    1020
gugggcgcca ccgccguuua cccgaucgac cucgugaaga cccggaugca gaaccaacgc    1080
ucgaccggca gcuuuggg cgagcugaug uacaagaaca gcuugacug cuucaagaaa    1140 gugcugaggu acgagggcuu uuuuggccug uaccgggcc ugcugcccca cuccugggc    1200 guggcccccg agaaggccau caagcugacc gugaacgacu cguccggga caaguucaug    1260 cacaaggacg ggccgucccc ccuggcgcc gagauccugg ccggggcug ugccggcggc    1320 ucccagguga ucuucaccaa ccccugagg aucgucaaga ucaggcugca gguggcaggc    1380
gagaucacca ccggccgcgc agucagcgcc uugagcgugg caggaucu gggcuucuuc    1440 gguaucuaca aaggcgccaa ggcgugcuuc ucccgggaua ucccguucuc cgccaucuau    1500
uuucccugcu acgcccacgu gaaggcuagc uucgccaacg aggacgggca agucagcccc    1560
ggcagccucc uccuggccgg agccaucgcc gggaugcccg ccgccagccu ggugacccc    1620 gccgacguga ucaagacgag gcuccaggug gccgccaggg ccgggcagac gacguacucc    1680
ggcgugaucg acugcuuccg caagauucug agggaggagg gccccaaagc ccuguggaag    1740
ggggccggcg cccggggguu ccggagcucc ccgcaguucg gggugacccu ccugaccuac    1800
```

| | |
|---|---:|
| gaacugcugc agcggugguu cuacaucgac uucggcggag ugaagcccau ggguagcgag | 1860 |
| ccugugccca aaagcagaau caaccuccce gcccccaacc ccgaccacgu cgggggcuac | 1920 |
| aagcucgccg uggcgaccuu cgccggcauc gaaaacaagu ucggcucuca ccucccccug | 1980 |
| uucaagccau ccgucagcac cagcaaagcc aucgggggag ccccc | 2025 |

```
<210> SEQ ID NO 27
<211> LENGTH: 2025
<212> TYPE: RNA
<213> ORGANISM: Artificial Sequence
<220> FEATURE:
<223> OTHER INFORMATION: Citrin-CO23

<400> SEQUENCE: 27
```

| | |
|---|---:|
| auggccgccg ccaaggucgc ccugaccaaa cgggccgacc ccgccgaacu gcggaccauc | 60 |
| uuccucaagu acgccagcau cgaaaagaac ggcgaauucu caugucccc caacgacuuc | 120 |
| gucaccaggu accugaacau cuucggcgaa ucccaaccca accccaagac cguggagcug | 180 |
| cugagcggcg uggucgacca gacaaaggau ggcucaucu ccuuucagga guucgucgcc | 240 |
| uucgaaagcg ugcugugcgc ccccgacgcc cuguucaugg uggccuucca gcuguucgac | 300 |
| aaggccggga agggcgaggu gaccuuugag gacgugaagc aggugUUugg gcagaccacg | 360 |
| auccaccagc acaucccauu uaacuGggac agcgaguucg ugcagcugca cuucggcaag | 420 |
| gaacgcaagc gccaccugac guacgcgag uuuacucagu uccugcugga gauccagcug | 480 |
| gaacacgcca agcaggccuu cgugcagagg gauaaugcgc gcaccggaag ggucaccgcc | 540 |
| aucgacuuca gggacaucau ggugaccauc aggcccacg uccugacccc cuucguagag | 600 |
| gagugucugg uggccgccgc cggcgggacc acgucccacc agguuagcuu uccuacuuc | 660 |
| aacggcuuca acucccugcu gaacaacaug gagcugauca ggaagaucua uagcacccug | 720 |
| gcuggcacca ggaaggacgu cgaggucacc aaggaggaau cgugcucgc cgcccagaag | 780 |
| uucgggcaag ugacccccau ggaggUGgac auacuguucc agcuggccga ucuguaugag | 840 |
| ccgcggggca ggaugacccu ggccgacauu gagcgaaucg ccccccugga ggagggcacc | 900 |
| cugcccuuua accuggccga ggcccaaagg cagaaggcca gcgggacag cgcaagaccg | 960 |
| guccugcugc aggugGccga aagcgccuac cgguucggcc ugggcagcgu ggccggagcc | 1020 |
| gucggcgcca ccgccgugua ccccaucgac cuggugaaaa cacgaugca gaaccagagg | 1080 |
| agcaccggca gcuucugggg cgagcugaug uauaagaaca gcuuugacug cuucaagaag | 1140 |
| guccugaggu acgagggcuu cucgggcuc uacagaggcc ugcucccca gcuccugggg | 1200 |
| gucgcccccg agaaagcaau caagcugacc gugaacgacu uugucaggga caaguucaug | 1260 |
| cacaaggacg gcuccgugcc ccucgccgcc gagauccugg ccggcggaug cgcgggggga | 1320 |
| agccagguga ucuuuacgaa ccccccucgag aucgucaaga uuaggcugca gguggccggg | 1380 |
| gagaucacca ccgggcccag gGUgagcgcc cugagcgugg ugcgcgaucu cggcuucuuc | 1440 |
| ggcaucuaca agggagccaa ggccugcuuc cugagggaca uccccuucag cgccaucuac | 1500 |
| uucccgUGUU acgccacgu gaaggccucg uucgccaacg aggacggcca ggugagcccc | 1560 |
| ggucgcucc uccuggcggg agccauagcc ggcaugccg ccgcucccu ggugacccca | 1620 |
| gcggacguga ucaagacccg gcuccagguG ccgccaggg ccgggcagac cacguauagc | 1680 |
| ggcgugaucg acugcuuccg aaaaauccug agggaggagg ccccaaggc ccuguggaaa | 1740 |
| ggcgcggggg ccagguGUu ccgcuccucc ccccaguucg ggugacgcu gcugacuuac | 1800 |
| gaguugcugc agaggUGGUU cuacaucgac uuuggcggcg ugaagcccau ggggagcgag | 1860 |

```
ccggugccca agagccggau caaccuccca gcccccaacc ccgaccacgu gggcggauac    1920
aagcuggccg uggccaccuu ugccggcauc gaaaacaagu ucggccucua ccucccgcug    1980
uucaagccca gcguguccac gagcaaggcc aucggcgggg ccccc                   2025
```

<210> SEQ ID NO 28
<211> LENGTH: 2025
<212> TYPE: RNA
<213> ORGANISM: Artificial Sequence
<220> FEATURE:
<223> OTHER INFORMATION: Citrin-CO24

<400> SEQUENCE: 28

```
auggccgccg ccaaagucgc ccugacaaag cgcgccgacc ccgccgagcu gcggaccauc      60
uuucugaagu acgccuccau cgagaagaac ggcgaguuuu ucaugagccc caacgacuuc     120
gugacccgcu accugaacau cuucggcgag agccaaccaa accccaagac cguggagcug     180
cugucuggug uggucgacca gaccaaggau ggccugauau cguuccagga guucguggcc     240
uucgagagcg uccugugcgc ccccgacgcc cuguucaugg uggccuucca gcuguucgac     300
aaagccggca agggcgaggu gaccuucgag gacgucaaac aggucuucgg ccagaccacc     360
auccaccaac acauaccguu caacugggau uccgaguucg uccagcuuca uucggaag       420 gaaaggaaga ggcaccugac cuaugccgag uuuacccagu uccuguugga gauccagcug     480
gagcacgcga agcaggccuu cgugcaacgg acaacgcccc ggaccgggag ggugaccgcc     540
aucgacuuca gagacauaau ggucaccauc aggccgcacg ugcucacccc cuucguggag     600
gaaugccugg uggccgccgc cggcgguacc accucccacc aggucagcuu cagcuacuuu     660
aacggcuuca cagccugcu gaacaacaug gagcugaucc gaaagauuua cagcaccug     720 gccggcacgc ggaaggacgu ggaagugacc aaggaggagu uguacuggc cgcccagaag     780 uucggccagg ugacgcccau ggagguggac aucuuauucc agcuggcgga uuuauacgag    840
ccccggggga ggaugacccu ggccgauauc gagaggaucg ccccccugga gagggcacc    900 cugcccuuca accuugccga ggcccagcgg caaaaagcua gcggcgacag ugcaaggccc    960
gugcugcugc agguggcgga gagcgccuac cgcuucggcc ugggcagcgu ggccggcgcc   1020
gucggagcca ccgccgugua ucccaucgac cuggucaaga ccaggaugca gaaccagcgg   1080
agcaccggca gcuucugggg ggaacugaug uacaagaaca gcuuugacug cuucaagaag   1140
gugcugaggu acgaagggu uuugggcug uacagagggc ugcugcccca gcugcugggu   1200
guggcccccg agaaggcaau caagcugacc gugaacgacu cgugaggga caaguucaug   1260 cacaaggacg gaucagugcc acuggccgcc gagauacugg ccggcggcug ugccgggggc   1320
agccaaguga ucuuccaccaa cccccuggag aucgugaaga uccgccugca ggucgccggc   1380
gagaucacca ccgggccuag ggugucccgcc cugagcgugg ugagggaccu gggcuucuuu   1440
gggaucuaua agggcgccaa ggccugcuuc cugcgcgaca ucccauucuc ugccauauac   1500
uucccuggcu acgccacgu gaaagccagc uucgccaacg aagacggcca ggugagcccc   1560 ggaagccuc ugcuggccgg cgccaucgcc ggaugcccg ccgccucccu ggugaccccg   1620
gccgacguga ucaagaccag gcugcagguc gccgcccgag ccgggcagac caccuauucc   1680
ggcgugauag acugcuuccg caagauccuc gagaggaag ucccaaggc ccugugaag   1740 ggcgccgggg cccggguguu caggagcccc ccgcaguucg gcgugacccu gcucaccuac   1800
gagcugcugc aaagguggu cuauaucgau uucggcggcg ugaagccgau gggcuccgag   1860
```

| | |
|---|---|
| cccgugccca agagccggau caaccugccc gcccccaacc ccgaccacgu aggcggcuau | 1920 |
| aagcuggcag uggcaaccuu cgccgggauc gaaaacaaau ucggccugua ccuccccccug | 1980 |
| uucaaaccca gcgugagcac gagcaaggcc aucggcggag gcccc | 2025 |

<210> SEQ ID NO 29
<211> LENGTH: 2025
<212> TYPE: RNA
<213> ORGANISM: Artificial Sequence
<220> FEATURE:
<223> OTHER INFORMATION: Citrin-CO25

<400> SEQUENCE: 29

| | |
|---|---|
| auggccgccg ccaaggucgc ccugaccaaa agggccgacc ccgccgagcu gcgaaccauc | 60 |
| uuccugaaau acgccagcau agagaagaac ggcgaguucu caugagcccc gaacgacuuc | 120 |
| gugacgcggu accugaacau cuucggggag agccagccca ccccaagac cguggagcug | 180 |
| cugagcggcg uggugaauca gaccaaggac gggcugauca guuccaaga guucguggcc | 240 |
| uucgagagcg ugcugcgc ccccgacgcc cuguucaugg uggcuuucca gcuguucgac | 300 |
| aaggccggga aggggaggu gacauucgag gacgugaagc agguguucgg gcagaccacg | 360 |
| auccaccagc acaucccccuu caacugggac uccgaauuug ugcagcugca uucggcaag | 420 |
| gagcggaaga ggcaccugac cuacgccgaa uucacccagu ccugcuggaa gauccagcug | 480 |
| gaacacgcca gcaggcauu cgugcagcgc gacaacgccc gcaccgguag ggugaccgcc | 540 |
| aucgacuucc gggacaucau ggugaccauc cggccgcacg ugcugacccc cuucguggag | 600 |
| gaaugccugg uggccgccgc cggcggcacc accagccacc aagugagcuu cagcuauuuc | 660 |
| aacggcuuca acagccugcu caacaauaug gagcugauca ggaaaaucua cagcacccug | 720 |
| gccgggacca ggaaggaugu ggaggugacc aaagaggaau uugugcucgc cgcccaaaag | 780 |
| ucggccagg ucaccccau ggaagucgac auccuguuuc agcuugccga ccucaugag | 840 |
| cccaggggga gaaugacccu ggccgacauc gagaggaucg cucccgga ggagggaaca | 900 |
| cugccguuca accuggccga ggcccagagg cagaaggcca gcggugacuc cgccaggccc | 960 |
| guacugcugc aagugcgga guccgccuau agguucgggc ugggcagcgu ggccggggcc | 1020 |
| gugggggcca ccgcggugua cccaauagac cuggugaaaa cccggaugca aaaccagagg | 1080 |
| agcacgggua gcuucguggg ggagcugaug uauaagaaua gcuucgauug cuucaagaag | 1140 |
| guccuccggu acgagggauu cuucggccug uaccggggcc ugcugcccca gcugcugggu | 1200 |
| gucgccccg agaaggccau aaagcugacc gugaacgauu cgugcggga caaguucaug | 1260 |
| cacaaggacg gcucggugcc ccuggccgcc gaaauacugg cgggcggggu ugccggcggg | 1320 |
| ucccagguga ucuucaccaa cccgcuggag aucgugaaga ccgucugca gguggccggc | 1380 |
| gagaucacca ccggccccag aguguccgcg cugagcgucg ugcgugaccu gggcuucuuc | 1440 |
| gggaucuaca agggagccaa agccugcuuu cugagggaca uccccuucuc cgccaucuac | 1500 |
| uuccccuguu acgccacgu uaaggccucc uuugccaacg aggacggcca ggugagcccc | 1560 |
| ggguucccugc ugcucgcagg cgccaucgcc ggcaugcccg ccgccagccu ggugaccccg | 1620 |
| gccgacguga ucaagacgag gcuccagguc gccgccaggu cggggcagac uaccuacagc | 1680 |
| ggcguuaucg acugcuuuag gaagauccug agggaggagg ggcccaaggc ccucuggaag | 1740 |
| ggcgccggag ccaggguguu caggagcagc cccaguuug ggguaacgcu ccugaccuac | 1800 |
| gagcugcugc agagguggu uuacaucgau uucggggcg ucaagcccau ggggucegag | 1860 |
| cccgugccca agagcaggau caaucugccc gcccccaauc ccgaccacgu ggggggcuac | 1920 |

```
aagcuggccg uggccacguu cgccgguauc gagaacaagu ucgggcugua ccugccccug    1980
uucaagcccu ccguauccac cagcaaggcg auaggagggg gaccc                   2025
```

<210> SEQ ID NO 30
<211> LENGTH: 47
<212> TYPE: RNA
<213> ORGANISM: Artificial Sequence
<220> FEATURE:
<223> OTHER INFORMATION: (5' UTR)

<400> SEQUENCE: 30

```
gggaaauaag agagaaaaga agaguaagaa gaaauauaag agccacc                   47
```

<210> SEQ ID NO 31
<211> LENGTH: 47
<212> TYPE: RNA
<213> ORGANISM: Artificial Sequence
<220> FEATURE:
<223> OTHER INFORMATION: 5'UTR-002

<400> SEQUENCE: 31

```
gggagaucag agagaaaaga agaguaagaa gaaauauaag agccacc                   47
```

<210> SEQ ID NO 32
<211> LENGTH: 145
<212> TYPE: RNA
<213> ORGANISM: Artificial Sequence
<220> FEATURE:
<223> OTHER INFORMATION: 5'UTR-003

<400> SEQUENCE: 32

```
ggaauaaaag ucucaacaca acauauacaa aacaaacgaa ucuaagcaa ucaagcauuc     60 uacuucuauu gcagcaauuu aaaucauuuc uuuuaaagca aaagcaauuu ucugaaaauu    120
uucaccauuu acgaacgaua gcaac                                          145
```

<210> SEQ ID NO 33
<211> LENGTH: 42
<212> TYPE: RNA
<213> ORGANISM: Artificial Sequence
<220> FEATURE:
<223> OTHER INFORMATION: 5'UTR-004

<400> SEQUENCE: 33

```
gggagacaag cuuggcauuc cgguacuguu gguaaagcca cc                       42
```

<210> SEQ ID NO 34
<211> LENGTH: 47
<212> TYPE: RNA
<213> ORGANISM: Artificial Sequence
<220> FEATURE:
<223> OTHER INFORMATION: 5'UTR-005

<400> SEQUENCE: 34

```
gggagaucag agagaaaaga agaguaagaa gaaauauaag agccacc                   47
```

<210> SEQ ID NO 35
<211> LENGTH: 145
<212> TYPE: RNA
<213> ORGANISM: Artificial Sequence
<220> FEATURE:
<223> OTHER INFORMATION: 5'UTR-006

<400> SEQUENCE: 35

```
ggaauaaaag ucucaacaca acauauacaa aacaaacgaa ucucaagcaa ucaagcauuc        60
uacuucuauu gcagcaauuu aaaucauuuc uuuuaaagca aaagcaauuu ucugaaaauu       120
uucaccauuu acgaacgaua gcaac                                            145
```

```
<210> SEQ ID NO 36
<211> LENGTH: 42
<212> TYPE: RNA
<213> ORGANISM: Artificial Sequence
<220> FEATURE:
<223> OTHER INFORMATION: 5'UTR-007

<400> SEQUENCE: 36
gggagacaag cuuggcauuc cgguacuguu gguaaagcca cc                          42
```

```
<210> SEQ ID NO 37
<211> LENGTH: 47
<212> TYPE: RNA
<213> ORGANISM: Artificial Sequence
<220> FEATURE:
<223> OTHER INFORMATION: 5'UTR-008

<400> SEQUENCE: 37
gggaauuaac agagaaaaga agaguaagaa gaaauauaag agccacc                     47
```

```
<210> SEQ ID NO 38
<211> LENGTH: 47
<212> TYPE: RNA
<213> ORGANISM: Artificial Sequence
<220> FEATURE:
<223> OTHER INFORMATION: 5'UTR-009

<400> SEQUENCE: 38
gggaaauuag acagaaaaga agaguaagaa gaaauauaag agccacc                     47
```

```
<210> SEQ ID NO 39
<211> LENGTH: 47
<212> TYPE: RNA
<213> ORGANISM: Artificial Sequence
<220> FEATURE:
<223> OTHER INFORMATION: 5'UTR-010

<400> SEQUENCE: 39
gggaaauaag agaguaaaga acaguaagaa gaaauauaag agccacc                     47
```

```
<210> SEQ ID NO 40
<211> LENGTH: 47
<212> TYPE: RNA
<213> ORGANISM: Artificial Sequence
<220> FEATURE:
<223> OTHER INFORMATION: 5'UTR-011

<400> SEQUENCE: 40
gggaaaaaag agagaaaaga agacuaagaa gaaauauaag agccacc                     47
```

```
<210> SEQ ID NO 41
<211> LENGTH: 47
<212> TYPE: RNA
<213> ORGANISM: Artificial Sequence
<220> FEATURE:
<223> OTHER INFORMATION: 5'UTR-012

<400> SEQUENCE: 41
gggaaauaag agagaaaaga agaguaagaa gauauauaag agccacc                     47
```

```
<210> SEQ ID NO 42
<211> LENGTH: 47
<212> TYPE: RNA
<213> ORGANISM: Artificial Sequence
<220> FEATURE:
<223> OTHER INFORMATION: 5'UTR-013

<400> SEQUENCE: 42
gggaaauaag agacaaaaca agaguaagaa gaaauauaag agccacc          47

<210> SEQ ID NO 43
<211> LENGTH: 47
<212> TYPE: RNA
<213> ORGANISM: Artificial Sequence
<220> FEATURE:
<223> OTHER INFORMATION: 5'UTR-014

<400> SEQUENCE: 43
gggaaauuag agaguaaaga acaguaagua gaauuaaaag agccacc          47

<210> SEQ ID NO 44
<211> LENGTH: 47
<212> TYPE: RNA
<213> ORGANISM: Artificial Sequence
<220> FEATURE:
<223> OTHER INFORMATION: 5'UTR-15

<400> SEQUENCE: 44
gggaaauaag agagaauaga agaguaagaa gaaauauaag agccacc          47

<210> SEQ ID NO 45
<211> LENGTH: 47
<212> TYPE: RNA
<213> ORGANISM: Artificial Sequence
<220> FEATURE:
<223> OTHER INFORMATION: 5'UTR-016

<400> SEQUENCE: 45
gggaaauaag agagaaaaga agaguaagaa gaaaauuaag agccacc          47

<210> SEQ ID NO 46
<211> LENGTH: 47
<212> TYPE: RNA
<213> ORGANISM: Artificial Sequence
<220> FEATURE:
<223> OTHER INFORMATION: 5'UTR-017

<400> SEQUENCE: 46
gggaaauaag agagaaaaga agaguaagaa gaaauuuaag agccacc          47

<210> SEQ ID NO 47
<211> LENGTH: 92
<212> TYPE: RNA
<213> ORGANISM: Artificial Sequence
<220> FEATURE:
<223> OTHER INFORMATION: 5'UTR-018

<400> SEQUENCE: 47
ucaagcuuuu ggacccucgu acagaagcua auacgacuca cuauagggaa auaagagaga          60
aaagaagagu aagaagaaau auaagagcca cc                                        92

<210> SEQ ID NO 48
<211> LENGTH: 142
<212> TYPE: RNA
<213> ORGANISM: Artificial Sequence
<220> FEATURE:
```

<223> OTHER INFORMATION: 3'UTR including miR142-3p binding site

<400> SEQUENCE: 48

```
ugauaauagu ccauaaagua ggaaacacua cagcuggagc cucgguggcc augcuucuug    60
ccccuugggc cuccccccag ccccuccucc ccuuccugca cccguacccc cguggucuuu   120
gaauaaaguc ugagugggcg gc                                            142
```

<210> SEQ ID NO 49
<211> LENGTH: 142
<212> TYPE: RNA
<213> ORGANISM: Artificial Sequence
<220> FEATURE:
<223> OTHER INFORMATION: 3'UTR including miR142-3p binding site

<400> SEQUENCE: 49

```
ugauaauagg cuggagccuc gguggcucca uaaaguagga aacacuacac augcuucuug    60
ccccuugggc cuccccccag ccccuccucc ccuuccugca cccguacccc cguggucuuu   120
gaauaaaguc ugagugggcg gc                                            142
```

<210> SEQ ID NO 50
<211> LENGTH: 142
<212> TYPE: RNA
<213> ORGANISM: Artificial Sequence
<220> FEATURE:
<223> OTHER INFORMATION: 3'UTR including miR142-3p binding site

<400> SEQUENCE: 50

```
ugauaauagg cuggagccuc gguggccaug cuucuugccc cuuccauaaa guaggaaaca    60
cuacaugggc cuccccccag ccccuccucc ccuuccugca cccguacccc cguggucuuu   120
gaauaaaguc ugagugggcg gc                                            142
```

<210> SEQ ID NO 51
<211> LENGTH: 142
<212> TYPE: RNA
<213> ORGANISM: Artificial Sequence
<220> FEATURE:
<223> OTHER INFORMATION: 3'UTR including miR142-3p binding site

<400> SEQUENCE: 51

```
ugauaauagg cuggagccuc gguggccaug cuucuugccc cuuggccuc ccccagucc     60
auaaaguagg aaacacuaca ccccuccucc ccuuccugca cccguacccc cguggucuuu   120
gaauaaaguc ugagugggcg gc                                            142
```

<210> SEQ ID NO 52
<211> LENGTH: 142
<212> TYPE: RNA
<213> ORGANISM: Artificial Sequence
<220> FEATURE:
<223> OTHER INFORMATION: 3'UTR including miR142-3p binding site

<400> SEQUENCE: 52

```
ugauaauagg cuggagccuc gguggccaug cuucuugccc cuuggccuc ccccagccc     60
cuccucccu ucuccauaaa guaggaaaca cuacacugca cccguacccc cguggucuuu   120
gaauaaaguc ugagugggcg gc                                            142
```

<210> SEQ ID NO 53
<211> LENGTH: 142
<212> TYPE: RNA
<213> ORGANISM: Artificial Sequence

```
<220> FEATURE:
<223> OTHER INFORMATION: 3'UTR including miR142-3p binding site

<400> SEQUENCE: 53
ugauaauagg cuggagccuc gguggccaug cuucuugccc cuugggccuc ccccagccc      60 cuccucccu uccugcaccc guaccccuc cauaaaguag gaaacacuac aguggucuuu     120
gaauaaaguc ugagugggcg gc                                            142

<210> SEQ ID NO 54
<211> LENGTH: 142
<212> TYPE: RNA
<213> ORGANISM: Artificial Sequence
<220> FEATURE:
<223> OTHER INFORMATION: 3'UTR including miR142-3p binding site

<400> SEQUENCE: 54
ugauaauagg cuggagccuc gguggccaug cuucuugccc cuugggccuc ccccagccc      60 cuccucccu uccugcaccc guaccccgu ggucuuugaa uaaaguucca uaaaguagga     120
aacacuacac ugagugggcg gc                                            142

<210> SEQ ID NO 55
<211> LENGTH: 371
<212> TYPE: RNA
<213> ORGANISM: Artificial Sequence
<220> FEATURE:
<223> OTHER INFORMATION: 3'UTR-001

<400> SEQUENCE: 55
gcgccugccc accugccacc gacugcugga acccagccag ugggagggcc uggcccacca     60
gaguccugcu cccucacucc ucgccccgcc cccuguccca gagucccacc uggggggcucu   120 cuccacccuu cucagaguuc caguuucaac cagaguucca accaaugggc uccauccucu    180
ggauucuggc caaugaaaua ucuccccuggc agggucccucu ucuuuuccca gagucccacc  240
ccaaccagga gcucuaguua auggagagcu cccagcacac ucggagcuug ugcuuugucu   300
ccacgcaaag cgauaaauaa aagcauuggu ggccuuuggu cuugaauaa agccugagua    360 ggaagucuag a                                                         371

<210> SEQ ID NO 56
<211> LENGTH: 568
<212> TYPE: RNA
<213> ORGANISM: Artificial Sequence
<220> FEATURE:
<223> OTHER INFORMATION: 3'UTR-002

<400> SEQUENCE: 56
gccccugccg cucccacccc cacccaucug ggccccgggu ucaagagaga gcggggucug     60
aucucgugua gccauauaga guuugcuucu gagugucugc uuuguuuagu agaggugggc   120
aggaggagcu gaggggcugg ggcuggggug uugaaguugg cuuugcaugc ccagcgaugc   180
gccucccugu gggaugucau cacccuggga accgggagug gcccuuggcu cacuguguuc   240
ugcaugguuu ggaucugaau uaauugccu ucuucuaaa ucccaaccga acuucuucca    300
accuccaaac uggcuguaac cccaaaucca agccauuaac uacaccugac aguagcaauu  360
gucugauuaa ucacuggccc cuugaagaca gcagaauguc ccuuugcaau gaggaggaga  420
ucugggcugg gcgggccagc uggggaagca uuugacuauc uggaacuugu gugugccucc  480
ucagguaugg cagugacuca ccugguuuua auaaaacaac cugcaacauc ucauggucuu  540
```

| | |
|---|---|
| ugaauaaagc cugaguagga agucuaga | 568 |

<210> SEQ ID NO 57
<211> LENGTH: 289
<212> TYPE: RNA
<213> ORGANISM: Artificial Sequence
<220> FEATURE:
<223> OTHER INFORMATION: 3'UTR-003

<400> SEQUENCE: 57

| | |
|---|---|
| acacacucca ccuccagcac gcgacuucuc aggacgacga aucuucucaa uggggggggcg | 60 |
| gcugagcucc agccaccccg cagucacuuu cuuuguaaca acuuccguug cugccaucgu | 120 |
| aaacugacac aguguuuaua acguguacau acauuaacuu auuaccucau uuuguuauuu | 180 |
| uucgaaacaa agcccugugg aagaaaaugg aaaacuugaa gaagcauuaa agucauucug | 240 |
| uuaagcugcg uaaauggucu uugaauaaag ccugaguagg aagucuaga | 289 |

<210> SEQ ID NO 58
<211> LENGTH: 379
<212> TYPE: RNA
<213> ORGANISM: Artificial Sequence
<220> FEATURE:
<223> OTHER INFORMATION: 3'UTR-004

<400> SEQUENCE: 58

| | |
|---|---|
| caucacauuu aaaagcaucu cagccuacca ugagaauaag agaaagaaaa ugaagaucaa | 60 |
| aagcuuauuc aucuguuuuu cuuuuucguu ggguguaaagc caacacccug ucuaaaaaac | 120 |
| auaaauuucu uuaaucauuu ugccucuuuu cucugugcuu caauuaauaa aaaauggaaa | 180 |
| gaaucuaaua gaguggguaca gcacuguuau uuucaaaga ugguugcua ccugaaaaau | 240 |
| ucuguagguu cuguggaagu uccaguguuc ucucuuauuc cacuucggua gaggauuucu | 300 |
| aguuucuugu gggcuaauua aauaaaucau uaauacucuu cuaauggucu uugaauaaag | 360 |
| ccugaguagg aagucuaga | 379 |

<210> SEQ ID NO 59
<211> LENGTH: 118
<212> TYPE: RNA
<213> ORGANISM: Artificial Sequence
<220> FEATURE:
<223> OTHER INFORMATION: 3'UTR-005

<400> SEQUENCE: 59

| | |
|---|---|
| gcugccuucu gcggggcuug ccuucuggcc augcccuucu ucucucccuu gcaccuguac | 60 |
| cucuuggucu uugaauaaag ccugaguagg aaggcggccg cucgagcaug caucuaga | 118 |

<210> SEQ ID NO 60
<211> LENGTH: 908
<212> TYPE: RNA
<213> ORGANISM: Artificial Sequence
<220> FEATURE:
<223> OTHER INFORMATION: 3'UTR-006

<400> SEQUENCE: 60

| | |
|---|---|
| gccaagcccu ccccauccca uguauuuauc ucuauuuaau auuuaugucu auuuaagccu | 60 |
| cauauuuaaa gacagggaag agcagaacgg agccccaggc cucuguguucc uucccugcau | 120 |
| uucugaguuu cauucuccug ccuguagcag ugagaaaaag cucccuguccu cccaucccu | 180 |
| ggacugggag guagauaggu aaauaccaag uauuuauuac uaugcacgcu ccccagcccu | 240 |
| ggcucugcaa ugggcacugg gaugagccgc ugugagcccc uggucccugag ggucccacc | 300 |

| | |
|---|---|
| ugggacccuu gagaguauca ggucuccac gugggagaca agaaaucccu guuuaauauu | 360 |
| uaaacagcag uguucccau cuggguccuu gcaccccuca cucuggccuc agccgacugc | 420 |
| acagcggccc cugcaucccc uuggcuguga ggcccuggaa caagcagagg uggccagagc | 480 |
| ugggaggcau ggcccugggg ucccacgaau ugcugggga aucucguuuu ucuucuuaag | 540 |
| acuuuuggga cauggguuga ucccgaaca ucaccgacgc gucuccuguu uuucuggggug | 600 |
| gccucgggac accugcccug ccccacgag ggucaggacu ugacucuuu uuagggccag | 660 |
| gcaggugccu ggacauuugc cuugcuggac ggggacuggg gaugugggag ggagcagaca | 720 |
| ggaggaauca ugucaggccu gugugugaaa ggaagcucca cugucacccu ccaccucuuc | 780 |
| accccccacu caccagugus cccuccacug ucacauugua acugaacuuc aggauaauaa | 840 |
| aguguuugcc uccauggucu ugaauaaag ccgaguagg aaggcggccg cucgagcaug | 900 |
| caucuaga | 908 |

<210> SEQ ID NO 61
<211> LENGTH: 835
<212> TYPE: RNA
<213> ORGANISM: Artificial Sequence
<220> FEATURE:
<223> OTHER INFORMATION: 3'UTR-007

<400> SEQUENCE: 61

| | |
|---|---|
| acucaaucua aauuaaaaaa gaaagaaauu ugaaaaaacu uucucuuugc cauuucuucu | 60 |
| ucuucuuuuu uaacgaaag cugaauccuu ccauuucuuc ugcacaucua cuugcuuaaa | 120 |
| uugugggcaa aagagaaaaa gaaggauuga ucagagcauu gucaauaca guucauuaa | 180 |
| cuccuucccc cgcucccca aaauuugaa uuuuuuuuc aacacucuua caccuguuau | 240 |
| ggaaaauguc aaccuuugua agaaaccaa aauaaaaauu gaaaauaaa aaccauaaac | 300 |
| auuugcacca cuuguggcuu uugaauaucu ccacagagg gaaguuuaaa acccaaacuu | 360 |
| ccaaagguuu aaacuaccuc aaaacacuuu cccaugagug ugauccacau uguuaggugc | 420 |
| ugaccuagac agagaugaac ugaggucuu guuuuguuuu guucauaaua caaaggugcu | 480 |
| aauuaauagu auucagaua cuugaagaau guugauggug cuagaagaau uugagaagaa | 540 |
| auacuccugu auugaguugu aucguguggu guauuuuuua aaaaauuuga uuuagcauuc | 600 |
| auauuuucca ucuauuuccc aauuaaaagu augcagauua uuugcccaaa ucuucucag | 660 |
| auucagcauu uguucuuugc cagucucauu ucaucuucu ccaugguuc cacagaagcu | 720 |
| uuguuucuug gcaagcaga aaauuaau guaccuauu uuguauaugu gagauguuua | 780 |
| aauaaauugu gaaaaaaug aaauaaagca uguuggguuu ccaaaagaa cauau | 835 |

<210> SEQ ID NO 62
<211> LENGTH: 297
<212> TYPE: RNA
<213> ORGANISM: Artificial Sequence
<220> FEATURE:
<223> OTHER INFORMATION: 3'UTR-008

<400> SEQUENCE: 62

| | |
|---|---|
| cgccgccgcc cgggcccgc agucgagggu cgugagccca ccccguccau ggugcuaagc | 60 |
| gggcccgggu cccacacggc cagcaccgcu gcucacucgg acgacgcccu gggccugcac | 120 |
| cucuccagcu ccucccacgg ggucccgua gccccggccc ccgccagcc ccaggucucc | 180 |
| ccaggcccuc cgcaggcugc ccggccuccc uccccugca gccaucccaa ggcuccugac | 240 |

| | |
|---|---|
| cuaccuggcc ccugagcucu ggagcaagcc cugacccaau aaaggcuuug aacccau | 297 |

<210> SEQ ID NO 63
<211> LENGTH: 602
<212> TYPE: RNA
<213> ORGANISM: Artificial Sequence
<220> FEATURE:
<223> OTHER INFORMATION: 3'UTR-009

<400> SEQUENCE: 63

| | |
|---|---|
| ggggcuagag cccucuccgc acagcgugga gacggggcaa ggaggggggu uauuaggauu | 60 |
| ggugguuuug uuuugcuuug uuuaaagccg ugggaaaaug gcacaacuuu accucugugg | 120 |
| gagaugcaac acugagagcc aaggggugg aguugggaua auuuuauau aaagaaguu | 180 |
| uuuccacuuu gaauugcuaa aagugggcauu uuuccuaugu gcagucacuc cucucauuuc | 240 |
| uaaaauaggg acguggccag gcacggugc ucaugccugu aaucccagca cuuugggagg | 300 |
| ccgaggcagg cggcucacga ggucaggaga ucgagacuau ccuggcuaac acgguaaaac | 360 |
| ccugucucua cuaaaaguac aaaaauuag cugggcgugg uggugggcac cuguaguccc | 420 |
| agcuacucgg gaggcugagg caggagaaag gcaugaaucc aagaggcaga gcuugcagug | 480 |
| agcugagauc acgccauugc acuccagccu gggcaacagu guuaagacuc ugucucaaau | 540 |
| auaaauaaau aaauaaauaa auaaauaaau aaauaaaaau aaagcgagau guugcccuca | 600 |
| aa | 602 |

<210> SEQ ID NO 64
<211> LENGTH: 785
<212> TYPE: RNA
<213> ORGANISM: Artificial Sequence
<220> FEATURE:
<223> OTHER INFORMATION: 3'UTR-010

<400> SEQUENCE: 64

| | |
|---|---|
| ggcccugccc cgucggacug cccccagaaa gccuccugcc cccugccagu gaaguccuuc | 60 |
| agugagcccc uccccagcca gcccuucccu gccccgccg gauguauaaa uguaaaaaug | 120 |
| aaggaauuac auuuuauaug ugagcgagca agccggcaag cgagcacagu auuauuucuc | 180 |
| caucccccucc cugccugcuc cuuggcaccc ccaugcugcc uucagggaga caggcaggga | 240 |
| gggcuugggg cugcaccucc uaccucccca ccagaacgca ccccacuggg agagcuggug | 300 |
| gugcagccuu cccccucccug uauaagacac uuugccaagg cucuccccuc ucgccccauc | 360 |
| ccugcuugcc cgcucccaca gcuuccugag ggcuaauucu gggaagggag aguucuuugc | 420 |
| ugccccugucu ggaagacgu ggcucugggu gagguaggcg ggaaaggaug gaguguuuua | 480 |
| guucuugggg gaggccaccc caaacccag ccccaacucc agggggcaccu augaauggc | 540 |
| caugcucaac ccccuccccca dacaggcccu cccugucucc agggccccca ccgagguucc | 600 |
| cagggcugga dacuuccucu gguaaacauu ccuccagccu ccccucccccu ggggacgcca | 660 |
| aggaggugg ccacacccag gaagggaaag cgggcagccc cguuugggg acgugaacgu | 720 |
| uuuaauaauu uugcugaauc uccuuuacaa cuaaauaaca cagauauugu uauaauaaaa | 780 |
| auugu | 785 |

<210> SEQ ID NO 65
<211> LENGTH: 3001
<212> TYPE: RNA
<213> ORGANISM: Artificial Sequence
<220> FEATURE:
<223> OTHER INFORMATION: 3'UTR-011

<400> SEQUENCE: 65

| | | | | | |
|---|---|---|---|---|---|
| auauuaagga | ucaagcuguu | agcuaauaau | gccaccucug | caguuuuggg | aacaggcaaa | 60 |
| uaaaguauca | guauacaugg | ugauguacau | cuguagcaaa | gcucuuggag | aaaaugaaga | 120 |
| cugaagaaag | caaagcaaaa | acuguauaga | gagauuuuuc | aaaagcagua | aucccucaau | 180 |
| uuuaaaaaag | gauugaaaau | ucuaaauguc | uuucugugca | uauuuuugu | guuaggaauc | 240 |
| aaaaguauuu | uauaaaagga | gaaagaacag | ccucauuuua | gauguagucc | uguuggauuu | 300 |
| uuuaugccuc | ucaguaacc | agaaauguuu | uaaaaacua | aguguuuagg | auuucaagac | 360 |
| aacauuauac | auggcucuga | auaucugac | acaauguaaa | cauugcaggc | accugcauuu | 420 |
| uauguuuuuu | uuucaacaa | augugacuaa | uuugaaacuu | uaugaacuu | cugagcuguc | 480 |
| cccuugcaau | ucaccgcag | uuugaauuaa | ucauaucaaa | ucaguuuaa | uuuuuaaau | 540 |
| uguacuucag | agucuauauu | ucaagggcac | auuuucucac | uacuauuuua | auacauuaaa | 600 |
| ggacuaaaua | aucuucaga | gaugcuggaa | acaaaucauu | ugcuuauau | guucauuag | 660 |
| aauaccaaug | aaacauacaa | cuugaaaauu | aguaauagua | uuuugaaga | ucccauuucu | 720 |
| aauuggagau | cucuuuaauu | ucgaucaacu | uauaauguu | aguacauau | uaagugcacu | 780 |
| ugaguggaau | ucaacauuug | acuaauaaa | ugaguucauc | auguuggcaa | gugaugguggc | 840 |
| aauuaucucu | ggugacaaaa | gaguaaaauc | aaauauuucu | gccuguuaca | aauucaagg | 900 |
| aagaccugcu | acuaugaaau | agaugacauu | aaucugucuu | cacuguuuau | aauacggaug | 960 |
| gauuuuuuu | caaaucagug | uguguuuuga | ggcuuaugu | aauugaugac | auuugagaga | 1020 |
| aauggugguucu | uuuuuagcu | accucuuugu | ucauuuaagc | accaguaaag | aucaugucuu | 1080 |
| uuuauagaag | uguagauuuu | cuuugugacu | ugcuaucgu | gccuaaagcu | cuaaauauag | 1140 |
| gugaaugugu | gaugaauacu | cagauuauu | gucucucuau | auaauuaguu | ugguacuaag | 1200 |
| uuucucaaaa | aauuauuaac | acaugaaaga | caaucucuaa | accagaaaaa | gaaguaguac | 1260 |
| aaauuuuguu | acuguaaugc | ucgcguuuag | ugaguuuaaa | acacacagua | ucuuuugguu | 1320 |
| uuauaaucag | uuucuauuuu | gcugugccug | agauuaagau | cuguauguu | gugugugugu | 1380 |
| gugugugcgu | uugugugua | aagcagaaaa | gacuuuuua | aaaguuuaa | gugauaaaug | 1440 |
| caauuuguua | auugaucuua | gaucacuagu | aaacucaggg | cugaauuaua | ccauguauau | 1500 |
| ucuauuagaa | gaaaguaaac | accaucuuua | uccugcccu | uuucuucuc | ucaaaguagu | 1560 |
| uguaguuaua | ucuagaaaga | agcaauuuug | auucuugaa | aagguaguuc | cugcacucag | 1620 |
| uuuaaacuaa | aaauaaucau | acuuggauuu | uauuauuuu | ugucauagua | aaauuuuaa | 1680 |
| uuuauauaua | uuuuauuua | guauuaucuu | auucuuugcu | auuugccaau | ccuuugucau | 1740 |
| caauuguguu | aaaugaauug | aaaauucaug | cccugucau | uuuauuuuac | uuuauuggu | 1800 |
| aggauauuua | aaggauuuuu | guauauaua | uuucuuaaau | uaauauucca | aaagguuagu | 1860 |
| ggacuuagau | uauaaauuau | ggcaaaaauc | uaaaaacaac | aaaaaugauu | uuauacauu | 1920 |
| cuauuucauu | auccucuuu | uuccaauaag | ucauacaauu | gguagauaug | acuuauuuua | 1980 |
| uuuuuguauu | auucacuaua | ucuuuaugau | auuuaaguau | aaauaauuaa | aaaaauuuau | 2040 |
| uguaccuuau | agcugucac | caaaaaaaaa | aaauuaucug | uagguaguga | aaugcuaaug | 2100 |
| uugauuuguc | uuuaagggcu | uguuaacuau | ccuuuauuuu | cucauuuguc | uuaaauuagg | 2160 |
| aguuuguguu | uaaauuacuc | aucuaagcaa | aaaaauguaua | uaaaucccau | uacugggguau | 2220 |
| auacccaaag | gauuauaaau | caugcugcua | uaaagacaca | ugcacacgua | uguuuauugc | 2280 |

| | | |
|---|---|---|
| agcacuauuc acaauagcaa agacuuggaa ccaacccaaa uguccaucaa ugauagacuu | 2340 |
| gauuaagaaa augugcacau auacaccaug gaauacuaug cagccauaaa aaaggaugag | 2400 |
| uucauguccu uuguagggac auggauaaag cuggaaacca ucauucugag caaacuauug | 2460 |
| caaggacaga aaaccaaaca cugcauguuc ucacucauag gugggaauug aacaaugaga | 2520 |
| acacuuggac acaaggugg gaacaccaca caccagggcc ugucauggggg uggggggagu | 2580 |
| ggggagggau agcauuagga gauauaccua auguaaauga ugaguuaaug ggugcagcac | 2640 |
| accaacaugg cacauguaua cauauguagc aaaccugcac guugugcaca uguacccuag | 2700 |
| aacuuaaagu auaauuaaaa aaaaaaagaa aacagaagcu auuuauaaag aaguuauuug | 2760 |
| cugaaauaaa ugugaucuuu cccauuaaaa aaauaaagaa auuuuggggu aaaaaaacac | 2820 |
| aauauauugu auucuugaaa aauucuaaga gagugaugu gaaguuucu caccacaaaa | 2880 |
| gugauaacua auugagguaa ugcacauauu aauuagaaag auuuugucau uccacaaugu | 2940 |
| auauauacuu aaaauaugu uauacacaau aaauacauac auuaaaaaau aaguaaaugu | 3000 |
| a | 3001 |

```
<210> SEQ ID NO 66
<211> LENGTH: 1037
<212> TYPE: RNA
<213> ORGANISM: Artificial Sequence
<220> FEATURE:
<223> OTHER INFORMATION: 3'UTR-012

<400> SEQUENCE: 66
```

| | | |
|---|---|---|
| cccacccugc acgccggcac caaacccugu ccucccaccc cucccacucu aucacuaaac | 60 |
| agaguaaaau gugaugcgaa uuucccgac caaccugauu cgcuagauuu uuuuaagga | 120 |
| aaagcuugga aagccaggac acaacgcugc ugccugcuuu gugcagggguc ucggggggcu | 180 |
| cagcccugag uuggcaucac cugcgcaggg cccucggggg cucagcccug agcuagugguc | 240 |
| accugcacag ggcccucuga ggcucagccc ugagcugggcg ucaccugugc agggcccucu | 300 |
| ggggcucagc ccugagcugg ccucaccugg guucccaccc cgggcucuc cugcccugcc | 360 |
| cuccugcccg cccucccucc ugccugcgca gcuccuuccc uaggcaccuc ugugcugcau | 420 |
| cccaccagcc ugagcaagac gcccucucgg ggccugugcc gcacuagccu cccucuccuc | 480 |
| ugucccaua gcugguuuuu cccaccaauc cucaccuaac aguuacuuua caauuaaacu | 540 |
| caaagcaagc ucuucuccuc agcuuggggc agccauuggc cucugucucg uuuugggaaa | 600 |
| ccaaggucag gaggccguug cagacauaaa ucucggcgac ucggccccgu uccugaggg | 660 |
| uccugcuggu gaccggccug gaccuuggcc cuacagcccu ggaggccgcu gcugaccagc | 720 |
| acugaccccg accucagaga guacucgcag gggcgcuggc ugcacucaag cccucgaga | 780 |
| uuaacggugc uaacccguc ugcuccuccc uccgcagag acugggggccu ggacuggaca | 840 |
| ugagagcccc uuggugccac agagggcugu gucuuacuag aaacaacgca aaccucuccu | 900 |
| uccucagaau agugaugugu ucgacguuuu aucaaaggcc cccuuucuau guucauguua | 960 |
| guuuugcucc uucuguguuu uuuucugaac cauauccaug uugcugacuu uccaaauaa | 1020 |
| agguuuucac uccucuc | 1037 |

```
<210> SEQ ID NO 67
<211> LENGTH: 577
<212> TYPE: RNA
<213> ORGANISM: Artificial Sequence
<220> FEATURE:
<223> OTHER INFORMATION: 3'UTR-013
```

<400> SEQUENCE: 67

```
agaggccugc cuccagggcu ggacugaggc cugagcgcuc cugccgcaga gcuggccgcg    60
ccaaauaaug ucucugugag acucgagaac uuucauuuuu uuccaggcug uucggauuu    120
ggggu ggauu uugguuuugu ucccccuccuc cacucccccc caccccccucc ccgcccuuuu  180
uuuuuuuuuu uuuuaaacug guauuuuauc uuugauucuc cuucagcccu caccccuggu   240
ucucaucuuu cuugaucaac aucuuuucuu gccucuguc ccuucucuca ucucuuagcu    300
cccccuccaac cuggggggca guggugugga aagccacag gccugagauu caucugcuc    360
uccuuccugg agcccagagg agggcagcag aaggggugg ugucuccaac cccccagcac   420
ugaggaagaa cggggcucuu ucauuucac ccucccuuu uccccugcc cccaggacug     480
ggccacuucu ggguggggca gugguccca gauuggcuca cacugagaau guaagaacua   540
caaacaaaau uucuauuaaa uuaaauuuug ugcucc                             577
```

<210> SEQ ID NO 68
<211> LENGTH: 2212
<212> TYPE: RNA
<213> ORGANISM: Artificial Sequence
<220> FEATURE:
<223> OTHER INFORMATION: 3'UTR-014

<400> SEQUENCE: 68

```
cucccuccau cccaaccugg cucccuccca cccaaccaac uuuccccca acccggaaac    60
agacaagcaa cccaaacuga acccccucaa aagccaaaaa augggagaca auuucacaug   120
gacuuuggaa aauauuuuuu uccuuugcau ucaucucuca aacuuaguuu uuaucuuuga   180
ccaaccgaac augaccaaaa accaaaagug cauucaaccu uaccaaaaaa aaaaaaaaa    240
aaagaauaaa uaaauaacuu uuuaaaaaag gaagcuuggu ccacuugcuu gaagacccau   300
gcgggggguaa gucccuuucu gcccguuggg cuuaugaaac cccaaugcug cccuuuucugc  360
uccuuucucc acacccccccu uggggccucc ccuccacucc uucccaaauc ugucuccccca  420
gaagacacag gaaacaaugu auugucugcc cagcaaucaa aggcaaugcu caaacacccca  480
aguggccccc acccucagcc cgcuccugcc cgcccagcac cccaggcccc uggggaccu    540
ggguucuca gacugccaaa gaagccuugc caucuggcgc ucccauggcu cuugcaacau   600
cuccccuucg uuuuugaggg ggucaugccg ggggagccac cagcccccuca cuggguucgg  660
aggagaguca ggaagggcca cgacaaagca gaaacaucgg auuuggggaa cgcgugucaa   720
ucccuugugc cgcagggcug ggcgggagag acguucugu uccugugua acuguguugc    780
ugaaagacua ccucguucuu gucuugaugu ucaccgggg caacugccug ggggcgggga  840
uggggcagg guggaagcgg cucccccauuu uauaccaaag gugcuacauc uaugugaugg  900
guggggugg gagggaauca cuggugcuau agaaauugag augcccccc aggccagcaa   960
auguuccuuu uuguucaaag ucuauuuuua uccuugauaa uuuuucuuuu uuuuuuuuu   1020
uuuuugugga ugggggacuug ugaauuuuuc uaaaggugcu auuuaacaug ggaggagagc  1080
gugugcggcu ccagcccagc ccgcugcuca cuuccacccc ucucuccacc ugccucuggc   1140
uucucaggcc ucugcucucc gaccucucuc cucugaaacc cuccuccaca gcugcagccc   1200
auccuccccgg cucccuccua gucuguccug cguccucugu cccggguuu cagagacaac   1260
uucccaaagc acaaagcagu uuuucccccu aggggugggga ggaagcaaaa gacucuguac  1320
cuauuuugua uguguauaau aauuugagau guuuuuaauu auuugauug cuggaauaaa   1380
```

```
gcaugoggaa augacccaaa cauaauccgc aguggccucc uaauuccuu cuuggagou   1440 gggggaggg uagacauggg aaggggcuu uggggugaug ggcuugccuu ccauuccugc   1500
ccuuccccuc cccacuauuc ucuucuagau cccuccauaa cccacuccc cuuucucuca   1560 cccuucuuau accgcaaacc uuucuacuuc ucuuucauu uucuauucu gcaauuccu    1620 ugcaccuuuu ccaauccuc uucuccccug caauaccaua caggcaaucc acgugcacaa  1680
cacacacaca cacucuucac aucuggggu guccaaaccu cauacccacu ccccuucaag  1740
cccauccacu uccacccccc uggaugcccu gcacuggug gcggugggau gcucauggau  1800
acugggaggg ugaggggagu ggaacccgug aggaggaccu gggggccucu ccuugaacug  1860
acaugaaggg ucaucuggcc ucugcucccu ucucacccac gcugaccucc ugccaagga   1920 gcaacgcaac aggagagggg ucugcugagc cuggcgaggg ucuggagggg accaggagga  1980
aggcgugcuc ccugcucgcu guccuggccc ugggggagug agggagacag acaccuggga  2040
gagcuguggg gaaggcacuc gcaccgugcu cuugggaagg aaggagaccu ggcccugcuc  2100
accacggacu gggugccucg accuccugaa ucccagaaac acaaccccc ugggcugggg   2160 uggucugggg aaccaucgug cccccgccuc cgccuacuc cuuuuaagc uu            2212
```

<210> SEQ ID NO 69
<211> LENGTH: 729
<212> TYPE: RNA
<213> ORGANISM: Artificial Sequence
<220> FEATURE:
<223> OTHER INFORMATION: 3'UTR-015

<400> SEQUENCE: 69

```
uuggccaggc cugacccucu uggaccuuuc uucuuugccg acaaccacug cccagcagcc   60
ucugggaccu cggggucca gggaaccag uccagccucc uggcuguuga cuucccauug   120
cucuuggagc caccaaucaa agagauucaa agagauuccu gcaggccaga ggcggaacac  180
accuuuaugg cugggcucu ccguggugu cuggacccag ccccuggaga caccauucac   240
uuuuacugcu uuguaguga cgugcucuc caaccugucu uccugaaaa ccaaggcccc    300 cuucccccac cucuuccaug gggugagacu ugagcagaac aggggcuucc ccaaguugcc  360
cagaaagacu gucugggga aagccaugg ccagagcuuc uucccaggcac aggguguug ca 420 ccagggacuu cugcuucaag uuuuggggua aagacaccug gaucagacuc caagggcugc  480
ccugagucug ggacuucugc cuccauggcu ggucaugaga gcaaaccgua guccccugga  540
gacagcgacu ccagagaacc ucuugggaga cagaagaggc aucugugcac agcucgaucu  600
ucuacuugcc ugugggagg ggagugacag guccacacac cacacugggu caccucugccc   660 uggaugccuc ugaagagagg gacagaccgu cagaaacugg agaguucua uuaaaggcuca 720 uuuaaacca                                                         729
```

<210> SEQ ID NO 70
<211> LENGTH: 847
<212> TYPE: RNA
<213> ORGANISM: Artificial Sequence
<220> FEATURE:
<223> OTHER INFORMATION: 3'UTR-016

<400> SEQUENCE: 70

```
uccuccggga cccagcccu caggauuccu gaugcuccaa ggcgacugau gggcgcugga    60
ugaaguggca cagucagcuu cccugggggc ugguguaug uugggcuccu ggggcggggg   120
cacggccugg cauuucacgc auugcugcca ccccaggucc accugucucc acuuucacag   180
```

-continued

```
ccuccaaguc uguggcucuu cccuucuguc cuccgagggg cuugccuucu cucgugucca     240
gugaggugcu cagugaucgg cuuaacuuag agaagcccgc ccccucccu ucuccgucug      300 ucccaagagg gucugcucug agccugcguu ccuaggugc ucggcucag cugccugggu      360 uguggccgcc cuagcauccu guaugccac agcuacugga auccccgcug cugcuccggg      420
ccaagcuucu gguugauuaa ugagggcaug ggguggucc ucaagaccuu ccccuaccuu      480
uuguggaacc agugaugccu caaagacagu gucccccuca cagcugggug ccaggggcag    540
gggauccuca guauagccgg ugaacccuga uaccaggagc cugggccucc cugaaccccu    600
ggcuuccagc caucucaucg ccagccuccu ccuggaccuc uuggcccca gcccuuccc      660 cacacagccc cagaaggguc ccagagcuga ccccacucca ggaccuaggc ccagcccuc     720 agccucaucu ggagcccug aagaccaguc ccacccaccu uucuggccuc aucgacacu      780 gcuccgcauc cugcugugug uccuguucca guuccgguu ccaucaaau acacuuucug      840 gaacaaa                                                              847

<210> SEQ ID NO 71
<211> LENGTH: 110
<212> TYPE: RNA
<213> ORGANISM: Artificial Sequence
<220> FEATURE:
<223> OTHER INFORMATION: 3'UTR-017

<400> SEQUENCE: 71
gcuggagccu cgguggccau gcuucuugcc ccuugggccu cccccagcc ccuccucccc      60 uuccugcacc cguaccccg uggucuuuga auaaagucug agugggcggc                 110

<210> SEQ ID NO 72
<211> LENGTH: 119
<212> TYPE: RNA
<213> ORGANISM: Artificial Sequence
<220> FEATURE:
<223> OTHER INFORMATION: 3' UTR no miR binding sites

<400> SEQUENCE: 72
ugauaauagg cuggagccuc ggguggccau gcuucuugcc cuugggccuc ccccagccc      60 cuccuccccu uccugcaccc guaccccgu ggucuuugaa uaaagucuga gugggcggc      119

<210> SEQ ID NO 73
<211> LENGTH: 87
<212> TYPE: RNA
<213> ORGANISM: Artificial Sequence
<220> FEATURE:
<223> OTHER INFORMATION: miR-142

<400> SEQUENCE: 73
gacagugcag ucacccauaa aguagaaagc acuacuaaca gcacuggagg guguaguguu     60
uccuacuuua uggaugagug uacugug                                         87

<210> SEQ ID NO 74
<211> LENGTH: 23
<212> TYPE: RNA
<213> ORGANISM: Artificial Sequence
<220> FEATURE:
<223> OTHER INFORMATION: miR-142-3p

<400> SEQUENCE: 74
uguaguguuu ccuacuuuau gga                                             23
```

<210> SEQ ID NO 75
<211> LENGTH: 23
<212> TYPE: RNA
<213> ORGANISM: Artificial Sequence
<220> FEATURE:
<223> OTHER INFORMATION: miR-142-3p binding site

<400> SEQUENCE: 75
uccauaaagu aggaaacacu aca                                           23

<210> SEQ ID NO 76
<211> LENGTH: 21
<212> TYPE: RNA
<213> ORGANISM: Artificial Sequence
<220> FEATURE:
<223> OTHER INFORMATION: miR-142-5p

<400> SEQUENCE: 76
cauaaaguag aaagcacuac u                                             21

<210> SEQ ID NO 77
<211> LENGTH: 21
<212> TYPE: RNA
<213> ORGANISM: Artificial Sequence
<220> FEATURE:
<223> OTHER INFORMATION: miR-142-5p binding site

<400> SEQUENCE: 77
aguagugcuu ucuacuuuau g                                             21

<210> SEQ ID NO 78
<211> LENGTH: 18
<212> TYPE: DNA
<213> ORGANISM: Artificial Sequence
<220> FEATURE:
<223> OTHER INFORMATION: Syn5 promoter

<400> SEQUENCE: 78
attgggcacc cgtaaggg                                                 18

<210> SEQ ID NO 79
<211> LENGTH: 92
<212> TYPE: RNA
<213> ORGANISM: Artificial Sequence
<220> FEATURE:
<223> OTHER INFORMATION: 5' UTR of Citrin in Example 12

<400> SEQUENCE: 79
ucaagcuuuu ggacccucgu acagaagcua auacgacuca cuauagggaa auaagagaga   60
aaagaagagu aagaagaaau auaagagcca cc                                 92

<210> SEQ ID NO 80
<211> LENGTH: 119
<212> TYPE: RNA
<213> ORGANISM: Artificial Sequence
<220> FEATURE:
<223> OTHER INFORMATION: 3' UTR of Citrin in Example 12

<400> SEQUENCE: 80
ugauaauagg cuggagccuc gguggccaug cuucuugccc cuugggccuc ccccagccc    60 cuccucccu uccugcaccc guaccccgu ggucuugaa uaaagucuga gugggcggc      119

<210> SEQ ID NO 81
<211> LENGTH: 133

```
<212> TYPE: RNA
<213> ORGANISM: Artificial Sequence
<220> FEATURE:
<223> OTHER INFORMATION: (3'UTR with miR 142-3p binding site)

<400> SEQUENCE: 81
gcuggagccu cgguggccau gcuucuugcc ccuugggccu cccccagcc ccuccuccc        60 uuccugcacc cguacccccu ccauaaagua ggaaacacua caguggucuu ugaauaaagu     120
cugagugggc ggc                                                        133

<210> SEQ ID NO 82
<211> LENGTH: 23
<212> TYPE: RNA
<213> ORGANISM: Artificial Sequence
<220> FEATURE:
<223> OTHER INFORMATION: (miR 142-3p binding site)

<400> SEQUENCE: 82
uccauaaagu aggaaacacu aca                                              23

<210> SEQ ID NO 83
<211> LENGTH: 23
<212> TYPE: RNA
<213> ORGANISM: Artificial Sequence
<220> FEATURE:
<223> OTHER INFORMATION: (miR 142-3p sequence)

<400> SEQUENCE: 83
uguaguguuu ccuacuuuau gga                                              23

<210> SEQ ID NO 84
<211> LENGTH: 21
<212> TYPE: RNA
<213> ORGANISM: Artificial Sequence
<220> FEATURE:
<223> OTHER INFORMATION: (miR 142-5p sequence)

<400> SEQUENCE: 84
cauaaaguag aaagcacuac u                                                21

<210> SEQ ID NO 85
<211> LENGTH: 22
<212> TYPE: RNA
<213> ORGANISM: Artificial Sequence
<220> FEATURE:
<223> OTHER INFORMATION: (miR 146-3p sequence)

<400> SEQUENCE: 85
ccucugaaau ucaguucuuc ag                                               22

<210> SEQ ID NO 86
<211> LENGTH: 22
<212> TYPE: RNA
<213> ORGANISM: Artificial Sequence
<220> FEATURE:
<223> OTHER INFORMATION: (miR 146-5p sequence)

<400> SEQUENCE: 86
ugagaacuga auuccauggg uu                                               22

<210> SEQ ID NO 87
<211> LENGTH: 22
<212> TYPE: RNA
<213> ORGANISM: Artificial Sequence
<220> FEATURE:
```

```
<223> OTHER INFORMATION: (miR 155-3p sequence)

<400> SEQUENCE: 87
cuccuacaua uuagcauuaa ca                                              22

<210> SEQ ID NO 88
<211> LENGTH: 23
<212> TYPE: RNA
<213> ORGANISM: Artificial Sequence
<220> FEATURE:
<223> OTHER INFORMATION: (miR 155-5p sequence)

<400> SEQUENCE: 88
uuaaugcuaa ucgugauagg ggu                                             23

<210> SEQ ID NO 89
<211> LENGTH: 22
<212> TYPE: RNA
<213> ORGANISM: Artificial Sequence
<220> FEATURE:
<223> OTHER INFORMATION: (miR 126-3p sequence)

<400> SEQUENCE: 89
ucguaccgug aguaauaaug cg                                              22

<210> SEQ ID NO 90
<211> LENGTH: 21
<212> TYPE: RNA
<213> ORGANISM: Artificial Sequence
<220> FEATURE:
<223> OTHER INFORMATION: (miR 126-5p sequence)

<400> SEQUENCE: 90
cauuauuacu uuugguacgc g                                               21

<210> SEQ ID NO 91
<211> LENGTH: 22
<212> TYPE: RNA
<213> ORGANISM: Artificial Sequence
<220> FEATURE:
<223> OTHER INFORMATION: (miR 16-3p sequence)

<400> SEQUENCE: 91
ccaguauuaa cugugcugcu ga                                              22

<210> SEQ ID NO 92
<211> LENGTH: 22
<212> TYPE: RNA
<213> ORGANISM: Artificial Sequence
<220> FEATURE:
<223> OTHER INFORMATION: (miR 16-5p sequence)

<400> SEQUENCE: 92
uagcagcacg uaaauauugg cg                                              22

<210> SEQ ID NO 93
<211> LENGTH: 21
<212> TYPE: RNA
<213> ORGANISM: Artificial Sequence
<220> FEATURE:
<223> OTHER INFORMATION: (miR 21-3p sequence)

<400> SEQUENCE: 93
caacaccagu cgaugggcug u                                               21
```

```
<210> SEQ ID NO 94
<211> LENGTH: 22
<212> TYPE: RNA
<213> ORGANISM: Artificial Sequence
<220> FEATURE:
<223> OTHER INFORMATION: (miR 21-5p sequence)

<400> SEQUENCE: 94
uagcuuauca gacugauguu ga                                              22

<210> SEQ ID NO 95
<211> LENGTH: 22
<212> TYPE: RNA
<213> ORGANISM: Artificial Sequence
<220> FEATURE:
<223> OTHER INFORMATION: (miR 223-3p sequence)

<400> SEQUENCE: 95
ugucaguuug ucaaauaccc ca                                              22

<210> SEQ ID NO 96
<211> LENGTH: 22
<212> TYPE: RNA
<213> ORGANISM: Artificial Sequence
<220> FEATURE:
<223> OTHER INFORMATION: (miR 223-5p sequence)

<400> SEQUENCE: 96
cguguauuug acaagcugag uu                                              22

<210> SEQ ID NO 97
<211> LENGTH: 22
<212> TYPE: RNA
<213> ORGANISM: Artificial Sequence
<220> FEATURE:
<223> OTHER INFORMATION: (miR 24-3p sequence)

<400> SEQUENCE: 97
uggcucaguu cagcaggaac ag                                              22

<210> SEQ ID NO 98
<211> LENGTH: 22
<212> TYPE: RNA
<213> ORGANISM: Artificial Sequence
<220> FEATURE:
<223> OTHER INFORMATION: (miR 24-5p sequence)

<400> SEQUENCE: 98
ugccuacuga gcugauauca gu                                              22

<210> SEQ ID NO 99
<211> LENGTH: 21
<212> TYPE: RNA
<213> ORGANISM: Artificial Sequence
<220> FEATURE:
<223> OTHER INFORMATION: (miR 27-3p sequence)

<400> SEQUENCE: 99
uucacagugg cuaaguuccg c                                               21

<210> SEQ ID NO 100
<211> LENGTH: 22
<212> TYPE: RNA
<213> ORGANISM: Artificial Sequence
<220> FEATURE:
<223> OTHER INFORMATION: (miR 27-5p sequence)
```

```
<400> SEQUENCE: 100
agggcuuagc ugcuugugag ca                                           22

<210> SEQ ID NO 101
<211> LENGTH: 22
<212> TYPE: RNA
<213> ORGANISM: Artificial Sequence
<220> FEATURE:
<223> OTHER INFORMATION: (miR 126-3p binding site)

<400> SEQUENCE: 101
cgcauuauua cucacgguac ga                                           22

<210> SEQ ID NO 102
<211> LENGTH: 141
<212> TYPE: RNA
<213> ORGANISM: Artificial Sequence
<220> FEATURE:
<223> OTHER INFORMATION: (3'UTR with miR 126-3p binding site)

<400> SEQUENCE: 102
ugauaauagg cuggagccuc gguggccaug cuucuugccc cuugggccuc ccccagccc    60 cucccccccu uccugcaccc guaccccccg cauuauuacu cacgguacga guggucuuug  120
aauaaagucu gagugggcgg c                                           141

<210> SEQ ID NO 103
<211> LENGTH: 142
<212> TYPE: RNA
<213> ORGANISM: Artificial Sequence
<220> FEATURE:
<223> OTHER INFORMATION: (3' UTR with miR 142-3p binding site)

<400> SEQUENCE: 103
ugauaauagg cuggagccuc gguggccaug cuucuugccc cuugggccuc ccccagccc    60 cucccccccu uccugcaccc guaccccccuc cauaaaguag aaacacuac aguggucuuu  120 gaauaaaguc ugagugggcg gc                                          142

<210> SEQ ID NO 104
<211> LENGTH: 141
<212> TYPE: RNA
<213> ORGANISM: Artificial Sequence
<220> FEATURE:
<223> OTHER INFORMATION: (3' UTR with miR 126-3p binding site)

<400> SEQUENCE: 104
ugauaauagg cuggagccuc gguggccaug cuucuugccc cuugggccuc ccccagccc    60 cucccccccu uccugcaccc guaccccccg cauuauuacu cacgguacga guggucuuug  120
aauaaagucu gagugggcgg c                                           141

<210> SEQ ID NO 105
<211> LENGTH: 164
<212> TYPE: RNA
<213> ORGANISM: Artificial Sequence
<220> FEATURE:
<223> OTHER INFORMATION: (3' UTR with miR 142-3p and miR 126-3p binding
      sites)

<400> SEQUENCE: 105
ugauaauagu ccauaaagua ggaaacacua cagcuggagc cucgguggcc augcuucuug   60
cccccuuggg c ucccccccag ccccuccucc ccuuccugca cccguacccc cgcauuauu  120
```

```
acucacggua cgaguggucu uugaauaaag ucugaguggg cggc                     164
```

```
<210> SEQ ID NO 106
<211> LENGTH: 23
<212> TYPE: RNA
<213> ORGANISM: Artificial Sequence
<220> FEATURE:
<223> OTHER INFORMATION: (miR 155-5p sequence)

<400> SEQUENCE: 106
uuaaugcuaa uugugauagg ggu                                            23
```

```
<210> SEQ ID NO 107
<211> LENGTH: 23
<212> TYPE: RNA
<213> ORGANISM: Artificial Sequence
<220> FEATURE:
<223> OTHER INFORMATION: (miR 155-5p binding site)

<400> SEQUENCE: 107
accccuauca caauuagcau uaa                                            23
```

```
<210> SEQ ID NO 108
<211> LENGTH: 188
<212> TYPE: RNA
<213> ORGANISM: Artificial Sequence
<220> FEATURE:
<223> OTHER INFORMATION: (3' UTR with 3 miR 142-3p binding sites)

<400> SEQUENCE: 108
ugauaauagu ccauaaagua ggaaacacua cagcuggagc cucgguggcc augcuucuug     60
ccccuugggc cuccauaaag uaggaaacac uacauccccc cagcccccuc ucccuuccu     120 gcacccguac ccccuccaua aaguaggaaa cacuacagug gucuuugaau aaagucugag    180
ugggcggc                                                            188
```

```
<210> SEQ ID NO 109
<211> LENGTH: 140
<212> TYPE: RNA
<213> ORGANISM: Artificial Sequence
<220> FEATURE:
<223> OTHER INFORMATION: (3'UTR with miR 142-5p binding site)

<400> SEQUENCE: 109
ugauaauagg cuggagccuc gguggccaug cuucuugccc cuugggccuc ccccagccc      60 cuccuccccu uccugcaccc guaccccag uagugcuuuc acuuuaugg uggucuuuga     120 auaaagucug agugggcggc                                               140
```

```
<210> SEQ ID NO 110
<211> LENGTH: 182
<212> TYPE: RNA
<213> ORGANISM: Artificial Sequence
<220> FEATURE:
<223> OTHER INFORMATION: (3'UTR with 3 miR 142-5p binding sites)

<400> SEQUENCE: 110
ugauaauaga guagugcuuu cuacuuuaug gcuggagccu cgguggccau gcuucuugcc     60
ccuugggcca guagugcuuu cuacuuuaug uccccccagc ccuccuccc cuuccugcac    120 ccguaccccc aguagugcuu ucuacuuuau gguggucuuu gaauaaaguc ugagugggcg    180
gc                                                                  182
```

```
<210> SEQ ID NO 111
<211> LENGTH: 184
<212> TYPE: RNA
<213> ORGANISM: Artificial Sequence
<220> FEATURE:
<223> OTHER INFORMATION: (3'UTR with 2 miR 142-5p binding sites and 1
      miR 142-3p binding site)

<400> SEQUENCE: 111
ugauaauaga guagugcuuu cuacuuuaug gcuggagccu cgguggccau gcuucuugcc      60
ccuugggccu ccauaaagua ggaaacacua caucccccca gcccccucuc cccuuccugc    120
acccguaccc ccaguagugc uuucuacuuu augguggucu uugaauaaag ucgagugggg    180
cggc                                                                 184

<210> SEQ ID NO 112
<211> LENGTH: 142
<212> TYPE: RNA
<213> ORGANISM: Artificial Sequence
<220> FEATURE:
<223> OTHER INFORMATION: (3'UTR with miR 155-5p binding site)

<400> SEQUENCE: 112
ugauaauagg cuggagccuc gguggccaug cuucuugccc cuugggccuc ccccagccc     60 cuccuccccu uccugcaccc guaccccac cccaucaca auuagcauua aguggucuuu     120
gaauaaaguc ugagugggcg gc                                            142

<210> SEQ ID NO 113
<211> LENGTH: 188
<212> TYPE: RNA
<213> ORGANISM: Artificial Sequence
<220> FEATURE:
<223> OTHER INFORMATION: (3' UTR with 3 miR 155-5p binding sites)

<400> SEQUENCE: 113
ugauaauaga ccccuaucac aauuagcauu aagcuggagc cucggguggcc augcuucuug    60 ccccuugggc caccccuauc acaauuagca uuaaucccc cagccccucc ucccuuccu     120 gcacccguac ccccacccu aucacaauua gcauuaagug gucuuugaau aaagucgag     180 ugggcggc                                                            188

<210> SEQ ID NO 114
<211> LENGTH: 188
<212> TYPE: RNA
<213> ORGANISM: Artificial Sequence
<220> FEATURE:
<223> OTHER INFORMATION: (3'UTR with 2 miR 155-5p binding sites and 1
      miR 142-3p binding site)

<400> SEQUENCE: 114
ugauaauaga ccccuaucac aauuagcauu aagcuggagc cucggguggcc augcuucuug    60 ccccuugggc cuccauaaag uaggaaacac uacauccccc cagccccucc ucccuuccu    120 gcacccguac ccccacccu aucacaauua gcauuaagug gucuuugaau aaagucgag     180 ugggcggc                                                            188

<210> SEQ ID NO 115
<211> LENGTH: 142
<212> TYPE: RNA
<213> ORGANISM: Artificial Sequence
<220> FEATURE:
<223> OTHER INFORMATION: (3'UTR with miR 142-3p binding site, P1
      insertion)
```

-continued

```
<400> SEQUENCE: 115
ugauaauagu ccauaaagua ggaaacacua cagcuggagc cucgguggcc augcuucuug      60
ccccuugggc cucccccag ccccuccucc ccuuccugca cccguacccc cguggucuuu      120
gaauaaaguc ugagugggcg gc                                              142

<210> SEQ ID NO 116
<211> LENGTH: 142
<212> TYPE: RNA
<213> ORGANISM: Artificial Sequence
<220> FEATURE:
<223> OTHER INFORMATION: (3'UTR with miR 142-3p binding site, P2
      insertion)

<400> SEQUENCE: 116
ugauaauagg cuggagccuc gguggcucca uaaaguagga aacacuacac augcuucuug      60
ccccuugggc cucccccag ccccuccucc ccuuccugca cccguacccc cguggucuuu      120
gaauaaaguc ugagugggcg gc                                              142

<210> SEQ ID NO 117
<211> LENGTH: 142
<212> TYPE: RNA
<213> ORGANISM: Artificial Sequence
<220> FEATURE:
<223> OTHER INFORMATION: (3'UTR with miR 142-3p binding site, P3
      insertion)

<400> SEQUENCE: 117
ugauaauagg cuggagccuc gguggccaug cuucuugccc cuuggccuc cauaaaguag       60 gaaacacuac aucccccag ccccuccucc ccuuccugca cccguacccc cguggucuuu      120
gaauaaaguc ugagugggcg gc                                              142

<210> SEQ ID NO 118
<211> LENGTH: 21
<212> TYPE: RNA
<213> ORGANISM: Artificial Sequence
<220> FEATURE:
<223> OTHER INFORMATION: (miR-142-5p binding site)

<400> SEQUENCE: 118
aguagugcuu ucuacuuuau g                                               21

<210> SEQ ID NO 119
<211> LENGTH: 87
<212> TYPE: RNA
<213> ORGANISM: Artificial Sequence
<220> FEATURE:
<223> OTHER INFORMATION: (miR-142)

<400> SEQUENCE: 119
gacagugcag ucacccauaa aguagaaagc acuacuaaca gcacuggagg guguaguguu      60
uccuacuuua uggaugagug uacugug                                         87

<210> SEQ ID NO 120
<211> LENGTH: 70
<212> TYPE: RNA
<213> ORGANISM: Artificial Sequence
<220> FEATURE:
<223> OTHER INFORMATION: (5' UTR with miR142-3p binding site at position
      p1)

<400> SEQUENCE: 120
```

```
gggaaauaag aguccauaaa guaggaaaca cuacaagaaa agaagaguaa gaagaaauau    60
aagagccacc                                                          70

<210> SEQ ID NO 121
<211> LENGTH: 70
<212> TYPE: RNA
<213> ORGANISM: Artificial Sequence
<220> FEATURE:
<223> OTHER INFORMATION: (5' UTR with miR142-3p binding site at position
      p2)

<400> SEQUENCE: 121
gggaaauaag agagaaaaga agaguaaucc auaaaguagg aaacacuaca gaagaaauau    60
aagagccacc                                                          70

<210> SEQ ID NO 122
<211> LENGTH: 70
<212> TYPE: RNA
<213> ORGANISM: Artificial Sequence
<220> FEATURE:
<223> OTHER INFORMATION: (5' UTR with miR142-3p binding site at position
      p3)

<400> SEQUENCE: 122
gggaaauaag agagaaaaga agaguaagaa gaaauauaau ccauaaagua ggaaacacua    60
cagagccacc                                                          70

<210> SEQ ID NO 123
<211> LENGTH: 23
<212> TYPE: RNA
<213> ORGANISM: Artificial Sequence
<220> FEATURE:
<223> OTHER INFORMATION: (miR 155-5p binding site)

<400> SEQUENCE: 123
accccuauca caauuagcau uaa                                           23

<210> SEQ ID NO 124
<211> LENGTH: 181
<212> TYPE: RNA
<213> ORGANISM: Artificial Sequence
<220> FEATURE:
<223> OTHER INFORMATION: (3'UTR with 3 miR 142-5p binding sites)

<400> SEQUENCE: 124
ugauaauaga guagugcuuu cuacuuuaug gcuggagccu cgguggccau gcuucuugcc    60
ccuugggcca guagugcuuu cuacuuuaug ucccccccagc cccucuccccc uuccugcacc   120 cguaccccca guagugcuuu cuacuuuaug guggucuuug aauaaagucu gagugggcgg   180
c                                                                  181

<210> SEQ ID NO 125
<211> LENGTH: 184
<212> TYPE: RNA
<213> ORGANISM: Artificial Sequence
<220> FEATURE:
<223> OTHER INFORMATION: (3'UTR with 2 miR 142-5p binding sites and 1
      miR 142-3p binding site)

<400> SEQUENCE: 125
ugauaauaga guagugcuuu cuacuuuaug gcuggagccu cgguggccau gcuucuugcc    60
ccuugggccu ccauaaagua ggaaacacua caucccccca gccccuccuc cccuuccugc   120
```

```
acccguaccc ccaguagugc uuucuacuuu augguggucu uugaauaaag ucgaguggg      180 cggc                                                                  184

<210> SEQ ID NO 126
<211> LENGTH: 70
<212> TYPE: RNA
<213> ORGANISM: Artificial Sequence
<220> FEATURE:
<223> OTHER INFORMATION: (5' UTR with miR142-3p binding site at position
      p1)

<400> SEQUENCE: 126
gggaaauaag aguccauaaa guaggaaaca cuacaagaaa agaagaguaa gaagaaauau      60
aagagccacc                                                            70

<210> SEQ ID NO 127
<211> LENGTH: 70
<212> TYPE: RNA
<213> ORGANISM: Artificial Sequence
<220> FEATURE:
<223> OTHER INFORMATION: (5' UTR with miR142-3p binding site at position
      p2)

<400> SEQUENCE: 127
gggaaauaag agagaaaaga agaguaaucc auaaaguagg aaacacuaca gaagaaauau      60
aagagccacc                                                            70

<210> SEQ ID NO 128
<211> LENGTH: 70
<212> TYPE: RNA
<213> ORGANISM: Artificial Sequence
<220> FEATURE:
<223> OTHER INFORMATION: (5' UTR with miR142-3p binding site at position
      p3)

<400> SEQUENCE: 128
gggaaauaag agagaaaaga agaguaagaa gaaauauaau ccauaaagua ggaaacacua      60
cagagccacc                                                            70

<210> SEQ ID NO 129
<211> LENGTH: 2025
<212> TYPE: RNA
<213> ORGANISM: Artificial Sequence
<220> FEATURE:
<223> OTHER INFORMATION: Construct #1 ORF of Citrin gene

<400> SEQUENCE: 129
auggccgccg ccaaggucgc ccucaccaag agggcggacc ccgcggagcu caggaccauc      60
uuucucaagu acgccuccau cgagaagaac ggggaguucu ucaugagccc gaacgauuuc     120
gucaccaggu accucaacau cuucggcgag agccagccca acccgaagac cguagagcuc     180
cucagcggcg ucgucgacca gacgaaggac ggacucauua gcuuccagga guucgucgcc     240
uucgagagcg uccucugcgc gcccgacgcc cucuucaugg ucgcguucca gcuguucgau     300
aaggccggca agggcgaggu gaccuuugaa gaugugaagc aggugucgg ucagaccacc      360 auccaccagc acaucccuuu uaacugggac ucagaauucg ccagcugca cuucggcaag      420 gaaaggaagc gccaucugac cuacgccgag uucacacagu uucuccugga gauccagcug     480
gaacacgcca acaggcguu cguucagcgg gacaacgcca ggaccggccg ggucaccgcg      540
aucgacuucc gugauaucau ggugaccauc aggccucacg uccugacgcc cuucguggaa     600
```

```
gagugccugg uggccgccgc ggguggggacc acgucccacc aggugagcuu cuccuauuuu    660
aacggguuca acagccuccu caacaacaug gagcugaucc ggaagaucua uagcacccug    720
gccgggacgc gcaaggacgu cgaggugacc aaggaagaau ucgugcuggc cgcccagaag    780
uuuggccagg ugacgcccau ggaggkuggac auccuguucc aacuggcgga ccuguacgaa    840
```

```
auaucauggu gaccaucagg ccucacgucc ugacgcccuu cguggaagag ugccuggugg    660
ccgccgcggg ugggaccacg ucccaccagg ugagcuucuc cuauuuuaac ggguucaaca    720
gccuccucaa caacauggag cugauccgga agaucuauag cacccuggcc gggacgcgca    780
aggacgucga ggugaccaag gaagaauucg ugcuggccgc ccagaaguuu ggccagguga    840
cgcccaugga gguggacauc cuguuccaac uggcggaccu guacgaaccc aggggccgga    900
ugacccuggc cgacaucgag cgcauugccc cgcucgagga gggcacccug cccuucaacc    960
uggcggaggc ccagcgccag aaggccagcg gggacagcgc caggcccguc cugcugcagg   1020
uggccgaguc cgcguacagg uucggucugg gagcgucgc gggagccgug ggugccaccg   1080
ccguguaucc gaucgaccuc gugaagaccc guaugcagaa ucagaggucc accggcagcu   1140
ucgugggcga gcucauguac aagaacuccu ucgacuguuu caagaagguu uccggguacg   1200
aggguucuu cggccucuac cggggacugc uaccccagcu gcucggcgug gcgcccgaga   1260
aggccaucaa gcucacgguc aacgacuuug ugcgggacaa guucaugcac aaggacggca   1320
gcgucccacu ggccgccgag auucuggcag gcggcugcgc cggaggcagc caggucaucu   1380
uuaccaaccc acuggagauc gugaagauca ggcugcaagu ggccggggag auuaccaccg   1440
gaccccgugu gagcgcccug agcguggga gggaccuugg cuucuuuggc auauacaagg   1500
gagccaaggc cugcuuucug agggacaucc cguuuccgc cauauacuuu cccugcuacg   1560
cccacgugaa agcgagcuuc gccaacgagg acgccaggu cagucccggc ucccuacugc   1620
uggccggagc caucgccggg augcccgccg ccagccuggu gacgcccgcg gacguuauca   1680
agaccaggcu gcaggugcg gccagggcgg ccagaccac cuacagcggc gugaucgacu   1740
gcuuccgcaa gauccugcgg gagggggc ccaaggcccu guggaaaggc gccgggcaa    1800
ggguguucag gagcagccca caguccgggg ugacccugcu uaccuacgaa cugcugcagc   1860
ggugguucua uaucgacuuc ggaggaguca agcccauggg cuccgagccu gugcccaaga   1920
gcaggaucaa ucugcccgcg cccaacccag accacguggg agguacaaaa cuggccgugg   1980
ccaccuucgc cggaaucgag aacaaguucg gccuguaucu gccccuguuc aaaccguccg   2040
ucuccaccag caaggccauc ggcggaggcc ccugauaaua guccauaaag uaggaaacac   2100
uacagcugga gccucggugg ccaugcuucu gccccuugg gccuccccc agccccuccu   2160
ccccuuccug cacccguacc ccccgcauua uuacucacgg uacgaguggu cuuugaauaa   2220
agucugagug ggcggc                                                   2236
```

<210> SEQ ID NO 131
<211> LENGTH: 675
<212> TYPE: PRT
<213> ORGANISM: Artificial Sequence
<220> FEATURE:
<223> OTHER INFORMATION: Construct #1 Amino acid sequence of Citrin gene

<400> SEQUENCE: 131

```
Met Ala Ala Ala Lys Val Ala Leu Thr Lys Arg Ala Asp Pro Ala Glu
1               5                   10                  15

Leu Arg Thr Ile Phe Leu Lys Tyr Ala Ser Ile Glu Lys Asn Gly Glu
            20                  25                  30

Phe Phe Met Ser Pro Asn Asp Phe Val Thr Arg Tyr Leu Asn Ile Phe
        35                  40                  45

Gly Glu Ser Gln Pro Asn Pro Lys Thr Val Glu Leu Leu Ser Gly Val
    50                  55                  60

Val Asp Gln Thr Lys Asp Gly Leu Ile Ser Phe Gln Glu Phe Val Ala
```

```
                65                  70                  75                  80
        Phe Glu Ser Val Leu Cys Ala Pro Asp Ala Leu Phe Met Val Ala Phe
                            85                  90                  95
        Gln Leu Phe Asp Lys Ala Gly Lys Gly Glu Val Thr Phe Glu Asp Val
                            100                 105                 110
        Lys Gln Val Phe Gly Gln Thr Thr Ile His Gln His Ile Pro Phe Asn
                            115                 120                 125
        Trp Asp Ser Glu Phe Val Gln Leu His Phe Gly Lys Glu Arg Lys Arg
                            130                 135                 140
        His Leu Thr Tyr Ala Glu Phe Thr Gln Phe Leu Leu Glu Ile Gln Leu
        145                 150                 155                 160
        Glu His Ala Lys Gln Ala Phe Val Gln Arg Asp Asn Ala Arg Thr Gly
                            165                 170                 175
        Arg Val Thr Ala Ile Asp Phe Arg Asp Ile Met Val Thr Ile Arg Pro
                            180                 185                 190
        His Val Leu Thr Pro Phe Val Glu Glu Cys Leu Val Ala Ala Ala Gly
                            195                 200                 205
        Gly Thr Thr Ser His Gln Val Ser Phe Ser Tyr Phe Asn Gly Phe Asn
                            210                 215                 220
        Ser Leu Leu Asn Asn Met Glu Leu Ile Arg Lys Ile Tyr Ser Thr Leu
        225                 230                 235                 240
        Ala Gly Thr Arg Lys Asp Val Glu Val Thr Lys Glu Glu Phe Val Leu
                            245                 250                 255
        Ala Ala Gln Lys Phe Gly Gln Val Thr Pro Met Glu Val Asp Ile Leu
                            260                 265                 270
        Phe Gln Leu Ala Asp Leu Tyr Glu Pro Arg Gly Arg Met Thr Leu Ala
                            275                 280                 285
        Asp Ile Glu Arg Ile Ala Pro Leu Glu Glu Gly Thr Leu Pro Phe Asn
                            290                 295                 300
        Leu Ala Glu Ala Gln Arg Gln Lys Ala Ser Gly Asp Ser Ala Arg Pro
        305                 310                 315                 320
        Val Leu Leu Gln Val Ala Glu Ser Ala Tyr Arg Phe Gly Leu Gly Ser
                            325                 330                 335
        Val Ala Gly Ala Val Gly Ala Thr Ala Val Tyr Pro Ile Asp Leu Val
                            340                 345                 350
        Lys Thr Arg Met Gln Asn Gln Arg Ser Thr Gly Ser Phe Val Gly Glu
                            355                 360                 365
        Leu Met Tyr Lys Asn Ser Phe Asp Cys Phe Lys Lys Val Leu Arg Tyr
                            370                 375                 380
        Glu Gly Phe Phe Gly Leu Tyr Arg Gly Leu Leu Pro Gln Leu Leu Gly
        385                 390                 395                 400
        Val Ala Pro Glu Lys Ala Ile Lys Leu Thr Val Asn Asp Phe Val Arg
                            405                 410                 415
        Asp Lys Phe Met His Lys Asp Gly Ser Val Pro Leu Ala Ala Glu Ile
                            420                 425                 430
        Leu Ala Gly Gly Cys Ala Gly Gly Ser Gln Val Ile Phe Thr Asn Pro
                            435                 440                 445
        Leu Glu Ile Val Lys Ile Arg Leu Gln Val Ala Gly Glu Ile Thr Thr
                            450                 455                 460
        Gly Pro Arg Val Ser Ala Leu Ser Val Val Arg Asp Leu Gly Phe Phe
        465                 470                 475                 480
        Gly Ile Tyr Lys Gly Ala Lys Ala Cys Phe Leu Arg Asp Ile Pro Phe
                            485                 490                 495
```

```
Ser Ala Ile Tyr Phe Pro Cys Tyr Ala His Val Lys Ala Ser Phe Ala
            500                 505                 510

Asn Glu Asp Gly Gln Val Ser Pro Gly Ser Leu Leu Leu Ala Gly Ala
            515                 520                 525

Ile Ala Gly Met Pro Ala Ala Ser Leu Val Thr Pro Ala Asp Val Ile
            530                 535                 540

Lys Thr Arg Leu Gln Val Ala Arg Ala Gly Gln Thr Thr Tyr Ser
545                 550                 555                 560

Gly Val Ile Asp Cys Phe Arg Lys Ile Leu Arg Glu Gly Pro Lys
                565                 570                 575

Ala Leu Trp Lys Gly Ala Gly Ala Arg Val Phe Arg Ser Ser Pro Gln
            580                 585                 590

Phe Gly Val Thr Leu Leu Thr Tyr Glu Leu Leu Gln Arg Trp Phe Tyr
            595                 600                 605

Ile Asp Phe Gly Gly Val Lys Pro Met Gly Ser Glu Pro Val Pro Lys
            610                 615                 620

Ser Arg Ile Asn Leu Pro Ala Pro Asn Pro Asp His Val Gly Gly Tyr
625                 630                 635                 640

Lys Leu Ala Val Ala Thr Phe Ala Gly Ile Glu Asn Lys Phe Gly Leu
                645                 650                 655

Tyr Leu Pro Leu Phe Lys Pro Ser Val Ser Thr Ser Lys Ala Ile Gly
            660                 665                 670

Gly Gly Pro
        675

<210> SEQ ID NO 132
<211> LENGTH: 2025
<212> TYPE: RNA
<213> ORGANISM: Artificial Sequence
<220> FEATURE:
<223> OTHER INFORMATION: Construct #2 ORF of Citrin gene

<400> SEQUENCE: 132
auggccgccg ccaaggucgc ccucaccaag agggcggacc ccgcggagcu caggaccauc      60
uuucucaagu acgccuccau cgagaagaac ggggaguucu ucaugagccc gaacgauuuc     120
gucaccaggu accucaacau cuucggcgag agccagccca acccgaagac cguagagcuc     180
cucagcggcg ucgucgacca gacgaaggac ggacucauua gcuuccagga guucgucgcc     240
uucgagagcg uccucugcgc ccccgacgcc cucuucaugg ucgcguucca gcuguucgau     300
aaggccggca agggcgaggu gaccuuugaa gaugugaagc aggugucgg ucagaccacc     360 auccaccagc acaucccuuu uaacugggac ucagaauucg uccagcugca cuucggcaag     420
gaaaggaagc gccaucugac cuacgccgag uucacacagu uucuccugga gaucagcug     480 gaacacgcca acaggcguu cguucagcgg acaacgcca ggaccggccg ggucaccgcg     540
aucgacuucc gugauaucau ggugaccauc aggccucacg uccugacccc cuucguggaa     600
gagugccugg uggccgccgc ggguggacc acgucccacc aggugagcuu cccuauuuu     660 aacgggiuica acagccuccu caacaacaug gagcugaucc ggaagaucua uagcacccug     720
gccgggacgc gcaaggacgu cgaggugacc aaggaagaau cgugcuggc cgcccagaag     780 uuuggccagg ugaccccau ggagguggac auccuguucc aacuggcgga ccuguacgaa     840
cccaggggcc ggaugacccu ggccgacauc gagcgcauug cccgcuga ggaggcacc     900 cugcccuuca accuggcgga ggcccagcgc cagaaggcca gcgggacag cgccagggccc     960
```

| | |
|---|---|
| guccugcugc agguggccga guccgcguac agguucgguc uggggagcgu cgcgggagcc | 1020 |
| gugggugcca ccgccgugua uccgaucgac cucgugaaga cccguaugca gaaucagagg | 1080 |
| uccaccggca gcuucguggg cgagcucaug uacaagaacu ccuucgacug uuucaagaag | 1140 |
| guucuccggu acgaggggu cuucggccuc uaccgggggc ugcuaccca gcugcucggc | 1200 |
| guggcgcccg agaaggccau caagcucacg gucaacgacu uugugcggga caaguucaug | 1260 |
| cacaaggacg gcagcgcccc ccuggccgcc gagauucugg caggcggcug cgccggaggc | 1320 |
| agccaggca ucuuuaccaa cccccuggag aucgugaaga ucaggcugca guggccgggg | 1380 |
| gagauuacca ccggacccg ugugagcgcc cugagcgugg ugagggaccu uggcuucuuu | 1440 |
| ggcauauaca agggagccaa ggccugcuuu cugagggaca ucccguuuuc cgccauauac | 1500 |
| uuucccugcu acgccacgu gaaagcgagc uucgccaacg aggacggcca ggucagcccc | 1560 |
| ggcucccuac ugcuggccgg agccaucgcc gggaugcccg ccgccagccu ggugacccc | 1620 |
| gcggacguua ucaagaccag gcugcaggug gcggccaggg cgggccagac caccacagc | 1680 |
| ggcgugaucg acugcuuccg caagauccug cgggaggag ggcccaaggc ccuggaaaa | 1740 |
| ggcgccgggg caaggguguu caggagcagc cccaguucg gggugacccu gcuuaccuac | 1800 |
| gaacugcugc agcgguggu cuauaucgac uucggggag ucaagcccau gggcuccgag | 1860 |
| ccugugccca agagcaggau caaucugccc gccccaacc cagaccacgu gggaggguac | 1920 |
| aaacuggccg uggccaccuu cgccggaauc gagaacaagu cggccugua ucugccccug | 1980 |
| uucaaaccgu ccgucuccac cagcaaggcc aucggcgggg gcccc | 2025 |

<210> SEQ ID NO 133
<211> LENGTH: 2236
<212> TYPE: RNA
<213> ORGANISM: Artificial Sequence
<220> FEATURE:
<223> OTHER INFORMATION: Construct #2 Full Citrin nucleic acid with UTRs

<400> SEQUENCE: 133

| | |
|---|---|
| gggaauaag agagaaaga agaguaagaa gaaauauaag agccaccaug gccgccgcca | 60 |
| aggucgcccu caccaagagg gcggaccccg cggagcucag gaccaucuuu ucaaguacg | 120 |
| ccuccaucga gaagaacggg gaguucuuca ugagcccgaa cgauuucguc accaggacc | 180 |
| ucaacaucuu cggcgagagc cagcccaacc cgaagaccgu agagcccuc agcggcgucg | 240 |
| ucgaccagac gaaggacgga cucauuagcu uccaggaguu cgucgccuuc gagagcgucc | 300 |
| ucugcgcccc cgacgcccuc uucauggucg cguccagcu guucgauaag gccggcaagg | 360 |
| gcgaggugac cuuugaagau gugaagcagg uguucgguca gaccaccauc caccagcaca | 420 |
| uccccuuuaa cugggacuca gaauucgucc agcugcacuu cggcaaggaa aggaagcgcc | 480 |
| aucugaccua cgccgaguuc acacaguuuc uccuggagau ccagcuggaa cacgccaaac | 540 |
| aggcguucgu ucagcgggac aacgccagga ccggccgggu caccgcgauc gacuuccgug | 600 |
| auaucauggu gaccaucagg ccucacgucc ugaccccuu cgugggaagag ugccugguug | 660 |
| ccgccgcggg ugggaccacg ucccaccagg ugagcuucuc cuauuuuaac ggguucaaca | 720 |
| gccuccucaa caacauggag cugauccgga agaucauaag caccggcc gggacgcgca | 780 |
| aggacgucga ggugaccaag gaagaauucg ugcuggccgc ccagaaguuu ggccaggua | 840 |
| ccccauggu gguggacauc cuguccaac uggcggaccu uacgaaccc aggggccgga | 900 |
| ugacccuggc cgacaucgag cgcauugccc cgcucgagga gggcacccug ccuucaaccc | 960 |
| uggcggaggc ccagcgccag aaggccagcg gggacagcgc caggcccguc cugcugcagg | 1020 |

```
uggccgaguc cgcguacagg uucggucugg ggagcgucgc gggagccgug ggugccaccg   1080
ccguguaucc gaucgaccuc gugaagaccc guaugcagaa ucagaggucc accggcagcu   1140
ucgugggcga gcucauguac aagaacuccu ucgacuguuu caagaagguu uccggguacg   1200 aggguucuu cggccucuac cggggcugc uaccccagcu gcucggcgug cgcgcccgaga   1260 aggccaucaa gcucacgguc aacgacuuug ugcgggacaa guucaugcac aaggacggca   1320
gcgucccccu ggccgccgag auucuggcag gcggcugcgc cggaggcagc caggucaucu   1380
uuaccaaccc ccuggagauc gugaagauca ggcugcaagu ggccggggag auuaccaccg   1440
gaccccgugu gagcgcccug agcgugguga gggaccuugg cuucuuuggc auauacaagg   1500
gagccaaggc cugcuuucug agggacaucc cguuuccgc cauauacuuu cccugcuacg   1560
cccacgugaa agcagcuuc gccaacgagg acggccaggu caguccggc ucccuacugc   1620 uggccggagc caucgccggg augcccgccg ccagccuggu gaccccgcg gacguuauca   1680 agaccaggcu gcagguggcg gccagggcgg gccagaccac cuacagcggc gugaucgacu   1740
gcuuccgcaa gauccugcgg gaggaggggc ccaaggcccu guggaaaggc gccggggcaa   1800
ggguguucag gagcagcccc caguucgggg ugaccccugcu uaccuacgaa cugcugcagc   1860 gguguucua uaucgacuuc gggggagucu agcccauggg cuccgagccu gugcccaaga   1920
gcaggaucaa ucugcccgcc cccaacccag accacguggg agguacaaa cuggccgugg   1980 ccaccuucgc cggaaucgag aacaaguucg gccuguaucu gccccuguuc aaaccguccg   2040
ucuccaccag caaggccauc ggcggggggcc ccugauaaua guccauaaag uaggaaacac   2100
uacagcugga gccucggugg ccaugcuucu ugccccuugg gccucccccc agccccuccu   2160 cccuuccug cacccguacc cccgcauua uuacucacgg uacgagguggu cuuugaauaa   2220 agucugagug ggcggc                                                   2236
```

<210> SEQ ID NO 134
<211> LENGTH: 675
<212> TYPE: PRT
<213> ORGANISM: Artificial Sequence
<220> FEATURE:
<223> OTHER INFORMATION: Construct #2 Amino acid sequence of Citrin gene

<400> SEQUENCE: 134

```
Met Ala Ala Ala Lys Val Ala Leu Thr Lys Arg Ala Asp Pro Ala Glu
1               5                   10                  15

Leu Arg Thr Ile Phe Leu Lys Tyr Ala Ser Ile Glu Lys Asn Gly Glu
            20                  25                  30

Phe Phe Met Ser Pro Asn Asp Phe Val Thr Arg Tyr Leu Asn Ile Phe
        35                  40                  45

Gly Glu Ser Gln Pro Asn Pro Lys Thr Val Glu Leu Leu Ser Gly Val
    50                  55                  60

Val Asp Gln Thr Lys Asp Gly Leu Ile Ser Phe Gln Glu Phe Val Ala
65                  70                  75                  80

Phe Glu Ser Val Leu Cys Ala Pro Asp Ala Leu Phe Met Val Ala Phe
                85                  90                  95

Gln Leu Phe Asp Lys Ala Gly Lys Gly Glu Val Thr Phe Glu Asp Val
            100                 105                 110

Lys Gln Val Phe Gly Gln Thr Thr Ile His Gln His Ile Pro Phe Asn
        115                 120                 125

Trp Asp Ser Glu Phe Val Gln Leu His Phe Gly Lys Glu Arg Lys Arg
    130                 135                 140
```

His Leu Thr Tyr Ala Glu Phe Thr Gln Phe Leu Leu Glu Ile Gln Leu
145                 150                 155                 160

Glu His Ala Lys Gln Ala Phe Val Gln Arg Asp Asn Ala Arg Thr Gly
                165                 170                 175

Arg Val Thr Ala Ile Asp Phe Arg Asp Ile Met Val Thr Ile Arg Pro
            180                 185                 190

His Val Leu Thr Pro Phe Val Glu Glu Cys Leu Val Ala Ala Ala Gly
        195                 200                 205

Gly Thr Thr Ser His Gln Val Ser Phe Ser Tyr Phe Asn Gly Phe Asn
    210                 215                 220

Ser Leu Leu Asn Asn Met Glu Leu Ile Arg Lys Ile Tyr Ser Thr Leu
225                 230                 235                 240

Ala Gly Thr Arg Lys Asp Val Glu Val Thr Lys Glu Glu Phe Val Leu
                245                 250                 255

Ala Ala Gln Lys Phe Gly Gln Val Thr Pro Met Glu Val Asp Ile Leu
                260                 265                 270

Phe Gln Leu Ala Asp Leu Tyr Glu Pro Arg Gly Arg Met Thr Leu Ala
            275                 280                 285

Asp Ile Glu Arg Ile Ala Pro Leu Glu Glu Gly Thr Leu Pro Phe Asn
290                 295                 300

Leu Ala Glu Ala Gln Arg Gln Lys Ala Ser Gly Asp Ser Ala Arg Pro
305                 310                 315                 320

Val Leu Leu Gln Val Ala Glu Ser Ala Tyr Arg Phe Gly Leu Gly Ser
                325                 330                 335

Val Ala Gly Ala Val Gly Ala Thr Ala Val Tyr Pro Ile Asp Leu Val
                340                 345                 350

Lys Thr Arg Met Gln Asn Gln Arg Ser Thr Gly Ser Phe Val Gly Glu
            355                 360                 365

Leu Met Tyr Lys Asn Ser Phe Asp Cys Phe Lys Val Leu Arg Tyr
370                 375                 380

Glu Gly Phe Phe Gly Leu Tyr Arg Gly Leu Leu Pro Gln Leu Leu Gly
385                 390                 395                 400

Val Ala Pro Glu Lys Ala Ile Lys Leu Thr Val Asn Asp Phe Val Arg
                405                 410                 415

Asp Lys Phe Met His Lys Asp Gly Ser Val Pro Leu Ala Ala Glu Ile
            420                 425                 430

Leu Ala Gly Gly Cys Ala Gly Gly Ser Gln Val Ile Phe Thr Asn Pro
        435                 440                 445

Leu Glu Ile Val Lys Ile Arg Leu Gln Val Ala Gly Glu Ile Thr Thr
450                 455                 460

Gly Pro Arg Val Ser Ala Leu Ser Val Val Arg Asp Leu Gly Phe Phe
465                 470                 475                 480

Gly Ile Tyr Lys Gly Ala Lys Ala Cys Phe Leu Arg Asp Ile Pro Phe
            485                 490                 495

Ser Ala Ile Tyr Phe Pro Cys Tyr Ala His Val Lys Ala Ser Phe Ala
        500                 505                 510

Asn Glu Asp Gly Gln Val Ser Pro Gly Ser Leu Leu Leu Ala Gly Ala
            515                 520                 525

Ile Ala Gly Met Pro Ala Ala Ser Leu Val Thr Pro Ala Asp Val Ile
        530                 535                 540

Lys Thr Arg Leu Gln Val Ala Ala Arg Ala Gly Gln Thr Thr Tyr Ser
545                 550                 555                 560

```
Gly Val Ile Asp Cys Phe Arg Lys Ile Leu Arg Glu Glu Gly Pro Lys
            565                 570                 575

Ala Leu Trp Lys Gly Ala Gly Ala Arg Val Phe Arg Ser Ser Pro Gln
        580                 585                 590

Phe Gly Val Thr Leu Leu Thr Tyr Glu Leu Leu Gln Arg Trp Phe Tyr
            595                 600                 605

Ile Asp Phe Gly Gly Val Lys Pro Met Gly Ser Glu Pro Val Pro Lys
        610                 615                 620

Ser Arg Ile Asn Leu Pro Ala Pro Asn Pro Asp His Val Gly Gly Tyr
625                 630                 635                 640

Lys Leu Ala Val Ala Thr Phe Ala Gly Ile Glu Asn Lys Phe Gly Leu
                645                 650                 655

Tyr Leu Pro Leu Phe Lys Pro Ser Val Ser Thr Ser Lys Ala Ile Gly
            660                 665                 670

Gly Gly Pro
        675

<210> SEQ ID NO 135
<211> LENGTH: 2025
<212> TYPE: RNA
<213> ORGANISM: Artificial Sequence
<220> FEATURE:
<223> OTHER INFORMATION: Construct #3 ORF of Citrin gene

<400> SEQUENCE: 135
auggccgccg ccaaggucgc acucaccaaa cgggccgacc ccgccgagcu caggaccauc      60
uuccucaagu acgccagcau cgagaagaac ggggaguucu ucaugagccc caacgacuuc     120
guaaccaggu accucaauau cuucggcgaa agccagccca acccgaagac cgucgagcuc     180
cucuccgggg ucgucgauca gaccaaggac gggcucaucu ccuuccagga guucguggcc     240
uucgaguccg uccucugcgc cccggacgcc cucuucaugg ucgccuucca acucuucgau     300
aaggccggga aaggcgaggu gaccuucgaa gaugugaagc agguuuucgg ccagaccacg     360
auccaccagc auauccccuu uaacugggac agcgaguucg ugcagcugca cuucggcaaa     420
gagaggaaga ggcaccucac cuaugccgaa uucacacaau uccugcucga auucagcugg     480
gagcaugcca acaagccuuu guccagcgg acaacgcca ggaccggcag ggucaccgcg      540
aucgacuuuc gcgauaucau ggugaccauc aggccccacg ugcucacccc cuuuguggag     600
gagugccugg ucgccgccgc cggcgggacg accagccacc aggugucccu ucauacuuc      660 aacggguuca cagccugcu gaacaacaug gagcugaucc gcaagaucua cuccaccug      720 gccggcacca ggaaggacgu ggaagugacc aaggaggagu ucguucucgc cgcccagaaa     780 uucgacagg ugaccccgau ggagguggac auccucuucc agcuggccga ucucuacgag      840
ccccggggca ggaugacgcu cgccgacauc gagcgaaucg cccccuugga ggaggguacc     900
cuucccuuca accuggccga ggcccagcga cagaaagcca gcggcgacag ugccaggccc     960
gugcuccugc aggugggcga auccgccuac agauuuggcc ugggcagcgu cgccggcgca    1020 guggggcgcca ccgccguguaa cccgaucgac cuggucaaga ccaggaugca gaaccagaga    1080
agcaccggcu ccuuugugg cgagcuuaug uacaagaaca gcuucgacug cuucaagaag    1140
guccugcguu acgagggcuu cuucgggcug uaccggggcc ugcugccgca gcugcuaggc    1200
gucgcgcccg agaaggccau uaagcugacc gugaacgacu ucuacggga caaauucaug    1260 cacaaggacg gcagugugcc ccuggccgca gagauccugg ccggggggcug ugccggcggg    1320 ucccagguga ucuuuacgaa ccccccuggag auagugaaga uccggcugca gguggccggg    1380
```

| | |
|---|---|
| gagaucacca ccggccccg ggugucogcc cugagcgucg ugagggaucu ggguucuuu | 1440 |
| ggcaucuaua agggugccaa ggccugcuuc cugcgugaca uucccuuuag cgccaucuac | 1500 |
| uuccccugcu acgccaugu caaggccagc uucgccaacg aagacggaca ggugagcccc | 1560 |
| ggucccugc ugcuggccgg cgccaucgca ggaugccgg ccgccucacu ggugaccccg | 1620 |
| gcggacguga uaaagacgag gcugcaggug gccgcccgcg caggccagac cacguacucg | 1680 |
| ggugugauag acugcuuccg gaagauccug agggaagaag gccccaaggc ccuguggaag | 1740 |
| ggggccggcg ccagggguguu ccgcagcagc ccccaguucg ggucacccu gcucacguac | 1800 |
| gagcuccugc agagguggu cuacaucgac uuuggcgggg ucaagcccau gggcagugag | 1860 |
| ccggugccca agagccggau caaucugccc gcccccaacc cugaccacgu cggcggguac | 1920 |
| aaacuggcgg uggccacccuu cgccggcauc gagaacaagu uggccugua ccugccgcug | 1980 |
| uuuaagccgu ccgugagcac cuccaaggcc aucgggggcg gccca | 2025 |

<210> SEQ ID NO 136
<211> LENGTH: 2236
<212> TYPE: RNA
<213> ORGANISM: Artificial Sequence
<220> FEATURE:
<223> OTHER INFORMATION: Construct #3 Full Citrin nucleic acid with UTRs

<400> SEQUENCE: 136

| | |
|---|---|
| gggaauaag agagaaaaga agaguaagaa gaaauauaag agccaccaug gccgccgcca | 60 |
| aggucgcacu caccaaacgg gccgaccccg ccgagcucag gaccaucuuc cucaaguacg | 120 |
| ccagcaucga gaagaacggg gaguucuuca ugagccccaa cgacuucgua accagguacc | 180 |
| ucaauaucuu cggcgaaagc cagcccaacc cgaagaccgu cgagcuccuc uccggggucg | 240 |
| ucgaucagac caaggacggg cucaucuccu uccaggaguu cguggccuuc gaguccgucc | 300 |
| ucugcgcccc ggacgcccuc uucauggucg ccuuccaacu cuucgauaag gccgggaaag | 360 |
| gcgaggugac cuucgaagau gugaagcagg uuuucggcca gaccacgauc caccagcaua | 420 |
| uccccuuuaa cugggacagc gaguucgugc agcugcacuu cggcaaagag aggaagaggc | 480 |
| accucaccua ugccgaauuc acacaauucc ugcucgagau ucagcuggag caugccaaac | 540 |
| aagccuuugu ccagcgggac aacgccagga ccggcagggu caccgcgauc gacuuucgcg | 600 |
| auaucauggu gaccaucagg ccccacgugc ucaccccccuu uguggaggag ugccuggucg | 660 |
| ccgccgccgg cgggacgacc agccaccagu guccuucuc auacuucaac ggguucaaca | 720 |
| gccugcugaa caacauggag cugauccgca agaucuacuc cacccuggcc ggcaccagga | 780 |
| aggacgugga agugaccaag gaggaguucg uucucgccgc ccagaaauuc ggacagguga | 840 |
| ccccgaugga gguggacauc ucuuccagc uggccgaucu cuacgagccc ggggcagga | 900 |
| ugacgcucgc cgacaucgag cgaaucgccc cccuggagga ggguacccuu cccuucaacc | 960 |
| uggccgaggc ccagcgacag aaagccagcg gcgacagugc caggcccgug cuccugcagg | 1020 |
| uggccgaauc cgccuacaga uuuggccugg gcagcgucgc cggcgcagug ggcgccaccg | 1080 |
| ccguguaccc gaucgaccug gucaagacca ggaugcagaa ccagagaagc accggcuccu | 1140 |
| uuguggggcga gcuuauguac aagaacagcu ucgacugcuu caagaagguc cugcguuacg | 1200 |
| agggcuucuu cgggcuguac cggggccugc ugccgcagcu gcuaggcguc gcgcccgaga | 1260 |
| aggccauuaa gcugaccgug aacgacuucg uacgggacaa auucaugcac aaggacggca | 1320 |
| gugugcccu ggccgcagag auccuggccg ggggcugugc cggcgggucc caggugaucu | 1380 |

-continued

```
uuacgaaccc ccuggagaua gugaagaucc ggcugcaggu ggccggggag aucaccaccg   1440
gcccccgggu guccgcccug agcgucguga gggaucuggg guucuuuggc aucuauaagg   1500
gugccaaggc cugcuuccug cgugacauuc ccuuuagcgc caucuacuuc cccugcuacg   1560
cccaugucaa ggccagcuuc gccaacgaag acggacaggu gagccccggg ucccugcugc   1620
uggccggcgc caucgcaggg augccggccg ccucacuggu gaccccggcg gacgugauaa   1680
agacgaggcu gcagguggcc gccgcgcag gccagaccac guacucgggu gugauagacu   1740
gcuuccggaa gauccugagg gaagaaggcc ccaaggcccu guggaagggg gccggcgcca   1800
ggguguuccg cagcagcccc caguucgggg ucacccugcu cacguacgag uccugcaga   1860 ggugguucua caucgacuuu ggcgggguca agcccauggg cagugagccg gugcccaaga   1920
gccggaucaa ucugcccgcc cccaacccug accacgucgg cggguacaaa cuggcggugg   1980
ccaccuucgc cggcaucgag aacaaguuug gccuguaccu gccgcuguuu aagccguccg   2040
ugagcaccuc caaggccauc ggggcggcc caugauaaua guccauaaag uaggaaacac   2100
uacagcugga gccucggugg ccaugcuucu ugccccuugg gccuccccc agccccuccu   2160 cccuuccug cacccguacc ccccgcauua uuacucacgg uacgaguggu cuugaauaa   2220 agucugagug ggcggc                                                    2236
```

<210> SEQ ID NO 137
<211> LENGTH: 675
<212> TYPE: PRT
<213> ORGANISM: Artificial Sequence
<220> FEATURE:
<223> OTHER INFORMATION: Construct #3 Amino acid sequence of Citrin gene

<400> SEQUENCE: 137

```
Met Ala Ala Ala Lys Val Ala Leu Thr Lys Arg Ala Asp Pro Ala Glu
1               5                   10                  15

Leu Arg Thr Ile Phe Leu Lys Tyr Ala Ser Ile Glu Lys Asn Gly Glu
            20                  25                  30

Phe Phe Met Ser Pro Asn Asp Phe Val Thr Arg Tyr Leu Asn Ile Phe
        35                  40                  45

Gly Glu Ser Gln Pro Asn Pro Lys Thr Val Glu Leu Leu Ser Gly Val
    50                  55                  60

Val Asp Gln Thr Lys Asp Gly Leu Ile Ser Phe Gln Glu Phe Val Ala
65                  70                  75                  80

Phe Glu Ser Val Leu Cys Ala Pro Asp Ala Leu Phe Met Val Ala Phe
                85                  90                  95

Gln Leu Phe Asp Lys Ala Gly Lys Gly Glu Val Thr Phe Glu Asp Val
            100                 105                 110

Lys Gln Val Phe Gly Gln Thr Thr Ile His Gln His Ile Pro Phe Asn
        115                 120                 125

Trp Asp Ser Glu Phe Val Gln Leu His Phe Gly Lys Glu Arg Lys Arg
    130                 135                 140

His Leu Thr Tyr Ala Glu Phe Thr Gln Phe Leu Leu Glu Ile Gln Leu
145                 150                 155                 160

Glu His Ala Lys Gln Ala Phe Val Gln Arg Asp Asn Ala Arg Thr Gly
                165                 170                 175

Arg Val Thr Ala Ile Asp Phe Arg Asp Ile Met Val Thr Ile Arg Pro
            180                 185                 190

His Val Leu Thr Pro Phe Val Glu Glu Cys Leu Val Ala Ala Ala Gly
        195                 200                 205
```

-continued

```
Gly Thr Thr Ser His Gln Val Ser Phe Ser Tyr Phe Asn Gly Phe Asn
    210                 215                 220
Ser Leu Leu Asn Asn Met Glu Leu Ile Arg Lys Ile Tyr Ser Thr Leu
225                 230                 235                 240
Ala Gly Thr Arg Lys Asp Val Glu Val Thr Lys Glu Glu Phe Val Leu
                245                 250                 255
Ala Ala Gln Lys Phe Gly Gln Val Thr Pro Met Glu Val Asp Ile Leu
            260                 265                 270
Phe Gln Leu Ala Asp Leu Tyr Glu Pro Arg Gly Arg Met Thr Leu Ala
        275                 280                 285
Asp Ile Glu Arg Ile Ala Pro Leu Glu Glu Gly Thr Leu Pro Phe Asn
290                 295                 300
Leu Ala Glu Ala Gln Arg Gln Lys Ala Ser Gly Asp Ser Ala Arg Pro
305                 310                 315                 320
Val Leu Leu Gln Val Ala Glu Ser Ala Tyr Arg Phe Gly Leu Gly Ser
                325                 330                 335
Val Ala Gly Ala Val Gly Ala Thr Ala Val Tyr Pro Ile Asp Leu Val
            340                 345                 350
Lys Thr Arg Met Gln Asn Gln Arg Ser Thr Gly Ser Phe Val Gly Glu
        355                 360                 365
Leu Met Tyr Lys Asn Ser Phe Asp Cys Phe Lys Lys Val Leu Arg Tyr
370                 375                 380
Glu Gly Phe Phe Gly Leu Tyr Arg Gly Leu Leu Pro Gln Leu Leu Gly
385                 390                 395                 400
Val Ala Pro Glu Lys Ala Ile Lys Leu Thr Val Asn Asp Phe Val Arg
                405                 410                 415
Asp Lys Phe Met His Lys Asp Gly Ser Val Pro Leu Ala Ala Glu Ile
            420                 425                 430
Leu Ala Gly Gly Cys Ala Gly Gly Ser Gln Val Ile Phe Thr Asn Pro
        435                 440                 445
Leu Glu Ile Val Lys Ile Arg Leu Gln Val Ala Gly Glu Ile Thr Thr
450                 455                 460
Gly Pro Arg Val Ser Ala Leu Ser Val Val Arg Asp Leu Gly Phe Phe
465                 470                 475                 480
Gly Ile Tyr Lys Gly Ala Lys Ala Cys Phe Leu Arg Asp Ile Pro Phe
                485                 490                 495
Ser Ala Ile Tyr Phe Pro Cys Tyr Ala His Val Lys Ala Ser Phe Ala
            500                 505                 510
Asn Glu Asp Gly Gln Val Ser Pro Gly Ser Leu Leu Leu Ala Gly Ala
        515                 520                 525
Ile Ala Gly Met Pro Ala Ala Ser Leu Val Thr Pro Ala Asp Val Ile
530                 535                 540
Lys Thr Arg Leu Gln Val Ala Ala Arg Ala Gly Gln Thr Thr Tyr Ser
545                 550                 555                 560
Gly Val Ile Asp Cys Phe Arg Lys Ile Leu Arg Glu Glu Gly Pro Lys
                565                 570                 575
Ala Leu Trp Lys Gly Ala Gly Ala Arg Val Phe Arg Ser Ser Pro Gln
            580                 585                 590
Phe Gly Val Thr Leu Leu Thr Tyr Glu Leu Leu Gln Arg Trp Phe Tyr
        595                 600                 605
Ile Asp Phe Gly Gly Val Lys Pro Met Gly Ser Glu Pro Val Pro Lys
610                 615                 620
Ser Arg Ile Asn Leu Pro Ala Pro Asn Pro Asp His Val Gly Gly Tyr
```

|  |  |  | 625 |  |  |  | 630 |  |  |  | 635 |  |  |  | 640 |
| --- | --- | --- | --- | --- | --- | --- | --- | --- | --- | --- | --- | --- | --- | --- | --- |
| Lys | Leu | Ala | Val | Ala | Thr | Phe | Ala | Gly | Ile | Glu | Asn | Lys | Phe | Gly | Leu |
|  |  |  |  | 645 |  |  |  | 650 |  |  |  | 655 |  |  |  |
| Tyr | Leu | Pro | Leu | Phe | Lys | Pro | Ser | Val | Ser | Thr | Ser | Lys | Ala | Ile | Gly |
|  |  |  | 660 |  |  |  | 665 |  |  |  | 670 |  |  |  |  |
| Gly | Gly | Pro |  |  |  |  |  |  |  |  |  |  |  |  |  |
|  |  | 675 |  |  |  |  |  |  |  |  |  |  |  |  |  |

<210> SEQ ID NO 138
<211> LENGTH: 2025
<212> TYPE: RNA
<213> ORGANISM: Artificial Sequence
<220> FEATURE:
<223> OTHER INFORMATION: Construct #4 ORF of Citrin gene

<400> SEQUENCE: 138

```
auggccgccg cuaaggucgc ccucacgaag cgggccgauc cgccgagcu     60
ccggaccauc
uuucucaaau acgccagcau cgagaagaac ggcgaguucu caugucccc    120
caacgacuuc
gucaccaggu accuaaacau cuucggcgag agccagccga accccaagac    180
cgucgaauug
cuaucgggcg ucgucgacca gaccaaggac gggcucauca gcuuccagga    240
guucgucgcc
uucgaguccg uccucugcgc ccccgacgcc cucuucaugg uagcauucca    300
guuguucgac
aaggccggaa agggggaggu gaccuucgag gacgugaagc aggucuuugg    360
ucagaccacc
auccaucagc acaucccguu uaacugggac ucggaguucg ugcagcucca    420
cuucggcaag
gaacgaaagc ggcaccucac cuacgccgag uucacccagu uccugcugga    480
gauccagcug
gaacacgcca gcaggccuu cgugcagcga gacaaugcga ggaccgggcg    540
cgugacugcc
aucgauuuca gggacaucau ggugaccauc cggcccacg ugcugacucc    600
cuucguggag
gagugccugg ucgcagccgc cggggguacc accucccacc aggugagcuu    660
cagcuacuuc
aacggcuuca cagccugcu caacaacaug aacugaucc gcaagaucua    720
uccacacuc
gccggcacca ggaaggaugu ggaggugacc aaggaggagu uugugcuggc    780
ggcccagaag
uuugggcagg ucaccccau ggagguggac auccucuucc agcuggccga    840
ccuuacgag
cccaggggca ggaugacccu ggccgacauc gaacgaaucg cccccuugga    900
ggagggcaca
cugcccuuca accuggccga ggcccagagg cagaaggccu ccggcgacag    960
cgcccgaccc
gugcuucugc aaguggccga gagcgccuac cgcuuuggcc uggauccgu   1020
ggccggcgcc
gucgguggcca cgccgugua cccaaucgac cuagugaaga cacgcaugca   1080
gaaccagcgc
agcaccggcu ccuuugucgg ggagcugaug uauaagaaca gcuucgacug   1140
cuucaagaag
gugcugcgcu acgagggcuu cuucggccug uacaggggc ugcugcccca   1200
acugcugggc
guggccccg agaaggccau caagcugacc guuaacgacu cgugcgaga   1260
caaguucaug
cacaaggacg gcagcgugcc cuuggccgca gagauacugg ccggggcug   1320
cgccggcggg
ucgcagguga ucuucaccaa ccccccugag aucguaaaga ucaggcuca   1380
aguggccggg
gagaucacca ccgccccag ggugccgcc cugucgguug ucagggaccu   1440
gggguucuuc
gggauauaca agggcgcgaa ggccgcuuc cugaggaca ucccuucag    1500
cgccaucuac
uuccugcu acgccacgu caggccagc uucgccaacg aggauggca   1560
ggucccccg
ggcucccgc uccuggccgg ugcuaucgcg ggaaugcccg ccgcgagccu    1620
ggugaccccc
gccgauguga ucaagaccag gcugcaaguc cggcgagggg ccggucagac   1680
caccuacucc
ggggucaucg auugcuuuag gaagauccuc cgggaggagg ggcccaaggc   1740
acuguggaag
```

```
gggggccgggg ccagggugul ccguagcucc ccccaguuug gcgugacccu gcugaccuac  1800
gaacugcugc agaggugguu cuacaucgac uucggggggcg ugaagcccau ggcuccgag   1860 ccggugccua agagccggau caaucugccc gccccaacc  ccgaccacgu gggggggcuac  1920 aagcuggccg uggcuaccuu cgccgguauc gagaacaagu ucggccugua ccugcccug   1980 uucaagcccu ccgugagcac gagcaaggcc aucgggggcg ccccc               2025
```

```
<210> SEQ ID NO 139
<211> LENGTH: 2236
<212> TYPE: RNA
<213> ORGANISM: Artificial Sequence
<220> FEATURE:
<223> OTHER INFORMATION: Construct #4 Full Citrin nucleic acid with UTRs

<400> SEQUENCE: 139
```

```
gggaauaaag agagaaaaga agaguaagaa gaaauauaag agccaccaug gccgccgcua   60
aggucgcccu cacgaagcgg gccgaucccg ccgagcuccg gaccaucuuu cucaaauacg   120
ccagcaucga gaagaacggc gaguucuuca ugucccccaa cgacuucguc accaguacc    180 uaaacaucuu cggcgagagc cagccgaacc caagaccgu  cgaauugcua ucgggcgucg   240
ucgaccagac caaggacggg cucaucagcu uccaggaguu cgucgccuuc gaguccgucc   300
ucugcgcccc cgacgcccuc uucaugguag cauuccaguu guucgacaag gccggaaagg   360
gggaggugac cuucgaggac gugaagcagg uguuggguca gaccaccauc caucagcaca   420
ucccguuuaa cuggacucg  gaguucgugc agcuccacuu cggcaaggaa cgaaagcggc   480
accucaccua cgccgaguuc acccaguucc ugcuggagau ccagcuggaa cacgccaagc   540
aggccuucgu gcagcgagac aaugcgagga ccgggcgcgu gacugccauc gauuucaggg   600
acaucauggu gaccauccgg ccccacgugc ugacucccuu cguggaggag ugccuggucg   660
cagccgccgg ggguaccacc ucccaccagg ugagcuucag cuacuucaac ggcuucaaca   720
gccugcucaa caacauggaa cugauccgca agaucuauuc cacacaucgcc ggcaccagga   780 aggaugugga ggugaccaag gaggaguuug ugcuggcggc ccagaaguuu gggcagguca   840
cccccaugga gguggacauc ucucuuccagc uggccgaccu uacgagccc  aggggcagga   900 ugacccuggc cgacaucgaa cgaaucgccc cccuggagga gggcacacug cccuucaacc   960
uggccgaggc ccagaggcag aaggccuccg gcgacagcgc ccgacccgug cuucugcaag   1020
uggccgagag cgccuaccgc uuuggccugg gauccgugc cggcgccguc ggugccaccg   1080
ccguguaccc aaucgaccua gugaagacac gcaugcagaa ccagcgcagc accggcuccu   1140
uugucgggga gcugauguau aagaacagcu ucgacugcuu caagaaggug cugcgcuacg   1200
agggcuucuu cggccuguac aggggggcugc ugccccaacu gcugggcgug gccccccgaga   1260 aggccaucaa gcugaccguu aacgacuucg ugcgagacaa guucaugcac aaggacggca   1320
gcgugcccuu ggccgcagag auacugggccg ggggcugcgc cggcgggucg cagguggaucu  1380 ucaccaaccc ccucgagauc guaaagauca ggcuccaagu ggccggggag aucaccaccg   1440
gccccagggu guccgcccug ucgguggucca gggaccuggg guucuucggg auauacaagg   1500
gcgcgaaggc cugcuuccug agggacaucc ccuucagcgc caucuacuuu cccugcuacg   1560
cccacgucaa ggccagcuuc gccaacgagg auggccaggu cccccgggc  ucccugcucc   1620 uggccggugc uaucgcggga augcccgccg cgagccuggu gaccccgcc  gaugugauca   1680 agaccaggcu gcaagucgcg gcgagggccg gucagaccac cuaccccggg gucaucgauu   1740
gcuuuaggaa gauccuccgg gaggaggggc ccaaggcacu gggaagggg  gccggggcca   1800
```

```
ggguguuccg uagcuccccc caguuuggcg ugacccugcu gaccuacgaa cugcugcaga    1860 gguguucua caucgacuuc gggggcguga agcccauggg cuccgagccg ugccuaaga     1920 gccggaucaa ucugcccgcc cccaaccccg accacguggg gggcuacaag cuggccgugg   1980
cuaccuucgc cgguaucgag aacaaguucg gccuguaccu gccccuguuc aagcccuccg   2040
ugagcacgag caaggccauc gggggcggcc ccugauaaua guccauaaag uaggaaacac   2100
uacagcugga gccucggugg ccaugcuucu gcccuuggcc cucccccc agccccuccu     2160 ccccuuccug cacccguacc ccccgcauua uuacucacgg uacgaguggu cuugaauaa    2220 agucugagug ggcggc                                                   2236
```

<210> SEQ ID NO 140
<211> LENGTH: 675
<212> TYPE: PRT
<213> ORGANISM: Artificial Sequence
<220> FEATURE:
<223> OTHER INFORMATION: Construct #4 Amino acid sequence of Citrin gene

<400> SEQUENCE: 140

```
Met Ala Ala Ala Lys Val Ala Leu Thr Lys Arg Ala Asp Pro Ala Glu
1               5                   10                  15

Leu Arg Thr Ile Phe Leu Lys Tyr Ala Ser Ile Glu Lys Asn Gly Glu
            20                  25                  30

Phe Phe Met Ser Pro Asn Asp Phe Val Thr Arg Tyr Leu Asn Ile Phe
        35                  40                  45

Gly Glu Ser Gln Pro Asn Pro Lys Thr Val Glu Leu Leu Ser Gly Val
    50                  55                  60

Val Asp Gln Thr Lys Asp Gly Leu Ile Ser Phe Gln Glu Phe Val Ala
65                  70                  75                  80

Phe Glu Ser Val Leu Cys Ala Pro Asp Ala Leu Phe Met Val Ala Phe
                85                  90                  95

Gln Leu Phe Asp Lys Ala Gly Lys Gly Glu Val Thr Phe Glu Asp Val
            100                 105                 110

Lys Gln Val Phe Gly Gln Thr Thr Ile His Gln His Ile Pro Phe Asn
        115                 120                 125

Trp Asp Ser Glu Phe Val Gln Leu His Phe Gly Lys Glu Arg Lys Arg
    130                 135                 140

His Leu Thr Tyr Ala Glu Phe Thr Gln Phe Leu Leu Glu Ile Gln Leu
145                 150                 155                 160

Glu His Ala Lys Gln Ala Phe Val Gln Arg Asp Asn Ala Arg Thr Gly
                165                 170                 175

Arg Val Thr Ala Ile Asp Phe Arg Asp Ile Met Val Thr Ile Arg Pro
            180                 185                 190

His Val Leu Thr Pro Phe Val Glu Glu Cys Leu Val Ala Ala Ala Gly
        195                 200                 205

Gly Thr Thr Ser His Gln Val Ser Phe Ser Tyr Phe Asn Gly Phe Asn
    210                 215                 220

Ser Leu Leu Asn Asn Met Glu Leu Ile Arg Lys Ile Tyr Ser Thr Leu
225                 230                 235                 240

Ala Gly Thr Arg Lys Asp Val Glu Val Thr Lys Glu Glu Phe Val Leu
                245                 250                 255

Ala Ala Gln Lys Phe Gly Gln Val Thr Pro Met Glu Val Asp Ile Leu
            260                 265                 270

Phe Gln Leu Ala Asp Leu Tyr Glu Pro Arg Gly Arg Met Thr Leu Ala
```

```
                275                 280                 285
Asp Ile Glu Arg Ile Ala Pro Leu Glu Glu Gly Thr Leu Pro Phe Asn
290                 295                 300

Leu Ala Glu Ala Gln Arg Gln Lys Ala Ser Gly Asp Ser Ala Arg Pro
305                 310                 315                 320

Val Leu Leu Gln Val Ala Glu Ser Ala Tyr Arg Phe Gly Leu Gly Ser
                325                 330                 335

Val Ala Gly Ala Val Gly Ala Thr Ala Val Tyr Pro Ile Asp Leu Val
                340                 345                 350

Lys Thr Arg Met Gln Asn Gln Arg Ser Thr Gly Ser Phe Val Gly Glu
                355                 360                 365

Leu Met Tyr Lys Asn Ser Phe Asp Cys Phe Lys Lys Val Leu Arg Tyr
370                 375                 380

Glu Gly Phe Phe Gly Leu Tyr Arg Gly Leu Leu Pro Gln Leu Leu Gly
385                 390                 395                 400

Val Ala Pro Glu Lys Ala Ile Lys Leu Thr Val Asn Asp Phe Val Arg
                405                 410                 415

Asp Lys Phe Met His Lys Asp Gly Ser Val Pro Leu Ala Ala Glu Ile
                420                 425                 430

Leu Ala Gly Gly Cys Ala Gly Gly Ser Gln Val Ile Phe Thr Asn Pro
                435                 440                 445

Leu Glu Ile Val Lys Ile Arg Leu Gln Val Ala Gly Glu Ile Thr Thr
450                 455                 460

Gly Pro Arg Val Ser Ala Leu Ser Val Val Arg Asp Leu Gly Phe Phe
465                 470                 475                 480

Gly Ile Tyr Lys Gly Ala Lys Ala Cys Phe Leu Arg Asp Ile Pro Phe
                485                 490                 495

Ser Ala Ile Tyr Phe Pro Cys Tyr Ala His Val Lys Ala Ser Phe Ala
                500                 505                 510

Asn Glu Asp Gly Gln Val Ser Pro Gly Ser Leu Leu Leu Ala Gly Ala
                515                 520                 525

Ile Ala Gly Met Pro Ala Ala Ser Leu Val Thr Pro Ala Asp Val Ile
                530                 535                 540

Lys Thr Arg Leu Gln Val Ala Ala Arg Ala Gly Gln Thr Thr Tyr Ser
545                 550                 555                 560

Gly Val Ile Asp Cys Phe Arg Lys Ile Leu Arg Glu Glu Gly Pro Lys
                565                 570                 575

Ala Leu Trp Lys Gly Ala Gly Ala Arg Val Phe Arg Ser Ser Pro Gln
                580                 585                 590

Phe Gly Val Thr Leu Leu Thr Tyr Glu Leu Leu Gln Arg Trp Phe Tyr
                595                 600                 605

Ile Asp Phe Gly Gly Val Lys Pro Met Gly Ser Glu Pro Val Pro Lys
            610                 615                 620

Ser Arg Ile Asn Leu Pro Ala Pro Asn Pro Asp His Val Gly Gly Tyr
625                 630                 635                 640

Lys Leu Ala Val Ala Thr Phe Ala Gly Ile Glu Asn Lys Phe Gly Leu
                645                 650                 655

Tyr Leu Pro Leu Phe Lys Pro Ser Val Ser Thr Ser Lys Ala Ile Gly
                660                 665                 670

Gly Gly Pro
            675

<210> SEQ ID NO 141
```

```
<211> LENGTH: 70
<212> TYPE: RNA
<213> ORGANISM: Artificial Sequence
<220> FEATURE:
<223> OTHER INFORMATION: mRNA encoding non-translated Factor IX (NTFIX

<400> SEQUENCE: 141
gggaauaaag agagaaaaga agaguaaucc auaaaguagg aaacacuaca gaagaaauau    60
aagagccacc                                                          70

<210> SEQ ID NO 142
<211> LENGTH: 85
<212> TYPE: RNA
<213> ORGANISM: Artificial Sequence
<220> FEATURE:
<223> OTHER INFORMATION: miR-126

<400> SEQUENCE: 142
cgcuggcgac gggacauuau uacuuuuggu acgcgcugug acacuucaaa cucguaccgu    60
gaguaauaau gcgccgucca cggca                                         85

<210> SEQ ID NO 143
<211> LENGTH: 22
<212> TYPE: RNA
<213> ORGANISM: Artificial Sequence
<220> FEATURE:
<223> OTHER INFORMATION: miR-126-3p

<400> SEQUENCE: 143
ucguaccgug aguaauaaug cg                                            22

<210> SEQ ID NO 144
<211> LENGTH: 22
<212> TYPE: RNA
<213> ORGANISM: Artificial Sequence
<220> FEATURE:
<223> OTHER INFORMATION: miR-126-3p binding site

<400> SEQUENCE: 144
cgcauuauua cucacgguac ga                                            22

<210> SEQ ID NO 145
<211> LENGTH: 21
<212> TYPE: RNA
<213> ORGANISM: Artificial Sequence
<220> FEATURE:
<223> OTHER INFORMATION: miR-126-5p

<400> SEQUENCE: 145
cauuauuacu uuggguacgc g                                             21

<210> SEQ ID NO 146
<211> LENGTH: 21
<212> TYPE: RNA
<213> ORGANISM: Artificial Sequence
<220> FEATURE:
<223> OTHER INFORMATION: miR-126-5p binding site

<400> SEQUENCE: 146
cgcguaccaa aaguaauaau g                                             21

<210> SEQ ID NO 147
<211> LENGTH: 166
<212> TYPE: RNA
<213> ORGANISM: Artificial Sequence
```

```
<220> FEATURE:
<223> OTHER INFORMATION: 3' UTR with miR 142-3p and miR 126-3p binding
      sites variant 2

<400> SEQUENCE: 147
ugauaauagu ccauaaagua ggaaacacua cagcuggagc cucgguggcc uagcuucuug      60
ccccuugggc cuccccccag ccccuccucc ccuccugca cccguacccc ccgcauuauu      120
acucacggua cgaguggucu uugaauaaag ucgagugggg cggcsd                    166

<210> SEQ ID NO 148
<211> LENGTH: 142
<212> TYPE: RNA
<213> ORGANISM: Artificial Sequence
<220> FEATURE:
<223> OTHER INFORMATION: 3' UTR with miR 142-3p binding site variant 2

<400> SEQUENCE: 148
ugauaauagg cuggagccuc gguggccuag cuucuugccc cuugggccuc ccccagccc      60 cuccuccccu uccugcaccc guaccccuc cauaaaguag gaaacacuac aguggucuuu      120
gaauaaaguc ugagugggcg gc                                              142

<210> SEQ ID NO 149
<211> LENGTH: 119
<212> TYPE: RNA
<213> ORGANISM: Artificial Sequence
<220> FEATURE:
<223> OTHER INFORMATION: 3' UTR, no miR binding sites variant 2

<400> SEQUENCE: 149
ugauaauagg cuggagccuc gguggccuag cuucuugccc cuugggccuc ccccagccc      60 cuccuccccu uccugcaccc guaccccgu ggucuuugaa uaaagucuga gugggcggc      119

<210> SEQ ID NO 150
<211> LENGTH: 141
<212> TYPE: RNA
<213> ORGANISM: Artificial Sequence
<220> FEATURE:
<223> OTHER INFORMATION: 3' UTR with miR 126-3p binding site variant 3

<400> SEQUENCE: 150
ugauaauagg cuggagccuc gguggccuag cuucuugccc cuugggccuc ccccagccc      60 cuccuccccu uccugcaccc guaccccccg cauuauuacu cacgguacga guggucuuug    120
aauaaagucu gagugggcgg c                                              141

<210> SEQ ID NO 151
<211> LENGTH: 188
<212> TYPE: RNA
<213> ORGANISM: Artificial Sequence
<220> FEATURE:
<223> OTHER INFORMATION: 3' UTR with 3 miR 142-3p binding sites variant
      2

<400> SEQUENCE: 151
ugauaauagu ccauaaagua ggaaacacua cagcuggagc cucgguggcc uagcuucuug      60
ccccuugggc cuccauaaag uaggaaacac uacaucccccc cagccccucc ucccuuccu    120 gcacccguac ccccuccaua aaguaggaaa cacuacagug gucuuugaau aaagucugag    180
ugggcggc                                                              188

<210> SEQ ID NO 152
```

```
<211> LENGTH: 142
<212> TYPE: RNA
<213> ORGANISM: Artificial Sequence
<220> FEATURE:
<223> OTHER INFORMATION: 3'UTR with miR 142-3p binding site, P1
      insertion variant 2

<400> SEQUENCE: 152
ugauaauagu ccauaaagua ggaaacacua cagcuggagc cucgguggcc uagcuucuug    60
ccccuugggc cuccccccag ccccuccucc ccuccugca cccguacccc cguggucuuu   120
gaauaaaguc ugagugggcg gc                                           142

<210> SEQ ID NO 153
<211> LENGTH: 142
<212> TYPE: RNA
<213> ORGANISM: Artificial Sequence
<220> FEATURE:
<223> OTHER INFORMATION: 3'UTR with miR 142-3p binding site, P2
      insertion variant 2

<400> SEQUENCE: 153
ugauaauagg cuggagccuc gguggcucca uaaaguagga aacacuacac uagcuucuug    60
ccccuugggc cuccccccag ccccuccucc ccuccugca cccguacccc cguggucuuu   120
gaauaaaguc ugagugggcg gc                                           142

<210> SEQ ID NO 154
<211> LENGTH: 142
<212> TYPE: RNA
<213> ORGANISM: Artificial Sequence
<220> FEATURE:
<223> OTHER INFORMATION: 3'UTR with miR 142-3p binding site, P3
      insertion variant 2

<400> SEQUENCE: 154
ugauaauagg cuggagccuc gguggccuag cuucuugccc cuugggccuc cauaaaguag    60
gaaacacuac auccccccag ccccuccucc ccuccugca cccguacccc cguggucuuu   120
gaauaaaguc ugagugggcg gc                                           142

<210> SEQ ID NO 155
<211> LENGTH: 142
<212> TYPE: RNA
<213> ORGANISM: Artificial Sequence
<220> FEATURE:
<223> OTHER INFORMATION: 3'UTR with miR 155-5p binding site variant 2

<400> SEQUENCE: 155
ugauaauagg cuggagccuc gguggccuag cuucuugccc cuugggccuc ccccagccc     60 cucccccu uccugcaccc guaccccac cccaucaca auuagcauua aguggucuuu      120
gaauaaaguc ugagugggcg gc                                           142

<210> SEQ ID NO 156
<211> LENGTH: 188
<212> TYPE: RNA
<213> ORGANISM: Artificial Sequence
<220> FEATURE:
<223> OTHER INFORMATION: 3' UTR with 3 miR 155-5p binding sites variant
      2

<400> SEQUENCE: 156
ugauaauaga cccuaucac aauuagcauu aagcuggagc cucgguggcc uagcuucuug     60
ccccuugggc caccccuauc acaauuagca uuaauccccc cagcccucc uccccuuccu   120
```

```
gcacccguac ccccaccccu aucacaauua gcauuaagug gucuuugaau aaagucugag    180
ugggcggc                                                            188

<210> SEQ ID NO 157
<211> LENGTH: 188
<212> TYPE: RNA
<213> ORGANISM: Artificial Sequence
<220> FEATURE:
<223> OTHER INFORMATION: 3'UTR with 2 miR 155-5p binding sites and 1 miR
      142-3p binding site variant 2

<400> SEQUENCE: 157
ugauaauaga ccccuaucac aauuagcauu aagcuggagc cucgguggcc uagcuucuug     60
ccccuugggc cuccauaaag uaggaaacac uacaucccc cagccccucc ucccccuuccu   120 gcacccguac ccccaccccu aucacaauua gcauuaagug gucuuugaau aaagucugag   180
ugggcggc                                                            188
```